US012691171B2

(12) United States Patent
Smith et al.

(10) Patent No.: US 12,691,171 B2
(45) Date of Patent: Jul. 28, 2026

(54) CORONAVIRUS VACCINE FORMULATIONS

(71) Applicant: Novavax, Inc., Gaithersburg, MD (US)

(72) Inventors: Gale Smith, Germantown, MD (US); Michael J. Massare, Mt. Airy, MD (US); Jing-Hui Tian, Germantown, MD (US)

(*) Notice: Subject to any disclaimer, the term of this patent is extended or adjusted under 35 U.S.C. 154(b) by 976 days.

(21) Appl. No.: 17/795,337

(22) PCT Filed: Jan. 27, 2021

(86) PCT No.: PCT/US2021/015220

§ 371 (c)(1),
(2) Date: Jul. 26, 2022

(87) PCT Pub. No.: WO2021/154812

PCT Pub. Date: Aug. 5, 2021

(65) Prior Publication Data

US 2023/0070886 A1     Mar. 9, 2023

Related U.S. Application Data

(63) Continuation-in-part of application No. 16/997,001, filed on Aug. 19, 2020, now Pat. No. 10,953,089.

(60) Provisional application No. 63/129,392, filed on Dec. 22, 2020, provisional application No. 63/054,182, filed on Jul. 20, 2020, provisional application No. 63/051,706, filed on Jul. 14, 2020, provisional
(Continued)

(51) Int. Cl.
| | |
|---|---|
| *C12N 7/00* | (2006.01) |
| *A61K 39/215* | (2006.01) |
| *A61P 31/14* | (2006.01) |
| *A61K 39/00* | (2006.01) |

(52) U.S. Cl.
CPC ............ *A61K 39/215* (2013.01); *A61P 31/14* (2018.01); *A61K 2039/545* (2013.01); *A61K 2039/55577* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 4,900,549 A | 2/1990 | De Vries et al. | |
| 4,911,928 A | 3/1990 | Wallach | |

(Continued)

FOREIGN PATENT DOCUMENTS

| | | | |
|---|---|---|---|
| AU | 2003245220 B2 | 4/2009 | |
| CA | 2491457 C | 9/2012 | |

(Continued)

OTHER PUBLICATIONS

"Safety Evaluation of Certain Food Additives and Contaminants Quillaia Extracts," WHO Food Additives Series:48, 14 pages (1996).
(Continued)

*Primary Examiner* — M Franco G Salvoza
(74) *Attorney, Agent, or Firm* — Carlson, Caspers, Vandenburgh & Lindquist, P.A.

(57) ABSTRACT

Disclosed herein are coronavirus Spike (S) proteins and nanoparticles comprising the same, which are suitable for use in vaccines. The nanoparticles present antigens from pathogens surrounded to and associated with a detergent core resulting in enhanced stability and good immunogenicity. Dosages, formulations, and methods for preparing the vaccines and nanoparticles are also disclosed.

30 Claims, 84 Drawing Sheets
Specification includes a Sequence Listing.

Related U.S. Application Data application No. 63/048,945, filed on Jul. 7, 2020, provisional application No. 62/983,180, filed on Feb. 28, 2020, provisional application No. 62/976,858, filed on Feb. 14, 2020, provisional application No. 62/966,271, filed on Jan. 27, 2020.

(56)               References Cited

U.S. PATENT DOCUMENTS

| | | | |
|---|---|---|---|
| 5,057,540 | A | 10/1991 | Kensil et al. |
| 5,620,690 | A | 4/1997 | Kersten et al. |
| 5,629,021 | A | 5/1997 | Wright |
| 6,231,859 | B1 | 5/2001 | Kensil |
| 6,352,697 | B1 | 3/2002 | Cox et al. |
| 6,387,373 | B1 | 5/2002 | Wright et al. |
| 6,428,807 | B1 | 8/2002 | Macfarlan et al. |
| 6,524,584 | B2 | 2/2003 | Kensil |
| 6,558,670 | B1 | 5/2003 | Friede et al. |
| 6,846,489 | B1 | 1/2005 | Garcon et al. |
| 7,776,343 | B1 | 8/2010 | Cox et al. |
| 8,173,141 | B2 | 5/2012 | Cox et al. |
| 8,541,003 | B2 | 9/2013 | Anderson et al. |
| 8,821,881 | B2 | 9/2014 | Morein et al. |
| 10,022,437 | B2 | 7/2018 | Pushko et al. |
| 10,426,829 | B2 | 10/2019 | Smith et al. |
| 10,485,863 | B2 | 11/2019 | Osterhaus et al. |
| 10,729,764 | B2 | 8/2020 | Morein et al. |
| 10,906,944 | B2 | 2/2021 | He et al. |
| 10,953,089 | B1 | 3/2021 | Smith et al. |
| 11,149,286 | B1 | 10/2021 | Barry |
| 11,253,586 | B2 | 2/2022 | Smith et al. |
| 11,541,112 | B2 | 1/2023 | Smith et al. |
| 11,896,664 | B2 | 2/2024 | Smith et al. |
| 2006/0121065 | A1 | 6/2006 | Morein et al. |
| 2006/0239963 | A1 | 10/2006 | Morein et al. |
| 2010/0017904 | A1 | 1/2010 | Abad et al. |
| 2012/0107353 | A1 | 5/2012 | Morein et al. |
| 2013/0129770 | A1 | 5/2013 | Osterhaus et al. |
| 2014/0335049 | A1 | 11/2014 | Morein et al. |
| 2015/0209425 | A1 | 7/2015 | Morein et al. |
| 2015/0265698 | A1 | 9/2015 | Pushko et al. |
| 2016/0008451 | A1 | 1/2016 | Stary et al. |
| 2016/0046675 | A1 | 2/2016 | Kwong |
| 2016/0184427 | A1 | 6/2016 | Morein et al. |
| 2016/0206729 | A1 | 7/2016 | Smith et al. |
| 2018/0346521 | A1 | 12/2018 | Langedijk |
| 2018/0369368 | A1 | 12/2018 | Morein et al. |
| 2020/0061185 | A1 | 2/2020 | Graham et al. |
| 2020/0215189 | A1 | 7/2020 | Morein et al. |
| 2020/0345840 | A1 | 11/2020 | Morein et al. |
| 2020/0407402 | A1 | 12/2020 | He et al. |
| 2021/0139543 | A1 | 5/2021 | He et al. |
| 2021/0228708 | A1 | 7/2021 | Smith et al. |
| 2021/0228709 | A1 | 7/2021 | Smith et al. |
| 2021/0246170 | A1 | 8/2021 | Langedijk et al. |
| 2022/0125914 | A1 | 4/2022 | Smith et al. |
| 2022/0332765 | A1 | 10/2022 | Smith et al. |
| 2022/0354944 | A1 | 11/2022 | Patel et al. |
| 2023/0070886 | A1 | 3/2023 | Smith et al. |
| 2023/0330216 | A1 | 10/2023 | Smith et al. |

FOREIGN PATENT DOCUMENTS

| | | | |
|---|---|---|---|
| CN | 1472332 | A | 2/2004 |
| CN | 111499692 | A | 8/2020 |
| EP | 0109942 | A2 | 5/1984 |
| EP | 0242380 | B1 | 4/1991 |
| EP | 0180564 | B1 | 7/1991 |
| EP | 0436620 | B1 | 8/1994 |
| EP | 0362279 | B1 | 1/1995 |
| EP | 0889736 | B1 | 12/2003 |
| EP | 1539231 | B1 | 6/2009 |
| JP | 2018532703 | A | 11/2018 |
| RU | 2403063 | C1 | 11/2010 |
| RU | 2639559 | C2 | 12/2017 |
| WO | WO-8809336 | A1 | 12/1988 |
| WO | WO-9003184 | A1 | 4/1990 |
| WO | WO-9611711 | A1 | 4/1996 |
| WO | WO-9730728 | A1 | 8/1997 |
| WO | WO-9836772 | A1 | 8/1998 |
| WO | WO-2004004762 | A1 | 1/2004 |
| WO | WO-2004085633 | A1 | 10/2004 |
| WO | WO-2005002620 | A1 | 1/2005 |
| WO | WO-2009081285 | A2 | 7/2009 |
| WO | WO-2013049342 | A1 | 4/2013 |
| WO | 2014153087 | A1 | 9/2014 |
| WO | WO-2015042373 | A1 | 3/2015 |
| WO | 2015080973 | A1 | 6/2015 |
| WO | WO-2017041100 | A2 | 3/2017 |
| WO | 2017161151 | A1 | 9/2017 |
| WO | WO-2018081318 | A1 | 5/2018 |
| WO | WO-2018170347 | A1 | 9/2018 |
| WO | WO 2021147025 | A1 | 7/2021 |
| WO | 2021154812 | A1 | 8/2021 |
| WO | WO-2021154763 | A1 | 8/2021 |
| WO | WO-2021155323 | A1 | 8/2021 |
| WO | WO-2022046634 | A1 | 3/2022 |

OTHER PUBLICATIONS

Ahlberg et al., Global transcriptional response to ISCOM-Matrix adjuvant at the site of administration and in the draining lymph node early after intramuscular injection in pigs, Developmental and Comparative Immunology, vol. 38, pp. 17-26 (2012), Elsevier Ltd.

Anonymous, "Novavax to Present at the 2013 Stifel Nicolaus Healthcare Conference," Reuters, 1 page http://in.reuters.com/article/2013/09/05/idUSnGNX7PTmrq+1d8+GNW20130905 (2013).

Anonymous, "Stifel 2013 Healthcare Conference," pp. 1-35, http://www.novavax.com/download/file/2013_09_12%20Novavax_Stifel_presentation.pdf (2013).

Barr et al., "ISCOMs and other saponin based adjuvants," Advanced Drug Delivery Reviews, (1998), 32: 247-271.

Behboudi et al., "Quillaja Saponin Formulations that Stimulate Proinflammatory Cytokines Elicit a Potent Acquired Cell-Mediated Immunity," Scand. J. Immunol. 50:371-377 (1999).

Bengtsson et al., Matrix-M adjuvant increases immunogenicity of seasonal influenza vaccine for the elderly, manuscript in preparation, pp. 1-27 (2014).

Bengtsson et al., "ISCOM technology-based Matrix™ adjuvant: success in future vaccines relies on formulation," Expert. Rev. Vaccines 10(4):401-403 (2011).

Boulter et al., Evaluation of recombinant sporozoite antigen SPAG-1 as a vaccine candidate against Theileria annulata by the use of different delivery systems, Tropical Medicine and International Health, vol. 4, pp. A71-A77 (1999), Blackwell Science, Ltd.

Chan et al., "Functional Characterization of Heptad Repeat 1 and 2 Mutants of theSpike Protein of Severe Acute Respiratory Syndrome Coronavirus," Journal of Virology 3225-3237 (2006).

Chatterjee et al., "The 2019 novel coronavirus disease (COVID-19) pandemic: A review of the current evidence," Indian J Med Res 151(2-3):147-159 (Year: 2020).

Chen et al., "RNA based mNGS approach identifies a novel human coronavirus from two individual pneumonia cases in 2019 Wuhan outbreak," Emerging Microbes & Infections 9(1):313-319 (2019).

Chen, Y. et al., "Emerging coronaviruses: Genome structure, replication, and pathogenesis"; Journal of Medical Virology; (Jan. 22, 2020); vol. 92; issue 4, pp. 418-423.

Cheng et al., "Use of convalescent plasma therapy in SARS patients in Hong Kong," Eur. J. Clin. Microbiol. Infect. Dis. 24(1):44-46 (2005).

Coleman et al., "Purified coronavirus spike protein nanoparticles induce coronavirus neutralizing antibodies in mice," Vaccine 32(26):3169-3174 (2014).

"Committee for Veterinary Medicinal Products, Quillaia Saponins, Summary Report", The European Agency for the rgJ Evaluation of Medicinal Products, EMEA/MRL/055/95-FINAL, Feb. 1996, pp. 1-2.

(56) References Cited

OTHER PUBLICATIONS

Copland et al., "Hydration of lipid films with an aqueous solution of Quil A: a simple method for the preparation of immune-stimulating complexes," International Journal of Pharmaceutics 196:135-139 (2000).

Coulter et al., Studies on experimental adjuvanted influenza vaccines: comparison of immune stimulating complexes(Iscoms) and oil-in-water vaccines; Vaccine, vol. 16, No. 11/12, pp. 1243-1253 (1998), Elsevier Science Ltd., Great Britain.

Cox et al., Development of an Influenza-ISCOM Vaccine, in Vaccine Design (eds. G. Gregoriadis et al.), Springer Science+Business Media, New York (1997), pp. 33-49.

Cox et al., Evaluation of a virosomal H5N1 vaccine formulated with Maxtrix M adjuvant in phase I clinical trial, Elsevier Ltd, Vaccine, 29, pp. 8049-8059, Aug. 22, 2011.

Cox et al., Prospects for the Development of New Vaccine Adjuvants, BioDrugs, vol. 12(6), pp. 439-453 (1999), Ad is International Limited.

Database UniProt [Online], "SubName: Full=S Protein {ECO:0000313|EMBL:AGN70973.1}," Ebi accession No. UNIPROT:R9UQ53, Database accession No. R9UQ53 (2013), 2 pages.

Delmas and Laude, "Assembly of Coronavirus Spike Protein into Trimers and Its Role in Epitope Expression," Journal of Virology 64(11):5367-5375 (1990).

Demana et al., "A comparison of pseudo-ternary diagrams of aqueous mixtures of Quil A, cholesterol and phospholipid prepared by lipid-film hydration and dialysis," Journal of Pharmacy and Pharmacology 56:573-580 (2004).

Demana et al., "Pseudo-ternary phase diagrams of aqueous mixtures of Quil A, cholesterol and phospholipid prepared by the lipid-film hydration method," International Journal of Pharmaceutics 270:229-239 (2004).

Drane et al., "Iscomatrix adjuvant for prophylactic and therapeutic vaccines," Expert Rev. Vaccines 6:761-772 (2007).

Du et al., "The spike protein of SRS-CpV—a target for vaccine and therapeutic development," Nat. Rev. Microbiol. 7(3):226-236 (2009).

Du, L., et al., "Identification of a Receptor-Binding Domain in the S Protein of the Novel Human Coronavirus Middle East Respiratory Syndrome Coronavirus as an Essential Target for Vaccine Development," J. Virol. 87(17):9939-9942 (2013).

Duan, et al., An overview of the novel coronavirus MERS-COV, Chin J Viral Dis, 3(4):245-249 (2013).

Eckert et al., "Mechanisms of Viral Membrane Fusion and Its Inhibition," Annual Review of Biochemistry 70:770-810 (2001).

Ekstrom et al., "Iscom and iscom-matrix enhance by intranasal route the IgA responses to OVA and rCTB in local and remote mucosal secretions," Vaccine 17:2690-2701 (1999).

Ennis et al., "Augmentation of Human Influenza A Virus-Specific Cytotoxic T Lymphocyte Memory by Influenza Vaccine and Adjuvanted Carriers (ISCOMS)," Virology 25:256-261 (1999).

Eyles et al., "Immunodominant Francisella tularensis antigens identified using proteome microarray," Proteomics 7:2172-2183 (2007).

Follis et al., "Furin cleavage of the SARS coronavirus spike glycoprotein enhances cell-cell fusion but does not affect virion entry," Virology 350(2):358-369 (2006).

Fossum et al., Early inflammatory response to the saponin adjuvant Matrix-M in the pig, Veterinary Immunology and Immunopathology, http://dx.doi.org/10.1016/j.vetimm.2013.07.007 (2013), pp. 1-9, Elsevier B.V.

Genocea Biosciences, Genocea Reports Positive Initial Phase 1/2A Results for GEN- 003, It's Pioneering Therapeutic Vaccine Candidate for the Treatment of Herpes Simplex Virus-2 (HSV-2), at ICAAC 2013, press release, Cambridge MA, Sep. 12,2013, pp. 1-3.

Gillim-Ross et al., "Emerging Respiratory Viruses: Challenges and Vaccine Strategies," Clin. Microbiol. Rev. 19(4):614-636 (2006).

Gonzalez-Reyes et al., "Cleavage of the human respiratory syncytial virus fusion protein at two distinct sites is required for activation of membrane fusion," Proc. Natl. Acad. Sci. USA 98(17):9859-9864 (2001).

Gretebeck et al., "Animal models for SARS and MERS coronaviruses," Virology, 13:123-129 (Year: 2015).

Gruenke et al., "New Insights into the Spring-Loaded Conformational Change of Influenza Virus Hemagglutinin," Journal of Virology, May 2002, 76:(9) 4456-4466 (2002).

Hilgenfeld et al., "From SARS to MERS: 10 years of research on highly pathogenic human coronaviruses," Antiviral Res. 100(1):286-295 (2013).

Hoffman, M et al., "Priming Time: How Cellular Proteases Arm Coronavirus Spike Proteins"; Coronavirus Spike Protein: Springer International Publishing AG; (2018); pp. 71-98; DOI: 10.1007/978-3-319-75474-1_4.

International Search Report and Written Opinion issued by the International Searching Authority for Application No. PCT/US21/15220, dated Jun. 30, 2021, 14 pages.

Jackson et al., "An mRNA Vaccine against SARS-CoV-2 Preliminary Report," The New England Journal of Medicine, pp. 1-12 (2020).

Jiang, et al., "A predicted receptor-binding and critical neutralizing domain in S protein of the novel human coronavirus HCoV-EMC", Journal of Infection (66):464-466 (2013).

Johansson et al., "Iscoms with different quillaja saponin components differ in their immunomodulating activities," Vaccine 17:2894-2900 (1999).

Kam et al., "Antibodies against trimeric S glycoprotein protect hamsters against SARS-CoV challenge despite their capacity to mediate FcgammaRII-dependent entry into B cells in vitro," Vaccine 25(4):729-740 (2007).

Karin Lovgren Bengtsson, Bror Morein & Albert Dme Osterhaus (2011) ISCOM technology-based Matrix M adjuvant: success in future vaccines relies on formulation, Expert Review of Vaccines, 10:4, 401-403, DOI: 10.1586/erv.11.25.

Kensil, Saponins as Vaccine Adjuvants, Critical Reviews in Therapeutic Drug Carrier Systems, vol. 13(1&2), pp. 1-55 (1996), Begell House, Inc.

Kersten et al., On the structure of immune-stimulating saponin-lipid complexes (iscoms) Biochimica et Biophysica Acta, 1062:165-171 (1991).

Kirchdoerfer et al., "Stabilized coronavirus spikes are resistant to conformational changes induced by receptor recognition or proteolysis," Scientific Reports, pp. 1-11 (2018).

Kleine-Weber et al., Functional analysis of potential cleavage sites in the MERS coronavirus spike protein, Scientific Reports vol. 8, No. 1, article 16597, pp. 1-11 (2018).

Korber et al., "Tracking Changes in SARS-CoV-2 Spike: Evidence that D614G Increases Infectivity of the COVID-19 Virus," Cell 182:1-16 (2020).

Kuroiwa, Y., et al., "Antigen-specific human polyclonal antibodies from hyperimmunized cattle," Nat. Biotechnol. 27(2):173-181 (2009).

Lavelle et al., "Cholera Toxin Promotes the Induction of Regulatory T Cells Specific for Bystander Antigens by Modulating Dendritic Cell Activation," Journal of Immunology 171:2384-2392 (2003).

Li et al., "Immunogenicity and Protection Efficacy of Monomeric and Trimeric Recombinant SARS Coronavirus Spike Protein Subunit Vaccine Candidates," Viral Immunology 26(2):126-132 (2013).

Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine 29(38):6606-6613 (2011).

Lovgren et al., The Requirement of Lipids for the Formation of Immunostimulating Complexes (Iscoms), Biotechnol. Appl. Biochem. 10:161-172 (1988).

Lovgren-Bengtsson, 6 Preparation and Use of Adjuvants; Methods in Microbiology, vol. 25, pp. 471-502 (1998), Academic Press Ltd.

Lovgren-Bengtsson et al., "4.5 Preparation and Use of Adjuvants," Methods in Microbiology 32:551-588 (2002).

Lu et al., "Immune responses against severe acute respiratory syndrome coronavirus induced by virus-like particles in mice," Immunol. 122:496-502 (2007).

Lucy et al., "Structure and Assembly of Macromolecular Lipid Complexes Composed of Globular Micelles," Journal of Molecular Biology, (1964), 8: 727-748.

(56)            References Cited

OTHER PUBLICATIONS

Magnusson et al., Immune enhancing properties of the novel Matrix-M adjuvant leads to potentiated immune responses to an influenza vaccine in mice, Vaccine, http://dx.doi.org/10.1 016/j.vaccine.2013.01.039 (2013), pp. 1-9, Elsevier Ltd.

Magnusson et al., Matrix-M adjuvanted envelope protein vaccine protects against lethal lineage 1 and 2 West Nile virus infection in mice, Vaccine vol. 32, pp. 800-808 (2014), Elsevier Ltd.

Matsushita et al., "Triple immunoglobulin gene knockout transchromosomic cattle: bovine lambda cluster deletion and its effect on fully human polyclonal antibody production," PLOS One 9(3):1-14 (2014).

McKenzie et al., ISCOMATRIX vaccines: Safety in human clinical studies, Human Vaccines, vol. 6, No. 3, pp. 237-246 (2010), Landes BioScience.

Morein et al., "Current status and potential application of ISCOMs in veterinary medicine," Advanced Drug Delivery Reviews 56:1367-1382 (2004).

NCT01669512, Adjuvanting Viral Vectored Malaria Vaccines with Matrix M, dated Mar. 9, 2014, pp. 14.

NCT04368988, Evaluation of the Safety and Immunogenicity of a SARS-CoV-2 rS Nanoparticle Vaccine With/Without Matrix-M Adjuvant, dated Apr. 30, 2020, 21 pages.

NCT04533399, A Study Looking at the Effectiveness and Safety of a COVID-19 Vaccine in South African Adults, dated Aug. 31, 2020, 18 pages.

NCT04583995, A Study Looking at the Effectiveness, Immune Response, and Safety of a COVID-19 Vaccine in Adults in the United Kingdom, dated Oct. 12, 2020, 11 pages.

NCT04611802, A Study to Evaluate the Efficacy, Immune Response, and Safety of a COVID-19 Vaccine in Adults â‰¥ 18 Years With a Pediatric Expansion in Adolescents (12 to 18 Years) at Risk for SARS-CoV-2, dated Nov. 2, 2020,18 pages.

NCT04834869, COVID-19 Vaccines Safety Tracking (CoVaST), dated Apr. 8, 2021, 11 pages.

NCT04889209, Delayed Heterologous SARS-CoV-2 Vaccine Dosing (Boost) After Receipt of EUA Vaccines, dated May 17, 2021, 16 pages.

NCT04961541, Evaluation of the Safety and Immunogenicity of Influenza and COVID-19 Combination Vaccine, dated Jul. 14, 2021, 14 pages.

NCT05029856, Evaluation of the Safety and Immunogenicity of SII Vaccine Constructs Based on the SARS-CoV-2 (COVID-19) Variant in Adults, dated Sep. 1, 2021, 13 pages.

NCT05112848, A Study to Evaluate Safety and Immunogenicity of a COVID-19 Vaccine in People Living With HIV at Risk for SARS-CoV-2 (COVID-19), dated Nov. 9, 2021, 16 pages.

NCT05236491, COvid-19 Vaccine Booster in Immunocompromised Rheumatic Diseases, dated Feb. 11, 2022, 9 pages.

NCT05249816, Phase 3 Study to Evaluate a Single Booster of the NVX-CoV2373 COVID19 Vaccine in Adults, dated Feb. 22, 2022, 11 pages.

NCT05372588, Phase 3 Booster Study for the SARS-COV-2 rS Vaccines, dated May 12, 2022, 12 pages.

Nord, "Novel acetylated triterpenoid saponins in a chromatographic fraction from Quilaja saponinaria Molina," Carb. Res. 329:817-829 (2000).

Ozel et al., "Quaternary Structure of the Immunostimulating Complex (Iscom), "Journal of Ultrastructure and Molecular Structure Research 102:240-248 (1989).

Pallesen et al., "Immunogenicity and structures of a rationally designed prefusion MERS-CoV spike antigen," PNAS E7348-E7357 (2017).

Parrish, "Novavax creates MERS-CoV vaccine candidate," http://vaccinenewsdaily.com/vaccine_development/325407-novavax-creates-mers-cov-vaccine-candidate/ (2013), 2 pages.

Pedersen et al., Matrix-M adjuvanted virosomal H5N1 vaccine confers protection against lethal viral challenge in a murine model, Influenza and Other Respiratory Viruses. DOI: 1 0.1111/j.1750-2659.2011.00256.x (2011 ), pp. 1-12, Blackwell Publishing Ltd.

Pedersen, et al.; T-Helper 1 Cells Elicited by H5N1 Vaccination Predict Seroprotection, Journal of Infectious Disease, 206, pp. 158-166, Jul. 15, 2016.

Poulsen et al., "Limits for Antibody Affinity Maturation and Repetoire Diversification in Hyper vaccinated Humans," J. Immunol. 187(8):4429-4235 (2011).

Ranade et al., "Rapid, high throughput protein estimation method for saponin and alhydrogel adjuvanted R21 VLP Malaria vaccine based on intrinsic fluorescence," Vaccine 40:600-601 (2022).

Rey, F. A. et al., "Common Features of Enveloped Viruses and Implications for Immunogen Design for Next-Generation Vaccines"; Cell; (Mar. 8, 2018); vol. 172; issue 6, pp. 1319-1334.

Rimmelzwaan. et al., A randomized, double blind study in young healthy adults comparing cell mediated and 1 humoral immune responses induced by influenza ISCOM vaccines and conventional vaccines; Vaccine, 2001, vol. 19, pp. 1180-1187, Elsevier Science Limited.

Ronnberg et al., "Adjuvant activity of non-toxic Quillaja saponaria Molina components for use in ISCOM matrix," Vaccine, vol. 13, No. 14, pp. 1375-1382 (1995).

Safety and Immunogenicity Study of Therapeutic HSV-2 Vaccine, Identifier NCT01667341, ClinicaiTrials.gov, U.S. National Institutes of Health; available at http://clinicaltrials.gov/ct2/show/NCT01667341 ?term=matrix+m&rank=3, Mar. 9, 2014, pp. 1-4.

Sekimukai et al., "Gold nanoparticle-adjuvanted S protein induces a strong antigen-specific IgG response against severe acute respiratory syndrome-related coronavirus infection, but fails to induce protective antibodies and limit eosinophilic infiltration in lungs, "Microbiology and Immunology, 64:33-51 (Year: 2020).

Shen, X. et al. Neutralization of SARS-CoV-2 Variants B.1.429 and B.1.351, N Engl J Med. (Apr. 7, 2021), 2 pages.

Shimizu, "Chapter 32. Routes of Administration," in The Laboratory Mouse, Hans Hedrich and Gillian Bullock, Eds., Elsevier Academic Press, 15 pages (2004).

Sjolander,, et al., ISCOMs: an adjuvant with multiple functions, Journal of Leukocyte Biology, vol. 64, pp. 713-723 (1998).

Sjolander, et al., Uptake and adjuvant activity of orally delivered saponin and ISCOM vaccines, Advanced Drug Delivery Reviews, vol. 34, pp. 321-338 (1998), Elsevier Science B.V.

Skoberne et al., An adjuvanted herpes simplex virus 2 subunit vaccine elicits a T cell response in mice and is an effective therapeutic vaccine in Guinea pigs, J. Virol. 87:3930-3942 (2013).

Song, F., et al., "Middle East Respiratory Syndrome Coronavirus Spike Protein Delivered by Modified Vaccinia Virus Ankara Efficiently Induces Virus-Neutralizing Antibodies," J. Virol. 87(21):11950-11954 (2013).

Sun et al., "Advances in saponin-based adjuvants," Vaccine 27:1787-1796 (2009).

Sun et al., "ISCOMs and ISOMATRIX," Vaccine 27:4388-4401 (2009).

Third Party Observation: Additional Comments in Respect of WO2021154812, Document #11 issued for International Application No. PCT/US2021/015220 on May 27, 2022, 2 pages.

Third Party Observation issued for International Application No. PCT/US2021/015220 on May 27, 2022, 11 pages.

Tian et al., "SARS-CoV-2 spike glycoprotein vaccine candidate NVX-CoV2373 elicits immunogenicity in baboons and protection in mice," Jun. 29, 2020, 50 pages.

Tian et al., "SARS-COV-2 spike glycoprotein vaccine candidate NVX-CoV2373 elicits immunogenicity in baboons and protection in mice," Nature Communications vol. 12, No. 1, Article 372, pp. 1-14 (2021).

Van Boheemen et al., "Genomic Characterization of a Newly Discovered Coronavirus Associated with Acute Respiratory Distress Syndrome in Humans," mBio 3(6):e00473-12, 9 pages (2012).

Van Doremalen N. et al. ChAdOx1 nCoV-19 vaccination prevents SARS-CoV-2 pneumonia in rhesus macaques. bioRxiv, 23 pages (2020).

Wald, "A Novel Therapeutic Vaccine (GEN003) for Genital Herpes Reduces HSV-2 Shedding: Initial Results of Clinical Trial GEN003-001," Presented at Interscience Conference on Antimicrobial Agents and Chemotherapy (ICAAC 2013), Denver, CO, Sep. 12, 2013, pp. 1-21.

(56)                    References Cited

OTHER PUBLICATIONS

Wald et al., Novel Therapeutic Vaccine for Genital Herpes Reduces Genital HSV-2 Shedding, in ICAAC 2013, Denver, CO, Sep. 2013, cover page and p. 279, Abstract 183(G).

Walls et al., "Functional Characterization of Heptad Repeat 1 and 2 Mutants of the Spike Protein of Severe Acute Respiratory Syndrome Coronavirus," Nature 531, 17 pages (2016).

Wang et al., "Subunit Vaccines Against Emerging Pathogenic Human Coronaviruses," Frontiers in Microbiology, 11:298, 19 pages (Year: 2020).

Wrapp et al., "Cryo EM Structure of the 2019 nCOV spike in the Prefusion Conformation," bioRxiv, posted Feb. 15, 2020 online at https://doi.org/10.1101/2020.02.11.944462, 30 pages.

Wrapp et al., Cryo EM Structure of the 2019 nCOV spike in the Prefusion Conformation Science 10.1126/science.abb2507 (2020), 9 pages.

Yeh, "Experience of using convalescent plasma for severe acute respiratory syndrome among healthcare workers in a Taiwan hospital," J. Antimicrob. Chemother. 56(5):919-922 (2005).

Japanese Patent Office, "Decision of Rejection," App. No. 2022-545141, Jul. 1, 2025 4 pgs. (w/English translation).

Liener, "The Lectins: Properties, Functions, and Applications in Biology and Medicine," Elsevier, 2012.

Pallesen J, et al. Immunogenicity and structures of a rationally designed prefusion MERS-CoV spike antigen. Proc Natl Acad Sci U S A. Aug. 29, 2017;114(35):E7348-E7357. doi: 10.1073/pnas.1707304114. Epub Aug. 14, 2017. PMID: 28807998; PMCID: PMC5584442.

Sharon, N. and Lis, H. (1990), Legume lectins—a large family of homologous proteins. The FASEB Journal, 4: 3198-3208.

Taiwan Intellectual Property Office, "Final Office Action", App. No. TW 110103013, Jun. 25, 2025, 7 pgs. (w/English Translation).

van Doremalen N. et al. A single dose of ChAdOx1 MERS provides protective immunity in rhesus macaques. Science Advances, 2020.

Dorr et al., "Detergent-free isolation, characterization, and functional reconstitution of a tetrameric K+ channel: The power or native nanodiscs," PNAS, vol. 111, No. 52: 18607-18612 (Year: 2014).

Federal Institute for Intellectual Property Rights (Rospatent), Office Action, App. No. 2022122879, Jan. 16, 2025, 6 pgs. (with English translation).

Frauenfeld et al., "A novel lipoprotein nanoparticle system for membrane proteins," Nat Methods 13(4): 345-351 (Year: 2016).

GenBank: "Wuhan seafood market pneumonia virus isolate Wuhan-Hu-1, Complete Genome," Accession No. MN908947.1; GenBank, Jan. 12, 2020, 11 pages.

Japanese Patent Office, "Office Action," App. No. 2022-545141, Dec. 6, 2024, 8 pgs. (w/English translation).

Taiwan Intellectual Property Office, "First Office Action", App. No. TW 110103013, Jan. 3, 2025, 11 pgs. (w/English Translation).

Thermoscientific, "Tech Tip #19: Remove detergent from protein samples," TRO0192 (Year: 2010), 3 pages.

United States Patent and Trademark Office, "Final Office Action", U.S. Appl. No. 18/061,831, filed Jan. 28, 2025, 8 pgs.

United States Patent And Trademark Office, "Non-Final Office Action", U.S. Appl. No. 18/526,015, filed Feb. 10, 2025, 11 pgs.

Canadian Intellectual Property Office, "First Office Action", App. No. 3,165,371, Apr. 4, 2024, 6 pgs.

Danaei et al., "Impact of particle Size and Polydispersity Index on the Clinical Applications of Lipidic nanocarrier Systems," Pharmaceutics, 2018, pp. 1-17, vol. 10.

Extended European Search Report for European Application No. EP21747453.5, dated Jan. 12, 2024, 16 pages.

United States Patent and Trademark Office, "Restriction Requirement", U.S. Appl. No. 18/526,015, filed Aug. 1, 2024, 6 pgs.

Federal Institute for Intellectual Property Rights (Rospatent), Office Action and Information Search Report, App. No. 2022122879, Jun. 4, 2024, 11 pgs. (w/English Translation).

United Arab Emirates Ministry of Economy, "Office Action Summary", App. No. P6001416/2022, Dec. 16, 2024, 7 pgs.

United Arab Emirates Ministry of Economy, "Search Report", App. No. P6001416/2022, Dec. 16, 2024, 4 pgs.

Canadian Intellectual Property Office, "Second Office Action", App. No. 3,165,371, Oct. 28, 2025, 5 pgs.

Intellectual Property Office of Singapore, "Search Report and Written Opinion," Appl. No. 11202251192E, Sep. 18, 2025, 11 pages.

Ministry of Intellectual Property, "Notice of Preliminary Rejection", App. No. 10-2022-7029337, Nov. 14, 2025, 11 pgs. (with English translation).

Fig. 1

MFVFLVLLPLVSSQCVNLTTRTQLPPAYTNSFTRGVYYPDKVFRSSVLHSTQDLFLPFFSN
VTWFHAIHVSGTNGTKRFDNPVLPFNDGVYFASTEKSNIIRGWIFGTTLDSKTQSLLIVNN
ATNVVIKVCEFQFCNDPFLGVYYHKNNKSWMESEFRVYSSANNCTFEYVSQPFLMDLEG
KQGNFKNLREFVFKNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALDPLSETKCTLK
SFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLP
DDFTGCVIAWNSNNLDSKVGGNYNYLYRLFRKSNLKPFERDISTEIYQAGSTPCNGVEGF
NCYFPLQSYGFQPTNGVGYQPYRVVVLSFELLHAPATVCGPKKSTNLVKNKCVNFNFNG
LTGTGVLTESNKKFLPFQQFGRDIADTTDAVRDPQTLEILDITPCSFGGVSVITPGTNTSNQ
VAVLYQDVNCTEVPVAIHADQLTPTWRVYSTGSNVFQTRAGCLIGAEHVNNSYECDIPIG
AGICASYQTQTNSPRRARSVASQSIIAYTMSLGAENSVAYSNNSIAIPTNFTISVTEILPVS
MTKTSVDCTMYICGDSTECSNLLLQYGSFCTQLNRALTGIAVEQDKNTQEVFAQVKQIYK
TPPIKDFGGFNFSQILPDPSKPSKRSFIEDLLFNKVTLADAGFIKQYGDCLGDIAARDLICA
QKFNGLTVLPPLLTDEMIAQYTSALLAGTITSGWTFGAGAALQIPFAMQMAYRFNGIGVT
QNVLYENQKLIANQFNSAIGKIQDSLSSTASALGKLQDVVNQNAQALNTLVKQLSSNFGA
ISSVLNDILSRLDKVEAEVQIDRLITGRLQSLQTYVTQQLIRAAEIRASANLAATKMSECV
LGQSKRVDFCGKGYHLMSFPQSAPHGVVFLHVTYVPAQEKNFTTAPAICHDGKAHFPRE
GVFVSNGTHWFVTQRNFYEPQIITTDNTFVSGNCDVVIGIVNNTVYDPLQPELDSFKEEL
DKYFKNHTSPDVDLGDISGINASVVNIQKEIDRLNEVAKNLNESLIDLQELGKYEQYIKWP
WYIWLGFIAGLIAIVMVTIMLCCMTSCCSCLKGCCSCGSCCKFDEDDSEPVLKGVKLHYT

BV2373

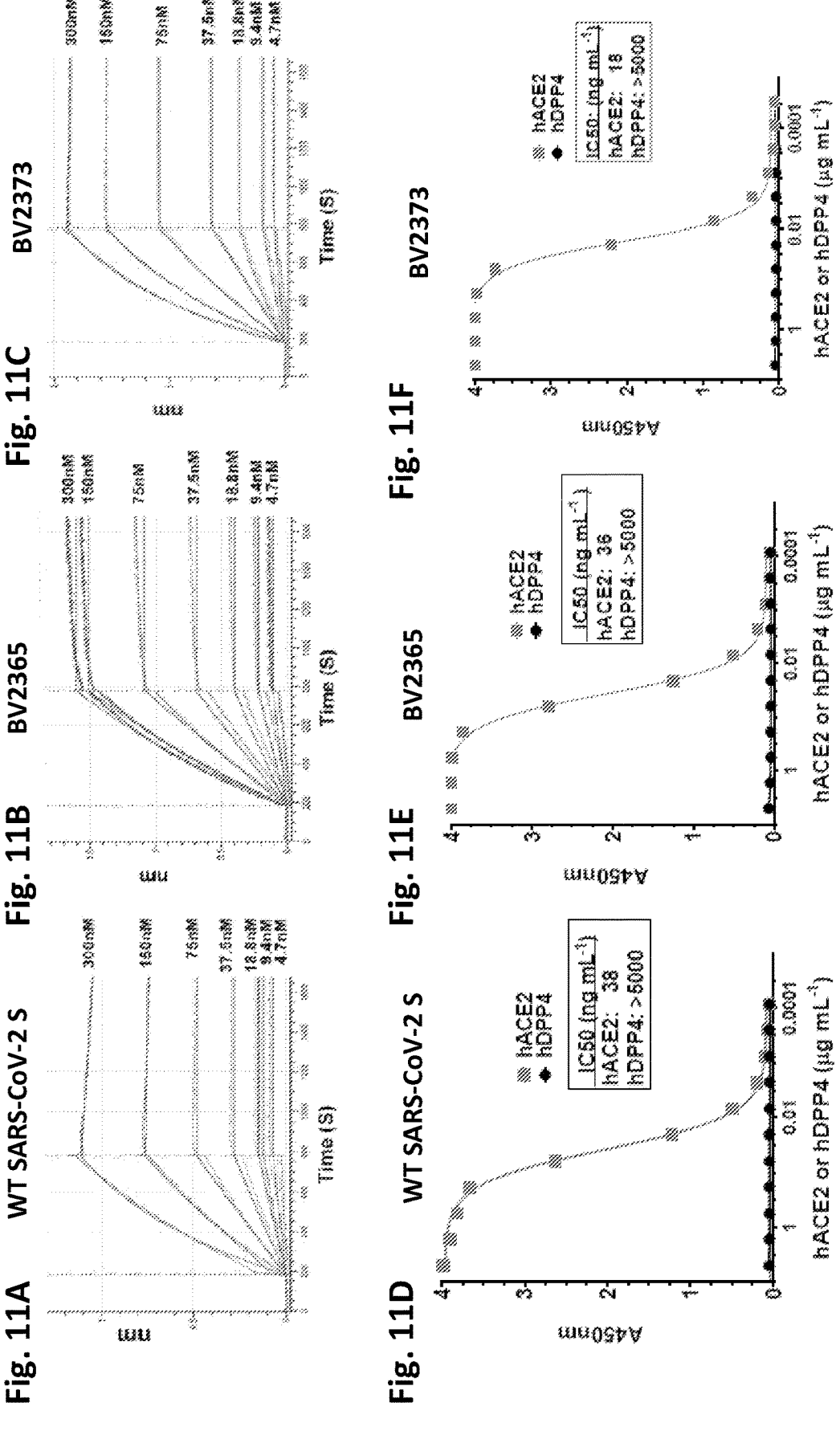

Fig. 12A
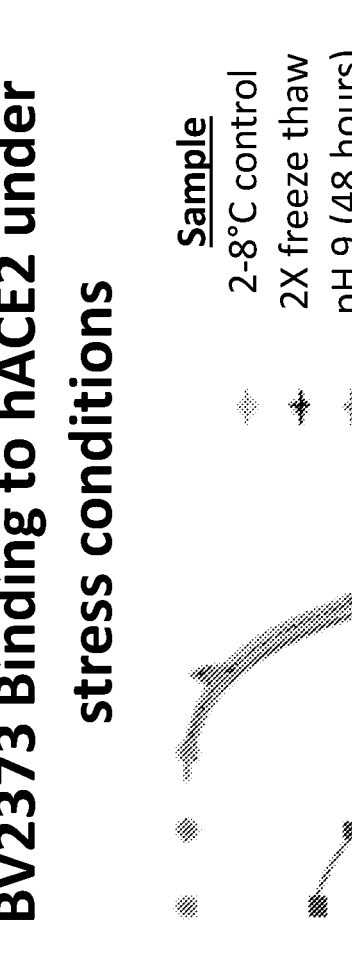
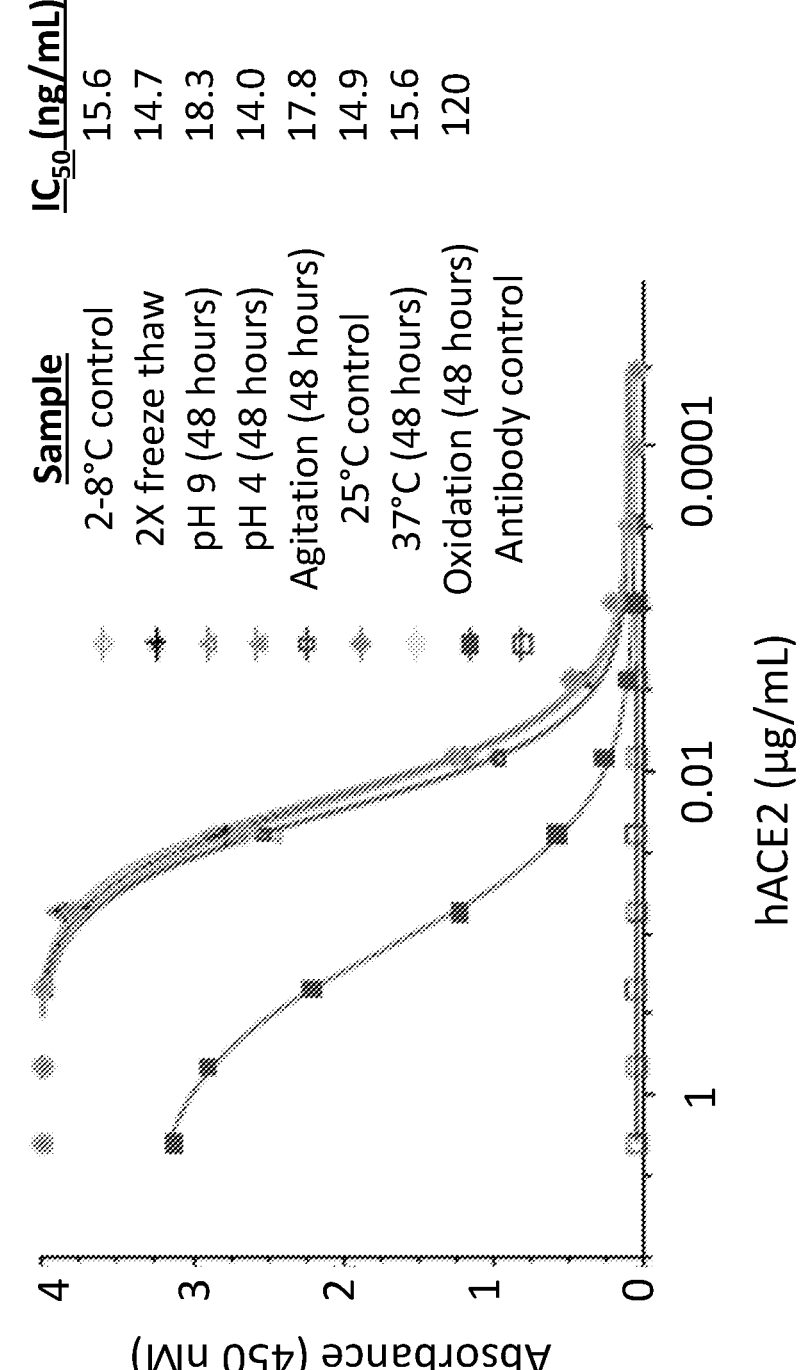
BV2373 Binding to hACE2 under stress conditions
| Sample | IC$_{50}$ (ng/mL) |
|---|---|
| 2-8°C control | 15.6 |
| 2X freeze thaw | 14.7 |
| pH 9 (48 hours) | 18.3 |
| pH 4 (48 hours) | 14.0 |
| Agitation (48 hours) | 17.8 |
| 25°C control | 14.9 |
| 37°C (48 hours) | 15.6 |
| Oxidation (48 hours) | 120 |
| Antibody control | |

BV2365 Binding to hACE2 under stress conditions

SARS-CoV-2 Neutralizing Antibody
(21 days post immunization)

% Weight Change (One Dose)

10 µg BV2373 + 5 µg Matrix-M™

Placebo

Bronchial

Vascular

Alveoli 4 days post infection

Fig. 18B

IFN-γ⁺ CD4⁺ T cells

TNF-α⁺ CD4⁺ T cells

IL-2⁺ CD4⁺ T cells

Two Cytokine⁺ CD4⁺ T cells

Two Cytokine⁺ CD8⁺ T cells

Fig. 25A

% Germinal Center (GC) B Cells

Anti-SARS-CoV-2 S IgG

Binding vs. Neutralization

Two Cytokine⁺ CD4⁺ T cells

IFN-γ⁺, TNF-α⁺, IL-2⁺ CD4⁺ T cells

Fig. 30

BV2384: CoV-2019/GSAS/K986P/V987P (SEQ ID NO: 109)

Isoelectric Pt (pI) 5.89

Signal
peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLPGDSSSGWTAGAAAYYVGYLQPRTFLLKYNENGTITDAVDCAL
DPLSETKCTLKSFTVEKGIYQTSNFRVQPTESIVRFPNITNLCPFGEVFNATRFASVYAWNRKRISNCVADYS
VLYNSASFSTFKCYGVSPTKLNDLCFTNVYADSFVIRGDEVRQIAPGQTGKIADYNYKLPDDFTGCVIAWNSN
NLDSKVGGNYNYLYRLFRKSNLKPFERDISTEIYQAGSTPCNGVEGFNCYFPLQSYGFQPTNGVGYQPYRVVV
LSFELLHAPATVCGPKKSTNLVKNKCVNFNFNGLTGTGVLTESNKKFLPFQQFGRDIADTTDAVRDPQTLEIL
DITPCSFGGVSVITPGTNTSNQVAVLYQDVNCTEVPVAIHADQLTPTWRVYSTGSNVFQTRAGCLIGAEHVNN
SYECDIPIGAGICASYQTQTNSPGSASSVVASQSIIAYTMSLGAENSVAYSNNSIAIPTNFTISVTTEILPVSM
TKTSVDCTMYICGDSTECSNLLLQYGSFCTQLNRALTGIAVEQDKNTQEVFAQVKQIYKTPPIKDFGGFNFSQ
ILPDPSKPSKRSFIEDLLFNKVTLADAGFIKQYGDCLGDIAARDLICAQKFNGLTVLPPLLTDEMIAQYTSAL
LAGTITSGWTFGAGAALQIPFAMQMAYRFNGIGVTQNVLYENQKLIANQFNSAIGKIQDSLSSTASALGKLQD
VVNQNAQALNTLVKQLSSNFGAISSVLNDILSRLDPPEAEVQIDRLITGRLQSLQTYVTQQLIRAAEIRASAN
LAATKMSECVLGQSKRVDFCGKGYHLMSFPQSAPHGVVFLHVTYVPAQEKNFTTAPAICHDGKAHFPREGVFV
SNGTHWFVTQRNFYEPQIITTDNTFVSGNCDVVIGIVNNTVYDPLQPELDSFKELDKYFKNHTSPDVDLGDIS
GINASVVNIQKEIDRLNEVAKNLNESLIDLQELGKYEQYIKWPWYIWLGFIAGLIAIVMVTIMLCCMTSCCSC
LKGCCSCGSCCKFDEDDSEPVLKGVKLHYT

Fig. 31

BV2373 (SEQ ID NO: 86)

CoV-2019/QQAQ/K986P/V987P

Inactive furin
cleavage site

Signal
peptide

MFVFLVLLPLVSSQCVNLTTRTQLPPAYTNSFTRGVYYPDKVFRSSVLHSTQDLFLPFFSNVTWFHAIHVSGT
NGTKRFDNPVLPFNDGVYFASTEKSNIIRGWIFGTTLDSKTQSLLIVNNATNVIKVCEFQFCNDPFLGVYYH
KNNKSWMESEFRVYSSANNCTFEYVSQPFLMDLEGKQGNFKNLREFVFKNIDGYFKIYSKHTPINLVRDLPQG
FSALEPLVDLPIGINITRFQTLLALHRSYLTPGDSSSGWTAGAAAYYVGYLQPRTFLLKYNENGTITDAVDCA
LDPLSETKCTLKSFTVEKGIYQTSNFRVQPTESIVRFPNITNLCPFGEVFNATRFASVYAWNRKRISNCVADY
SVLYNSASFSTFKCYGVSPTKLNDLCFTNVYADSFVIRGDEVRQIAPGQTGKIADYNYKLPDDFTGCVIAWNS
NNLDSKVGGNYNYLYRLFRKSNLKPFERDISTEIYQAGSTPCNGVEGFNCYFPLQSYGFQPTNGVGYQPYRVV
VLSFELLHAPATVCGPKKSTNLVKNKCVNFNFNGLTGTGVLTESNKKFLPFQQFGRDIADTTDAVRDPQTLEI
LDITPCSFGGVSVITPGTNTSNQVAVLYQDVNCTEVPVAIHADQLTPTWRVYSTGSNVFQTRAGCLIGAEHVN
NSYECDIPIGAGICASYQTQTNSPQQAQSVASQSIIAYTMSLGAENSVAYSNNSIAIPTNFTISVTTEILPVS
MTKTSVDCTMYICGDSTECSNLLLQYGSFCTQLNRALTGIAVEQDKNTQEVFAQVKQIYKTPPIKDFGGFNFS
QILPDPSKPSKRSFIEDLLFNKVTLADAGFIKQYGDCLGDIAARDLICAQKFNGLTVLPPLLTDEMIAQYTSA
LLAGTITSGWTFGAGAALQIPFAMQMAYRFNGIGVTQNVLYENQKLIANQFNSAIGKIQDSLSSTASALGKLQ
DVVNQNAQALNTLVKQLSSNFGAISSVLNDILSRLDPPEAEVQIDRLITGRLQSLQTYVTQQLIRAAEIRASA
NLAATKMSECVLGQSKRVDFCGKGYHLMSFPQSAPHGVVFLHVTYVPAQEKNFTTAPAICHDGKAHFPREGVF
VSNGTHWFVTQRNFYEPQIITDNTFVSGNCDVVIGIVNNTVYDPLQPELDSFKEELDKYFKNHTSPDVDLGD
ISGINASVVNIQKEIDRLNEVAKNLNESLIDLQELGKYEQYIKWPWYIWLGFIAGLIAIVMVTIMLCCMTSCC
SCLKGCCSCGSCCKFDEDDSEPVLKGVKLHYT

Fig. 32

Purity: 38.5%

Densitometry

Protein concentration:

A280(0.9226) - A340(0.187) = 0.7356 /1.067 = 0.6894 mg/mL

Total Volume: 19.0mL X 0.6894 mg/mL = 13.098 mg

Yield: 13.098mg/4.8 liter = 2.728 mg/L

Densitometry

Purity: 94.8%

Protein concentration:

A280(0.8368) - A340(0.0248) = 0.8142 /1.067 = 0.761 mg/mL

Total Volume: 42.47mL X 0.761 mg/mL = 42.32 mg

Yield: 42.32mg/5 liter = 6.4 mg/L

Correlation of Anti-S IgG Titer and hACE2 Receptor Inhibition in macaques

SARS-CoV-2 Neutralizing Titers by CPE (100% neutralization)

SARS-CoV-2 Neutralizing Titers by PRNT (EC90 titers)

Fig. 45A
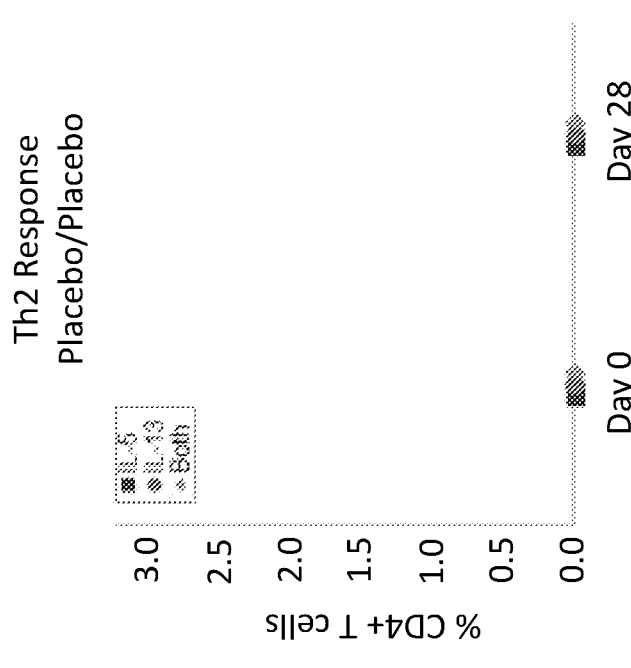
Th2 Response
Placebo/Placebo
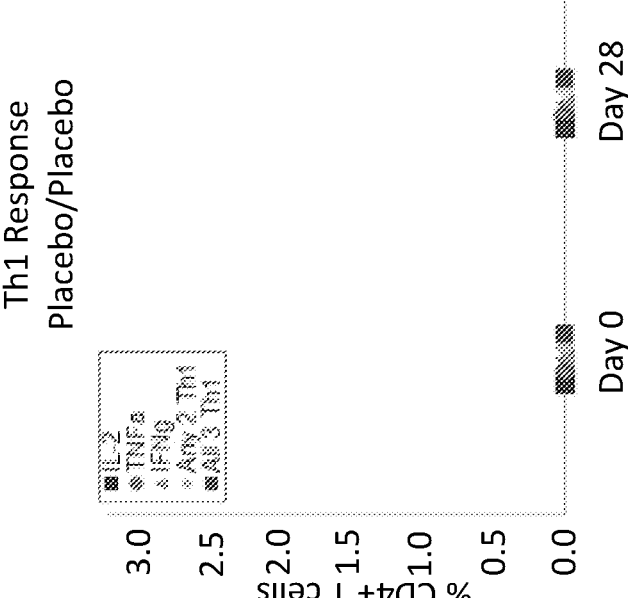
Th1 Response
Placebo/Placebo

Fig. 45D
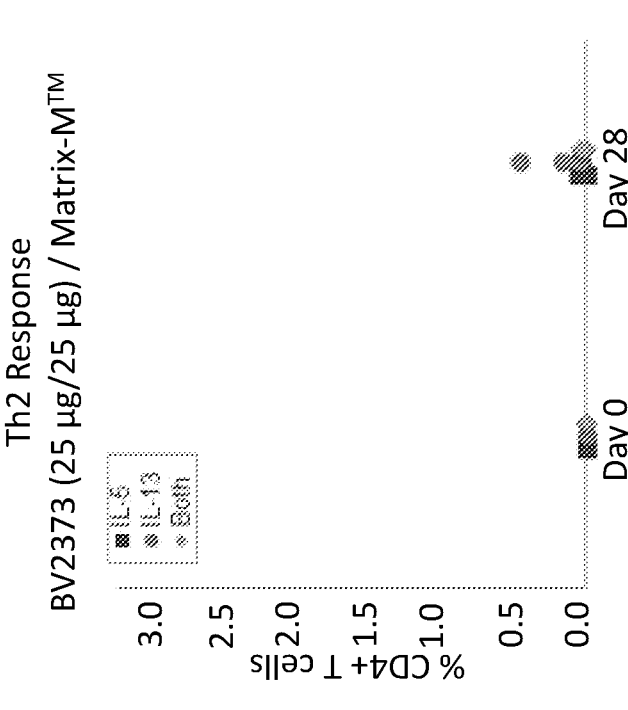
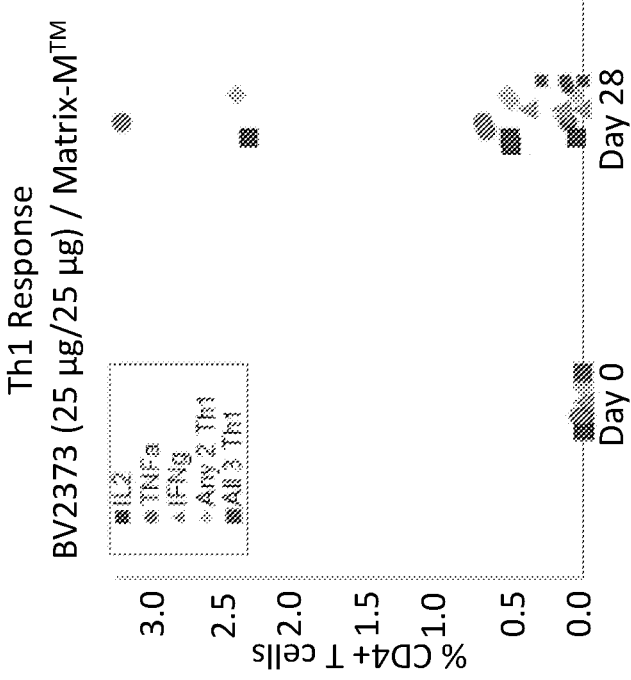

SEQUENCE LISTING

<160> NUMBER OF SEQ ID NOS: 126

<210> SEQ ID NO 1
<211> LENGTH: 1273
<212> TYPE: PRT
<213> ORGANISM: Betacoronavirus severe acute respiratory syndrome
      coronavirus 2

<400> SEQUENCE: 1

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190
```

-continued

```
Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
```

-continued

```
        610              615              620
His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
             645              650              655

Asn Asn Ser Tyr Glu Cys Asp Ile Pro Ile Gly Ala Gly Ile Cys Ala
             660              665              670

Ser Tyr Gln Thr Gln Thr Asn Ser Pro Arg Arg Ala Arg Ser Val Ala
             675              680              685

Ser Gln Ser Ile Ile Ala Tyr Thr Met Ser Leu Gly Ala Glu Asn Ser
             690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
             725              730              735

Asp Cys Thr Met Tyr Ile Cys Gly Asp Ser Thr Glu Cys Ser Asn Leu
             740              745              750

Leu Leu Gln Tyr Gly Ser Phe Cys Thr Gln Leu Asn Arg Ala Leu Thr
             755              760              765

Gly Ile Ala Val Glu Gln Asp Lys Asn Thr Gln Glu Val Phe Ala Gln
770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
             805              810              815

Phe Ile Glu Asp Leu Leu Phe Asn Lys Val Thr Leu Ala Asp Ala Gly
             820              825              830

Phe Ile Lys Gln Tyr Gly Asp Cys Leu Gly Asp Ile Ala Ala Arg Asp
             835              840              845

Leu Ile Cys Ala Gln Lys Phe Asn Gly Leu Thr Val Leu Pro Pro Leu
             850              855              860

Leu Thr Asp Glu Met Ile Ala Gln Tyr Thr Ser Ala Leu Leu Ala Gly
865              870              875              880

Thr Ile Thr Ser Gly Trp Thr Phe Gly Ala Gly Ala Ala Leu Gln Ile
             885              890              895

Pro Phe Ala Met Gln Met Ala Tyr Arg Phe Asn Gly Ile Gly Val Thr
             900              905              910

Gln Asn Val Leu Tyr Glu Asn Gln Lys Leu Ile Ala Asn Gln Phe Asn
             915              920              925

Ser Ala Ile Gly Lys Ile Gln Asp Ser Leu Ser Ser Thr Ala Ser Ala
             930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
             965              970              975

Leu Asn Asp Ile Leu Ser Arg Leu Asp Lys Val Glu Ala Glu Val Gln
             980              985              990

Ile Asp Arg Leu Ile Thr Gly Arg  Leu Gln Ser Leu Gln  Thr Tyr Val
             995              1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
    1025             1030             1035
```

-continued

```
Arg Val Asp Phe Cys Gly Lys  Gly Tyr His Leu Met  Ser Phe Pro
    1040            1045              1050

Gln Ser Ala Pro His Gly Val  Val Phe Leu His Val  Thr Tyr Val
    1055            1060              1065

Pro Ala Gln Glu Lys Asn Phe  Thr Thr Ala Pro Ala  Ile Cys His
    1070            1075              1080

Asp Gly Lys Ala His Phe Pro  Arg Glu Gly Val Phe  Val Ser Asn
    1085            1090              1095

Gly Thr His Trp Phe Val Thr  Gln Arg Asn Phe Tyr  Glu Pro Gln
    1100            1105              1110

Ile Ile Thr Thr Asp Asn Thr  Phe Val Ser Gly Asn  Cys Asp Val
    1115            1120              1125

Val Ile Gly Ile Val Asn Asn  Thr Val Tyr Asp Pro  Leu Gln Pro
    1130            1135              1140

Glu Leu Asp Ser Phe Lys Glu  Glu Leu Asp Lys Tyr  Phe Lys Asn
    1145            1150              1155

His Thr Ser Pro Asp Val Asp  Leu Gly Asp Ile Ser  Gly Ile Asn
    1160            1165              1170

Ala Ser Val Val Asn Ile Gln  Lys Glu Ile Asp Arg  Leu Asn Glu
    1175            1180              1185

Val Ala Lys Asn Leu Asn Glu  Ser Leu Ile Asp Leu  Gln Glu Leu
    1190            1195              1200

Gly Lys Tyr Glu Gln Tyr Ile  Lys Trp Pro Trp Tyr  Ile Trp Leu
    1205            1210              1215

Gly Phe Ile Ala Gly Leu Ile  Ala Ile Val Met Val  Thr Ile Met
    1220            1225              1230

Leu Cys Cys Met Thr Ser Cys  Cys Ser Cys Leu Lys  Gly Cys Cys
    1235            1240              1245

Ser Cys Gly Ser Cys Cys Lys  Phe Asp Glu Asp Asp  Ser Glu Pro
    1250            1255              1260

Val Leu Lys Gly Val Lys Leu  His Tyr Thr
    1265            1270
```

```
<210> SEQ ID NO 2
<211> LENGTH: 1260
<212> TYPE: PRT
<213> ORGANISM: Betacoronavirus severe acute respiratory syndrome
      coronavirus 2

<400> SEQUENCE: 2
```

```
Gln Cys Val Asn Leu Thr Thr Arg Thr Gln Leu Pro Pro Ala Tyr Thr
1               5               10              15

Asn Ser Phe Thr Arg Gly Val Tyr Tyr Pro Asp Lys Val Phe Arg Ser
            20              25              30

Ser Val Leu His Ser Thr Gln Asp Leu Phe Leu Pro Phe Phe Ser Asn
        35              40              45

Val Thr Trp Phe His Ala Ile His Val Ser Gly Thr Asn Gly Thr Lys
    50              55              60

Arg Phe Asp Asn Pro Val Leu Pro Phe Asn Asp Gly Val Tyr Phe Ala
65              70              75              80

Ser Thr Glu Lys Ser Asn Ile Ile Arg Gly Trp Ile Phe Gly Thr Thr
            85              90              95

Leu Asp Ser Lys Thr Gln Ser Leu Leu Ile Val Asn Asn Ala Thr Asn
            100             105             110
```

-continued

```
Val Val Ile Lys Val Cys Glu Phe Gln Phe Cys Asn Asp Pro Phe Leu
        115             120             125

Gly Val Tyr Tyr His Lys Asn Asn Lys Ser Trp Met Glu Ser Glu Phe
        130             135             140

Arg Val Tyr Ser Ser Ala Asn Asn Cys Thr Phe Glu Tyr Val Ser Gln
145             150             155             160

Pro Phe Leu Met Asp Leu Glu Gly Lys Gln Gly Asn Phe Lys Asn Leu
                165             170             175

Arg Glu Phe Val Phe Lys Asn Ile Asp Gly Tyr Phe Lys Ile Tyr Ser
                180             185             190

Lys His Thr Pro Ile Asn Leu Val Arg Asp Leu Pro Gln Gly Phe Ser
        195             200             205

Ala Leu Glu Pro Leu Val Asp Leu Pro Ile Gly Ile Asn Ile Thr Arg
        210             215             220

Phe Gln Thr Leu Leu Ala Leu His Arg Ser Tyr Leu Thr Pro Gly Asp
225             230             235             240

Ser Ser Ser Gly Trp Thr Ala Gly Ala Ala Ala Tyr Tyr Val Gly Tyr
                245             250             255

Leu Gln Pro Arg Thr Phe Leu Leu Lys Tyr Asn Glu Asn Gly Thr Ile
                260             265             270

Thr Asp Ala Val Asp Cys Ala Leu Asp Pro Leu Ser Glu Thr Lys Cys
        275             280             285

Thr Leu Lys Ser Phe Thr Val Glu Lys Gly Ile Tyr Gln Thr Ser Asn
        290             295             300

Phe Arg Val Gln Pro Thr Glu Ser Ile Val Arg Phe Pro Asn Ile Thr
305             310             315             320

Asn Leu Cys Pro Phe Gly Glu Val Phe Asn Ala Thr Arg Phe Ala Ser
                325             330             335

Val Tyr Ala Trp Asn Arg Lys Arg Ile Ser Asn Cys Val Ala Asp Tyr
                340             345             350

Ser Val Leu Tyr Asn Ser Ala Ser Phe Ser Thr Phe Lys Cys Tyr Gly
        355             360             365

Val Ser Pro Thr Lys Leu Asn Asp Leu Cys Phe Thr Asn Val Tyr Ala
        370             375             380

Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
                405             410             415

Thr Gly Cys Val Ile Ala Trp Asn Ser Asn Asn Leu Asp Ser Lys Val
                420             425             430

Gly Gly Asn Tyr Asn Tyr Leu Tyr Arg Leu Phe Arg Lys Ser Asn Leu
        435             440             445

Lys Pro Phe Glu Arg Asp Ile Ser Thr Glu Ile Tyr Gln Ala Gly Ser
        450             455             460

Thr Pro Cys Asn Gly Val Glu Gly Phe Asn Cys Tyr Phe Pro Leu Gln
465             470             475             480

Ser Tyr Gly Phe Gln Pro Thr Asn Gly Val Gly Tyr Gln Pro Tyr Arg
                485             490             495

Val Val Val Leu Ser Phe Glu Leu Leu His Ala Pro Ala Thr Val Cys
                500             505             510

Gly Pro Lys Lys Ser Thr Asn Leu Val Lys Asn Lys Cys Val Asn Phe
        515             520             525

Asn Phe Asn Gly Leu Thr Gly Thr Gly Val Leu Thr Glu Ser Asn Lys
```

-continued

```
                 530                   535                   540
Lys Phe Leu Pro Phe Gln Gln Phe Gly Arg Asp Ile Ala Asp Thr Thr
545                   550                   555                   560

Asp Ala Val Arg Asp Pro Gln Thr Leu Glu Ile Leu Asp Ile Thr Pro
                565                   570                   575

Cys Ser Phe Gly Gly Val Ser Val Ile Thr Pro Gly Thr Asn Thr Ser
                580                   585                   590

Asn Gln Val Ala Val Leu Tyr Gln Asp Val Asn Cys Thr Glu Val Pro
            595                   600                   605

Val Ala Ile His Ala Asp Gln Leu Thr Pro Thr Trp Arg Val Tyr Ser
            610                   615                   620

Thr Gly Ser Asn Val Phe Gln Thr Arg Ala Gly Cys Leu Ile Gly Ala
625                   630                   635                   640

Glu His Val Asn Asn Ser Tyr Glu Cys Asp Ile Pro Ile Gly Ala Gly
                645                   650                   655

Ile Cys Ala Ser Tyr Gln Thr Gln Thr Asn Ser Pro Arg Arg Ala Arg
                660                   665                   670

Ser Val Ala Ser Gln Ser Ile Ile Ala Tyr Thr Met Ser Leu Gly Ala
                675                   680                   685

Glu Asn Ser Val Ala Tyr Ser Asn Asn Ser Ile Ala Ile Pro Thr Asn
            690                   695                   700

Phe Thr Ile Ser Val Thr Thr Glu Ile Leu Pro Val Ser Met Thr Lys
705                   710                   715                   720

Thr Ser Val Asp Cys Thr Met Tyr Ile Cys Gly Asp Ser Thr Glu Cys
                725                   730                   735

Ser Asn Leu Leu Leu Gln Tyr Gly Ser Phe Cys Thr Gln Leu Asn Arg
                740                   745                   750

Ala Leu Thr Gly Ile Ala Val Glu Gln Asp Lys Asn Thr Gln Glu Val
                755                   760                   765

Phe Ala Gln Val Lys Gln Ile Tyr Lys Thr Pro Pro Ile Lys Asp Phe
            770                   775                   780

Gly Gly Phe Asn Phe Ser Gln Ile Leu Pro Asp Pro Ser Lys Pro Ser
785                   790                   795                   800

Lys Arg Ser Phe Ile Glu Asp Leu Leu Phe Asn Lys Val Thr Leu Ala
                805                   810                   815

Asp Ala Gly Phe Ile Lys Gln Tyr Gly Asp Cys Leu Gly Asp Ile Ala
                820                   825                   830

Ala Arg Asp Leu Ile Cys Ala Gln Lys Phe Asn Gly Leu Thr Val Leu
                835                   840                   845

Pro Pro Leu Leu Thr Asp Glu Met Ile Ala Gln Tyr Thr Ser Ala Leu
            850                   855                   860

Leu Ala Gly Thr Ile Thr Ser Gly Trp Thr Phe Gly Ala Gly Ala Ala
865                   870                   875                   880

Leu Gln Ile Pro Phe Ala Met Gln Met Ala Tyr Arg Phe Asn Gly Ile
                885                   890                   895

Gly Val Thr Gln Asn Val Leu Tyr Glu Asn Gln Lys Leu Ile Ala Asn
                900                   905                   910

Gln Phe Asn Ser Ala Ile Gly Lys Ile Gln Asp Ser Leu Ser Ser Thr
            915                   920                   925

Ala Ser Ala Leu Gly Lys Leu Gln Asp Val Val Asn Gln Asn Ala Gln
            930                   935                   940

Ala Leu Asn Thr Leu Val Lys Gln Leu Ser Ser Asn Phe Gly Ala Ile
945                   950                   955                   960
```

-continued

```
Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                 1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065

Cys His  Asp Gly Lys Ala His  Phe Pro Arg Glu Gly  Val Phe Val
    1070                 1075                 1080

Ser Asn  Gly Thr His Trp Phe  Val Thr Gln Arg Asn  Phe Tyr Glu
    1085                 1090                 1095

Pro Gln  Ile Ile Thr Thr Asp  Asn Thr Phe Val Ser  Gly Asn Cys
    1100                 1105                 1110

Asp Val  Val Ile Gly Ile Val  Asn Asn Thr Val Tyr  Asp Pro Leu
    1115                 1120                 1125

Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185

Glu Leu  Gly Lys Tyr Glu Gln  Tyr Ile Lys Trp Pro  Trp Tyr Ile
    1190                 1195                 1200

Trp Leu  Gly Phe Ile Ala Gly  Leu Ile Ala Ile Val  Met Val Thr
    1205                 1210                 1215

Ile Met  Leu Cys Cys Met Thr  Ser Cys Cys Ser Cys  Leu Lys Gly
    1220                 1225                 1230

Cys Cys  Ser Cys Gly Ser Cys  Cys Lys Phe Asp Glu  Asp Asp Ser
    1235                 1240                 1245

Glu Pro  Val Leu Lys Gly Val  Lys Leu His Tyr Thr
    1250                 1255                 1260
```

```
<210> SEQ ID NO 3
<211> LENGTH: 1273
<212> TYPE: PRT
<213> ORGANISM: Artificial Sequence
<220> FEATURE:
<223> OTHER INFORMATION: RECOMBINANT S PROTEIN

<400> SEQUENCE: 3

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45
```

-continued

```
His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
            85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
        355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460
```

-continued

```
Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
                485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
            530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
            610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gln Gln Ala Gln Ser Val Ala
            675             680             685

Ser Gln Ser Ile Ile Ala Tyr Thr Met Ser Leu Gly Ala Glu Asn Ser
            690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
            770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
            850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
```

-continued

```
                885              890              895

Pro Phe Ala Met Gln Met Ala Tyr Arg Phe Asn Gly Ile Gly Val Thr
            900              905              910

Gln Asn Val Leu Tyr Glu Asn Gln Lys Leu Ile Ala Asn Gln Phe Asn
        915              920              925

Ser Ala Ile Gly Lys Ile Gln Asp Ser Leu Ser Ser Thr Ala Ser Ala
    930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
            965              970              975

Leu Asn Asp Ile Leu Ser Arg Leu Asp Lys Val Glu Ala Glu Val Gln
            980              985              990

Ile Asp Arg Leu Ile Thr Gly Arg  Leu Gln Ser Leu Gln  Thr Tyr Val
        995              1000              1005

Thr Gln  Gln Leu Ile Arg Ala  Ala Glu Ile Arg Ala  Ser Ala Asn
    1010              1015              1020

Leu Ala  Ala Thr Lys Met Ser  Glu Cys Val Leu Gly  Gln Ser Lys
    1025              1030              1035

Arg Val  Asp Phe Cys Gly Lys  Gly Tyr His Leu Met  Ser Phe Pro
    1040              1045              1050

Gln Ser  Ala Pro His Gly Val  Val Phe Leu His Val  Thr Tyr Val
    1055              1060              1065

Pro Ala  Gln Glu Lys Asn Phe  Thr Thr Ala Pro Ala  Ile Cys His
    1070              1075              1080

Asp Gly  Lys Ala His Phe Pro  Arg Glu Gly Val Phe  Val Ser Asn
    1085              1090              1095

Gly Thr  His Trp Phe Val Thr  Gln Arg Asn Phe Tyr  Glu Pro Gln
    1100              1105              1110

Ile Ile  Thr Thr Asp Asn Thr  Phe Val Ser Gly Asn  Cys Asp Val
    1115              1120              1125

Val Ile  Gly Ile Val Asn Asn  Thr Val Tyr Asp Pro  Leu Gln Pro
    1130              1135              1140

Glu Leu  Asp Ser Phe Lys Glu  Glu Leu Asp Lys Tyr  Phe Lys Asn
    1145              1150              1155

His Thr  Ser Pro Asp Val Asp  Leu Gly Asp Ile Ser  Gly Ile Asn
    1160              1165              1170

Ala Ser  Val Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro Trp Tyr  Ile Trp Leu
    1205              1210              1215

Gly Phe  Ile Ala Gly Leu Ile  Ala Ile Val Met Val  Thr Ile Met
    1220              1225              1230

Leu Cys  Cys Met Thr Ser Cys  Cys Ser Cys Leu Lys  Gly Cys Cys
    1235              1240              1245

Ser Cys  Gly Ser Cys Cys Lys  Phe Asp Glu Asp Asp  Ser Glu Pro
    1250              1255              1260

Val Leu  Lys Gly Val Lys Leu  His Tyr Thr
    1265              1270
```

<210> SEQ ID NO 4

-continued

```
<211> LENGTH: 1260
<212> TYPE: PRT
<213> ORGANISM: Artificial Sequence
<220> FEATURE:
<223> OTHER INFORMATION: RECOMBINANT S PROTEIN

<400> SEQUENCE: 4

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380
```

```
Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
            405             410             415

Thr Gly Cys Val Ile Ala Trp Asn Ser Asn Asn Leu Asp Ser Lys Val
        420             425             430

Gly Gly Asn Tyr Asn Tyr Leu Tyr Arg Leu Phe Arg Lys Ser Asn Leu
        435             440             445

Lys Pro Phe Glu Arg Asp Ile Ser Thr Glu Ile Tyr Gln Ala Gly Ser
    450             455             460

Thr Pro Cys Asn Gly Val Glu Gly Phe Asn Cys Tyr Phe Pro Leu Gln
465             470             475             480

Ser Tyr Gly Phe Gln Pro Thr Asn Gly Val Gly Tyr Gln Pro Tyr Arg
            485             490             495

Val Val Val Leu Ser Phe Glu Leu Leu His Ala Pro Ala Thr Val Cys
        500             505             510

Gly Pro Lys Lys Ser Thr Asn Leu Val Lys Asn Lys Cys Val Asn Phe
        515             520             525

Asn Phe Asn Gly Leu Thr Gly Thr Gly Val Leu Thr Glu Ser Asn Lys
    530             535             540

Lys Phe Leu Pro Phe Gln Gln Phe Gly Arg Asp Ile Ala Asp Thr Thr
545             550             555             560

Asp Ala Val Arg Asp Pro Gln Thr Leu Glu Ile Leu Asp Ile Thr Pro
            565             570             575

Cys Ser Phe Gly Gly Val Ser Val Ile Thr Pro Gly Thr Asn Thr Ser
            580             585             590

Asn Gln Val Ala Val Leu Tyr Gln Asp Val Asn Cys Thr Glu Val Pro
        595             600             605

Val Ala Ile His Ala Asp Gln Leu Thr Pro Thr Trp Arg Val Tyr Ser
    610             615             620

Thr Gly Ser Asn Val Phe Gln Thr Arg Ala Gly Cys Leu Ile Gly Ala
625             630             635             640

Glu His Val Asn Asn Ser Tyr Glu Cys Asp Ile Pro Ile Gly Ala Gly
            645             650             655

Ile Cys Ala Ser Tyr Gln Thr Gln Thr Asn Ser Pro Gln Gln Ala Gln
            660             665             670

Ser Val Ala Ser Gln Ser Ile Ile Ala Tyr Thr Met Ser Leu Gly Ala
        675             680             685

Glu Asn Ser Val Ala Tyr Ser Asn Asn Ser Ile Ala Ile Pro Thr Asn
    690             695             700

Phe Thr Ile Ser Val Thr Thr Glu Ile Leu Pro Val Ser Met Thr Lys
705             710             715             720

Thr Ser Val Asp Cys Thr Met Tyr Ile Cys Gly Asp Ser Thr Glu Cys
            725             730             735

Ser Asn Leu Leu Leu Gln Tyr Gly Ser Phe Cys Thr Gln Leu Asn Arg
            740             745             750

Ala Leu Thr Gly Ile Ala Val Glu Gln Asp Lys Asn Thr Gln Glu Val
        755             760             765

Phe Ala Gln Val Lys Gln Ile Tyr Lys Thr Pro Pro Ile Lys Asp Phe
    770             775             780

Gly Gly Phe Asn Phe Ser Gln Ile Leu Pro Asp Pro Ser Lys Pro Ser
785             790             795             800
```

```
Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
            820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
```

-continued

```
        1205                1210                1215

Ile Met  Leu Cys Cys Met Thr  Ser Cys Cys Ser Cys  Leu Lys Gly
        1220                1225                1230

Cys Cys  Ser Cys Gly Ser Cys  Cys Lys Phe Asp Glu  Asp Asp Ser
        1235                1240                1245

Glu Pro  Val Leu Lys Gly Val  Lys Leu His Tyr Thr
        1250                1255                1260

<210> SEQ ID NO 5
<211> LENGTH: 13
<212> TYPE: PRT
<213> ORGANISM: Artificial Sequence
<220> FEATURE:
<223> OTHER INFORMATION: SIGNAL PEPTIDE

<400> SEQUENCE: 5

Met Phe Val Phe Leu Val Leu Leu Pro Leu Val Ser Ser
1               5               10

<210> SEQ ID NO 6
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 6

Arg Arg Ala Arg
1

<210> SEQ ID NO 7
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 7

Gln Gln Ala Gln
1

<210> SEQ ID NO 8
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 8

Gln Arg Ala Arg
1

<210> SEQ ID NO 9
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 9

Arg Gln Ala Arg
1

<210> SEQ ID NO 10
<211> LENGTH: 4
```

```
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 10

Arg Arg Ala Gln
1

<210> SEQ ID NO 11
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 11

Gln Gln Ala Arg
1

<210> SEQ ID NO 12
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 12

Arg Gln Ala Gln
1

<210> SEQ ID NO 13
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 13

Gln Arg Ala Gln
1

<210> SEQ ID NO 14
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 14

Asn Asn Ala Asn
1

<210> SEQ ID NO 15
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 15

Asn Arg Ala Arg
1

<210> SEQ ID NO 16
<211> LENGTH: 4
<212> TYPE: PRT
```

```
<213> ORGANISM: Artificial Sequence
<220> FEATURE:
<223> OTHER INFORMATION: RECOMBINANT FURIN CLEAVAGE SITE

<400> SEQUENCE: 16

Arg Asn Ala Arg
1

<210> SEQ ID NO 17
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 17

Arg Arg Ala Asn
1

<210> SEQ ID NO 18
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 18

Asn Asn Ala Arg
1

<210> SEQ ID NO 19
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 19

Arg Asn Ala Asn
1

<210> SEQ ID NO 20
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 20

Asn Arg Ala Asn
1

<210> SEQ ID NO 21
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 21

Ala Ala Ala Ala
1

<210> SEQ ID NO 22
<211> LENGTH: 4
<212> TYPE: PRT
<213> ORGANISM: Artificial Sequence
```

```
<220> FEATURE:
<223> OTHER INFORMATION: RECOMBINANT FURIN CLEAVAGE SITE

<400> SEQUENCE: 22

Ala Arg Ala Arg
1

<210> SEQ ID NO 23
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 23

Arg Ala Ala Arg
1

<210> SEQ ID NO 24
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 24

Arg Arg Ala Ala
1

<210> SEQ ID NO 25
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 25

Ala Ala Ala Arg
1

<210> SEQ ID NO 26
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 26

Arg Ala Ala Ala
1

<210> SEQ ID NO 27
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 27

Ala Arg Ala Ala
1

<210> SEQ ID NO 28
<211> LENGTH: 4
<212> TYPE: PRT
<213> ORGANISM: Artificial Sequence
<220> FEATURE:
```

-continued

<223> OTHER INFORMATION: RECOMBINANT FURIN CLEAVAGE SITE

<400> SEQUENCE: 28

Gly Gly Ala Gly
1

<210> SEQ ID NO 29
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 29

Gly Arg Ala Arg
1

<210> SEQ ID NO 30
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 30

Arg Gly Ala Arg
1

<210> SEQ ID NO 31
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 31

Arg Arg Ala Gly
1

<210> SEQ ID NO 32
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 32

Gly Gly Ala Arg
1

<210> SEQ ID NO 33
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE

<400> SEQUENCE: 33

Arg Gly Ala Gly
1

<210> SEQ ID NO 34
<211> LENGTH: 4
<212> TYPE: PRT
<213> ORGANISM: Artificial Sequence
<220> FEATURE:
<223> OTHER INFORMATION: RECOMBINANT FURIN CLEAVAGE SITE -continued

```
<400> SEQUENCE: 34

Gly Arg Ala Gly
1

<210> SEQ ID NO 35
<211> LENGTH: 3819
<212> TYPE: DNA
<213> ORGANISM: Artificial Sequence
<220> FEATURE:
<223> OTHER INFORMATION: RECOMBINANT SPIKE PROTEIN

<400> SEQUENCE: 35
atgttcgtct tcctggtgct gctgcccctg gtgtccagcc agtgcgtgaa cctgaccact      60
aggactcagc tgcctcccgc ttacaccaac tcattcactc gcggtgtgta ctaccctgac     120
aaggtcttcc gttcttcagt gctgcactca actcaggacc tgttcctgcc cttcttctcc     180
aacgtcacct ggttccacgc catccacgtg tccggcacca acggcactaa gcgcttcgac     240
aacccagtgc tgcctttcaa cgacggtgtc tacttcgctt caaccgagaa gtccaacatc     300
atccgtggat ggatcttcgg caccactctg gacagcaaga ctcagtctct gctgatcgtc     360
aacaacgcca ccaacgtggt catcaaggtc tgcgaattcc agttctgcaa cgacccattc     420
ctgggcgtct actaccacaa gaacaacaag tcatggatgg agtccgaatt ccgcgtctac     480
tccagcgcta caactgcac tttcgagtac gtgtcccagc ctttcctgat ggacctggaa     540
ggaaagcagg gtaacttcaa gaacctgagg gagttcgtgt tcaagaacat cgacggatac     600
ttcaagattt acagcaagca cacccccaatc aacctggtgc gcgacctgcc tcagggtttc     660
tctgctctgg agccactggt ggacctgcct atcggcatca acatcacccg cttccagact     720
ctgctggctc tgcaccgttc ctacctgact ccaggcgact catcttctgg atggactgct     780
ggagctgctg cttactacgt gggctacctg cagcctcgca ccttcctgct gaagtacaac     840
gaaaacggaa ccatcactga cgccgtcgac tgcgctctgg accctctgtc agaaaccaag     900
tgcactctga gtccttcac cgtggagaag ggcatctacc agacttcaaa cttcagggtg     960
cagcccaccg aatccatcgt cagattccct aacatcacta acctgtgccc cttcggagag    1020
gtcttcaacg ccacccgctt cgcttccgtg tacgcctgga caggaagag aatctcaaac    1080 tgcgtcgctg actactccgt gctgtacaac tcagcctcct tcagcacctt caagtgctac    1140
ggcgtgtcac caactaagct gaacgacctg tgcttcacca acgtctacgc cgactccttc    1200
gtgatcaggg gagacgaggt cagacagatc gctcctggcc agactggaaa gatcgccgac    1260
tacaactaca gctgcccga cgacttcacc ggttgcgtca tcgcttggaa cagcaacaac    1320
ctggactcta aagtgggtgg caactacaac tacctgtacc gcctgttccg taagtcaaac    1380
ctgaagccat tcgagaggga catcagcact gaaatctacc aggccggatc taccccttgc    1440
aacggtgtcg agggcttcaa ctgctacttc ccctgcagt cctacggttt ccagccaact    1500
aacggtgtgg gctaccagcc ttacagagtg gtcgtgctga gcttcgaact gctccacgct    1560
cctgctactg tgtgcggtcc aaagaagtct accaacctgg tcaagaacaa gtgcgtgaac    1620
ttcaacttca cggcctgac cggaactggt gtcctgaccg agagcaacaa gaagttcctg    1680 ccccttccagc agttcggaag ggacatcgct gacaccactg acgctgtgcg cgaccctcag    1740
accctggaaa tcctggacat cactccatgc tcattcggag tgtctccgt gatcacccct    1800 ggcaccaaca cttctaacca ggtcgctgtg ctgtaccagg acgtcaactg caccgaggtc    1860
cctgtggcca tccacgctga ccagctgacc cccacttggc gcgtgtactc caccggcagc    1920
```

```
aacgtgttcc agactcgtgc tggttgcctg atcggcgccg agcacgtgaa caacagctac    1980
gaatgcgaca tccccatcgg cgctggaatc tgcgcctctt accagaccca gactaacagc    2040
ccacgcaggg ctcgctctgt ggcctctcag tcaatcatcg cttacaccat gtcactgggc    2100
gctgaaaact ccgtggccta ctctaacaac tcaatcgcca tccccaccaa cttcactatc    2160
agcgtgacca ctgagatcct gccagtcagc atgaccaaga cttctgtgga ctgcactatg    2220
tacatctgcg gagacagcac cgaatgctct aacctgctgc tgcagtacgg ctctttctgc    2280
acccagctga accgtgctct gactggaatc gccgtggagc aggacaagaa cactcaggaa    2340
gtcttcgctc aggtgaagca aatctacaag accccaccta tcaaggactt cggcggattc    2400
aacttctccc agatcctgcc tgacccctcc aagccaagca agcgctcttt catcgaggac    2460
ctgctgttca acaaggtcac tctggccgac gctggattca tcaagcagta cggagactgc    2520
ctgggtgaca tcgccgctcg tgacctgatc tgcgctcaga agttcaacgg tctgaccgtg    2580
ctgcccccac tgctgactga cgaaatgatc gcccagtaca ctagcgccct gctggctgga    2640
accatcactt ctggttggac cttcggtgct ggcgccgctc tgcagatccc tttcgctatg    2700
cagatggcct accgtttcaa cggaatcggt gtcacccaga acgtgctgta cgagaaccag    2760
aagctgatcg ctaaccagtt caactcagcc atcggaaaga tccaggacag cctgagctct    2820
actgcctctg ctctgggcaa gctgcaggac gtcgtgaacc agaacgccca ggctctgaac    2880 acccctggtca agcagctgtc atccaacttc ggtgctatca gctctgtgct gaacgacatc    2940
ctgtcccgcc tggacaaggt cgaggccgaa gtgcagatcg accgcctgat cactggccgt    3000
ctgcagtcac tgcagaccta cgtgactcag cagctgatca gggccgctga aatcagagcc    3060
tccgctaacc tggccgctac caagatgagc gagtgcgtcc tgggtcaatc taagcgtgtg    3120
gacttctgcg gcaagggata ccacctgatg tcattccctc agtctgctcc ccacggtgtg    3180
gtgttcctgc acgtcaccta cgtgccagcc caggagaaga acttcaccac tgcccctgct    3240
atctgccacg acggcaaggc tcacttcccc agggaaggtg tcttcgtgag caacggcacc    3300
cactggttcg tcactcagag aaacttctac gagccacaga tcatcaccac tgacaacact    3360
ttcgtgtctg aaactgcga cgtggtcatc ggtatcgtca acaacaccgt gtacgacccc    3420
ctgcagccag agctggactc attcaaggag gaactggaca agtacttcaa gaaccacacc    3480
tcccctgacg tcgacctggg cgacatctca ggaatcaacg cttccgtcgt gaacatccag    3540
aaggagatcg accgcctgaa cgaagtggcc aagaacctga cgaaagcct gatcgacctg    3600 caggagctgg gcaagtacga acagtacatc aagtggcctt ggtacatctg gctgggtttc    3660
atcgctggcc tcatcgctat cgtgatggtg accatcatgc tgtgctgcat gacttcatgc    3720
tgctcctgcc tgaagggctg ctgcagctgc ggatcttgct gcaagttcga cgaggacgac    3780
tctgaacccg tcctgaaggg cgtgaagctg cactacacc                            3819
```

<210> SEQ ID NO 36
<211> LENGTH: 1279
<212> TYPE: PRT
<213> ORGANISM: Artificial Sequence
<220> FEATURE:
<223> OTHER INFORMATION: RECOMBINANT SPIKE PROTEIN

<400> SEQUENCE: 36

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
```

-continued

```
                20                25                30
Thr Arg Gly Val Tyr Tyr Pro Asp Lys Val Phe Arg Ser Ser Val Leu
            35                40                45
His Ser Thr Gln Asp Leu Phe Leu Pro Phe Phe Ser Asn Val Thr Trp
        50                55                60
Phe His Ala Ile His Val Ser Gly Thr Asn Gly Thr Lys Arg Phe Asp
65                70                75                80
Asn Pro Val Leu Pro Phe Asn Asp Gly Val Tyr Phe Ala Ser Thr Glu
                85                90                95
Lys Ser Asn Ile Ile Arg Gly Trp Ile Phe Gly Thr Thr Leu Asp Ser
                100               105               110
Lys Thr Gln Ser Leu Leu Ile Val Asn Asn Ala Thr Asn Val Val Ile
            115               120               125
Lys Val Cys Glu Phe Gln Phe Cys Asn Asp Pro Phe Leu Gly Val Tyr
            130               135               140
Tyr His Lys Asn Asn Lys Ser Trp Met Glu Ser Glu Phe Arg Val Tyr
145               150               155               160
Ser Ser Ala Asn Asn Cys Thr Phe Glu Tyr Val Ser Gln Pro Phe Leu
            165               170               175
Met Asp Leu Glu Gly Lys Gln Gly Asn Phe Lys Asn Leu Arg Glu Phe
            180               185               190
Val Phe Lys Asn Ile Asp Gly Tyr Phe Lys Ile Tyr Ser Lys His Thr
            195               200               205
Pro Ile Asn Leu Val Arg Asp Leu Pro Gln Gly Phe Ser Ala Leu Glu
    210               215               220
Pro Leu Val Asp Leu Pro Ile Gly Ile Asn Ile Thr Arg Phe Gln Thr
225               230               235               240
Leu Leu Ala Leu His Arg Ser Tyr Leu Thr Pro Gly Asp Ser Ser Ser
            245               250               255
Gly Trp Thr Ala Gly Ala Ala Ala Tyr Tyr Val Gly Tyr Leu Gln Pro
            260               265               270
Arg Thr Phe Leu Leu Lys Tyr Asn Glu Asn Gly Thr Ile Thr Asp Ala
            275               280               285
Val Asp Cys Ala Leu Asp Pro Leu Ser Glu Thr Lys Cys Thr Leu Lys
    290               295               300
Ser Phe Thr Val Glu Lys Gly Ile Tyr Gln Thr Ser Asn Phe Arg Val
305               310               315               320
Gln Pro Thr Glu Ser Ile Val Arg Phe Pro Asn Ile Thr Asn Leu Cys
            325               330               335
Pro Phe Gly Glu Val Phe Asn Ala Thr Arg Phe Ala Ser Val Tyr Ala
            340               345               350
Trp Asn Arg Lys Arg Ile Ser Asn Cys Val Ala Asp Tyr Ser Val Leu
            355               360               365
Tyr Asn Ser Ala Ser Phe Ser Thr Phe Lys Cys Tyr Gly Val Ser Pro
    370               375               380
Thr Lys Leu Asn Asp Leu Cys Phe Thr Asn Val Tyr Ala Asp Ser Phe
385               390               395               400
Val Ile Arg Gly Asp Glu Val Arg Gln Ile Ala Pro Gly Gln Thr Gly
                405               410               415
Lys Ile Ala Asp Tyr Asn Tyr Lys Leu Pro Asp Asp Phe Thr Gly Cys
            420               425               430
Val Ile Ala Trp Asn Ser Asn Asn Leu Asp Ser Lys Val Gly Gly Asn
            435               440               445
```

-continued

```
Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
    675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
    755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
    850                 855                 860
```

-continued

```
Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000            1005

Thr Gln  Gln Leu Ile Arg Ala  Ala Glu Ile Arg Ala  Ser Ala Asn
    1010            1015            1020

Leu Ala  Ala Thr Lys Met Ser  Glu Cys Val Leu Gly  Gln Ser Lys
    1025            1030            1035

Arg Val  Asp Phe Cys Gly Lys  Gly Tyr His Leu Met  Ser Phe Pro
    1040            1045            1050

Gln Ser  Ala Pro His Gly Val  Val Phe Leu His Val  Thr Tyr Val
    1055            1060            1065

Pro Ala  Gln Glu Lys Asn Phe  Thr Thr Ala Pro Ala  Ile Cys His
    1070            1075            1080

Asp Gly  Lys Ala His Phe Pro  Arg Glu Gly Val Phe  Val Ser Asn
    1085            1090            1095

Gly Thr  His Trp Phe Val Thr  Gln Arg Asn Phe Tyr  Glu Pro Gln
    1100            1105            1110

Ile Ile  Thr Thr Asp Asn Thr  Phe Val Ser Gly Asn  Cys Asp Val
    1115            1120            1125

Val Ile  Gly Ile Val Asn Asn  Thr Val Tyr Asp Pro  Leu Gln Pro
    1130            1135            1140

Glu Leu  Asp Ser Phe Lys Glu  Glu Leu Asp Lys Tyr  Phe Lys Asn
    1145            1150            1155

His Thr  Ser Pro Asp Val Asp  Leu Gly Asp Ile Ser  Gly Ile Asn
    1160            1165            1170

Ala Ser  Val Val Asn Ile Gln  Lys Glu Ile Asp Arg  Leu Asn Glu
    1175            1180            1185

Val Ala  Lys Asn Leu Asn Glu  Ser Leu Ile Asp Leu  Gln Glu Leu
    1190            1195            1200

Gly Lys  Tyr Glu Gln Tyr Ile  Lys Trp Pro Trp Tyr  Ile Trp Leu
    1205            1210            1215

Gly Phe  Ile Ala Gly Leu Ile  Ala Ile Val Met Val  Thr Ile Met
    1220            1225            1230

Leu Cys  Cys Met Thr Ser Cys  Cys Ser Cys Leu Lys  Gly Cys Cys
    1235            1240            1245

Ser Cys  Gly Ser Cys Cys Lys  Phe Asp Glu Asp Asp  Ser Glu Pro
    1250            1255            1260

Val Leu  Lys Gly Val Lys Leu  His Tyr Thr His His  His His His
```

-continued

```
             1265                1270                1275

His

<210> SEQ ID NO 37
<211> LENGTH: 3837
<212> TYPE: DNA
<213> ORGANISM: Artificial Sequence
<220> FEATURE:
<223> OTHER INFORMATION: RECOMBINANT SPIKE PROTEIN

<400> SEQUENCE: 37
atgttcgtct tcctggtgct gctgcccctg gtgtccagcc agtgcgtgaa cctgaccact        60
aggactcagc tgcctcccgc ttacaccaac tcattcactc gcggtgtgta ctaccctgac       120
aaggtcttcc gttcttcagt gctgcactca actcaggacc tgttcctgcc cttcttctcc       180
aacgtcacct ggttccacgc catccacgtg tccggcacca acggcactaa gcgcttcgac       240
aacccagtgc tgcctttcaa cgacggtgtc tacttcgctt caaccgagaa gtccaacatc       300
atccgtggat ggatcttcgg caccactctg gacagcaaga ctcagtctct gctgatcgtc       360
aacaacgcca ccaacgtggt catcaaggtc tgcgaattcc agttctgcaa cgacccattc       420
ctgggcgtct actaccacaa gaacaacaag tcatggatgg agtccgaatt ccgcgtctac       480
tccagcgcta caactgcac tttcgagtac gtgtcccagc ctttcctgat ggacctggaa       540
ggaaagcagg gtaacttcaa gaacctgagg gagttcgtgt tcaagaacat cgacggatac       600
ttcaagattt acagcaagca caccccaatc aacctggtgc gcgacctgcc tcagggtttc       660
tctgctctgg agccactggt ggacctgcct atcggcatca acatcacccg cttccagact       720
ctgctggctc tgcaccgttc ctacctgact ccaggcgact atcttctgg atggactgct       780 ggagctgctc cttactacgt gggctacctg cagcctcgca ccttcctgct gaagtacaac       840
gaaaacggaa ccatcactga cgccgtcgac tgcgctctgg accctctgtc agaaaccaag       900
tgcactctga gtccttcac cgtggagaag ggcatctacc agacttcaaa cttcagggtg       960
cagcccaccg aatccatcgt cagattccct aacatcacta acctgtgccc cttcggagag      1020
gtcttcaacg ccacccgctt cgcttccgtg tacgcctgga acaggaagag aatctcaaac      1080
tgcgtcgctg actactccgt gctgtacaac tcagcctcct tcagcacctt caagtgctac      1140
ggcgtgtcac caactaagct gaacgacctg tgcttcacca cgtctacgc cgactccttc      1200 gtgatcaggg gagacgaggt cagacagatc gctcctggcc agactggaaa gatcgccgac      1260
tacaactaca agctgcccga cgacttcacc ggttgcgtca tcgcttggaa cagcaacaac      1320
ctggactcta aagtgggtgg caactacaac tacctgtacc gcctgttccg taagtcaaac      1380
ctgaagccat tcgagaggga catcagcact gaaatctacc aggccggatc taccccttgc      1440
aacggtgtcg agggcttcaa ctgctacttc ccctgcagt cctacggttt ccagccaact      1500
aacggtgtgg gctaccagcc ttacagagtg gtcgtgctga cttcgaact gctccacgct      1560 cctgctactg tgtgcggtcc aaagaagtct accaacctgg tcaagaacaa gtgcgtgaac      1620
ttcaacttca cggcctgac cggaactggt gtcctgaccg agagcaacaa gaagttcctg      1680
cccttccagc agtccggaag ggacatcgct gacaccactg acgctgtgcg cgaccctcag      1740
accctggaaa tcctggacat cactccatgc tcattcggag gtgtctccgt gatcacccct      1800
ggcaccaaca cttctaacca ggtcgctgtg ctgtaccagg acgtcaactg caccgaggtc      1860
cctgtggcca tccacgctga ccagctgacc cccacttggc gcgtgtactc caccggcagc      1920
aacgtgttcc agactcgtgc tggttgcctg atcggcgccg agcacgtgaa caacagctac      1980
```

-continued

```
gaatgcgaca tccccatcgg cgctggaatc tgcgcctctt accagaccca gactaacagc        2040
ccacgcaggg ctcgctctgt ggcctctcag tcaatcatcg cttacaccat gtcactgggc        2100
gctgaaaact ccgtggccta ctctaacaac tcaatcgcca tccccaccaa cttcactatc        2160
agcgtgacca ctgagatcct gccagtcagc atgaccaaga cttctgtgga ctgcactatg        2220
tacatctgcg gagacagcac cgaatgctct aacctgctgc tgcagtacgg ctctttctgc        2280
acccagctga accgtgctct gactggaatc gccgtggagc aggacaagaa cactcaggaa        2340
gtcttcgctc aggtgaagca aatctacaag accccaccta tcaaggactt cggcggattc        2400
aacttctccc agatcctgcc tgaccctcc aagccaagca agcgctcttt catcgaggac        2460
ctgctgttca acaaggtcac tctggccgac gctggattca tcaagcagta cggagactgc        2520
ctgggtgaca tcgccgctcg tgacctgatc tgcgctcaga agttcaacgg tctgaccgtg        2580 ctgccccac tgctgactga cgaaatgatc gcccagtaca ctagcgccct gctggctgga        2640
accatcactt ctggttggac cttcggtgct ggcgccgctc tgcagatccc tttcgctatg        2700
cagatggcct accgtttcaa cggaatcggt gtcacccaga acgtgctgta cgagaaccag        2760
aagctgatcg ctaaccagtt caactcagcc atcggaaaga tccaggacag cctgagctct        2820
actgcctctg ctctgggcaa gctgcaggac gtcgtgaacc agaacgccca ggctctgaac        2880
accctggtca agcagctgtc atccaacttc ggtgctatca gctctgtgct gaacgacatc        2940
ctgtcccgcc tggacaaggt cgaggccgaa gtgcagatcg accgcctgat cactggccgt        3000
ctgcagtcac tgcagaccta cgtgactcag cagctgatca gggccgctga aatcagagcc        3060
tccgctaacc tggccgctac caagatgagc gagtgcgtcc tgggtcaatc taagcgtgtg        3120
gacttctgcg gcaagggata ccacctgatg tcattccctc agtctgctcc ccacggtgtg        3180
gtgttcctgc acgtcaccta cgtgccagcc caggagaaga acttcaccac tgccctgct        3240 atctgccacg acggcaaggc tcacttcccc agggaaggtg tcttcgtgag caacggcacc        3300
cactggttcg tcactcagag aaacttctac gagccacaga tcatcaccac tgacaacact        3360
ttcgtgtctg aaactgcga cgtggtcatc ggtatcgtca acaacaccgt gtacgacccc        3420
ctgcagccag agctggactc attcaaggag gaactggaca agtacttcaa gaaccacacc        3480
tcccctgacg tcgacctggg cgacatctca ggaatcaacg cttccgtcgt gaacatccag        3540
aaggagatcg accgcctgaa cgaagtggcc aagaacctga cgaaagcct gatcgacctg        3600 caggagctgg gcaagtacga acagtacatc aagtggcctt ggtacatctg gctgggtttc        3660
atcgctggcc tcatcgctat cgtgatggtg accatcatgc tgtgctgcat gacttcatgc        3720
tgctcctgcc tgaagggctg ctgcagctgc ggatcttgct gcaagttcga cgaggacgac        3780
tctgaacccg tcctgaaggg cgtgaagctg cactacaccc accaccacca ccaccac        3837
```

<210> SEQ ID NO 38
<211> LENGTH: 1266
<212> TYPE: PRT
<213> ORGANISM: Artificial Sequence
<220> FEATURE:
<223> OTHER INFORMATION: RECOMBINANT SPIKE PROTEIN

<400> SEQUENCE: 38

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30
```

-continued

```
Ser Val Leu His Ser Thr Gln Asp Leu Phe Leu Pro Phe Phe Ser Asn
    35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
```

-continued

```
      450              455              460

Thr Pro Cys Asn Gly Val Glu Gly Phe Asn Cys Tyr Phe Pro Leu Gln
465              470              475              480

Ser Tyr Gly Phe Gln Pro Thr Asn Gly Val Gly Tyr Gln Pro Tyr Arg
              485              490              495

Val Val Val Leu Ser Phe Glu Leu Leu His Ala Pro Ala Thr Val Cys
              500              505              510

Gly Pro Lys Lys Ser Thr Asn Leu Val Lys Asn Lys Cys Val Asn Phe
              515              520              525

Asn Phe Asn Gly Leu Thr Gly Thr Gly Val Leu Thr Glu Ser Asn Lys
              530              535              540

Lys Phe Leu Pro Phe Gln Gln Phe Gly Arg Asp Ile Ala Asp Thr Thr
545              550              555              560

Asp Ala Val Arg Asp Pro Gln Thr Leu Glu Ile Leu Asp Ile Thr Pro
              565              570              575

Cys Ser Phe Gly Gly Val Ser Val Ile Thr Pro Gly Thr Asn Thr Ser
              580              585              590

Asn Gln Val Ala Val Leu Tyr Gln Asp Val Asn Cys Thr Glu Val Pro
              595              600              605

Val Ala Ile His Ala Asp Gln Leu Thr Pro Thr Trp Arg Val Tyr Ser
              610              615              620

Thr Gly Ser Asn Val Phe Gln Thr Arg Ala Gly Cys Leu Ile Gly Ala
625              630              635              640

Glu His Val Asn Asn Ser Tyr Glu Cys Asp Ile Pro Ile Gly Ala Gly
              645              650              655

Ile Cys Ala Ser Tyr Gln Thr Gln Thr Asn Ser Pro Arg Arg Ala Arg
              660              665              670

Ser Val Ala Ser Gln Ser Ile Ile Ala Tyr Thr Met Ser Leu Gly Ala
              675              680              685

Glu Asn Ser Val Ala Tyr Ser Asn Asn Ser Ile Ala Ile Pro Thr Asn
              690              695              700

Phe Thr Ile Ser Val Thr Thr Glu Ile Leu Pro Val Ser Met Thr Lys
705              710              715              720

Thr Ser Val Asp Cys Thr Met Tyr Ile Cys Gly Asp Ser Thr Glu Cys
              725              730              735

Ser Asn Leu Leu Leu Gln Tyr Gly Ser Phe Cys Thr Gln Leu Asn Arg
              740              745              750

Ala Leu Thr Gly Ile Ala Val Glu Gln Asp Lys Asn Thr Gln Glu Val
              755              760              765

Phe Ala Gln Val Lys Gln Ile Tyr Lys Thr Pro Pro Ile Lys Asp Phe
              770              775              780

Gly Gly Phe Asn Phe Ser Gln Ile Leu Pro Asp Pro Ser Lys Pro Ser
785              790              795              800

Lys Arg Ser Phe Ile Glu Asp Leu Leu Phe Asn Lys Val Thr Leu Ala
              805              810              815

Asp Ala Gly Phe Ile Lys Gln Tyr Gly Asp Cys Leu Gly Asp Ile Ala
              820              825              830

Ala Arg Asp Leu Ile Cys Ala Gln Lys Phe Asn Gly Leu Thr Val Leu
              835              840              845

Pro Pro Leu Leu Thr Asp Glu Met Ile Ala Gln Tyr Thr Ser Ala Leu
850              855              860

Leu Ala Gly Thr Ile Thr Ser Gly Trp Thr Phe Gly Ala Gly Ala Ala
865              870              875              880
```

-continued

```
Leu Gln Ile Pro Phe Ala Met Gln Met Ala Tyr Arg Phe Asn Gly Ile
            885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
            915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
            965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
            995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr  His His His
    1250                1255                1260

His His  His
    1265
```

<210> SEQ ID NO 39
<211> LENGTH: 60
<212> TYPE: PRT
<213> ORGANISM: Artificial Sequence
<220> FEATURE:
<223> OTHER INFORMATION: RECOMBINANT SPIKE PROTEIN

<400> SEQUENCE: 39

Trp Tyr Ile Trp Leu Gly Phe Ile Ala Gly Leu Ile Ala Ile Val Met
1               5                   10                  15

Val Thr Ile Met Leu Cys Cys Met Thr Ser Cys Cys Ser Cys Leu Lys
                20                  25                  30

Gly Cys Cys Ser Cys Gly Ser Cys Cys Lys Phe Asp Glu Asp Asp Ser
            35                  40                  45

Glu Pro Val Leu Lys Gly Val Lys Leu His Tyr Thr
        50                  55                  60

<210> SEQ ID NO 40
<211> LENGTH: 1213
<212> TYPE: PRT
<213> ORGANISM: Artificial Sequence
<220> FEATURE:
<223> OTHER INFORMATION: RECOMBINANT SPIKE PROTEIN

<400> SEQUENCE: 40

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
        130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

-continued

```
Gly Trp Thr Ala Gly Ala Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
        660                 665                 670
```

-continued

```
Ser Tyr Gln Thr Gln Thr Asn Ser Pro Arg Arg Ala Arg Ser Val Ala
        675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
        850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000                1005

Thr Gln  Gln Leu Ile Arg Ala  Ala Glu Ile Arg Ala  Ser Ala Asn
    1010            1015            1020

Leu Ala  Ala Thr Lys Met Ser  Glu Cys Val Leu Gly  Gln Ser Lys
    1025            1030            1035

Arg Val  Asp Phe Cys Gly Lys  Gly Tyr His Leu Met  Ser Phe Pro
    1040            1045            1050

Gln Ser  Ala Pro His Gly Val  Val Phe Leu His Val  Thr Tyr Val
    1055            1060            1065

Pro Ala  Gln Glu Lys Asn Phe  Thr Thr Ala Pro Ala  Ile Cys His
    1070            1075            1080

Asp Gly  Lys Ala His Phe Pro  Arg Glu Gly Val Phe  Val Ser Asn
```

-continued

```
    1085              1090              1095

Gly Thr His Trp Phe Val Thr Gln Arg Asn Phe Tyr Glu Pro Gln
    1100              1105              1110

Ile Ile Thr Thr Asp Asn Thr Phe Val Ser Gly Asn Cys Asp Val
    1115              1120              1125

Val Ile Gly Ile Val Asn Asn Thr Val Tyr Asp Pro Leu Gln Pro
    1130              1135              1140

Glu Leu Asp Ser Phe Lys Glu Glu Leu Asp Lys Tyr Phe Lys Asn
    1145              1150              1155

His Thr Ser Pro Asp Val Asp Leu Gly Asp Ile Ser Gly Ile Asn
    1160              1165              1170

Ala Ser Val Val Asn Ile Gln Lys Glu Ile Asp Arg Leu Asn Glu
    1175              1180              1185

Val Ala Lys Asn Leu Asn Glu Ser Leu Ile Asp Leu Gln Glu Leu
    1190              1195              1200

Gly Lys Tyr Glu Gln Tyr Ile Lys Trp Pro
    1205              1210

<210> SEQ ID NO 41
<211> LENGTH: 1200
<212> TYPE: PRT
<213> ORGANISM: Artificial Sequence
<220> FEATURE:
<223> OTHER INFORMATION: RECOMBINANT SPIKE PROTEIN

<400> SEQUENCE: 41

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
```

-continued

```
225                230                235                240

Ser Ser Ser Gly Trp Thr Ala Gly Ala Ala Ala Tyr Tyr Val Gly Tyr
            245                250                255

Leu Gln Pro Arg Thr Phe Leu Leu Lys Tyr Asn Glu Asn Gly Thr Ile
            260                265                270

Thr Asp Ala Val Asp Cys Ala Leu Asp Pro Leu Ser Glu Thr Lys Cys
            275                280                285

Thr Leu Lys Ser Phe Thr Val Glu Lys Gly Ile Tyr Gln Thr Ser Asn
    290                295                300

Phe Arg Val Gln Pro Thr Glu Ser Ile Val Arg Phe Pro Asn Ile Thr
305                310                315                320

Asn Leu Cys Pro Phe Gly Glu Val Phe Asn Ala Thr Arg Phe Ala Ser
            325                330                335

Val Tyr Ala Trp Asn Arg Lys Arg Ile Ser Asn Cys Val Ala Asp Tyr
            340                345                350

Ser Val Leu Tyr Asn Ser Ala Ser Phe Ser Thr Phe Lys Cys Tyr Gly
            355                360                365

Val Ser Pro Thr Lys Leu Asn Asp Leu Cys Phe Thr Asn Val Tyr Ala
    370                375                380

Asp Ser Phe Val Ile Arg Gly Asp Glu Val Arg Gln Ile Ala Pro Gly
385                390                395                400

Gln Thr Gly Lys Ile Ala Asp Tyr Asn Tyr Lys Leu Pro Asp Asp Phe
            405                410                415

Thr Gly Cys Val Ile Ala Trp Asn Ser Asn Asn Leu Asp Ser Lys Val
            420                425                430

Gly Gly Asn Tyr Asn Tyr Leu Tyr Arg Leu Phe Arg Lys Ser Asn Leu
            435                440                445

Lys Pro Phe Glu Arg Asp Ile Ser Thr Glu Ile Tyr Gln Ala Gly Ser
    450                455                460

Thr Pro Cys Asn Gly Val Glu Gly Phe Asn Cys Tyr Phe Pro Leu Gln
465                470                475                480

Ser Tyr Gly Phe Gln Pro Thr Asn Gly Val Gly Tyr Gln Pro Tyr Arg
            485                490                495

Val Val Val Leu Ser Phe Glu Leu Leu His Ala Pro Ala Thr Val Cys
            500                505                510

Gly Pro Lys Lys Ser Thr Asn Leu Val Lys Asn Lys Cys Val Asn Phe
            515                520                525

Asn Phe Asn Gly Leu Thr Gly Thr Gly Val Leu Thr Glu Ser Asn Lys
    530                535                540

Lys Phe Leu Pro Phe Gln Gln Phe Gly Arg Asp Ile Ala Asp Thr Thr
545                550                555                560

Asp Ala Val Arg Asp Pro Gln Thr Leu Glu Ile Leu Asp Ile Thr Pro
            565                570                575

Cys Ser Phe Gly Gly Val Ser Val Ile Thr Pro Gly Thr Asn Thr Ser
            580                585                590

Asn Gln Val Ala Val Leu Tyr Gln Asp Val Asn Cys Thr Glu Val Pro
            595                600                605

Val Ala Ile His Ala Asp Gln Leu Thr Pro Thr Trp Arg Val Tyr Ser
            610                615                620

Thr Gly Ser Asn Val Phe Gln Thr Arg Ala Gly Cys Leu Ile Gly Ala
625                630                635                640

Glu His Val Asn Asn Ser Tyr Glu Cys Asp Ile Pro Ile Gly Ala Gly
            645                650                655
```

-continued

```
Ile Cys Ala Ser Tyr Gln Thr Gln Thr Asn Ser Pro Arg Arg Ala Arg
        660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
        930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Lys Val Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile  Arg Ala Ala Glu Ile  Arg Ala Ser
        995                 1000                 1005

Ala Asn  Leu Ala Ala Thr Lys  Met Ser Glu Cys Val  Leu Gly Gln
    1010                 1015                 1020

Ser Lys  Arg Val Asp Phe Cys  Gly Lys Gly Tyr His  Leu Met Ser
    1025                 1030                 1035

Phe Pro  Gln Ser Ala Pro His  Gly Val Val Phe Leu  His Val Thr
    1040                 1045                 1050

Tyr Val  Pro Ala Gln Glu Lys  Asn Phe Thr Thr Ala  Pro Ala Ile
    1055                 1060                 1065
```

-continued

```
Cys His  Asp Gly Lys Ala His  Phe Pro Arg Glu Gly  Val Phe Val
    1070             1075             1080

Ser Asn  Gly Thr His Trp Phe  Val Thr Gln Arg Asn  Phe Tyr Glu
    1085             1090             1095

Pro Gln  Ile Ile Thr Thr Asp  Asn Thr Phe Val Ser  Gly Asn Cys
    1100             1105             1110

Asp Val  Val Ile Gly Ile Val  Asn Asn Thr Val Tyr  Asp Pro Leu
    1115             1120             1125

Gln Pro  Glu Leu Asp Ser Phe  Lys Glu Glu Leu Asp  Lys Tyr Phe
    1130             1135             1140

Lys Asn  His Thr Ser Pro Asp  Val Asp Leu Gly Asp  Ile Ser Gly
    1145             1150             1155

Ile Asn  Ala Ser Val Val Asn  Ile Gln Lys Glu Ile  Asp Arg Leu
    1160             1165             1170

Asn Glu  Val Ala Lys Asn Leu  Asn Glu Ser Leu Ile  Asp Leu Gln
    1175             1180             1185

Glu Leu  Gly Lys Tyr Glu Gln  Tyr Ile Lys Trp Pro
    1190             1195             1200

<210> SEQ ID NO 42
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 42

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220
```

-continued

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
```

-continued

```
                   645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
                770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065
```

-continued

```
Pro Ala  Gln Glu Lys Asn Phe  Thr Thr Ala Pro Ala  Ile Cys His
    1070             1075             1080

Asp Gly  Lys Ala His Phe Pro  Arg Glu Gly Val Phe  Val Ser Asn
    1085             1090             1095

Gly Thr  His Trp Phe Val Thr  Gln Arg Asn Phe Tyr  Glu Pro Gln
    1100             1105             1110

Ile Ile  Thr Thr Asp Asn Thr  Phe Val Ser Gly Asn  Cys Asp Val
    1115             1120             1125

Val Ile  Gly Ile Val Asn Asn  Thr Val Tyr Asp Pro  Leu Gln Pro
    1130             1135             1140

Glu Leu  Asp Ser Phe Lys Glu  Glu Leu Asp Lys Tyr  Phe Lys Asn
    1145             1150             1155

His Thr  Ser Pro Asp Val Asp  Leu Gly Asp Ile Ser  Gly Ile Asn
    1160             1165             1170

Ala Ser  Val Val Asn Ile Gln  Lys Glu Ile Asp Arg  Leu Asn Glu
    1175             1180             1185

Val Ala  Lys Asn Leu Asn Glu  Ser Leu Ile Asp Leu  Gln Glu Leu
    1190             1195             1200

Gly Lys  Tyr Glu Gln Tyr Ile  Lys Trp Pro His His  His His His
    1205             1210             1215

His
```

<210> SEQ ID NO 43
<211> LENGTH: 3657
<212> TYPE: DNA
<213> ORGANISM: Artificial Sequence
<220> FEATURE:
<223> OTHER INFORMATION: RECOMBINANT SPIKE PROTEIN

<400> SEQUENCE: 43

```
atgttcgtct tcctggtgct gctgcccctg gtgtccagcc agtgcgtgaa cctgaccact      60
aggactcagc tgcctcccgc ttacaccaac tcattcactc gcggtgtgta ctaccctgac     120
aaggtcttcc gttcttcagt gctgcactca actcaggacc tgttcctgcc cttcttctcc     180
aacgtcacct ggttccacgc catccacgtg tccggcacca acggcactaa cgcgcttcgac    240 aacccagtgc tgcctttcaa cgacggtgtc tacttcgctt caaccgagaa gtccaacatc     300
atccgtggat ggatcttcgg caccactctg gacagcaaga ctcagtctct gctgatcgtc     360
aacaacgcca ccaacgtggt catcaaggtc tgcgaattcc agttctgcaa cgacccattc     420
ctgggcgtct actaccacaa gaacaacaag tcatggatgg agtccgaatt ccgcgtctac     480
tccagcgcta caactgcac tttcgagtac gtgtcccagc ctttcctgat ggacctggaa     540
ggaaagcagg gtaacttcaa gaacctgagg gagttcgtgt tcaagaacat cgacggatac     600
ttcaagattt acagcaagca cacccccaatc aacctggtgc gcgacctgcc tcagggtttc     660
tctgctctgg agccactggt ggacctgcct atcggcatca acatcacccg cttccagact     720
ctgctggctc tgcaccgttc ctacctgact ccaggcgact catcttctgg atggactgct     780
ggagctgctg cttactacgt gggctacctg cagcctcgca ccttcctgct gaagtacaac     840
gaaaacggaa ccatcactga cgccgtcgac tgcgctctgg accctctgtc agaaaccaag     900
tgcactctga gtccttcac cgtggagaag ggcatctacc agacttcaaa cttcagggtg     960
cagcccaccg aatccatcgt cagattccct aacatcacta acctgtgccc cttcggagag    1020
gtcttcaacg ccaccgctt cgcttccgtg tacgcctgga acaggaagag aatctcaaac    1080
```

-continued

```
tgcgtcgctg actactccgt gctgtacaac tcagcctcct tcagcacctt caagtgctac      1140
ggcgtgtcac caactaagct gaacgacctg tgcttcacca acgtctacgc cgactccttc      1200
gtgatcaggg gagacgaggt cagacagatc gctcctggcc agactggaaa gatcgccgac      1260
tacaactaca agctgcccga cgacttcacc ggttgcgtca tcgcttggaa cagcaacaac      1320
ctggactcta aagtgggtgg caactacaac tacctgtacc gcctgttccg taagtcaaac      1380
ctgaagccat tcgagaggga catcagcact gaaatctacc aggccggatc tacccccttgc     1440 aacggtgtcg agggcttcaa ctgctacttc cccctgcagt cctacggttt ccagccaact      1500
aacggtgtgg gctaccagcc ttacagagtg gtcgtgctga gcttcgaact gctccacgct      1560
cctgctactg tgtgcggtcc aaagaagtct accaacctgg tcaagaacaa gtgcgtgaac      1620
ttcaacttca acggcctgac cggaactggt gtcctgaccg agagcaacaa gaagttcctg      1680
cccttccagc agttcggaag ggacatcgct gacaccactg acgctgtgcg cgaccctcag      1740
accctggaaa tcctggacat cactccatgc tcattcggag gtgtctccgt gatcacccct      1800
ggcaccaaca cttctaacca ggtcgctgtg ctgtaccagg acgtcaactg caccgaggtc      1860
cctgtggcca tccacgctga ccagctgacc cccacttggc gcgtgtactc caccggcagc      1920
aacgtgttcc agactcgtgc tggttgcctg atcggcgccg agcacgtgaa caacagctac      1980
gaatgcgaca tcccccatcgg cgctggaatc tgcgcctctt accagaccca gactaacagc      2040
ccacgcaggg ctcgctctgt ggcctctcag tcaatcatcg cttacaccat gtcactgggc      2100
gctgaaaact ccgtggccta ctctaacaac tcaatcgcca tccccaccaa cttcactatc      2160
agcgtgacca ctgagatcct gccagtcagc atgaccaaga cttctgtgga ctgcactatg      2220
tacatctgcg gagacagcac cgaatgctct aacctgctgc tgcagtacgg ctctttctgc      2280
acccagctga ccgtgctctc gactggaatc gccgtggagc aggacaagaa cactcaggaa      2340
gtcttcgctc aggtgaagca aatctacaag accccaccta tcaaggactt cggcggattc      2400
aacttctccc agatcctgcc tgacccctcc aagccaagca gcgctctttt catcgaggac      2460
ctgctgttca caaggtcac tctggccgac gctggattca tcaagcagta cggagactgc      2520
ctgggtgaca tcgccgctcg tgacctgatc tgcgctcaga agttcaacgg tctgaccgtg      2580
ctgcccccac tgctgactga cgaaatgatc gcccagtaca ctagcgccct gctggctgga      2640
accatcactt ctggttggac cttcggtgct ggcgccgctc tgcagatccc tttcgctatg      2700
cagatggcct accgtttcaa cggaatcggt gtcacccaga acgtgctgta cgagaaccag      2760
aagctgatcg ctaaccagtt caactcagcc atcggaaaga tccaggacag cctgagctct      2820
actgcctctg ctctgggcaa gctgcaggac gtcgtgaacc agaacgccca ggctctgaac      2880
accctggtca agcagctgtc atccaacttc ggtgctatca gctctgtgct gaacgacatc      2940
ctgtcccgcc tggacaaggt cgaggccgaa gtgcagatcg accgcctgat cactggccgt      3000
ctgcagtcac tgcagaccta cgtgactcag cagctgatcc gggccgctga aatcagagcc      3060
tccgctaacc tggccgctac caagatgagc gagtgcgtcc tgggtcaatc taagcgtgtg      3120
gacttctgcg gcaagggata ccacctgatg tcattccctc agtctgctcc ccacggtgtg      3180
gtgttcctgc acgtcacta cgtgccagcc aggagaaga acttcaccac tgccctgct      3240 atctgccacg acggcaaggc tcacttcccc agggaaggtg tcttcgtgag caacggcacc      3300
cactggttcg tcactcagag aaacttctac gagccacaga tcatcaccac tgacaacact      3360
ttcgtgtctg gaaactgcga cgtggtcatc ggtatcgtca caacaccgt gtacgacccc      3420 ctgcagccag agctggactc attcaaggag gaactggaca agtacttcaa gaaccacacc      3480
```

-continued

```
tcccctgacg tcgacctggg cgacatctca ggaatcaacg cttccgtcgt gaacatccag      3540
aaggagatcg accgcctgaa cgaagtggcc aagaacctga acgaaagcct gatcgacctg      3600
caggagctgg gcaagtacga acagtacatc aagtggcctc accaccacca ccaccac        3657
```

<210> SEQ ID NO 44
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 44

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750
```

```
Leu Leu Gln Tyr Gly Ser Phe Cys Thr Gln Leu Asn Arg Ala Leu Thr
        755              760                 765

Gly Ile Ala Val Glu Gln Asp Lys Asn Thr Gln Glu Val Phe Ala Gln
770              775                 780

Val Lys Gln Ile Tyr Lys Thr Pro Pro Ile Lys Asp Phe Gly Gly Phe
785                  790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
            885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
            965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
```

```
       1160              1165              1170

Ala Ser  Val Val Asn Ile Gln  Lys Glu Ile Asp Arg  Leu Asn Glu
    1175              1180              1185

Val Ala  Lys Asn Leu Asn Glu  Ser Leu Ile Asp Leu  Gln Glu Leu
    1190              1195              1200

Gly Lys  Tyr Glu Gln Tyr Ile  Lys Trp Pro His His  His His His
    1205              1210              1215

His
```

```
<210> SEQ ID NO 45
<211> LENGTH: 318
<212> TYPE: PRT
<213> ORGANISM: Artificial Sequence
<220> FEATURE:
<223> OTHER INFORMATION: RECOMBINANT SPIKE PROTEIN

<400> SEQUENCE: 45

Gln Cys Val Asn Leu Thr Thr Arg Thr Gln Leu Pro Pro Ala Tyr Thr
1               5                  10                 15

Asn Ser Phe Thr Arg Gly Val Tyr Tyr Pro Asp Lys Val Phe Arg Ser
            20                 25                 30

Ser Val Leu His Ser Thr Gln Asp Leu Phe Leu Pro Phe Phe Ser Asn
        35                 40                 45

Val Thr Trp Phe His Ala Ile His Val Ser Gly Thr Asn Gly Thr Lys
    50                 55                 60

Arg Phe Asp Asn Pro Val Leu Pro Phe Asn Asp Gly Val Tyr Phe Ala
65                 70                 75                 80

Ser Thr Glu Lys Ser Asn Ile Ile Arg Gly Trp Ile Phe Gly Thr Thr
                85                 90                 95

Leu Asp Ser Lys Thr Gln Ser Leu Leu Ile Val Asn Asn Ala Thr Asn
            100                105                110

Val Val Ile Lys Val Cys Glu Phe Gln Phe Cys Asn Asp Pro Phe Leu
        115                120                125

Gly Val Tyr Tyr His Lys Asn Asn Lys Ser Trp Met Glu Ser Glu Phe
    130                135                140

Arg Val Tyr Ser Ser Ala Asn Asn Cys Thr Phe Glu Tyr Val Ser Gln
145                150                155                160

Pro Phe Leu Met Asp Leu Glu Gly Lys Gln Gly Asn Phe Lys Asn Leu
                165                170                175

Arg Glu Phe Val Phe Lys Asn Ile Asp Gly Tyr Phe Lys Ile Tyr Ser
            180                185                190

Lys His Thr Pro Ile Asn Leu Val Arg Asp Leu Pro Gln Gly Phe Ser
            195                200                205

Ala Leu Glu Pro Leu Val Asp Leu Pro Ile Gly Ile Asn Ile Thr Arg
    210                215                220

Phe Gln Thr Leu Leu Ala Leu His Arg Ser Tyr Leu Thr Pro Gly Asp
225                230                235                240

Ser Ser Ser Gly Trp Thr Ala Gly Ala Ala Ala Tyr Tyr Val Gly Tyr
                245                250                255

Leu Gln Pro Arg Thr Phe Leu Leu Lys Tyr Asn Glu Asn Gly Thr Ile
            260                265                270

Thr Asp Ala Val Asp Cys Ala Leu Asp Pro Leu Ser Glu Thr Lys Cys
            275                280                285

Thr Leu Lys Ser Phe Thr Val Glu Lys Gly Ile Tyr Gln Thr Ser Asn
290                295                300
```

-continued

```
Phe Arg Val Gln Pro Thr Glu Ser Ile Val Arg Phe Pro Asn
305             310             315

<210> SEQ ID NO 46
<211> LENGTH: 955
<212> TYPE: PRT
<213> ORGANISM: Artificial Sequence
<220> FEATURE:
<223> OTHER INFORMATION: RECOMBINANT SPIKE PROTEIN

<400> SEQUENCE: 46

Met Phe Val Phe Leu Val Leu Leu Pro Leu Val Ser Ser Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65              70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe Asn
        210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
                260                 265                 270

Ser Phe Gly Gly Val Ser Val Ile Thr Pro Gly Thr Asn Thr Ser Asn
            275                 280                 285

Gln Val Ala Val Leu Tyr Gln Asp Val Asn Cys Thr Glu Val Pro Val
        290                 295                 300

Ala Ile His Ala Asp Gln Leu Thr Pro Thr Trp Arg Val Tyr Ser Thr
305                 310                 315                 320

Gly Ser Asn Val Phe Gln Thr Arg Ala Gly Cys Leu Ile Gly Ala Glu
                325                 330                 335

His Val Asn Asn Ser Tyr Glu Cys Asp Ile Pro Ile Gly Ala Gly Ile
            340                 345                 350
```

-continued

```
Cys Ala Ser Tyr Gln Thr Gln Thr Asn Ser Pro Arg Arg Ala Arg Ser
        355             360             365

Val Ala Ser Gln Ser Ile Ile Ala Tyr Thr Met Ser Leu Gly Ala Glu
        370             375             380

Asn Ser Val Ala Tyr Ser Asn Asn Ser Ile Ala Ile Pro Thr Asn Phe
385             390             395             400

Thr Ile Ser Val Thr Thr Glu Ile Leu Pro Val Ser Met Thr Lys Thr
            405             410             415

Ser Val Asp Cys Thr Met Tyr Ile Cys Gly Asp Ser Thr Glu Cys Ser
            420             425             430

Asn Leu Leu Leu Gln Tyr Gly Ser Phe Cys Thr Gln Leu Asn Arg Ala
            435             440             445

Leu Thr Gly Ile Ala Val Glu Gln Asp Lys Asn Thr Gln Glu Val Phe
        450             455             460

Ala Gln Val Lys Gln Ile Tyr Lys Thr Pro Pro Ile Lys Asp Phe Gly
465             470             475             480

Gly Phe Asn Phe Ser Gln Ile Leu Pro Asp Pro Ser Lys Pro Ser Lys
            485             490             495

Arg Ser Phe Ile Glu Asp Leu Leu Phe Asn Lys Val Thr Leu Ala Asp
            500             505             510

Ala Gly Phe Ile Lys Gln Tyr Gly Asp Cys Leu Gly Asp Ile Ala Ala
            515             520             525

Arg Asp Leu Ile Cys Ala Gln Lys Phe Asn Gly Leu Thr Val Leu Pro
        530             535             540

Pro Leu Leu Thr Asp Glu Met Ile Ala Gln Tyr Thr Ser Ala Leu Leu
545             550             555             560

Ala Gly Thr Ile Thr Ser Gly Trp Thr Phe Gly Ala Gly Ala Ala Leu
            565             570             575

Gln Ile Pro Phe Ala Met Gln Met Ala Tyr Arg Phe Asn Gly Ile Gly
            580             585             590

Val Thr Gln Asn Val Leu Tyr Glu Asn Gln Lys Leu Ile Ala Asn Gln
        595             600             605

Phe Asn Ser Ala Ile Gly Lys Ile Gln Asp Ser Leu Ser Ser Thr Ala
        610             615             620

Ser Ala Leu Gly Lys Leu Gln Asp Val Val Asn Gln Asn Ala Gln Ala
625             630             635             640

Leu Asn Thr Leu Val Lys Gln Leu Ser Ser Asn Phe Gly Ala Ile Ser
            645             650             655

Ser Val Leu Asn Asp Ile Leu Ser Arg Leu Asp Lys Val Glu Ala Glu
            660             665             670

Val Gln Ile Asp Arg Leu Ile Thr Gly Arg Leu Gln Ser Leu Gln Thr
        675             680             685

Tyr Val Thr Gln Gln Leu Ile Arg Ala Ala Glu Ile Arg Ala Ser Ala
        690             695             700

Asn Leu Ala Ala Thr Lys Met Ser Glu Cys Val Leu Gly Gln Ser Lys
705             710             715             720

Arg Val Asp Phe Cys Gly Lys Gly Tyr His Leu Met Ser Phe Pro Gln
            725             730             735

Ser Ala Pro His Gly Val Val Phe Leu His Val Thr Tyr Val Pro Ala
            740             745             750

Gln Glu Lys Asn Phe Thr Thr Ala Pro Ala Ile Cys His Asp Gly Lys
            755             760             765
```

```
Ala His Phe Pro Arg Glu Gly Val Phe Val Ser Asn Gly Thr His Trp
    770             775             780

Phe Val Thr Gln Arg Asn Phe Tyr Glu Pro Gln Ile Ile Thr Thr Asp
785             790             795             800

Asn Thr Phe Val Ser Gly Asn Cys Asp Val Val Ile Gly Ile Val Asn
                805             810             815

Asn Thr Val Tyr Asp Pro Leu Gln Pro Glu Leu Asp Ser Phe Lys Glu
            820             825             830

Glu Leu Asp Lys Tyr Phe Lys Asn His Thr Ser Pro Asp Val Asp Leu
            835             840             845

Gly Asp Ile Ser Gly Ile Asn Ala Ser Val Val Asn Ile Gln Lys Glu
    850             855             860

Ile Asp Arg Leu Asn Glu Val Ala Lys Asn Leu Asn Glu Ser Leu Ile
865             870             875             880

Asp Leu Gln Glu Leu Gly Lys Tyr Glu Gln Tyr Ile Lys Trp Pro Trp
            885             890             895

Tyr Ile Trp Leu Gly Phe Ile Ala Gly Leu Ile Ala Ile Val Met Val
            900             905             910

Thr Ile Met Leu Cys Cys Met Thr Ser Cys Cys Ser Cys Leu Lys Gly
    915             920             925

Cys Cys Ser Cys Gly Ser Cys Cys Lys Phe Asp Glu Asp Asp Ser Glu
    930             935             940

Pro Val Leu Lys Gly Val Lys Leu His Tyr Thr
945             950             955
```

```
<210> SEQ ID NO 47
<211> LENGTH: 2868
<212> TYPE: DNA
<213> ORGANISM: Artificial Sequence
<220> FEATURE:
<223> OTHER INFORMATION: RECOMBINANT SPIKE PROTEIN

<400> SEQUENCE: 47
atgttcgtct tcctggtgct gctgcccctg gtgtccagca tcactaacct gtgccccttc      60
ggagaggtct tcaacgccac cgcttcgct tccgtgtacg cctggaacag gaagagaatc     120
tcaaactgcg tcgctgacta ctccgtgctg tacaactcag cctccttcag caccttcaag     180
tgctacggcg tgtcaccaac taagctgaac gacctgtgct tcaccaacgt ctacgccgac     240
tccttcgtga tcaggggaga cgaggtcaga cagatcgctc ctggccagac tggaaagatc     300
gccgactaca actacaagct gcccgacgac ttcaccggtt gcgtcatcgc ttggaacagc     360
aacaacctgg actctaaagt gggtggcaac tacaactacc tgtaccgcct gttccgtaag     420
tcaaacctga agccattcga gaggacatc agcactgaaa tctaccaggc cggatctacc     480
ccttgcaacg gtgtcgaggg cttcaactgc tacttccccc tgcagtccta cggtttccag     540
ccaactaacg gtgtgggcta ccagccttac agagtggtcg tgctgagctt cgaactgctc     600
cacgctcctg ctactgtgtg cggtccaaag aagtctacca acctggtcaa gaacaagtgc     660
gtgaacttca acttcaacgg cctgaccgga actggtgtcc tgaccgagag caacaagaag     720
ttcctgccct ccagcagtt cggaagggac atcgctgaca ccactgacgc tgtgcgcgac     780
cctcagaccc tggaaatcct ggacatcact ccatgctcat cggaggtgt ctccgtgatc     840 acccctggca ccaacacttc taaccaggtc gctgtgctgt accaggacgt caactgcacc     900
gaggtccctg tggccatcca cgctgaccag ctgaccccca cttggcgcgt gtactccacc     960
ggcagcaacg tgttccagac tcgtgctggt tgcctgatcg gcgccgagca cgtgaacaac    1020
```

```
agctacgaat gcgacatccc catcggcgct ggaatctgcg cctcttacca gacccagact     1080
aacagcccac gcagggctcg ctctgtggcc tctcagtcaa tcatcgctta caccatgtca     1140
ctgggcgctg aaaactccgt ggcctactct aacaactcaa tcgccatccc caccaacttc     1200
actatcagcg tgaccactga gatcctgcca gtcagcatga ccaagacttc tgtggactgc     1260
actatgtaca tctgcggaga cagcaccgaa tgctctaacc tgctgctgca gtacggctct     1320
ttctgcaccc agctgaaccg tgctctgact ggaatcgccg tggagcagga caagaacact     1380
caggaagtct tcgctcaggt gaagcaaatc tacaagaccc acctatcaa ggacttcggc       1440 ggattcaact tctcccagat cctgcctgac ccctccaagc caagcaagcg ctctttcatc     1500
gaggacctgc tgttcaacaa ggtcactctg ccgacgctg gattcatcaa gcagtacgga       1560
gactgcctgg gtgacatcgc cgctcgtgac ctgatctgcg ctcagaagtt caacggtctg     1620
accgtgctgc ccccactgct gactgacgaa atgatcgccc agtacactag cgccctgctg     1680
gctggaacca tcacttctgg ttggaccttc ggtgctggcg ccgctctgca gatccctttc     1740
gctatgcaga tggcctaccg tttcaacgga atcggtgtca cccagaacgt gctgtacgag     1800
aaccagaagc tgatcgctaa ccagttcaac tcagccatcg aaagatcca ggacagcctg       1860 agctctactg cctctgctct gggcaagctg caggacgtcg tgaaccagaa cgcccaggct     1920
ctgaacaccc tggtcaagca gctgtcatcc aacttcggtg ctatcagctc tgtgctgaac     1980
gacatcctgt cccgcctgga caaggtcgag gccgaagtgc agatcgaccg cctgatcact     2040
ggccgtctgc agtcactgca gacctacgtg actcagcagc tgatcagggc cgctgaaatc     2100
agagcctccg ctaacctggc cgctaccaag atgagcgagt gcgtcctggg tcaatctaag     2160
cgtgtggact ctgcggcaa gggataccac ctgatgtcat ccctcagtc tgctcccac       2220 ggtgtggtgt tcctgcacgt cacctacgtg ccagcccagg agaagaactt caccactgcc     2280
cctgctatct gccacgacgg caaggctcac ttccccaggg aaggtgtctt cgtgagcaac     2340
ggcacccact ggttcgtcac tcagagaaac ttctacgagc cacagatcat caccactgac     2400
aacactttcg tgtctggaaa ctgcgacgtg gtcatcggta tcgtcaacaa caccgtgtac     2460
gaccccctgc agccagagct ggactcattc aaggaggaac tggacaagta cttcaagaac     2520
cacacctccc ctgacgtcga cctgggcgac atctcaggaa tcaacgcttc cgtcgtgaac     2580
atccagaagg agatcgaccg cctgaacgaa gtggccaaga acctgaacga aagcctgatc     2640
gacctgcagg agctgggcaa gtacgaacag tacatcaagt ggccttggta catctggctg     2700
ggtttcatcg ctggcctcat cgctatcgtg atggtgacca tcatgctgtg ctgcatgact     2760
tcatgctgct cctgcctgaa gggctgctgc agctgcggat cttgctgcaa gttcgacgag     2820
gacgactctg aacccgtcct gaagggcgtg aagctgcact acacctaa                   2868
```

<210> SEQ ID NO 48
<211> LENGTH: 942
<212> TYPE: PRT
<213> ORGANISM: Artificial Sequence
<220> FEATURE:
<223> OTHER INFORMATION: RECOMBINANT SPIKE PROTEIN

<400> SEQUENCE: 48

```
Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30
```

-continued

```
Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
                100                 105                 110

Lys Val Gly Gly Asn Tyr Asn Tyr Leu Tyr Arg Leu Phe Arg Lys Ser
                115                 120                 125

Asn Leu Lys Pro Phe Glu Arg Asp Ile Ser Thr Glu Ile Tyr Gln Ala
        130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
                180                 185                 190

Val Cys Gly Pro Lys Lys Ser Thr Asn Leu Val Lys Asn Lys Cys Val
                195                 200                 205

Asn Phe Asn Phe Asn Gly Leu Thr Gly Thr Gly Val Leu Thr Glu Ser
        210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
                245                 250                 255

Thr Pro Cys Ser Phe Gly Gly Val Ser Val Ile Thr Pro Gly Thr Asn
                260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
        290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
                325                 330                 335

Ala Gly Ile Cys Ala Ser Tyr Gln Thr Gln Thr Asn Ser Pro Arg Arg
                340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
        370                 375                 380

Thr Asn Phe Thr Ile Ser Val Thr Thr Glu Ile Leu Pro Val Ser Met
385                 390                 395                 400

Thr Lys Thr Ser Val Asp Cys Thr Met Tyr Ile Cys Gly Asp Ser Thr
                405                 410                 415

Glu Cys Ser Asn Leu Leu Leu Gln Tyr Gly Ser Phe Cys Thr Gln Leu
                420                 425                 430

Asn Arg Ala Leu Thr Gly Ile Ala Val Glu Gln Asp Lys Asn Thr Gln
        435                 440                 445

Glu Val Phe Ala Gln Val Lys Gln Ile Tyr Lys Thr Pro Pro Ile Lys
```

-continued

```
      450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
                500                 505                 510

Ile Ala Ala Arg Asp Leu Ile Cys Ala Gln Lys Phe Asn Gly Leu Thr
                515                 520                 525

Val Leu Pro Pro Leu Leu Thr Asp Glu Met Ile Ala Gln Tyr Thr Ser
530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
                580                 585                 590

Ala Asn Gln Phe Asn Ser Ala Ile Gly Lys Ile Gln Asp Ser Leu Ser
                595                 600                 605

Ser Thr Ala Ser Ala Leu Gly Lys Leu Gln Asp Val Val Asn Gln Asn
    610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
                660                 665                 670

Leu Gln Thr Tyr Val Thr Gln Gln Leu Ile Arg Ala Ala Glu Ile Arg
                675                 680                 685

Ala Ser Ala Asn Leu Ala Ala Thr Lys Met Ser Glu Cys Val Leu Gly
    690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
                740                 745                 750

Asp Gly Lys Ala His Phe Pro Arg Glu Gly Val Phe Val Ser Asn Gly
                755                 760                 765

Thr His Trp Phe Val Thr Gln Arg Asn Phe Tyr Glu Pro Gln Ile Ile
    770                 775                 780

Thr Thr Asp Asn Thr Phe Val Ser Gly Asn Cys Asp Val Val Ile Gly
785                 790                 795                 800

Ile Val Asn Asn Thr Val Tyr Asp Pro Leu Gln Pro Glu Leu Asp Ser
                805                 810                 815

Phe Lys Glu Glu Leu Asp Lys Tyr Phe Lys Asn His Thr Ser Pro Asp
                820                 825                 830

Val Asp Leu Gly Asp Ile Ser Gly Ile Asn Ala Ser Val Val Asn Ile
                835                 840                 845

Gln Lys Glu Ile Asp Arg Leu Asn Glu Val Ala Lys Asn Leu Asn Glu
    850                 855                 860

Ser Leu Ile Asp Leu Gln Glu Leu Gly Lys Tyr Glu Gln Tyr Ile Lys
865                 870                 875                 880
```

-continued

Trp Pro Trp Tyr Ile Trp Leu Gly Phe Ile Ala Gly Leu Ile Ala Ile
            885             890             895

Val Met Val Thr Ile Met Leu Cys Cys Met Thr Ser Cys Cys Ser Cys
            900             905             910

Leu Lys Gly Cys Cys Ser Cys Gly Ser Cys Cys Lys Phe Asp Glu Asp
        915             920             925

Asp Ser Glu Pro Val Leu Lys Gly Val Lys Leu His Tyr Thr
    930             935             940

<210> SEQ ID NO 49
<211> LENGTH: 960
<212> TYPE: PRT
<213> ORGANISM: Artificial Sequence
<220> FEATURE:
<223> OTHER INFORMATION: RECOMBINANT SPIKE PROTEIN

<400> SEQUENCE: 49

Met Phe Val Phe Leu Val Leu Leu Pro Leu Val Ser Ser Ile Thr Asn
1               5               10              15

Leu Cys Pro Phe Gly Glu Val Phe Asn Ala Thr Arg Phe Ala Ser Val
            20              25              30

Tyr Ala Trp Asn Arg Lys Arg Ile Ser Asn Cys Val Ala Asp Tyr Ser
        35              40              45

Val Leu Tyr Asn Ser Ala Ser Phe Ser Thr Phe Lys Cys Tyr Gly Val
    50              55              60

Ser Pro Thr Lys Leu Asn Asp Leu Cys Phe Thr Asn Val Tyr Ala Asp
65              70              75              80

Ser Phe Val Ile Arg Gly Asp Glu Val Arg Gln Ile Ala Pro Gly Gln
            85              90              95

Thr Gly Lys Ile Ala Asp Tyr Asn Tyr Lys Leu Pro Asp Asp Phe Thr
            100             105             110

Gly Cys Val Ile Ala Trp Asn Ser Asn Asn Leu Asp Ser Lys Val Gly
        115             120             125

Gly Asn Tyr Asn Tyr Leu Tyr Arg Leu Phe Arg Lys Ser Asn Leu Lys
    130             135             140

Pro Phe Glu Arg Asp Ile Ser Thr Glu Ile Tyr Gln Ala Gly Ser Thr
145             150             155             160

Pro Cys Asn Gly Val Glu Gly Phe Asn Cys Tyr Phe Pro Leu Gln Ser
            165             170             175

Tyr Gly Phe Gln Pro Thr Asn Gly Val Gly Tyr Gln Pro Tyr Arg Val
            180             185             190

Val Val Leu Ser Phe Glu Leu Leu His Ala Pro Ala Thr Val Cys Gly
        195             200             205

Pro Lys Lys Ser Thr Asn Leu Val Lys Asn Lys Cys Val Asn Phe Asn
    210             215             220

Phe Asn Gly Leu Thr Gly Thr Gly Val Leu Thr Glu Ser Asn Lys Lys
225             230             235             240

Phe Leu Pro Phe Gln Gln Phe Gly Arg Asp Ile Ala Asp Thr Thr Asp
            245             250             255

Ala Val Arg Asp Pro Gln Thr Leu Glu Ile Leu Asp Ile Thr Pro Cys
            260             265             270

Ser Phe Gly Gly Val Ser Val Ile Thr Pro Gly Thr Asn Thr Ser Asn
        275             280             285

Gln Val Ala Val Leu Tyr Gln Asp Val Asn Cys Thr Glu Val Pro Val
    290             295             300

```
Ala Ile His Ala Asp Gln Leu Thr Pro Thr Trp Arg Val Tyr Ser Thr
305             310             315             320

Gly Ser Asn Val Phe Gln Thr Arg Ala Gly Cys Leu Ile Gly Ala Glu
            325             330             335

His Val Asn Asn Ser Tyr Glu Cys Asp Ile Pro Ile Gly Ala Gly Ile
            340             345             350

Cys Ala Ser Tyr Gln Thr Gln Thr Asn Ser Pro Arg Arg Ala Arg Ser
            355             360             365

Val Ala Ser Gln Ser Ile Ile Ala Tyr Thr Met Ser Leu Gly Ala Glu
            370             375             380

Asn Ser Val Ala Tyr Ser Asn Asn Ser Ile Ala Ile Pro Thr Asn Phe
305             390             395             400

Thr Ile Ser Val Thr Thr Glu Ile Leu Pro Val Ser Met Thr Lys Thr
            405             410             415

Ser Val Asp Cys Thr Met Tyr Ile Cys Gly Asp Ser Thr Glu Cys Ser
            420             425             430

Asn Leu Leu Leu Gln Tyr Gly Ser Phe Cys Thr Gln Leu Asn Arg Ala
            435             440             445

Leu Thr Gly Ile Ala Val Glu Gln Asp Lys Asn Thr Gln Glu Val Phe
            450             455             460

Ala Gln Val Lys Gln Ile Tyr Lys Thr Pro Pro Ile Lys Asp Phe Gly
465             470             475             480

Gly Phe Asn Phe Ser Gln Ile Leu Pro Asp Pro Ser Lys Pro Ser Lys
            485             490             495

Arg Ser Phe Ile Glu Asp Leu Leu Phe Asn Lys Val Thr Leu Ala Asp
            500             505             510

Ala Gly Phe Ile Lys Gln Tyr Gly Asp Cys Leu Gly Asp Ile Ala Ala
            515             520             525

Arg Asp Leu Ile Cys Ala Gln Lys Phe Asn Gly Leu Thr Val Leu Pro
            530             535             540

Pro Leu Leu Thr Asp Glu Met Ile Ala Gln Tyr Thr Ser Ala Leu Leu
545             550             555             560

Ala Gly Thr Ile Thr Ser Gly Trp Thr Phe Gly Ala Gly Ala Ala Leu
            565             570             575

Gln Ile Pro Phe Ala Met Gln Met Ala Tyr Arg Phe Asn Gly Ile Gly
            580             585             590

Val Thr Gln Asn Val Leu Tyr Glu Asn Gln Lys Leu Ile Ala Asn Gln
            595             600             605

Phe Asn Ser Ala Ile Gly Lys Ile Gln Asp Ser Leu Ser Ser Thr Ala
            610             615             620

Ser Ala Leu Gly Lys Leu Gln Asp Val Val Asn Gln Asn Ala Gln Ala
625             630             635             640

Leu Asn Thr Leu Val Lys Gln Leu Ser Ser Asn Phe Gly Ala Ile Ser
            645             650             655

Ser Val Leu Asn Asp Ile Leu Ser Arg Leu Asp Lys Val Glu Ala Glu
            660             665             670

Val Gln Ile Asp Arg Leu Ile Thr Gly Arg Leu Gln Ser Leu Gln Thr
            675             680             685

Tyr Val Thr Gln Gln Leu Ile Arg Ala Ala Glu Ile Arg Ala Ser Ala
            690             695             700

Asn Leu Ala Ala Thr Lys Met Ser Glu Cys Val Leu Gly Gln Ser Lys
705             710             715             720
```

Arg Val Asp Phe Cys Gly Lys Gly Tyr His Leu Met Ser Phe Pro Gln
                725             730             735

Ser Ala Pro His Gly Val Val Phe Leu His Val Thr Tyr Val Pro Ala
            740             745             750

Gln Glu Lys Asn Phe Thr Thr Ala Pro Ala Ile Cys His Asp Gly Lys
            755             760             765

Ala His Phe Pro Arg Glu Gly Val Phe Val Ser Asn Gly Thr His Trp
    770             775             780

Phe Val Thr Gln Arg Asn Phe Tyr Glu Pro Gln Ile Ile Thr Thr Asp
785             790             795             800

Asn Thr Phe Val Ser Gly Asn Cys Asp Val Val Ile Gly Ile Val Asn
            805             810             815

Asn Thr Val Tyr Asp Pro Leu Gln Pro Glu Leu Asp Ser Phe Lys Glu
            820             825             830

Glu Leu Asp Lys Tyr Phe Lys Asn His Thr Ser Pro Asp Val Asp Leu
            835             840             845

Gly Asp Ile Ser Gly Ile Asn Ala Ser Val Val Asn Ile Gln Lys Glu
    850             855             860

Ile Asp Arg Leu Asn Glu Val Ala Lys Asn Leu Asn Glu Ser Leu Ile
865             870             875             880

Asp Leu Gln Glu Leu Gly Lys Tyr Glu Gln Tyr Ile Lys Trp Pro Trp
            885             890             895

Tyr Ile Trp Leu Gly Phe Ile Ala Gly Leu Ile Ala Ile Val Met Val
            900             905             910

Thr Ile Met Leu Cys Cys Met Thr Ser Cys Cys Ser Cys Leu Lys Gly
            915             920             925

Cys Cys Ser Cys Gly Ser Cys Cys Lys Phe Asp Glu Asp Asp Ser Glu
    930             935             940

Pro Val Leu Lys Gly Val Lys Leu His Tyr Thr His His His His His
945             950             955             960

<210> SEQ ID NO 50
<211> LENGTH: 2883
<212> TYPE: DNA
<213> ORGANISM: Artificial Sequence
<220> FEATURE:
<223> OTHER INFORMATION: RECOMBINANT SPIKE PROTEIN

<400> SEQUENCE: 50
atgttcgtct tcctggtgct gctgcccctg gtgtccagca tcactaacct gtgcccttc        60 ggagaggtct tcaacgccac ccgcttcgct tccgtgtacg cctggaacag gaagagaatc       120
tcaaactgcg tcgctgacta ctccgtgctg tacaactcag cctccttcag caccttcaag       180
tgctacggcg tgtcaccaac taagctgaac gacctgtgct tcaccaacgt ctacgccgac       240
tccttcgtga tcaggggaga cgaggtcaga cagatcgctc ctggccagac tggaaagatc       300
gccgactaca actacaagct gcccgacgac ttcaccggtt cgtcatcgc ttggaacagc        360 aacaacctgg actctaaagt gggtggcaac tacaactacc tgtaccgcct gttccgtaag       420
tcaaacctga gccattcga gaggacatc agcactgaaa tctaccaggc cggatctacc        480
ccttgcaacg gtgtcgaggg cttcaactgc tacttccccc tgcagtccta cggtttccag       540
ccaactaacg gtgtgggcta ccagccttac agagtggtcg tgctgagctt cgaactgctc       600
cacgctcctg ctactgtgtg cggtccaaag aagtctacca acctggtcaa gaacaagtgc       660
gtgaacttca acttcaacgg cctgaccgga actggtgtcc tgaccgagag caacaagaag       720

```
ttcctgccct tccagcagtt cggaagggac atcgctgaca ccactgacgc tgtgcgcgac        780
cctcagaccc tggaaatcct ggacatcact ccatgctcat tcggaggtgt ctccgtgatc        840
acccctggca ccaacacttc taaccaggtc gctgtgctgt accaggacgt caactgcacc        900
gaggtccctg tggccatcca cgctgaccag ctgaccccca cttggcgcgt gtactccacc        960
ggcagcaacg tgttccagac tcgtgctggt tgcctgatcg gcgccgagca cgtgaacaac       1020
agctacgaat gcgacatccc catcggcgct ggaatctgcg cctcttacca gacccagact       1080
aacagcccac gcagggctcg ctctgtggcc tctcagtcaa tcatcgctta caccatgtca       1140
ctgggcgctg aaaactccgt ggcctactct aacaactcaa tcgccatccc caccaacttc       1200
actatcagcg tgaccactga gatcctgcca gtcagcatga ccaagacttc tgtggactgc       1260
actatgtaca tctgcggaga cagcaccgaa tgctctaacc tgctgctgca gtacggctct       1320
ttctgcaccc agctgaaccg tgctctgact ggaatcgccg tggagcagga caagaacact       1380
caggaagtct tcgctcaggt gaagcaaatc tacaagaccc cacctatcaa ggacttcggc       1440
ggattcaact tctcccagat cctgcctgac ccctccaagc caagcaagcg ctctttcatc       1500
gaggacctgc tgttcaacaa ggtcactctg gccgacgctg gattcatcaa gcagtacgga       1560
gactgcctgg gtgacatcgc cgctcgtgac ctgatctgcg ctcagaagtt caacggtctg       1620
accgtgctgc ccccactgct gactgacgaa atgatcgccc agtacactag cgccctgctg       1680
gctggaacca tcacttctgg ttggaccttc ggtgctggcg ccgctctgca gatccctttc       1740
gctatgcaga tggcctaccg tttcaacgga atcggtgtca cccagaacgt gctgtacgag       1800
aaccagaagc tgatcgctaa ccagttcaac tcagccatcg gaaagatcca ggacagcctg       1860
agctctactg cctctgctct gggcaagctg caggacgtcg tgaaccagaa cgcccaggct       1920
ctgaacaccc tggtcaagca gctgtcatcc aacttcggtg ctatcagctc tgtgctgaac       1980
gacatcctgt cccgcctgga caaggtcgag gccgaagtgc agatcgaccg cctgatcact       2040
ggccgtctgc agtcactgca gacctacgtg actcagcagc tgatcagggc cgctgaaatc       2100
agagcctccg ctaacctggc cgctaccaag atgagcgagt gcgtcctggg tcaatctaag       2160
cgtgtggact ctgcggcaa gggataccac ctgatgtcat tccctcagtc tgctccccac        2220
ggtgtggtgt tcctgcacgt cacctacgtg ccagcccagg agaagaactt caccactgcc       2280
cctgctatct gccacgacgg caaggctcac ttccccaggg aaggtgtctt cgtgagcaac       2340
ggcacccact ggttcgtcac tcagagaaac ttctacgagc cacagatcat caccactgac       2400 aacacttctcg tgtctggaaa ctgcgacgtg gtcatcggta tcgtcaacaa caccgtgtac       2460 gacccccctgc agccagagct ggactcattc aaggaggaac tggacaagta cttcaagaac       2520
cacacctccc ctgacgtcga cctgggcgac atctcaggaa tcaacgcttc cgtcgtgaac       2580
atccagaagg agatcgaccg cctgaacgaa gtggccaaga acctgaacga aagcctgatc       2640
gacctgcagg agctgggcaa gtacgaacag tacatcaagt ggccttggta catctggctg       2700
ggtttcatcg ctggcctcat cgctatcgtg atggtgacca tcatgctgtg ctgcatgact       2760
tcatgctgct cctgcctgaa gggctgctgc agctgcggat cttgctgcaa gttcgacgag       2820
gacgactctg aacccgtcct gaagggcgtg aagctgcact acacccacca ccaccaccac       2880
cac                                                                       2883
```

<210> SEQ ID NO 51
<211> LENGTH: 947
<212> TYPE: PRT
<213> ORGANISM: Artificial Sequence

```
<220> FEATURE:
<223> OTHER INFORMATION: RECOMBINANT SPIKE PROTEIN

<400> SEQUENCE: 51

Ile Thr Asn Leu Cys Pro Phe Gly Glu Val Phe Asn Ala Thr Arg Phe
1               5                   10                  15

Ala Ser Val Tyr Ala Trp Asn Arg Lys Arg Ile Ser Asn Cys Val Ala
            20                  25                  30

Asp Tyr Ser Val Leu Tyr Asn Ser Ala Ser Phe Ser Thr Phe Lys Cys
        35                  40                  45

Tyr Gly Val Ser Pro Thr Lys Leu Asn Asp Leu Cys Phe Thr Asn Val
    50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
            195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
            245                 250                 255

Thr Pro Cys Ser Phe Gly Gly Val Ser Val Ile Thr Pro Gly Thr Asn
            260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
    290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
            325                 330                 335

Ala Gly Ile Cys Ala Ser Tyr Gln Thr Gln Thr Asn Ser Pro Arg Arg
            340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
    370                 375                 380

Thr Asn Phe Thr Ile Ser Val Thr Thr Glu Ile Leu Pro Val Ser Met
385                 390                 395                 400
```

-continued

```
Thr Lys Thr Ser Val Asp Cys Thr Met Tyr Ile Cys Gly Asp Ser Thr
            405                 410                 415

Glu Cys Ser Asn Leu Leu Leu Gln Tyr Gly Ser Phe Cys Thr Gln Leu
            420                 425                 430

Asn Arg Ala Leu Thr Gly Ile Ala Val Glu Gln Asp Lys Asn Thr Gln
            435                 440                 445

Glu Val Phe Ala Gln Val Lys Gln Ile Tyr Lys Thr Pro Pro Ile Lys
            450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
            500                 505                 510

Ile Ala Ala Arg Asp Leu Ile Cys Ala Gln Lys Phe Asn Gly Leu Thr
            515                 520                 525

Val Leu Pro Pro Leu Leu Thr Asp Glu Met Ile Ala Gln Tyr Thr Ser
        530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
            580                 585                 590

Ala Asn Gln Phe Asn Ser Ala Ile Gly Lys Ile Gln Asp Ser Leu Ser
            595                 600                 605

Ser Thr Ala Ser Ala Leu Gly Lys Leu Gln Asp Val Val Asn Gln Asn
        610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
            660                 665                 670

Leu Gln Thr Tyr Val Thr Gln Gln Leu Ile Arg Ala Ala Glu Ile Arg
            675                 680                 685

Ala Ser Ala Asn Leu Ala Ala Thr Lys Met Ser Glu Cys Val Leu Gly
        690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
            740                 745                 750

Asp Gly Lys Ala His Phe Pro Arg Glu Gly Val Phe Val Ser Asn Gly
            755                 760                 765

Thr His Trp Phe Val Thr Gln Arg Asn Phe Tyr Glu Pro Gln Ile Ile
        770                 775                 780

Thr Thr Asp Asn Thr Phe Val Ser Gly Asn Cys Asp Val Val Ile Gly
785                 790                 795                 800

Ile Val Asn Asn Thr Val Tyr Asp Pro Leu Gln Pro Glu Leu Asp Ser
                805                 810                 815
```

-continued

```
Phe Lys Glu Glu Leu Asp Lys Tyr Phe Lys Asn His Thr Ser Pro Asp
            820             825             830

Val Asp Leu Gly Asp Ile Ser Gly Ile Asn Ala Ser Val Val Asn Ile
            835             840             845

Gln Lys Glu Ile Asp Arg Leu Asn Glu Val Ala Lys Asn Leu Asn Glu
    850             855             860

Ser Leu Ile Asp Leu Gln Glu Leu Gly Lys Tyr Glu Gln Tyr Ile Lys
865             870             875             880

Trp Pro Trp Tyr Ile Trp Leu Gly Phe Ile Ala Gly Leu Ile Ala Ile
                885             890             895

Val Met Val Thr Ile Met Leu Cys Cys Met Thr Ser Cys Cys Ser Cys
            900             905             910

Leu Lys Gly Cys Cys Ser Cys Gly Ser Cys Cys Lys Phe Asp Glu Asp
            915             920             925

Asp Ser Glu Pro Val Leu Lys Gly Val Lys Leu His Tyr Thr His His
    930             935             940

His His His
945

<210> SEQ ID NO 52
<211> LENGTH: 901
<212> TYPE: PRT
<213> ORGANISM: Artificial Sequence
<220> FEATURE:
<223> OTHER INFORMATION: RECOMBINANT SPIKE PROTEIN

<400> SEQUENCE: 52

Met Phe Val Phe Leu Val Leu Leu Pro Leu Val Ser Ser Ile Thr Asn
1               5               10              15

Leu Cys Pro Phe Gly Glu Val Phe Asn Ala Thr Arg Phe Ala Ser Val
            20              25              30

Tyr Ala Trp Asn Arg Lys Arg Ile Ser Asn Cys Val Ala Asp Tyr Ser
            35              40              45

Val Leu Tyr Asn Ser Ala Ser Phe Ser Thr Phe Lys Cys Tyr Gly Val
    50              55              60

Ser Pro Thr Lys Leu Asn Asp Leu Cys Phe Thr Asn Val Tyr Ala Asp
65              70              75              80

Ser Phe Val Ile Arg Gly Asp Glu Val Arg Gln Ile Ala Pro Gly Gln
            85              90              95

Thr Gly Lys Ile Ala Asp Tyr Asn Tyr Lys Leu Pro Asp Asp Phe Thr
            100             105             110

Gly Cys Val Ile Ala Trp Asn Ser Asn Asn Leu Asp Ser Lys Val Gly
            115             120             125

Gly Asn Tyr Asn Tyr Leu Tyr Arg Leu Phe Arg Lys Ser Asn Leu Lys
    130             135             140

Pro Phe Glu Arg Asp Ile Ser Thr Glu Ile Tyr Gln Ala Gly Ser Thr
145             150             155             160

Pro Cys Asn Gly Val Glu Gly Phe Asn Cys Tyr Phe Pro Leu Gln Ser
                165             170             175

Tyr Gly Phe Gln Pro Thr Asn Gly Val Gly Tyr Gln Pro Tyr Arg Val
            180             185             190

Val Val Leu Ser Phe Glu Leu Leu His Ala Pro Ala Thr Val Cys Gly
            195             200             205

Pro Lys Lys Ser Thr Asn Leu Val Lys Asn Lys Cys Val Asn Phe Asn
    210             215             220
```

```
Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
                260                 265                 270

Ser Phe Gly Gly Val Ser Val Ile Thr Pro Gly Thr Asn Thr Ser Asn
                275                 280                 285

Gln Val Ala Val Leu Tyr Gln Asp Val Asn Cys Thr Glu Val Pro Val
        290                 295                 300

Ala Ile His Ala Asp Gln Leu Thr Pro Thr Trp Arg Val Tyr Ser Thr
305                 310                 315                 320

Gly Ser Asn Val Phe Gln Thr Arg Ala Gly Cys Leu Ile Gly Ala Glu
                325                 330                 335

His Val Asn Asn Ser Tyr Glu Cys Asp Ile Pro Ile Gly Ala Gly Ile
                340                 345                 350

Cys Ala Ser Tyr Gln Thr Gln Thr Asn Ser Pro Arg Arg Ala Arg Ser
        355                 360                 365

Val Ala Ser Gln Ser Ile Ile Ala Tyr Thr Met Ser Leu Gly Ala Glu
        370                 375                 380

Asn Ser Val Ala Tyr Ser Asn Asn Ser Ile Ala Ile Pro Thr Asn Phe
385                 390                 395                 400

Thr Ile Ser Val Thr Thr Glu Ile Leu Pro Val Ser Met Thr Lys Thr
                405                 410                 415

Ser Val Asp Cys Thr Met Tyr Ile Cys Gly Asp Ser Thr Glu Cys Ser
                420                 425                 430

Asn Leu Leu Leu Gln Tyr Gly Ser Phe Cys Thr Gln Leu Asn Arg Ala
        435                 440                 445

Leu Thr Gly Ile Ala Val Glu Gln Asp Lys Asn Thr Gln Glu Val Phe
        450                 455                 460

Ala Gln Val Lys Gln Ile Tyr Lys Thr Pro Pro Ile Lys Asp Phe Gly
465                 470                 475                 480

Gly Phe Asn Phe Ser Gln Ile Leu Pro Asp Pro Ser Lys Pro Ser Lys
                485                 490                 495

Arg Ser Phe Ile Glu Asp Leu Leu Phe Asn Lys Val Thr Leu Ala Asp
                500                 505                 510

Ala Gly Phe Ile Lys Gln Tyr Gly Asp Cys Leu Gly Asp Ile Ala Ala
        515                 520                 525

Arg Asp Leu Ile Cys Ala Gln Lys Phe Asn Gly Leu Thr Val Leu Pro
        530                 535                 540

Pro Leu Leu Thr Asp Glu Met Ile Ala Gln Tyr Thr Ser Ala Leu Leu
545                 550                 555                 560

Ala Gly Thr Ile Thr Ser Gly Trp Thr Phe Gly Ala Gly Ala Ala Leu
                565                 570                 575

Gln Ile Pro Phe Ala Met Gln Met Ala Tyr Arg Phe Asn Gly Ile Gly
                580                 585                 590

Val Thr Gln Asn Val Leu Tyr Glu Asn Gln Lys Leu Ile Ala Asn Gln
        595                 600                 605

Phe Asn Ser Ala Ile Gly Lys Ile Gln Asp Ser Leu Ser Ser Thr Ala
        610                 615                 620

Ser Ala Leu Gly Lys Leu Gln Asp Val Val Asn Gln Asn Ala Gln Ala
625                 630                 635                 640

Leu Asn Thr Leu Val Lys Gln Leu Ser Ser Asn Phe Gly Ala Ile Ser
```

-continued

```
                645               650               655
Ser Val Leu Asn Asp Ile Leu Ser Arg Leu Asp Lys Val Glu Ala Glu
                660               665               670

Val Gln Ile Asp Arg Leu Ile Thr Gly Arg Leu Gln Ser Leu Gln Thr
                675               680               685

Tyr Val Thr Gln Gln Leu Ile Arg Ala Ala Glu Ile Arg Ala Ser Ala
            690               695               700

Asn Leu Ala Ala Thr Lys Met Ser Glu Cys Val Leu Gly Gln Ser Lys
705               710               715               720

Arg Val Asp Phe Cys Gly Lys Gly Tyr His Leu Met Ser Phe Pro Gln
                725               730               735

Ser Ala Pro His Gly Val Val Phe Leu His Val Thr Tyr Val Pro Ala
                740               745               750

Gln Glu Lys Asn Phe Thr Thr Ala Pro Ala Ile Cys His Asp Gly Lys
            755               760               765

Ala His Phe Pro Arg Glu Gly Val Phe Val Ser Asn Gly Thr His Trp
            770               775               780

Phe Val Thr Gln Arg Asn Phe Tyr Glu Pro Gln Ile Ile Thr Thr Asp
785               790               795               800

Asn Thr Phe Val Ser Gly Asn Cys Asp Val Val Ile Gly Ile Val Asn
                805               810               815

Asn Thr Val Tyr Asp Pro Leu Gln Pro Glu Leu Asp Ser Phe Lys Glu
                820               825               830

Glu Leu Asp Lys Tyr Phe Lys Asn His Thr Ser Pro Asp Val Asp Leu
            835               840               845

Gly Asp Ile Ser Gly Ile Asn Ala Ser Val Val Asn Ile Gln Lys Glu
            850               855               860

Ile Asp Arg Leu Asn Glu Val Ala Lys Asn Leu Asn Glu Ser Leu Ile
865               870               875               880

Asp Leu Gln Glu Leu Gly Lys Tyr Glu Gln Tyr Ile Lys Trp Pro His
                885               890               895

His His His His His
                900
```

```
<210> SEQ ID NO 53
<211> LENGTH: 2706
<212> TYPE: DNA
<213> ORGANISM: Artificial Sequence
<220> FEATURE:
<223> OTHER INFORMATION: RECOMBINANT SPIKE PROTEIN

<400> SEQUENCE: 53
atgttcgtct tcctggtgct gctgcccctg gtgtccagca tcactaacct gtgcccttc      60 ggagaggtct tcaacgccac ccgcttcgct tccgtgtacg cctggaacag gaagagaatc      120
tcaaactgcg tcgctgacta ctccgtgctg tacaactcag cctccttcag caccttcaag      180
tgctacggcg tgtcaccaac taagctgaac gacctgtgct tcaccaacgt ctacgccgac      240
tccttcgtga tcaggggaga cgaggtcaga cagatcgctc ctggccagac tggaaagatc      300
gccgactaca actacaagct gcccgacgac ttcaccggtt cgtcatcgc ttggaacagc      360 aacaacctgg actctaaagt gggtggcaac tacaactacc tgtaccgcct gttccgtaag      420
tcaaacctga gccattcga gaggacatc agcactgaaa tctaccaggc cggatctacc      480
ccttgcaacg tgtcgaggg cttcaactgc tacttcccc tgcagtccta cggtttccag      540
ccaactaacg gtgtgggcta ccagccttac agagtggtcg tgctgagctt cgaactgctc      600
```

-continued

```
cacgctcctg ctactgtgtg cggtccaaag aagtctacca acctggtcaa gaacaagtgc    660
gtgaacttca acttcaacgg cctgaccgga actggtgtcc tgaccgagag caacaagaag    720
ttcctgccct tccagcagtt cggaagggac atcgctgaca ccactgacgc tgtgcgcgac    780
cctcagaccc tggaaatcct ggacatcact ccatgctcat tcggaggtgt ctccgtgatc    840 accccctggca ccaacacttc taaccaggtc gctgtgctgt accaggacgt caactgcacc    900
gaggtccctg tggccatcca cgctgaccag ctgacccca cttggcgcgt gtactccacc    960
ggcagcaacg tgttccagac tcgtgctggt tgcctgatcg cgcgccagca cgtgaacaac    1020
agctacgaat gcgacatccc catcggcgct ggaatctgcg cctcttacca gacccagact    1080
aacagcccac gcagggctcg ctctgtggcc tctcagtcaa tcatcgctta caccatgtca    1140
ctgggcgctg aaaactccgt ggcctactct aacaactcaa tcgccatccc caccaacttc    1200
actatcagcg tgaccactga tcctgcca gtcagcatga ccaagacttc tgtggactgc    1260
actatgtaca tctgcggaga cagcaccgaa tgctctaacc tgctgctgca gtacggctct    1320
ttctgcaccc agctgaaccg tgctctgact ggaatcgccg tggagcagga caagaacact    1380
caggaagtct tcgctcaggt gaagcaaatc tacaagaccc cacctatcaa ggacttcggc    1440
ggattcaact tctcccagat cctgcctgac ccctccaagc caagcaagcg ctctttcatc    1500
gaggacctgc tgttcaacaa ggtcactctg gccgacgctg gattcatcaa gcagtacgga    1560
gactgcctgg gtgacatcgc cgctcgtgac ctgatctgcg ctcagaagtt caacggtctg    1620
accgtgctgc ccccactgct gactgacgaa atgatcgccc agtacactag cgccctgctg    1680
gctggaacca tcacttctgg ttggaccttc ggtgctggcg ccgctctgca gatcccttc    1740 gctatgcaga tggcctaccg tttcaacgga atcggtgtca cccagaacgt gctgtacgag    1800
aaccagaagc tgatcgctaa ccagttcaac tcagccatcg aaagatcca ggacagcctg    1860 agctctactg cctctgctct gggcaagctg caggacgtcg tgaaccagaa cgcccaggct    1920
ctgaacaccc tggtcaagca gctgtcatcc aacttcggtg ctatcagctc tgtgctgaac    1980
gacatcctgt cccgcctgga caaggtcgag gccgaagtgc agatcgaccg cctgatcact    2040
ggccgtctgc agtcactgca gacctacgtg actcagcagc tgatcaggc cgctgaaatc    2100 agagcctccg ctaacctggc cgctaccaag atgagcgagt gcgtcctggg tcaatctaag    2160
cgtgtggact tctgcggcaa gggataccac ctgatgtcat tccctcagtc tgctccccac    2220
ggtgtggtgt tcctgcacgt cacctacgtg ccagcccagg agaagaactt caccactgcc    2280
cctgctatct gccacgacgg caaggctcac ttccccaggg aaggtgtctt cgtgagcaac    2340
ggcacccact ggttcgtcac tcagagaaac ttctacgagc cacagatcat caccactgac    2400
aacactttcg tgtctggaaa ctgcgacgtg gtcatcggta tcgtcaacaa caccgtgtac    2460
gaccccctgc agccagagct ggactcattc aaggaggaac tggacaagta cttcaagaac    2520
cacacctccc ctgacgtcga cctgggcgac atctcaggaa tcaacgcttc cgtcgtgaac    2580
atccagaagg agatcgaccg cctgaacgaa gtggccaaga acctgaacga aagcctgatc    2640
gacctgcagg agctgggcaa gtacgaacag tacatcaagt ggcctcacca ccaccaccac    2700
caccac                                                              2706
```

<210> SEQ ID NO 54
<211> LENGTH: 888
<212> TYPE: PRT
<213> ORGANISM: Artificial Sequence
<220> FEATURE:

<223> OTHER INFORMATION: RECOMBINANT SPIKE PROTEIN

<400> SEQUENCE: 54

```
Ile Thr Asn Leu Cys Pro Phe Gly Glu Val Phe Asn Ala Thr Arg Phe
1                   5                   10                  15

Ala Ser Val Tyr Ala Trp Asn Arg Lys Arg Ile Ser Asn Cys Val Ala
                20                  25                  30

Asp Tyr Ser Val Leu Tyr Asn Ser Ala Ser Phe Ser Thr Phe Lys Cys
            35                  40                  45

Tyr Gly Val Ser Pro Thr Lys Leu Asn Asp Leu Cys Phe Thr Asn Val
        50                  55                  60

Tyr Ala Asp Ser Phe Val Ile Arg Gly Asp Glu Val Arg Gln Ile Ala
65                  70                  75                  80

Pro Gly Gln Thr Gly Lys Ile Ala Asp Tyr Asn Tyr Lys Leu Pro Asp
                85                  90                  95

Asp Phe Thr Gly Cys Val Ile Ala Trp Asn Ser Asn Asn Leu Asp Ser
            100                 105                 110

Lys Val Gly Gly Asn Tyr Asn Tyr Leu Tyr Arg Leu Phe Arg Lys Ser
        115                 120                 125

Asn Leu Lys Pro Phe Glu Arg Asp Ile Ser Thr Glu Ile Tyr Gln Ala
    130                 135                 140

Gly Ser Thr Pro Cys Asn Gly Val Glu Gly Phe Asn Cys Tyr Phe Pro
145                 150                 155                 160

Leu Gln Ser Tyr Gly Phe Gln Pro Thr Asn Gly Val Gly Tyr Gln Pro
                165                 170                 175

Tyr Arg Val Val Val Leu Ser Phe Glu Leu Leu His Ala Pro Ala Thr
            180                 185                 190

Val Cys Gly Pro Lys Lys Ser Thr Asn Leu Val Lys Asn Lys Cys Val
        195                 200                 205

Asn Phe Asn Phe Asn Gly Leu Thr Gly Thr Gly Val Leu Thr Glu Ser
    210                 215                 220

Asn Lys Lys Phe Leu Pro Phe Gln Gln Phe Gly Arg Asp Ile Ala Asp
225                 230                 235                 240

Thr Thr Asp Ala Val Arg Asp Pro Gln Thr Leu Glu Ile Leu Asp Ile
            245                 250                 255

Thr Pro Cys Ser Phe Gly Gly Val Ser Val Ile Thr Pro Gly Thr Asn
            260                 265                 270

Thr Ser Asn Gln Val Ala Val Leu Tyr Gln Asp Val Asn Cys Thr Glu
        275                 280                 285

Val Pro Val Ala Ile His Ala Asp Gln Leu Thr Pro Thr Trp Arg Val
    290                 295                 300

Tyr Ser Thr Gly Ser Asn Val Phe Gln Thr Arg Ala Gly Cys Leu Ile
305                 310                 315                 320

Gly Ala Glu His Val Asn Asn Ser Tyr Glu Cys Asp Ile Pro Ile Gly
            325                 330                 335

Ala Gly Ile Cys Ala Ser Tyr Gln Thr Gln Thr Asn Ser Pro Arg Arg
        340                 345                 350

Ala Arg Ser Val Ala Ser Gln Ser Ile Ile Ala Tyr Thr Met Ser Leu
        355                 360                 365

Gly Ala Glu Asn Ser Val Ala Tyr Ser Asn Asn Ser Ile Ala Ile Pro
    370                 375                 380

Thr Asn Phe Thr Ile Ser Val Thr Thr Glu Ile Leu Pro Val Ser Met
385                 390                 395                 400
```

```
Thr Lys Thr Ser Val Asp Cys Thr Met Tyr Ile Cys Gly Asp Ser Thr
            405                 410                 415

Glu Cys Ser Asn Leu Leu Leu Gln Tyr Gly Ser Phe Cys Thr Gln Leu
            420                 425                 430

Asn Arg Ala Leu Thr Gly Ile Ala Val Glu Gln Asp Lys Asn Thr Gln
            435                 440                 445

Glu Val Phe Ala Gln Val Lys Gln Ile Tyr Lys Thr Pro Pro Ile Lys
        450                 455                 460

Asp Phe Gly Gly Phe Asn Phe Ser Gln Ile Leu Pro Asp Pro Ser Lys
465                 470                 475                 480

Pro Ser Lys Arg Ser Phe Ile Glu Asp Leu Leu Phe Asn Lys Val Thr
                485                 490                 495

Leu Ala Asp Ala Gly Phe Ile Lys Gln Tyr Gly Asp Cys Leu Gly Asp
            500                 505                 510

Ile Ala Ala Arg Asp Leu Ile Cys Ala Gln Lys Phe Asn Gly Leu Thr
            515                 520                 525

Val Leu Pro Pro Leu Leu Thr Asp Glu Met Ile Ala Gln Tyr Thr Ser
        530                 535                 540

Ala Leu Leu Ala Gly Thr Ile Thr Ser Gly Trp Thr Phe Gly Ala Gly
545                 550                 555                 560

Ala Ala Leu Gln Ile Pro Phe Ala Met Gln Met Ala Tyr Arg Phe Asn
                565                 570                 575

Gly Ile Gly Val Thr Gln Asn Val Leu Tyr Glu Asn Gln Lys Leu Ile
            580                 585                 590

Ala Asn Gln Phe Asn Ser Ala Ile Gly Lys Ile Gln Asp Ser Leu Ser
            595                 600                 605

Ser Thr Ala Ser Ala Leu Gly Lys Leu Gln Asp Val Val Asn Gln Asn
        610                 615                 620

Ala Gln Ala Leu Asn Thr Leu Val Lys Gln Leu Ser Ser Asn Phe Gly
625                 630                 635                 640

Ala Ile Ser Ser Val Leu Asn Asp Ile Leu Ser Arg Leu Asp Lys Val
                645                 650                 655

Glu Ala Glu Val Gln Ile Asp Arg Leu Ile Thr Gly Arg Leu Gln Ser
            660                 665                 670

Leu Gln Thr Tyr Val Thr Gln Gln Leu Ile Arg Ala Ala Glu Ile Arg
            675                 680                 685

Ala Ser Ala Asn Leu Ala Ala Thr Lys Met Ser Glu Cys Val Leu Gly
        690                 695                 700

Gln Ser Lys Arg Val Asp Phe Cys Gly Lys Gly Tyr His Leu Met Ser
705                 710                 715                 720

Phe Pro Gln Ser Ala Pro His Gly Val Val Phe Leu His Val Thr Tyr
                725                 730                 735

Val Pro Ala Gln Glu Lys Asn Phe Thr Thr Ala Pro Ala Ile Cys His
            740                 745                 750

Asp Gly Lys Ala His Phe Pro Arg Glu Gly Val Phe Val Ser Asn Gly
            755                 760                 765

Thr His Trp Phe Val Thr Gln Arg Asn Phe Tyr Glu Pro Gln Ile Ile
        770                 775                 780

Thr Thr Asp Asn Thr Phe Val Ser Gly Asn Cys Asp Val Val Ile Gly
785                 790                 795                 800

Ile Val Asn Asn Thr Val Tyr Asp Pro Leu Gln Pro Glu Leu Asp Ser
                805                 810                 815

Phe Lys Glu Glu Leu Asp Lys Tyr Phe Lys Asn His Thr Ser Pro Asp
```

-continued

```
               820              825              830
Val Asp Leu Gly Asp Ile Ser Gly Ile Asn Ala Ser Val Val Asn Ile
        835              840              845

Gln Lys Glu Ile Asp Arg Leu Asn Glu Val Ala Lys Asn Leu Asn Glu
    850              855              860

Ser Leu Ile Asp Leu Gln Glu Leu Gly Lys Tyr Glu Gln Tyr Ile Lys
865              870              875              880

Trp Pro His His His His His His
            885

<210> SEQ ID NO 55
<211> LENGTH: 3819
<212> TYPE: DNA
<213> ORGANISM: Artificial Sequence
<220> FEATURE:
<223> OTHER INFORMATION: RECOMBINANT SPIKE PROTEIN

<400> SEQUENCE: 55
atgttcgtct tcctggtgct gctgcccctg gtgtccagcc agtgcgtgaa cctgaccact      60
aggactcagc tgcctcccgc ttacaccaac tcattcactc gcggtgtgta ctaccctgac     120
aaggtcttcc gttcttcagt gctgcactca actcaggacc tgttcctgcc cttcttctcc     180
aacgtcacct ggttccacgc catccacgtg tccggcacca acggcactaa gcgcttcgac     240
aacccagtgc tgcctttcaa cgacggtgtc tacttcgctt caaccgagaa gtccaacatc     300
atccgtggat ggatcttcgg caccactctg gacagcaaga ctcagtctct gctgatcgtc     360
aacaacgcca ccaacgtggt catcaaggtc tgcgaattcc agttctgcaa cgacccattc     420
ctgggcgtct actaccacaa gaacaacaag tcatggatgg agtccgaatt ccgcgtctac     480
tccagcgcta caactgcac tttcgagtac gtgtcccagc ctttcctgat ggacctggaa     540
ggaaagcagg gtaacttcaa gaacctgagg gagttcgtgt tcaagaacat cgacggatac     600
ttcaagattt acagcaagca caccccaatc aacctggtgc gcgacctgcc tcagggtttc     660
tctgctctgg agccactggt ggacctgcct atcggcatca acatcacccg cttccagact     720
ctgctggctc tgcaccgttc ctacctgact ccaggcgact atctctctgg atggactgct     780
ggagctgctg cttactacgt gggctacctg cagcctcgca ccttcctgct gaagtacaac     840
gaaaacggaa ccatcactga cgccgtcgac tgcgctctgg accctctgtc agaaaccaag     900
tgcactctga gtccttcac cgtggagaag ggcatctacc agacttcaaa cttcagggtg     960
cagcccaccg aatccatcgt cagattccct aacatcacta acctgtgccc cttcggagag    1020
gtcttcaacg ccacccgctt cgcttccgtg tacgcctgga acaggaagag aatctcaaac    1080
tgcgtcgctg actactccgt gctgtacaac tcagcctcct tcagcacctt caagtgctac    1140
ggcgtgtcac caactaagct gaacgacctg tgcttcacca cgtctacgc cgactccttc    1200 gtgatcaggg gagacgaggt cagacagatc gctcctggcc agactggaaa gatcgccgac    1260
tacaactaca agctgcccga cgacttcacc ggttgcgtca tcgcttggaa cagcaacaac    1320
ctggactcta aagtgggtgg caactacaac tacctgtacc gcctgttccg taagtcaaac    1380
ctgaagccat tcgagaggga catcagcact gaaatctacc aggccggatc tacccccttgc    1440 aacggtgtcg agggcttcaa ctgctacttc cccctgcagt cctacggttt ccagccaact    1500
aacggtgtgg ctaccagcc ttacagagtg tcgtgctga gcttcgaact gctccacgct    1560
cctgctactg tgtgcggtcc aaagaagtct accaacctgg tcaagaacaa gtgcgtgaac    1620
ttcaacttca cggcctgac cggaactggt gtcctgaccg agagcaacaa gaagttcctg    1680
```

-continued

```
cccttccagc agttcggaag ggacatcgct gacaccactg acgctgtgcg cgaccctcag      1740
accctggaaa tcctggacat cactccatgc tcattcggag gtgtctccgt gatcacccct      1800
ggcaccaaca cttctaacca ggtcgctgtg ctgtaccagg acgtcaactg caccgaggtc      1860
cctgtggcca tccacgctga ccagctgacc cccacttggc gcgtgtactc caccggcagc      1920
aacgtgttcc agactcgtgc tggttgcctg atcggcgccg agcacgtgaa caacagctac      1980
gaatgcgaca tccccatcgg cgctggaatc tgcgcctctt accagaccca gactaacagc      2040
ccacagcagg ctcagtctgt ggcctctcag tcaatcatcg cttacaccat gtcactgggc      2100
gctgaaaact ccgtggccta ctctaacaac tcaatcgcca tccccaccaa cttcactatc      2160
agcgtgacca ctgagatcct gccagtcagc atgaccaaga cttctgtgga ctgcactatg      2220
tacatctgcg gagacagcac cgaatgctct aacctgctgc tgcagtacgg ctctttctgc      2280
acccagctga accgtgctct gactggaatc gccgtggagc aggacaagaa cactcaggaa      2340
gtcttcgctc aggtgaagca aatctacaag accccaccta tcaaggactt cggcggattc      2400
aacttctccc agatcctgcc tgacccctcc aagccaagca agcgctcttt catcgaggac      2460
ctgctgttca acaaggtcac tctggccgac gctggattca tcaagcagta cggagactgc      2520
ctgggtgaca tcgccgctcg tgacctgatc tgcgctcaga agttcaacgg tctgaccgtg      2580
ctgcccccac tgctgactga cgaaatgatc gcccagtaca ctagcgccct gctggctgga      2640
accatcactt ctggttggac cttcggtgct ggcgccgctc tgcagatccc tttcgctatg      2700
cagatggcct accgtttcaa cggaatcggt gtcacccaga acgtgctgta cgagaaccag      2760
aagctgatcg ctaaccagtt caactcagcc atcggaaaga tccaggacag cctgagctct      2820
actgcctctg ctctgggcaa gctgcaggac gtcgtgaacc agaacgccca ggctctgaac      2880
accctggtca agcagctgtc atccaacttc ggtgctatca gctctgtgct gaacgacatc      2940
ctgtcccgcc tggacaaggt cgaggccgaa gtgcagatcg accgcctgat cactggccgt      3000
ctgcagtcac tgcagaccta cgtgactcag cagctgatca gggccgctga aatcagagcc      3060
tccgctaacc tggccgctac caagatgagc gagtgcgtcc tgggtcaatc taagcgtgtg      3120
gacttctgcg gcaagggata ccacctgatg tcattccctc agtctgctcc ccacggtgtg      3180
gtgttcctgc acgtcaccta cgtgccagcc caggagaaga acttcaccac tgccctgct      3240 atctgccacg acggcaaggc tcacttcccc agggaaggtg tcttcgtgag caacggcacc      3300
cactggttcg tcactcagag aaacttctac gagccacaga tcatcaccac tgacaacact      3360
ttcgtgtctg gaaactgcga cgtggtcatc ggtatcgtca acaacaccgt gtacgacccc      3420
ctgcagccag agctggactc attcaaggag gaactggaca gtacttcaa gaaccacacc      3480 tcccctgacg tcgacctggg cgacatctca ggaatcaacg cttccgtcgt gaacatccag      3540
aaggagatcg accgcctgaa cgaagtggcc aagaacctga acgaaagcct gatcgacctg      3600
caggagctgg gcaagtacga acagtacatc aagtggcctt ggtacatctg ctgggtttc      3660 atcgctggcc tcatcgctat cgtgatggtg accatcatgc tgtgctgcat gacttcatgc      3720
tgctcctgcc tgaagggctg ctgcagctgc ggatcttgct gcaagttcga cgaggacgac      3780
tctgaacccg tcctgaaggg cgtgaagctg cactacacc                             3819
```

<210> SEQ ID NO 56
<211> LENGTH: 1279
<212> TYPE: PRT
<213> ORGANISM: Artificial Sequence
<220> FEATURE:

<223> OTHER INFORMATION: RECOMBINANT SPIKE PROTEIN

<400> SEQUENCE: 56

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400
```

-continued

```
Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Gln Gln Ala Gln Ser Val Ala
        675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
```

-continued

```
                820                825               830
Phe Ile Lys Gln Tyr Gly Asp Cys Leu Gly Asp Ile Ala Ala Arg Asp
        835                840                845
Leu Ile Cys Ala Gln Lys Phe Asn Gly Leu Thr Val Leu Pro Pro Leu
    850                855                860
Leu Thr Asp Glu Met Ile Ala Gln Tyr Thr Ser Ala Leu Leu Ala Gly
865                870                875                880
Thr Ile Thr Ser Gly Trp Thr Phe Gly Ala Gly Ala Ala Leu Gln Ile
                885                890                895
Pro Phe Ala Met Gln Met Ala Tyr Arg Phe Asn Gly Ile Gly Val Thr
            900                905                910
Gln Asn Val Leu Tyr Glu Asn Gln Lys Leu Ile Ala Asn Gln Phe Asn
        915                920                925
Ser Ala Ile Gly Lys Ile Gln Asp Ser Leu Ser Ser Thr Ala Ser Ala
        930                935                940
Leu Gly Lys Leu Gln Asp Val Val Asn Gln Asn Ala Gln Ala Leu Asn
945                950                955                960
Thr Leu Val Lys Gln Leu Ser Ser Asn Phe Gly Ala Ile Ser Ser Val
            965                970                975
Leu Asn Asp Ile Leu Ser Arg Leu Asp Lys Val Glu Ala Glu Val Gln
            980                985                990
Ile Asp Arg Leu Ile Thr Gly Arg  Leu Gln Ser Leu Gln  Thr Tyr Val
        995                1000                1005
Thr Gln  Gln Leu Ile Arg Ala  Ala Glu Ile Arg Ala  Ser Ala Asn
    1010                1015                1020
Leu Ala  Ala Thr Lys Met Ser  Glu Cys Val Leu Gly  Gln Ser Lys
    1025                1030                1035
Arg Val  Asp Phe Cys Gly Lys  Gly Tyr His Leu Met  Ser Phe Pro
    1040                1045                1050
Gln Ser  Ala Pro His Gly Val  Val Phe Leu His Val  Thr Tyr Val
    1055                1060                1065
Pro Ala  Gln Glu Lys Asn Phe  Thr Thr Ala Pro Ala  Ile Cys His
    1070                1075                1080
Asp Gly  Lys Ala His Phe Pro  Arg Glu Gly Val Phe  Val Ser Asn
    1085                1090                1095
Gly Thr  His Trp Phe Val Thr  Gln Arg Asn Phe Tyr  Glu Pro Gln
    1100                1105                1110
Ile Ile  Thr Thr Asp Asn Thr  Phe Val Ser Gly Asn  Cys Asp Val
    1115                1120                1125
Val Ile  Gly Ile Val Asn Asn  Thr Val Tyr Asp Pro  Leu Gln Pro
    1130                1135                1140
Glu Leu  Asp Ser Phe Lys Glu  Glu Leu Asp Lys Tyr  Phe Lys Asn
    1145                1150                1155
His Thr  Ser Pro Asp Val Asp  Leu Gly Asp Ile Ser  Gly Ile Asn
    1160                1165                1170
Ala Ser  Val Val Asn Ile Gln  Lys Glu Ile Asp Arg  Leu Asn Glu
    1175                1180                1185
Val Ala  Lys Asn Leu Asn Glu  Ser Leu Ile Asp Leu  Gln Glu Leu
    1190                1195                1200
Gly Lys  Tyr Glu Gln Tyr Ile  Lys Trp Pro Trp Tyr  Ile Trp Leu
    1205                1210                1215
Gly Phe  Ile Ala Gly Leu Ile  Ala Ile Val Met Val  Thr Ile Met
    1220                1225                1230
```

-continued

```
Leu Cys  Cys Met Thr Ser Cys  Cys Ser Cys Leu Lys  Gly Cys Cys
    1235             1240              1245

Ser Cys  Gly Ser Cys Cys Lys  Phe Asp Glu Asp Asp  Ser Glu Pro
    1250             1255              1260

Val Leu  Lys Gly Val Lys Leu  His Tyr Thr His His  His His His
    1265             1270              1275

His
```

```
<210> SEQ ID NO 57
<211> LENGTH: 3837
<212> TYPE: DNA
<213> ORGANISM: Artificial Sequence
<220> FEATURE:
<223> OTHER INFORMATION: RECOMBINANT SPIKE PROTEIN

<400> SEQUENCE: 57
atgttcgtct tcctggtgct gctgcccctg gtgtccagcc agtgcgtgaa cctgaccact      60
aggactcagc tgcctcccgc ttacaccaac tcattcactc gcggtgtgta ctaccctgac     120
aaggtcttcc gttcttcagt gctgcactca actcaggacc tgttcctgcc cttcttctcc     180
aacgtcacct ggttccacgc catccacgtg tccggcacca acggcactaa gcgcttcgac     240
aacccagtgc tgcctttcaa cgacggtgtc tacttcgctt caaccgagaa gtccaacatc     300
atccgtggat ggatcttcgg caccactctg gacagcaaga ctcagtctct gctgatcgtc     360
aacaacgcca ccaacgtggt catcaaggtc tgcgaattcc agttctgcaa cgacccattc     420
ctgggcgtct actaccacaa gaacaacaag tcatggatgg agtccgaatt ccgcgtctac     480
tccagcgcta caactgcac tttcgagtac gtgtcccagc ctttcctgat ggacctggaa     540
ggaaagcagg gtaacttcaa gaacctgagg gagttcgtgt tcaagaacat cgacggatac     600
ttcaagattt acagcaagca cacccccaatc aacctggtgc gcgacctgcc tcagggtttc     660
tctgctctgg agccactggt ggacctgcct atcggcatca acatcacccg cttccagact     720
ctgctggctc tgcaccgttc ctacctgact ccaggcgact catcttctgg atggactgct     780
ggagctgctg cttactacgt gggctacctg cagcctcgca ccttcctgct gaagtacaac     840
gaaaacggaa ccatcactga cgccgtcgac tgcgctctgg accctctgtc agaaaccaag     900
tgcactctga gtccttcac cgtggagaag ggcatctacc agacttcaaa cttcagggtg     960
cagcccaccg aatccatcgt cagattccct aacatcacta acctgtgccc cttcggagag    1020
gtcttcaacg ccacccgctt cgcttccgtg tacgcctgga caggaagag aatctcaaac    1080 tgcgtcgctg actactccgt gctgtacaac tcagcctcct cagcaccttt caagtgctac    1140
ggcgtgtcac caactaagct gaacgacctg tgcttcacca cgtctacgc cgactccttc    1200 gtgatcaggg gagacgaggt cagacagatc gctcctggcc agactggaaa gatcgccgac    1260
tacaactaca gctgcccga cgacttcacc ggttgcgtca tcgcttggaa cagcaacaac    1320
ctggactcta aagtgggtgg caactacaac tacctgtacc gcctgttccg taagtcaaac    1380
ctgaagccat tcgagaggga catcagcact gaaatctacc aggccggatc tacccccttgc    1440 aacggtgtcg agggcttcaa ctgctacttc ccctgcagt cctacggttt ccagccaact    1500
aacggtgtgg gctaccagcc ttacagagtg gtcgtgctga gcttcgaact gctccacgct    1560
cctgctactg tgtgcggtcc aaagaagtct accaacctgg tcaagaacaa gtgcgtgaac    1620
ttcaacttca cggcctgac cggaactggt gtcctgaccg agagcaacaa gaagttcctg    1680
cccttccagc agttcggaag ggacatcgct gacaccactg acgctgtgcg cgaccctcag    1740
```

-continued

```
accctggaaa tcctggacat cactccatgc tcattcggag gtgtctccgt gatcacccct    1800
ggcaccaaca cttctaacca ggtcgctgtg ctgtaccagg acgtcaactg caccgaggtc    1860
cctgtggcca tccacgctga ccagctgacc cccacttggc gcgtgtactc caccggcagc    1920
aacgtgttcc agactcgtgc tggttgcctg atcggcgccg agcacgtgaa caacagctac    1980
gaatgcgaca tccccatcgg cgctggaatc tgcgcctctt accagaccca gactaacagc    2040
ccacagcagg ctcagtctgt ggcctctcag tcaatcatcg cttacaccat gtcactgggc    2100
gctgaaaact ccgtggccta ctctaacaac tcaatcgcca tccccaccaa cttcactatc    2160
agcgtgacca ctgagatcct gccagtcagc atgaccaaga cttctgtgga ctgcactatg    2220
tacatctgcg gagacagcac cgaatgctct aacctgctgc tgcagtacgg ctctttctgc    2280
acccagctga accgtgctct gactggaatc gccgtggagc aggacaagaa cactcaggaa    2340
gtcttcgctc aggtgaagca aatctacaag accccaccta tcaaggactt cggcggattc    2400
aacttctccc agatcctgcc tgaccctcc aagccaagca agcgctcttt catcgaggac    2460
ctgctgttca acaaggtcac tctggccgac gctggattca tcaagcagta cggagactgc    2520
ctgggtgaca tcgccgctcg tgacctgatc tgcgctcaga agttcaacgg tctgaccgtg    2580 ctgccccac tgctgactga cgaaatgatc gcccagtaca ctagcgccct gctggctgga    2640
accatcactt ctggttggac cttcggtgct ggcgccgctc tgcagatccc tttcgctatg    2700
cagatggcct accgtttcaa cggaatcggt gtcacccaga acgtgctgta cgagaaccag    2760
aagctgatcg ctaaccagtt caactcagcc atcggaaaga tccaggacag cctgagctct    2820
actgcctctg ctctgggcaa gctgcaggac gtcgtgaacc agaacgccca ggctctgaac    2880
accctggtca agcagctgtc atccaacttc ggtgctatca gctctgtgct gaacgacatc    2940
ctgtcccgcc tggacaaggt cgaggccgaa gtgcagatcg accgcctgat cactggccgt    3000
ctgcagtcac tgcagaccta cgtgactcag cagctgatca gggccgctga aatcagagcc    3060
tccgctaacc tggccgctac caagatgagc gagtgcgtcc tgggtcaatc taagcgtgtg    3120
gacttctgcg gcaagggata ccacctgatg tcattccctc agtctgctcc ccacggtgtg    3180
gtgttcctgc acgtcaccta cgtgccagcc caggagaaga acttcaccac tgcccctgct    3240
atctgccacg acggcaaggc tcacttcccc agggaaggtg tcttcgtgag caacggcacc    3300
cactggttcg tcactcagag aaacttctac gagccacaga tcatcaccac tgacaacact    3360
ttcgtgtctg aaactgcga cgtggtcatc ggtatcgtca caacaccgt gtacgacccc    3420 ctgcagccag agctggactc attcaaggag gaactggaca gtacttcaa gaaccacacc    3480 tcccctgacg tcgacctggg cgacatctca ggaatcaacg cttccgtcgt gaacatccag    3540
aaggagatcg accgcctgaa cgaagtggcc aagaacctga cgaaagcct gatcgacctg    3600 caggagctgg gcaagtacga acagtacatc aagtggcctt ggtacatctg gctgggtttc    3660
atcgctggcc tcatcgctat cgtgatggtg accatcatgc tgtgctgcat gacttcatgc    3720
tgctcctgcc tgaagggctg ctgcagctgc ggatcttgct gcaagttcga cgaggacgac    3780
tctgaacccg tcctgaaggg cgtgaagctg cactacaccc accaccacca ccaccac    3837
```

```
<210> SEQ ID NO 58
<211> LENGTH: 1266
<212> TYPE: PRT
<213> ORGANISM: Artificial Sequence
<220> FEATURE:
<223> OTHER INFORMATION: RECOMBINANT SPIKE PROTEIN
```

-continued

```
<400> SEQUENCE: 58

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
        290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415
```

```
Thr Gly Cys Val Ile Ala Trp Asn Ser Asn Asn Leu Asp Ser Lys Val
        420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
        500                 505                 510

Gly Pro Lys Lys Ser Thr Asn Leu Val Lys Asn Lys Cys Val Asn Phe
        515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
                660                 665                 670

Ser Val Ala Ser Gln Ser Ile Ile Ala Tyr Thr Met Ser Leu Gly Ala
        675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830
```

-continued

```
Ala Arg Asp Leu Ile Cys Ala Gln Lys Phe Asn Gly Leu Thr Val Leu
        835             840             845

Pro Pro Leu Leu Thr Asp Glu Met Ile Ala Gln Tyr Thr Ser Ala Leu
    850             855             860

Leu Ala Gly Thr Ile Thr Ser Gly Trp Thr Phe Gly Ala Gly Ala Ala
865             870             875             880

Leu Gln Ile Pro Phe Ala Met Gln Met Ala Tyr Arg Phe Asn Gly Ile
            885             890             895

Gly Val Thr Gln Asn Val Leu Tyr Glu Asn Gln Lys Leu Ile Ala Asn
        900             905             910

Gln Phe Asn Ser Ala Ile Gly Lys Ile Gln Asp Ser Leu Ser Ser Thr
        915             920             925

Ala Ser Ala Leu Gly Lys Leu Gln Asp Val Val Asn Gln Asn Ala Gln
    930             935             940

Ala Leu Asn Thr Leu Val Lys Gln Leu Ser Ser Asn Phe Gly Ala Ile
945             950             955             960

Ser Ser Val Leu Asn Asp Ile Leu Ser Arg Leu Asp Lys Val Glu Ala
            965             970             975

Glu Val Gln Ile Asp Arg Leu Ile Thr Gly Arg Leu Gln Ser Leu Gln
        980             985             990

Thr Tyr Val Thr Gln Gln Leu Ile  Arg Ala Ala Glu Ile  Arg Ala Ser
        995             1000            1005

Ala Asn  Leu Ala Ala Thr Lys  Met Ser Glu Cys Val  Leu Gly Gln
    1010            1015            1020

Ser Lys  Arg Val Asp Phe Cys  Gly Lys Gly Tyr His  Leu Met Ser
    1025            1030            1035

Phe Pro  Gln Ser Ala Pro His  Gly Val Val Phe Leu  His Val Thr
    1040            1045            1050

Tyr Val  Pro Ala Gln Glu Lys  Asn Phe Thr Thr Ala  Pro Ala Ile
    1055            1060            1065

Cys His  Asp Gly Lys Ala His  Phe Pro Arg Glu Gly  Val Phe Val
    1070            1075            1080

Ser Asn  Gly Thr His Trp Phe  Val Thr Gln Arg Asn  Phe Tyr Glu
    1085            1090            1095

Pro Gln  Ile Ile Thr Thr Asp  Asn Thr Phe Val Ser  Gly Asn Cys
    1100            1105            1110

Asp Val  Val Ile Gly Ile Val  Asn Asn Thr Val Tyr  Asp Pro Leu
    1115            1120            1125

Gln Pro  Glu Leu Asp Ser Phe  Lys Glu Glu Leu Asp  Lys Tyr Phe
    1130            1135            1140

Lys Asn  His Thr Ser Pro Asp  Val Asp Leu Gly Asp  Ile Ser Gly
    1145            1150            1155

Ile Asn  Ala Ser Val Val Asn  Ile Gln Lys Glu Ile  Asp Arg Leu
    1160            1165            1170

Asn Glu  Val Ala Lys Asn Leu  Asn Glu Ser Leu Ile  Asp Leu Gln
    1175            1180            1185

Glu Leu  Gly Lys Tyr Glu Gln  Tyr Ile Lys Trp Pro  Trp Tyr Ile
    1190            1195            1200

Trp Leu  Gly Phe Ile Ala Gly  Leu Ile Ala Ile Val  Met Val Thr
    1205            1210            1215

Ile Met  Leu Cys Cys Met Thr  Ser Cys Cys Ser Cys  Leu Lys Gly
    1220            1225            1230

Cys Cys  Ser Cys Gly Ser Cys  Cys Lys Phe Asp Glu  Asp Asp Ser
```

-continued

```
        1235             1240             1245

Glu Pro  Val Leu Lys Gly Val  Lys Leu His Tyr Thr  His His His
    1250             1255             1260

His His  His
    1265

<210> SEQ ID NO 59
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 59

Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
            85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
```

-continued

```
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
            370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
            450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
            530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gln Gln Ala Gln Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750
```

Leu Leu Gln Tyr Gly Ser Phe Cys Thr Gln Leu Asn Arg Ala Leu Thr
        755                760                765

Gly Ile Ala Val Glu Gln Asp Lys Asn Thr Gln Glu Val Phe Ala Gln
    770                775                780

Val Lys Gln Ile Tyr Lys Thr Pro Pro Ile Lys Asp Phe Gly Gly Phe
785                790                795                800

Asn Phe Ser Gln Ile Leu Pro Asp Pro Ser Lys Pro Ser Lys Arg Ser
            805                810                815

Phe Ile Glu Asp Leu Leu Phe Asn Lys Val Thr Leu Ala Asp Ala Gly
            820                825                830

Phe Ile Lys Gln Tyr Gly Asp Cys Leu Gly Asp Ile Ala Ala Arg Asp
            835                840                845

Leu Ile Cys Ala Gln Lys Phe Asn Gly Leu Thr Val Leu Pro Pro Leu
    850                855                860

Leu Thr Asp Glu Met Ile Ala Gln Tyr Thr Ser Ala Leu Leu Ala Gly
865                870                875                880

Thr Ile Thr Ser Gly Trp Thr Phe Gly Ala Gly Ala Ala Leu Gln Ile
            885                890                895

Pro Phe Ala Met Gln Met Ala Tyr Arg Phe Asn Gly Ile Gly Val Thr
            900                905                910

Gln Asn Val Leu Tyr Glu Asn Gln Lys Leu Ile Ala Asn Gln Phe Asn
    915                920                925

Ser Ala Ile Gly Lys Ile Gln Asp Ser Leu Ser Ser Thr Ala Ser Ala
    930                935                940

Leu Gly Lys Leu Gln Asp Val Val Asn Gln Asn Ala Gln Ala Leu Asn
945                950                955                960

Thr Leu Val Lys Gln Leu Ser Ser Asn Phe Gly Ala Ile Ser Ser Val
            965                970                975

Leu Asn Asp Ile Leu Ser Arg Leu Asp Lys Val Glu Ala Glu Val Gln
            980                985                990

Ile Asp Arg Leu Ile Thr Gly Arg  Leu Gln Ser Leu Gln  Thr Tyr Val
            995                1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

-continued

```
His Thr Ser Pro Asp Val Asp Leu Gly Asp Ile Ser Gly Ile Asn
    1160             1165             1170

Ala Ser Val Val Asn Ile Gln Lys Glu Ile Asp Arg Leu Asn Glu
    1175             1180             1185

Val Ala Lys Asn Leu Asn Glu Ser Leu Ile Asp Leu Gln Glu Leu
    1190             1195             1200

Gly Lys Tyr Glu Gln Tyr Ile Lys Trp Pro His His His His
    1205             1210             1215

His
```

<210> SEQ ID NO 60
<211> LENGTH: 3657
<212> TYPE: DNA
<213> ORGANISM: Artificial Sequence
<220> FEATURE:
<223> OTHER INFORMATION: RECOMBINANT SPIKE PROTEIN

<400> SEQUENCE: 60

```
atgttcgtct tcctggtgct gctgcccctg gtgtccagcc agtgcgtgaa cctgaccact      60
aggactcagc tgcctcccgc ttacaccaac tcattcactc gcggtgtgta ctaccctgac     120
aaggtcttcc gttcttcagt gctgcactca actcaggacc tgttcctgcc cttcttctcc     180
aacgtcacct ggttccacgc catccacgtg tccggcacca acggcactaa gcgcttcgac     240
aacccagtgc tgccttttcaa cgacggtgtc tacttcgctt caaccgagaa gtccaacatc     300
atccgtggat ggatcttcgg caccactctg gacagcaaga ctcagtctct gctgatcgtc     360
aacaacgcca ccaacgtggt catcaaggtc tgcgaattcc agttctgcaa cgacccattc     420
ctgggcgtct actaccacaa gaacaacaag tcatggatgg agtccgaatt ccgcgtctac     480
tccagcgcta caactgcac tttcgagtac gtgtcccagc ctttcctgat ggacctggaa     540
ggaaagcagg gtaacttcaa gaacctgagg gagttcgtgt tcaagaacat cgacggatac     600
ttcaagattt acagcaagca cacccccaatc aacctggtgc gcgacctgcc tcagggtttc     660
tctgctctgg agccactggt ggacctgcct atcggcatca acatcacccg cttccagact     720
ctgctggctc tgcaccgttc ctacctgact ccaggcgact atctccttctgg atggactgct     780 ggagctgctg cttactacgt gggctacctg cagcctcgca ccttcctgct gaagtacaac     840
gaaaacggaa ccatcactga cgccgtcgac tgcgctctgg accctctgtc agaaaccaag     900
tgcactctga gtccttcac cgtggagaag ggcatctacc agacttcaaa cttcagggtg     960
cagcccaccg aatccatcgt cagattccct aacatcacta acctgtgccc cttcggagag    1020
gtcttcaacg ccaccgctt cgcttccgtg tacgcctgga caggaagag aatctcaaac    1080 tgcgtcgctg actactccgt gctgtacaac tcagcctcct tcagcacctt caagtgctac    1140
ggcgtgtcac caactaagct gaacgacctg tgcttcacca cgtctacgc cgactccttc    1200 gtgatcaggg gagacgaggt cagacagatc gctcctggcc agactggaaa gatcgccgac    1260
tacaactaca gctgcccga cgacttcacc ggttgcgtca tcgcttggaa cagcaacaac    1320
ctggactcta aagtgggtgg caactacaac tacctgtacc gcctgttccg taagtcaaac    1380
ctgaagccat cgagaggga catcagcact gaaatctacc aggccggatc tacccccttgc    1440 aacggtgtcg agggcttcaa ctgctacttc ccctgcagt cctacggttt ccagccaact    1500
aacggtgtgg ctaccagcc ttacagagtg tcgtgctga gcttcgaact gctccacgct    1560
cctgctactg tgtgcggtcc aaagaagtct accaacctgg tcaagaacaa gtgcgtgaac    1620
ttcaacttca cggcctgac cggaactggt gtcctgaccg agagcaacaa gaagttcctg    1680
```

```
cccttccagc agttcggaag ggacatcgct gacaccactg acgctgtgcg cgaccctcag       1740
accctggaaa tcctggacat cactccatgc tcattcggag gtgtctccgt gatcacccct       1800
ggcaccaaca cttctaacca ggtcgctgtg ctgtaccagg acgtcaactg caccgaggtc       1860
cctgtggcca tccacgctga ccagctgacc cccacttggc gcgtgtactc caccggcagc       1920
aacgtgttcc agactcgtgc tggttgcctg atcggcgccg agcacgtgaa caacagctac       1980
gaatgcgaca tccccatcgg cgctggaatc tgcgcctctt accagaccca gactaacagc       2040
ccacagcagg ctcagtctgt ggcctctcag tcaatcatcg cttacaccat gtcactgggc       2100
gctgaaaact ccgtggccta ctctaacaac tcaatcgcca tccccaccaa cttcactatc       2160
agcgtgacca ctgagatcct gccagtcagc atgaccaaga cttctgtgga ctgcactatg       2220
tacatctgcg gagacagcac cgaatgctct aacctgctgc tgcagtacgg ctctttctgc       2280
acccagctga accgtgctct gactggaatc gccgtggagc aggacaagaa cactcaggaa       2340
gtcttcgctc aggtgaagca aatctacaag accccaccta tcaaggactt cggcggattc       2400
aacttctccc agatcctgcc tgaccctcc aagccaagca gcgctctttt catcgaggac       2460
ctgctgttca acaaggtcac tctggccgac gctggattca tcaagcagta cggagactgc       2520
ctgggtgaca tcgccgctcg tgacctgatc tgcgctcaga gttcaacggt ctgaccgtg       2580 ctgcccccac tgctgactga cgaaatgatc gcccagtaca ctagcgccct gctggctgga       2640
accatcactt ctggttggac cttcggtgct ggcgccgctc tgcagatccc tttcgctatg       2700
cagatggcct accgtttcaa cggaatcggt gtcacccaga acgtgctgta cgagaaccag       2760
aagctgatcg ctaaccagtt caactcagcc atcggaaaga tccaggacag cctgagctct       2820
actgcctctg ctctgggcaa gctgcaggac gtcgtgaacc agaacgccca ggctctgaac       2880
accctggtca agcagctgtc atccaacttc ggtgctatca gctctgtgct gaacgacatc       2940
ctgtcccgcc tggacaaggt cgaggccgaa gtgcagatcg accgcctgat cactggccgt       3000
ctgcagtcac tgcagaccta cgtgactcag cagctgatca gggccgctga aatcagagcc       3060
tccgctaacc tggccgctac caagatgagc gagtgcgtcc tgggtcaatc taagcgtgtg       3120
gacttctgcg gcaagggata ccacctgatg tcattccctc agtctgctcc ccacggtgtg       3180
gtgttcctgc acgtcaccta cgtgccagcc caggagaaga acttcaccac tgcccctgct       3240
atctgccacg acggcaaggc tcacttcccc agggaaggtg tcttcgtgag caacggcacc       3300
cactggttcg tcactcagag aaacttctac gagccacaga tcatcaccac tgacaacact       3360
ttcgtgtctg gaaactgcga cgtggtcatc ggtatcgtca acaacaccgt gtacgacccc       3420
ctgcagccag agctggactc attcaaggag gaactggaca gtacttcaa gaaccacacc       3480 tcccctgacg tcgacctggg cgacatctca ggaatcaacg cttccgtcgt gaacatccag       3540
aaggagatcg accgcctgaa cgaagtggcc aagaacctga cgaaagcct gatcgacctg       3600 caggagctgg gcaagtacga acagtacatc aagtggcctc accaccacca ccaccac          3657
```

<210> SEQ ID NO 61
<211> LENGTH: 1205
<212> TYPE: PRT
<213> ORGANISM: Artificial Sequence
<220> FEATURE:
<223> OTHER INFORMATION: RECOMBINANT SPIKE PROTEIN
<400> SEQUENCE: 61

```
Cys Val Asn Leu Thr Thr Arg Thr Gln Leu Pro Pro Ala Tyr Thr Asn
1               5                   10                  15
```

-continued

```
Ser Phe Thr Arg Gly Val Tyr Tyr Pro Asp Lys Val Phe Arg Ser Ser
        20                  25                  30

Val Leu His Ser Thr Gln Asp Leu Phe Leu Pro Phe Phe Ser Asn Val
        35                  40                  45

Thr Trp Phe His Ala Ile His Val Ser Gly Thr Asn Gly Thr Lys Arg
        50                  55                  60

Phe Asp Asn Pro Val Leu Pro Phe Asn Asp Gly Val Tyr Phe Ala Ser
65                  70                  75                  80

Thr Glu Lys Ser Asn Ile Ile Arg Gly Trp Ile Phe Gly Thr Thr Leu
                85                  90                  95

Asp Ser Lys Thr Gln Ser Leu Leu Ile Val Asn Asn Ala Thr Asn Val
                100                 105                 110

Val Ile Lys Val Cys Glu Phe Gln Phe Cys Asn Asp Pro Phe Leu Gly
                115                 120                 125

Val Tyr Tyr His Lys Asn Asn Lys Ser Trp Met Glu Ser Glu Phe Arg
        130                 135                 140

Val Tyr Ser Ser Ala Asn Asn Cys Thr Phe Glu Tyr Val Ser Gln Pro
145                 150                 155                 160

Phe Leu Met Asp Leu Glu Gly Lys Gln Gly Asn Phe Lys Asn Leu Arg
                165                 170                 175

Glu Phe Val Phe Lys Asn Ile Asp Gly Tyr Phe Lys Ile Tyr Ser Lys
                180                 185                 190

His Thr Pro Ile Asn Leu Val Arg Asp Leu Pro Gln Gly Phe Ser Ala
                195                 200                 205

Leu Glu Pro Leu Val Asp Leu Pro Ile Gly Ile Asn Ile Thr Arg Phe
        210                 215                 220

Gln Thr Leu Leu Ala Leu His Arg Ser Tyr Leu Thr Pro Gly Asp Ser
225                 230                 235                 240

Ser Ser Gly Trp Thr Ala Gly Ala Ala Ala Tyr Tyr Val Gly Tyr Leu
                245                 250                 255

Gln Pro Arg Thr Phe Leu Leu Lys Tyr Asn Glu Asn Gly Thr Ile Thr
                260                 265                 270

Asp Ala Val Asp Cys Ala Leu Asp Pro Leu Ser Glu Thr Lys Cys Thr
        275                 280                 285

Leu Lys Ser Phe Thr Val Glu Lys Gly Ile Tyr Gln Thr Ser Asn Phe
        290                 295                 300

Arg Val Gln Pro Thr Glu Ser Ile Val Arg Phe Pro Asn Ile Thr Asn
305                 310                 315                 320

Leu Cys Pro Phe Gly Glu Val Phe Asn Ala Thr Arg Phe Ala Ser Val
                325                 330                 335

Tyr Ala Trp Asn Arg Lys Arg Ile Ser Asn Cys Val Ala Asp Tyr Ser
                340                 345                 350

Val Leu Tyr Asn Ser Ala Ser Phe Ser Thr Phe Lys Cys Tyr Gly Val
        355                 360                 365

Ser Pro Thr Lys Leu Asn Asp Leu Cys Phe Thr Asn Val Tyr Ala Asp
        370                 375                 380

Ser Phe Val Ile Arg Gly Asp Glu Val Arg Gln Ile Ala Pro Gly Gln
385                 390                 395                 400

Thr Gly Lys Ile Ala Asp Tyr Asn Tyr Lys Leu Pro Asp Asp Phe Thr
                405                 410                 415

Gly Cys Val Ile Ala Trp Asn Ser Asn Asn Leu Asp Ser Lys Val Gly
                420                 425                 430
```

-continued

```
Gly Asn Tyr Asn Tyr Leu Tyr Arg Leu Phe Arg Lys Ser Asn Leu Lys
    435                 440                 445

Pro Phe Glu Arg Asp Ile Ser Thr Glu Ile Tyr Gln Ala Gly Ser Thr
    450                 455                 460

Pro Cys Asn Gly Val Glu Gly Phe Asn Cys Tyr Phe Pro Leu Gln Ser
465                 470                 475                 480

Tyr Gly Phe Gln Pro Thr Asn Gly Val Gly Tyr Gln Pro Tyr Arg Val
                485                 490                 495

Val Val Leu Ser Phe Glu Leu Leu His Ala Pro Ala Thr Val Cys Gly
                500                 505                 510

Pro Lys Lys Ser Thr Asn Leu Val Lys Asn Lys Cys Val Asn Phe Asn
            515                 520                 525

Phe Asn Gly Leu Thr Gly Thr Gly Val Leu Thr Glu Ser Asn Lys Lys
    530                 535                 540

Phe Leu Pro Phe Gln Gln Phe Gly Arg Asp Ile Ala Asp Thr Thr Asp
545                 550                 555                 560

Ala Val Arg Asp Pro Gln Thr Leu Glu Ile Leu Asp Ile Thr Pro Cys
                565                 570                 575

Ser Phe Gly Gly Val Ser Val Ile Thr Pro Gly Thr Asn Thr Ser Asn
                580                 585                 590

Gln Val Ala Val Leu Tyr Gln Asp Val Asn Cys Thr Glu Val Pro Val
            595                 600                 605

Ala Ile His Ala Asp Gln Leu Thr Pro Thr Trp Arg Val Tyr Ser Thr
    610                 615                 620

Gly Ser Asn Val Phe Gln Thr Arg Ala Gly Cys Leu Ile Gly Ala Glu
625                 630                 635                 640

His Val Asn Asn Ser Tyr Glu Cys Asp Ile Pro Ile Gly Ala Gly Ile
                645                 650                 655

Cys Ala Ser Tyr Gln Thr Gln Thr Asn Ser Pro Gln Gln Ala Gln Ser
                660                 665                 670

Val Ala Ser Gln Ser Ile Ile Ala Tyr Thr Met Ser Leu Gly Ala Glu
            675                 680                 685

Asn Ser Val Ala Tyr Ser Asn Asn Ser Ile Ala Ile Pro Thr Asn Phe
    690                 695                 700

Thr Ile Ser Val Thr Thr Glu Ile Leu Pro Val Ser Met Thr Lys Thr
705                 710                 715                 720

Ser Val Asp Cys Thr Met Tyr Ile Cys Gly Asp Ser Thr Glu Cys Ser
                725                 730                 735

Asn Leu Leu Leu Gln Tyr Gly Ser Phe Cys Thr Gln Leu Asn Arg Ala
            740                 745                 750

Leu Thr Gly Ile Ala Val Glu Gln Asp Lys Asn Thr Gln Glu Val Phe
    755                 760                 765

Ala Gln Val Lys Gln Ile Tyr Lys Thr Pro Pro Ile Lys Asp Phe Gly
    770                 775                 780

Gly Phe Asn Phe Ser Gln Ile Leu Pro Asp Pro Ser Lys Pro Ser Lys
785                 790                 795                 800

Arg Ser Phe Ile Glu Asp Leu Leu Phe Asn Lys Val Thr Leu Ala Asp
                805                 810                 815

Ala Gly Phe Ile Lys Gln Tyr Gly Asp Cys Leu Gly Asp Ile Ala Ala
                820                 825                 830

Arg Asp Leu Ile Cys Ala Gln Lys Phe Asn Gly Leu Thr Val Leu Pro
    835                 840                 845

Pro Leu Leu Thr Asp Glu Met Ile Ala Gln Tyr Thr Ser Ala Leu Leu
```

-continued

```
            850                  855                  860

Ala Gly Thr Ile Thr Ser Gly Trp Thr Phe Gly Ala Gly Ala Ala Leu
865                  870                  875                  880

Gln Ile Pro Phe Ala Met Gln Met Ala Tyr Arg Phe Asn Gly Ile Gly
                885                  890                  895

Val Thr Gln Asn Val Leu Tyr Glu Asn Gln Lys Leu Ile Ala Asn Gln
                900                  905                  910

Phe Asn Ser Ala Ile Gly Lys Ile Gln Asp Ser Leu Ser Ser Thr Ala
                915                  920                  925

Ser Ala Leu Gly Lys Leu Gln Asp Val Val Asn Gln Asn Ala Gln Ala
        930                  935                  940

Leu Asn Thr Leu Val Lys Gln Leu Ser Ser Asn Phe Gly Ala Ile Ser
945                  950                  955                  960

Ser Val Leu Asn Asp Ile Leu Ser Arg Leu Asp Lys Val Glu Ala Glu
                965                  970                  975

Val Gln Ile Asp Arg Leu Ile Thr Gly Arg Leu Gln Ser Leu Gln Thr
                980                  985                  990

Tyr Val Thr Gln Gln Leu Ile Arg  Ala Ala Glu Ile Arg  Ala Ser Ala
            995                  1000                 1005

Asn Leu  Ala Ala Thr Lys Met  Ser Glu Cys Val Leu  Gly Gln Ser
    1010                 1015                 1020

Lys Arg  Val Asp Phe Cys Gly  Lys Gly Tyr His Leu  Met Ser Phe
    1025                 1030                 1035

Pro Gln  Ser Ala Pro His Gly  Val Val Phe Leu His  Val Thr Tyr
    1040                 1045                 1050

Val Pro  Ala Gln Glu Lys Asn  Phe Thr Thr Ala Pro  Ala Ile Cys
    1055                 1060                 1065

His Asp  Gly Lys Ala His Phe  Pro Arg Glu Gly Val  Phe Val Ser
    1070                 1075                 1080

Asn Gly  Thr His Trp Phe Val  Thr Gln Arg Asn Phe  Tyr Glu Pro
    1085                 1090                 1095

Gln Ile  Ile Thr Thr Asp Asn  Thr Phe Val Ser Gly  Asn Cys Asp
    1100                 1105                 1110

Val Val  Ile Gly Ile Val Asn  Asn Thr Val Tyr Asp  Pro Leu Gln
    1115                 1120                 1125

Pro Glu  Leu Asp Ser Phe Lys  Glu Glu Leu Asp Lys  Tyr Phe Lys
    1130                 1135                 1140

Asn His  Thr Ser Pro Asp Val  Asp Leu Gly Asp Ile  Ser Gly Ile
    1145                 1150                 1155

Asn Ala  Ser Val Val Asn Ile  Gln Lys Glu Ile Asp  Arg Leu Asn
    1160                 1165                 1170

Glu Val  Ala Lys Asn Leu Asn  Glu Ser Leu Ile Asp  Leu Gln Glu
    1175                 1180                 1185

Leu Gly  Lys Tyr Glu Gln Tyr  Ile Lys Trp Pro His  His His His
    1190                 1195                 1200

His His
    1205
```

<210> SEQ ID NO 62
<211> LENGTH: 1263
<212> TYPE: PRT
<213> ORGANISM: Artificial Sequence
<220> FEATURE:
<223> OTHER INFORMATION: RECOMBINANT SPIKE PROTEIN

```
<400> SEQUENCE: 62

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415
```

```
Lys Ile Ala Asp Tyr Asn Tyr Lys Leu Pro Asp Asp Phe Thr Gly Cys
        420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
        500             505             510

Leu Ser Phe Glu Leu Leu His Ala Pro Ala Thr Val Cys Gly Pro Lys
        515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gln Gln Ala Gln Ser Val Ala
        675             680             685

Leu Gly Ala Glu Asn Ser Val Ala Tyr Ser Asn Asn Ser Ile Ala Ile
    690             695             700

Pro Thr Asn Phe Thr Ile Ser Val Thr Thr Glu Ile Leu Pro Val Ser
705             710             715             720

Met Thr Lys Thr Ser Val Asp Cys Thr Met Tyr Ile Cys Gly Asp Ser
            725             730             735

Thr Glu Cys Ser Asn Leu Leu Leu Gln Tyr Gly Ser Phe Cys Thr Gln
        740             745             750

Leu Asn Arg Ala Leu Thr Gly Ile Ala Val Glu Gln Asp Lys Asn Thr
        755             760             765

Gln Glu Val Phe Ala Gln Val Lys Gln Ile Tyr Lys Thr Pro Pro Ile
    770             775             780

Lys Asp Phe Gly Gly Phe Asn Phe Ser Gln Ile Leu Pro Asp Pro Ser
785             790             795             800

Lys Pro Ser Lys Arg Ser Phe Ile Glu Asp Leu Leu Phe Asn Lys Val
            805             810             815

Thr Leu Ala Asp Ala Gly Phe Ile Lys Gln Tyr Gly Asp Cys Leu Gly
        820             825             830
```

```
Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                 1005

Arg Ala  Ser Ala Asn Leu Ala  Ala Thr Lys Met Ser  Glu Cys Val
    1010                 1015                 1020

Leu Gly Gln Ser Lys Arg Val  Asp Phe Cys Gly Lys  Gly Tyr His
    1025                 1030                 1035

Leu Met  Ser Phe Pro Gln Ser  Ala Pro His Gly Val  Val Phe Leu
    1040                 1045                 1050

His Val  Thr Tyr Val Pro Ala  Gln Glu Lys Asn Phe  Thr Thr Ala
    1055                 1060                 1065

Pro Ala  Ile Cys His Asp Gly  Lys Ala His Phe Pro  Arg Glu Gly
    1070                 1075                 1080

Val Phe  Val Ser Asn Gly Thr  His Trp Phe Val Thr  Gln Arg Asn
    1085                 1090                 1095

Phe Tyr  Glu Pro Gln Ile Ile  Thr Thr Asp Asn Thr  Phe Val Ser
    1100                 1105                 1110

Gly Asn  Cys Asp Val Val Ile  Gly Ile Val Asn Asn  Thr Val Tyr
    1115                 1120                 1125

Asp Pro  Leu Gln Pro Glu Leu  Asp Ser Phe Lys Glu  Glu Leu Asp
    1130                 1135                 1140

Lys Tyr  Phe Lys Asn His Thr  Ser Pro Asp Val Asp  Leu Gly Asp
    1145                 1150                 1155

Ile Ser  Gly Ile Asn Ala Ser  Val Val Asn Ile Gln  Lys Glu Ile
    1160                 1165                 1170

Asp Arg  Leu Asn Glu Val Ala  Lys Asn Leu Asn Glu  Ser Leu Ile
    1175                 1180                 1185

Asp Leu  Gln Glu Leu Gly Lys  Tyr Glu Gln Tyr Ile  Lys Trp Pro
    1190                 1195                 1200

Trp Tyr  Ile Trp Leu Gly Phe  Ile Ala Gly Leu Ile  Ala Ile Val
    1205                 1210                 1215

Met Val  Thr Ile Met Leu Cys  Cys Met Thr Ser Cys  Cys Ser Cys
    1220                 1225                 1230

Leu Lys  Gly Cys Cys Ser Cys  Gly Ser Cys Cys Lys  Phe Asp Glu
```

```
    1235              1240              1245

Asp Asp Ser Glu Pro Val Leu Lys Gly Val Lys Leu His Tyr Thr
    1250              1255              1260

<210> SEQ ID NO 63
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 63

Gln Cys Val Asn Leu Thr Thr Arg Thr Gln Leu Pro Pro Ala Tyr Thr
1            5             10            15

Asn Ser Phe Thr Arg Gly Val Tyr Tyr Pro Asp Lys Val Phe Arg Ser
        20            25            30

Ser Val Leu His Ser Thr Gln Asp Leu Phe Leu Pro Phe Phe Ser Asn
        35            40            45

Val Thr Trp Phe His Ala Ile His Val Ser Gly Thr Asn Gly Thr Lys
    50            55            60

Arg Phe Asp Asn Pro Val Leu Pro Phe Asn Asp Gly Val Tyr Phe Ala
65            70            75            80

Ser Thr Glu Lys Ser Asn Ile Ile Arg Gly Trp Ile Phe Gly Thr Thr
            85            90            95

Leu Asp Ser Lys Thr Gln Ser Leu Leu Ile Val Asn Asn Ala Thr Asn
            100           105           110

Val Val Ile Lys Val Cys Glu Phe Gln Phe Cys Asn Asp Pro Phe Leu
            115           120           125

Gly Val Tyr Tyr His Lys Asn Asn Lys Ser Trp Met Glu Ser Glu Phe
    130           135           140

Arg Val Tyr Ser Ser Ala Asn Asn Cys Thr Phe Glu Tyr Val Ser Gln
145           150           155           160

Pro Phe Leu Met Asp Leu Glu Gly Lys Gln Gly Asn Phe Lys Asn Leu
            165           170           175

Arg Glu Phe Val Phe Lys Asn Ile Asp Gly Tyr Phe Lys Ile Tyr Ser
            180           185           190

Lys His Thr Pro Ile Asn Leu Val Arg Asp Leu Pro Gln Gly Phe Ser
        195           200           205

Ala Leu Glu Pro Leu Val Asp Leu Pro Ile Gly Ile Asn Ile Thr Arg
    210           215           220

Phe Gln Thr Leu Leu Ala Leu His Arg Ser Tyr Leu Thr Pro Gly Asp
225           230           235           240

Ser Ser Ser Gly Trp Thr Ala Gly Ala Ala Ala Tyr Tyr Val Gly Tyr
        245           250           255

Leu Gln Pro Arg Thr Phe Leu Leu Lys Tyr Asn Glu Asn Gly Thr Ile
        260           265           270

Thr Asp Ala Val Asp Cys Ala Leu Asp Pro Leu Ser Glu Thr Lys Cys
        275           280           285

Thr Leu Lys Ser Phe Thr Val Glu Lys Gly Ile Tyr Gln Thr Ser Asn
    290           295           300

Phe Arg Val Gln Pro Thr Glu Ser Ile Val Arg Phe Pro Asn Ile Thr
305           310           315           320

Asn Leu Cys Pro Phe Gly Glu Val Phe Asn Ala Thr Arg Phe Ala Ser
            325           330           335

Val Tyr Ala Trp Asn Arg Lys Arg Ile Ser Asn Cys Val Ala Asp Tyr
```

-continued

```
                340                 345                 350
Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
        595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
                660                 665                 670

Ser Val Ala Leu Gly Ala Glu Asn Ser Val Ala Tyr Ser Asn Asn Ser
                675                 680                 685

Ile Ala Ile Pro Thr Asn Phe Thr Ile Ser Val Thr Thr Glu Ile Leu
        690                 695                 700

Pro Val Ser Met Thr Lys Thr Ser Val Asp Cys Thr Met Tyr Ile Cys
705                 710                 715                 720

Gly Asp Ser Thr Glu Cys Ser Asn Leu Leu Leu Gln Tyr Gly Ser Phe
                725                 730                 735

Cys Thr Gln Leu Asn Arg Ala Leu Thr Gly Ile Ala Val Glu Gln Asp
                740                 745                 750

Lys Asn Thr Gln Glu Val Phe Ala Gln Val Lys Gln Ile Tyr Lys Thr
                755                 760                 765
```

```
Pro Pro Ile Lys Asp Phe Gly Gly Phe Asn Phe Ser Gln Ile Leu Pro
    770             775             780

Asp Pro Ser Lys Pro Ser Lys Arg Ser Phe Ile Glu Asp Leu Leu Phe
785             790             795             800

Asn Lys Val Thr Leu Ala Asp Ala Gly Phe Ile Lys Gln Tyr Gly Asp
            805             810             815

Cys Leu Gly Asp Ile Ala Ala Arg Asp Leu Ile Cys Ala Gln Lys Phe
            820             825             830

Asn Gly Leu Thr Val Leu Pro Pro Leu Leu Thr Asp Glu Met Ile Ala
            835             840             845

Gln Tyr Thr Ser Ala Leu Leu Ala Gly Thr Ile Thr Ser Gly Trp Thr
    850             855             860

Phe Gly Ala Gly Ala Ala Leu Gln Ile Pro Phe Ala Met Gln Met Ala
865             870             875             880

Tyr Arg Phe Asn Gly Ile Gly Val Thr Gln Asn Val Leu Tyr Glu Asn
            885             890             895

Gln Lys Leu Ile Ala Asn Gln Phe Asn Ser Ala Ile Gly Lys Ile Gln
    900             905             910

Asp Ser Leu Ser Ser Thr Ala Ser Ala Leu Gly Lys Leu Gln Asp Val
    915             920             925

Val Asn Gln Asn Ala Gln Ala Leu Asn Thr Leu Val Lys Gln Leu Ser
    930             935             940

Ser Asn Phe Gly Ala Ile Ser Ser Val Leu Asn Asp Ile Leu Ser Arg
945             950             955             960

Leu Asp Lys Val Glu Ala Glu Val Gln Ile Asp Arg Leu Ile Thr Gly
            965             970             975

Arg Leu Gln Ser Leu Gln Thr Tyr Val Thr Gln Gln Leu Ile Arg Ala
            980             985             990

Ala Glu Ile Arg Ala Ser Ala Asn  Leu Ala Ala Thr Lys  Met Ser Glu
    995             1000                1005

Cys Val  Leu Gly Gln Ser Lys  Arg Val Asp Phe Cys  Gly Lys Gly
    1010             1015                1020

Tyr His  Leu Met Ser Phe Pro  Gln Ser Ala Pro His  Gly Val Val
    1025             1030                1035

Phe Leu  His Val Thr Tyr Val  Pro Ala Gln Glu Lys  Asn Phe Thr
    1040             1045                1050

Thr Ala  Pro Ala Ile Cys His  Asp Gly Lys Ala His  Phe Pro Arg
    1055             1060                1065

Glu Gly  Val Phe Val Ser Asn  Gly Thr His Trp Phe  Val Thr Gln
    1070             1075                1080

Arg Asn  Phe Tyr Glu Pro Gln  Ile Ile Thr Thr Asp  Asn Thr Phe
    1085             1090                1095

Val Ser  Gly Asn Cys Asp Val  Val Ile Gly Ile Val  Asn Asn Thr
    1100             1105                1110

Val Tyr  Asp Pro Leu Gln Pro  Glu Leu Asp Ser Phe  Lys Glu Glu
    1115             1120                1125

Leu Asp  Lys Tyr Phe Lys Asn  His Thr Ser Pro Asp  Val Asp Leu
    1130             1135                1140

Gly Asp  Ile Ser Gly Ile Asn  Ala Ser Val Val Asn  Ile Gln Lys
    1145             1150                1155

Glu Ile  Asp Arg Leu Asn Glu  Val Ala Lys Asn Leu  Asn Glu Ser
    1160             1165                1170
```

-continued

```
Leu Ile  Asp Leu Gln Glu Leu  Gly Lys Tyr Glu Gln  Tyr Ile Lys
    1175             1180             1185

Trp Pro  Trp Tyr Ile Trp Leu  Gly Phe Ile Ala Gly  Leu Ile Ala
    1190             1195             1200

Ile Val  Met Val Thr Ile Met  Leu Cys Cys Met Thr  Ser Cys Cys
    1205             1210             1215

Ser Cys  Leu Lys Gly Cys Cys  Ser Cys Gly Ser Cys  Cys Lys Phe
    1220             1225             1230

Asp Glu  Asp Asp Ser Glu Pro  Val Leu Lys Gly Val  Lys Leu His
    1235             1240             1245

Tyr Thr
    1250
```

```
<210> SEQ ID NO 64
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 64
```

```
Met Phe Val Phe Leu Val Leu Leu Pro Leu Val Ser Ser Gln Cys Val
1                5                10               15

Asn Leu Thr Thr Arg Thr Gln Leu Pro Pro Ala Tyr Thr Asn Ser Phe
            20               25               30

Thr Arg Gly Val Tyr Tyr Pro Asp Lys Val Phe Arg Ser Ser Val Leu
        35               40               45

His Ser Thr Gln Asp Leu Phe Leu Pro Phe Phe Ser Asn Val Thr Trp
    50               55               60

Phe His Ala Ile His Val Ser Gly Thr Asn Gly Thr Lys Arg Phe Asp
65               70               75               80

Asn Pro Val Leu Pro Phe Asn Asp Gly Val Tyr Phe Ala Ser Thr Glu
                85               90               95

Lys Ser Asn Ile Ile Arg Gly Trp Ile Phe Gly Thr Thr Leu Asp Ser
            100              105              110

Lys Thr Gln Ser Leu Leu Ile Val Asn Asn Ala Thr Asn Val Val Ile
        115              120              125

Lys Val Cys Glu Phe Gln Phe Cys Asn Asp Pro Phe Leu Gly Val Tyr
    130              135              140

Tyr His Lys Asn Asn Lys Ser Trp Met Glu Ser Glu Phe Arg Val Tyr
145              150              155              160

Ser Ser Ala Asn Asn Cys Thr Phe Glu Tyr Val Ser Gln Pro Phe Leu
            165              170              175

Met Asp Leu Glu Gly Lys Gln Gly Asn Phe Lys Asn Leu Arg Glu Phe
        180              185              190

Val Phe Lys Asn Ile Asp Gly Tyr Phe Lys Ile Tyr Ser Lys His Thr
        195              200              205

Pro Ile Asn Leu Val Arg Asp Leu Pro Gln Gly Phe Ser Ala Leu Glu
    210              215              220

Pro Leu Val Asp Leu Pro Ile Gly Ile Asn Ile Thr Arg Phe Gln Thr
225              230              235              240

Leu Leu Ala Leu His Arg Ser Tyr Leu Thr Pro Gly Asp Ser Ser Ser
            245              250              255

Gly Trp Thr Ala Gly Ala Ala Ala Tyr Tyr Val Gly Tyr Leu Gln Pro
            260              265              270
```

-continued

```
Arg Thr Phe Leu Leu Lys Tyr Asn Glu Asn Gly Thr Ile Thr Asp Ala
        275                 280             285

Val Asp Cys Ala Leu Asp Pro Leu Ser Glu Thr Lys Cys Thr Leu Lys
    290                 295             300

Ser Phe Thr Val Glu Lys Gly Ile Tyr Gln Thr Ser Asn Phe Arg Val
305                 310             315                 320

Gln Pro Thr Glu Ser Ile Val Arg Phe Pro Asn Ile Thr Asn Leu Cys
                325             330                 335

Pro Phe Gly Glu Val Phe Asn Ala Thr Arg Phe Ala Ser Val Tyr Ala
            340                 345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gln Gln Ala Gln Ser Val Ala
            675             680             685

Ser Gln Ser Ile Ile Ala Tyr Thr Met Ser Leu Gly Ala Glu Asn Ser
```

-continued

```
              690             695              700
Val Ala Tyr Ser Asn Asn Ser Ile Ala Ile Glu Ile Leu Pro Val Ser
705             710             715              720

Met Thr Lys Thr Ser Val Asp Cys Thr Met Tyr Ile Cys Gly Asp Ser
            725             730             735

Thr Glu Cys Ser Asn Leu Leu Leu Gln Tyr Gly Ser Phe Cys Thr Gln
            740             745             750

Leu Asn Arg Ala Leu Thr Gly Ile Ala Val Glu Gln Asp Lys Asn Thr
            755             760             765

Gln Glu Val Phe Ala Gln Val Lys Gln Ile Tyr Lys Thr Pro Pro Ile
    770             775             780

Lys Asp Phe Gly Gly Phe Asn Phe Ser Gln Ile Leu Pro Asp Pro Ser
785             790             795             800

Lys Pro Ser Lys Arg Ser Phe Ile Glu Asp Leu Leu Phe Asn Lys Val
            805             810             815

Thr Leu Ala Asp Ala Gly Phe Ile Lys Gln Tyr Gly Asp Cys Leu Gly
            820             825             830

Asp Ile Ala Ala Arg Asp Leu Ile Cys Ala Gln Lys Phe Asn Gly Leu
            835             840             845

Thr Val Leu Pro Pro Leu Leu Thr Asp Glu Met Ile Ala Gln Tyr Thr
    850             855             860

Ser Ala Leu Leu Ala Gly Thr Ile Thr Ser Gly Trp Thr Phe Gly Ala
865             870             875             880

Gly Ala Ala Leu Gln Ile Pro Phe Ala Met Gln Met Ala Tyr Arg Phe
            885             890             895

Asn Gly Ile Gly Val Thr Gln Asn Val Leu Tyr Glu Asn Gln Lys Leu
            900             905             910

Ile Ala Asn Gln Phe Asn Ser Ala Ile Gly Lys Ile Gln Asp Ser Leu
            915             920             925

Ser Ser Thr Ala Ser Ala Leu Gly Lys Leu Gln Asp Val Val Asn Gln
    930             935             940

Asn Ala Gln Ala Leu Asn Thr Leu Val Lys Gln Leu Ser Ser Asn Phe
945             950             955             960

Gly Ala Ile Ser Ser Val Leu Asn Asp Ile Leu Ser Arg Leu Asp Lys
            965             970             975

Val Glu Ala Glu Val Gln Ile Asp Arg Leu Ile Thr Gly Arg Leu Gln
            980             985             990

Ser Leu Gln Thr Tyr Val Thr Gln  Gln Leu Ile Arg Ala  Ala Glu Ile
    995             1000            1005

Arg Ala  Ser Ala Asn Leu Ala  Ala Thr Lys Met Ser  Glu Cys Val
    1010            1015            1020

Leu Gly  Gln Ser Lys Arg Val  Asp Phe Cys Gly Lys  Gly Tyr His
    1025            1030            1035

Leu Met  Ser Phe Pro Gln Ser  Ala Pro His Gly Val  Val Phe Leu
    1040            1045            1050

His Val  Thr Tyr Val Pro Ala  Gln Glu Lys Asn Phe  Thr Thr Ala
    1055            1060            1065

Pro Ala  Ile Cys His Asp Gly  Lys Ala His Phe Pro  Arg Glu Gly
    1070            1075            1080

Val Phe  Val Ser Asn Gly Thr  His Trp Phe Val Thr  Gln Arg Asn
    1085            1090            1095

Phe Tyr  Glu Pro Gln Ile Ile  Thr Thr Asp Asn Thr  Phe Val Ser
    1100            1105            1110
```

-continued

```
Gly Asn Cys Asp Val Val Ile  Gly Ile Val Asn Asn  Thr Val Tyr
    1115              1120              1125

Asp Pro Leu Gln Pro Glu Leu  Asp Ser Phe Lys Glu  Glu Leu Asp
    1130              1135              1140

Lys Tyr  Phe Lys Asn His Thr  Ser Pro Asp Val Asp  Leu Gly Asp
    1145              1150              1155

Ile Ser  Gly Ile Asn Ala Ser  Val Val Asn Ile Gln  Lys Glu Ile
    1160              1165              1170

Asp Arg  Leu Asn Glu Val Ala  Lys Asn Leu Asn Glu  Ser Leu Ile
    1175              1180              1185

Asp Leu  Gln Glu Leu Gly Lys  Tyr Glu Gln Tyr Ile  Lys Trp Pro
    1190              1195              1200

Trp Tyr  Ile Trp Leu Gly Phe  Ile Ala Gly Leu Ile  Ala Ile Val
    1205              1210              1215

Met Val  Thr Ile Met Leu Cys  Cys Met Thr Ser Cys  Cys Ser Cys
    1220              1225              1230

Leu Lys  Gly Cys Cys Ser Cys  Gly Ser Cys Cys Lys  Phe Asp Glu
    1235              1240              1245

Asp Asp  Ser Glu Pro Val Leu  Lys Gly Val Lys Leu  His Tyr Thr
    1250              1255              1260
```

```
<210> SEQ ID NO 65
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 65

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
        195                 200                 205
```

-continued

```
Ala Leu Glu Pro Leu Val Asp Leu Pro Ile Gly Ile Asn Ile Thr Arg
    210             215             220

Phe Gln Thr Leu Leu Ala Leu His Arg Ser Tyr Leu Thr Pro Gly Asp
225             230             235             240

Ser Ser Ser Gly Trp Thr Ala Gly Ala Ala Tyr Tyr Val Gly Tyr
            245             250             255

Leu Gln Pro Arg Thr Phe Leu Leu Lys Tyr Asn Glu Asn Gly Thr Ile
            260             265             270

Thr Asp Ala Val Asp Cys Ala Leu Asp Pro Leu Ser Glu Thr Lys Cys
        275             280             285

Thr Leu Lys Ser Phe Thr Val Glu Lys Gly Ile Tyr Gln Thr Ser Asn
    290             295             300

Phe Arg Val Gln Pro Thr Glu Ser Ile Val Arg Phe Pro Asn Ile Thr
305             310             315             320

Asn Leu Cys Pro Phe Gly Glu Val Phe Asn Ala Thr Arg Phe Ala Ser
            325             330             335

Val Tyr Ala Trp Asn Arg Lys Arg Ile Ser Asn Cys Val Ala Asp Tyr
            340             345             350

Ser Val Leu Tyr Asn Ser Ala Ser Phe Ser Thr Phe Lys Cys Tyr Gly
        355             360             365

Val Ser Pro Thr Lys Leu Asn Asp Leu Cys Phe Thr Asn Val Tyr Ala
    370             375             380

Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
            405             410             415

Thr Gly Cys Val Ile Ala Trp Asn Ser Asn Asn Leu Asp Ser Lys Val
            420             425             430

Gly Gly Asn Tyr Asn Tyr Leu Tyr Arg Leu Phe Arg Lys Ser Asn Leu
        435             440             445

Lys Pro Phe Glu Arg Asp Ile Ser Thr Glu Ile Tyr Gln Ala Gly Ser
    450             455             460

Thr Pro Cys Asn Gly Val Glu Gly Phe Asn Cys Tyr Phe Pro Leu Gln
465             470             475             480

Ser Tyr Gly Phe Gln Pro Thr Asn Gly Val Gly Tyr Gln Pro Tyr Arg
            485             490             495

Val Val Val Leu Ser Phe Glu Leu Leu His Ala Pro Ala Thr Val Cys
            500             505             510

Gly Pro Lys Lys Ser Thr Asn Leu Val Lys Asn Lys Cys Val Asn Phe
        515             520             525

Asn Phe Asn Gly Leu Thr Gly Thr Gly Val Leu Thr Glu Ser Asn Lys
    530             535             540

Lys Phe Leu Pro Phe Gln Gln Phe Gly Arg Asp Ile Ala Asp Thr Thr
545             550             555             560

Asp Ala Val Arg Asp Pro Gln Thr Leu Glu Ile Leu Asp Ile Thr Pro
            565             570             575

Cys Ser Phe Gly Gly Val Ser Val Ile Thr Pro Gly Thr Asn Thr Ser
            580             585             590

Asn Gln Val Ala Val Leu Tyr Gln Asp Val Asn Cys Thr Glu Val Pro
        595             600             605

Val Ala Ile His Ala Asp Gln Leu Thr Pro Thr Trp Arg Val Tyr Ser
    610             615             620
```

-continued

```
Thr Gly Ser Asn Val Phe Gln Thr Arg Ala Gly Cys Leu Ile Gly Ala
625             630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Glu Ile Leu
    690                 695                 700

Pro Val Ser Met Thr Lys Thr Ser Val Asp Cys Thr Met Tyr Ile Cys
705                 710                 715                 720

Gly Asp Ser Thr Glu Cys Ser Asn Leu Leu Leu Gln Tyr Gly Ser Phe
                725                 730                 735

Cys Thr Gln Leu Asn Arg Ala Leu Thr Gly Ile Ala Val Glu Gln Asp
                740                 745                 750

Lys Asn Thr Gln Glu Val Phe Ala Gln Val Lys Gln Ile Tyr Lys Thr
            755                 760                 765

Pro Pro Ile Lys Asp Phe Gly Gly Phe Asn Phe Ser Gln Ile Leu Pro
    770                 775                 780

Asp Pro Ser Lys Pro Ser Lys Arg Ser Phe Ile Glu Asp Leu Leu Phe
785                 790                 795                 800

Asn Lys Val Thr Leu Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
                820                 825                 830

Asn Gly Leu Thr Val Leu Pro Pro Leu Leu Thr Asp Glu Met Ile Ala
            835                 840                 845

Gln Tyr Thr Ser Ala Leu Leu Ala Gly Thr Ile Thr Ser Gly Trp Thr
    850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
            915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
            980                 985                 990

Ala Glu Ile Arg Ala Ser Ala Asn  Leu Ala Ala Thr Lys  Met Ser Glu
        995                 1000                1005

Cys Val  Leu Gly Gln Ser Lys  Arg Val Asp Phe Cys  Gly Lys Gly
    1010                1015                1020

Tyr His  Leu Met Ser Phe Pro  Gln Ser Ala Pro His  Gly Val Val
    1025                1030                1035

Phe Leu  His Val Thr Tyr Val  Pro Ala Gln Glu Lys  Asn Phe Thr
```

-continued

```
          1040                1045                1050

Thr Ala  Pro Ala Ile Cys His  Asp Gly Lys Ala His  Phe Pro Arg
    1055                1060                1065

Glu Gly  Val Phe Val Ser Asn  Gly Thr His Trp Phe  Val Thr Gln
    1070                1075                1080

Arg Asn  Phe Tyr Glu Pro Gln  Ile Ile Thr Thr Asp  Asn Thr Phe
    1085                1090                1095

Val Ser  Gly Asn Cys Asp Val  Val Ile Gly Ile Val  Asn Asn Thr
    1100                1105                1110

Val Tyr  Asp Pro Leu Gln Pro  Glu Leu Asp Ser Phe  Lys Glu Glu
    1115                1120                1125

Leu Asp  Lys Tyr Phe Lys Asn  His Thr Ser Pro Asp  Val Asp Leu
    1130                1135                1140

Gly Asp  Ile Ser Gly Ile Asn  Ala Ser Val Val Asn  Ile Gln Lys
    1145                1150                1155

Glu Ile  Asp Arg Leu Asn Glu  Val Ala Lys Asn Leu  Asn Glu Ser
    1160                1165                1170

Leu Ile  Asp Leu Gln Glu Leu  Gly Lys Tyr Glu Gln  Tyr Ile Lys
    1175                1180                1185

Trp Pro  Trp Tyr Ile Trp Leu  Gly Phe Ile Ala Gly  Leu Ile Ala
    1190                1195                1200

Ile Val  Met Val Thr Ile Met  Leu Cys Cys Met Thr  Ser Cys Cys
    1205                1210                1215

Ser Cys  Leu Lys Gly Cys Cys  Ser Cys Gly Ser Cys  Cys Lys Phe
    1220                1225                1230

Asp Glu  Asp Asp Ser Glu Pro  Val Leu Lys Gly Val  Lys Leu His
    1235                1240                1245

Tyr Thr
    1250

<210> SEQ ID NO 66
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 66

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
```

-continued

```
         130               135               140

Tyr His Lys Asn Asn Lys Ser Trp Met Glu Ser Glu Phe Arg Val Tyr
145               150               155               160

Ser Ser Ala Asn Asn Cys Thr Phe Glu Tyr Val Ser Gln Pro Phe Leu
              165               170               175

Met Asp Leu Glu Gly Lys Gln Gly Asn Phe Lys Asn Leu Arg Glu Phe
          180               185               190

Val Phe Lys Asn Ile Asp Gly Tyr Phe Lys Ile Tyr Ser Lys His Thr
          195               200               205

Pro Ile Asn Leu Val Arg Asp Leu Pro Gln Gly Phe Ser Ala Leu Glu
      210               215               220

Pro Leu Val Asp Leu Pro Ile Gly Ile Asn Ile Thr Arg Phe Gln Thr
225               230               235               240

Leu Leu Ala Leu His Arg Ser Tyr Leu Thr Pro Gly Asp Ser Ser Ser
              245               250               255

Gly Trp Thr Ala Gly Ala Ala Ala Tyr Tyr Val Gly Tyr Leu Gln Pro
          260               265               270

Arg Thr Phe Leu Leu Lys Tyr Asn Glu Asn Gly Thr Ile Thr Asp Ala
      275               280               285

Val Asp Cys Ala Leu Asp Pro Leu Ser Glu Thr Lys Cys Thr Leu Lys
      290               295               300

Ser Phe Thr Val Glu Lys Gly Ile Tyr Gln Thr Ser Asn Phe Arg Val
305               310               315               320

Gln Pro Thr Glu Ser Ile Val Arg Phe Pro Asn Ile Thr Asn Leu Cys
              325               330               335

Pro Phe Gly Glu Val Phe Asn Ala Thr Arg Phe Ala Ser Val Tyr Ala
          340               345               350

Trp Asn Arg Lys Arg Ile Ser Asn Cys Val Ala Asp Tyr Ser Val Leu
          355               360               365

Tyr Asn Ser Ala Ser Phe Ser Thr Phe Lys Cys Tyr Gly Val Ser Pro
      370               375               380

Thr Lys Leu Asn Asp Leu Cys Phe Thr Asn Val Tyr Ala Asp Ser Phe
385               390               395               400

Val Ile Arg Gly Asp Glu Val Arg Gln Ile Ala Pro Gly Gln Thr Gly
          405               410               415

Lys Ile Ala Asp Tyr Asn Tyr Lys Leu Pro Asp Asp Phe Thr Gly Cys
          420               425               430

Val Ile Ala Trp Asn Ser Asn Asn Leu Asp Ser Lys Val Gly Gly Asn
          435               440               445

Tyr Asn Tyr Leu Tyr Arg Leu Phe Arg Lys Ser Asn Leu Lys Pro Phe
      450               455               460

Glu Arg Asp Ile Ser Thr Glu Ile Tyr Gln Ala Gly Ser Thr Pro Cys
465               470               475               480

Asn Gly Val Glu Gly Phe Asn Cys Tyr Phe Pro Leu Gln Ser Tyr Gly
              485               490               495

Phe Gln Pro Thr Asn Gly Val Gly Tyr Gln Pro Tyr Arg Val Val Val
          500               505               510

Leu Ser Phe Glu Leu Leu His Ala Pro Ala Thr Val Cys Gly Pro Lys
          515               520               525

Lys Ser Thr Asn Leu Val Lys Asn Lys Cys Val Asn Phe Asn Phe Asn
      530               535               540

Gly Leu Thr Gly Thr Gly Val Leu Thr Glu Ser Asn Lys Lys Phe Leu
545               550               555               560
```

-continued

```
Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gln Gln Ala Gln Ser Val Ala
            675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Ala Asp Ala Gly Phe Ile Lys Gln Tyr Gly Asp Cys Leu Gly
            820             825             830

Asp Ile Ala Ala Arg Asp Leu Ile Cys Ala Gln Lys Phe Asn Gly Leu
    835             840             845

Thr Val Leu Pro Pro Leu Leu Thr Asp Glu Met Ile Ala Gln Tyr Thr
    850             855             860

Ser Ala Leu Leu Ala Gly Thr Ile Thr Ser Gly Trp Thr Phe Gly Ala
865             870             875             880

Gly Ala Ala Leu Gln Ile Pro Phe Ala Met Gln Met Ala Tyr Arg Phe
            885             890             895

Asn Gly Ile Gly Val Thr Gln Asn Val Leu Tyr Glu Asn Gln Lys Leu
            900             905             910

Ile Ala Asn Gln Phe Asn Ser Ala Ile Gly Lys Ile Gln Asp Ser Leu
    915             920             925

Ser Ser Thr Ala Ser Ala Leu Gly Lys Leu Gln Asp Val Val Asn Gln
    930             935             940

Asn Ala Gln Ala Leu Asn Thr Leu Val Lys Gln Leu Ser Ser Asn Phe
945             950             955             960

Gly Ala Ile Ser Ser Val Leu Asn Asp Ile Leu Ser Arg Leu Asp Lys
            965             970             975
```

-continued

```
Val Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
            995                 1000                1005

Arg Ala  Ser Ala Asn Leu Ala  Ala Thr Lys Met Ser  Glu Cys Val
            1010                1015                1020

Leu Gly  Gln Ser Lys Arg Val  Asp Phe Cys Gly Lys  Gly Tyr His
            1025                1030                1035

Leu Met  Ser Phe Pro Gln Ser  Ala Pro His Gly Val  Val Phe Leu
            1040                1045                1050

His Val  Thr Tyr Val Pro Ala  Gln Glu Lys Asn Phe  Thr Thr Ala
            1055                1060                1065

Pro Ala  Ile Cys His Asp Gly  Lys Ala His Phe Pro  Arg Glu Gly
            1070                1075                1080

Val Phe  Val Ser Asn Gly Thr  His Trp Phe Val Thr  Gln Arg Asn
            1085                1090                1095

Phe Tyr  Glu Pro Gln Ile Ile  Thr Thr Asp Asn Thr  Phe Val Ser
            1100                1105                1110

Gly Asn  Cys Asp Val Val Ile  Gly Ile Val Asn Asn  Thr Val Tyr
            1115                1120                1125

Asp Pro  Leu Gln Pro Glu Leu  Asp Ser Phe Lys Glu  Glu Leu Asp
            1130                1135                1140

Lys Tyr  Phe Lys Asn His Thr  Ser Pro Asp Val Asp  Leu Gly Asp
            1145                1150                1155

Ile Ser  Gly Ile Asn Ala Ser  Val Val Asn Ile Gln  Lys Glu Ile
            1160                1165                1170

Asp Arg  Leu Asn Glu Val Ala  Lys Asn Leu Asn Glu  Ser Leu Ile
            1175                1180                1185

Asp Leu  Gln Glu Leu Gly Lys  Tyr Glu Gln Tyr Ile  Lys Trp Pro
            1190                1195                1200

Trp Tyr  Ile Trp Leu Gly Phe  Ile Ala Gly Leu Ile  Ala Ile Val
            1205                1210                1215

Met Val  Thr Ile Met Leu Cys  Cys Met Thr Ser Cys  Cys Ser Cys
            1220                1225                1230

Leu Lys  Gly Cys Cys Ser Cys  Gly Ser Cys Cys Lys  Phe Asp Glu
            1235                1240                1245

Asp Asp  Ser Glu Pro Val Leu  Lys Gly Val Lys Leu  His Tyr Thr
            1250                1255                1260
```

<210> SEQ ID NO 67
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 67

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60
```

-continued

```
Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
        355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
        435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
```

-continued

```
                   485                 490                 495
Val Val Val Leu Ser Phe Glu Leu Leu His Ala Pro Ala Thr Val Cys
                   500                 505                 510
Gly Pro Lys Lys Ser Thr Asn Leu Val Lys Asn Lys Cys Val Asn Phe
                   515                 520                 525
Asn Phe Asn Gly Leu Thr Gly Thr Gly Val Leu Thr Glu Ser Asn Lys
                   530                 535                 540
Lys Phe Leu Pro Phe Gln Gln Phe Gly Arg Asp Ile Ala Asp Thr Thr
545                550                 555                 560
Asp Ala Val Arg Asp Pro Gln Thr Leu Glu Ile Leu Asp Ile Thr Pro
                   565                 570                 575
Cys Ser Phe Gly Gly Val Ser Val Ile Thr Pro Gly Thr Asn Thr Ser
                   580                 585                 590
Asn Gln Val Ala Val Leu Tyr Gln Asp Val Asn Cys Thr Glu Val Pro
                   595                 600                 605
Val Ala Ile His Ala Asp Gln Leu Thr Pro Thr Trp Arg Val Tyr Ser
                   610                 615                 620
Thr Gly Ser Asn Val Phe Gln Thr Arg Ala Gly Cys Leu Ile Gly Ala
625                630                 635                 640
Glu His Val Asn Asn Ser Tyr Glu Cys Asp Ile Pro Ile Gly Ala Gly
                   645                 650                 655
Ile Cys Ala Ser Tyr Gln Thr Gln Thr Asn Ser Pro Gln Gln Ala Gln
                   660                 665                 670
Ser Val Ala Ser Gln Ser Ile Ile Ala Tyr Thr Met Ser Leu Gly Ala
                   675                 680                 685
Glu Asn Ser Val Ala Tyr Ser Asn Asn Ser Ile Ala Ile Pro Thr Asn
                   690                 695                 700
Phe Thr Ile Ser Val Thr Thr Glu Ile Leu Pro Val Ser Met Thr Lys
705                710                 715                 720
Thr Ser Val Asp Cys Thr Met Tyr Ile Cys Gly Asp Ser Thr Glu Cys
                   725                 730                 735
Ser Asn Leu Leu Leu Gln Tyr Gly Ser Phe Cys Thr Gln Leu Asn Arg
                   740                 745                 750
Ala Leu Thr Gly Ile Ala Val Glu Gln Asp Lys Asn Thr Gln Glu Val
                   755                 760                 765
Phe Ala Gln Val Lys Gln Ile Tyr Lys Thr Pro Pro Ile Lys Asp Phe
                   770                 775                 780
Gly Gly Phe Asn Phe Ser Gln Ile Leu Pro Asp Pro Ser Lys Pro Ser
785                790                 795                 800
Lys Arg Ser Phe Ile Ala Asp Ala Gly Phe Ile Lys Gln Tyr Gly Asp
                   805                 810                 815
Cys Leu Gly Asp Ile Ala Ala Arg Asp Leu Ile Cys Ala Gln Lys Phe
                   820                 825                 830
Asn Gly Leu Thr Val Leu Pro Pro Leu Leu Thr Asp Glu Met Ile Ala
                   835                 840                 845
Gln Tyr Thr Ser Ala Leu Leu Ala Gly Thr Ile Thr Ser Gly Trp Thr
                   850                 855                 860
Phe Gly Ala Gly Ala Ala Leu Gln Ile Pro Phe Ala Met Gln Met Ala
865                870                 875                 880
Tyr Arg Phe Asn Gly Ile Gly Val Thr Gln Asn Val Leu Tyr Glu Asn
                   885                 890                 895
Gln Lys Leu Ile Ala Asn Gln Phe Asn Ser Ala Ile Gly Lys Ile Gln
                   900                 905                 910
```

-continued

```
Asp Ser Leu Ser Ser Thr Ala Ser Ala Leu Gly Lys Leu Gln Asp Val
        915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
                980                 985                 990

Ala Glu Ile Arg Ala Ser Ala Asn  Leu Ala Ala Thr Lys  Met Ser Glu
        995                 1000                 1005

Cys Val  Leu Gly Gln Ser Lys  Arg Val Asp Phe Cys  Gly Lys Gly
    1010                 1015                 1020

Tyr His  Leu Met Ser Phe Pro  Gln Ser Ala Pro His  Gly Val Val
    1025                 1030                 1035

Phe Leu  His Val Thr Tyr Val  Pro Ala Gln Glu Lys  Asn Phe Thr
    1040                 1045                 1050

Thr Ala  Pro Ala Ile Cys His  Asp Gly Lys Ala His  Phe Pro Arg
    1055                 1060                 1065

Glu Gly  Val Phe Val Ser Asn  Gly Thr His Trp Phe  Val Thr Gln
    1070                 1075                 1080

Arg Asn  Phe Tyr Glu Pro Gln  Ile Ile Thr Thr Asp  Asn Thr Phe
    1085                 1090                 1095

Val Ser  Gly Asn Cys Asp Val  Val Ile Gly Ile Val  Asn Asn Thr
    1100                 1105                 1110

Val Tyr  Asp Pro Leu Gln Pro  Glu Leu Asp Ser Phe  Lys Glu Glu
    1115                 1120                 1125

Leu Asp  Lys Tyr Phe Lys Asn  His Thr Ser Pro Asp  Val Asp Leu
    1130                 1135                 1140

Gly Asp  Ile Ser Gly Ile Asn  Ala Ser Val Val Asn  Ile Gln Lys
    1145                 1150                 1155

Glu Ile  Asp Arg Leu Asn Glu  Val Ala Lys Asn Leu  Asn Glu Ser
    1160                 1165                 1170

Leu Ile  Asp Leu Gln Glu Leu  Gly Lys Tyr Glu Gln  Tyr Ile Lys
    1175                 1180                 1185

Trp Pro  Trp Tyr Ile Trp Leu  Gly Phe Ile Ala Gly  Leu Ile Ala
    1190                 1195                 1200

Ile Val  Met Val Thr Ile Met  Leu Cys Cys Met Thr  Ser Cys Cys
    1205                 1210                 1215

Ser Cys  Leu Lys Gly Cys Cys  Ser Cys Gly Ser Cys  Cys Lys Phe
    1220                 1225                 1230

Asp Glu  Asp Asp Ser Glu Pro  Val Leu Lys Gly Val  Lys Leu His
    1235                 1240                 1245

Tyr Thr
    1250
```

```
<210> SEQ ID NO 68
<211> LENGTH: 31
<212> TYPE: PRT
<213> ORGANISM: Artificial Sequence
<220> FEATURE:
<223> OTHER INFORMATION: Foldon

<400> SEQUENCE: 68
```

```
Ser Ala Ile Gly Gly Tyr Ile Pro Glu Ala Pro Arg Asp Gly Gln Ala
1               5                   10                  15

Tyr Val Arg Lys Asp Gly Glu Trp Val Leu Leu Ser Thr Phe Leu
            20                  25                  30

<210> SEQ ID NO 69
<211> LENGTH: 202
<212> TYPE: PRT
<213> ORGANISM: Betacoronavirus severe acute respiratory syndrome
      coronavirus 2

<400> SEQUENCE: 69

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
        35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
            115                 120                 125

Phe Arg Lys Ser Asn Leu Lys Pro Phe Glu Arg Asp Ile Ser Thr Glu
        130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys
        195                 200

<210> SEQ ID NO 70
<211> LENGTH: 201
<212> TYPE: PRT
<213> ORGANISM: Betacoronavirus Severe acute respiratory syndrome-
      related coronavirus

<400> SEQUENCE: 70

Arg Phe Pro Asn Ile Thr Asn Leu Cys Pro Phe Gly Glu Val Phe Asn
1               5                   10                  15

Ala Thr Lys Phe Pro Ser Val Tyr Ala Trp Glu Arg Lys Lys Ile Ser
            20                  25                  30

Asn Cys Val Ala Asp Tyr Ser Val Leu Tyr Asn Ser Thr Phe Phe Ser
        35                  40                  45

Thr Phe Lys Cys Tyr Gly Val Ser Ala Thr Lys Leu Asn Asp Leu Cys
    50                  55                  60

Phe Ser Asn Val Tyr Ala Asp Ser Phe Val Val Lys Gly Asp Asp Val
65                  70                  75                  80
```

-continued

```
Arg Gln Ile Ala Pro Gly Gln Thr Gly Val Ile Ala Asp Tyr Asn Tyr
            85              90              95

Lys Leu Pro Asp Asp Phe Met Gly Cys Val Leu Ala Trp Asn Thr Arg
            100             105             110

Asn Ile Asp Ala Thr Ser Thr Gly Asn Tyr Asn Tyr Lys Tyr Arg Tyr
            115             120             125

Leu Arg His Gly Lys Leu Arg Pro Phe Glu Arg Asp Ile Ser Asn Val
    130             135             140

Pro Phe Ser Pro Asp Gly Lys Pro Cys Thr Pro Pro Ala Leu Asn Cys
145             150             155             160

Tyr Trp Pro Leu Asn Asp Tyr Gly Phe Tyr Thr Thr Thr Gly Ile Gly
            165             170             175

Tyr Gln Pro Tyr Arg Val Val Val Leu Ser Phe Glu Leu Leu Asn Ala
            180             185             190

Pro Ala Thr Val Cys Gly Pro Lys Leu
            195             200
```

```
<210> SEQ ID NO 71
<211> LENGTH: 239
<212> TYPE: PRT
<213> ORGANISM: Betacoronavirus Middle East respiratory syndrome-related
      coronavirus

<400> SEQUENCE: 71
```

```
Phe Glu Ala Lys Pro Ser Gly Ser Val Val Ala Glu Gly Val Glu Cys
1               5               10              15

Asp Phe Ser Pro Leu Leu Ser Gly Thr Pro Pro Gln Val Tyr Asn Phe
            20              25              30

Lys Arg Leu Val Phe Thr Asn Cys Asn Tyr Asn Leu Thr Lys Leu Leu
        35              40              45

Ser Leu Phe Ser Val Asn Asp Phe Thr Cys Ser Gln Ile Ser Pro Ala
    50              55              60

Ala Ile Ala Ser Asn Cys Tyr Ser Ser Leu Ile Leu Asp Tyr Phe Ser
65              70              75              80

Tyr Pro Leu Ser Met Lys Ser Asp Leu Ser Val Ser Ser Ala Gly Pro
            85              90              95

Ile Ser Gln Phe Asn Tyr Lys Gln Ser Phe Ser Asn Pro Thr Cys Leu
            100             105             110

Ile Leu Ala Thr Val Pro His Asn Leu Thr Thr Ile Thr Lys Pro Leu
            115             120             125

Lys Tyr Ser Tyr Ile Asn Lys Cys Ser Arg Leu Leu Ser Asp Asp Arg
    130             135             140

Thr Glu Val Pro Gln Leu Val Asn Ala Asn Gln Tyr Ser Pro Cys Val
145             150             155             160

Ser Ile Val Pro Ser Thr Val Trp Glu Asp Gly Asp Tyr Tyr Arg Lys
            165             170             175

Gln Leu Ser Pro Leu Glu Gly Gly Gly Trp Leu Val Ala Ser Gly Ser
            180             185             190

Thr Val Ala Met Thr Glu Gln Leu Gln Met Gly Phe Gly Ile Thr Val
            195             200             205

Gln Tyr Gly Thr Asp Thr Asn Ser Val Cys Pro Lys Leu Glu Phe Ala
            210             215             220

Asn Asp Thr Lys Ile Ala Ser Gln Leu Gly Asn Cys Val Glu Tyr
225             230             235
```

<210> SEQ ID NO 72
<211> LENGTH: 544
<212> TYPE: PRT
<213> ORGANISM: Artificial Sequence
<220> FEATURE:
<223> OTHER INFORMATION: RECOMBINANT SPIKE PROTEIN

<400> SEQUENCE: 72

```
Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
            20                  25                  30

Phe Ala Ser Val Tyr Ala Trp Asn Arg Lys Arg Ile Ser Asn Cys Val
        35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
            115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
            195                 200                 205

Thr Val Cys Gly Pro Lys Lys Ser Thr Asn Leu Val Lys Asn Lys Cys
    210                 215                 220

Val Asn Phe Asn Phe Asn Gly Leu Thr Gly Thr Gly Val Leu Thr Glu
225                 230                 235                 240

Ser Asn Lys Lys Phe Leu Pro Phe Gln Gln Phe Gly Arg Asp Ile Ala
                245                 250                 255

Asp Thr Thr Asp Ala Val Arg Asp Pro Gln Thr Leu Glu Ile Leu Asp
            260                 265                 270

Ile Thr Pro Cys Ser Phe Gly Gly Val Ser Val Ile Thr Pro Gly Thr
            275                 280                 285

Asn Thr Ser Asn Gln Val Ala Val Leu Tyr Gln Asp Val Asn Cys Thr
    290                 295                 300

Glu Arg Phe Pro Asn Ile Thr Asn Leu Cys Pro Phe Gly Glu Val Phe
305                 310                 315                 320

Asn Ala Thr Arg Phe Ala Ser Val Tyr Ala Trp Asn Arg Lys Arg Ile
                325                 330                 335

Ser Asn Cys Val Ala Asp Tyr Ser Val Leu Tyr Asn Ser Ala Ser Phe
            340                 345                 350

Ser Thr Phe Lys Cys Tyr Gly Val Ser Pro Thr Lys Leu Asn Asp Leu
            355                 360                 365

Cys Phe Thr Asn Val Tyr Ala Asp Ser Phe Val Ile Arg Gly Asp Glu
```

-continued

```
                370                 375                 380
Val Arg Gln Ile Ala Pro Gly Gln Thr Gly Lys Ile Ala Asp Tyr Asn
385                 390                 395                 400

Tyr Lys Leu Pro Asp Asp Phe Thr Gly Cys Val Ile Ala Trp Asn Ser
                405                 410                 415

Asn Asn Leu Asp Ser Lys Val Gly Gly Asn Tyr Asn Tyr Leu Tyr Arg
                420                 425                 430

Leu Phe Arg Lys Ser Asn Leu Lys Pro Phe Glu Arg Asp Ile Ser Thr
                435                 440                 445

Glu Ile Tyr Gln Ala Gly Ser Thr Pro Cys Asn Gly Val Glu Gly Phe
            450                 455                 460

Asn Cys Tyr Phe Pro Leu Gln Ser Tyr Gly Phe Gln Pro Thr Asn Gly
465                 470                 475                 480

Val Gly Tyr Gln Pro Tyr Arg Val Val Val Leu Ser Phe Glu Leu Leu
                485                 490                 495

His Ala Pro Ala Thr Val Cys Gly Pro Lys Lys Ser Ala Ile Gly Gly
                500                 505                 510

Tyr Ile Pro Glu Ala Pro Arg Asp Gly Gln Ala Tyr Val Arg Lys Asp
                515                 520                 525

Gly Glu Trp Val Leu Leu Ser Thr Phe Leu His His His His His His
                530                 535                 540

<210> SEQ ID NO 73
<211> LENGTH: 531
<212> TYPE: PRT
<213> ORGANISM: Artificial Sequence
<220> FEATURE:
<223> OTHER INFORMATION: RECOMBINANT SPIKE PROTEIN

<400> SEQUENCE: 73

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
                20                  25                  30

Asn Cys Val Ala Asp Tyr Ser Val Leu Tyr Asn Ser Ala Ser Phe Ser
            35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
                100                 105                 110

Asn Leu Asp Ser Lys Val Gly Gly Asn Tyr Asn Tyr Leu Tyr Arg Leu
                115                 120                 125

Phe Arg Lys Ser Asn Leu Lys Pro Phe Glu Arg Asp Ile Ser Thr Glu
            130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
                180                 185                 190

Ala Pro Ala Thr Val Cys Gly Pro Lys Lys Ser Thr Asn Leu Val Lys
```

-continued

```
               195                 200                 205

Asn Lys Cys Val Asn Phe Asn Phe Asn Gly Leu Thr Gly Thr Gly Val
    210                 215                 220

Leu Thr Glu Ser Asn Lys Lys Phe Leu Pro Phe Gln Gln Phe Gly Arg
225                 230                 235                 240

Asp Ile Ala Asp Thr Thr Asp Ala Val Arg Asp Pro Gln Thr Leu Glu
                245                 250                 255

Ile Leu Asp Ile Thr Pro Cys Ser Phe Gly Gly Val Ser Val Ile Thr
                260                 265                 270

Pro Gly Thr Asn Thr Ser Asn Gln Val Ala Val Leu Tyr Gln Asp Val
                275                 280                 285

Asn Cys Thr Glu Arg Phe Pro Asn Ile Thr Asn Leu Cys Pro Phe Gly
    290                 295                 300

Glu Val Phe Asn Ala Thr Arg Phe Ala Ser Val Tyr Ala Trp Asn Arg
305                 310                 315                 320

Lys Arg Ile Ser Asn Cys Val Ala Asp Tyr Ser Val Leu Tyr Asn Ser
                325                 330                 335

Ala Ser Phe Ser Thr Phe Lys Cys Tyr Gly Val Ser Pro Thr Lys Leu
                340                 345                 350

Asn Asp Leu Cys Phe Thr Asn Val Tyr Ala Asp Ser Phe Val Ile Arg
                355                 360                 365

Gly Asp Glu Val Arg Gln Ile Ala Pro Gly Gln Thr Gly Lys Ile Ala
    370                 375                 380

Asp Tyr Asn Tyr Lys Leu Pro Asp Asp Phe Thr Gly Cys Val Ile Ala
385                 390                 395                 400

Trp Asn Ser Asn Asn Leu Asp Ser Lys Val Gly Gly Asn Tyr Asn Tyr
                405                 410                 415

Leu Tyr Arg Leu Phe Arg Lys Ser Asn Leu Lys Pro Phe Glu Arg Asp
                420                 425                 430

Ile Ser Thr Glu Ile Tyr Gln Ala Gly Ser Thr Pro Cys Asn Gly Val
                435                 440                 445

Glu Gly Phe Asn Cys Tyr Phe Pro Leu Gln Ser Tyr Gly Phe Gln Pro
    450                 455                 460

Thr Asn Gly Val Gly Tyr Gln Pro Tyr Arg Val Val Val Leu Ser Phe
465                 470                 475                 480

Glu Leu Leu His Ala Pro Ala Thr Val Cys Gly Pro Lys Lys Ser Ala
                485                 490                 495

Ile Gly Gly Tyr Ile Pro Glu Ala Pro Arg Asp Gly Gln Ala Tyr Val
                500                 505                 510

Arg Lys Asp Gly Glu Trp Val Leu Leu Ser Thr Phe Leu His His His
    515                 520                 525

His His His
    530
```

```
<210> SEQ ID NO 74
<211> LENGTH: 544
<212> TYPE: PRT
<213> ORGANISM: Artificial Sequence
<220> FEATURE:
<223> OTHER INFORMATION: RECOMBINANT SPIKE PROTEIN

<400> SEQUENCE: 74
```

```
Met Phe Val Phe Leu Val Leu Leu Pro Leu Val Ser Ser Arg Phe Pro
1               5                  10                  15

Asn Ile Thr Asn Leu Cys Pro Phe Gly Glu Val Phe Asn Ala Thr Arg
```

-continued

```
                20                 25                 30

Phe Ala Ser Val Tyr Ala Trp Asn Arg Lys Arg Ile Ser Asn Cys Val
            35                 40                 45

Ala Asp Tyr Ser Val Leu Tyr Asn Ser Ala Ser Phe Ser Thr Phe Lys
        50                 55                 60

Cys Tyr Gly Val Ser Pro Thr Lys Leu Asn Asp Leu Cys Phe Thr Asn
65                 70                 75                 80

Val Tyr Ala Asp Ser Phe Val Ile Arg Gly Asp Glu Val Arg Gln Ile
                85                 90                 95

Ala Pro Gly Gln Thr Gly Lys Ile Ala Asp Tyr Asn Tyr Lys Leu Pro
            100                105                110

Asp Asp Phe Thr Gly Cys Val Ile Ala Trp Asn Ser Asn Asn Leu Asp
            115                120                125

Ser Lys Val Gly Gly Asn Tyr Asn Tyr Leu Tyr Arg Leu Phe Arg Lys
        130                135                140

Ser Asn Leu Lys Pro Phe Glu Arg Asp Ile Ser Thr Glu Ile Tyr Gln
145                150                155                160

Ala Gly Ser Thr Pro Cys Asn Gly Val Glu Gly Phe Asn Cys Tyr Phe
            165                170                175

Pro Leu Gln Ser Tyr Gly Phe Gln Pro Thr Asn Gly Val Gly Tyr Gln
            180                185                190

Pro Tyr Arg Val Val Val Leu Ser Phe Glu Leu Leu His Ala Pro Ala
            195                200                205

Thr Val Cys Gly Pro Lys Lys Ser Thr Asn Leu Val Lys Asn Lys Cys
        210                215                220

Val Asn Phe Asn Phe Asn Gly Leu Thr Gly Thr Gly Val Leu Thr Glu
225                230                235                240

Ser Asn Lys Lys Phe Leu Pro Phe Gln Gln Phe Gly Arg Asp Ile Ala
            245                250                255

Asp Thr Thr Asp Ala Val Arg Asp Pro Gln Thr Leu Glu Ile Leu Asp
            260                265                270

Ile Thr Pro Cys Ser Phe Gly Gly Val Ser Val Ile Thr Pro Gly Thr
            275                280                285

Asn Thr Ser Asn Gln Val Ala Val Leu Tyr Gln Asp Val Asn Cys Thr
        290                295                300

Glu Arg Phe Pro Asn Ile Thr Asn Leu Cys Pro Phe Gly Glu Val Phe
305                310                315                320

Asn Ala Thr Arg Phe Ala Ser Val Tyr Ala Trp Asn Arg Lys Arg Ile
            325                330                335

Ser Asn Cys Val Ala Asp Tyr Ser Val Leu Tyr Asn Ser Ala Ser Phe
            340                345                350

Ser Thr Phe Lys Cys Tyr Gly Val Ser Pro Thr Lys Leu Asn Asp Leu
            355                360                365

Cys Phe Thr Asn Val Tyr Ala Asp Ser Phe Val Ile Arg Gly Asp Glu
        370                375                380

Val Arg Gln Ile Ala Pro Gly Gln Thr Gly Lys Ile Ala Asp Tyr Asn
385                390                395                400

Tyr Lys Leu Pro Asp Asp Phe Thr Gly Cys Val Ile Ala Trp Asn Ser
            405                410                415

Asn Asn Leu Asp Ser Lys Val Gly Gly Asn Tyr Asn Tyr Leu Tyr Arg
            420                425                430

Leu Phe Arg Lys Ser Asn Leu Lys Pro Phe Glu Arg Asp Ile Ser Thr
            435                440                445
```

-continued

```
Glu Ile Tyr Gln Ala Gly Ser Thr Pro Cys Asn Gly Val Glu Gly Phe
    450                 455                 460

Asn Cys Tyr Phe Pro Leu Gln Ser Tyr Gly Phe Gln Pro Thr Asn Gly
465                 470                 475                 480

Val Gly Tyr Gln Pro Tyr Arg Val Val Val Leu Ser Phe Glu Leu Leu
                485                 490                 495

His Ala Pro Ala Thr Val Cys Gly Pro Lys Lys Ser Ala Ile Gly Gly
                500                 505                 510

Tyr Ile Pro Glu Ala Pro Arg Asp Gly Gln Ala Tyr Val Arg Lys Asp
            515                 520                 525

Gly Glu Trp Val Leu Leu Ser Thr Phe Leu His His His His His His
    530                 535                 540

<210> SEQ ID NO 75
<211> LENGTH: 531
<212> TYPE: PRT
<213> ORGANISM: Artificial Sequence
<220> FEATURE:
<223> OTHER INFORMATION: RECOMBINANT SPIKE PROTEIN

<400> SEQUENCE: 75

Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
                20                  25                  30

Asn Cys Val Ala Asp Tyr Ser Val Leu Tyr Asn Ser Ala Ser Phe Ser
            35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
            115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys Ser Thr Asn Leu Val Lys
            195                 200                 205

Asn Lys Cys Val Asn Phe Asn Phe Asn Gly Leu Thr Gly Thr Gly Val
    210                 215                 220

Leu Thr Glu Ser Asn Lys Lys Phe Leu Pro Phe Gln Gln Phe Gly Arg
225                 230                 235                 240

Asp Ile Ala Asp Thr Thr Asp Ala Val Arg Asp Pro Gln Thr Leu Glu
                245                 250                 255

Ile Leu Asp Ile Thr Pro Cys Ser Phe Gly Gly Val Ser Val Ile Thr
            260                 265                 270
```

```
Pro Gly Thr Asn Thr Ser Asn Gln Val Ala Val Leu Tyr Gln Asp Val
        275                 280                 285

Asn Cys Thr Glu Arg Phe Pro Asn Ile Thr Asn Leu Cys Pro Phe Gly
    290                 295                 300

Glu Val Phe Asn Ala Thr Arg Phe Ala Ser Val Tyr Ala Trp Asn Arg
305                 310                 315                 320

Lys Arg Ile Ser Asn Cys Val Ala Asp Tyr Ser Val Leu Tyr Asn Ser
                325                 330                 335

Ala Ser Phe Ser Thr Phe Lys Cys Tyr Gly Val Ser Pro Thr Lys Leu
                340                 345                 350

Asn Asp Leu Cys Phe Thr Asn Val Tyr Ala Asp Ser Phe Val Ile Arg
                355                 360                 365

Gly Asp Glu Val Arg Gln Ile Ala Pro Gly Gln Thr Gly Lys Ile Ala
        370                 375                 380

Asp Tyr Asn Tyr Lys Leu Pro Asp Asp Phe Thr Gly Cys Val Ile Ala
385                 390                 395                 400

Trp Asn Ser Asn Asn Leu Asp Ser Lys Val Gly Gly Asn Tyr Asn Tyr
                405                 410                 415

Leu Tyr Arg Leu Phe Arg Lys Ser Asn Leu Lys Pro Phe Glu Arg Asp
        420                 425                 430

Ile Ser Thr Glu Ile Tyr Gln Ala Gly Ser Thr Pro Cys Asn Gly Val
        435                 440                 445

Glu Gly Phe Asn Cys Tyr Phe Pro Leu Gln Ser Tyr Gly Phe Gln Pro
    450                 455                 460

Thr Asn Gly Val Gly Tyr Gln Pro Tyr Arg Val Val Val Leu Ser Phe
465                 470                 475                 480

Glu Leu Leu His Ala Pro Ala Thr Val Cys Gly Pro Lys Lys Ser Ala
                485                 490                 495

Ile Gly Gly Tyr Ile Pro Glu Ala Pro Arg Asp Gly Gln Ala Tyr Val
                500                 505                 510

Arg Lys Asp Gly Glu Trp Val Leu Leu Ser Thr Phe Leu His His His
        515                 520                 525

His His His
    530

<210> SEQ ID NO 76
<211> LENGTH: 470
<212> TYPE: PRT
<213> ORGANISM: Artificial Sequence
<220> FEATURE:
<223> OTHER INFORMATION: RECOMBINANT SPIKE PROTEIN

<400> SEQUENCE: 76

Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
                20                  25                  30

Phe Ala Ser Val Tyr Ala Trp Asn Arg Lys Arg Ile Ser Asn Cys Val
            35                  40                  45

Ala Asp Tyr Ser Val Leu Tyr Asn Ser Ala Ser Phe Ser Thr Phe Lys
    50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95
```

-continued

```
Ala Pro Gly Gln Thr Gly Lys Ile Ala Asp Tyr Asn Tyr Lys Leu Pro
            100                 105                 110

Asp Asp Phe Thr Gly Cys Val Ile Ala Trp Asn Ser Asn Asn Leu Asp
            115                 120                 125

Ser Lys Val Gly Gly Asn Tyr Asn Tyr Leu Tyr Arg Leu Phe Arg Lys
130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
                180                 185                 190

Pro Tyr Arg Val Val Val Leu Ser Phe Glu Leu Leu His Ala Pro Ala
                195                 200                 205

Thr Val Cys Gly Pro Lys Lys Ser Gly Gly Gly Ser Gly Gly Gly Ser
            210                 215                 220

Gly Gly Gly Ser Gly Gly Gly Ser Arg Phe Pro Asn Ile Thr Asn Leu
225                 230                 235                 240

Cys Pro Phe Gly Glu Val Phe Asn Ala Thr Lys Phe Pro Ser Val Tyr
                245                 250                 255

Ala Trp Glu Arg Lys Lys Ile Ser Asn Cys Val Ala Asp Tyr Ser Val
                260                 265                 270

Leu Tyr Asn Ser Thr Phe Phe Ser Thr Phe Lys Cys Tyr Gly Val Ser
            275                 280                 285

Ala Thr Lys Leu Asn Asp Leu Cys Phe Ser Asn Val Tyr Ala Asp Ser
            290                 295                 300

Phe Val Val Lys Gly Asp Asp Val Arg Gln Ile Ala Pro Gly Gln Thr
305                 310                 315                 320

Gly Val Ile Ala Asp Tyr Asn Tyr Lys Leu Pro Asp Asp Phe Met Gly
                325                 330                 335

Cys Val Leu Ala Trp Asn Thr Arg Asn Ile Asp Ala Thr Ser Thr Gly
            340                 345                 350

Asn Tyr Asn Tyr Lys Tyr Arg Tyr Leu Arg His Gly Lys Leu Arg Pro
            355                 360                 365

Phe Glu Arg Asp Ile Ser Asn Val Pro Phe Ser Pro Asp Gly Lys Pro
370                 375                 380

Cys Thr Pro Pro Ala Leu Asn Cys Tyr Trp Pro Leu Asn Asp Tyr Gly
385                 390                 395                 400

Phe Tyr Thr Thr Thr Gly Ile Gly Tyr Gln Pro Tyr Arg Val Val Val
                405                 410                 415

Leu Ser Phe Glu Leu Leu Asn Ala Pro Ala Thr Val Cys Gly Pro Lys
            420                 425                 430

Leu Ser Ala Ile Gly Gly Tyr Ile Pro Glu Ala Pro Arg Asp Gly Gln
            435                 440                 445

Ala Tyr Val Arg Lys Asp Gly Glu Trp Val Leu Leu Ser Thr Phe Leu
450                 455                 460

His His His His His His
465                 470
```

<210> SEQ ID NO 77
<211> LENGTH: 464
<212> TYPE: PRT
<213> ORGANISM: Artificial Sequence
<220> FEATURE:

<223> OTHER INFORMATION: RECOMBINANT SPIKE PROTEIN

<400> SEQUENCE: 77

```
Met Phe Val Phe Leu Val Leu Leu Pro Leu Val Ser Ser Arg Phe Pro
1               5                   10                  15

Asn Ile Thr Asn Leu Cys Pro Phe Gly Glu Val Phe Asn Ala Thr Arg
                20                  25                  30

Phe Ala Ser Val Tyr Ala Trp Asn Arg Lys Arg Ile Ser Asn Cys Val
            35                  40                  45

Ala Asp Tyr Ser Val Leu Tyr Asn Ser Ala Ser Phe Ser Thr Phe Lys
        50                  55                  60

Cys Tyr Gly Val Ser Pro Thr Lys Leu Asn Asp Leu Cys Phe Thr Asn
65                  70                  75                  80

Val Tyr Ala Asp Ser Phe Val Ile Arg Gly Asp Glu Val Arg Gln Ile
                85                  90                  95

Ala Pro Gly Gln Thr Gly Lys Ile Ala Asp Tyr Asn Tyr Lys Leu Pro
                100                 105                 110

Asp Asp Phe Thr Gly Cys Val Ile Ala Trp Asn Ser Asn Asn Leu Asp
            115                 120                 125

Ser Lys Val Gly Gly Asn Tyr Asn Tyr Leu Tyr Arg Leu Phe Arg Lys
        130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
            195                 200                 205

Thr Val Cys Gly Pro Lys Lys Ser Gly Gly Gly Ser Gly Gly Gly Ser
        210                 215                 220

Gly Gly Gly Ser Gly Gly Gly Ser Arg Phe Pro Asn Ile Thr Asn Leu
225                 230                 235                 240

Cys Pro Phe Gly Glu Val Phe Asn Ala Thr Lys Phe Pro Ser Val Tyr
                245                 250                 255

Ala Trp Glu Arg Lys Lys Ile Ser Asn Cys Val Ala Asp Tyr Ser Val
            260                 265                 270

Leu Tyr Asn Ser Thr Phe Phe Ser Thr Phe Lys Cys Tyr Gly Val Ser
        275                 280                 285

Ala Thr Lys Leu Asn Asp Leu Cys Phe Ser Asn Val Tyr Ala Asp Ser
        290                 295                 300

Phe Val Val Lys Gly Asp Asp Val Arg Gln Ile Ala Pro Gly Gln Thr
305                 310                 315                 320

Gly Val Ile Ala Asp Tyr Asn Tyr Lys Leu Pro Asp Asp Phe Met Gly
            325                 330                 335

Cys Val Leu Ala Trp Asn Thr Arg Asn Ile Asp Ala Thr Ser Thr Gly
            340                 345                 350

Asn Tyr Asn Tyr Lys Tyr Arg Tyr Leu Arg His Gly Lys Leu Arg Pro
            355                 360                 365

Phe Glu Arg Asp Ile Ser Asn Val Pro Phe Ser Pro Asp Gly Lys Pro
        370                 375                 380

Cys Thr Pro Pro Ala Leu Asn Cys Tyr Trp Pro Leu Asn Asp Tyr Gly
385                 390                 395                 400
```

Phe Tyr Thr Thr Thr Gly Ile Gly Tyr Gln Pro Tyr Arg Val Val Val
                405             410             415

Leu Ser Phe Glu Leu Leu Asn Ala Pro Ala Thr Val Cys Gly Pro Lys
            420             425             430

Leu Ser Ala Ile Gly Gly Tyr Ile Pro Glu Ala Pro Arg Asp Gly Gln
        435             440             445

Ala Tyr Val Arg Lys Asp Gly Glu Trp Val Leu Leu Ser Thr Phe Leu
    450             455             460

<210> SEQ ID NO 78
<211> LENGTH: 457
<212> TYPE: PRT
<213> ORGANISM: Artificial Sequence
<220> FEATURE:
<223> OTHER INFORMATION: RECOMBINANT SPIKE PROTEIN

<400> SEQUENCE: 78

Arg Phe Pro Asn Ile Thr Asn Leu Cys Pro Phe Gly Glu Val Phe Asn
1               5               10              15

Ala Thr Arg Phe Ala Ser Val Tyr Ala Trp Asn Arg Lys Arg Ile Ser
            20              25              30

Asn Cys Val Ala Asp Tyr Ser Val Leu Tyr Asn Ser Ala Ser Phe Ser
        35              40              45

Thr Phe Lys Cys Tyr Gly Val Ser Pro Thr Lys Leu Asn Asp Leu Cys
    50              55              60

Phe Thr Asn Val Tyr Ala Asp Ser Phe Val Ile Arg Gly Asp Glu Val
65              70              75              80

Arg Gln Ile Ala Pro Gly Gln Thr Gly Lys Ile Ala Asp Tyr Asn Tyr
                85              90              95

Lys Leu Pro Asp Asp Phe Thr Gly Cys Val Ile Ala Trp Asn Ser Asn
            100             105             110

Asn Leu Asp Ser Lys Val Gly Gly Asn Tyr Asn Tyr Leu Tyr Arg Leu
        115             120             125

Phe Arg Lys Ser Asn Leu Lys Pro Phe Glu Arg Asp Ile Ser Thr Glu
    130             135             140

Ile Tyr Gln Ala Gly Ser Thr Pro Cys Asn Gly Val Glu Gly Phe Asn
145             150             155             160

Cys Tyr Phe Pro Leu Gln Ser Tyr Gly Phe Gln Pro Thr Asn Gly Val
                165             170             175

Gly Tyr Gln Pro Tyr Arg Val Val Val Leu Ser Phe Glu Leu Leu His
            180             185             190

Ala Pro Ala Thr Val Cys Gly Pro Lys Lys Ser Gly Gly Gly Ser Gly
        195             200             205

Gly Gly Ser Gly Gly Gly Ser Gly Gly Gly Ser Arg Phe Pro Asn Ile
    210             215             220

Thr Asn Leu Cys Pro Phe Gly Glu Val Phe Asn Ala Thr Lys Phe Pro
225             230             235             240

Ser Val Tyr Ala Trp Glu Arg Lys Lys Ile Ser Asn Cys Val Ala Asp
                245             250             255

Tyr Ser Val Leu Tyr Asn Ser Thr Phe Phe Ser Thr Phe Lys Cys Tyr
            260             265             270

Gly Val Ser Ala Thr Lys Leu Asn Asp Leu Cys Phe Ser Asn Val Tyr
        275             280             285

Ala Asp Ser Phe Val Val Lys Gly Asp Asp Val Arg Gln Ile Ala Pro
    290             295             300

```
Gly Gln Thr Gly Val Ile Ala Asp Tyr Asn Tyr Lys Leu Pro Asp Asp
305             310             315             320

Phe Met Gly Cys Val Leu Ala Trp Asn Thr Arg Asn Ile Asp Ala Thr
            325             330             335

Ser Thr Gly Asn Tyr Asn Tyr Lys Tyr Arg Tyr Leu Arg His Gly Lys
            340             345             350

Leu Arg Pro Phe Glu Arg Asp Ile Ser Asn Val Pro Phe Ser Pro Asp
            355             360             365

Gly Lys Pro Cys Thr Pro Pro Ala Leu Asn Cys Tyr Trp Pro Leu Asn
            370             375             380

Asp Tyr Gly Phe Tyr Thr Thr Thr Gly Ile Gly Tyr Gln Pro Tyr Arg
385             390             395             400

Val Val Val Leu Ser Phe Glu Leu Leu Asn Ala Pro Ala Thr Val Cys
                405             410             415

Gly Pro Lys Leu Ser Ala Ile Gly Gly Tyr Ile Pro Glu Ala Pro Arg
            420             425             430

Asp Gly Gln Ala Tyr Val Arg Lys Asp Gly Glu Trp Val Leu Leu Ser
            435             440             445

Thr Phe Leu His His His His His His
    450             455
```

```
<210> SEQ ID NO 79
<211> LENGTH: 451
<212> TYPE: PRT
<213> ORGANISM: Artificial Sequence
<220> FEATURE:
<223> OTHER INFORMATION: RECOMBINANT SPIKE PROTEIN

<400> SEQUENCE: 79

Arg Phe Pro Asn Ile Thr Asn Leu Cys Pro Phe Gly Glu Val Phe Asn
1               5               10              15

Ala Thr Arg Phe Ala Ser Val Tyr Ala Trp Asn Arg Lys Arg Ile Ser
            20              25              30

Asn Cys Val Ala Asp Tyr Ser Val Leu Tyr Asn Ser Ala Ser Phe Ser
            35              40              45

Thr Phe Lys Cys Tyr Gly Val Ser Pro Thr Lys Leu Asn Asp Leu Cys
    50              55              60

Phe Thr Asn Val Tyr Ala Asp Ser Phe Val Ile Arg Gly Asp Glu Val
65              70              75              80

Arg Gln Ile Ala Pro Gly Gln Thr Gly Lys Ile Ala Asp Tyr Asn Tyr
            85              90              95

Lys Leu Pro Asp Asp Phe Thr Gly Cys Val Ile Ala Trp Asn Ser Asn
            100             105             110

Asn Leu Asp Ser Lys Val Gly Gly Asn Tyr Asn Tyr Leu Tyr Arg Leu
            115             120             125

Phe Arg Lys Ser Asn Leu Lys Pro Phe Glu Arg Asp Ile Ser Thr Glu
    130             135             140

Ile Tyr Gln Ala Gly Ser Thr Pro Cys Asn Gly Val Glu Gly Phe Asn
145             150             155             160

Cys Tyr Phe Pro Leu Gln Ser Tyr Gly Phe Gln Pro Thr Asn Gly Val
            165             170             175

Gly Tyr Gln Pro Tyr Arg Val Val Val Leu Ser Phe Glu Leu Leu His
            180             185             190

Ala Pro Ala Thr Val Cys Gly Pro Lys Lys Ser Gly Gly Gly Ser Gly
            195             200             205
```

```
Gly Gly Ser Gly Gly Gly Ser Gly Gly Gly Ser Arg Phe Pro Asn Ile
    210             215             220

Thr Asn Leu Cys Pro Phe Gly Glu Val Phe Asn Ala Thr Lys Phe Pro
225             230             235             240

Ser Val Tyr Ala Trp Glu Arg Lys Lys Ile Ser Asn Cys Val Ala Asp
            245             250             255

Tyr Ser Val Leu Tyr Asn Ser Thr Phe Phe Ser Thr Phe Lys Cys Tyr
            260             265             270

Gly Val Ser Ala Thr Lys Leu Asn Asp Leu Cys Phe Ser Asn Val Tyr
            275             280             285

Ala Asp Ser Phe Val Val Lys Gly Asp Asp Val Arg Gln Ile Ala Pro
    290             295             300

Gly Gln Thr Gly Val Ile Ala Asp Tyr Asn Tyr Lys Leu Pro Asp Asp
305             310             315             320

Phe Met Gly Cys Val Leu Ala Trp Asn Thr Arg Asn Ile Asp Ala Thr
            325             330             335

Ser Thr Gly Asn Tyr Asn Tyr Lys Tyr Arg Tyr Leu Arg His Gly Lys
            340             345             350

Leu Arg Pro Phe Glu Arg Asp Ile Ser Asn Val Pro Phe Ser Pro Asp
    355             360             365

Gly Lys Pro Cys Thr Pro Pro Ala Leu Asn Cys Tyr Trp Pro Leu Asn
    370             375             380

Asp Tyr Gly Phe Tyr Thr Thr Thr Gly Ile Gly Tyr Gln Pro Tyr Arg
385             390             395             400

Val Val Val Leu Ser Phe Glu Leu Leu Asn Ala Pro Ala Thr Val Cys
            405             410             415

Gly Pro Lys Leu Ser Ala Ile Gly Gly Tyr Ile Pro Glu Ala Pro Arg
            420             425             430

Asp Gly Gln Ala Tyr Val Arg Lys Asp Gly Glu Trp Val Leu Leu Ser
    435             440             445

Thr Phe Leu
    450

<210> SEQ ID NO 80
<211> LENGTH: 726
<212> TYPE: PRT
<213> ORGANISM: Artificial Sequence
<220> FEATURE:
<223> OTHER INFORMATION: RECOMBINANT SPIKE PROTEIN

<400> SEQUENCE: 80

Met Phe Val Phe Leu Val Leu Leu Pro Leu Val Ser Ser Arg Phe Pro
1               5               10              15

Asn Ile Thr Asn Leu Cys Pro Phe Gly Glu Val Phe Asn Ala Thr Arg
            20              25              30

Phe Ala Ser Val Tyr Ala Trp Asn Arg Lys Arg Ile Ser Asn Cys Val
            35              40              45

Ala Asp Tyr Ser Val Leu Tyr Asn Ser Ala Ser Phe Ser Thr Phe Lys
    50              55              60

Cys Tyr Gly Val Ser Pro Thr Lys Leu Asn Asp Leu Cys Phe Thr Asn
65              70              75              80

Val Tyr Ala Asp Ser Phe Val Ile Arg Gly Asp Glu Val Arg Gln Ile
            85              90              95

Ala Pro Gly Gln Thr Gly Lys Ile Ala Asp Tyr Asn Tyr Lys Leu Pro
            100             105             110
```

```
Asp Asp Phe Thr Gly Cys Val Ile Ala Trp Asn Ser Asn Asn Leu Asp
        115                 120                 125

Ser Lys Val Gly Gly Asn Tyr Asn Tyr Leu Tyr Arg Leu Phe Arg Lys
    130                 135                 140

Ser Asn Leu Lys Pro Phe Glu Arg Asp Ile Ser Thr Glu Ile Tyr Gln
145                 150                 155                 160

Ala Gly Ser Thr Pro Cys Asn Gly Val Glu Gly Phe Asn Cys Tyr Phe
                165                 170                 175

Pro Leu Gln Ser Tyr Gly Phe Gln Pro Thr Asn Gly Val Gly Tyr Gln
            180                 185                 190

Pro Tyr Arg Val Val Val Leu Ser Phe Glu Leu Leu His Ala Pro Ala
            195                 200                 205

Thr Val Cys Gly Pro Lys Lys Ser Gly Gly Gly Ser Gly Gly Gly Ser
    210                 215                 220

Gly Gly Gly Ser Gly Gly Gly Ser Phe Glu Ala Lys Pro Ser Gly Ser
225                 230                 235                 240

Val Val Ala Glu Gly Val Glu Cys Asp Phe Ser Pro Leu Leu Ser Gly
            245                 250                 255

Thr Pro Pro Gln Val Tyr Asn Phe Lys Arg Leu Val Phe Thr Asn Cys
            260                 265                 270

Asn Tyr Asn Leu Thr Lys Leu Leu Ser Leu Phe Ser Val Asn Asp Phe
    275                 280                 285

Thr Cys Ser Gln Ile Ser Pro Ala Ala Ile Ala Ser Asn Cys Tyr Ser
    290                 295                 300

Ser Leu Ile Leu Asp Tyr Phe Ser Tyr Pro Leu Ser Met Lys Ser Asp
305                 310                 315                 320

Leu Ser Val Ser Ser Ala Gly Pro Ile Ser Gln Phe Asn Tyr Lys Gln
            325                 330                 335

Ser Phe Ser Asn Pro Thr Cys Leu Ile Leu Ala Thr Val Pro His Asn
            340                 345                 350

Leu Thr Thr Ile Thr Lys Pro Leu Lys Tyr Ser Tyr Ile Asn Lys Cys
            355                 360                 365

Ser Arg Leu Leu Ser Asp Asp Arg Thr Glu Val Pro Gln Leu Val Asn
    370                 375                 380

Ala Asn Gln Tyr Ser Pro Cys Val Ser Ile Val Pro Ser Thr Val Trp
385                 390                 395                 400

Glu Asp Gly Asp Tyr Tyr Arg Lys Gln Leu Ser Pro Leu Glu Gly Gly
            405                 410                 415

Gly Trp Leu Val Ala Ser Gly Ser Thr Val Ala Met Thr Glu Gln Leu
            420                 425                 430

Gln Met Gly Phe Gly Ile Thr Val Gln Tyr Gly Thr Asp Thr Asn Ser
            435                 440                 445

Val Cys Pro Lys Leu Glu Phe Ala Asn Asp Thr Lys Ile Ala Ser Gln
    450                 455                 460

Leu Gly Asn Cys Val Glu Tyr Ser Gly Gly Gly Ser Gly Gly Gly Ser
465                 470                 475                 480

Gly Gly Gly Ser Gly Gly Gly Ser Arg Phe Pro Asn Ile Thr Asn Leu
            485                 490                 495

Cys Pro Phe Gly Glu Val Phe Asn Ala Thr Lys Phe Pro Ser Val Tyr
            500                 505                 510

Ala Trp Glu Arg Lys Lys Ile Ser Asn Cys Val Ala Asp Tyr Ser Val
            515                 520                 525

Leu Tyr Asn Ser Thr Phe Phe Ser Thr Phe Lys Cys Tyr Gly Val Ser
```

```
          530              535              540

Ala Thr Lys Leu Asn Asp Leu Cys Phe Ser Asn Val Tyr Ala Asp Ser
545                  550              555                  560

Phe Val Val Lys Gly Asp Asp Val Arg Gln Ile Ala Pro Gly Gln Thr
                 565              570              575

Gly Val Ile Ala Asp Tyr Asn Tyr Lys Leu Pro Asp Asp Phe Met Gly
                 580              585              590

Cys Val Leu Ala Trp Asn Thr Arg Asn Ile Asp Ala Thr Ser Thr Gly
                 595              600              605

Asn Tyr Asn Tyr Lys Tyr Arg Tyr Leu Arg His Gly Lys Leu Arg Pro
             610              615              620

Phe Glu Arg Asp Ile Ser Asn Val Pro Phe Ser Pro Asp Gly Lys Pro
625                  630              635                  640

Cys Thr Pro Pro Ala Leu Asn Cys Tyr Trp Pro Leu Asn Asp Tyr Gly
                 645              650              655

Phe Tyr Thr Thr Thr Gly Ile Gly Tyr Gln Pro Tyr Arg Val Val Val
                 660              665              670

Leu Ser Phe Glu Leu Leu Asn Ala Pro Ala Thr Val Cys Gly Pro Lys
                 675              680              685

Leu Ser Ala Ile Gly Gly Tyr Ile Pro Glu Ala Pro Arg Asp Gly Gln
             690              695              700

Ala Tyr Val Arg Lys Asp Gly Glu Trp Val Leu Leu Ser Thr Phe Leu
705                  710              715                  720

His His His His His His
                 725
```

```
<210> SEQ ID NO 81
<211> LENGTH: 720
<212> TYPE: PRT
<213> ORGANISM: Artificial Sequence
<220> FEATURE:
<223> OTHER INFORMATION: RECOMBINANT SPIKE PROTEIN

<400> SEQUENCE: 81

Met Phe Val Phe Leu Val Leu Leu Pro Leu Val Ser Ser Arg Phe Pro
1                5                10               15

Asn Ile Thr Asn Leu Cys Pro Phe Gly Glu Val Phe Asn Ala Thr Arg
                 20               25               30

Phe Ala Ser Val Tyr Ala Trp Asn Arg Lys Arg Ile Ser Asn Cys Val
                 35               40               45

Ala Asp Tyr Ser Val Leu Tyr Asn Ser Ala Ser Phe Ser Thr Phe Lys
     50               55               60

Cys Tyr Gly Val Ser Pro Thr Lys Leu Asn Asp Leu Cys Phe Thr Asn
65                   70               75                   80

Val Tyr Ala Asp Ser Phe Val Ile Arg Gly Asp Glu Val Arg Gln Ile
                 85               90               95

Ala Pro Gly Gln Thr Gly Lys Ile Ala Asp Tyr Asn Tyr Lys Leu Pro
                 100              105              110

Asp Asp Phe Thr Gly Cys Val Ile Ala Trp Asn Ser Asn Asn Leu Asp
                 115              120              125

Ser Lys Val Gly Gly Asn Tyr Asn Tyr Leu Tyr Arg Leu Phe Arg Lys
             130              135              140

Ser Asn Leu Lys Pro Phe Glu Arg Asp Ile Ser Thr Glu Ile Tyr Gln
145                  150              155                  160

Ala Gly Ser Thr Pro Cys Asn Gly Val Glu Gly Phe Asn Cys Tyr Phe
```

```
                165               170               175

Pro Leu Gln Ser Tyr Gly Phe Gln Pro Thr Asn Gly Val Gly Tyr Gln
            180               185               190

Pro Tyr Arg Val Val Val Leu Ser Phe Glu Leu Leu His Ala Pro Ala
            195               200               205

Thr Val Cys Gly Pro Lys Lys Ser Gly Gly Gly Ser Gly Gly Gly Ser
    210               215               220

Gly Gly Gly Ser Gly Gly Gly Ser Phe Glu Ala Lys Pro Ser Gly Ser
225               230               235               240

Val Val Ala Glu Gly Val Glu Cys Asp Phe Ser Pro Leu Leu Ser Gly
            245               250               255

Thr Pro Pro Gln Val Tyr Asn Phe Lys Arg Leu Val Phe Thr Asn Cys
            260               265               270

Asn Tyr Asn Leu Thr Lys Leu Leu Ser Leu Phe Ser Val Asn Asp Phe
            275               280               285

Thr Cys Ser Gln Ile Ser Pro Ala Ala Ile Ala Ser Asn Cys Tyr Ser
    290               295               300

Ser Leu Ile Leu Asp Tyr Phe Ser Tyr Pro Leu Ser Met Lys Ser Asp
305               310               315               320

Leu Ser Val Ser Ser Ala Gly Pro Ile Ser Gln Phe Asn Tyr Lys Gln
            325               330               335

Ser Phe Ser Asn Pro Thr Cys Leu Ile Leu Ala Thr Val Pro His Asn
            340               345               350

Leu Thr Thr Ile Thr Lys Pro Leu Lys Tyr Ser Tyr Ile Asn Lys Cys
            355               360               365

Ser Arg Leu Leu Ser Asp Asp Arg Thr Glu Val Pro Gln Leu Val Asn
    370               375               380

Ala Asn Gln Tyr Ser Pro Cys Val Ser Ile Val Pro Ser Thr Val Trp
385               390               395               400

Glu Asp Gly Asp Tyr Tyr Arg Lys Gln Leu Ser Pro Leu Glu Gly Gly
            405               410               415

Gly Trp Leu Val Ala Ser Gly Ser Thr Val Ala Met Thr Glu Gln Leu
            420               425               430

Gln Met Gly Phe Gly Ile Thr Val Gln Tyr Gly Thr Asp Thr Asn Ser
            435               440               445

Val Cys Pro Lys Leu Glu Phe Ala Asn Asp Thr Lys Ile Ala Ser Gln
    450               455               460

Leu Gly Asn Cys Val Glu Tyr Ser Gly Gly Gly Ser Gly Gly Gly Ser
465               470               475               480

Gly Gly Gly Ser Gly Gly Gly Ser Arg Phe Pro Asn Ile Thr Asn Leu
            485               490               495

Cys Pro Phe Gly Glu Val Phe Asn Ala Thr Lys Phe Pro Ser Val Tyr
            500               505               510

Ala Trp Glu Arg Lys Lys Ile Ser Asn Cys Val Ala Asp Tyr Ser Val
            515               520               525

Leu Tyr Asn Ser Thr Phe Phe Ser Thr Phe Lys Cys Tyr Gly Val Ser
            530               535               540

Ala Thr Lys Leu Asn Asp Leu Cys Phe Ser Asn Val Tyr Ala Asp Ser
545               550               555               560

Phe Val Val Lys Gly Asp Asp Val Arg Gln Ile Ala Pro Gly Gln Thr
            565               570               575

Gly Val Ile Ala Asp Tyr Asn Tyr Lys Leu Pro Asp Asp Phe Met Gly
            580               585               590
```

-continued

```
Cys Val Leu Ala Trp Asn Thr Arg Asn Ile Asp Ala Thr Ser Thr Gly
        595               600               605

Asn Tyr Asn Tyr Lys Tyr Arg Tyr Leu Arg His Gly Lys Leu Arg Pro
        610               615               620

Phe Glu Arg Asp Ile Ser Asn Val Pro Phe Ser Pro Asp Gly Lys Pro
625               630               635               640

Cys Thr Pro Pro Ala Leu Asn Cys Tyr Trp Pro Leu Asn Asp Tyr Gly
                645               650               655

Phe Tyr Thr Thr Thr Gly Ile Gly Tyr Gln Pro Tyr Arg Val Val Val
                660               665               670

Leu Ser Phe Glu Leu Leu Asn Ala Pro Ala Thr Val Cys Gly Pro Lys
        675               680               685

Leu Ser Ala Ile Gly Gly Tyr Ile Pro Glu Ala Pro Arg Asp Gly Gln
        690               695               700

Ala Tyr Val Arg Lys Asp Gly Glu Trp Val Leu Leu Ser Thr Phe Leu
705               710               715               720
```

```
<210> SEQ ID NO 82
<211> LENGTH: 713
<212> TYPE: PRT
<213> ORGANISM: Artificial Sequence
<220> FEATURE:
<223> OTHER INFORMATION: RECOMBINANT SPIKE PROTEIN

<400> SEQUENCE: 82
```

```
Arg Phe Pro Asn Ile Thr Asn Leu Cys Pro Phe Gly Glu Val Phe Asn
1               5               10               15

Ala Thr Arg Phe Ala Ser Val Tyr Ala Trp Asn Arg Lys Arg Ile Ser
                20               25               30

Asn Cys Val Ala Asp Tyr Ser Val Leu Tyr Asn Ser Ala Ser Phe Ser
        35               40               45

Thr Phe Lys Cys Tyr Gly Val Ser Pro Thr Lys Leu Asn Asp Leu Cys
        50               55               60

Phe Thr Asn Val Tyr Ala Asp Ser Phe Val Ile Arg Gly Asp Glu Val
65               70               75               80

Arg Gln Ile Ala Pro Gly Gln Thr Gly Lys Ile Ala Asp Tyr Asn Tyr
                85               90               95

Lys Leu Pro Asp Asp Phe Thr Gly Cys Val Ile Ala Trp Asn Ser Asn
        100               105               110

Asn Leu Asp Ser Lys Val Gly Gly Asn Tyr Asn Tyr Leu Tyr Arg Leu
        115               120               125

Phe Arg Lys Ser Asn Leu Lys Pro Phe Glu Arg Asp Ile Ser Thr Glu
        130               135               140

Ile Tyr Gln Ala Gly Ser Thr Pro Cys Asn Gly Val Glu Gly Phe Asn
145               150               155               160

Cys Tyr Phe Pro Leu Gln Ser Tyr Gly Phe Gln Pro Thr Asn Gly Val
                165               170               175

Gly Tyr Gln Pro Tyr Arg Val Val Val Leu Ser Phe Glu Leu Leu His
                180               185               190

Ala Pro Ala Thr Val Cys Gly Pro Lys Lys Ser Gly Gly Gly Ser Gly
        195               200               205

Gly Gly Ser Gly Gly Gly Ser Gly Gly Gly Ser Phe Glu Ala Lys Pro
        210               215               220

Ser Gly Ser Val Val Ala Glu Gly Val Glu Cys Asp Phe Ser Pro Leu
225               230               235               240
```

-continued

```
Leu Ser Gly Thr Pro Pro Gln Val Tyr Asn Phe Lys Arg Leu Val Phe
            245             250             255

Thr Asn Cys Asn Tyr Asn Leu Thr Lys Leu Leu Ser Leu Phe Ser Val
            260             265             270

Asn Asp Phe Thr Cys Ser Gln Ile Ser Pro Ala Ala Ile Ala Ser Asn
            275             280             285

Cys Tyr Ser Ser Leu Ile Leu Asp Tyr Phe Ser Tyr Pro Leu Ser Met
    290             295             300

Lys Ser Asp Leu Ser Val Ser Ser Ala Gly Pro Ile Ser Gln Phe Asn
305             310             315             320

Tyr Lys Gln Ser Phe Ser Asn Pro Thr Cys Leu Ile Leu Ala Thr Val
            325             330             335

Pro His Asn Leu Thr Thr Ile Thr Lys Pro Leu Lys Tyr Ser Tyr Ile
            340             345             350

Asn Lys Cys Ser Arg Leu Leu Ser Asp Asp Arg Thr Glu Val Pro Gln
            355             360             365

Leu Val Asn Ala Asn Gln Tyr Ser Pro Cys Val Ser Ile Val Pro Ser
    370             375             380

Thr Val Trp Glu Asp Gly Asp Tyr Tyr Arg Lys Gln Leu Ser Pro Leu
385             390             395             400

Glu Gly Gly Gly Trp Leu Val Ala Ser Gly Ser Thr Val Ala Met Thr
            405             410             415

Glu Gln Leu Gln Met Gly Phe Gly Ile Thr Val Gln Tyr Gly Thr Asp
            420             425             430

Thr Asn Ser Val Cys Pro Lys Leu Glu Phe Ala Asn Asp Thr Lys Ile
            435             440             445

Ala Ser Gln Leu Gly Asn Cys Val Glu Tyr Ser Gly Gly Gly Ser Gly
    450             455             460

Gly Gly Ser Gly Gly Gly Ser Gly Gly Gly Ser Arg Phe Pro Asn Ile
465             470             475             480

Thr Asn Leu Cys Pro Phe Gly Glu Val Phe Asn Ala Thr Lys Phe Pro
            485             490             495

Ser Val Tyr Ala Trp Glu Arg Lys Lys Ile Ser Asn Cys Val Ala Asp
            500             505             510

Tyr Ser Val Leu Tyr Asn Ser Thr Phe Phe Ser Thr Phe Lys Cys Tyr
            515             520             525

Gly Val Ser Ala Thr Lys Leu Asn Asp Leu Cys Phe Ser Asn Val Tyr
    530             535             540

Ala Asp Ser Phe Val Val Lys Gly Asp Asp Val Arg Gln Ile Ala Pro
545             550             555             560

Gly Gln Thr Gly Val Ile Ala Asp Tyr Asn Tyr Lys Leu Pro Asp Asp
            565             570             575

Phe Met Gly Cys Val Leu Ala Trp Asn Thr Arg Asn Ile Asp Ala Thr
            580             585             590

Ser Thr Gly Asn Tyr Asn Tyr Lys Tyr Arg Tyr Leu Arg His Gly Lys
            595             600             605

Leu Arg Pro Phe Glu Arg Asp Ile Ser Asn Val Pro Phe Ser Pro Asp
    610             615             620

Gly Lys Pro Cys Thr Pro Pro Ala Leu Asn Cys Tyr Trp Pro Leu Asn
625             630             635             640

Asp Tyr Gly Phe Tyr Thr Thr Thr Gly Ile Gly Tyr Gln Pro Tyr Arg
            645             650             655
```

-continued

```
Val Val Val Leu Ser Phe Glu Leu Leu Asn Ala Pro Ala Thr Val Cys
            660                 665                 670

Gly Pro Lys Leu Ser Ala Ile Gly Gly Tyr Ile Pro Glu Ala Pro Arg
            675                 680                 685

Asp Gly Gln Ala Tyr Val Arg Lys Asp Gly Glu Trp Val Leu Leu Ser
    690                 695                 700

Thr Phe Leu His His His His His His
705                 710
```

```
<210> SEQ ID NO 83
<211> LENGTH: 707
<212> TYPE: PRT
<213> ORGANISM: Artificial Sequence
<220> FEATURE:
<223> OTHER INFORMATION: RECOMBINANT SPIKE PROTEIN

<400> SEQUENCE: 83
```

```
Arg Phe Pro Asn Ile Thr Asn Leu Cys Pro Phe Gly Glu Val Phe Asn
1               5                   10                  15

Ala Thr Arg Phe Ala Ser Val Tyr Ala Trp Asn Arg Lys Arg Ile Ser
            20                  25                  30

Asn Cys Val Ala Asp Tyr Ser Val Leu Tyr Asn Ser Ala Ser Phe Ser
            35                  40                  45

Thr Phe Lys Cys Tyr Gly Val Ser Pro Thr Lys Leu Asn Asp Leu Cys
    50                  55                  60

Phe Thr Asn Val Tyr Ala Asp Ser Phe Val Ile Arg Gly Asp Glu Val
65                  70                  75                  80

Arg Gln Ile Ala Pro Gly Gln Thr Gly Lys Ile Ala Asp Tyr Asn Tyr
                85                  90                  95

Lys Leu Pro Asp Asp Phe Thr Gly Cys Val Ile Ala Trp Asn Ser Asn
            100                 105                 110

Asn Leu Asp Ser Lys Val Gly Gly Asn Tyr Asn Tyr Leu Tyr Arg Leu
            115                 120                 125

Phe Arg Lys Ser Asn Leu Lys Pro Phe Glu Arg Asp Ile Ser Thr Glu
    130                 135                 140

Ile Tyr Gln Ala Gly Ser Thr Pro Cys Asn Gly Val Glu Gly Phe Asn
145                 150                 155                 160

Cys Tyr Phe Pro Leu Gln Ser Tyr Gly Phe Gln Pro Thr Asn Gly Val
                165                 170                 175

Gly Tyr Gln Pro Tyr Arg Val Val Val Leu Ser Phe Glu Leu Leu His
            180                 185                 190

Ala Pro Ala Thr Val Cys Gly Pro Lys Lys Ser Gly Gly Gly Ser Gly
    195                 200                 205

Gly Gly Ser Gly Gly Gly Ser Gly Gly Gly Ser Phe Glu Ala Lys Pro
    210                 215                 220

Ser Gly Ser Val Val Ala Glu Gly Val Glu Cys Asp Phe Ser Pro Leu
225                 230                 235                 240

Leu Ser Gly Thr Pro Pro Gln Val Tyr Asn Phe Lys Arg Leu Val Phe
                245                 250                 255

Thr Asn Cys Asn Tyr Asn Leu Thr Lys Leu Leu Ser Leu Phe Ser Val
            260                 265                 270

Asn Asp Phe Thr Cys Ser Gln Ile Ser Pro Ala Ala Ile Ala Ser Asn
            275                 280                 285

Cys Tyr Ser Ser Leu Ile Leu Asp Tyr Phe Ser Tyr Pro Leu Ser Met
    290                 295                 300
```

```
Lys Ser Asp Leu Ser Val Ser Ser Ala Gly Pro Ile Ser Gln Phe Asn
305             310             315             320

Tyr Lys Gln Ser Phe Ser Asn Pro Thr Cys Leu Ile Leu Ala Thr Val
            325             330             335

Pro His Asn Leu Thr Thr Ile Thr Lys Pro Leu Lys Tyr Ser Tyr Ile
            340             345             350

Asn Lys Cys Ser Arg Leu Leu Ser Asp Asp Arg Thr Glu Val Pro Gln
            355             360             365

Leu Val Asn Ala Asn Gln Tyr Ser Pro Cys Val Ser Ile Val Pro Ser
            370             375             380

Thr Val Trp Glu Asp Gly Asp Tyr Tyr Arg Lys Gln Leu Ser Pro Leu
385             390             395             400

Glu Gly Gly Gly Trp Leu Val Ala Ser Gly Ser Thr Val Ala Met Thr
                405             410             415

Glu Gln Leu Gln Met Gly Phe Gly Ile Thr Val Gln Tyr Gly Thr Asp
            420             425             430

Thr Asn Ser Val Cys Pro Lys Leu Glu Phe Ala Asn Asp Thr Lys Ile
            435             440             445

Ala Ser Gln Leu Gly Asn Cys Val Glu Tyr Ser Gly Gly Gly Ser Gly
    450             455             460

Gly Gly Ser Gly Gly Gly Ser Gly Gly Gly Ser Arg Phe Pro Asn Ile
465             470             475             480

Thr Asn Leu Cys Pro Phe Gly Glu Val Phe Asn Ala Thr Lys Phe Pro
            485             490             495

Ser Val Tyr Ala Trp Glu Arg Lys Lys Ile Ser Asn Cys Val Ala Asp
            500             505             510

Tyr Ser Val Leu Tyr Asn Ser Thr Phe Phe Ser Thr Phe Lys Cys Tyr
            515             520             525

Gly Val Ser Ala Thr Lys Leu Asn Asp Leu Cys Phe Ser Asn Val Tyr
            530             535             540

Ala Asp Ser Phe Val Val Lys Gly Asp Asp Val Arg Gln Ile Ala Pro
545             550             555             560

Gly Gln Thr Gly Val Ile Ala Asp Tyr Asn Tyr Lys Leu Pro Asp Asp
            565             570             575

Phe Met Gly Cys Val Leu Ala Trp Asn Thr Arg Asn Ile Asp Ala Thr
            580             585             590

Ser Thr Gly Asn Tyr Asn Tyr Lys Tyr Arg Tyr Leu Arg His Gly Lys
            595             600             605

Leu Arg Pro Phe Glu Arg Asp Ile Ser Asn Val Pro Phe Ser Pro Asp
    610             615             620

Gly Lys Pro Cys Thr Pro Pro Ala Leu Asn Cys Tyr Trp Pro Leu Asn
625             630             635             640

Asp Tyr Gly Phe Tyr Thr Thr Thr Gly Ile Gly Tyr Gln Pro Tyr Arg
            645             650             655

Val Val Val Leu Ser Phe Glu Leu Leu Asn Ala Pro Ala Thr Val Cys
            660             665             670

Gly Pro Lys Leu Ser Ala Ile Gly Gly Tyr Ile Pro Glu Ala Pro Arg
            675             680             685

Asp Gly Gln Ala Tyr Val Arg Lys Asp Gly Glu Trp Val Leu Leu Ser
    690             695             700

Thr Phe Leu
705
```

-continued

<210> SEQ ID NO 84
<211> LENGTH: 1273
<212> TYPE: PRT
<213> ORGANISM: Artificial Sequence
<220> FEATURE:
<223> OTHER INFORMATION: RECOMBINANT SPIKE PROTEIN

<400> SEQUENCE: 84

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
```

-continued

```
                370                 375                 380
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
                450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
                675                 680                 685

Ser Gln Ser Ile Ile Ala Tyr Thr Met Ser Leu Gly Ala Glu Asn Ser
                690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
                770                 775                 780

Val Lys Gln Ile Tyr Lys Thr Pro Pro Ile Lys Asp Phe Gly Gly Phe
785                 790                 795                 800
```

-continued

```
Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200
```

```
Gly Lys Tyr Glu Gln Tyr Ile  Lys Trp Pro Trp Tyr  Ile Trp Leu
    1205            1210             1215

Gly Phe Ile Ala Gly Leu Ile  Ala Ile Val Met Val  Thr Ile Met
    1220            1225             1230

Leu Cys Cys Met Thr Ser Cys  Cys Ser Cys Leu Lys  Gly Cys Cys
    1235            1240             1245

Ser Cys Gly Ser Cys Cys Lys  Phe Asp Glu Asp Asp  Ser Glu Pro
    1250            1255             1260

Val Leu Lys Gly Val Lys Leu  His Tyr Thr
    1265            1270

<210> SEQ ID NO 85
<211> LENGTH: 1260
<212> TYPE: PRT
<213> ORGANISM: Artificial Sequence
<220> FEATURE:
<223> OTHER INFORMATION: RECOMBINANT SPIKE PROTEIN

<400> SEQUENCE: 85

Gln Cys Val Asn Leu Thr Thr Arg Thr Gln Leu Pro Pro Ala Tyr Thr
1                5                  10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
            85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
            165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
            245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285
```

-continued

```
Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
```

```
705                    710                    715                    720

Thr Ser Val Asp Cys Thr Met Tyr Ile Cys Gly Asp Ser Thr Glu Cys
                725                    730                    735

Ser Asn Leu Leu Leu Gln Tyr Gly Ser Phe Cys Thr Gln Leu Asn Arg
                740                    745                    750

Ala Leu Thr Gly Ile Ala Val Glu Gln Asp Lys Asn Thr Gln Glu Val
                755                    760                    765

Phe Ala Gln Val Lys Gln Ile Tyr Lys Thr Pro Pro Ile Lys Asp Phe
        770                    775                    780

Gly Gly Phe Asn Phe Ser Gln Ile Leu Pro Asp Pro Ser Lys Pro Ser
785                    790                    795                    800

Lys Arg Ser Phe Ile Glu Asp Leu Leu Phe Asn Lys Val Thr Leu Ala
                805                    810                    815

Asp Ala Gly Phe Ile Lys Gln Tyr Gly Asp Cys Leu Gly Asp Ile Ala
                820                    825                    830

Ala Arg Asp Leu Ile Cys Ala Gln Lys Phe Asn Gly Leu Thr Val Leu
                835                    840                    845

Pro Pro Leu Leu Thr Asp Glu Met Ile Ala Gln Tyr Thr Ser Ala Leu
        850                    855                    860

Leu Ala Gly Thr Ile Thr Ser Gly Trp Thr Phe Gly Ala Gly Ala Ala
865                    870                    875                    880

Leu Gln Ile Pro Phe Ala Met Gln Met Ala Tyr Arg Phe Asn Gly Ile
                885                    890                    895

Gly Val Thr Gln Asn Val Leu Tyr Glu Asn Gln Lys Leu Ile Ala Asn
                900                    905                    910

Gln Phe Asn Ser Ala Ile Gly Lys Ile Gln Asp Ser Leu Ser Ser Thr
        915                    920                    925

Ala Ser Ala Leu Gly Lys Leu Gln Asp Val Val Asn Gln Asn Ala Gln
        930                    935                    940

Ala Leu Asn Thr Leu Val Lys Gln Leu Ser Ser Asn Phe Gly Ala Ile
945                    950                    955                    960

Ser Ser Val Leu Asn Asp Ile Leu Ser Arg Leu Asp Pro Pro Glu Ala
                965                    970                    975

Glu Val Gln Ile Asp Arg Leu Ile Thr Gly Arg Leu Gln Ser Leu Gln
                980                    985                    990

Thr Tyr Val Thr Gln Gln Leu Ile Arg Ala Ala Glu Ile Arg Ala Ser
        995                    1000                    1005

Ala Asn Leu Ala Ala Thr Lys Met Ser Glu Cys Val Leu Gly Gln
        1010                    1015                    1020

Ser Lys Arg Val Asp Phe Cys Gly Lys Gly Tyr His Leu Met Ser
        1025                    1030                    1035

Phe Pro Gln Ser Ala Pro His Gly Val Val Phe Leu His Val Thr
        1040                    1045                    1050

Tyr Val Pro Ala Gln Glu Lys Asn Phe Thr Thr Ala Pro Ala Ile
        1055                    1060                    1065

Cys His Asp Gly Lys Ala His Phe Pro Arg Glu Gly Val Phe Val
        1070                    1075                    1080

Ser Asn Gly Thr His Trp Phe Val Thr Gln Arg Asn Phe Tyr Glu
        1085                    1090                    1095

Pro Gln Ile Ile Thr Thr Asp Asn Thr Phe Val Ser Gly Asn Cys
        1100                    1105                    1110

Asp Val Val Ile Gly Ile Val Asn Asn Thr Val Tyr Asp Pro Leu
        1115                    1120                    1125
```

-continued

```
Gln Pro  Glu Leu Asp Ser Phe  Lys Glu Glu Leu Asp  Lys Tyr Phe
    1130             1135              1140

Lys Asn  His Thr Ser Pro Asp  Val Asp Leu Gly Asp  Ile Ser Gly
    1145             1150              1155

Ile Asn  Ala Ser Val Val Asn  Ile Gln Lys Glu Ile  Asp Arg Leu
    1160             1165              1170

Asn Glu  Val Ala Lys Asn Leu  Asn Glu Ser Leu Ile  Asp Leu Gln
    1175             1180              1185

Glu Leu  Gly Lys Tyr Glu Gln  Tyr Ile Lys Trp Pro  Trp Tyr Ile
    1190             1195              1200

Trp Leu  Gly Phe Ile Ala Gly  Leu Ile Ala Ile Val  Met Val Thr
    1205             1210              1215

Ile Met  Leu Cys Cys Met Thr  Ser Cys Cys Ser Cys  Leu Lys Gly
    1220             1225              1230

Cys Cys  Ser Cys Gly Ser Cys  Cys Lys Phe Asp Glu  Asp Asp Ser
    1235             1240              1245

Glu Pro  Val Leu Lys Gly Val  Lys Leu His Tyr Thr
    1250             1255              1260
```

```
<210> SEQ ID NO 86
<211> LENGTH: 1273
<212> TYPE: PRT
<213> ORGANISM: Artificial Sequence
<220> FEATURE:
<223> OTHER INFORMATION: RECOMBINANT SPIKE PROTEIN

<400> SEQUENCE: 86

Met Phe Val Phe Leu Val Leu Leu Pro Leu Val Ser Ser Gln Cys Val
1                5               10               15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
            85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220
```

-continued

```
Pro Leu Val Asp Leu Pro Ile Gly Ile Asn Ile Thr Arg Phe Gln Thr
225             230                 235             240

Leu Leu Ala Leu His Arg Ser Tyr Leu Thr Pro Gly Asp Ser Ser Ser
            245                 250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
        290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
        370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
        450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
        530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
        610             615             620

His Ala Asp Gln Leu Thr Pro Thr Trp Arg Val Tyr Ser Thr Gly Ser
625             630             635             640
```

-continued

```
Asn Val Phe Gln Thr Arg Ala Gly Cys Leu Ile Gly Ala Glu His Val
              645               650               655

Asn Asn Ser Tyr Glu Cys Asp Ile Pro Ile Gly Ala Gly Ile Cys Ala
              660               665               670

Ser Tyr Gln Thr Gln Thr Asn Ser Pro Gln Gln Ala Gln Ser Val Ala
              675               680               685

Ser Gln Ser Ile Ile Ala Tyr Thr Met Ser Leu Gly Ala Glu Asn Ser
     690               695               700

Val Ala Tyr Ser Asn Asn Ser Ile Ala Ile Pro Thr Asn Phe Thr Ile
705               710               715               720

Ser Val Thr Thr Glu Ile Leu Pro Val Ser Met Thr Lys Thr Ser Val
              725               730               735

Asp Cys Thr Met Tyr Ile Cys Gly Asp Ser Thr Glu Cys Ser Asn Leu
              740               745               750

Leu Leu Gln Tyr Gly Ser Phe Cys Thr Gln Leu Asn Arg Ala Leu Thr
              755               760               765

Gly Ile Ala Val Glu Gln Asp Lys Asn Thr Gln Glu Val Phe Ala Gln
     770               775               780

Val Lys Gln Ile Tyr Lys Thr Pro Pro Ile Lys Asp Phe Gly Gly Phe
785               790               795               800

Asn Phe Ser Gln Ile Leu Pro Asp Pro Ser Lys Pro Ser Lys Arg Ser
              805               810               815

Phe Ile Glu Asp Leu Leu Phe Asn Lys Val Thr Leu Ala Asp Ala Gly
              820               825               830

Phe Ile Lys Gln Tyr Gly Asp Cys Leu Gly Asp Ile Ala Ala Arg Asp
              835               840               845

Leu Ile Cys Ala Gln Lys Phe Asn Gly Leu Thr Val Leu Pro Pro Leu
     850               855               860

Leu Thr Asp Glu Met Ile Ala Gln Tyr Thr Ser Ala Leu Leu Ala Gly
865               870               875               880

Thr Ile Thr Ser Gly Trp Thr Phe Gly Ala Gly Ala Ala Leu Gln Ile
              885               890               895

Pro Phe Ala Met Gln Met Ala Tyr Arg Phe Asn Gly Ile Gly Val Thr
              900               905               910

Gln Asn Val Leu Tyr Glu Asn Gln Lys Leu Ile Ala Asn Gln Phe Asn
              915               920               925

Ser Ala Ile Gly Lys Ile Gln Asp Ser Leu Ser Ser Thr Ala Ser Ala
     930               935               940

Leu Gly Lys Leu Gln Asp Val Val Asn Gln Asn Ala Gln Ala Leu Asn
945               950               955               960

Thr Leu Val Lys Gln Leu Ser Ser Asn Phe Gly Ala Ile Ser Ser Val
              965               970               975

Leu Asn Asp Ile Leu Ser Arg Leu Asp Pro Pro Glu Ala Glu Val Gln
              980               985               990

Ile Asp Arg Leu Ile Thr Gly Arg  Leu Gln Ser Leu Gln  Thr Tyr Val
          995               1000               1005

Thr Gln  Gln Leu Ile Arg Ala  Ala Glu Ile Arg Ala  Ser Ala Asn
    1010               1015               1020

Leu Ala  Ala Thr Lys Met Ser  Glu Cys Val Leu Gly  Gln Ser Lys
    1025               1030               1035

Arg Val  Asp Phe Cys Gly Lys  Gly Tyr His Leu Met  Ser Phe Pro
    1040               1045               1050

Gln Ser  Ala Pro His Gly Val  Val Phe Leu His Val  Thr Tyr Val
```

-continued

```
        1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Tyr Ile  Lys Trp Pro Trp Tyr  Ile Trp Leu
    1205                1210                1215

Gly Phe  Ile Ala Gly Leu Ile  Ala Ile Val Met Val  Thr Ile Met
    1220                1225                1230

Leu Cys  Cys Met Thr Ser Cys  Cys Ser Cys Leu Lys  Gly Cys Cys
    1235                1240                1245

Ser Cys  Gly Ser Cys Cys Lys  Phe Asp Glu Asp Asp  Ser Glu Pro
    1250                1255                1260

Val Leu  Lys Gly Val Lys Leu  His Tyr Thr
    1265                1270
```

```
<210> SEQ ID NO 87
<211> LENGTH: 1260
<212> TYPE: PRT
<213> ORGANISM: Artificial Sequence
<220> FEATURE:
<223> OTHER INFORMATION: RECOMBINANT SPIKE PROTEIN

<400> SEQUENCE: 87

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
```

-continued

```
        130                  135                  140

Arg Val Tyr Ser Ser Ala Asn Asn Cys Thr Phe Glu Tyr Val Ser Gln
145                 150                  155                  160

Pro Phe Leu Met Asp Leu Glu Gly Lys Gln Gly Asn Phe Lys Asn Leu
                165                  170                  175

Arg Glu Phe Val Phe Lys Asn Ile Asp Gly Tyr Phe Lys Ile Tyr Ser
                180                  185                  190

Lys His Thr Pro Ile Asn Leu Val Arg Asp Leu Pro Gln Gly Phe Ser
                195                  200                  205

Ala Leu Glu Pro Leu Val Asp Leu Pro Ile Gly Ile Asn Ile Thr Arg
        210                  215                  220

Phe Gln Thr Leu Leu Ala Leu His Arg Ser Tyr Leu Thr Pro Gly Asp
225                 230                  235                  240

Ser Ser Ser Gly Trp Thr Ala Gly Ala Ala Ala Tyr Tyr Val Gly Tyr
                245                  250                  255

Leu Gln Pro Arg Thr Phe Leu Leu Lys Tyr Asn Glu Asn Gly Thr Ile
                260                  265                  270

Thr Asp Ala Val Asp Cys Ala Leu Asp Pro Leu Ser Glu Thr Lys Cys
                275                  280                  285

Thr Leu Lys Ser Phe Thr Val Glu Lys Gly Ile Tyr Gln Thr Ser Asn
        290                  295                  300

Phe Arg Val Gln Pro Thr Glu Ser Ile Val Arg Phe Pro Asn Ile Thr
305                 310                  315                  320

Asn Leu Cys Pro Phe Gly Glu Val Phe Asn Ala Thr Arg Phe Ala Ser
                325                  330                  335

Val Tyr Ala Trp Asn Arg Lys Arg Ile Ser Asn Cys Val Ala Asp Tyr
                340                  345                  350

Ser Val Leu Tyr Asn Ser Ala Ser Phe Ser Thr Phe Lys Cys Tyr Gly
                355                  360                  365

Val Ser Pro Thr Lys Leu Asn Asp Leu Cys Phe Thr Asn Val Tyr Ala
        370                  375                  380

Asp Ser Phe Val Ile Arg Gly Asp Glu Val Arg Gln Ile Ala Pro Gly
385                 390                  395                  400

Gln Thr Gly Lys Ile Ala Asp Tyr Asn Tyr Lys Leu Pro Asp Asp Phe
                405                  410                  415

Thr Gly Cys Val Ile Ala Trp Asn Ser Asn Asn Leu Asp Ser Lys Val
                420                  425                  430

Gly Gly Asn Tyr Asn Tyr Leu Tyr Arg Leu Phe Arg Lys Ser Asn Leu
                435                  440                  445

Lys Pro Phe Glu Arg Asp Ile Ser Thr Glu Ile Tyr Gln Ala Gly Ser
        450                  455                  460

Thr Pro Cys Asn Gly Val Glu Gly Phe Asn Cys Tyr Phe Pro Leu Gln
465                 470                  475                  480

Ser Tyr Gly Phe Gln Pro Thr Asn Gly Val Gly Tyr Gln Pro Tyr Arg
                485                  490                  495

Val Val Val Leu Ser Phe Glu Leu Leu His Ala Pro Ala Thr Val Cys
                500                  505                  510

Gly Pro Lys Lys Ser Thr Asn Leu Val Lys Asn Lys Cys Val Asn Phe
                515                  520                  525

Asn Phe Asn Gly Leu Thr Gly Thr Gly Val Leu Thr Glu Ser Asn Lys
        530                  535                  540

Lys Phe Leu Pro Phe Gln Gln Phe Gly Arg Asp Ile Ala Asp Thr Thr
545                 550                  555                  560
```

```
Asp Ala Val Arg Asp Pro Gln Thr Leu Glu Ile Leu Asp Ile Thr Pro
            565             570             575

Cys Ser Phe Gly Gly Val Ser Val Ile Thr Pro Gly Thr Asn Thr Ser
            580             585             590

Asn Gln Val Ala Val Leu Tyr Gln Asp Val Asn Cys Thr Glu Val Pro
        595             600             605

Val Ala Ile His Ala Asp Gln Leu Thr Pro Thr Trp Arg Val Tyr Ser
        610             615             620

Thr Gly Ser Asn Val Phe Gln Thr Arg Ala Gly Cys Leu Ile Gly Ala
625             630             635             640

Glu His Val Asn Asn Ser Tyr Glu Cys Asp Ile Pro Ile Gly Ala Gly
            645             650             655

Ile Cys Ala Ser Tyr Gln Thr Gln Thr Asn Ser Pro Gln Gln Ala Gln
            660             665             670

Ser Val Ala Ser Gln Ser Ile Ile Ala Tyr Thr Met Ser Leu Gly Ala
            675             680             685

Glu Asn Ser Val Ala Tyr Ser Asn Asn Ser Ile Ala Ile Pro Thr Asn
        690             695             700

Phe Thr Ile Ser Val Thr Thr Glu Ile Leu Pro Val Ser Met Thr Lys
705             710             715             720

Thr Ser Val Asp Cys Thr Met Tyr Ile Cys Gly Asp Ser Thr Glu Cys
            725             730             735

Ser Asn Leu Leu Leu Gln Tyr Gly Ser Phe Cys Thr Gln Leu Asn Arg
            740             745             750

Ala Leu Thr Gly Ile Ala Val Glu Gln Asp Lys Asn Thr Gln Glu Val
            755             760             765

Phe Ala Gln Val Lys Gln Ile Tyr Lys Thr Pro Pro Ile Lys Asp Phe
        770             775             780

Gly Gly Phe Asn Phe Ser Gln Ile Leu Pro Asp Pro Ser Lys Pro Ser
785             790             795             800

Lys Arg Ser Phe Ile Glu Asp Leu Leu Phe Asn Lys Val Thr Leu Ala
            805             810             815

Asp Ala Gly Phe Ile Lys Gln Tyr Gly Asp Cys Leu Gly Asp Ile Ala
            820             825             830

Ala Arg Asp Leu Ile Cys Ala Gln Lys Phe Asn Gly Leu Thr Val Leu
            835             840             845

Pro Pro Leu Leu Thr Asp Glu Met Ile Ala Gln Tyr Thr Ser Ala Leu
        850             855             860

Leu Ala Gly Thr Ile Thr Ser Gly Trp Thr Phe Gly Ala Gly Ala Ala
865             870             875             880

Leu Gln Ile Pro Phe Ala Met Gln Met Ala Tyr Arg Phe Asn Gly Ile
            885             890             895

Gly Val Thr Gln Asn Val Leu Tyr Glu Asn Gln Lys Leu Ile Ala Asn
            900             905             910

Gln Phe Asn Ser Ala Ile Gly Lys Ile Gln Asp Ser Leu Ser Ser Thr
            915             920             925

Ala Ser Ala Leu Gly Lys Leu Gln Asp Val Val Asn Gln Asn Ala Gln
        930             935             940

Ala Leu Asn Thr Leu Val Lys Gln Leu Ser Ser Asn Phe Gly Ala Ile
945             950             955             960

Ser Ser Val Leu Asn Asp Ile Leu Ser Arg Leu Asp Pro Pro Glu Ala
            965             970             975
```

-continued

```
Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155

Ile Asn  Ala Ser Val Val Asn  Ile Gln Lys Glu Ile  Asp Arg Leu
    1160                1165                1170

Asn Glu  Val Ala Lys Asn Leu  Asn Glu Ser Leu Ile  Asp Leu Gln
    1175                1180                1185

Glu Leu  Gly Lys Tyr Glu Gln  Tyr Ile Lys Trp Pro  Trp Tyr Ile
    1190                1195                1200

Trp Leu  Gly Phe Ile Ala Gly  Leu Ile Ala Ile Val  Met Val Thr
    1205                1210                1215

Ile Met  Leu Cys Cys Met Thr  Ser Cys Cys Ser Cys  Leu Lys Gly
    1220                1225                1230

Cys Cys  Ser Cys Gly Ser Cys  Cys Lys Phe Asp Glu  Asp Asp Ser
    1235                1240                1245

Glu Pro  Val Leu Lys Gly Val  Lys Leu His Tyr Thr
    1250                1255                1260
```

```
<210> SEQ ID NO 88
<211> LENGTH: 1219
<212> TYPE: PRT
<213> ORGANISM: Artificial Sequence
<220> FEATURE:
<223> OTHER INFORMATION: RECOMBINANT SPIKE PROTEIN

<400> SEQUENCE: 88

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

-continued

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
        130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
        370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly

-continued

```
                    485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
        530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
        610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gln Gln Ala Gln Ser Val Ala
            675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
        850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910
```

-continued

```
Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn
        1010                1015                1020

Leu Ala Ala Thr Lys Met Ser Glu Cys Val Leu Gly Gln Ser Lys
        1025                1030                1035

Arg Val Asp Phe Cys Gly Lys Gly Tyr His Leu Met Ser Phe Pro
        1040                1045                1050

Gln Ser Ala Pro His Gly Val Val Phe Leu His Val Thr Tyr Val
        1055                1060                1065

Pro Ala Gln Glu Lys Asn Phe Thr Thr Ala Pro Ala Ile Cys His
        1070                1075                1080

Asp Gly Lys Ala His Phe Pro Arg Glu Gly Val Phe Val Ser Asn
        1085                1090                1095

Gly Thr His Trp Phe Val Thr Gln Arg Asn Phe Tyr Glu Pro Gln
        1100                1105                1110

Ile Ile Thr Thr Asp Asn Thr Phe Val Ser Gly Asn Cys Asp Val
        1115                1120                1125

Val Ile Gly Ile Val Asn Asn Thr Val Tyr Asp Pro Leu Gln Pro
        1130                1135                1140

Glu Leu Asp Ser Phe Lys Glu Glu Leu Asp Lys Tyr Phe Lys Asn
        1145                1150                1155

His Thr Ser Pro Asp Val Asp Leu Gly Asp Ile Ser Gly Ile Asn
        1160                1165                1170

Ala Ser Val Val Asn Ile Gln Lys Glu Ile Asp Arg Leu Asn Glu
        1175                1180                1185

Val Ala Lys Asn Leu Asn Glu Ser Leu Ile Asp Leu Gln Glu Leu
        1190                1195                1200

Gly Lys Tyr Glu Gln Tyr Ile Lys Trp Pro His His His His His
        1205                1210                1215

His
```

```
<210> SEQ ID NO 89
<211> LENGTH: 1206
<212> TYPE: PRT
<213> ORGANISM: Artificial Sequence
<220> FEATURE:
<223> OTHER INFORMATION: RECOMBINANT SPIKE PROTEIN

<400> SEQUENCE: 89

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30
```

-continued

```
Ser Val Leu His Ser Thr Gln Asp Leu Phe Leu Pro Phe Phe Ser Asn
        35              40              45

Val Thr Trp Phe His Ala Ile His Val Ser Gly Thr Asn Gly Thr Lys
    50              55              60

Arg Phe Asp Asn Pro Val Leu Pro Phe Asn Asp Gly Val Tyr Phe Ala
65              70              75              80

Ser Thr Glu Lys Ser Asn Ile Ile Arg Gly Trp Ile Phe Gly Thr Thr
            85              90              95

Leu Asp Ser Lys Thr Gln Ser Leu Leu Ile Val Asn Asn Ala Thr Asn
            100             105             110

Val Val Ile Lys Val Cys Glu Phe Gln Phe Cys Asn Asp Pro Phe Leu
            115             120             125

Gly Val Tyr Tyr His Lys Asn Asn Lys Ser Trp Met Glu Ser Glu Phe
    130             135             140

Arg Val Tyr Ser Ser Ala Asn Asn Cys Thr Phe Glu Tyr Val Ser Gln
145             150             155             160

Pro Phe Leu Met Asp Leu Glu Gly Lys Gln Gly Asn Phe Lys Asn Leu
            165             170             175

Arg Glu Phe Val Phe Lys Asn Ile Asp Gly Tyr Phe Lys Ile Tyr Ser
            180             185             190

Lys His Thr Pro Ile Asn Leu Val Arg Asp Leu Pro Gln Gly Phe Ser
    195             200             205

Ala Leu Glu Pro Leu Val Asp Leu Pro Ile Gly Ile Asn Ile Thr Arg
    210             215             220

Phe Gln Thr Leu Leu Ala Leu His Arg Ser Tyr Leu Thr Pro Gly Asp
225             230             235             240

Ser Ser Ser Gly Trp Thr Ala Gly Ala Ala Ala Tyr Tyr Val Gly Tyr
            245             250             255

Leu Gln Pro Arg Thr Phe Leu Leu Lys Tyr Asn Glu Asn Gly Thr Ile
            260             265             270

Thr Asp Ala Val Asp Cys Ala Leu Asp Pro Leu Ser Glu Thr Lys Cys
            275             280             285

Thr Leu Lys Ser Phe Thr Val Glu Lys Gly Ile Tyr Gln Thr Ser Asn
    290             295             300

Phe Arg Val Gln Pro Thr Glu Ser Ile Val Arg Phe Pro Asn Ile Thr
305             310             315             320

Asn Leu Cys Pro Phe Gly Glu Val Phe Asn Ala Thr Arg Phe Ala Ser
            325             330             335

Val Tyr Ala Trp Asn Arg Lys Arg Ile Ser Asn Cys Val Ala Asp Tyr
            340             345             350

Ser Val Leu Tyr Asn Ser Ala Ser Phe Ser Thr Phe Lys Cys Tyr Gly
            355             360             365

Val Ser Pro Thr Lys Leu Asn Asp Leu Cys Phe Thr Asn Val Tyr Ala
    370             375             380

Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
            405             410             415

Thr Gly Cys Val Ile Ala Trp Asn Ser Asn Asn Leu Asp Ser Lys Val
            420             425             430

Gly Gly Asn Tyr Asn Tyr Leu Tyr Arg Leu Phe Arg Lys Ser Asn Leu
            435             440             445

Lys Pro Phe Glu Arg Asp Ile Ser Thr Glu Ile Tyr Gln Ala Gly Ser
```

```
          450               455               460
Thr Pro Cys Asn Gly Val Glu Gly Phe Asn Cys Tyr Phe Pro Leu Gln
465               470               475               480

Ser Tyr Gly Phe Gln Pro Thr Asn Gly Val Gly Tyr Gln Pro Tyr Arg
              485               490               495

Val Val Val Leu Ser Phe Glu Leu Leu His Ala Pro Ala Thr Val Cys
              500               505               510

Gly Pro Lys Lys Ser Thr Asn Leu Val Lys Asn Lys Cys Val Asn Phe
              515               520               525

Asn Phe Asn Gly Leu Thr Gly Thr Gly Val Leu Thr Glu Ser Asn Lys
              530               535               540

Lys Phe Leu Pro Phe Gln Gln Phe Gly Arg Asp Ile Ala Asp Thr Thr
545               550               555               560

Asp Ala Val Arg Asp Pro Gln Thr Leu Glu Ile Leu Asp Ile Thr Pro
              565               570               575

Cys Ser Phe Gly Gly Val Ser Val Ile Thr Pro Gly Thr Asn Thr Ser
              580               585               590

Asn Gln Val Ala Val Leu Tyr Gln Asp Val Asn Cys Thr Glu Val Pro
              595               600               605

Val Ala Ile His Ala Asp Gln Leu Thr Pro Thr Trp Arg Val Tyr Ser
              610               615               620

Thr Gly Ser Asn Val Phe Gln Thr Arg Ala Gly Cys Leu Ile Gly Ala
625               630               635               640

Glu His Val Asn Asn Ser Tyr Glu Cys Asp Ile Pro Ile Gly Ala Gly
              645               650               655

Ile Cys Ala Ser Tyr Gln Thr Gln Thr Asn Ser Pro Gln Gln Ala Gln
              660               665               670

Ser Val Ala Ser Gln Ser Ile Ile Ala Tyr Thr Met Ser Leu Gly Ala
              675               680               685

Glu Asn Ser Val Ala Tyr Ser Asn Asn Ser Ile Ala Ile Pro Thr Asn
              690               695               700

Phe Thr Ile Ser Val Thr Thr Glu Ile Leu Pro Val Ser Met Thr Lys
705               710               715               720

Thr Ser Val Asp Cys Thr Met Tyr Ile Cys Gly Asp Ser Thr Glu Cys
              725               730               735

Ser Asn Leu Leu Leu Gln Tyr Gly Ser Phe Cys Thr Gln Leu Asn Arg
              740               745               750

Ala Leu Thr Gly Ile Ala Val Glu Gln Asp Lys Asn Thr Gln Glu Val
              755               760               765

Phe Ala Gln Val Lys Gln Ile Tyr Lys Thr Pro Pro Ile Lys Asp Phe
              770               775               780

Gly Gly Phe Asn Phe Ser Gln Ile Leu Pro Asp Pro Ser Lys Pro Ser
785               790               795               800

Lys Arg Ser Phe Ile Glu Asp Leu Leu Phe Asn Lys Val Thr Leu Ala
              805               810               815

Asp Ala Gly Phe Ile Lys Gln Tyr Gly Asp Cys Leu Gly Asp Ile Ala
              820               825               830

Ala Arg Asp Leu Ile Cys Ala Gln Lys Phe Asn Gly Leu Thr Val Leu
              835               840               845

Pro Pro Leu Leu Thr Asp Glu Met Ile Ala Gln Tyr Thr Ser Ala Leu
              850               855               860

Leu Ala Gly Thr Ile Thr Ser Gly Trp Thr Phe Gly Ala Gly Ala Ala
865               870               875               880
```

```
Leu Gln Ile Pro Phe Ala Met Gln Met Ala Tyr Arg Phe Asn Gly Ile
            885             890             895

Gly Val Thr Gln Asn Val Leu Tyr Glu Asn Gln Lys Leu Ile Ala Asn
            900             905             910

Gln Phe Asn Ser Ala Ile Gly Lys Ile Gln Asp Ser Leu Ser Ser Thr
            915             920             925

Ala Ser Ala Leu Gly Lys Leu Gln Asp Val Val Asn Gln Asn Ala Gln
    930             935             940

Ala Leu Asn Thr Leu Val Lys Gln Leu Ser Ser Asn Phe Gly Ala Ile
945             950             955             960

Ser Ser Val Leu Asn Asp Ile Leu Ser Arg Leu Asp Pro Pro Glu Ala
            965             970             975

Glu Val Gln Ile Asp Arg Leu Ile Thr Gly Arg Leu Gln Ser Leu Gln
            980             985             990

Thr Tyr Val Thr Gln Gln Leu Ile  Arg Ala Ala Glu Ile  Arg Ala Ser
        995             1000                1005

Ala Asn  Leu Ala Ala Thr Lys  Met Ser Glu Cys Val  Leu Gly Gln
    1010            1015            1020

Ser Lys  Arg Val Asp Phe Cys  Gly Lys Gly Tyr His  Leu Met Ser
    1025            1030            1035

Phe Pro  Gln Ser Ala Pro His  Gly Val Val Phe Leu  His Val Thr
    1040            1045            1050

Tyr Val  Pro Ala Gln Glu Lys  Asn Phe Thr Thr Ala  Pro Ala Ile
    1055            1060            1065

Cys His  Asp Gly Lys Ala His  Phe Pro Arg Glu Gly  Val Phe Val
    1070            1075            1080

Ser Asn  Gly Thr His Trp Phe  Val Thr Gln Arg Asn  Phe Tyr Glu
    1085            1090            1095

Pro Gln  Ile Ile Thr Thr Asp  Asn Thr Phe Val Ser  Gly Asn Cys
    1100            1105            1110

Asp Val  Val Ile Gly Ile Val  Asn Asn Thr Val Tyr  Asp Pro Leu
    1115            1120            1125

Gln Pro  Glu Leu Asp Ser Phe  Lys Glu Glu Leu Asp  Lys Tyr Phe
    1130            1135            1140

Lys Asn  His Thr Ser Pro Asp  Val Asp Leu Gly Asp  Ile Ser Gly
    1145            1150            1155

Ile Asn  Ala Ser Val Val Asn  Ile Gln Lys Glu Ile  Asp Arg Leu
    1160            1165            1170

Asn Glu  Val Ala Lys Asn Leu  Asn Glu Ser Leu Ile  Asp Leu Gln
    1175            1180            1185

Glu Leu  Gly Lys Tyr Glu Gln  Tyr Ile Lys Trp Pro  His His His
    1190            1195            1200

His His  His
    1205

<210> SEQ ID NO 90
<211> LENGTH: 17
<212> TYPE: PRT
<213> ORGANISM: Artificial Sequence
<220> FEATURE:
<223> OTHER INFORMATION: Linker

<400> SEQUENCE: 90

Ser Gly Gly Gly Ser Gly Gly Gly Ser Gly Gly Gly Ser Gly Gly Gly
1               5               10              15
```

-continued

Ser

```
<210> SEQ ID NO 91
<211> LENGTH: 4
<212> TYPE: PRT
<213> ORGANISM: Artificial Sequence
<220> FEATURE:
<223> OTHER INFORMATION: Linker

<400> SEQUENCE: 91

Ser Gly Gly Gly
1

<210> SEQ ID NO 92
<211> LENGTH: 4
<212> TYPE: PRT
<213> ORGANISM: Artificial Sequence
<220> FEATURE:
<223> OTHER INFORMATION: Linker

<400> SEQUENCE: 92

Gly Gly Gly Ser
1

<210> SEQ ID NO 93
<211> LENGTH: 5
<212> TYPE: PRT
<213> ORGANISM: Artificial Sequence
<220> FEATURE:
<223> OTHER INFORMATION: Linker

<400> SEQUENCE: 93

Gly Gly Gly Gly Ser
1               5

<210> SEQ ID NO 94
<211> LENGTH: 90
<212> TYPE: PRT
<213> ORGANISM: Artificial Sequence
<220> FEATURE:
<223> OTHER INFORMATION: RECOMBINANT SPIKE PROTEIN

<400> SEQUENCE: 94

Ser Thr Asn Leu Val Lys Asn Lys Cys Val Asn Phe Asn Phe Asn Gly
1               5                   10                  15

Leu Thr Gly Thr Gly Val Leu Thr Glu Ser Asn Lys Lys Phe Leu Pro
                20                  25                  30

Phe Gln Gln Phe Gly Arg Asp Ile Ala Asp Thr Thr Asp Ala Val Arg
            35                  40                  45

Asp Pro Gln Thr Leu Glu Ile Leu Asp Ile Thr Pro Cys Ser Phe Gly
        50                  55                  60

Gly Val Ser Val Ile Thr Pro Gly Thr Asn Thr Ser Asn Gln Val Ala
65                  70                  75                  80

Val Leu Tyr Gln Asp Val Asn Cys Thr Glu
                85                  90

<210> SEQ ID NO 95
<211> LENGTH: 3639
<212> TYPE: DNA
<213> ORGANISM: Artificial Sequence
<220> FEATURE:
<223> OTHER INFORMATION: RECOMBINANT SPIKE PROTEIN

<400> SEQUENCE: 95
```

```
atgttcgtct tcctggtgct gctgcccctg gtgtccagcc agtgcgtgaa cctgaccact    60
aggactcagc tgcctcccgc ttacaccaac tcattcactc gcggtgtgta ctaccctgac   120
aaggtcttcc gttcttcagt gctgcactca actcaggacc tgttcctgcc cttcttctcc   180
aacgtcacct ggttccacgc catccacgtg tccggcacca acggcactaa gcgcttcgac   240
aacccagtgc tgcctttcaa cgacggtgtc tacttcgctt caaccgagaa gtccaacatc   300
atccgtggat ggatcttcgg caccactctg gacagcaaga ctcagtctct gctgatcgtc   360
aacaacgcca ccaacgtggt catcaaggtc tgcgaattcc agttctgcaa cgacccattc   420
ctgggcgtct actaccacaa gaacaacaag tcatggatgg agtccgaatt ccgcgtctac   480
tccagcgcta caactgcac tttcgagtac gtgtcccagc ctttcctgat ggacctggaa   540
ggaaagcagg gtaacttcaa gaacctgagg gagttcgtgt tcaagaacat cgacggatac   600
ttcaagattt acagcaagca cacccccaatc aacctggtgc gcgacctgcc tcagggtttc   660
tctgctctgg agccactggt ggacctgcct atcggcatca acatcacccg cttccagact   720
ctgctggctc tgcaccgttc ctacctgact ccaggcgact catcttctgg atggactgct   780
ggagctgctg cttactacgt gggctacctg cagcctcgca ccttcctgct gaagtacaac   840
gaaaacggaa ccatcactga cgccgtcgac tgcgctctgg accctctgtc agaaaccaag   900
tgcactctga gtccttcac cgtggagaag ggcatctacc agacttcaaa cttcagggtg   960
cagcccaccg aatccatcgt cagattccct aacatcacta acctgtgccc cttcggagag  1020
gtcttcaacg ccacccgctt cgcttccgtg tacgcctgga caggaagag aatctcaaac  1080 tgcgtcgctg actactccgt gctgtacaac tcagcctcct tcagcacctt caagtgctac  1140
ggcgtgtcac caactaagct gaacgacctg tgcttcacca acgtctacgc cgactccttc  1200
gtgatcaggg gagacgaggt cagacagatc gctcctggcc agactggaaa gatcgccgac  1260
tacaactaca agctgcccga cgacttcacc ggttgcgtca tcgcttggaa cagcaacaac  1320
ctggactcta aagtgggtgg caactacaac tacctgtacc gcctgttccg taagtcaaac  1380
ctgaagccat tcgagaggga catcagcact gaaatctacc aggccggatc tacccccttgc  1440 aacggtgtcg agggcttcaa ctgctacttc ccctgcagt cctacggttt ccagccaact  1500
aacggtgtgg ctaccagcc ttacagagtg gtcgtgctga gcttcgaact gctccacgct  1560
cctgctactg tgtgcggtcc aaagaagtct accaacctgg tcaagaacaa gtgcgtgaac  1620
ttcaacttca acggcctgac cggaactggt gtcctgaccg agagcaacaa gaagttcctg  1680
cccttccagc agttcggaag ggacatcgct gacaccactg acgctgtgcg cgaccctcag  1740
accctggaaa tcctggacat cactccatgc tcattcggag gtgtctccgt gatcacccct  1800
ggcaccaaca cttctaacca ggtcgctgtg ctgtaccagg acgtcaactg caccgaggtc  1860
cctgtggcca tccacgctga ccagctgacc cccacttggc gcgtgtactc caccggcagc  1920
aacgtgttcc agactcgtgc tggttgcctg atcggcgccg agcacgtgaa caacagctac  1980
gaatgcgaca tccccatcgg cgctggaatc tgcgcctctt accagaccca gactaacagc  2040
ccacgcaggg ctcgctctgt ggcctctcag tcaatcatcg cttacaccat gtcactgggc  2100
gctgaaaact ccgtggccta ctctaacaac tcaatcgcca tccccaccaa cttcactatc  2160
agcgtgacca ctgagatcct gccagtcagc atgaccaaga cttctgtgga ctgcactatg  2220
tacatctgcg gagacagcac cgaatgctct aacctgctgc tgcagtacgg ctctttctgc  2280
acccagctga accgtgctct gactggaatc gccgtggagc aggacaagaa cactcaggaa  2340
```

-continued

```
gtcttcgctc aggtgaagca aatctacaag accccaccta tcaaggactt cggcggattc    2400
aacttctccc agatcctgcc tgacccctcc aagccaagca agcgctcttt catcgaggac    2460
ctgctgttca acaaggtcac tctggccgac gctggattca tcaagcagta cggagactgc    2520
ctgggtgaca tcgccgctcg tgacctgatc tgcgctcaga agttcaacgg tctgaccgtg    2580 ctgccccac tgctgactga cgaaatgatc gcccagtaca ctagcgccct gctggctgga    2640
accatcactt ctggttggac cttcggtgct ggcgccgctc tgcagatccc tttcgctatg    2700
cagatggcct accgtttcaa cggaatcggt gtcacccaga acgtgctgta cgagaaccag    2760
aagctgatcg ctaaccagtt caactcagcc atcggaaaga tccaggacag cctgagctct    2820
actgcctctg ctctgggcaa gctgcaggac gtcgtgaacc agaacgccca ggctctgaac    2880
accctggtca agcagctgtc atccaacttc ggtgctatca gctctgtgct gaacgacatc    2940
ctgtcccgcc tggacaaggt cgaggccgaa gtgcagatcg accgcctgat cactggccgt    3000
ctgcagtcac tgcagaccta cgtgactcag cagctgatca gggccgctga aatcagagcc    3060
tccgctaacc tggccgctac caagatgagc gagtgcgtcc tgggtcaatc taagcgtgtg    3120
gacttctgcg gcaagggata ccacctgatg tcattccctc agtctgctcc ccacggtgtg    3180
gtgttcctgc acgtcaccta cgtgccagcc caggagaaga acttcaccac tgccctgct    3240 atctgccacg acggcaaggc tcacttcccc agggaaggtg tcttcgtgag caacggcacc    3300
cactggttcg tcactcagag aaacttctac gagccacaga tcatcaccac tgacaacact    3360
ttcgtgtctg gaaactgcga cgtggtcatc ggtatcgtca caacaccgt gtacgacccc    3420 ctgcagccag agctggactc attcaaggag gaactggaca gtacttcaa gaaccacacc    3480 tcccctgacg tcgacctggg cgacatctca ggaatcaacg cttccgtcgt gaacatccag    3540
aaggagatcg accgcctgaa cgaagtggcc aagaacctga cgaaagcct gatcgacctg    3600 caggagctgg gcaagtacga acagtacatc aagtggcct                          3639
```

<210> SEQ ID NO 96
<211> LENGTH: 3822
<212> TYPE: DNA
<213> ORGANISM: Artificial Sequence
<220> FEATURE:
<223> OTHER INFORMATION: RECOMBINANT SPIKE PROTEIN

<400> SEQUENCE: 96

```
atgttcgtct tcctggtgct gctgcccctg gtgtccagcc agtgcgtgaa cctgaccact     60
aggactcagc tgcctcccgc ttacaccaac tcattcactc gcggtgtgta ctaccctgac    120
aaggtcttcc gttcttcagt gctgcactca actcaggacc tgttcctgcc cttcttctcc    180
aacgtcacct ggttccacgc catccacgtg tccggcacca acggcactaa gcgcttcgac    240
aacccagtgc tgccttttcaa cgacggtgtc tacttcgctt caaccgagaa gtccaacatc    300
atccgtggat ggatcttcgg caccactctg gacagcaaga ctcagtctct gctgatcgtc    360
aacaacgcca ccaacgtggt catcaaggtc tgcgaattcc agttctgcaa cgacccattc    420
ctgggcgtct actaccacaa gaacaacaag tcatggatgg agtccgaatt ccgcgtctac    480
tccagcgcta acaactgcac tttcgagtac gtgtcccagc ctttcctgat ggacctggaa    540
ggaaagcagg gtaacttcaa gaacctgagg gagttcgtgt tcaagaacat cgacggatac    600
ttcaagattt acagcaagca cacccccaatc aacctggtgc gcgacctgcc tcagggtttc    660
tctgctctgg agccactggt ggacctgcct atcggcatca acatcacccg cttccagact    720
ctgctggctc tgcaccgttc ctacctgact ccaggcgact catcttctgg atggactgct    780
```

-continued

```
ggagctgctg cttactacgt gggctacctg cagcctcgca ccttcctgct gaagtacaac        840
gaaaacggaa ccatcactga cgccgtcgac tgcgctctgg accctctgtc agaaaccaag        900
tgcactctga agtccttcac cgtggagaag ggcatctacc agacttcaaa cttcagggtg        960
cagcccaccg aatccatcgt cagattccct aacatcacta acctgtgccc cttcggagag       1020
gtcttcaacg ccacccgctt cgcttccgtg tacgcctgga acaggaagag aatctcaaac       1080
tgcgtcgctg actactccgt gctgtacaac tcagcctcct tcagcacctt caagtgctac       1140
ggcgtgtcac caactaagct gaacgacctg tgcttcacca acgtctacgc cgactccttc       1200
gtgatcaggg gagacgaggt cagacagatc gctcctggcc agactggaaa gatcgccgac       1260
tacaactaca agctgcccga cgacttcacc ggttgcgtca tcgcttggaa cagcaacaac       1320
ctggactcta aagtgggtgg caactacaac tacctgtacc gcctgttccg taagtcaaac       1380
ctgaagccat tcgagaggga catcagcact gaaatctacc aggccggatc taccccttgc       1440
aacggtgtcg agggcttcaa ctgctacttc ccctgcagt cctacggttt ccagccaact        1500
aacggtgtgg gctaccagcc ttacagagtg gtcgtgctga gcttcgaact gctccacgct       1560
cctgctactg tgtgcggtcc aaagaagtct accaacctgg tcaagaacaa gtgcgtgaac       1620
ttcaacttca cggcctgac cggaactggt gtcctgaccg agagcaacaa gaagttcctg        1680
cccttccagc agttcggaag ggacatcgct gacaccactg acgctgtgcg cgaccctcag       1740
accctggaaa tcctggacat cactccatgc tcattcggag gtgtctccgt gatcacccct       1800
ggcaccaaca cttctaacca ggtcgctgtg ctgtaccagg acgtcaactg caccgaggtc       1860
cctgtggcca tccacgctga ccagctgacc cccacttggc gcgtgtactc caccggcagc       1920
aacgtgttcc agactcgtgc tggttgcctg atcggcgccg agcacgtgaa caacagctac       1980
gaatgcgaca tccccatcgg cgctggaatc tgcgcctctt accagaccca gactaacagc       2040
ccacagcagg ctcagtctgt ggcctctcag tcaatcatcg cttacaccat gtcactgggc       2100
gctgaaaact ccgtggccta ctctaacaac tcaatcgcca tccccaccaa cttcactatc       2160
agcgtgacca ctgagatcct gccagtcagc atgaccaaga cttctgtgga ctgcactatg       2220
tacatctgcg gagacagcac cgaatgctct aacctgctgc tgcagtacgg ctctttctgc       2280
acccagctga ccgtgctct gactggaatc gccgtggagc aggacaagaa cactcaggaa        2340
gtcttcgctc aggtgaagca aatctacaag accccaccta tcaaggactt cggcggattc       2400
aacttctccc agatcctgcc tgaccctcc aagccaagca gcgctctttt catcgaggac        2460
ctgctgttca acaaggtcac tctggccgac gctggattca tcaagcagta cggagactgc       2520
ctgggtgaca tcgccgctcg tgacctgatc tgcgctcaga gttcaacgg tctgaccgtg        2580 ctgcccccac tgctgactga cgaaatgatc gcccagtaca ctagcgccct gctggctgga       2640
accatcactt ctggttggac cttcggtgct ggcgccgctc tgcagatccc tttcgctatg       2700
cagatggcct accgtttcaa cggaatcggt gtcacccaga acgtgctgta cgagaaccag       2760
aagctgatcg ctaaccagtt caactcagcc atcggaaaga tccaggacag cctgagctct       2820
actgcctctg ctctgggcaa gctgcaggac gtcgtgaacc agaacgccca ggctctgaac       2880
accctggtca agcagctgtc atccaacttc ggtgctatca ctctgtgct gaacgacatc        2940 ctgtcccgcc tggaccctcc cgaggccgaa gtgcagatcg accgcctgat cactggccgt       3000
ctgcagtcac tgcagaccta cgtgactcag cagctgatca gggccgctga aatcagagcc       3060
tccgctaacc tggccgctac caagatgagc gagtgcgtcc tgggtcaatc taagcgtgtg       3120
```

```
gacttctgcg gcaagggata ccacctgatg tcattccctc agtctgctcc ccacggtgtg      3180
gtgttcctgc acgtcaccta cgtgccagcc caggagaaga acttcaccac tgcccctgct      3240
atctgccacg acggcaaggc tcacttcccc agggaaggtg tcttcgtgag caacggcacc      3300
cactggttcg tcactcagag aaacttctac gagccacaga tcatcaccac tgacaacact      3360
ttcgtgtctg aaactgcga cgtggtcatc ggtatcgtca acaacaccgt gtacgacccc      3420
ctgcagccag agctggactc attcaaggag gaactggaca agtacttcaa gaaccacacc      3480
tcccctgacg tcgacctggg cgacatctca ggaatcaacg cttccgtcgt gaacatccag      3540
aaggagatcg accgcctgaa cgaagtggcc aagaacctga cgaaagcct gatcgacctg      3600 caggagctgg gcaagtacga acagtacatc aagtggcctt ggtacatctg gctgggtttc      3660
atcgctggcc tcatcgctat cgtgatggtg accatcatgc tgtgctgcat gacttcatgc      3720
tgctcctgcc tgaagggctg ctgcagctgc ggatcttgct gcaagttcga cgaggacgac      3780
tctgaacccg tcctgaaggg cgtgaagctg cactacacct aa                        3822
```

```
<210> SEQ ID NO 97
<211> LENGTH: 4
<212> TYPE: PRT
<213> ORGANISM: Artificial Sequence
<220> FEATURE:
<223> OTHER INFORMATION: Recombinant Furin Cleavage Site

<400> SEQUENCE: 97

Gly Ser Ala Ser
1

<210> SEQ ID NO 98
<211> LENGTH: 8
<212> TYPE: PRT
<213> ORGANISM: Artificial Sequence
<220> FEATURE:
<223> OTHER INFORMATION: HRV3C Cleavage Site

<400> SEQUENCE: 98

Leu Glu Val Leu Phe Gln Gly Pro
1               5

<210> SEQ ID NO 99
<211> LENGTH: 8
<212> TYPE: PRT
<213> ORGANISM: Artificial Sequence
<220> FEATURE:
<223> OTHER INFORMATION: Strep-tag

<400> SEQUENCE: 99

Trp Ser His Pro Gln Phe Glu Lys
1               5

<210> SEQ ID NO 100
<211> LENGTH: 6
<212> TYPE: PRT
<213> ORGANISM: Artificial Sequence
<220> FEATURE:
<223> OTHER INFORMATION: 6X-His Tag

<400> SEQUENCE: 100

His His His His His His
1               5

<210> SEQ ID NO 101
<211> LENGTH: 10
```

<212> TYPE: PRT
<213> ORGANISM: Artificial Sequence
<220> FEATURE:
<223> OTHER INFORMATION: His-Tag
<220> FEATURE:
<221> NAME/KEY: MISC_FEATURE
<222> LOCATION: (6)..(6)
<223> OTHER INFORMATION: May be present or absent
<220> FEATURE:
<221> NAME/KEY: MISC_FEATURE
<222> LOCATION: (7)..(7)
<223> OTHER INFORMATION: May be present or absent
<220> FEATURE:
<221> NAME/KEY: MISC_FEATURE
<222> LOCATION: (8)..(8)
<223> OTHER INFORMATION: May be present or absent
<220> FEATURE:
<221> NAME/KEY: MISC_FEATURE
<222> LOCATION: (9)..(9)
<223> OTHER INFORMATION: May be present or absent
<220> FEATURE:
<221> NAME/KEY: MISC_FEATURE
<222> LOCATION: (10)..(10)
<223> OTHER INFORMATION: May be present or absent

<400> SEQUENCE: 101

His His His His His His His His His His
1               5                   10

<210> SEQ ID NO 102
<211> LENGTH: 8
<212> TYPE: PRT
<213> ORGANISM: Artificial Sequence
<220> FEATURE:
<223> OTHER INFORMATION: 8X-His Tag

<400> SEQUENCE: 102

His His His His His His His His
1               5

<210> SEQ ID NO 103
<211> LENGTH: 30
<212> TYPE: PRT
<213> ORGANISM: Artificial Sequence
<220> FEATURE:
<223> OTHER INFORMATION: FOLDON

<400> SEQUENCE: 103

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu Ser Pro Ala
            20                  25                  30

<210> SEQ ID NO 104
<211> LENGTH: 10
<212> TYPE: PRT
<213> ORGANISM: Artificial Sequence
<220> FEATURE:
<223> OTHER INFORMATION: RECOMBINANT SPIKE PROTEIN

<400> SEQUENCE: 104

Glu Asp Leu Leu Phe Asn Lys Val Thr Leu
1               5                   10

<210> SEQ ID NO 105
<211> LENGTH: 1263
<212> TYPE: PRT
<213> ORGANISM: Artificial Sequence
<220> FEATURE:
<223> OTHER INFORMATION: RECOMBINANT SPIKE PROTEIN -continued

<400> SEQUENCE: 105

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
```

-continued

```
                 405              410              415

Lys Ile Ala Asp Tyr Asn Tyr Lys Leu Pro Asp Asp Phe Thr Gly Cys
             420              425              430

Val Ile Ala Trp Asn Ser Asn Asn Leu Asp Ser Lys Val Gly Gly Asn
             435              440              445

Tyr Asn Tyr Leu Tyr Arg Leu Phe Arg Lys Ser Asn Leu Lys Pro Phe
     450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
             485              490              495

Phe Gln Pro Thr Asn Gly Val Gly Tyr Gln Pro Tyr Arg Val Val Val
             500              505              510

Leu Ser Phe Glu Leu Leu His Ala Pro Ala Thr Val Cys Gly Pro Lys
             515              520              525

Lys Ser Thr Asn Leu Val Lys Asn Lys Cys Val Asn Phe Asn Phe Asn
     530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
             565              570              575

Arg Asp Pro Gln Thr Leu Glu Ile Leu Asp Ile Thr Pro Cys Ser Phe
             580              585              590

Gly Gly Val Ser Val Ile Thr Pro Gly Thr Asn Thr Ser Asn Gln Val
             595              600              605

Ala Val Leu Tyr Gln Asp Val Asn Cys Thr Glu Val Pro Val Ala Ile
     610              615              620

His Ala Asp Gln Leu Thr Pro Thr Trp Arg Val Tyr Ser Thr Gly Ser
625              630              635              640

Asn Val Phe Gln Thr Arg Ala Gly Cys Leu Ile Gly Ala Glu His Val
             645              650              655

Asn Asn Ser Tyr Glu Cys Asp Ile Pro Ile Gly Ala Gly Ile Cys Ala
             660              665              670

Ser Tyr Gln Thr Gln Thr Asn Ser Pro Gln Gln Ala Gln Ser Val Ala
             675              680              685

Ser Gln Ser Ile Ile Ala Tyr Thr Met Ser Leu Gly Ala Glu Asn Ser
     690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
             725              730              735

Asp Cys Thr Met Tyr Ile Cys Gly Asp Ser Thr Glu Cys Ser Asn Leu
             740              745              750

Leu Leu Gln Tyr Gly Ser Phe Cys Thr Gln Leu Asn Arg Ala Leu Thr
             755              760              765

Gly Ile Ala Val Glu Gln Asp Lys Asn Thr Gln Glu Val Phe Ala Gln
     770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
             805              810              815

Phe Ile Ala Asp Ala Gly Phe Ile Lys Gln Tyr Gly Asp Cys Leu Gly
             820              825              830
```

-continued

```
Asp Ile Ala Ala Arg Asp Leu Ile Cys Ala Gln Lys Phe Asn Gly Leu
        835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
            900                 905                 910

Ile Ala Asn Gln Phe Asn Ser Ala Ile Gly Lys Ile Gln Asp Ser Leu
        915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Pro
                965                 970                 975

Pro Glu Ala Glu Val Gln Ile Asp Arg Leu Ile Thr Gly Arg Leu Gln
            980                 985                 990

Ser Leu Gln Thr Tyr Val Thr Gln  Gln Leu Ile Arg Ala  Ala Glu Ile
        995                 1000                1005

Arg Ala  Ser Ala Asn Leu Ala  Ala Thr Lys Met Ser  Glu Cys Val
    1010                1015                1020

Leu Gly  Gln Ser Lys Arg Val  Asp Phe Cys Gly Lys  Gly Tyr His
    1025                1030                1035

Leu Met  Ser Phe Pro Gln Ser  Ala Pro His Gly Val  Val Phe Leu
    1040                1045                1050

His Val  Thr Tyr Val Pro Ala  Gln Glu Lys Asn Phe  Thr Thr Ala
    1055                1060                1065

Pro Ala  Ile Cys His Asp Gly  Lys Ala His Phe Pro  Arg Glu Gly
    1070                1075                1080

Val Phe  Val Ser Asn Gly Thr  His Trp Phe Val Thr  Gln Arg Asn
    1085                1090                1095

Phe Tyr  Glu Pro Gln Ile Ile  Thr Thr Asp Asn Thr  Phe Val Ser
    1100                1105                1110

Gly Asn  Cys Asp Val Val Ile  Gly Ile Val Asn Asn  Thr Val Tyr
    1115                1120                1125

Asp Pro  Leu Gln Pro Glu Leu  Asp Ser Phe Lys Glu  Glu Leu Asp
    1130                1135                1140

Lys Tyr  Phe Lys Asn His Thr  Ser Pro Asp Val Asp  Leu Gly Asp
    1145                1150                1155

Ile Ser  Gly Ile Asn Ala Ser  Val Val Asn Ile Gln  Lys Glu Ile
    1160                1165                1170

Asp Arg  Leu Asn Glu Val Ala  Lys Asn Leu Asn Glu  Ser Leu Ile
    1175                1180                1185

Asp Leu  Gln Glu Leu Gly Lys  Tyr Glu Gln Tyr Ile  Lys Trp Pro
    1190                1195                1200

Trp Tyr  Ile Trp Leu Gly Phe  Ile Ala Gly Leu Ile  Ala Ile Val
    1205                1210                1215

Met Val  Thr Ile Met Leu Cys  Cys Met Thr Ser Cys  Cys Ser Cys
    1220                1225                1230
```

-continued

```
Leu Lys  Gly Cys Cys Ser Cys  Gly Ser Cys Cys Lys  Phe Asp Glu
    1235             1240              1245

Asp Asp  Ser Glu Pro Val Leu  Lys Gly Val Lys Leu  His Tyr Thr
    1250             1255              1260

<210> SEQ ID NO 106
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 106

Gln Cys Val Asn Leu Thr Thr Arg Thr Gln Leu Pro Pro Ala Tyr Thr
1                 5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
                35                  40                  45

Val Thr Trp Phe His Ala Ile His Val Ser Gly Thr Asn Gly Thr Lys
            50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
            195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
        290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335
```

-continued

```
Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
            660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750

Ala Leu Thr Gly Ile Ala Val Glu Gln Asp Lys Asn Thr Gln Glu Val
```

-continued

```
          755            760            765

Phe Ala Gln Val Lys Gln Ile Tyr Lys Thr Pro Pro Ile Lys Asp Phe
    770            775            780

Gly Gly Phe Asn Phe Ser Gln Ile Leu Pro Asp Pro Ser Lys Pro Ser
785            790            795            800

Lys Arg Ser Phe Ile Ala Asp Ala Gly Phe Ile Lys Gln Tyr Gly Asp
            805            810            815

Cys Leu Gly Asp Ile Ala Ala Arg Asp Leu Ile Cys Ala Gln Lys Phe
            820            825            830

Asn Gly Leu Thr Val Leu Pro Pro Leu Leu Thr Asp Glu Met Ile Ala
            835            840            845

Gln Tyr Thr Ser Ala Leu Leu Ala Gly Thr Ile Thr Ser Gly Trp Thr
    850            855            860

Phe Gly Ala Gly Ala Ala Leu Gln Ile Pro Phe Ala Met Gln Met Ala
865            870            875            880

Tyr Arg Phe Asn Gly Ile Gly Val Thr Gln Asn Val Leu Tyr Glu Asn
            885            890            895

Gln Lys Leu Ile Ala Asn Gln Phe Asn Ser Ala Ile Gly Lys Ile Gln
            900            905            910

Asp Ser Leu Ser Ser Thr Ala Ser Ala Leu Gly Lys Leu Gln Asp Val
            915            920            925

Val Asn Gln Asn Ala Gln Ala Leu Asn Thr Leu Val Lys Gln Leu Ser
    930            935            940

Ser Asn Phe Gly Ala Ile Ser Ser Val Leu Asn Asp Ile Leu Ser Arg
945            950            955            960

Leu Asp Pro Pro Glu Ala Glu Val Gln Ile Asp Arg Leu Ile Thr Gly
            965            970            975

Arg Leu Gln Ser Leu Gln Thr Tyr Val Thr Gln Gln Leu Ile Arg Ala
            980            985            990

Ala Glu Ile Arg Ala Ser Ala Asn  Leu Ala Ala Thr Lys  Met Ser Glu
    995            1000            1005

Cys Val  Leu Gly Gln Ser Lys  Arg Val Asp Phe Cys  Gly Lys Gly
    1010            1015            1020

Tyr His  Leu Met Ser Phe Pro  Gln Ser Ala Pro His  Gly Val Val
    1025            1030            1035

Phe Leu  His Val Thr Tyr Val  Pro Ala Gln Glu Lys  Asn Phe Thr
    1040            1045            1050

Thr Ala  Pro Ala Ile Cys His  Asp Gly Lys Ala His  Phe Pro Arg
    1055            1060            1065

Glu Gly  Val Phe Val Ser Asn  Gly Thr His Trp Phe  Val Thr Gln
    1070            1075            1080

Arg Asn  Phe Tyr Glu Pro Gln  Ile Ile Thr Thr Asp  Asn Thr Phe
    1085            1090            1095

Val Ser  Gly Asn Cys Asp Val  Val Ile Gly Ile Val  Asn Asn Thr
    1100            1105            1110

Val Tyr  Asp Pro Leu Gln Pro  Glu Leu Asp Ser Phe  Lys Glu Glu
    1115            1120            1125

Leu Asp  Lys Tyr Phe Lys Asn  His Thr Ser Pro Asp  Val Asp Leu
    1130            1135            1140

Gly Asp  Ile Ser Gly Ile Asn  Ala Ser Val Val Asn  Ile Gln Lys
    1145            1150            1155

Glu Ile  Asp Arg Leu Asn Glu  Val Ala Lys Asn Leu  Asn Glu Ser
    1160            1165            1170
```

```
Leu Ile  Asp Leu Gln Glu Leu  Gly Lys Tyr Glu Gln  Tyr Ile Lys
    1175             1180              1185

Trp Pro  Trp Tyr Ile Trp Leu  Gly Phe Ile Ala Gly  Leu Ile Ala
    1190             1195              1200

Ile Val  Met Val Thr Ile Met  Leu Cys Cys Met Thr  Ser Cys Cys
    1205             1210              1215

Ser Cys  Leu Lys Gly Cys Cys  Ser Cys Gly Ser Cys  Cys Lys Phe
    1220             1225              1230

Asp Gly  Asp Asp Ser Glu Pro  Val Leu Lys Gly Val  Lys Leu His
    1235             1240              1245

Tyr Thr
    1250

<210> SEQ ID NO 107
<211> LENGTH: 1263
<212> TYPE: PRT
<213> ORGANISM: Artificial Sequence
<220> FEATURE:
<223> OTHER INFORMATION: RECOMBINANT SPIKE PROTEIN

<400> SEQUENCE: 107

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270
```

-continued

```
Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Arg Ala Arg Ser Val Ala
    675                 680                 685
```

-continued

---

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Ala Asp Ala Gly Phe Ile Lys Gln Tyr Gly Asp Cys Leu Gly
                820                 825                 830

Asp Ile Ala Ala Arg Asp Leu Ile Cys Ala Gln Lys Phe Asn Gly Leu
                835                 840                 845

Thr Val Leu Pro Pro Leu Leu Thr Asp Glu Met Ile Ala Gln Tyr Thr
    850                 855                 860

Ser Ala Leu Leu Ala Gly Thr Ile Thr Ser Gly Trp Thr Phe Gly Ala
865                 870                 875                 880

Gly Ala Ala Leu Gln Ile Pro Phe Ala Met Gln Met Ala Tyr Arg Phe
                885                 890                 895

Asn Gly Ile Gly Val Thr Gln Asn Val Leu Tyr Glu Asn Gln Lys Leu
                900                 905                 910

Ile Ala Asn Gln Phe Asn Ser Ala Ile Gly Lys Ile Gln Asp Ser Leu
                915                 920                 925

Ser Ser Thr Ala Ser Ala Leu Gly Lys Leu Gln Asp Val Val Asn Gln
    930                 935                 940

Asn Ala Gln Ala Leu Asn Thr Leu Val Lys Gln Leu Ser Ser Asn Phe
945                 950                 955                 960

Gly Ala Ile Ser Ser Val Leu Asn Asp Ile Leu Ser Arg Leu Asp Lys
                965                 970                 975

Val Glu Ala Glu Val Gln Ile Asp Arg Leu Ile Thr Gly Arg Leu Gln
                980                 985                 990

Ser Leu Gln Thr Tyr Val Thr Gln  Gln Leu Ile Arg Ala  Ala Glu Ile
    995                 1000                1005

Arg Ala  Ser Ala Asn Leu Ala  Ala Thr Lys Met Ser  Glu Cys Val
    1010                1015                1020

Leu Gly  Gln Ser Lys Arg Val  Asp Phe Cys Gly Lys  Gly Tyr His
    1025                1030                1035

Leu Met  Ser Phe Pro Gln Ser  Ala Pro His Gly Val  Val Phe Leu
    1040                1045                1050

His Val  Thr Tyr Val Pro Ala  Gln Glu Lys Asn Phe  Thr Thr Ala
    1055                1060                1065

Pro Ala  Ile Cys His Asp Gly  Lys Ala His Phe Pro  Arg Glu Gly
    1070                1075                1080

Val Phe  Val Ser Asn Gly Thr  His Trp Phe Val Thr  Gln Arg Asn
    1085                1090                1095

Phe Tyr  Glu Pro Gln Ile Ile  Thr Thr Asp Asn Thr  Phe Val Ser

-continued

```
              1100              1105              1110

Gly Asn  Cys Asp Val Val Ile  Gly Ile Val Asn Asn  Thr Val Tyr
   1115              1120              1125

Asp Pro  Leu Gln Pro Glu Leu  Asp Ser Phe Lys Glu  Glu Leu Asp
   1130              1135              1140

Lys Tyr  Phe Lys Asn His Thr  Ser Pro Asp Val Asp  Leu Gly Asp
   1145              1150              1155

Ile Ser  Gly Ile Asn Ala Ser  Val Val Asn Ile Gln  Lys Glu Ile
   1160              1165              1170

Asp Arg  Leu Asn Glu Val Ala  Lys Asn Leu Asn Glu  Ser Leu Ile
   1175              1180              1185

Asp Leu  Gln Glu Leu Gly Lys  Tyr Glu Gln Tyr Ile  Lys Trp Pro
   1190              1195              1200

Trp Tyr  Ile Trp Leu Gly Phe  Ile Ala Gly Leu Ile  Ala Ile Val
   1205              1210              1215

Met Val  Thr Ile Met Leu Cys  Cys Met Thr Ser Cys  Cys Ser Cys
   1220              1225              1230

Leu Lys  Gly Cys Cys Ser Cys  Gly Ser Cys Cys Lys  Phe Asp Glu
   1235              1240              1245

Asp Asp  Ser Glu Pro Val Leu  Lys Gly Val Lys Leu  His Tyr Thr
   1250              1255              1260
```

```
<210> SEQ ID NO 108
<211> LENGTH: 1250
<212> TYPE: PRT
<213> ORGANISM: Artificial Sequence
<220> FEATURE:
<223> OTHER INFORMATION: RECOMBINANT SPIKE PROTEIN

<400> SEQUENCE: 108
```

```
Gln Cys Val Asn Leu Thr Thr Arg Thr Gln Leu Pro Pro Ala Tyr Thr
1            5              10             15

Asn Ser Phe Thr Arg Gly Val Tyr Tyr Pro Asp Lys Val Phe Arg Ser
            20             25             30

Ser Val Leu His Ser Thr Gln Asp Leu Phe Leu Pro Phe Phe Ser Asn
         35             40             45

Val Thr Trp Phe His Ala Ile His Val Ser Gly Thr Asn Gly Thr Lys
      50             55             60

Arg Phe Asp Asn Pro Val Leu Pro Phe Asn Asp Gly Val Tyr Phe Ala
65             70             75             80

Ser Thr Glu Lys Ser Asn Ile Ile Arg Gly Trp Ile Phe Gly Thr Thr
            85             90             95

Leu Asp Ser Lys Thr Gln Ser Leu Leu Ile Val Asn Asn Ala Thr Asn
            100            105            110

Val Val Ile Lys Val Cys Glu Phe Gln Phe Cys Asn Asp Pro Phe Leu
         115            120            125

Gly Val Tyr Tyr His Lys Asn Asn Lys Ser Trp Met Glu Ser Glu Phe
      130            135            140

Arg Val Tyr Ser Ser Ala Asn Asn Cys Thr Phe Glu Tyr Val Ser Gln
145            150            155            160

Pro Phe Leu Met Asp Leu Glu Gly Lys Gln Gly Asn Phe Lys Asn Leu
               165            170            175

Arg Glu Phe Val Phe Lys Asn Ile Asp Gly Tyr Phe Lys Ile Tyr Ser
            180            185            190

Lys His Thr Pro Ile Asn Leu Val Arg Asp Leu Pro Gln Gly Phe Ser
```

-continued

```
            195               200               205

Ala Leu Glu Pro Leu Val Asp Leu Pro Ile Gly Ile Asn Ile Thr Arg
    210               215               220

Phe Gln Thr Leu Leu Ala Leu His Arg Ser Tyr Leu Thr Pro Gly Asp
225               230               235               240

Ser Ser Ser Gly Trp Thr Ala Gly Ala Ala Ala Tyr Tyr Val Gly Tyr
                245               250               255

Leu Gln Pro Arg Thr Phe Leu Leu Lys Tyr Asn Glu Asn Gly Thr Ile
                260               265               270

Thr Asp Ala Val Asp Cys Ala Leu Asp Pro Leu Ser Glu Thr Lys Cys
                275               280               285

Thr Leu Lys Ser Phe Thr Val Glu Lys Gly Ile Tyr Gln Thr Ser Asn
    290               295               300

Phe Arg Val Gln Pro Thr Glu Ser Ile Val Arg Phe Pro Asn Ile Thr
305               310               315               320

Asn Leu Cys Pro Phe Gly Glu Val Phe Asn Ala Thr Arg Phe Ala Ser
                325               330               335

Val Tyr Ala Trp Asn Arg Lys Arg Ile Ser Asn Cys Val Ala Asp Tyr
                340               345               350

Ser Val Leu Tyr Asn Ser Ala Ser Phe Ser Thr Phe Lys Cys Tyr Gly
                355               360               365

Val Ser Pro Thr Lys Leu Asn Asp Leu Cys Phe Thr Asn Val Tyr Ala
    370               375               380

Asp Ser Phe Val Ile Arg Gly Asp Glu Val Arg Gln Ile Ala Pro Gly
385               390               395               400

Gln Thr Gly Lys Ile Ala Asp Tyr Asn Tyr Lys Leu Pro Asp Asp Phe
                405               410               415

Thr Gly Cys Val Ile Ala Trp Asn Ser Asn Asn Leu Asp Ser Lys Val
                420               425               430

Gly Gly Asn Tyr Asn Tyr Leu Tyr Arg Leu Phe Arg Lys Ser Asn Leu
                435               440               445

Lys Pro Phe Glu Arg Asp Ile Ser Thr Glu Ile Tyr Gln Ala Gly Ser
    450               455               460

Thr Pro Cys Asn Gly Val Glu Gly Phe Asn Cys Tyr Phe Pro Leu Gln
465               470               475               480

Ser Tyr Gly Phe Gln Pro Thr Asn Gly Val Gly Tyr Gln Pro Tyr Arg
                485               490               495

Val Val Val Leu Ser Phe Glu Leu Leu His Ala Pro Ala Thr Val Cys
                500               505               510

Gly Pro Lys Lys Ser Thr Asn Leu Val Lys Asn Lys Cys Val Asn Phe
                515               520               525

Asn Phe Asn Gly Leu Thr Gly Thr Gly Val Leu Thr Glu Ser Asn Lys
    530               535               540

Lys Phe Leu Pro Phe Gln Gln Phe Gly Arg Asp Ile Ala Asp Thr Thr
545               550               555               560

Asp Ala Val Arg Asp Pro Gln Thr Leu Glu Ile Leu Asp Ile Thr Pro
                565               570               575

Cys Ser Phe Gly Gly Val Ser Val Ile Thr Pro Gly Thr Asn Thr Ser
                580               585               590

Asn Gln Val Ala Val Leu Tyr Gln Asp Val Asn Cys Thr Glu Val Pro
                595               600               605

Val Ala Ile His Ala Asp Gln Leu Thr Pro Thr Trp Arg Val Tyr Ser
    610               615               620
```

-continued

```
Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
                660                 665                 670

Ser Val Ala Ser Gln Ser Ile Ile Ala Tyr Thr Met Ser Leu Gly Ala
                675                 680                 685

Glu Asn Ser Val Ala Tyr Ser Asn Asn Ser Ile Ala Ile Pro Thr Asn
            690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
                740                 745                 750

Ala Leu Thr Gly Ile Ala Val Glu Gln Asp Lys Asn Thr Gln Glu Val
                755                 760                 765

Phe Ala Gln Val Lys Gln Ile Tyr Lys Thr Pro Pro Ile Lys Asp Phe
            770                 775                 780

Gly Gly Phe Asn Phe Ser Gln Ile Leu Pro Asp Pro Ser Lys Pro Ser
785                 790                 795                 800

Lys Arg Ser Phe Ile Ala Asp Ala Gly Phe Ile Lys Gln Tyr Gly Asp
                805                 810                 815

Cys Leu Gly Asp Ile Ala Ala Arg Asp Leu Ile Cys Ala Gln Lys Phe
                820                 825                 830

Asn Gly Leu Thr Val Leu Pro Pro Leu Leu Thr Asp Glu Met Ile Ala
                835                 840                 845

Gln Tyr Thr Ser Ala Leu Leu Ala Gly Thr Ile Thr Ser Gly Trp Thr
            850                 855                 860

Phe Gly Ala Gly Ala Ala Leu Gln Ile Pro Phe Ala Met Gln Met Ala
865                 870                 875                 880

Tyr Arg Phe Asn Gly Ile Gly Val Thr Gln Asn Val Leu Tyr Glu Asn
                885                 890                 895

Gln Lys Leu Ile Ala Asn Gln Phe Asn Ser Ala Ile Gly Lys Ile Gln
            900                 905                 910

Asp Ser Leu Ser Ser Thr Ala Ser Ala Leu Gly Lys Leu Gln Asp Val
            915                 920                 925

Val Asn Gln Asn Ala Gln Ala Leu Asn Thr Leu Val Lys Gln Leu Ser
    930                 935                 940

Ser Asn Phe Gly Ala Ile Ser Ser Val Leu Asn Asp Ile Leu Ser Arg
945                 950                 955                 960

Leu Asp Lys Val Glu Ala Glu Val Gln Ile Asp Arg Leu Ile Thr Gly
                965                 970                 975

Arg Leu Gln Ser Leu Gln Thr Tyr Val Thr Gln Gln Leu Ile Arg Ala
                980                 985                 990

Ala Glu Ile Arg Ala Ser Ala Asn  Leu Ala Ala Thr Lys  Met Ser Glu
            995                 1000                1005

Cys Val  Leu Gly Gln Ser Lys  Arg Val Asp Phe Cys  Gly Lys Gly
    1010                1015                1020

Tyr His  Leu Met Ser Phe Pro  Gln Ser Ala Pro His  Gly Val Val
    1025                1030                1035
```

-continued

```
Phe Leu His Val Thr Tyr Val  Pro Ala Gln Glu Lys  Asn Phe Thr
    1040              1045              1050

Thr Ala Pro Ala Ile Cys His  Asp Gly Lys Ala His  Phe Pro Arg
    1055              1060              1065

Glu Gly Val Phe Val Ser Asn  Gly Thr His Trp Phe  Val Thr Gln
    1070              1075              1080

Arg Asn Phe Tyr Glu Pro Gln  Ile Ile Thr Thr Asp  Asn Thr Phe
    1085              1090              1095

Val Ser Gly Asn Cys Asp Val  Val Ile Gly Ile Val  Asn Asn Thr
    1100              1105              1110

Val Tyr Asp Pro Leu Gln Pro  Glu Leu Asp Ser Phe  Lys Glu Glu
    1115              1120              1125

Leu Asp Lys Tyr Phe Lys Asn  His Thr Ser Pro Asp  Val Asp Leu
    1130              1135              1140

Gly Asp Ile Ser Gly Ile Asn  Ala Ser Val Val Asn  Ile Gln Lys
    1145              1150              1155

Glu Ile Asp Arg Leu Asn Glu  Val Ala Lys Asn Leu  Asn Glu Ser
    1160              1165              1170

Leu Ile Asp Leu Gln Glu Leu  Gly Lys Tyr Glu Gln  Tyr Ile Lys
    1175              1180              1185

Trp Pro Trp Tyr Ile Trp Leu  Gly Phe Ile Ala Gly  Leu Ile Ala
    1190              1195              1200

Ile Val Met Val Thr Ile Met  Leu Cys Cys Met Thr  Ser Cys Cys
    1205              1210              1215

Ser Cys Leu Lys Gly Cys Cys  Ser Cys Gly Ser Cys  Cys Lys Phe
    1220              1225              1230

Asp Glu Asp Asp Ser Glu Pro  Val Leu Lys Gly Val  Lys Leu His
    1235              1240              1245

Tyr Thr
    1250
```

```
<210> SEQ ID NO 109
<211> LENGTH: 1273
<212> TYPE: PRT
<213> ORGANISM: Artificial Sequence
<220> FEATURE:
<223> OTHER INFORMATION: Recombinant CoV S polypeptide

<400> SEQUENCE: 109

Met Phe Val Phe Leu Val Leu  Leu Pro Leu Val Ser  Ser Gln Cys Val
1               5               10              15

Asn Leu Thr Thr Arg Thr Gln  Leu Pro Pro Ala Tyr  Thr Asn Ser Phe
            20              25              30

Thr Arg Gly Val Tyr Tyr Pro  Asp Lys Val Phe Arg  Ser Ser Val Leu
        35              40              45

His Ser Thr Gln Asp Leu Phe  Leu Pro Phe Phe Ser  Asn Val Thr Trp
    50              55              60

Phe His Ala Ile His Val Ser  Gly Thr Asn Gly Thr  Lys Arg Phe Asp
65              70              75              80

Asn Pro Val Leu Pro Phe Asn  Asp Gly Val Tyr Phe  Ala Ser Thr Glu
                85              90              95

Lys Ser Asn Ile Ile Arg Gly  Trp Ile Phe Gly Thr  Thr Leu Asp Ser
            100             105             110

Lys Thr Gln Ser Leu Leu Ile  Val Asn Asn Ala Thr  Asn Val Val Ile
            115             120             125
```

-continued

```
Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
            195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
    275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
```

-continued

```
545               550               555               560

Pro Phe Gln Gln Phe Gly Arg Asp Ile Ala Asp Thr Thr Asp Ala Val
                565               570               575

Arg Asp Pro Gln Thr Leu Glu Ile Leu Asp Ile Thr Pro Cys Ser Phe
                580               585               590

Gly Gly Val Ser Val Ile Thr Pro Gly Thr Asn Thr Ser Asn Gln Val
                595               600               605

Ala Val Leu Tyr Gln Asp Val Asn Cys Thr Glu Val Pro Val Ala Ile
                610               615               620

His Ala Asp Gln Leu Thr Pro Thr Trp Arg Val Tyr Ser Thr Gly Ser
625               630               635               640

Asn Val Phe Gln Thr Arg Ala Gly Cys Leu Ile Gly Ala Glu His Val
                645               650               655

Asn Asn Ser Tyr Glu Cys Asp Ile Pro Ile Gly Ala Gly Ile Cys Ala
                660               665               670

Ser Tyr Gln Thr Gln Thr Asn Ser Pro Gly Ser Ala Ser Ser Val Ala
                675               680               685

Ser Gln Ser Ile Ile Ala Tyr Thr Met Ser Leu Gly Ala Glu Asn Ser
                690               695               700

Val Ala Tyr Ser Asn Asn Ser Ile Ala Ile Pro Thr Asn Phe Thr Ile
705               710               715               720

Ser Val Thr Thr Glu Ile Leu Pro Val Ser Met Thr Lys Thr Ser Val
                725               730               735

Asp Cys Thr Met Tyr Ile Cys Gly Asp Ser Thr Glu Cys Ser Asn Leu
                740               745               750

Leu Leu Gln Tyr Gly Ser Phe Cys Thr Gln Leu Asn Arg Ala Leu Thr
                755               760               765

Gly Ile Ala Val Glu Gln Asp Lys Asn Thr Gln Glu Val Phe Ala Gln
                770               775               780

Val Lys Gln Ile Tyr Lys Thr Pro Pro Ile Lys Asp Phe Gly Gly Phe
785               790               795               800

Asn Phe Ser Gln Ile Leu Pro Asp Pro Ser Lys Pro Ser Lys Arg Ser
                805               810               815

Phe Ile Glu Asp Leu Leu Phe Asn Lys Val Thr Leu Ala Asp Ala Gly
                820               825               830

Phe Ile Lys Gln Tyr Gly Asp Cys Leu Gly Asp Ile Ala Ala Arg Asp
                835               840               845

Leu Ile Cys Ala Gln Lys Phe Asn Gly Leu Thr Val Leu Pro Pro Leu
                850               855               860

Leu Thr Asp Glu Met Ile Ala Gln Tyr Thr Ser Ala Leu Leu Ala Gly
865               870               875               880

Thr Ile Thr Ser Gly Trp Thr Phe Gly Ala Gly Ala Ala Leu Gln Ile
                885               890               895

Pro Phe Ala Met Gln Met Ala Tyr Arg Phe Asn Gly Ile Gly Val Thr
                900               905               910

Gln Asn Val Leu Tyr Glu Asn Gln Lys Leu Ile Ala Asn Gln Phe Asn
                915               920               925

Ser Ala Ile Gly Lys Ile Gln Asp Ser Leu Ser Ser Thr Ala Ser Ala
                930               935               940

Leu Gly Lys Leu Gln Asp Val Val Asn Gln Asn Ala Gln Ala Leu Asn
945               950               955               960

Thr Leu Val Lys Gln Leu Ser Ser Asn Phe Gly Ala Ile Ser Ser Val
                965               970               975
```

-continued

```
Leu Asn Asp Ile Leu Ser Arg Leu Asp Pro Pro Glu Ala Glu Val Gln
            980                 985                 990

Ile Asp Arg Leu Ile Thr Gly Arg  Leu Gln Ser Leu Gln  Thr Tyr Val
            995                 1000                1005

Thr Gln  Gln Leu Ile Arg Ala  Ala Glu Ile Arg Ala  Ser Ala Asn
            1010                1015                1020

Leu Ala  Ala Thr Lys Met Ser  Glu Cys Val Leu Gly  Gln Ser Lys
            1025                1030                1035

Arg Val  Asp Phe Cys Gly Lys  Gly Tyr His Leu Met  Ser Phe Pro
            1040                1045                1050

Gln Ser  Ala Pro His Gly Val  Val Phe Leu His Val  Thr Tyr Val
            1055                1060                1065

Pro Ala  Gln Glu Lys Asn Phe  Thr Thr Ala Pro Ala  Ile Cys His
            1070                1075                1080

Asp Gly  Lys Ala His Phe Pro  Arg Glu Gly Val Phe  Val Ser Asn
            1085                1090                1095

Gly Thr  His Trp Phe Val Thr  Gln Arg Asn Phe Tyr  Glu Pro Gln
            1100                1105                1110

Ile Ile  Thr Thr Asp Asn Thr  Phe Val Ser Gly Asn  Cys Asp Val
            1115                1120                1125

Val Ile  Gly Ile Val Asn Asn  Thr Val Tyr Asp Pro  Leu Gln Pro
            1130                1135                1140

Glu Leu  Asp Ser Phe Lys Glu  Glu Leu Asp Lys Tyr  Phe Lys Asn
            1145                1150                1155

His Thr  Ser Pro Asp Val Asp  Leu Gly Asp Ile Ser  Gly Ile Asn
            1160                1165                1170

Ala Ser  Val Val Asn Ile Gln  Lys Glu Ile Asp Arg  Leu Asn Glu
            1175                1180                1185

Val Ala  Lys Asn Leu Asn Glu  Ser Leu Ile Asp Leu  Gln Glu Leu
            1190                1195                1200

Gly Lys  Tyr Glu Gln Tyr Ile  Lys Trp Pro Trp Tyr  Ile Trp Leu
            1205                1210                1215

Gly Phe  Ile Ala Gly Leu Ile  Ala Ile Val Met Val  Thr Ile Met
            1220                1225                1230

Leu Cys  Cys Met Thr Ser Cys  Cys Ser Cys Leu Lys  Gly Cys Cys
            1235                1240                1245

Ser Cys  Gly Ser Cys Cys Lys  Phe Asp Glu Asp Asp  Ser Glu Pro
            1250                1255                1260

Val Leu  Lys Gly Val Lys Leu  His Tyr Thr
            1265                1270
```

<210> SEQ ID NO 110
<211> LENGTH: 1260
<212> TYPE: PRT
<213> ORGANISM: Artificial Sequence
<220> FEATURE:
<223> OTHER INFORMATION: Recombinant CoV S polypeptide

<400> SEQUENCE: 110

```
Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
            35                  40                  45
```

-continued

```
Val Thr Trp Phe His Ala Ile His Val Ser Gly Thr Asn Gly Thr Lys
    50              55              60

Arg Phe Asp Asn Pro Val Leu Pro Phe Asn Asp Gly Val Tyr Phe Ala
65              70              75              80

Ser Thr Glu Lys Ser Asn Ile Ile Arg Gly Trp Ile Phe Gly Thr Thr
                85              90              95

Leu Asp Ser Lys Thr Gln Ser Leu Leu Ile Val Asn Asn Ala Thr Asn
            100             105             110

Val Val Ile Lys Val Cys Glu Phe Gln Phe Cys Asn Asp Pro Phe Leu
            115             120             125

Gly Val Tyr Tyr His Lys Asn Asn Lys Ser Trp Met Glu Ser Glu Phe
    130             135             140

Arg Val Tyr Ser Ser Ala Asn Asn Cys Thr Phe Glu Tyr Val Ser Gln
145             150             155             160

Pro Phe Leu Met Asp Leu Glu Gly Lys Gln Gly Asn Phe Lys Asn Leu
                165             170             175

Arg Glu Phe Val Phe Lys Asn Ile Asp Gly Tyr Phe Lys Ile Tyr Ser
            180             185             190

Lys His Thr Pro Ile Asn Leu Val Arg Asp Leu Pro Gln Gly Phe Ser
            195             200             205

Ala Leu Glu Pro Leu Val Asp Leu Pro Ile Gly Ile Asn Ile Thr Arg
    210             215             220

Phe Gln Thr Leu Leu Ala Leu His Arg Ser Tyr Leu Thr Pro Gly Asp
225             230             235             240

Ser Ser Ser Gly Trp Thr Ala Gly Ala Ala Ala Tyr Tyr Val Gly Tyr
                245             250             255

Leu Gln Pro Arg Thr Phe Leu Leu Lys Tyr Asn Glu Asn Gly Thr Ile
            260             265             270

Thr Asp Ala Val Asp Cys Ala Leu Asp Pro Leu Ser Glu Thr Lys Cys
            275             280             285

Thr Leu Lys Ser Phe Thr Val Glu Lys Gly Ile Tyr Gln Thr Ser Asn
    290             295             300

Phe Arg Val Gln Pro Thr Glu Ser Ile Val Arg Phe Pro Asn Ile Thr
305             310             315             320

Asn Leu Cys Pro Phe Gly Glu Val Phe Asn Ala Thr Arg Phe Ala Ser
                325             330             335

Val Tyr Ala Trp Asn Arg Lys Arg Ile Ser Asn Cys Val Ala Asp Tyr
            340             345             350

Ser Val Leu Tyr Asn Ser Ala Ser Phe Ser Thr Phe Lys Cys Tyr Gly
            355             360             365

Val Ser Pro Thr Lys Leu Asn Asp Leu Cys Phe Thr Asn Val Tyr Ala
    370             375             380

Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
                405             410             415

Thr Gly Cys Val Ile Ala Trp Asn Ser Asn Asn Leu Asp Ser Lys Val
            420             425             430

Gly Gly Asn Tyr Asn Tyr Leu Tyr Arg Leu Phe Arg Lys Ser Asn Leu
            435             440             445

Lys Pro Phe Glu Arg Asp Ile Ser Thr Glu Ile Tyr Gln Ala Gly Ser
    450             455             460
```

```
Thr Pro Cys Asn Gly Val Glu Gly Phe Asn Cys Tyr Phe Pro Leu Gln
465             470             475             480

Ser Tyr Gly Phe Gln Pro Thr Asn Gly Val Gly Tyr Gln Pro Tyr Arg
                485             490             495

Val Val Val Leu Ser Phe Glu Leu Leu His Ala Pro Ala Thr Val Cys
            500             505             510

Gly Pro Lys Lys Ser Thr Asn Leu Val Lys Asn Lys Cys Val Asn Phe
            515             520             525

Asn Phe Asn Gly Leu Thr Gly Thr Gly Val Leu Thr Glu Ser Asn Lys
        530             535             540

Lys Phe Leu Pro Phe Gln Gln Phe Gly Arg Asp Ile Ala Asp Thr Thr
545             550             555             560

Asp Ala Val Arg Asp Pro Gln Thr Leu Glu Ile Leu Asp Ile Thr Pro
                565             570             575

Cys Ser Phe Gly Gly Val Ser Val Ile Thr Pro Gly Thr Asn Thr Ser
            580             585             590

Asn Gln Val Ala Val Leu Tyr Gln Asp Val Asn Cys Thr Glu Val Pro
            595             600             605

Val Ala Ile His Ala Asp Gln Leu Thr Pro Thr Trp Arg Val Tyr Ser
            610             615             620

Thr Gly Ser Asn Val Phe Gln Thr Arg Ala Gly Cys Leu Ile Gly Ala
625             630             635             640

Glu His Val Asn Asn Ser Tyr Glu Cys Asp Ile Pro Ile Gly Ala Gly
                645             650             655

Ile Cys Ala Ser Tyr Gln Thr Gln Thr Asn Ser Pro Gly Ser Ala Ser
            660             665             670

Ser Val Ala Ser Gln Ser Ile Ile Ala Tyr Thr Met Ser Leu Gly Ala
            675             680             685

Glu Asn Ser Val Ala Tyr Ser Asn Asn Ser Ile Ala Ile Pro Thr Asn
            690             695             700

Phe Thr Ile Ser Val Thr Thr Glu Ile Leu Pro Val Ser Met Thr Lys
705             710             715             720

Thr Ser Val Asp Cys Thr Met Tyr Ile Cys Gly Asp Ser Thr Glu Cys
                725             730             735

Ser Asn Leu Leu Leu Gln Tyr Gly Ser Phe Cys Thr Gln Leu Asn Arg
            740             745             750

Ala Leu Thr Gly Ile Ala Val Glu Gln Asp Lys Asn Thr Gln Glu Val
            755             760             765

Phe Ala Gln Val Lys Gln Ile Tyr Lys Thr Pro Pro Ile Lys Asp Phe
            770             775             780

Gly Gly Phe Asn Phe Ser Gln Ile Leu Pro Asp Pro Ser Lys Pro Ser
785             790             795             800

Lys Arg Ser Phe Ile Glu Asp Leu Leu Phe Asn Lys Val Thr Leu Ala
                805             810             815

Asp Ala Gly Phe Ile Lys Gln Tyr Gly Asp Cys Leu Gly Asp Ile Ala
            820             825             830

Ala Arg Asp Leu Ile Cys Ala Gln Lys Phe Asn Gly Leu Thr Val Leu
            835             840             845

Pro Pro Leu Leu Thr Asp Glu Met Ile Ala Gln Tyr Thr Ser Ala Leu
            850             855             860

Leu Ala Gly Thr Ile Thr Ser Gly Trp Thr Phe Gly Ala Gly Ala Ala
865             870             875             880

Leu Gln Ile Pro Phe Ala Met Gln Met Ala Tyr Arg Phe Asn Gly Ile
```

-continued

```
                885                 890                 895

Gly Val Thr Gln Asn Val Leu Tyr Glu Asn Gln Lys Leu Ile Ala Asn
            900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
            980                 985                 990

Thr Tyr Val Thr Gln Gln Leu Ile  Arg Ala Ala Glu Ile  Arg Ala Ser
        995                 1000                 1005

Ala Asn  Leu Ala Ala Thr Lys  Met Ser Glu Cys Val  Leu Gly Gln
    1010             1015                 1020

Ser Lys  Arg Val Asp Phe Cys  Gly Lys Gly Tyr His  Leu Met Ser
    1025             1030                 1035

Phe Pro  Gln Ser Ala Pro His  Gly Val Val Phe Leu  His Val Thr
    1040             1045                 1050

Tyr Val  Pro Ala Gln Glu Lys  Asn Phe Thr Thr Ala  Pro Ala Ile
    1055             1060                 1065

Cys His  Asp Gly Lys Ala His  Phe Pro Arg Glu Gly  Val Phe Val
    1070             1075                 1080

Ser Asn  Gly Thr His Trp Phe  Val Thr Gln Arg Asn  Phe Tyr Glu
    1085             1090                 1095

Pro Gln  Ile Ile Thr Thr Asp  Asn Thr Phe Val Ser  Gly Asn Cys
    1100             1105                 1110

Asp Val  Val Ile Gly Ile Val  Asn Asn Thr Val Tyr  Asp Pro Leu
    1115             1120                 1125

Gln Pro  Glu Leu Asp Ser Phe  Lys Glu Glu Leu Asp  Lys Tyr Phe
    1130             1135                 1140

Lys Asn  His Thr Ser Pro Asp  Val Asp Leu Gly Asp  Ile Ser Gly
    1145             1150                 1155

Ile Asn  Ala Ser Val Val Asn  Ile Gln Lys Glu Ile  Asp Arg Leu
    1160             1165                 1170

Asn Glu  Val Ala Lys Asn Leu  Asn Glu Ser Leu Ile  Asp Leu Gln
    1175             1180                 1185

Glu Leu  Gly Lys Tyr Glu Gln  Tyr Ile Lys Trp Pro  Trp Tyr Ile
    1190             1195                 1200

Trp Leu  Gly Phe Ile Ala Gly  Leu Ile Ala Ile Val  Met Val Thr
    1205             1210                 1215

Ile Met  Leu Cys Cys Met Thr  Ser Cys Cys Ser Cys  Leu Lys Gly
    1220             1225                 1230

Cys Cys  Ser Cys Gly Ser Cys  Cys Lys Phe Asp Glu  Asp Asp Ser
    1235             1240                 1245

Glu Pro  Val Leu Lys Gly Val  Lys Leu His Tyr Thr
    1250             1255                 1260
```

<210> SEQ ID NO 111
<211> LENGTH: 4
<212> TYPE: PRT
<213> ORGANISM: Artificial Sequence -continued

```
<220> FEATURE:
<223> OTHER INFORMATION: Recombinant Furin Cleavage Site

<400> SEQUENCE: 111

Gly Ser Gly Ala
1

<210> SEQ ID NO 112
<211> LENGTH: 1260
<212> TYPE: PRT
<213> ORGANISM: Artificial Sequence
<220> FEATURE:
<223> OTHER INFORMATION: Recombinant SARS-CoV-2 spike protein

<400> SEQUENCE: 112

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
        210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
            275                 280                 285

Thr Leu Lys Ser Phe Thr Val Glu Lys Gly Ile Tyr Gln Thr Ser Asn
        290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
```

-continued

```
                325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Gln Gln Ala Gln
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
    690                 695                 700

Phe Thr Ile Ser Val Thr Thr Glu Ile Leu Pro Val Ser Met Thr Lys
705                 710                 715                 720

Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
            740                 745                 750
```

-continued

```
Ala Leu Thr Gly Ile Ala Val Glu Gln Asp Lys Asn Thr Gln Glu Val
        755                 760                 765

Phe Ala Gln Val Lys Gln Ile Tyr Lys Thr Pro Pro Ile Lys Asp Phe
    770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
        835                 840                 845

Pro Pro Leu Leu Thr Asp Glu Met Ile Ala Gln Tyr Thr Ser Ala Leu
    850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
    930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile  Arg Ala Ala Glu Ile  Arg Ala Ser
        995                 1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095

Pro Gln  Ile Ile Thr Thr Asp  Asn Thr Phe Val Ser  Gly Asn Cys
    1100                1105                1110

Asp Val  Val Ile Gly Ile Val  Asn Asn Thr Val Tyr  Asp Pro Leu
    1115                1120                1125

Gln Pro  Glu Leu Asp Ser Phe  Lys Glu Glu Leu Asp  Lys Tyr Phe
    1130                1135                1140

Lys Asn  His Thr Ser Pro Asp  Val Asp Leu Gly Asp  Ile Ser Gly
    1145                1150                1155
```

-continued

```
Ile Asn  Ala Ser Val Val Asn  Ile Gln Lys Glu Ile  Asp Arg Leu
    1160              1165              1170

Asn Glu  Val Ala Lys Asn Leu  Asn Glu Ser Leu Ile  Asp Leu Gln
    1175              1180              1185

Glu Leu  Gly Lys Tyr Glu Gln  Tyr Ile Lys Trp Pro  Trp Tyr Ile
    1190              1195              1200

Trp Leu  Gly Phe Ile Ala Gly  Leu Ile Ala Ile Val  Met Val Thr
    1205              1210              1215

Ile Met  Leu Cys Cys Met Thr  Ser Cys Cys Ser Cys  Leu Lys Gly
    1220              1225              1230

Cys Cys  Ser Cys Gly Ser Cys  Cys Lys Phe Asp Glu  Asp Asp Ser
    1235              1240              1245

Glu Pro  Val Leu Lys Gly Val  Lys Leu His Tyr Thr
    1250              1255              1260
```

<210> SEQ ID NO 113
<211> LENGTH: 1260
<212> TYPE: PRT
<213> ORGANISM: Artificial Sequence
<220> FEATURE:
<223> OTHER INFORMATION: Recombinant SARS-CoV-2 spike protein

<400> SEQUENCE: 113

```
Gln Cys Val Asn Leu Thr Thr Arg Thr Gln Leu Pro Pro Ala Tyr Thr
1               5               10              15

Asn Ser Phe Thr Arg Gly Val Tyr Tyr Pro Asp Lys Val Phe Arg Ser
            20              25              30

Ser Val Leu His Ser Thr Gln Asp Leu Phe Leu Pro Phe Phe Ser Asn
            35              40              45

Val Thr Trp Phe His Ala Ile His Val Ser Gly Thr Asn Gly Thr Lys
    50              55              60

Arg Phe Asp Asn Pro Val Leu Pro Phe Asn Asp Gly Val Tyr Phe Ala
65              70              75              80

Ser Thr Glu Lys Ser Asn Ile Ile Arg Gly Trp Ile Phe Gly Thr Thr
            85              90              95

Leu Asp Ser Lys Thr Gln Ser Leu Leu Ile Val Asn Asn Ala Thr Asn
            100             105             110

Val Val Ile Lys Val Cys Glu Phe Gln Phe Cys Asn Asp Pro Phe Leu
            115             120             125

Gly Val Tyr Tyr His Lys Asn Asn Lys Ser Trp Met Glu Ser Glu Phe
            130             135             140

Arg Val Tyr Ser Ser Ala Asn Asn Cys Thr Phe Glu Tyr Val Ser Gln
145             150             155             160

Pro Phe Leu Met Asp Leu Glu Gly Lys Gln Gly Asn Phe Lys Asn Leu
            165             170             175

Arg Glu Phe Val Phe Lys Asn Ile Asp Gly Tyr Phe Lys Ile Tyr Ser
            180             185             190

Lys His Thr Pro Ile Asn Leu Val Arg Asp Leu Pro Gln Gly Phe Ser
            195             200             205

Ala Leu Glu Pro Leu Val Asp Leu Pro Ile Gly Ile Asn Ile Thr Arg
            210             215             220

Phe Gln Thr Leu Leu Ala Leu His Arg Ser Tyr Leu Thr Pro Gly Asp
225             230             235             240

Ser Ser Ser Gly Trp Thr Ala Gly Ala Ala Ala Tyr Tyr Val Gly Tyr
            245             250             255
```

-continued

```
Leu Gln Pro Arg Thr Phe Leu Leu Lys Tyr Asn Glu Asn Gly Thr Ile
            260             265             270

Thr Asp Ala Val Asp Cys Ala Leu Asp Pro Leu Ser Glu Thr Lys Cys
            275             280             285

Thr Leu Lys Ser Phe Thr Val Glu Lys Gly Ile Tyr Gln Thr Ser Asn
    290             295             300

Phe Arg Val Gln Pro Thr Glu Ser Ile Val Arg Phe Pro Asn Ile Thr
305             310             315             320

Asn Leu Cys Pro Phe Gly Glu Val Phe Asn Ala Thr Arg Phe Ala Ser
            325             330             335

Val Tyr Ala Trp Asn Arg Lys Arg Ile Ser Asn Cys Val Ala Asp Tyr
            340             345             350

Ser Val Leu Tyr Asn Ser Ala Ser Phe Ser Thr Phe Lys Cys Tyr Gly
            355             360             365

Val Ser Pro Thr Lys Leu Asn Asp Leu Cys Phe Thr Asn Val Tyr Ala
    370             375             380

Asp Ser Phe Val Ile Arg Gly Asp Glu Val Arg Gln Ile Ala Pro Gly
385             390             395             400

Gln Thr Gly Lys Ile Ala Asp Tyr Asn Tyr Lys Leu Pro Asp Asp Phe
            405             410             415

Thr Gly Cys Val Ile Ala Trp Asn Ser Asn Asn Leu Asp Ser Lys Val
            420             425             430

Gly Gly Asn Tyr Asn Tyr Leu Tyr Arg Leu Phe Arg Lys Ser Asn Leu
            435             440             445

Lys Pro Phe Glu Arg Asp Ile Ser Thr Glu Ile Tyr Gln Ala Gly Ser
    450             455             460

Thr Pro Cys Asn Gly Val Glu Gly Phe Asn Cys Tyr Phe Pro Leu Gln
465             470             475             480

Ser Tyr Gly Phe Gln Pro Thr Tyr Gly Val Gly Tyr Gln Pro Tyr Arg
            485             490             495

Val Val Val Leu Ser Phe Glu Leu Leu His Ala Pro Ala Thr Val Cys
            500             505             510

Gly Pro Lys Lys Ser Thr Asn Leu Val Lys Asn Lys Cys Val Asn Phe
            515             520             525

Asn Phe Asn Gly Leu Thr Gly Thr Gly Val Leu Thr Glu Ser Asn Lys
    530             535             540

Lys Phe Leu Pro Phe Gln Gln Phe Gly Arg Asp Ile Ala Asp Thr Thr
545             550             555             560

Asp Ala Val Arg Asp Pro Gln Thr Leu Glu Ile Leu Asp Ile Thr Pro
            565             570             575

Cys Ser Phe Gly Gly Val Ser Val Ile Thr Pro Gly Thr Asn Thr Ser
            580             585             590

Asn Gln Val Ala Val Leu Tyr Gln Gly Val Asn Cys Thr Glu Val Pro
            595             600             605

Val Ala Ile His Ala Asp Gln Leu Thr Pro Thr Trp Arg Val Tyr Ser
            610             615             620

Thr Gly Ser Asn Val Phe Gln Thr Arg Ala Gly Cys Leu Ile Gly Ala
625             630             635             640

Glu His Val Asn Asn Ser Tyr Glu Cys Asp Ile Pro Ile Gly Ala Gly
            645             650             655

Ile Cys Ala Ser Tyr Gln Thr Gln Thr Asn Ser Pro Gln Gln Ala Gln
            660             665             670

Ser Val Ala Ser Gln Ser Ile Ile Ala Tyr Thr Met Ser Leu Gly Ala
```

-continued

```
                 675                680                685

Glu Asn Ser Val Ala Tyr Ser Asn Asn Ser Ile Ala Ile Pro Thr Asn
    690                695                700

Phe Thr Ile Ser Val Thr Thr Glu Ile Leu Pro Val Ser Met Thr Lys
705                710                715                720

Thr Ser Val Asp Cys Thr Met Tyr Ile Cys Gly Asp Ser Thr Glu Cys
                725                730                735

Ser Asn Leu Leu Leu Gln Tyr Gly Ser Phe Cys Thr Gln Leu Asn Arg
            740                745                750

Ala Leu Thr Gly Ile Ala Val Glu Gln Asp Lys Asn Thr Gln Glu Val
            755                760                765

Phe Ala Gln Val Lys Gln Ile Tyr Lys Thr Pro Pro Ile Lys Asp Phe
    770                775                780

Gly Gly Phe Asn Phe Ser Gln Ile Leu Pro Asp Pro Ser Lys Pro Ser
785                790                795                800

Lys Arg Ser Phe Ile Glu Asp Leu Leu Phe Asn Lys Val Thr Leu Ala
                805                810                815

Asp Ala Gly Phe Ile Lys Gln Tyr Gly Asp Cys Leu Gly Asp Ile Ala
                820                825                830

Ala Arg Asp Leu Ile Cys Ala Gln Lys Phe Asn Gly Leu Thr Val Leu
            835                840                845

Pro Pro Leu Leu Thr Asp Glu Met Ile Ala Gln Tyr Thr Ser Ala Leu
    850                855                860

Leu Ala Gly Thr Ile Thr Ser Gly Trp Thr Phe Gly Ala Gly Ala Ala
865                870                875                880

Leu Gln Ile Pro Phe Ala Met Gln Met Ala Tyr Arg Phe Asn Gly Ile
                885                890                895

Gly Val Thr Gln Asn Val Leu Tyr Glu Asn Gln Lys Leu Ile Ala Asn
            900                905                910

Gln Phe Asn Ser Ala Ile Gly Lys Ile Gln Asp Ser Leu Ser Ser Thr
            915                920                925

Ala Ser Ala Leu Gly Lys Leu Gln Asp Val Val Asn Gln Asn Ala Gln
    930                935                940

Ala Leu Asn Thr Leu Val Lys Gln Leu Ser Ser Asn Phe Gly Ala Ile
945                950                955                960

Ser Ser Val Leu Asn Asp Ile Leu Ser Arg Leu Asp Pro Pro Glu Ala
                965                970                975

Glu Val Gln Ile Asp Arg Leu Ile Thr Gly Arg Leu Gln Ser Leu Gln
            980                985                990

Thr Tyr Val Thr Gln Gln Leu Ile  Arg Ala Ala Glu Ile  Arg Ala Ser
        995                1000                1005

Ala Asn  Leu Ala Ala Thr Lys  Met Ser Glu Cys Val  Leu Gly Gln
    1010                1015                1020

Ser Lys  Arg Val Asp Phe Cys  Gly Lys Gly Tyr His  Leu Met Ser
    1025                1030                1035

Phe Pro  Gln Ser Ala Pro His  Gly Val Val Phe Leu  His Val Thr
    1040                1045                1050

Tyr Val  Pro Ala Gln Glu Lys  Asn Phe Thr Thr Ala  Pro Ala Ile
    1055                1060                1065

Cys His  Asp Gly Lys Ala His  Phe Pro Arg Glu Gly  Val Phe Val
    1070                1075                1080

Ser Asn  Gly Thr His Trp Phe  Val Thr Gln Arg Asn  Phe Tyr Glu
    1085                1090                1095
```

-continued

```
Pro Gln Ile Ile Thr Thr Asp  Asn Thr Phe Val Ser  Gly Asn Cys
    1100            1105           1110

Asp Val Val Ile Gly Ile Val  Asn Asn Thr Val Tyr  Asp Pro Leu
    1115            1120           1125

Gln Pro Glu Leu Asp Ser Phe  Lys Glu Glu Leu Asp  Lys Tyr Phe
    1130            1135           1140

Lys Asn His Thr Ser Pro Asp  Val Asp Leu Gly Asp  Ile Ser Gly
    1145            1150           1155

Ile Asn Ala Ser Val Val Asn  Ile Gln Lys Glu Ile  Asp Arg Leu
    1160            1165           1170

Asn Glu Val Ala Lys Asn Leu  Asn Glu Ser Leu Ile  Asp Leu Gln
    1175            1180           1185

Glu Leu Gly Lys Tyr Glu Gln  Tyr Ile Lys Trp Pro  Trp Tyr Ile
    1190            1195           1200

Trp Leu Gly Phe Ile Ala Gly  Leu Ile Ala Ile Val  Met Val Thr
    1205            1210           1215

Ile Met Leu Cys Cys Met Thr  Ser Cys Cys Ser Cys  Leu Lys Gly
    1220            1225           1230

Cys Cys Ser Cys Gly Ser Cys  Cys Lys Phe Asp Glu  Asp Asp Ser
    1235            1240           1245

Glu Pro Val Leu Lys Gly Val  Lys Leu His Tyr Thr
    1250            1255           1260

<210> SEQ ID NO 114
<211> LENGTH: 1257
<212> TYPE: PRT
<213> ORGANISM: Artificial Sequence
<220> FEATURE:
<223> OTHER INFORMATION: Recombinant SARS-CoV-2 spike protein

<400> SEQUENCE: 114

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile Ser Gly Thr Asn Gly Thr Lys Arg Phe
    50                  55                  60

Asp Asn Pro Val Leu Pro Phe Asn Asp Gly Val Tyr Phe Ala Ser Thr
65                  70                  75                  80

Glu Lys Ser Asn Ile Ile Arg Gly Trp Ile Phe Gly Thr Thr Leu Asp
                85                  90                  95

Ser Lys Thr Gln Ser Leu Leu Ile Val Asn Asn Ala Thr Asn Val Val
            100                 105                 110

Ile Lys Val Cys Glu Phe Gln Phe Cys Asn Asp Pro Phe Leu Gly Val
        115                 120                 125

Tyr His Lys Asn Asn Lys Ser Trp Met Glu Ser Glu Phe Arg Val Tyr
    130                 135                 140

Ser Ser Ala Asn Asn Cys Thr Phe Glu Tyr Val Ser Gln Pro Phe Leu
145                 150                 155                 160

Met Asp Leu Glu Gly Lys Gln Gly Asn Phe Lys Asn Leu Arg Glu Phe
                165                 170                 175

Val Phe Lys Asn Ile Asp Gly Tyr Phe Lys Ile Tyr Ser Lys His Thr
            180                 185                 190
```

```
Pro Ile Asn Leu Val Arg Asp Leu Pro Gln Gly Phe Ser Ala Leu Glu
        195                 200                 205

Pro Leu Val Asp Leu Pro Ile Gly Ile Asn Ile Thr Arg Phe Gln Thr
    210                 215                 220

Leu Leu Ala Leu His Arg Ser Tyr Leu Thr Pro Gly Asp Ser Ser Ser
225                 230                 235                 240

Gly Trp Thr Ala Gly Ala Ala Ala Tyr Tyr Val Gly Tyr Leu Gln Pro
                245                 250                 255

Arg Thr Phe Leu Leu Lys Tyr Asn Glu Asn Gly Thr Ile Thr Asp Ala
                260                 265                 270

Val Asp Cys Ala Leu Asp Pro Leu Ser Glu Thr Lys Cys Thr Leu Lys
        275                 280                 285

Ser Phe Thr Val Glu Lys Gly Ile Tyr Gln Thr Ser Asn Phe Arg Val
    290                 295                 300

Gln Pro Thr Glu Ser Ile Val Arg Phe Pro Asn Ile Thr Asn Leu Cys
305                 310                 315                 320

Pro Phe Gly Glu Val Phe Asn Ala Thr Arg Phe Ala Ser Val Tyr Ala
                325                 330                 335

Trp Asn Arg Lys Arg Ile Ser Asn Cys Val Ala Asp Tyr Ser Val Leu
                340                 345                 350

Tyr Asn Ser Ala Ser Phe Ser Thr Phe Lys Cys Tyr Gly Val Ser Pro
                355                 360                 365

Thr Lys Leu Asn Asp Leu Cys Phe Thr Asn Val Tyr Ala Asp Ser Phe
    370                 375                 380

Val Ile Arg Gly Asp Glu Val Arg Gln Ile Ala Pro Gly Gln Thr Gly
385                 390                 395                 400

Lys Ile Ala Asp Tyr Asn Tyr Lys Leu Pro Asp Asp Phe Thr Gly Cys
                405                 410                 415

Val Ile Ala Trp Asn Ser Asn Asn Leu Asp Ser Lys Val Gly Gly Asn
                420                 425                 430

Tyr Asn Tyr Leu Tyr Arg Leu Phe Arg Lys Ser Asn Leu Lys Pro Phe
                435                 440                 445

Glu Arg Asp Ile Ser Thr Glu Ile Tyr Gln Ala Gly Ser Thr Pro Cys
    450                 455                 460

Asn Gly Val Glu Gly Phe Asn Cys Tyr Phe Pro Leu Gln Ser Tyr Gly
465                 470                 475                 480

Phe Gln Pro Thr Tyr Gly Val Gly Tyr Gln Pro Tyr Arg Val Val Val
                485                 490                 495

Leu Ser Phe Glu Leu Leu His Ala Pro Ala Thr Val Cys Gly Pro Lys
                500                 505                 510

Lys Ser Thr Asn Leu Val Lys Asn Lys Cys Val Asn Phe Asn Phe Asn
                515                 520                 525

Gly Leu Thr Gly Thr Gly Val Leu Thr Glu Ser Asn Lys Lys Phe Leu
    530                 535                 540

Pro Phe Gln Gln Phe Gly Arg Asp Ile Asp Asp Thr Thr Asp Ala Val
545                 550                 555                 560

Arg Asp Pro Gln Thr Leu Glu Ile Leu Asp Ile Thr Pro Cys Ser Phe
                565                 570                 575

Gly Gly Val Ser Val Ile Thr Pro Gly Thr Asn Thr Ser Asn Gln Val
                580                 585                 590

Ala Val Leu Tyr Gln Gly Val Asn Cys Thr Glu Val Pro Val Ala Ile
                595                 600                 605
```

-continued

```
His Ala Asp Gln Leu Thr Pro Thr Trp Arg Val Tyr Ser Thr Gly Ser
    610             615             620
Asn Val Phe Gln Thr Arg Ala Gly Cys Leu Ile Gly Ala Glu His Val
625             630             635             640
Asn Asn Ser Tyr Glu Cys Asp Ile Pro Ile Gly Ala Gly Ile Cys Ala
            645             650             655
Ser Tyr Gln Thr Gln Thr Asn Ser His Gln Gln Ala Gln Ser Val Ala
            660             665             670
Ser Gln Ser Ile Ile Ala Tyr Thr Met Ser Leu Gly Ala Glu Asn Ser
        675             680             685
Val Ala Tyr Ser Asn Asn Ser Ile Ala Ile Pro Ile Asn Phe Thr Ile
    690             695             700
Ser Val Thr Thr Glu Ile Leu Pro Val Ser Met Thr Lys Thr Ser Val
705             710             715             720
Asp Cys Thr Met Tyr Ile Cys Gly Asp Ser Thr Glu Cys Ser Asn Leu
            725             730             735
Leu Leu Gln Tyr Gly Ser Phe Cys Thr Gln Leu Asn Arg Ala Leu Thr
            740             745             750
Gly Ile Ala Val Glu Gln Asp Lys Asn Thr Gln Glu Val Phe Ala Gln
        755             760             765
Val Lys Gln Ile Tyr Lys Thr Pro Pro Ile Lys Asp Phe Gly Gly Phe
    770             775             780
Asn Phe Ser Gln Ile Leu Pro Asp Pro Ser Lys Pro Ser Lys Arg Ser
785             790             795             800
Phe Ile Glu Asp Leu Leu Phe Asn Lys Val Thr Leu Ala Asp Ala Gly
            805             810             815
Phe Ile Lys Gln Tyr Gly Asp Cys Leu Gly Asp Ile Ala Ala Arg Asp
            820             825             830
Leu Ile Cys Ala Gln Lys Phe Asn Gly Leu Thr Val Leu Pro Pro Leu
        835             840             845
Leu Thr Asp Glu Met Ile Ala Gln Tyr Thr Ser Ala Leu Leu Ala Gly
    850             855             860
Thr Ile Thr Ser Gly Trp Thr Phe Gly Ala Gly Ala Ala Leu Gln Ile
865             870             875             880
Pro Phe Ala Met Gln Met Ala Tyr Arg Phe Asn Gly Ile Gly Val Thr
            885             890             895
Gln Asn Val Leu Tyr Glu Asn Gln Lys Leu Ile Ala Asn Gln Phe Asn
            900             905             910
Ser Ala Ile Gly Lys Ile Gln Asp Ser Leu Ser Ser Thr Ala Ser Ala
        915             920             925
Leu Gly Lys Leu Gln Asp Val Val Asn Gln Asn Ala Gln Ala Leu Asn
    930             935             940
Thr Leu Val Lys Gln Leu Ser Ser Asn Phe Gly Ala Ile Ser Ser Val
945             950             955             960
Leu Asn Asp Ile Leu Ala Arg Leu Asp Pro Pro Glu Ala Glu Val Gln
            965             970             975
Ile Asp Arg Leu Ile Thr Gly Arg Leu Gln Ser Leu Gln Thr Tyr Val
            980             985             990
Thr Gln Gln Leu Ile Arg Ala Ala  Glu Ile Arg Ala Ser  Ala Asn Leu
        995             1000             1005
Ala Ala  Thr Lys Met Ser Glu  Cys Val Leu Gly Gln  Ser Lys Arg
    1010             1015             1020
Val Asp  Phe Cys Gly Lys Gly  Tyr His Leu Met Ser  Phe Pro Gln
```

```
          1025                1030                1035

Ser Ala  Pro His Gly Val Val  Phe Leu His Val Thr  Tyr Val Pro
    1040         1045                1050

Ala Gln  Glu Lys Asn Phe Thr  Thr Ala Pro Ala Ile  Cys His Asp
    1055         1060                1065

Gly Lys  Ala His Phe Pro Arg  Glu Gly Val Phe Val  Ser Asn Gly
    1070         1075                1080

Thr His  Trp Phe Val Thr Gln  Arg Asn Phe Tyr Glu  Pro Gln Ile
    1085         1090                1095

Ile Thr  Thr His Asn Thr Phe  Val Ser Gly Asn Cys  Asp Val Val
    1100         1105                1110

Ile Gly  Ile Val Asn Asn Thr  Val Tyr Asp Pro Leu  Gln Pro Glu
    1115         1120                1125

Leu Asp  Ser Phe Lys Glu Glu  Leu Asp Lys Tyr Phe  Lys Asn His
    1130         1135                1140

Thr Ser  Pro Asp Val Asp Leu  Gly Asp Ile Ser Gly  Ile Asn Ala
    1145         1150                1155

Ser Val  Val Asn Ile Gln Lys  Glu Ile Asp Arg Leu  Asn Glu Val
    1160         1165                1170

Ala Lys  Asn Leu Asn Glu Ser  Leu Ile Asp Leu Gln  Glu Leu Gly
    1175         1180                1185

Lys Tyr  Glu Gln Tyr Ile Lys  Trp Pro Trp Tyr Ile  Trp Leu Gly
    1190         1195                1200

Phe Ile  Ala Gly Leu Ile Ala  Ile Val Met Val Thr  Ile Met Leu
    1205         1210                1215

Cys Cys  Met Thr Ser Cys Cys  Ser Cys Leu Lys Gly  Cys Cys Ser
    1220         1225                1230

Cys Gly  Ser Cys Cys Lys Phe  Asp Glu Asp Asp Ser  Glu Pro Val
    1235         1240                1245

Leu Lys  Gly Val Lys Leu His  Tyr Thr
    1250         1255

<210> SEQ ID NO 115
<211> LENGTH: 1260
<212> TYPE: PRT
<213> ORGANISM: Artificial Sequence
<220> FEATURE:
<223> OTHER INFORMATION: Recombinant SARS-CoV-2 spike protein

<400> SEQUENCE: 115

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Ala Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
```

-continued

```
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Gly Leu Pro Gln Gly Phe Ser
                195                 200                 205

Ala Leu Glu Pro Leu Val Asp Leu Pro Ile Gly Ile Asn Ile Thr Arg
    210                 215                 220

Phe Gln Thr Leu His Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Asn Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
    450                 455                 460

Thr Pro Cys Asn Gly Val Lys Gly Phe Asn Cys Tyr Phe Pro Leu Gln
465                 470                 475                 480

Ser Tyr Gly Phe Gln Pro Thr Tyr Gly Val Gly Tyr Gln Pro Tyr Arg
                485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
                515                 520                 525

Asn Phe Asn Gly Leu Thr Gly Thr Gly Val Leu Thr Glu Ser Asn Lys
    530                 535                 540
```

-continued

```
Lys Phe Leu Pro Phe Gln Gln Phe Gly Arg Asp Ile Ala Asp Thr Thr
545             550             555             560

Asp Ala Val Arg Asp Pro Gln Thr Leu Glu Ile Leu Asp Ile Thr Pro
            565             570             575

Cys Ser Phe Gly Gly Val Ser Val Ile Thr Pro Gly Thr Asn Thr Ser
            580             585             590

Asn Gln Val Ala Val Leu Tyr Gln Gly Val Asn Cys Thr Glu Val Pro
            595             600             605

Val Ala Ile His Ala Asp Gln Leu Thr Pro Thr Trp Arg Val Tyr Ser
        610             615             620

Thr Gly Ser Asn Val Phe Gln Thr Arg Ala Gly Cys Leu Ile Gly Ala
625             630             635             640

Glu His Val Asn Asn Ser Tyr Glu Cys Asp Ile Pro Ile Gly Ala Gly
            645             650             655

Ile Cys Ala Ser Tyr Gln Thr Gln Thr Asn Ser Pro Gln Gln Ala Gln
            660             665             670

Ser Val Ala Ser Gln Ser Ile Ile Ala Tyr Thr Met Ser Leu Gly Val
            675             680             685

Glu Asn Ser Val Ala Tyr Ser Asn Asn Ser Ile Ala Ile Pro Thr Asn
        690             695             700

Phe Thr Ile Ser Val Thr Thr Glu Ile Leu Pro Val Ser Met Thr Lys
705             710             715             720

Thr Ser Val Asp Cys Thr Met Tyr Ile Cys Gly Asp Ser Thr Glu Cys
            725             730             735

Ser Asn Leu Leu Leu Gln Tyr Gly Ser Phe Cys Thr Gln Leu Asn Arg
            740             745             750

Ala Leu Thr Gly Ile Ala Val Glu Gln Asp Lys Asn Thr Gln Glu Val
            755             760             765

Phe Ala Gln Val Lys Gln Ile Tyr Lys Thr Pro Pro Ile Lys Asp Phe
        770             775             780

Gly Gly Phe Asn Phe Ser Gln Ile Leu Pro Asp Pro Ser Lys Pro Ser
785             790             795             800

Lys Arg Ser Phe Ile Glu Asp Leu Leu Phe Asn Lys Val Thr Leu Ala
            805             810             815

Asp Ala Gly Phe Ile Lys Gln Tyr Gly Asp Cys Leu Gly Asp Ile Ala
            820             825             830

Ala Arg Asp Leu Ile Cys Ala Gln Lys Phe Asn Gly Leu Thr Val Leu
        835             840             845

Pro Pro Leu Leu Thr Asp Glu Met Ile Ala Gln Tyr Thr Ser Ala Leu
        850             855             860

Leu Ala Gly Thr Ile Thr Ser Gly Trp Thr Phe Gly Ala Gly Ala Ala
865             870             875             880

Leu Gln Ile Pro Phe Ala Met Gln Met Ala Tyr Arg Phe Asn Gly Ile
            885             890             895

Gly Val Thr Gln Asn Val Leu Tyr Glu Asn Gln Lys Leu Ile Ala Asn
            900             905             910

Gln Phe Asn Ser Ala Ile Gly Lys Ile Gln Asp Ser Leu Ser Ser Thr
            915             920             925

Ala Ser Ala Leu Gly Lys Leu Gln Asp Val Val Asn Gln Asn Ala Gln
        930             935             940

Ala Leu Asn Thr Leu Val Lys Gln Leu Ser Ser Asn Phe Gly Ala Ile
945             950             955             960
```

-continued

Ser Ser Val Leu Asn Asp Ile Leu Ser Arg Leu Asp Pro Pro Glu Ala
              965                970                975

Glu Val Gln Ile Asp Arg Leu Ile Thr Gly Arg Leu Gln Ser Leu Gln
              980                985                990

Thr Tyr Val Thr Gln Gln Leu Ile Arg Ala Ala Glu Ile Arg Ala Ser
         995                1000                1005

Ala Asn Leu Ala Ala Thr Lys Met Ser Glu Cys Val Leu Gly Gln
    1010                1015                1020

Ser Lys Arg Val Asp Phe Cys Gly Lys Gly Tyr His Leu Met Ser
    1025                1030                1035

Phe Pro Gln Ser Ala Pro His Gly Val Val Phe Leu His Val Thr
    1040                1045                1050

Tyr Val Pro Ala Gln Glu Lys Asn Phe Thr Thr Ala Pro Ala Ile
    1055                1060                1065

Cys His Asp Gly Lys Ala His Phe Pro Arg Glu Gly Val Phe Val
    1070                1075                1080

Ser Asn Gly Thr His Trp Phe Val Thr Gln Arg Asn Phe Tyr Glu
    1085                1090                1095

Pro Gln Ile Ile Thr Thr Asp Asn Thr Phe Val Ser Gly Asn Cys
    1100                1105                1110

Asp Val Val Ile Gly Ile Val Asn Asn Thr Val Tyr Asp Pro Leu
    1115                1120                1125

Gln Pro Glu Leu Asp Ser Phe Lys Glu Glu Leu Asp Lys Tyr Phe
    1130                1135                1140

Lys Asn His Thr Ser Pro Asp Val Asp Leu Gly Asp Ile Ser Gly
    1145                1150                1155

Ile Asn Ala Ser Val Val Asn Ile Gln Lys Glu Ile Asp Arg Leu
    1160                1165                1170

Asn Glu Val Ala Lys Asn Leu Asn Glu Ser Leu Ile Asp Leu Gln
    1175                1180                1185

Glu Leu Gly Lys Tyr Glu Gln Tyr Ile Lys Trp Pro Trp Tyr Ile
    1190                1195                1200

Trp Leu Gly Phe Ile Ala Gly Leu Ile Ala Ile Val Met Val Thr
    1205                1210                1215

Ile Met Leu Cys Cys Met Thr Ser Cys Cys Ser Cys Leu Lys Gly
    1220                1225                1230

Cys Cys Ser Cys Gly Ser Cys Cys Lys Phe Asp Glu Asp Asp Ser
    1235                1240                1245

Glu Pro Val Leu Lys Gly Val Lys Leu His Tyr Thr
    1250                1255                1260

<210> SEQ ID NO 116
<211> LENGTH: 196
<212> TYPE: PRT
<213> ORGANISM: Betacoronavirus severe acute respiratory syndrome
      coronavirus 2

<400> SEQUENCE: 116

Leu Cys Pro Phe Gly Glu Val Phe Asn Ala Thr Arg Phe Ala Ser Val
1               5                10                15

Tyr Ala Trp Asn Arg Lys Arg Ile Ser Asn Cys Val Ala Asp Tyr Ser
              20                25                30

Val Leu Tyr Asn Ser Ala Ser Phe Ser Thr Phe Lys Cys Tyr Gly Val
         35                40                45

Ser Pro Thr Lys Leu Asn Asp Leu Cys Phe Thr Asn Val Tyr Ala Asp

-continued

```
        50                  55                  60

Ser Phe Val Ile Arg Gly Asp Glu Val Arg Gln Ile Ala Pro Gly Gln
65                  70                  75                  80

Thr Gly Lys Ile Ala Asp Tyr Asn Tyr Lys Leu Pro Asp Asp Phe Thr
                85                  90                  95

Gly Cys Val Ile Ala Trp Asn Ser Asn Asn Leu Asp Ser Lys Val Gly
                100                 105                 110

Gly Asn Tyr Asn Tyr Leu Tyr Arg Leu Phe Arg Lys Ser Asn Leu Lys
            115                 120                 125

Pro Phe Glu Arg Asp Ile Ser Thr Glu Ile Tyr Gln Ala Gly Ser Thr
        130                 135                 140

Pro Cys Asn Gly Val Glu Gly Phe Asn Cys Tyr Phe Pro Leu Gln Ser
145                 150                 155                 160

Tyr Gly Phe Gln Pro Thr Asn Gly Val Gly Tyr Gln Pro Tyr Arg Val
                165                 170                 175

Val Val Leu Ser Phe Glu Leu Leu His Ala Pro Ala Thr Val Cys Gly
                180                 185                 190

Pro Lys Lys Ser
            195

<210> SEQ ID NO 117
<211> LENGTH: 13
<212> TYPE: PRT
<213> ORGANISM: Artificial Sequence
<220> FEATURE:
<223> OTHER INFORMATION: signal peptide

<400> SEQUENCE: 117

Met Phe Val Phe Leu Val Leu Leu Pro Leu Val Ser Ile
1               5                   10

<210> SEQ ID NO 118
<211> LENGTH: 292
<212> TYPE: PRT
<213> ORGANISM: Betacoronavirus severe acute respiratory syndrome
      coronavirus 2

<400> SEQUENCE: 118

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
                20                  25                  30

Ser Val Leu His Ser Thr Gln Asp Leu Phe Leu Pro Phe Phe Ser Asn
            35                  40                  45

Val Thr Trp Phe His Ala Ile His Val Ser Gly Thr Asn Gly Thr Lys
        50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
            115                 120                 125

Gly Val Tyr Tyr His Lys Asn Asn Lys Ser Trp Met Glu Ser Glu Phe
        130                 135                 140

Arg Val Tyr Ser Ser Ala Asn Asn Cys Thr Phe Glu Tyr Val Ser Gln
```

-continued

```
145               150               155               160

Pro Phe Leu Met Asp Leu Glu Gly Lys Gln Gly Asn Phe Lys Asn Leu
              165               170               175

Arg Glu Phe Val Phe Lys Asn Ile Asp Gly Tyr Phe Lys Ile Tyr Ser
              180               185               190

Lys His Thr Pro Ile Asn Leu Val Arg Asp Leu Pro Gln Gly Phe Ser
              195               200               205

Ala Leu Glu Pro Leu Val Asp Leu Pro Ile Gly Ile Asn Ile Thr Arg
              210               215               220

Phe Gln Thr Leu Leu Ala Leu His Arg Ser Tyr Leu Thr Pro Gly Asp
          225               230               235               240

Ser Ser Ser Gly Trp Thr Ala Gly Ala Ala Ala Tyr Tyr Val Gly Tyr
              245               250               255

Leu Gln Pro Arg Thr Phe Leu Leu Lys Tyr Asn Glu Asn Gly Thr Ile
              260               265               270

Thr Asp Ala Val Asp Cys Ala Leu Asp Pro Leu Ser Glu Thr Lys Cys
              275               280               285

Thr Leu Lys Ser
      290

<210> SEQ ID NO 119
<211> LENGTH: 83
<212> TYPE: PRT
<213> ORGANISM: Betacoronavirus severe acute respiratory syndrome
      coronavirus 2

<400> SEQUENCE: 119

Met Ala Tyr Arg Phe Asn Gly Ile Gly Val Thr Gln Asn Val Leu Tyr
1               5               10               15

Glu Asn Gln Lys Leu Ile Ala Asn Gln Phe Asn Ser Ala Ile Gly Lys
              20               25               30

Ile Gln Asp Ser Leu Ser Ser Thr Ala Ser Ala Leu Gly Lys Leu Gln
          35               40               45

Asp Val Val Asn Gln Asn Ala Gln Ala Leu Asn Thr Leu Val Lys Gln
      50               55               60

Leu Ser Ser Asn Phe Gly Ala Ile Ser Ser Val Leu Asn Asp Ile Leu
65               70               75               80

Ser Arg Leu

<210> SEQ ID NO 120
<211> LENGTH: 588
<212> TYPE: PRT
<213> ORGANISM: Betacoronavirus severe acute respiratory syndrome
      coronavirus 2

<400> SEQUENCE: 120

Ser Val Ala Ser Gln Ser Ile Ile Ala Tyr Thr Met Ser Leu Gly Ala
1               5               10               15

Glu Asn Ser Val Ala Tyr Ser Asn Asn Ser Ile Ala Ile Pro Thr Asn
              20               25               30

Phe Thr Ile Ser Val Thr Thr Glu Ile Leu Pro Val Ser Met Thr Lys
          35               40               45

Thr Ser Val Asp Cys Thr Met Tyr Ile Cys Gly Asp Ser Thr Glu Cys
      50               55               60

Ser Asn Leu Leu Leu Gln Tyr Gly Ser Phe Cys Thr Gln Leu Asn Arg
65               70               75               80
```

```
Ala Leu Thr Gly Ile Ala Val Glu Gln Asp Lys Asn Thr Gln Glu Val
                 85                  90                  95

Phe Ala Gln Val Lys Gln Ile Tyr Lys Thr Pro Pro Ile Lys Asp Phe
            100                 105                 110

Gly Gly Phe Asn Phe Ser Gln Ile Leu Pro Asp Pro Ser Lys Pro Ser
        115                 120                 125

Lys Arg Ser Phe Ile Glu Asp Leu Leu Phe Asn Lys Val Thr Leu Ala
    130                 135                 140

Asp Ala Gly Phe Ile Lys Gln Tyr Gly Asp Cys Leu Gly Asp Ile Ala
145                 150                 155                 160

Ala Arg Asp Leu Ile Cys Ala Gln Lys Phe Asn Gly Leu Thr Val Leu
                165                 170                 175

Pro Pro Leu Leu Thr Asp Glu Met Ile Ala Gln Tyr Thr Ser Ala Leu
            180                 185                 190

Leu Ala Gly Thr Ile Thr Ser Gly Trp Thr Phe Gly Ala Gly Ala Ala
        195                 200                 205

Leu Gln Ile Pro Phe Ala Met Gln Met Ala Tyr Arg Phe Asn Gly Ile
    210                 215                 220

Gly Val Thr Gln Asn Val Leu Tyr Glu Asn Gln Lys Leu Ile Ala Asn
225                 230                 235                 240

Gln Phe Asn Ser Ala Ile Gly Lys Ile Gln Asp Ser Leu Ser Ser Thr
                245                 250                 255

Ala Ser Ala Leu Gly Lys Leu Gln Asp Val Val Asn Gln Asn Ala Gln
            260                 265                 270

Ala Leu Asn Thr Leu Val Lys Gln Leu Ser Ser Asn Phe Gly Ala Ile
        275                 280                 285

Ser Ser Val Leu Asn Asp Ile Leu Ser Arg Leu Asp Lys Val Glu Ala
    290                 295                 300

Glu Val Gln Ile Asp Arg Leu Ile Thr Gly Arg Leu Gln Ser Leu Gln
305                 310                 315                 320

Thr Tyr Val Thr Gln Gln Leu Ile Arg Ala Ala Glu Ile Arg Ala Ser
                325                 330                 335

Ala Asn Leu Ala Ala Thr Lys Met Ser Glu Cys Val Leu Gly Gln Ser
            340                 345                 350

Lys Arg Val Asp Phe Cys Gly Lys Gly Tyr His Leu Met Ser Phe Pro
        355                 360                 365

Gln Ser Ala Pro His Gly Val Val Phe Leu His Val Thr Tyr Val Pro
    370                 375                 380

Ala Gln Glu Lys Asn Phe Thr Thr Ala Pro Ala Ile Cys His Asp Gly
385                 390                 395                 400

Lys Ala His Phe Pro Arg Glu Gly Val Phe Val Ser Asn Gly Thr His
                405                 410                 415

Trp Phe Val Thr Gln Arg Asn Phe Tyr Glu Pro Gln Ile Ile Thr Thr
            420                 425                 430

Asp Asn Thr Phe Val Ser Gly Asn Cys Asp Val Val Ile Gly Ile Val
        435                 440                 445

Asn Asn Thr Val Tyr Asp Pro Leu Gln Pro Glu Leu Asp Ser Phe Lys
    450                 455                 460

Glu Glu Leu Asp Lys Tyr Phe Lys Asn His Thr Ser Pro Asp Val Asp
465                 470                 475                 480

Leu Gly Asp Ile Ser Gly Ile Asn Ala Ser Val Val Asn Ile Gln Lys
                485                 490                 495

Glu Ile Asp Arg Leu Asn Glu Val Ala Lys Asn Leu Asn Glu Ser Leu
```

```
                 500              505                510
Ile Asp Leu Gln Glu Leu Gly Lys Tyr Glu Gln Tyr Ile Lys Trp Pro
        515              520              525

Trp Tyr Ile Trp Leu Gly Phe Ile Ala Gly Leu Ile Ala Ile Val Met
    530              535              540

Val Thr Ile Met Leu Cys Cys Met Thr Ser Cys Cys Ser Cys Leu Lys
545              550              555              560

Gly Cys Cys Ser Cys Gly Ser Cys Cys Lys Phe Asp Glu Asp Asp Ser
            565              570              575

Glu Pro Val Leu Lys Gly Val Lys Leu His Tyr Thr
        580              585

<210> SEQ ID NO 121
<211> LENGTH: 672
<212> TYPE: PRT
<213> ORGANISM: Betacoronavirus severe acute respiratory syndrome
      coronavirus 2

<400> SEQUENCE: 121

Gln Cys Val Asn Leu Thr Thr Arg Thr Gln Leu Pro Pro Ala Tyr Thr
1               5                10               15

Asn Ser Phe Thr Arg Gly Val Tyr Tyr Pro Asp Lys Val Phe Arg Ser
            20               25               30

Ser Val Leu His Ser Thr Gln Asp Leu Phe Leu Pro Phe Phe Ser Asn
        35               40               45

Val Thr Trp Phe His Ala Ile His Val Ser Gly Thr Asn Gly Thr Lys
    50               55               60

Arg Phe Asp Asn Pro Val Leu Pro Phe Asn Asp Gly Val Tyr Phe Ala
65               70               75               80

Ser Thr Glu Lys Ser Asn Ile Ile Arg Gly Trp Ile Phe Gly Thr Thr
            85               90               95

Leu Asp Ser Lys Thr Gln Ser Leu Leu Ile Val Asn Asn Ala Thr Asn
            100              105              110

Val Val Ile Lys Val Cys Glu Phe Gln Phe Cys Asn Asp Pro Phe Leu
        115              120              125

Gly Val Tyr Tyr His Lys Asn Asn Lys Ser Trp Met Glu Ser Glu Phe
    130              135              140

Arg Val Tyr Ser Ser Ala Asn Asn Cys Thr Phe Glu Tyr Val Ser Gln
145              150              155              160

Pro Phe Leu Met Asp Leu Glu Gly Lys Gln Gly Asn Phe Lys Asn Leu
            165              170              175

Arg Glu Phe Val Phe Lys Asn Ile Asp Gly Tyr Phe Lys Ile Tyr Ser
            180              185              190

Lys His Thr Pro Ile Asn Leu Val Arg Asp Leu Pro Gln Gly Phe Ser
        195              200              205

Ala Leu Glu Pro Leu Val Asp Leu Pro Ile Gly Ile Asn Ile Thr Arg
    210              215              220

Phe Gln Thr Leu Leu Ala Leu His Arg Ser Tyr Leu Thr Pro Gly Asp
225              230              235              240

Ser Ser Ser Gly Trp Thr Ala Gly Ala Ala Ala Tyr Tyr Val Gly Tyr
            245              250              255

Leu Gln Pro Arg Thr Phe Leu Leu Lys Tyr Asn Glu Asn Gly Thr Ile
            260              265              270

Thr Asp Ala Val Asp Cys Ala Leu Asp Pro Leu Ser Glu Thr Lys Cys
        275              280              285
```

-continued

```
Thr Leu Lys Ser Phe Thr Val Glu Lys Gly Ile Tyr Gln Thr Ser Asn
    290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
            325                 330                 335

Val Tyr Ala Trp Asn Arg Lys Arg Ile Ser Asn Cys Val Ala Asp Tyr
            340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
    370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                405                 410                 415

Thr Gly Cys Val Ile Ala Trp Asn Ser Asn Asn Leu Asp Ser Lys Val
            420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
    450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                485                 490                 495

Val Val Val Leu Ser Phe Glu Leu Leu His Ala Pro Ala Thr Val Cys
            500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
    530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                565                 570                 575

Cys Ser Phe Gly Gly Val Ser Val Ile Thr Pro Gly Thr Asn Thr Ser
            580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
    610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                645                 650                 655

Ile Cys Ala Ser Tyr Gln Thr Gln Thr Asn Ser Pro Arg Arg Ala Arg
            660                 665                 670
```

<210> SEQ ID NO 122
<211> LENGTH: 140
<212> TYPE: PRT
<213> ORGANISM: Betacoronavirus severe acute respiratory syndrome
    coronavirus 2

-continued

<400> SEQUENCE: 122

Asn Phe Asn Gly Leu Thr Gly Thr Gly Val Leu Thr Glu Ser Asn Lys
1               5                   10                  15

Lys Phe Leu Pro Phe Gln Gln Phe Gly Arg Asp Ile Ala Asp Thr Thr
                20                  25                  30

Asp Ala Val Arg Asp Pro Gln Thr Leu Glu Ile Leu Asp Ile Thr Pro
            35                  40                  45

Cys Ser Phe Gly Gly Val Ser Val Ile Thr Pro Gly Thr Asn Thr Ser
        50                  55                  60

Asn Gln Val Ala Val Leu Tyr Gln Asp Val Asn Cys Thr Glu Val Pro
65                  70                  75                  80

Val Ala Ile His Ala Asp Gln Leu Thr Pro Thr Trp Arg Val Tyr Ser
                85                  90                  95

Thr Gly Ser Asn Val Phe Gln Thr Arg Ala Gly Cys Leu Ile Gly Ala
                100                 105                 110

Glu His Val Asn Asn Ser Tyr Glu Cys Asp Ile Pro Ile Gly Ala Gly
            115                 120                 125

Ile Cys Ala Ser Tyr Gln Thr Gln Thr Asn Ser Pro
    130                 135                 140

<210> SEQ ID NO 123
<211> LENGTH: 24
<212> TYPE: PRT
<213> ORGANISM: Betacoronavirus severe acute respiratory syndrome
      coronavirus 2

<400> SEQUENCE: 123

Trp Tyr Ile Trp Leu Gly Phe Ile Ala Gly Leu Ile Ala Ile Val Met
1               5                   10                  15

Val Thr Ile Met Leu Cys Cys Met
                20

<210> SEQ ID NO 124
<211> LENGTH: 36
<212> TYPE: PRT
<213> ORGANISM: Betacoronavirus severe acute respiratory syndrome
      coronavirus 2

<400> SEQUENCE: 124

Thr Ser Cys Cys Ser Cys Leu Lys Gly Cys Cys Ser Cys Gly Ser Cys
1               5                   10                  15

Cys Lys Phe Asp Glu Asp Asp Ser Glu Pro Val Leu Lys Gly Val Lys
                20                  25                  30

Leu His Tyr Thr
        35

<210> SEQ ID NO 125
<211> LENGTH: 51
<212> TYPE: PRT
<213> ORGANISM: Betacoronavirus severe acute respiratory syndrome
      coronavirus 2

<400> SEQUENCE: 125

Asp Val Asp Leu Gly Asp Ile Ser Gly Ile Asn Ala Ser Val Val Asn
1               5                   10                  15

Ile Gln Lys Glu Ile Asp Arg Leu Asn Glu Val Ala Lys Asn Leu Asn
                20                  25                  30

Glu Ser Leu Ile Asp Leu Gln Glu Leu Gly Lys Tyr Glu Gln Tyr Ile

-continued

```
            35              40              45

Lys Trp Pro
    50

<210> SEQ ID NO 126
<211> LENGTH: 197
<212> TYPE: PRT
<213> ORGANISM: Betacoronavirus severe acute respiratory syndrome
      coronavirus 2

<400> SEQUENCE: 126

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
            85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
            115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
            165                 170                 175

Pro Tyr Arg Val Val Val Leu Ser Phe Glu Leu Leu His Ala Pro Ala
            180                 185                 190

Thr Val Cys Gly Pro
            195
```

CORONAVIRUS VACCINE FORMULATIONS

CROSS REFERENCE TO RELATED APPLICATIONS

This application is a U.S. National Phase application, filed under 35 U.S.C. § 371 (c) of International Application No. PCT/US2021/015220, filed Jan. 27, 2021, which claims priority to the following applications, each of which is incorporated by reference in its entirety for all purposes: U.S. Provisional Application No. 62/966,271, filed Jan. 27, 2020; U.S. Provisional Application No. 62/976,858, filed Feb. 14, 2020; U.S. Provisional Application No. 62/983,180, filed Feb. 28, 2020; U.S. Provisional Application No. 63/048,945, filed Jul. 7, 2020; U.S. Provisional Application No. 63/051,706, filed Jul. 14, 2020; U.S. Provisional Application No. 63/054,182, filed Jul. 20, 2020; U.S. Provisional Application No. 63/129,392, filed Dec. 22, 2020; and U.S. Non-Provisional application Ser. No. 16/997,001, filed Aug. 19, 2020, now U.S. Pat. No. 10,953,089. International Application No. PCT/US2021/015220 is a continuation-in-part of U.S. Non-Provisional application Ser. No. 16/997,001, now U.S. Pat. No. 10,953,089, which claims priority to the following applications: U.S. Provisional Application No. 62/966,271, filed Jan. 27, 2020; U.S. Provisional Application No. 62/976,858, filed Feb. 14, 2020; U.S. Provisional Application No. 62/983,180, filed Feb. 28, 2020; U.S. Provisional Application No. 63/048,945, filed Jul. 7, 2020; U.S. Provisional Application No. 63/051,706, filed Jul. 14, 2020; and U.S. Provisional Application No. 63/054,182, filed Jul. 20, 2020.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_088_08WO_SeqList_ST25.txt, date recorded: Jan. 26, 2021; file size: 577 kilobytes).

FIELD

The present disclosure is generally related to non-naturally occurring coronavirus (CoV) Spike (5) polypeptides and nanoparticles and vaccines comprising the same, which are useful for stimulating immune responses. The nanoparticles provide antigens, for example, glycoprotein antigens, optionally associated with a detergent core and are typically produced using recombinant approaches. The nanoparticles have improved stability and enhanced epitope presentation. The disclosure also provides compositions containing the nanoparticles, methods for producing them, and methods of stimulating immune responses.

BACKGROUND OF THE INVENTION

Infectious diseases remain a problem throughout the world. While progress has been made on developing vaccines against some pathogens, many remain a threat to human health. The outbreak of sudden acute respiratory syndrome coronavirus 2 (SARS-CoV-2) (also called Wuhan coronavirus and SARS-CoV-2) has infected more than 2000 people in China and killed at least 17 people. Recently, the SARS-CoV-2 coronavirus has spread to the United States, Thailand, South Korea, Taiwan, and Japan. The SARS-CoV-2 coronavirus belongs to the same family of viruses as severe acute respiratory syndrome coronavirus (SARS-CoV) and Middle East respiratory syndrome coronavirus (MERS-CoV), which have killed hundreds of people in the past 17 years. SARS-CoV-2 causes the disease COVID-19.

The development of vaccines that prevent or reduce the severity of life-threatening infectious diseases like the SARS-CoV-2 coronavirus is desirable. However, human vaccine development remains challenging because of the highly sophisticated evasion mechanisms of pathogens and difficulties stabilizing vaccines. Optimally, a vaccine must both induce antibodies that block or neutralize infectious agents and remain stable in various environments, including environments that do not enable refrigeration.

SUMMARY OF THE INVENTION

The present disclosure provides non-naturally occurring CoV S polypeptides suitable for inducing immune responses against SARS-CoV-2 (also called Wuhan CoV and 2019-nCoV)). The disclosure also provides nanoparticles containing the glycoproteins as well as methods of stimulating immune responses.

The present disclosure also provides CoV S polypeptides suitable for inducing immune responses against multiple coronaviruses, including SARS-CoV-2, Middle East Respiratory Syndrome (MERS), and Severe Acute Respiratory Syndrome (SARS).

BRIEF DESCRIPTION OF THE DRAWINGS

FIG. 1 shows a schematic of the wild-type amino acid sequence of the SARS-CoV-2 Spike (5) protein (SEQ ID NO: 1). The furin cleavage site RRAR (SEQ ID NO: 6) is highlighted in bold, and the signal peptide is underlined.

FIGS. 11A-F show that the CoV S Spike polypeptides BV2365 and BV2373 bind to hACE2. Bio-layer interferometry reveals that BV2365 (FIG. 11B) and BV2373 (FIG. 11C) bind to hACE2 with similar dissociation kinetics to the wild-type CoV S polypeptide (FIG. 11A) ELISA shows that the wild-type CoV S polypeptide (FIG. 11D) and BV2365 (FIG. 11E) bind to hACE2 with similar affinity while BV2373 binds to hACE2 at a higher affinity (FIG. 11F).

FIGS. 12A-B show the effect of stress conditions, such as temperature, two freeze/thaw cycles, oxidation, agitation, and pH extremes on binding of the CoV S polypeptides BV2373 (FIG. 12A) and BV2365 (FIG. 12B) to hACE2.

FIG. 17A shows the effect of immunization on weight loss with a single 0.01 μg, 0.1 μg, 1 μg, or 10 μg of BV2373 plus MATRIX-M™. FIG. 17B shows the effect of immunization on weight loss with two doses of BV2373 (0.01 μg, 0.1 μg, 1 μg) plus MATRIX-M™. FIG. 17C shows the effect of immunization on weight loss with two doses of BV2373 (10 μg) in the presence or absence of MATRIX-M™.

FIGS. 18A-B shows the effect of BV2373 on lung histopathology of mice four days (FIG. 18A) or seven days (FIG. 18B) after infection with SARS-CoV-2.

FIG. 20A shows the frequency of IFN-γ secreting CD4+ T cells. FIG. 20B shows the frequency of TNF-α secreting CD4+ T cells. FIG. 20C shows the frequency of IL-2 secreting CD4+ T cells. FIG. 20D shows the frequency of CD4+ T cells that secrete two cytokines selected from IFN-γ, INF-α, and IL-2. FIG. 20E shows the frequency of CD4+ T cells that express IFN-γ, TNF-α, and IL-2.

FIG. 21A shows the frequency of IFN-γ secreting CD8+ T cells. FIG. 21B shows the frequency of TNF-α secreting CD8+ T cells. FIG. 21C shows the frequency of IL-2 secreting CD8+ T cells. FIG. 20D shows the frequency of CD8+ T cells that secrete two cytokines selected from IFN-γ, TNF-α, and IL-2. FIG. 21E shows the frequency of CD8+ T cells that express IFN-γ, TNF-α, and IL-2.

FIG. 23A shows the frequency of IL-4 secreting cells. FIG. 23B shows the frequency of IL-5 CD4+ secreting cells. FIG. 23C shows the ratio of IFN-γ secreting to IL-4 secreting CD4+ T cells.

FIG. 24A shows frequency of CD4+ T follicular helper cells in spleens, and FIG. 24B shows the phenotype (e.g. CD4+ CXCR5+ PD-1+) of the CD4+ T follicular helper cells.

Figure 25A:
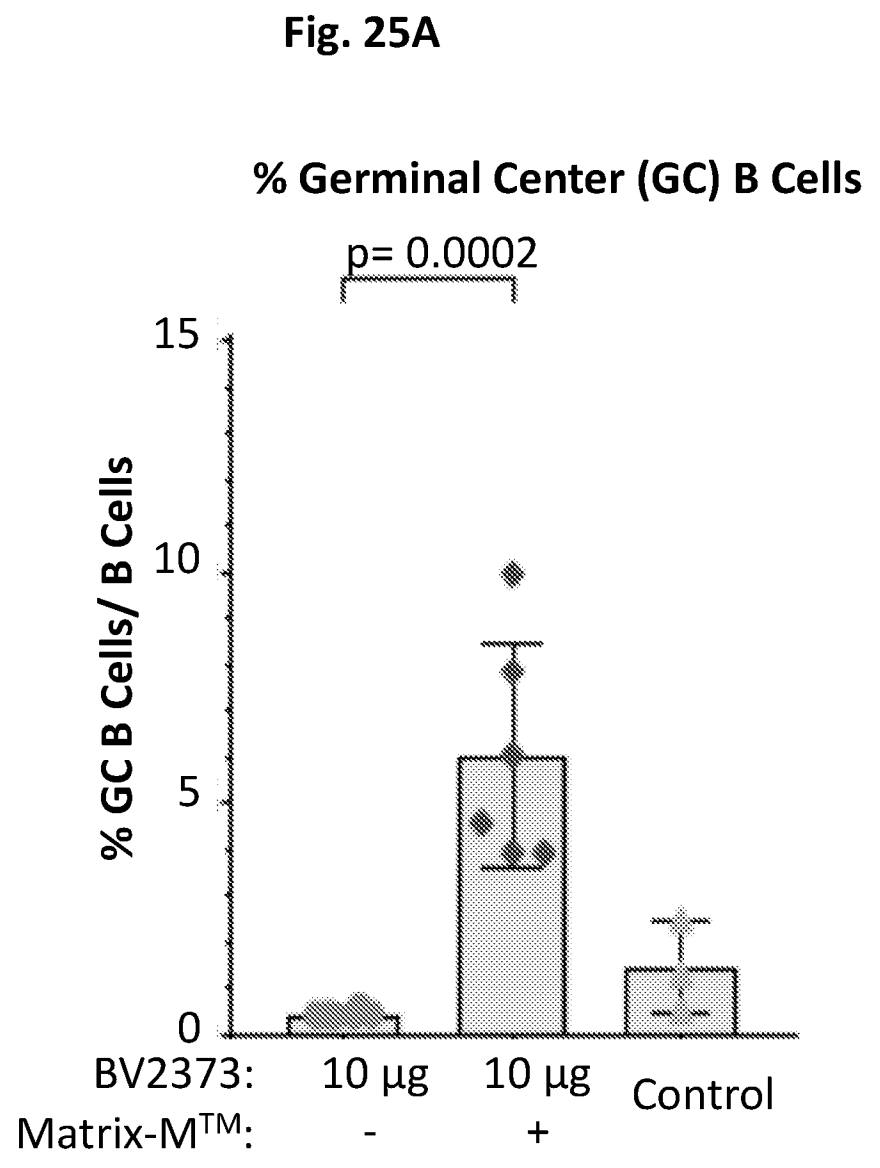

FIGS. 25A-B illustrate the effect of mouse immunization with BV2373 in the presence or absence of MATRIX-M™ on germinal center formation by assessing the presence of germinal center (GC) B cells. FIG. 25A shows the frequency of GC B cells in spleens, and FIG. 25B reveals the phenotype (e.g. CD19+ GL7+ CD-95+) of the CD4+ T follicular helper cells.

FIG. 26A shows the anti-SARS-CoV-2 S polypeptide IgG titer in baboons after immunization with BV2373. FIG. 26B shows the presence of hACE2 receptor blocking antibodies in baboons following a single immunization with 5 μg or 25 μg of BV2373 in the presence of MATRIX-M™. FIG. 26C shows the titer of virus neutralizing antibodies following a single immunization with BV2373 and MATRIX-M™.

FIG. 29A shows the frequency of IFN-γ secreting CD4+ T cells. FIG. 29B shows the frequency of IL-2 secreting CD4+ T cells. FIG. 29C shows the frequency of TNF-α secreting CD4+ T cells. FIG. 29D shows the frequency of CD4+ T cells that secrete two cytokines selected from IFN-γ, TNF-α, and IL-2. FIG. 29E shows the frequency of CD4+ T cells that express IFN-γ, TNF-α, and IL-2.

FIG. 30 shows a schematic of the coronavirus Spike (5) protein (SEQ ID NO: 109) (BV2384). The furin cleavage site GSAS (SEQ ID NO: 97) is underlined once, and the K986P and V987P mutations are underlined twice.

FIG. 31 shows a schematic of the coronavirus Spike (S) protein (SEQ ID NO: 86) (BV2373). The furin cleavage site QQAQ (SEQ ID NO: 7) is underlined once, and the K986P and V987P mutations are underlined twice.

FIG. 32 shows purification of the CoV S polypeptides BV2373 (SEQ ID NO: 87) and BV2384 (SEQ ID NO: 109).

FIGS. 45A-D show the frequencies of antigen-specific CD4$^+$ T cells producing T helper 1 (Th1) cytokines interferon-gamma (IFN-γ), tumor necrosis factor-alpha (TNF-α), and interleukin (IL)-2 and T helper 2 (Th2) cytokines IL-5 and IL-13 indicated cytokines from participants in Groups A (placebo, FIG. 45A), B (25 µg BV2373, FIG. 45B), C (5 µg BV2373 and 50 µg MATRIX-M™, FIG. 45C), and D (25 µg BV2373 and 50 µg MATRIX-M™, FIG. 45D) following stimulation with BV2373. "Any 2" in Th1 cytokine panel means CD4$^+$ T cells that can produce two types of Th1 cytokines at the same time. "All 3" indicates CD4$^+$ T cells that produce IFN-γ, TNF-α, and IL-2 simultaneously. "Both" in Th2 panel means CD4$^+$ T cells that can produce Th2 cytokines IL-5 and IL-13 at the same time.

DETAILED DESCRIPTION OF THE INVENTION

Definitions

Figure 2:
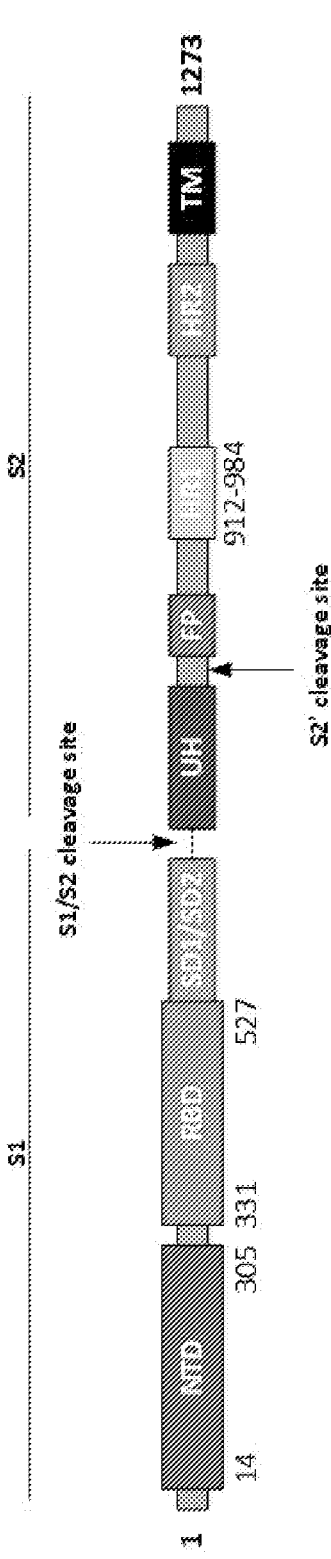
FIG. 2 shows the primary structure of a SARS-CoV-2 S polypeptide, which has an inactive furin cleavage site, a fusion peptide deletion, and K986P and V987P mutations. The domain positions are numbered with respect to the amino acid sequence of the wild-type CoV S polypeptide from SARS-CoV-2 containing a signal peptide (SEQ ID NO: 1).

As used herein, and in the appended claims, the singular forms "a", "an", and "the" include plural referents unless the context clearly dictates otherwise. Thus, for example, reference to "a protein" can refer to one protein or to mixtures of such protein, and reference to "the method" includes reference to equivalent steps and/or methods known to those skilled in the art, and so forth.

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the term "about" or "approximately" when preceding a numerical value indicates the value plus or minus a range of 10%. For example, "about 100" encompasses 90 and 110.

As used herein, the terms "immunogen," "antigen," and "epitope" refer to substances such as proteins, including glycoproteins; and peptides that are capable of eliciting an immune response.

As used herein; an "immunogenic composition" is a composition that comprises an antigen where administration of the composition to a subject results in the development in the subject of a humoral and/or a cellular immune response to the antigen.

As used herein, a "subunit" composition, for example a vaccine, that includes one or more selected antigens but not all antigens from a pathogen. Such a composition is substantially free of intact virus or the lysate of such cells or particles and is typically prepared from at least partially purified, often substantially purified immunogenic polypeptides from the pathogen. The antigens in the subunit composition disclosed herein are typically prepared recombinantly, often using a baculovirus system.

As used herein, "substantially" refers to isolation of a substance (e.g. a compound, polynucleotide, or polypeptide) such that the substance forms the majority percent of the sample in which it is contained. For example, in a sample, a substantially purified component comprises 85%, preferably 85%-90%, more preferably at least 95%-99.5%, and most preferably at least 99% of the sample. If a component is substantially replaced the amount remaining in a sample is less than or equal to about 0.5% to about 10%, preferably less than about 0.5% to about 1.0%.

The terms "treat," "treatment," and "treating," as used herein, refer to an approach for obtaining beneficial or desired results, for example, clinical results. For the purposes of this disclosure, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of pathogen infection. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to an immunogenic composition, such as an immunogen derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a subject to produce protective immunity.

As used herein, the term "subject" includes humans and other animals. Typically, the subject is a human. For example, the subject may be an adult, a teenager, a child (2 years to 14 years of age), an infant (birth to 2 year), or a neonate (up to 2 months). In particular aspects, the subject is up to 4 months old, or up to 6 months old. In some aspects, the adults are seniors about 65 years or older, or about 60 years or older. In some aspects, the subject is a pregnant woman or a woman intending to become pregnant. In other aspects, subject is not a human; for example a non-human primate; for example, a baboon, a chimpanzee, a gorilla, or a macaque. In certain aspects, the subject may be a pet, such as a dog or cat.

As used herein, the term "pharmaceutically acceptable" means being approved by a regulatory agency of a U.S. Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

As used herein, the term "about" means plus or minus 10% of the indicated numerical value.

As used herein, the term "NVX-CoV2373" refers to a vaccine composition comprising the BV2373 Spike glycoprotein (SEQ ID NO: 87) and Fraction A and Fraction C iscom matrix (e.g., MATRIX-M™).

As used herein, the term "modification" as it refers to a CoV S polypeptide refers to mutation, deletion, or addition of one or more amino acids of the CoV S polypeptide. The location of a modification within a CoV S polypeptide can be determined based on aligning the sequence of the polypeptide to SEQ ID NO: 1 (CoV S polypeptide containing signal peptide) or SEQ ID NO: 2 (mature CoV S polypeptide lacking a signal peptide).

Vaccine Compositions Containing Coronavirus (CoV) Spike (S) Proteins

The disclosure provides non-naturally occurring coronavirus (CoV) Spike (S) polypeptides, nanoparticles containing CoV S polypeptides, and immunogenic compositions and vaccine compositions containing either non-naturally occurring CoV S polypeptides or nanoparticles containing CoV S polypeptides. In embodiments, provided herein are methods of using CoV S polypeptides, nanoparticles, immunogenic compositions, and vaccine compositions to stimulate an immune response.

Also provided herein are methods of manufacturing the nanoparticles and vaccine compositions. Advantageously, the methods provide nanoparticles that are substantially free from contamination by other proteins, such as proteins associated with recombinant expression of proteins in insect cells. In embodiments, expression occurs in baculovirus/Sf9 systems.

CoV S Polypeptide Antigens

The vaccine compositions of the disclosure contain non-naturally occurring CoV S polypeptides. CoV S polypeptides may be derived from coronaviruses, including but not limited to SARS-CoV-2, for example from SARS-CoV-2, from MERS CoV, and from SARS CoV. In embodiments, the CoV S polypeptide is derived from a variant of SARS-CoV-2. In embodiments, the variant of SARS-CoV-2 is SARS-CoV-2 VUI 202012/01, B. 1.1.7, 501Y.V2, Cal.20C, or P.1. In contrast to the SARS-CoV S protein, the SARS-CoV-2 S protein has a four amino acid insertion in the S1/S2 cleavage site resulting in a polybasic RRAR furin-like cleavage motif. The SARS-CoV-2 S protein is synthesized as an inactive precursor (S0) that is proteolytically cleaved at the furin cleavage site into S1 and S2 subunits which remain non-covalently linked to form prefusion trimers. The S2 domain of the SARS-CoV-2 S protein comprises a fusion peptide (FP), two heptad repeats (HR1 and HR2), a transmembrane (TM) domain, and a cytoplasmic tail (CT). The S1 domain of the SARS-CoV-2 S protein folds into four distinct domains: the N-terminal domain (NTD) and the C-terminal domain, which contains the receptor binding domain (RBD) and two subdomains SD1 and SD2. The prefusion SARS-CoV-2 S protein trimers undergo a structural rearrangement from a prefusion to a postfusion conformation upon S-protein receptor binding and cleavage.

Figure 3:
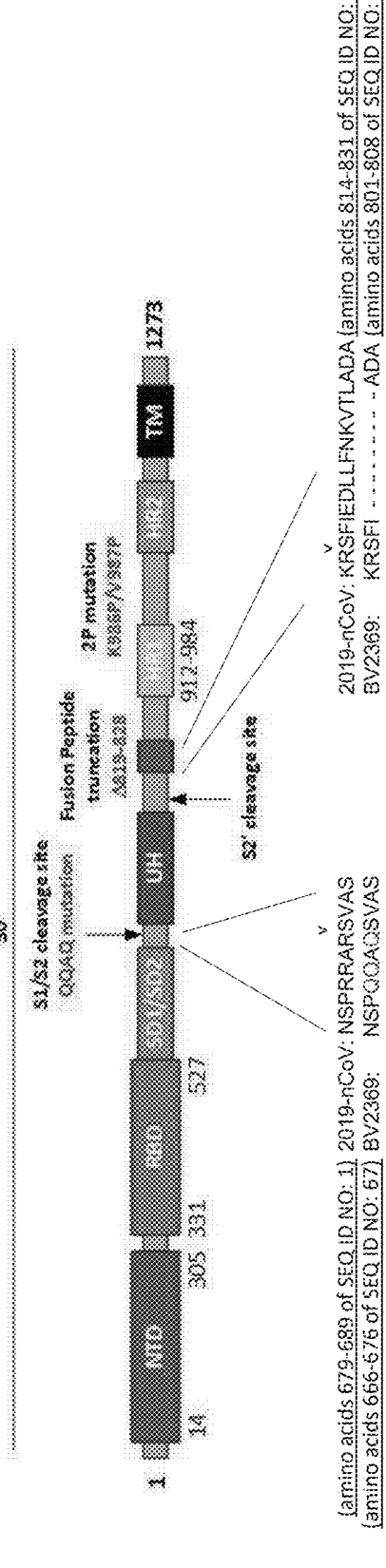
FIG. 3 shows the primary structure of the BV2378 CoV S polypeptide, which has an inactive furin cleavage site, a fusion peptide deletion of amino acids 819-828, and K986P and V987P mutations. The domain positions are numbered with respect to the amino acid sequence of the wild-type CoV S polypeptide from SARS-CoV-2 containing a signal peptide (SEQ ID NO: 1).
Figures 46A, 46B:
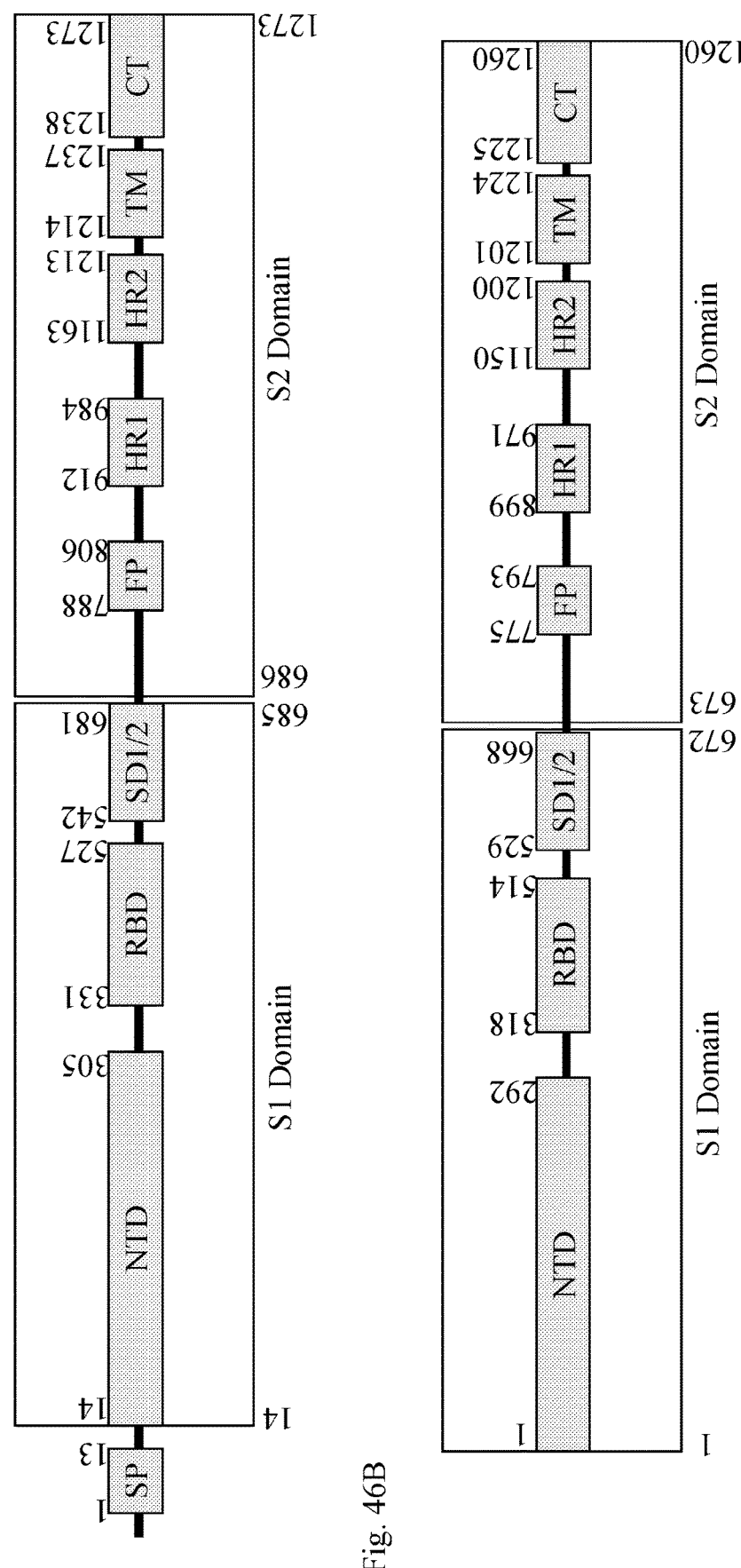
FIG. 46A shows the primary structure of a wild-type SARS-CoV-2 S polypeptide, containing a signal peptide, numbered with respect to SEQ ID NO: 1.
FIG. 46B shows the primary structure of a wild-type SARS-CoV-2 S polypeptide, without a signal peptide, numbered with respect to SEQ ID NO: 2.

In embodiments, the CoV S polypeptides are glycoproteins, due to post-translational glycosylation. The glycoproteins comprise one or more of a signal peptide, an S1 subunit, an S2 subunit, a NTD, a, RBD, two subdomains (SD1 and SD2, labeled SD1/2 in FIGS. 46A-B and referred to as "SD1/2" herein), an intact or modified fusion peptide, an HR1 domain, an HR2 domain, a TM, and a CD. In embodiments, the amino acids for each domain are given in FIG. 2 and FIG. 46A (shown according to SEQ ID NO: 1), FIG. 46B (shown according to SEQ ID NO: 2), and FIG. 3 (shown corresponding to SEQ ID NO: 1). In embodiments, each domain may have at least 95%, at least 96%, at least 97%, at least 98%, at least 99%, or at least 99.5% identity to the sequences for each domain as in SEQ ID NO: 1 or SEQ ID NO: 2. Each domain may have a deletion, an insertion, or mutation of up to about 1, up to about 2, up to about 3, up to about 4, up to about 5, up to about 10, up to about 20, or up to about 30 amino acids compared to those shown in SEQ ID NO: 1 or SEQ ID NO: 2. Each domain may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to those shown in SEQ ID NO: 1 or SEQ ID NO: 2. Note that FIGS. 2 and 3 illustrate the 13-amino acid N-terminal signal peptide that is absent from the mature peptide. The CoV S polypeptides may be used to stimulate immune responses against the native CoV Spike (S) polypeptide.

In embodiments, the native CoV Spike (S) polypeptide (SEQ ID NO: 2) is modified resulting in non-naturally occurring CoV Spike (S) polypeptides (FIG. 1). In embodiments, the CoV Spike (S) glycoproteins comprise a S1 subunit and a S2 subunit, wherein the 51 subunit comprises an NTD, an RBD, a SD1/2, and an inactive furin cleavage site (amino acids 669-672), and wherein the S2 subunit comprises mutations of amino acids 973 and 974;

wherein the NTD (amino acids 1-318) optionally comprises one or more modifications selected from the group consisting of:

(a) deletion of one or more amino acids from the NTD, optionally wherein the one or more modifications are selected from the group consisting of amino acid 56, 57, 131, 132, 229, 230, 231, and combinations thereof; and (b) mutation of one or more amino acids selected from the group consisting of amino acid 67, 229, 202, 139, 5, 233, 7, 13, 125, 177, or combinations thereof;

wherein the RBD optionally comprises mutation of one or more amino acids selected from the group consisting of amino acid 488, 404, 471, 439, 426, 440, and combinations thereof;

wherein the SD1/2 optionally comprises mutation of one or more amino acids selected from the group consisting of 601, 557, 668, 642, and combinations thereof; and wherein the S2 subunit optionally comprises one or more modifications selected from the group consisting of:

(a) deletion of one or more amino acids from 676-702, 702-711, 775-793;

(b) deletion of one or more amino acids from the fusion peptide (amino acids 806-815);

(c) mutation of one or more amino acids selected from the group consisting of 973, 974, 703, 1105, 688, 969, and 1014; and (d) deletion of one or more amino acids from the transmembrane and cytoplasmic domain (TMCT) (amino acids 1201-1260), wherein the amino acids of the CoV S glycoprotein are numbered with respect to SEQ ID NO: 2. FIG. 3 shows a CoV S polypeptide called BV2378, which has an inactive furin cleavage site, deleted fusion peptide (e.g., deletion of amino acids 819-828), a K986P, and a V987 mutation, wherein the amino acids are numbered with respect to SEQ ID NO: 1. The mature BV2378 polypeptide lacks one or more amino acids of the signal peptide, which are amino acids 1-13 of SEQ ID NO: 1.

In embodiments, the CoV S polypeptides described herein exist in a prefusion conformation. In embodiments, the CoV S polypeptides described herein comprise a flexible HR2 domain. Unless otherwise mentioned, the flexibility of a domain is determined by transition electron microscopy (TEM) and 2D class averaging. A reduction in electron density corresponds to a flexible domain.

CoV S Polypeptide Antigens—Modifications to S1 Subunit

In embodiments, the CoV S polypeptides contain one or more modifications to the 51 subunit having an amino acid sequence of SEQ ID NO: 121.

The amino acid sequence of the S1 subunit (SEQ ID NO: 121) is shown below.

QCVNLTTRTQLPPAYTNSFTRGVYYPDKVFRSSVLHSTQDLFLPFFSNVT

WFHAIHVSGTNGTKRFDNPVLPFNDGVYFASTEKSNIIRGWIFGTTLDSK

TQSLLIVNNATNVVIKVCEFQFCNDPFLGVYYHKNNKSWMESEFRVYSSA

NNCTFEYVSQPFLMDLEGKQGNFKNLREFVFKNIDGYFKIYSKHTPINLV

RDLPQGFSALEPLVDLPIGINITRFQTLLALHRSYLTPGDSSSGWTAGAA

AYYVGYLQPRTFLLKYNENGTITDAVDCALDPLSETKCTLKSFTVEKGIY

QTSNFRVQPTESIVRFPNITNLCPFGEVFNATRFASVYAWNRKRISNCVA

DYSVLYNSASFSTFKCYGVSPTKLNDLCFTNVYADSFVIRGDEVRQIAPG

QTGKIADYNYKLPDDFTGCVIAWNSNNLDSKVGGNYNYLYRLFRKSNLKP

FERDISTEIYQAGSTPCNGVEGFNCYFPLQSYGFQPTNGVGYQPYRVVVL

SFELLHAPATVCGPKKSTNLVKNKCVNFNFNGLTGTGVLTESNKKFLPFQ

QFGRDIADTTDAVRDPQTLEILDITPCSFGGVSVITPGTNTSNQVAVLYQ

DVNCTEVPVAIHADQLTPTWRVYSTGSNVFQTRAGCLIGAEHVNNSYECD

IPIGAGICASYQTQTNSPRRAR

Underlined regions of SEQ ID NO: 121 represent amino acids within the S1 subunit that may be modified.

In embodiments, the CoV S polypeptides described herein comprise an S1 subunit with at least 95%, at least 96%, at least 97%, at least 98%, at least 99%, or at least 99.5%, identity to the S1 subunit of SEQ ID NO: 1 or SEQ ID NO: 2. The S1 subunit may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the 51 subunit of SEQ ID NO: 1 or SEQ ID NO: 2. The S1 subunit may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the S1 subunit of SEQ ID NO: 1 or SEQ ID NO: 2.

In embodiments, the S1 subunit may contain any combination of modifications shown in Table 1A.

TABLE 1A

| Modifications to S1 (SEQ ID NO: 121) * amino acids 14-685 of SEQ ID NO: 1 and amino acids 1-672 of SEQ ID NO: 2 | | | |
| --- | --- | --- | --- |
| Position within SEQ ID NO: 1 | Position within SEQ ID NO: 2 | Position within SEQ ID NO: 121 | Potential Modifications |
| 69 | 56 | 56 | Deletion of amino acid |
| 70 | 57 | 57 | Deletion of amino acid |
| 144 | 131 | 131 | Deletion of amino acid |
| 145 | 132 | 132 | Deletion of amino acid |
| 80 | 67 | 67 | mutation to alanine mutation to glycine |
| 242 | 229 | 229 | mutation to histidine mutation to lysine mutation to arginine |
| 215 | 202 | 202 | mutation to glycine mutation to alanine |

TABLE 1A-continued

| Modifications to S1 (SEQ ID NO: 121) * amino acids 14-685 of SEQ ID NO: 1 and amino acids 1-672 of SEQ ID NO: 2 | | | |
| --- | --- | --- | --- |
| Position within SEQ ID NO: 1 | Position within SEQ ID NO: 2 | Position within SEQ ID NO: 121 | Potential Modifications |
| 152 | 139 | 139 | mutation to cysteine mutation to methionine mutation to serine mutation to threonine |
| 18 | 5 | 5 | mutation to phenylalanine mutation to tyrosine mutation to tryptophan |
| 242-244 | 229-231 | 229-231 | deletion of amino acids 229-231 deletions of amino acids 229-230 deletion of amino acids 230-231 deletion of amino acids 229 and 231 deletion of amino acid 229 deletion of amino acid 230 deletion of amino acid 231 |
| 246 | 233 | 233 | mutation to beta-branched amino acid mutation to isoleucine mutation to valine mutation to threonine |
| 20 | 7 | 7 | mutation to asparagine mutation to glutamine mutation to isoleucine mutation to valine |
| 26 | 13 | 13 | mutation to serine mutation to threonine |
| 138 | 125 | 125 | mutation to tyrosine mutation to phenylalanine mutation to tryptophan |
| 190 | 177 | 177 | mutation to serine mutation to threonine mutation to cysteine |
| 14-305 | 1-292 | 1-292 | deletion of up to about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 292 amino acids |
| 501 | 488 | 183 | mutation to tyrosine mutation to phenylalanine mutation to tryptophan |
| 417 | 404 | 99 | mutation to asparagine mutation to threonine mutation to isoleucine mutation to valine mutation to serine mutation to glutamine mutation to beta-branched amino acid |
| 484 | 471 | 166 | mutation to lysine mutation to arginine mutation to histidine |
| 452 | 439 | 134 | mutation to arginine mutation to lysine mutation to histidine |
| 439 | 426 | 121 | mutation to lysine mutation to arginine mutation to histidine |
| 453 | 440 | 135 | mutation to phenylalanine mutation to tryptophan |
| 682-685 | 669-672 | 141-144 | inactive furin cleavage site (See Table IE) |
| 614 | 601 | 73 | Mutation to glycine Mutation to alanine |
| 570 | 557 | 29 | Mutation to aspartic acid Mutation to glutamic acid |
| 681 | 668 | 140 | Mutation to histidine Mutation to lysine Mutation to arginine |
| 655 | 642 | 114 | Mutation to tyrosine Mutation to phenylalanine Mutation to tryptophan |

13

14

CoV S Polypeptide Antigens—Modifications to S1 Sub-unit—NTD

In embodiments, the CoV S polypeptides contain one or more modifications to the NTD. In embodiments, the NTD has an amino acid sequence of SEQ ID NO: 118, which corresponds to amino acids 14-305 of SEQ ID NO: 1 or amino acids 1-292 of SEQ ID NO: 2.

The amino acid sequence of an NTD (SEQ ID NO: 118) is shown below.

QCVNL<u>TT</u>RTQLPPAYTNSFTRGVYYPDKVFRSSVLHSTQDLFLPFFSNVT

WFHAI<u>H</u>VSGTNGTKRF<u>D</u>NPVLPFNDGVYFASTEKSNIIRGWIFGTTLDSK

TQSLLIVNNATNVVIKVCEFQFCND<u>P</u>FLGV<u>YY</u>HKNNKS<u>W</u>MESEFRVYSSA

NNCTFEYVSQPFLMDLEGKQGNFK<u>NLR</u>EFVFKNIDGYFKIYSKHTPINLV

RDLPQGFSALEPLVDLPIGINITRFQTL<u>L</u>AL<u>HR</u>SYLTPGDS<u>SSG</u>WTAGAA

AYYVGYLQPRTFLLKYNENGTITDAVDCALDPLSETKCTLKS

Underlined regions of SEQ ID NO: 118 represent amino acids within the NTD that may be modified.

In embodiments, the NTD has an amino acid sequence of SEQ ID NO: 45, which corresponds to amino acids 14 to 331 of SEQ ID NO: 1 or amino acids 1-318 of SEQ ID NO: 2. The amino acid sequence of an NTD (SEQ ID NO: 45) is shown below.

QCVNL<u>TT</u>RTQLP<u>P</u>AYTNSFTRGVYYPDKVFRSSVLHSTQDLFLPFFSNVT

WFHAI<u>H</u>VSGTNGTKRF<u>D</u>NPVLPFNDGVYFASTEKSNIIRGWIFGTTLDSK

TQSLLIVNNATNVVIKVCEFQFCND<u>P</u>FLGV<u>YY</u>HKNNKS<u>W</u>MESEFRVYSSA

NNCTFEYVSQPFLMDLEGKQGNFK<u>NLR</u>EFVFKNIDGYFKIYSKHTPINLV

RDLPQGFSALEPLVDLPIGINITRFQTL<u>L</u>AL<u>HR</u>SYLTPGDS<u>SSG</u>WTAGAA

AYYVGYLQPRTFLLKYNENGTITDAVDCALDPLSETKCTLKSFTVEKGIY

QTSNFRVQPTESIVRFPN

In embodiments, the NTD and RBD overlap by up to about 1 amino acid, up to about 5 amino acids, up to about 10 amino acids, or up to about 20 amino acids.

In embodiments, an NTD as provided herein may be extended at the C-terminus by up to 5, up to 10, up to 15, up to 20, up to 25, or up to 30 amino acids.

In embodiments, the CoV S polypeptides described herein comprise a NTD with at least 95%, at least 96%, at least 97%, at least 98%, at least 99%, or at least 99.5%, identity to the NTD of SEQ ID NO: 1 or SEQ ID NO: 2. The NTD may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the NTD of SEQ ID NO: 1 or SEQ ID NO: 2. The NTD may have a deletion, an insertion, or mutation of between about 1 and about 5 amino acids, between about 3 and about 10 amino acids, between about 5 and 10 amino acids, between about 8 and 17 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the NTD of SEQ ID NO: 1 or SEQ ID NO: 2.

In embodiments, the CoV S polypeptides contain a deletion of one or more amino acids from the N-terminal domain (NTD) (corresponding to amino acids 1-292 of SEQ ID NO: 2. In some embodiments, the CoV S polypeptides contain a deletion of up to about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 292 amino acids of the NTD.

In some embodiments, the CoV S polypeptides contain a deletion of one or more amino acids from the NTD (corresponding to amino acids 1-318 of SEQ ID NO: 2). In embodiments, the CoV S polypeptides contain a deletion of amino acids 1-318 of the NTD of SEQ ID NO: 2. In embodiments, deletion of the NTD enhances protein expression of the CoV Spike (S) polypeptide. In embodiments, the CoV S polypeptides which have an NTD deletion have amino acid sequences represented by SEQ ID NOS: 46, 48, 49, 51, 52, and 54. In embodiments, the CoV S polypeptides which have an NTD deletion are encoded by an isolated nucleic acid sequence selected from the group consisting of SEQ ID NO: 47, SEQ ID NO: 50, and SEQ ID NO: 53.

In embodiments, the NTD may contain any combination of modifications shown in Table 1B. The modifications are shown with respect to SEQ ID NO:2, the mature S polypeptide sequence for reference.

TABLE 1B

| Modifications to NTD (SEQ ID NO: 118) * amino acids 14-305 of SEQ ID NO: 1 and amino acids 1-292 of SEQ ID NO: 2 | | | |
|---|---|---|---|
| Position within SEQ ID NO: 1 | SEQ ID NO: 2 residue | SEQ ID NO: 121 or SEQ ID NO: 45 residue | Modifications |
| 69 | 56 | 56 | Deletion of amino acid |
| 70 | 57 | 57 | Deletion of amino acid |
| 144 | 131 | 131 | Deletion of amino acid |
| 145 | 132 | 132 | Deletion of amino acid |
| 80 | 67 | 67 | mutation to alanine |
| | | | mutation to glycine |
| 242 | 229 | 229 | mutation to histidine |
| | | | mutation to lysine |
| | | | mutation to arginine |
| 215 | 202 | 202 | mutation to glycine |
| | | | mutation to alanine |
| 152 | 139 | 139 | mutation to cysteine |
| | | | mutation to methionine |
| | | | mutation to serine |
| | | | mutation to threonine |
| 18 | 5 | 5 | mutation to phenylalanine |
| | | | mutation to tyrosine |
| | | | mutation to tryptophan |
| 242-244 | 229-231 | 229-231 | deletion of amino acids 229-231 |
| | | | deletions of amino acids 229-230 |
| | | | deletion of amino acids 230-231 |
| | | | deletion of amino acids 229 and 231 |
| | | | deletion of amino acid 229 |
| | | | deletion of amino acid 230 |
| | | | deletion of amino acid 231 |
| 246 | 233 | 233 | mutation to beta-branched amino acid |
| | | | mutation to isoleucine |
| | | | mutation to valine |
| | | | mutation to threonine |
| 20 | 7 | 7 | mutation to asparagine |
| | | | mutation to glutamine |
| | | | mutation to isoleucine |
| | | | mutation to valine |
| 26 | 13 | 13 | mutation to serine |
| | | | mutation to threonine |
| 138 | 125 | 125 | mutation to tyrosine |
| | | | mutation to phenylalanine |
| | | | mutation to tryptophan |

TABLE 1B-continued

| Modifications to NTD (SEQ ID NO: 118) * amino acids 14-305 of SEQ ID NO: 1 and amino acids 1-292 of SEQ ID NO: 2 | | | |
|---|---|---|---|
| Position within SEQ ID NO: 1 | SEQ ID NO: 2 residue | SEQ ID NO: 121 or SEQ ID NO: 45 residue | Modifications |
| 190 | 177 | 177 | mutation to serine mutation to threonine mutation to cysteine |

CoV S Polypeptide Antigens—Modifications to S1 Subunit—RBD

In embodiments, the CoV S polypeptides contain one or more modifications to the RBD.

In embodiments, the RBD has an amino acid sequence of SEQ ID NO: 126, which corresponds to amino acids 331-527 of SEQ ID NO: 1 or amino acids 318-514 of SEQ ID NO: 2.

The amino acid sequence of the RBD (SEQ ID NO: 126) is shown below:

NITNLCPFGEVFNATRFASVYAWNRKRISNCVADYSVLYNSASFSTFKCY

GVSPTKLNDLCFTNVYADSFVIRGDEVRQIAPGQTGKIADYNYKLPDDFT

GCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGP

Underlined regions of SEQ ID NO: 126 represent amino acids within the RBD subunit that may be modified.

In embodiments, the RBD has an amino acid sequence of SEQ ID NO: 116, which corresponds to amino acids 335-530 of SEQ ID NO: 1 or amino acids 322-517 of SEQ ID NO: 2.

The amino acid sequence of the RBD (SEQ ID NO: 116) is shown below.

LCPFGEVFNATRFASVYAWNRKRISNCVADYSVLYNSASFSTFKCYGVSP

TKLNDLCFTNVYADSFVIRGDEVRQIAPGQTGKIADYNYKLPDDFTGCVI

AWNSNNLDSKVGGNYNYLYRLFRKSNLKPFERDISTEIYQAGSTPCNGVE

GFNCYFPLQSYGFQPTNGVGYQPYRVVVLSFELLHAPATVCGPKKS

Underlined regions of SEQ ID NO: 116 represent amino acids within the RBD subunit that may be modified.

In embodiments, an RBD as provided herein may be extended at the N-terminus or C-terminus by up to 1 amino acid, up to 5 amino acids, up to 10 amino acids, up to 15 amino acids, up to 20 amino acids, up to 25 amino acids, or up to 30 amino acids.

In embodiments, the CoV S polypeptides described herein comprise a RBD with at least 95%, at least 96%, at least 97%, at least 98%, at least 99%, or at least 99.5%, identity to the RBD of SEQ ID NO: 1 or SEQ ID NO: 2. The RBD may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the RBD of SEQ ID NO: 1 or SEQ ID NO: 2. The RBD may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the RBD of SEQ ID NO: 1 or SEQ ID NO: 2.

In embodiments, the CoV S polypeptide has at least one, at least two, at least three, at least four, at least 5, at least 6, at least 7, at least 8, at least 9, at least 10, at least 11, at least 12, at least 13, at least 14, at least 15, at least 16, at least 17, at least 18, at least 19, or at least 20 mutations in the RBD. In embodiments, the RBD may contain any combination of modifications as shown in Table 1C.

TABLE 1C

| Modifications to RBD (SEQ ID NO: 126) * amino acids 331-527 of SEQ ID NO: 1 and amino acids 318-514 of SEQ ID NO: 2 | | | |
|---|---|---|---|
| Position within SEQ ID NO: 1 | Position within SEQ ID NO: 2 | Position within SEQ ID NO: 126 | Potential Modifications |
| 501 | 488 | 171 | mutation to tyrosine mutation to phenylalanine mutation to tryptophan |
| 417 | 404 | 87 | mutation to asparagine mutation to threonine mutation to isoleucine mutation to valine mutation to serine mutation to glutamine mutation to beta-branched amino acid |
| 484 | 471 | 154 | mutation to lysine mutation to arginine mutation to histidine |
| 452 | 439 | 122 | mutation to arginine mutation to lysine mutation to histidine |
| 439 | 426 | 109 | mutation to lysine mutation to arginine mutation to histidine |
| 453 | 440 | 123 | mutation to phenylalanine mutation to tryptophan |

CoV S Polypeptide Antigens—Modifications to SD1/2

In embodiments, the CoV S polypeptides contain one or more modifications to the SD1/2 having an amino acid sequence of SEQ ID NO: 122, which corresponds to amino acids 542-681 of SEQ ID NO: 1 or amino acids 529-668 of SEQ ID NO: 2.

The amino acid sequence of the SD1/2 (SEQ ID NO: 122) is shown below.

NFNGLTGTGVLTESNKKFLPFQQFGRDIADTTDAVRDPQTLEILDITPCS

FGGVSVITPGTNTSNQVAVLYQDVNCTEVPVAIHADQLTPTWRVYSTGSN

VFQTRAGCLIGAEHVNNSYECDIPIGAGICASYQTQTNSP

Underlined regions of SEQ ID NO: 122 represent amino acids within SD1/2 that may be modified.

In embodiments, the CoV S polypeptides described herein comprise a SD1/2 with at least 95%, at least 96%, at least 97%, at least 98%, at least 99%, or at least 99.5%, identity to the SD1/2 of SEQ ID NO: 1 or SEQ ID NO: 2. The SD1/2 may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the SD1/2 of SEQ ID NO: 1 or SEQ ID NO: 2. The SD1/2 may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the SD1/2 of SEQ ID NO: 1 or SEQ ID NO: 2.

In embodiments, the CoV S polypeptide has at least one, at least two, at least three, at least four, at least four, at least 5, at least 6, at least 7, at least 8, at least 9, at least 10, at least 11, at least 12, at least 13, at least 14, at least 15, at least 16, at least 17, at least 18, at least 19, or at least 20 mutations in the SD1/2. In embodiments, the SD1/2 may contain any combination of modifications as shown in Table 1D.

TABLE 1D

Modifications to SD1/2 (SEQ ID NO: 122)
* amino acids 542-681 of SEQ ID NO: 1 or
amino acids 529-668 of SEQ ID NO: 2

| Position within SEQID NO: 1 | Position within SEQ ID NO: 2 | Position within SEQID NO: 122 | Potential Modifications |
|---|---|---|---|
| 614 | 601 | 73 | Mutation to glycine |
| | | | Mutation to alanine |
| 570 | 557 | 29 | Mutation to aspartic acid |
| | | | Mutation to glutamic acid |
| 681 | 668 | 140 | Mutation to histidine |
| | | | Mutation to lysine |
| | | | Mutation to arginine |
| 655 | 642 | 114 | Mutation to tyrosine |
| | | | Mutation to phenylalanine |
| | | | Mutation to tryptophan |

CoV S Polypeptide Antigens—Modifications to Furin Cleavage Site

In embodiments, the CoV S polypeptides contain a furin site (RRAR), which corresponds to amino acids 682-685 of SEQ ID NO: 1 or amino acids 669-672 of SEQ ID NO: 2, that is inactivated by one or more mutations. Inactivation of the furin cleavage site prevents furin from cleaving the CoV S polypeptide. In embodiments, the CoV S polypeptides described herein which contain an inactivated furin cleavage site are expressed as a single chain.

In embodiments, one or more of the amino acids comprising the native furin cleavage site is mutated to any natural amino acid. In embodiments, the amino acids are L-amino acids. Non-limiting examples of amino acids include alanine, arginine, glycine, asparagine, aspartic acid, cysteine, glutamine, glutamic acid, serine, threonine, histidine, lysine, methionine, proline, valine, isoleucine, leucine, tyrosine, tryptophan, and phenylalanine.

In embodiments, one or more of the amino acids comprising the native furin cleavage site is mutated to glutamine. In embodiments, 1, 2, 3, or 4 amino acids may be mutated to glutamine. In embodiments, one of the arginines comprising the native furin cleavage site is mutated to glutamine. In embodiments, two of the arginines comprising the native furin cleavage site are mutated to glutamine. In embodiments, three of the arginines comprising the native furin cleavage site are mutated to glutamine.

In embodiments, one or more of the amino acids comprising the native furin cleavage site, is mutated to alanine.

In embodiments, 1, 2, 3, or 4 amino acids may be mutated to alanine. embodiments, one of the arginines comprising the native furin cleavage site is mutated to alanine. In embodiments, two of the arginines comprising the native furin cleavage site are mutated to alanine. In embodiments, three of the arginines comprising the native furin cleavage site are mutated to alanine.

In embodiments, one or more of the amino acids comprising the native furin cleavage site is mutated to glycine. In embodiments, 1, 2, 3, or 4 amino acids may be mutated to glycine. In embodiments, one of the arginines of the native furin cleavage site is mutated to glycine. In embodiments, two of the arginines comprising the native furin cleavage site are mutated to glycine. In embodiments, three of the arginines comprising the native furin cleavage site are mutated to glycine.

In embodiments, one or more of the amino acids comprising the native furin cleavage site, is mutated to asparagine. For example 1, 2, 3, or 4 amino acids may be mutated to asparagine. In embodiments, one of the arginines comprising the native furin cleavage site is mutated to asparagine. In embodiments, two of the arginines comprising the native furin cleavage site are mutated to asparagine. In embodiments, three of the arginines comprising the native furin cleavage site are mutated to asparagine.

Non-limiting examples of the amino acid sequences of the inactivated furin sites contained within the CoV S polypeptides are found in Table 1E.

TABLE 1E

Inactivated Furin Cleavage Sites

| Amino Acid Sequence of Furin Cleavage Site | Active or Inactive Furin Cleavage Site |
|---|---|
| RRAR (SEQ ID NO: 6) | Active |
| QQAQ (SEQ ID NO: 7) | Inactive |
| QRAR (SEQ ID NO: 8) | Inactive |
| RQAR (SEQ ID NO: 9) | Inactive |
| RRAQ (SEQ ID NO: 10) | Inactive |
| QQAR (SEQ ID NO: 11) | Inactive |
| RQAQ (SEQ ID NO: 12) | Inactive |
| QRAQ (SEQ ID NO: 13) | Inactive |
| NNAN (SEQ ID NO: 14) | Inactive |
| NRAR (SEQ ID NO: 15) | Inactive |
| RNAR (SEQ ID NO: 16) | Inactive |
| RRAN (SEQ ID NO: 17) | Inactive |
| NNAR (SEQ ID NO: 18) | Inactive |
| RNAN (SEQ ID NO: 19) | Inactive |
| NRAN (SEQ ID NO: 20) | Inactive |
| AAAA (SEQ ID NO: 21) | Inactive |
| ARAR (SEQ ID NO: 22) | Inactive |
| RAAR (SEQ ID NO: 23) | Inactive |
| RRAA (SEQ ID NO: 24) | Inactive |
| AAAR (SEQ ID NO: 25) | Inactive |

TABLE 1E-continued

Inactivated Furin Cleavage Sites

| Amino Acid Sequence of Furin Cleavage Site | Active or Inactive Furin Cleavage Site |
|---|---|
| RAAA (SEQ ID NO: 26) | Inactive |
| ARAA (SEQ ID NO: 27) | Inactive |
| GGAG (SEQ ID NO: 28) | Inactive |
| GRAR (SEQ ID NO: 29) | Inactive |
| RGAR (SEQ ID NO: 30) | Inactive |
| RRAG (SEQ ID NO: 31) | Inactive |
| GGAR (SEQ ID NO: 32) | Inactive |
| RGAG (SEQ ID NO: 33) | Inactive |
| GRAG (SEQ ID NO: 34) | Inactive |
| GSAS (SEQ ID NO: 97) | Inactive |
| GSGA (SEQ ID NO: 111) | Inactive |

In embodiments, in lieu of an active furin cleavage site (SEQ ID NO: 6) the CoV S polypeptides described herein contain an inactivated furin cleavage site. In embodiments, the amino acid sequence of the inactivated furin cleavage site is represented by any one of SEQ ID NO: 7-34 or SEQ ID NO: 97. In embodiments, the amino acid sequence of the inactivated furin cleavage site is QQAQ (SEQ ID NO: 7). In embodiments, the amino acid sequence of the inactivated furin cleavage site is GSAS (SEQ ID NO: 97). In embodiments, the amino acid sequence of the inactivated furin cleavage site is GSGA (SEQ ID NO: 111).

CoV S Polypeptide Antigens—Modifications to S2 Subunit

In embodiments, the CoV S polypeptides contain one or more modifications to the S2 subunit having an amino acid sequence of SEQ ID NO: 120, which corresponds to amino acids 686-1273 of SEQ ID NO: 1 or amino acids 673-1260 of SEQ ID NO: 2.

The amino acid sequence of the S2 subunit (SEQ ID NO: 120) is shown below.

SVASQSIIAYTMSLGAENSVAYSNNSIAIPTNFTISVTTEILPVSMTK

TSVDCTMYICGDSTECSNLLLQYGSFCTQLNRALTGIAVEODKNTQEV

FAQVKQIYKTPPIKDFGGFNFSQILPDPSKPSKRSFIEDLLFNKVTLA

DAGFIKQYGDCLGDIAARDLICAQKFNGLTVLPPLLTDEMIAQYTSAL

LAGTITSGWTFGAGAALQIPFAMQMAYRFNGIGVTQNVLYENQKLIAN

QFNSAIGKIQDSLSSTASALGKLQDVVNQNAQALNTLVKQLSSNFGAI

SSVLNDILSRLDKVEAEVQIDRLITGRLQSLQTYVTQQLIRAAEIRAS

ANLAATKMSECVLGQSKRVDFCGKGYHLMSFPQSAPHGVVFLHVTYVP

AQEKNFTTAPAICHDGKAHFPREGVFVSNGTHWFVTQRNFYEPQIITT

DNTFVSGNCDVVIGIVNNTVYDPLQPELDSFKEELDKYFKNHTSPDVD

LGDISGINASVVNIQKEIDRLNEVAKNLNESLIDLQELGKYEQYIKWP

WYIWLGFIAGLIAIVMVTIMLCCMTSCCSCLKGCCSCGSCCKFDEDDS

EPVLKGVKLHYT

Underlined regions of SEQ ID NO: 120 represent amino acids within the S2 subunit that may be modified.

In embodiments, the CoV S polypeptides described herein comprise an S2 subunit with at least 95%, at least 96%, at least 97%, at least 98%, at least 99%, or at least 99.5%, identity to the S2 subunit of SEQ ID NO: 1 or SEQ ID NO: 2. The S2 subunit may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the S2 subunit of SEQ ID NO: 1 or SEQ ID NO: 2. The S2 subunit may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the S2 subunit of SEQ ID NO: 1 or SEQ ID NO: 2.

In embodiments, the S2 subunit may contain any combination of modifications as shown in Table IF.

TABLE 1F

Modifications to S2 (SEQ ID NO: 120)
* amino acids 686-1273 of SEQ ID NO: 1 and
amino acids 673-1260 of SEQ ID NO: 2

| Position within SEQ ID NO: 1 | Position within SEQ ID NO: 2 | Position within SEQ ID NO: 120 | Possible Modifications |
|---|---|---|---|
| 689-698 | 676-685 | 4-13 | Deletion of up to about 1, up to about 2, up to about 3, up to about 4, up to about 5, up to about 6, up to about 7, up to about 8, up to about 9, or up to about 10 amino acids |
| 715-724 | 702-711 | 30-39 | Deletion of up to about 1, up to about 2, up to about 3, up to about 4, up to about 5, up to about 6, up to about 7, up to about 8, up to about 9, or up to about 10 amino acids |
| 788-806 | 775-793 | 103-121 | Deletion of up to about 1, up to about 2, up to about 3, up to about 4, up to about 5, up to about 6, up to about 7, up to about 8, up to about 9, up to about 10, up to about 11, up to about 12, up to about 13, up to about 14, up to about 15, up to about 16, up to about 17, up to about 18, or up to about 19 amino acids |
| 819-828 | 806-815 | 194-203 | Deletion of up to about 1, up to about 2, up to about 3, up to about 4, up to about 5, up to about 6, up to about 7, up to about 8, up to about 9, or up to about 10 amino acids |
| 986 | 973 | 301 | Mutation to proline Mutation to glycine |
| 987 | 974 | 302 | Mutation to proline Mutation to glycine |
| 716 | 703 | 31 | Mutation to beta-branched amino acid Mutation to valine Mutation to isoleucine |

TABLE 1F-continued

| Modifications to S2 (SEQ ID NO: 120) * amino acids 686-1273 of SEQ ID NO: 1 and amino acids 673-1260 of SEQ ID NO: 2 | | | |
|---|---|---|---|
| Position within SEQ ID NO: 1 | Position within SEQ ID NO: 2 | Position within SEQ ID NO: 120 | Possible Modifications |
| 1118 | 1105 | 433 | Mutation to histidine Mutation to lysine Mutation to arginine Mutation to asparagine Mutation to glutamine |
| 701 | 688 | 16 | Mutation to beta-branched amino acid Mutation to valine Mutation to isoleucine Mutation to threonine |
| 1027 | 1014 | 342 | Mutation to isoleucine Mutation to valine Mutation to serine |
| 982 | 969 | 297 | Mutation to alanine Mutation to glycine Mutation to threonine |
| 1214-1237 | 1201-1224 | 1-24 | Deletion of one or more amino acids of TM |
| 1238-1273 | 1225-1260 | 1-36 | Deletion of one or more amino acids of CD |

In embodiments, the CoV S polypeptides contain a deletion, corresponding to one or more deletions within amino acids 676-685 of the native CoV Spike (S) polypeptide (SEQ ID NO: 2). In embodiments, 1, 2, 3, 4, 5, 6, 7, 8, 9, or 10 amino acids of amino acids 676-685 of the native CoV Spike (S) polypeptide (SEQ ID NO:2) are deleted. In embodiments, the deletions of amino acids within amino acids 676-685 are consecutive e g amino acids 676 and 677 are deleted or amino acids 680 and 681 are deleted. In embodiments, the deletions of amino acids within amino acids 676-685 are non-consecutive e.g. amino acids 676 and 680 are deleted or amino acids 677 and 682 are deleted. In embodiments, CoV S polypeptides containing a deletion, corresponding to one or more deletions within amino acids 676-685, have an amino acid sequence selected from the group consisting of SEQ ID NO: 62 and SEQ ID NO: 63.

In embodiments, the CoV S polypeptides contain a deletion, corresponding to one or more deletions within amino acids 702-711 of the native CoV Spike (S) polypeptide (SEQ ID NO: 2). In embodiments, 1, 2, 3, 4, 5, 6, 7, 8, 9, or 10 amino acids of amino acids 702-711 of the native SARS-CoV-2 Spike (5) polypeptide (SEQ ID NO:2) are deleted. In embodiments, the one or more deletions of amino acids within amino acids 702-711 are consecutive e.g. amino acids 702 and 703 are deleted or amino acids 708 and 709 are deleted. In embodiments, the deletions of amino acids within amino acids 702-711 are non-consecutive e.g. amino acids 702 and 704 are deleted or amino acids 707 and 710 are deleted. In embodiments, the CoV S polypeptides containing a deletion, corresponding to one or more deletions within amino acids 702-711, have an amino acid sequence selected from the group consisting of SEQ ID NO: 64 and SEQ ID NO: 65.

In embodiments, the CoV S polypeptides contain a deletion, corresponding to one or more deletions within amino acids 775-793 of the native CoV S polypeptide (SEQ ID NO: 2). In embodiments, up to about 1, 2, 3, 4, 5, 6, 7, 8, 9, 10, 11, 12, 13, 14, 15, 16, 17, 18, or 19 amino acids of amino acids 775-793 of the native SARS-CoV-2 Spike (S) polypeptide (SEQ ID NO:2) are deleted. In embodiments, the one or more deletions of amino acids within amino acids 775-793 are consecutive e.g. amino acids 776 and 777 are deleted or amino acids 780 and 781 are deleted. In embodiments, the deletions of amino acids within amino acids 775-793 are non-consecutive e.g. amino acids 775 and 790 are deleted or amino acids 777 and 781 are deleted.

In embodiments, the CoV S polypeptides contain a deletion of the fusion peptide (SEQ ID NO: 104), which corresponds to amino acids 806-815 of SEQ ID NO: 2. In embodiments, 1, 2, 3, 4, 5, 6, 7, 8, 9, or 10 amino acids of the fusion peptide of the CoV Spike (S) polypeptide (SEQ ID NO:2) are deleted. In embodiments, the deletions of amino acids within the fusion peptide are consecutive e.g. amino acids 806 and 807 are deleted or amino acids 809 and 810 are deleted. In embodiments, the deletions of amino acids within the fusion peptide are non-consecutive e.g. amino acids 806 and 808 are deleted or amino acids 810 and 813 are deleted. In embodiments, the CoV S polypeptides containing a deletion, corresponding to one or more amino acids of the fusion peptide, have an amino acid sequence selected from SEQ ID NOS: 66, 77, and 105-108.

In embodiments, the CoV S polypeptides contain a mutation at Lys-973 of the native CoV Spike (S) polypeptide (SEQ ID NO: 2). In embodiments, Lys-973 is mutated to any natural amino acid. In embodiments, Lys-973 is mutated to proline. In embodiments, Lys-973 is mutated to glycine. In embodiments, the CoV S polypeptides containing a mutation at amino acid 973 are selected from the group consisting of SEQ ID NO: 84-89, 105-106, and 109-110.

In embodiments, the CoV S polypeptides contain a mutation at Val-974 of the native CoV Spike (S) polypeptide (SEQ ID NO: 2). In embodiments, Val-974 is mutated to any natural amino acid. In embodiments, Val-974 is mutated to proline. In embodiments, Val-974 is mutated to glycine. In embodiments, the CoV S polypeptides containing a mutation at amino acid 974 are selected from the group consisting of SEQ ID NO: 84-89, 105-106, and 109-110.

In embodiments, the CoV S polypeptides contain a mutation at Lys-973 and Val-974 of the native CoV Spike (S) polypeptide (SEQ ID NO: 2). In embodiments, Lys-973 and Val-974 are mutated to any natural amino acid. In embodiments, Lys-973 and Val-974 are mutated to proline. In embodiments, the CoV S polypeptides containing a mutation at amino acids 973 and 974 are selected from SEQ ID NOS: 84-89, 105-106, and 109-110.

CoV S Polypeptide Antigens—Modifications to S2 Subunit—HR1 Domain

In embodiments, the CoV S polypeptides contain one or more modifications to the HR1 domain having an amino acid sequence of SEQ ID NO: 119, which corresponds to amino acids 912-984 of SEQ ID NO: 1 or amino acids 889-971 of SEQ ID NO: 2.

The amino acid sequence of the HR1 domain (SEQ ID NO: 119) is shown below.

```
MAYRFNGIGVTQNVLYENQKLIANQFNSAIGKIQDSLSSTASALGKLQD

VVNQNAQALNTLVKQLSSNFGAISSVLNDILSRL
```

Underlined regions of SEQ ID NO: 119 represent amino acids within the HR1 domain that may be modified.

In embodiments, the CoV S polypeptides described herein comprise an HR1 domain with at least 95%, at least 96%, at least 97%, at least 98%, at least 99%, or at least 99.5%, identity to the HR1 domain of SEQ ID NO: 1 or SEQ ID NO: 2. The HR1 domain may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the HR1 domain of SEQ ID NO: 1 or SEQ ID NO: 2. The HR1 domain may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the HR1 domain of SEQ ID NO: 1 or SEQ ID NO: 2.

In embodiments, the HR1 domain may contain any combination of modifications as shown in Table 1G.

TABLE 1G

| Modifications to HR1 (SEQ ID NO: 119) * amino acids 912-984 of SEQ ID NO: 1 and amino acids 889-971 of SEQ ID NO: 2) | | | |
|---|---|---|---|
| Position within SEQ ID NO: 1 | Position within SEQ ID NO: 2 | Position within SEQ ID NO: 119 | Possible Modifications |
| 982 | 969 | 81 | Mutation to alanine Mutation to glycine Mutation to threonine |

CoV S Polypeptide Antigens—Modifications to S2 Subunit—HR2 Domain

In embodiments, the CoV S polypeptides contain one or more modifications to the HR2 domain having an amino acid sequence of SEQ ID NO: 125, which corresponds to amino acids 1163-1213 of SEQ ID NO: 1 or amino acids 1150-1200 of SEQ ID NO: 2.

The amino acid sequence of the HR2 domain (SEQ ID NO: 125) is shown below.

DVDLGDISGINASVVNIQKEIDRLNEVAKNLNESLIDLQELGKYEQYIK

WP

In embodiments, the CoV S polypeptides described herein comprise an HR2 domain with at least 95%, at least 96%, at least 97%, at least 98%, at least 99%, or at least 99.5%, identity to the HR2 domain of SEQ ID NO: 1 or SEQ ID NO: 2. The HR2 domain may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the HR2 domain of SEQ ID NO: 1 or SEQ ID NO: 2. The HR2 domain may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the HR2 domain of SEQ ID NO: 1 or SEQ ID NO: 2.

CoV S Polypeptide Antigens—Modifications to the TM Domain

In embodiments, the CoV S polypeptides contain one or more modifications to the TM domain having an amino acid sequence of SEQ ID NO: 123, which corresponds to amino acids 1214-1237 of SEQ ID NO: 1 or amino acids 1201-1224 of SEQ ID NO: 2.

The amino acid sequence of the TM domain (SEQ ID NO: 123) is shown below.

WYIWLGFIAGLIAIVMVTIMLCCM

In embodiments, the CoV S polypeptides described herein comprise a TM domain with at least 95%, at least 96%, at least 97%, at least 98%, at least 99%, or at least 99.5%, identity to the TM domain of SEQ ID NO: 1 or SEQ ID NO: 2. The TM domain may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the TM domain of SEQ ID NO: 1 or SEQ ID NO: 2. The TM domain may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the TM domain of SEQ ID NO: 1 or SEQ ID NO: 2.

In embodiments, the CoV S polypeptides described herein lack the entire TM domain. In embodiments, the CoV S polypeptides comprise the TM domain.

CoV S Polypeptide Antigens—Modifications to the CT

In embodiments, the CoV S polypeptides contain one or more modifications to the CT having an amino acid sequence of SEQ ID NO: 124, which corresponds to amino acids 1238-1273 of SEQ ID NO: 1 or amino acids 1225-1260 of SEQ ID NO: 2.

The amino acid sequence of the CT (SEQ ID NO: 124) is shown below:

TSCCSCLKGCCSCGSCCKFDEDDSEPVLKGVKLHYT

In embodiments, the CoV S polypeptides described herein comprise a CT with at least 95%, at least 96%, at least 97%, at least 98%, at least 99%, or at least 99.5%, identity to the CT of SEQ ID NO: 1 or SEQ ID NO: 2. The CT may have a deletion, an insertion, or mutation of up to about 1, up to about 2, up to about 3, up to about 4, up to about 5, up to about 10, up to about 15, up to about 20, up to about 25, or up to about 30 amino acids compared to the amino acid sequence of the CT of SEQ ID NO: 1 or SEQ ID NO: 2. The CT may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, or between about 25 and 30 amino acids as compared to the CT of SEQ ID NO: 1 or SEQ ID NO: 2.

In embodiments, the CoV S polypeptides described herein lack a CT. In embodiments, the CoV S polypeptides comprise the CT.

In embodiments, the CoV S polypeptides comprise a TM and a CT. In embodiments, the CoV Spike (S) polypeptides contain a deletion of one or more amino acids from the transmembrane and cytoplasmic tail (TMCT) (corresponding to amino acids 1201-1260). The amino acid sequence of the TMCT is represented by SEQ ID NO: 39. In embodiments, the CoV S polypeptides which have a deletion of one or more residues of the TMCT have enhanced protein expression. In embodiments, the CoV Spike (5) polypeptides which have one or more deletions from the TMCT have an amino acid sequence selected from the group consisting of SEQ ID NO: 40, 41, 42, 52, 54, 59, 61, 88, and 89. In embodiments, the CoV S polypeptides which have one or more deletions from the TM-CD are encoded by an isolated nucleic acid sequence selected from the group consisting of SEQ ID NO: 39, 43, 53, and 60.

CoV S Polypeptide Antigens—Non-Limiting Combinations of Mutations

In embodiments, the CoV S polypeptides contain a deletion of amino acids 56 and 57 of the native CoV Spike (5) polypeptide (SEQ ID NO: 2).

In embodiments, the CoV S polypeptides contain deletions of amino acids 131 and 132 of the native CoV Spike (S) polypeptide (SEQ ID NO: 2).

In embodiments, the CoV S polypeptides contain a deletion of amino acids 56 and 131 of the native CoV Spike (5) polypeptide (SEQ ID NO: 2). In embodiments, the CoV S polypeptides contain a deletion of amino acids 57 and 131 of the native CoV Spike (S) polypeptide (SEQ ID NO: 2).

In embodiments, the CoV S polypeptides contain a deletion of amino acids 56, 57, and 131 of the native CoV Spike (S) polypeptide (SEQ ID NO: 2).

In embodiments, the CoV S polypeptides contain a deletion of amino acids 56 and 132 of the native CoV Spike (S) polypeptide (SEQ ID NO: 2).

In embodiments, the CoV S polypeptides contain a deletion of amino acids 57 and 132 of the native CoV Spike (S) polypeptide (SEQ ID NO: 2).

In embodiments, the CoV S polypeptides contain a deletion of amino acids 56, 57, and 132 of the native CoV Spike (S) polypeptide (SEQ ID NO: 2).

In embodiments, the CoV S polypeptides contain a deletion of amino acids 56, 57, 131, and 132 of the native CoV Spike (S) polypeptide (SEQ ID NO: 2).

In embodiments, the CoV S polypeptides contain mutations that stabilize the prefusion conformation of the CoV S polypeptide. In embodiments, the CoV S polypeptides contain proline or glycine substitutions which stabilize the prefusion conformation. This strategy has been utilized for to develop a prefusion stabilized MERS-CoV S protein as described in the following documents which are each incorporated by reference herein in their entirety: Proc Natl Acad Sci USA. 2017 Aug. 29; 114(35):E7348-E7357; Sci Rep. 2018 Oct. 24; 8(1):15701; U.S. Publication No. 2020/0061185; and PCT Application No. PCT/US2017/058370.

Figure 8:
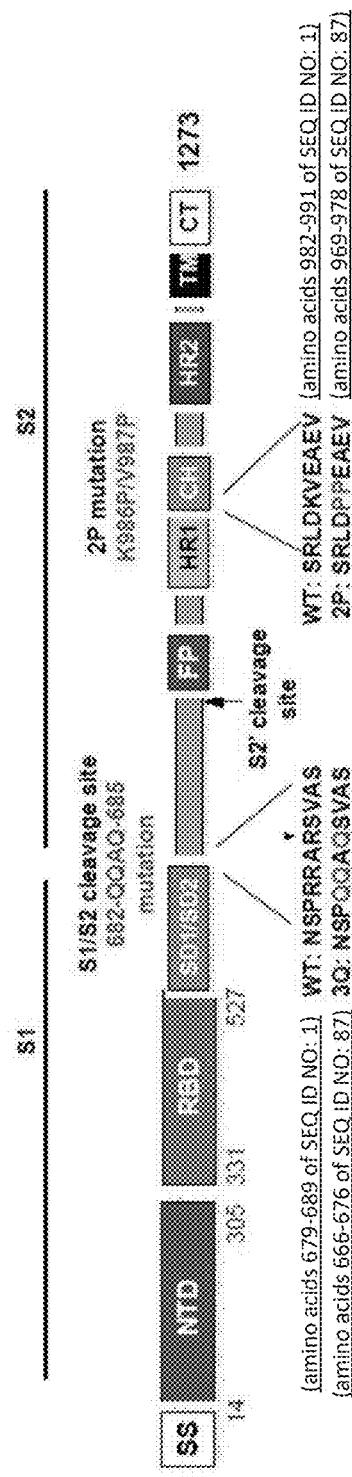
FIG. 8 shows the primary structure of the BV2373 CoV S polypeptide and modifications to the furin cleavage site, K986P, and V987P.

In embodiments, the CoV S polypeptides contain a mutation at Lys-973 and Val-974 and an inactivated furin cleavage site. In embodiments, the CoV S polypeptides contain mutations of Lys-973 and Val-974 to proline and an inactivated furin cleavage site, having the amino acid sequence of QQAQ (SEQ ID NO: 7) or GSAS (SEQ ID NO: 96). An exemplary CoV S polypeptide containing a mutation at Lys-973 and Val-974 and an inactivated furin cleavage site is depicted in FIG. 8. In embodiments, the CoV S polypeptides containing mutations of Lys-973 and Val-974 to proline and an inactivated furin cleavage site have an amino acid sequences of SEQ ID NOS: 86 or 87 and a nucleic acid sequence of SEQ ID NO: 96.

In embodiments, the CoV S polypeptides contain a mutation at Lys-973 and Val-974, an inactivated furin cleavage site, and a deletion of one or more amino acids of the fusion peptide. In embodiments, the CoV S polypeptides contain mutations of Lys-973 and Val-974 to proline, an inactivated furin cleavage site having the amino acid sequence of QQAQ (SEQ ID NO: 7) or GSAS (SEQ ID NO: 96), and deletion of one or more amino acids of the fusion peptide. In embodiments, the CoV S polypeptides containing mutations of Lys-973 and Val-974 to proline, an inactivated furin cleavage site, and deletion of one or more amino acids of the fusion peptide has an amino acid sequence of SEQ ID NO: 105 or 106. In embodiments, the CoV S polypeptide contains a mutation of Leu-5 to phenylalanine, mutation of Thr-7 to asparagine, mutation of Pro-13 to serine, mutation of Asp-125 to tyrosine, mutation of Arg-177 to serine, mutation of Lys-404 to threonine, mutation of Glu-471 to lysine, mutation of Asn-488 to tyrosine, mutation of His-642 to tyrosine, mutation of Thr-1014 to isoleucine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2).

In embodiments, the CoV S polypeptide contains a mutation of Trp-139 to cysteine, mutation of Leu-439 to arginine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2). In embodiments, the CoV S polypeptide contains a mutation of Trp-152 to cysteine, mutation of Leu-452 to arginine, mutation of Ser-13 to isoleucine, mutations of Lys-986 and Val-987 to proline, and an inactivated furin cleavage site having the amino acid sequence of QQAQ (SEQ ID NO: 7) or GSAS (SEQ ID NO: 96) relative to the native CoV Spike (5) polypeptide (SEQ ID NO: 1).

In embodiments, the CoV S polypeptide contains a mutation of Lys-404 to threonine or asparagine, mutation of Glu-471 to lysine, mutation of Asn-488 to tyrosine, mutation of Leu-5 to phenylalanine, mutation of Asp-67 to alanine, mutation of Asp-202 to glycine, deletion of one or more of amino acids 229-231, mutation of Arg-233 to isoleucine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2).

In embodiments, the CoV S polypeptide contains a mutation of Asn-488 to tyrosine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2). In embodiments, the CoV S polypeptide having a mutation of Asn-488 to tyrosine, mutations of Lys-973 and Val-974 to proline, and an inactivated furin cleavage site having the amino acid sequence of QQAQ (SEQ ID NO: 7) or GSAS (SEQ ID NO: 96) comprises an amino acid sequence of SEQ ID NO: 112.

In embodiments, the CoV S polypeptide contains a mutation of Asp-601 to glycine, a mutation of Asn-488 to tyrosine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2). In embodiments, the CoV S polypeptide having a mutation of Asn-488 to tyrosine, mutations of Lys-973 and Val-974 to proline, and an inactivated furin cleavage site having the amino acid sequence of QQAQ (SEQ ID NO: 7) or GSAS (SEQ ID NO: 96) comprises an amino acid sequence of SEQ ID NO: 113.

In embodiments, the CoV S polypeptide contains deletion of amino acids 56, 57, and 131, mutation of Asn-488 to tyrosine, a mutation of Ala-557 to aspartate, mutation of Asp-601 to glycine, mutation of Pro-668 to histidine, mutation of Thr-703 to isoleucine, mutation of Ser-969 to alanine, mutation of Asp-1105 to histidine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2). In embodiments, the CoV S polypeptide having deletion of amino acids 56, 57, and 131, mutation of Asn-488 to tyrosine, a mutation of Ala-557 to aspartate, mutation of Asp-601 to glycine, mutation of Pro-668 to histidine, mutation of Thr-703 to isoleucine, mutation of Ser-969 to alanine, mutation of Asp-1105 to histidine, mutations of Lys-973 and Val-974 to proline, and an inactivated furin cleavage site having the amino acid sequence of QQAQ (SEQ ID NO: 7) or GSAS (SEQ ID NO: 96) comprises an amino acid sequence of SEQ ID NO: 114.

In embodiments, the CoV S polypeptide contains deletion of amino acids 56, 57, and 132, mutation of Asn-488 to tyrosine, a mutation of Ala-557 to aspartate, mutation of Asp-601 to glycine, mutation of Pro-668 to histidine, mutation of Thr-703 to isoleucine, mutation of Ser-969 to alanine, mutation of Asp-1105 to histidine, mutations of Lys-973 and Val-974 to proline, and an inactivated furin cleavage site having the amino acid sequence of QQAQ (SEQ ID NO: 7) or GSAS (SEQ ID NO: 96 relative to the native CoV Spike (5) polypeptide (SEQ ID NO: 2). In embodiments, the CoV S polypeptide having a deletion of amino acids 56, 57, and 132, mutation of Asn-488 to tyrosine, a mutation of Ala-557 to aspartate, mutation of Asp-601 to glycine, mutation of Pro-668 to histidine, mutation of Thr-703 to isoleucine, mutation of Ser-969 to alanine, mutation of Asp-1105 to histidine, mutations of Lys-973 and Val-974 to proline, and an inactivated furin cleavage site having the amino acid sequence of QQAQ (SEQ ID NO: 7) or GSAS (SEQ ID NO: 96) comprises an amino acid sequence of SEQ ID NO: 114.

In embodiments, the CoV S polypeptide contains mutation of Asn-488 to tyrosine, mutation of Asp-67 to alanine, mutation of Leu-229 to histidine, mutation of Asp-202 to glycine, mutation of Lys-404 to asparagine, mutation of Glu-471 to lysine, mutation of Ala-688 to valine, mutation of Asp-601 to glycine, mutations of Lys-973 and Val-974 to proline, and an inactivated furin cleavage site having the amino acid sequence of QQAQ (SEQ ID NO: 7) or GSAS (SEQ ID NO: 96) relative to the native CoV Spike (S) polypeptide (SEQ ID NO: 2). In embodiments, the CoV S polypeptide having a mutation of Asn-488 to tyrosine, mutation of Asp-67 to alanine, mutation of Leu-229 to histidine, mutation of Asp-202 to glycine, mutation of Lys-404 to asparagine, mutation of Glu-471 to lysine, mutation of Ala-688 to valine, mutation of Asp-601 to glycine, mutations of Lys-973 and Val-974 to proline, and an inactivated furin cleavage site having the amino acid sequence of QQAQ (SEQ ID NO: 7) or GSAS (SEQ ID NO: 96) comprises an amino acid sequence of SEQ ID NO: 115.

In embodiments, the CoV Spike (S) polypeptides comprise a polypeptide linker. In embodiments, the polypeptide linker contains glycine and serine. In embodiments, the linker has about 50%, about 55%, about 60%, about 65%, about 70%, about 75%, about 80%, about 85%, about 90%, about 95%, or about 100% glycine.

In embodiments, the polypeptide linker has a repeat of (SGGG)$_n$ (SEQ ID NO: 91), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50). In embodiments, the polypeptide linker has an amino acid sequence corresponding to SEQ ID NO: 90.

In embodiments, the polypeptide linker has a repeat of (GGGGS)$_n$ (SEQ ID NO: 93), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In embodiments, the polypeptide linker has a repeat of (GGGS)$_n$ (SEQ ID NO: 92), wherein n is an integer from 1 to 50 (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50).

In some aspects, the polypeptide linker is a poly-(Gly)n linker, wherein n is 1, 2, 3, 4, 5, 6, 7, 8, 9, 10, 15, 16, 17, 18, 19, or 20. In other embodiments, the linker is selected from the group consisting of: dipeptides, tripeptides, and quadripeptides. In embodiments, the linker is a dipeptide selected from the group consisting of alanine-serine (AS), leucine-glutamic acid (LE), and serine-arginine (SR).

In embodiments, the polypeptide linker comprises between 1 to 100 contiguous amino acids of a naturally occurring CoV S polypeptide or of a CoV S polypeptide disclosed herein. In embodiments, the polypeptide linker has an amino acid sequence corresponding to SEQ ID NO: 94.

In embodiments, the CoV Spike (S) polypeptides comprise a foldon. In embodiments, the TMCT is replaced with a foldon. In embodiments, a foldon causes trimerization of the CoV Spike (S) polypeptide. In embodiments, the foldon is an amino acid sequence known in the art. In embodiments, the foldon has an amino acid sequence of SEQ ID NO: 68. In embodiments, the foldon is a T4 fibritin trimerization motif. In embodiments, the T4 fibritin trimerization domain has an amino acid sequence of SEQ ID NO: 103. In embodiments, the foldon is separated in amino acid sequence from the CoV Spike (S) polypeptide by a polypeptide linker. Non-limiting examples of polypeptide linkers are found throughout this disclosure.

In embodiments, the disclosure provides CoV S polypeptides comprising a fragment of a coronavirus S protein and nanoparticles and vaccines comprising the same. In embodiments, the fragment of the coronavirus S protein is between 10 and 1500 amino acids in length (e.g. about 10, about 20, about 30, about 40, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, or about 1500 amino acids in length). In embodiments, the fragment of the coronavirus S protein is selected from the group consisting of the receptor binding domain (RBD), subdomain 1, subdomain 2, upper helix, fusion peptide, connecting region, heptad repeat 1, central helix, heptad repeat 2, NTD, and TMCT.

In embodiments, the CoV S polypeptide comprises an RBD and a subdomain 1. In embodiments, the CoV S polypeptide comprising an RBD and a subdomain 1 is amino acids 319 to 591 of SEQ ID NO: 1.

In embodiments, the CoV S polypeptide contains a fragment of a coronavirus S protein, wherein the fragment of the coronavirus S protein is the RBD. Non-limiting examples of RBDs include the RBD of SARS-CoV-2 (amino acid sequence=SEQ ID NO: 69), the RBD of SARS (amino acid sequence=SEQ ID NO: 70), and the RBD of MERS, (amino acid sequence=SEQ ID NO: 71).

In embodiments, the CoV S polypeptide contains two or more RBDs, which are connected by a polypeptide linker. In embodiments, the polypeptide linker has an amino acid sequence of SEQ ID NO: 90 or SEQ ID NO: 94.

In embodiments, the CoV S polypeptide contains 1, 2, 3, 4, 5, 6, 7, 8, 9, 10, 11, 12, 13, 14, 15, 16, 17, 18, 19, or 20 RBDs.

In some embodiments, the CoV S polypeptide contains two or more SARS-CoV-2 RBDs, which are connected by a polypeptide linker. In embodiments, the antigen containing two or more SARS-CoV-2 RBDs has an amino acid sequence corresponding to one of SEQ ID NOS: 72-75.

In embodiments, the CoV S polypeptide contains a SARS-CoV-2 RBD and a SARS RBD. In embodiments, the CoV S polypeptide comprises a SARS-CoV-2 RBD and a SARS RBD, wherein each RBD is separated by a polypeptide linker. In embodiments, the CoV S polypeptide comprising a SARS-CoV-2 RBD and a SARS RBD has an amino acid sequence selected from the group consisting of SEQ ID NOS: 76-79.

In embodiments, the CoV S polypeptide contains a SARS-CoV-2 RBD and a MERS RBD. In embodiments, the CoV S polypeptide comprises a SARS-CoV-2 RBD and a MERS RBD, wherein each RBD is separated by a polypeptide linker.

In embodiments, the CoV S polypeptide comprises a SARS RBD and a MERS RBD. In embodiments, the CoV S polypeptide comprises a SARS RBD and a MERS RBD, wherein each RBD is separated by a polypeptide linker.

In embodiments, the CoV S polypeptide contains a SARS-CoV-2 RBD, a SARS RBD, and a MERS RBD. In embodiments, the CoV S polypeptide contains a SARS-CoV-2 RBD, a SARS RBD, and a MERS RBD, wherein each RBD is separated by a polypeptide linker. In embodiments, the CoV S polypeptide comprising a SARS-CoV-2 RBD, a SARS RBD, and a MERS RBD has an amino acid sequence selected from the group consisting of SEQ ID NOS: 80-83.

In embodiments, the CoV S polypeptides described herein are expressed with an N-terminal signal peptide. In embodiments, the N-terminal signal peptide has an amino acid sequence of SEQ ID NO: 5 (MFVFLVLLPLVSS). In embodiments, the N-terminal signal peptide has an amino acid sequence of SEQ ID NO: 117 (MIFVFLVLLPLVSI). In embodiments, the signal peptide may be replaced with any signal peptide that enables expression of the CoV S protein. In embodiments, one or more of the CoV S protein signal peptide amino acids may be deleted or mutated. An initiating methionine residue is maintained to initiate expression. In embodiments, the CoV S polypeptides are encoded by a nucleic acid sequence selected from the group consisting of SEQ ID NO: 35, SEQ ID NO: 37, SEQ ID NO: 95, SEQ ID NO: 43, SEQ ID NO: 47, SEQ ID NO: 50, SEQ ID NO: 53, SEQ ID NO: 55, SEQ ID NO: 57, SEQ ID NO: 96, and SEQ ID NO: 60. In embodiments, the N-terminal signal peptide of the CoV S polypeptide contains a mutation at Ser-13 relative to the native CoV Spike (S) signal polypeptide (SEQ ID NO: 5). In embodiments, Ser-13 is mutated to any natural amino acid. In embodiments, Ser-13 is mutated to alanine, methionine, isoleucine, leucine, threonine, or valine. In embodiments, Ser-13 is mutated to isoleucine.

Following expression of the CoV S protein in a host cell, the N-terminal signal peptide is cleaved to provide the mature CoV protein sequence (SEQ ID NOS: 2, 4, 38, 41, 44, 48, 51, 54, 58, 61, 63, 65, 67, 73, 75, 78, 79, 82, 83, 85, 87, 89, 106, and 110). In embodiments, the signal peptide is cleaved by host cell proteases. In aspects, the full-length protein may be isolated from the host cell and the signal peptide cleaved subsequently.

Following cleavage of the signal peptide from the CoV Spike (S) polypeptide with an amino acid sequence corresponding to SEQ ID NOS: 1, 3, 36, 40, 42, 46, 49, 52, 56, 59, 62, 64, 66, 72, 74, 76, 77, 80, 81, 84, 86, 87, 105, 107, 88, and 109 during expression and purification, a mature polypeptide having an amino acid sequence selected from the group consisting of SEQ ID NOS: 2, 4, 38, 41, 44, 48, 51, 54, 58, 61, 63, 65, 67, 73, 75, 78, 79, 82, 83, 85, 106, 108, 89, and 110, or 112-115 is obtained and used to produce a CoV S nanoparticle vaccine or CoV S nanoparticles.

Advantageously, the disclosed CoV S polypeptides may have enhanced protein expression and stability relative to the native CoV Spike (S) protein.

In embodiments, the CoV S polypeptides described herein contain further modifications from the native coronavirus S protein (SEQ ID NO: 2). In embodiments, the coronavirus S proteins described herein exhibit at least 80%, or at least 90%, or at least 95%, or at least 97%, or at least 99% identity to the native coronavirus S protein. A person of skill in the art would use known techniques to calculate the percent identity of the recombinant coronavirus S protein to the native protein or to any of the CoV S polypeptides described herein. For example, percentage identity can be calculated using the tools CLUSTALW2 or Basic Local Alignment Search Tool (BLAST), which are available online. The following default parameters may be used for CLUSTALW2 Pairwise alignment: Protein Weight Matrix=Gonnet; Gap Open=10; Gap Extension=0.1.

In embodiments, the CoV S polypeptides described herein are at least 95%, at least 96%, at least 97%, at least 98%, at least 99%, or at least 99.5% identical to the CoV S polypeptide having an amino acid sequence of SEQ ID NO: 87. A CoV S polypeptide may have a deletion, an insertion, or mutation of up to about 1, up to about 2, up to about 3, up to about 4, up to about 5, up to about 10, up to about 15, up to about 20, up to about 25, up to about 30, up to about 35, up to about 40, up to about 45, or up to about 50 amino acids compared to the amino acid sequence of the CoV S polypeptide having an amino acid sequence of SEQ ID NO: 87. A CoV S polypeptide may have may have a deletion, an insertion, or mutation of between about 1 and about 5 amino acids, between about 3 and about 10 amino acids, between about 5 and 10 amino acids, between about 8 and 12 amino acids, between about 10 and 15 amino acids, between about 12 and 17 amino acids, between about 15 and 20 amino acids, between about 18 and 23 amino acids, between about 20 and 25 amino acids, between about 22 and about 27 amino acids, between about 25 and 30 amino acids, between about 30 and 35 amino acids, between about 35 and 40 amino acids, between about 40 and 45 amino acids, or between about 45 and 50 amino acids, as compared to the CoV S polypeptide having an amino acid sequence of SEQ ID NO: 87. In embodiments, the CoV S polypeptides described herein comprise about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, or about 25 substitutions compared to the coronavirus S protein (SEQ ID NO: 87).

In embodiments, the coronavirus S polypeptide is extended at the N-terminus, the C-terminus, or both the N-terminus and the C-terminus. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines) (SEQ ID NO: 101), a hexahistidine tag (SEQ ID NO: 100), an 8×-His-tag (having eight histidines) (SEQ ID NO: 102), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included. In embodiments, the tag is a protease cleavage site. Non-limiting examples of protease cleavage sites include the HRV3C protease cleavage site, chymotrypsin, trypsin, elastase, endopeptidase, caspase-1, caspase-2, caspase-3, caspase-4, caspase-5, caspase-6, caspase-7, caspase-8, caspase-9, caspase-10, enterokinase, factor Xa, Granzyme B, TEV protease, and thrombin. In embodiments, the protease cleavage site is an HRV3C protease cleavage site. In embodiments, the protease cleavage site comprises an amino acid sequence of SEQ ID NO: 98.

In embodiments, the CoV S glycoprotein comprises a fusion protein. In embodiments, the CoV S glycoprotein comprises an N-terminal fusion protein. In embodiments, the Cov S glycoprotein comprises a C-terminal fusion protein. In embodiments, the fusion protein encompasses a tag useful for protein expression, purification, or detection. In embodiments, the tag is a polyHis-tag (having about 5-10 histidines), a Myc-tag, a Glutathione-S-transferase-tag, a Green fluorescent protein-tag, Maltose binding protein-tag, a Thioredoxin-tag, a Strep-tag, a Twin-Strep-tag, or an Fc-tag. In embodiments, the tag is an Fc-tag. In embodiments, the Fc-tag is monomeric, dimeric, or trimeric. In embodiments, the tag is a hexahistidine tag, e.g. a polyHis-tag which contains six histidines (SEQ ID NO: 100). In embodiments, the tag is a Twin-Strep-tag with an amino acid sequence of SEQ ID NO: 99.

In embodiments, the CoV S polypeptide is a fusion protein comprising another coronavirus protein. In embodiments, the other coronavirus protein is from the same coronavirus. In embodiments, the other coronavirus protein is from a different coronavirus.

In some aspects, the CoV S protein may be truncated. For example, the N-terminus may be truncated by about 10 amino acids, about 30 amino acids, about 50 amino acids, about 75 amino acids, about 100 amino acids, or about 200 amino acids. The C-terminus may be truncated instead of or in addition to the N-terminus. For example, the C-terminus may be truncated by about 10 amino acids, about 30 amino acids, about 50 amino acids, about 75 amino acids, about 100 amino acids, or about 200 amino acids. For purposes of calculating identity to the protein having truncations, identity is measured over the remaining portion of the protein.

Nanoparticles Containing CoV Spike (5) Polypeptides

In embodiments, the mature CoV S polypeptide antigens are used to produce a vaccine comprising coronavirus S nanoparticles. In embodiments, nanoparticles of the present disclosure comprise the CoV S polypeptides described herein. In embodiments, the nanoparticles of the present disclosure comprise CoV S polypeptides associated with a detergent core. The presence of the detergent facilitates formation of the nanoparticles by forming a core that

Figure 10:
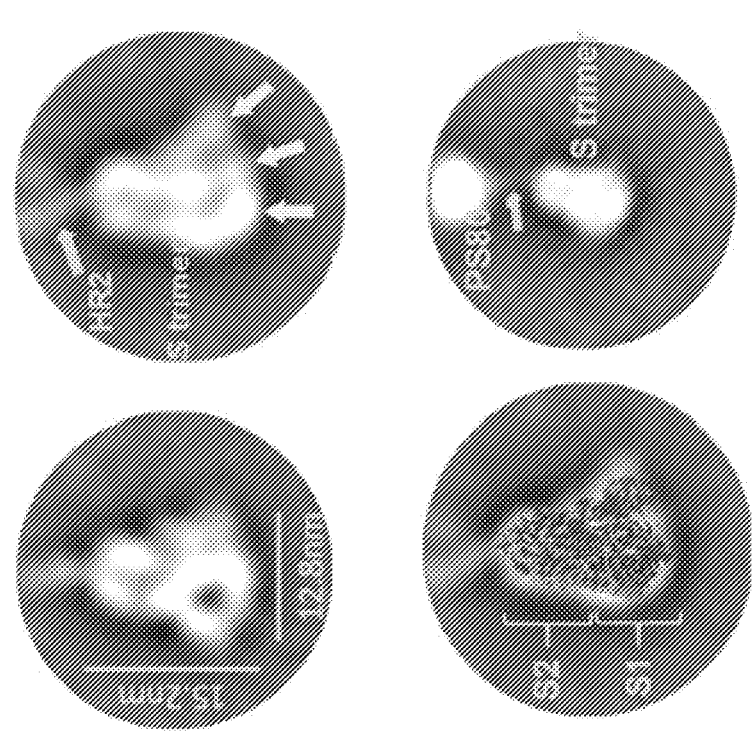
FIG. 10 shows a cryo-electron microscopy (cryoEM) structure of the BV2373 CoV S polypeptide overlaid on the cryoEM structure of the SARS-CoV-2 spike protein (EMB ID: 21374).

32 organizes and presents the antigens. In embodiments, the nanoparticles may contain the CoV S polypeptides assembled into multi-oligomeric glycoprotein-detergent (e.g. PS80) nanoparticles with the head regions projecting outward and hydrophobic regions and PS80 detergent forming a central core surrounded by the glycoprotein. In embodiments, the CoV S polypeptide inherently contains or is adapted to contain a transmembrane domain to promote association of the protein into a detergent core. In embodiments, the CoV S polypeptide contains a head domain. FIG. 10 shows an exemplary structure of a CoV S polypeptide of the disclosure. Primarily the transmembrane domains of a CoV S polypeptide trimer associate with detergent; however, other portions of the polypeptide may also interact. Advantageously, the nanoparticles have improved resistance to environmental stresses such that they provide enhanced stability and/or improved presentation to the immune system due to organization of multiple copies of the protein around the detergent.

In embodiments, the detergent core is a non-ionic detergent core. In embodiments, the CoV S polypeptide is associated with the non-ionic detergent core. In embodiments, the detergent is selected from the group consisting of polysorbate-20 (PS20), polysorbate-40 (PS40), polysorbate-60 (PS60), polysorbate-65 (PS65) and polysorbate-80 (PS80). In embodiments, the detergent is PS80.

In embodiments, the CoV S polypeptide forms a trimer. In embodiments, the CoV S polypeptide nanoparticles are composed of multiple polypeptide trimers surrounding a non-ionic detergent core. In embodiments, the nanoparticles contain at least about 1 trimer or more. In embodiments, the nanoparticles contain at least about 5 trimers to about 30 trimers of the Spike protein. In embodiments, each nanoparticle may contain 1, 2, 3, 4, 5, 6, 7, 8, 9, 10, 11, 12, or 15, 20, 25, or 30 trimers, including all values and ranges in between. Compositions disclosed herein may contain nanoparticles having different numbers of trimers. For example, a composition may contain nanoparticles where the number of trimers ranges from 2-9; in embodiments, the nanoparticles in a composition may contain from 2-6 trimers. In embodiments, the compositions contain a heterogeneous population of nanoparticles having 2 to 6 trimers per nanoparticle, or 2 to 9 trimers per nanoparticle. In embodiments, the compositions may contain a substantially homogenous population of nanoparticles. For example, the population may contain about 95% nanoparticles having 5 trimers.

The nanoparticles disclosed herein range in particle size. In embodiments, the nanoparticles disclosed herein range in particle size from a Z-ave size from about 20 nm to about 60 nm, about 20 nm to about 50 nm, about 20 nm to about 45 mu, about 20 nm to about 35 nm, about 20 nm to about 30 mu, about 25 nm to about 35 nm, or about 25 nm to about 45 nm. Particle size (Z-ave) is measured by dynamic light scattering (DLS) using a Zetasizer NanoZS (Malvern, UK), unless otherwise specified.

In embodiments, the nanoparticles comprising the CoV S polypeptides disclosed herein have a reduced particle size compared to nanoparticles comprising a wild-type CoV S polypeptide. In embodiments, the CoV S polypeptides are at least about 40% smaller in particle size, for example, at least about 40%, at least about 45%, at least about 50%, at least about 55%, at least about 60%, at least about 65%, at least about 70%, at least about 75%, at least about 80%, or at least about 85% smaller in particle size.

The nanoparticles comprising CoV S polypeptides disclosed herein are more homogenous in size, shape, and mass than nanoparticles comprising a wild-type CoV S polypeptide. The polydispersity index (PDI), which is a measure of heterogeneity, is measured by dynamic light scattering using a Malvern Setasizer unless otherwise specified. In embodiments, the particles measured herein have a PDI from about 0.2 to about 0.45, for example, about 0.2, about 0.25, about 0.29, about 0.3, about 0.35, about 0.40, or about 0.45. In embodiments, the nanoparticles measured herein have a PDI that is at least about 25% smaller than the PDI of nanoparticles comprising the wild-type CoV S polypeptide, for example, at least about 25%, at least about 30%, at least about 35%, at least about 40%, at least about 45%, at least about 50%, at least about 55%, or at least about 60%, smaller.

The CoV S polypeptides and nanoparticles comprising the same have improved thermal stability as compared to the wild-type CoV S polypeptide or a nanoparticle thereof. The thermal stability of the CoV S polypeptides is measured using differential scanning calorimetry (DSC) unless otherwise specified. The enthalpy of transition ($\Delta$Hcal) is the energy required to unfold a CoV S polypeptide. In embodiments, the CoV S polypeptides have an increased $\Delta$Hcal as compared to the wild-type CoV S polypeptide. In embodiments, the $\Delta$Hcal of a CoV S polypeptide is about 2-fold, about 3-fold, about 4-fold, about 5-fold, about 6-fold, about 7-fold, about 8-fold, about 9-fold, or about 10-fold greater than the $\Delta$Hcal of a wild-type CoV S polypeptide.

Several nanoparticle types may be included in vaccine compositions disclosed herein. In some aspects, the nanoparticle type is in the form of an anisotropic rod, which may be a dimer or a monomer. In other aspects, the nanoparticle type is a spherical oligomer. In yet other aspects, the nanoparticle may be described as an intermediate nanoparticle, having sedimentation properties intermediate between the first two types. Formation of nanoparticle types may be regulated by controlling detergent and protein concentration during the production process. Nanoparticle type may be determined by measuring sedimentation co-efficient.

Production of Nanoparticles Containing CoV S Polypeptide Antigens

The nanoparticles of the present disclosure are non-naturally occurring products, the components of which do not occur together in nature. Generally, the methods disclosed herein use a detergent exchange approach wherein a first detergent is used to isolate a protein and then that first detergent is exchanged for a second detergent to form the nanoparticles.

The antigens contained in the nanoparticles are typically produced by recombinant expression in host cells. Standard recombinant techniques may be used. In embodiments, the CoV S polypeptides are expressed in insect host cells using a baculovirus system. In embodiments, the baculovirus is a cathepsin-L knock-out baculovirus, a chitinase knock-out baculovirus. Optionally, the baculovirus is a double knock-out for both cathepsin-L and chitinase. High level expression may be obtained in insect cell expression systems. Non limiting examples of insect cells are, *Spodoptera frugiperda* (Sf) cells, e.g. Sf9, Sf21, Trichoplusiani cells, e.g. High Five cells, and *Drosophila* S2 cells. In embodiments, the CoV S polypeptide described herein are produced in any suitable host cell. In embodiments, the host cell is an insect cell. In embodiments, the insect cell is an Sf9 cell.

Typical transfection and cell growth methods can be used to culture the cells. Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 3500 L bags.

Extraction and Purification of Nanoparticles Containing CoV Spike (S) Protein Antigens After growth of the host cells, the protein may be harvested from the host cells using detergents and purification protocols. Once the host cells have grown for 48 to 96 hours, the cells are isolated from the media and a detergent-containing solution is added to solubilize the cell membrane, releasing the protein in a detergent extract. Triton X-100 and TERGITOL® nonylphenol ethoxylate, also known as NP-9, are each preferred detergents for extraction. The detergent may be added to a final concentration of about 0.1% to about 1.0%. For example, the concentration may be about 0.1%, about 0.2%, about 0.3%, about 0.5%, about 0.7%, about 0.8%, or about 1.0%. The range may be about 0.1% to about 0.3%. In aspects, the concentration is about 0.5%.

In other aspects, different first detergents may be used to isolate the protein from the host cell. For example, the first detergent may be Bis(polyethylene glycol bis[imidazoylcarbonyl]), nonoxynol-9, Bis(polyethylene glycol bis[imidazoyl carbonyl]), BRIJ® Polyethylene glycol dodecyl ether 35, BRIJ® Polyethylene glycol (3) cetyl ether 56, BRIJ® alcohol ethoxylate 72, BRIJ® Polyoxyl 2 stearyl ether 76, BRIJ® polyethylene glycol monoolelyl ether 92V, BRIJ® Polyoxyethylene (10) oleyl ether 97, BRIJ® Polyethylene glycol hexadecyl ether 58P, CREMOPHOR® EL Macrogolglycerol ricinoleate, Decaethyleneglycol monododecyl ether, N-Decanoyl-N-methylglucamine, n-Decyl alpha-Dglucopyranoside, Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-0-(N-heptylcarbamoyl)-alpha-D-glucopyranoside, Nonaethylene glycol monododecyl ether, N-Nonanoyl-N-methylglucamine, N-NonanoylN-methylglucamine, Octaethylene glycol monodecyl ether, Octaethylene glycolmonododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene

35

10 tridecyl ether, Polyoxyethylene 100 stearate, Polyoxy-
ethylene 20 isohexadecyl ether, Polyoxyethylene 20 oleyl
ether, Polyoxyethylene 40 stearate, Polyoxyethylene 50
stearate, Polyoxyethylene 8 stearate, Polyoxyethylene bis
(imidazolyl carbonyl), Polyoxyethylene 25 propylene glycol
stearate, Saponin from *Quillaja* bark, SPAN® 20 sorbitan
laurate, SPAN® 40 sorbitan monopalmitate, SPAN® 60
sorbitan stearate, SPAN® 65 sorbitan tristearate, SPAN® 80
sorbitane monooleate, SPAN® 85 sorbitane trioleate, TER-
GITOL® secondary alcohol ethoxylate Type 15-S-12, TER-
GITOL® secondary alcohol ethoxylate Type 15-S-30, TER-
GITOL® secondary alcohol ethoxylate Type 15-S-5,
TERGITOL® secondary alcohol ethoxylate Type 15-S-7,
TERGITOL® secondary alcohol ethoxylate Type 15-S-9,
TERGITOL® nonylphenol ethoxylate Type NP-10, TER-
GITOL® nonylphenol ethoxylate Type NP-4, TERGITOL®
nonylphenol ethoxylate Type NP-40, TERGITOL® non-
ylphenol ethoxylate Type NP-7, TERGITOL® nonylphenol
ethoxylate Type NP-9, TERGITOL® branched secondary
alcohol ethoxylate Type TMN-10, TERGITOL® branched
secondary alcohol ethoxylate Type TMN-6, TRITON™
X-100 Polyethylene glycol tert-octylphenyl ether or combi-
nations thereof.

The nanoparticles may then be isolated from cellular
debris using centrifugation. In embodiments, gradient cen-
trifugation, such as using cesium chloride, sucrose and
iodixanol, may be used. Other techniques may be used as
alternatives or in addition, such as standard purification
techniques including, e.g., ion exchange, affinity, and gel
filtration chromatography.

For example, the first column may be an ion exchange
chromatography resin, such as FRACTOGEL® EMD meth-
acrylate based polymeric beads TMAE (EMD Millipore),
the second column may be a lentil (*Lens culinaris*) lectin
affinity resin, and the third column may be a cation exchange
column such as a FRACTOGEL® EMD methacrylate based
polymeric beads SO3 (EMD Millipore) resin. In other
aspects, the cation exchange column may be an MMC
column or a Nuvia C Prime column (Bio-Rad Laboratories,
Inc). Preferably, the methods disclosed herein do not use a
detergent extraction column; for example a hydrophobic
interaction column. Such a column is often used to remove
detergents during purification but may negatively impact the
methods disclosed here.

Detergent Exchange of Nanoparticles Containing CoV S
Polypeptide Antigens

To form nanoparticles, the first detergent, used to extract
the protein from the host cell is substantially replaced with
a second detergent to arrive at the nanoparticle structure.
NP-9 is a preferred extraction detergent. Typically, the
nanoparticles do not contain detectable NP-9 when mea-
sured by HPLC. The second detergent is typically selected
from the group consisting of PS20, PS40, PS60, PS65, and
PS80. Preferably, the second detergent is PS80.

In particular aspects, detergent exchange is performed
using affinity chromatography to bind glycoproteins via their
carbohydrate moiety. For example, the affinity chromatog-
raphy may use a legume lectin column. Legume lectins are
proteins originally identified in plants and found to interact
specifically and reversibly with carbohydrate residues. See,
for example, Sharon and Lis, "Legume lectins—a large
family of homologous proteins," FASEB J. 1990 November;
4(14):3198-208; Liener, "The Lectins: Properties, Func-
tions, and Applications in Biology and Medicine," Elsevier,
2012. Suitable lectins include concanavalin A (con A), pea
lectin, sainfoin lect, and lentil lectin. Lentil lectin is a
preferred column for detergent exchange due to its binding properties. Lectin columns are commercially available; for
example, Capto Lentil Lectin, is available from GE Health-
care. In certain aspects, the lentil lectin column may use a
recombinant lectin. At the molecular level, it is thought that
the carbohydrate moieties bind to the lentil lectin, freeing the
amino acids of the protein to coalesce around the detergent
resulting in the formation of a detergent core providing
nanoparticles having multiple copies of the antigen, e.g.,
glycoprotein oligomers which can be dimers, trimers, or
tetramers anchored in the detergent. In embodiments, the
CoV S polypeptides form trimers. In embodiments, the CoV
S polypeptide trimers are anchored in detergent. In embodi-
ments, each CoV S polypeptide nanoparticle contains at
least one trimer associated with a non-ionic core.

The detergent, when incubated with the protein to form
the nanoparticles during detergent exchange, may be present
at up to about 0.1% (w/v) during early purifications steps
and this amount is lowered to achieve the final nanoparticles
having optimum stability. For example, the non-ionic deter-
gent (e.g., PS80) may be about 0.005% (v/v) to about 0.1%
(v/v), for example, about 0.005% (v/v), about 0.006% (v/v),
about 0.007% (v/v), about 0.008% (v/v), about 0.009%
(v/v), about 0.01% (v/v), about 0.015% (v/v), about 0.02%
(v/v), about 0.025% (v/v), about 0.03% (v/v), about 0.035%
(v/v), about 0.04% (v/v), about 0.045% (v/v), about 0.05%
(v/v), about 0.055% (v/v), about 0.06% (v/v), about 0.065%
(v/v), about 0.07% (v/v), about 0.075% (v/v), about 0.08%
(v/v), about 0.085% (v/v), about 0.09% (v/v), about 0.095%
(v/v), or about 0.1% (v/v) PS80. In embodiments, the
nanoparticle contains about 0.03% to about 0.05% PS80. In
embodiments, the nanoparticle contains about 0.01% (v/v)
PS80.

In embodiments, purified CoV S polypeptides are dia-
lyzed. In embodiments, dialysis occurs after purification. In
embodiments, the CoV S polypeptides are dialyzed in a
solution comprising sodium phosphate, NaCl, and PS80. In
embodiments, the dialysis solution comprising sodium phos-
phate contains between about 5 mM and about 100 mM of
sodium phosphate, for example, about 5 mM, about 10 mM,
about 15 mM, about 20 mM, about 25 mM, about 30 mM,
about 35 mM, about 40 mM, about 45 mM, about 50 mM,
about 55 mM, about 60 mM, about 65 mM, about 70 mM,
about 75 mM, about 80 mM, about 85 mM, about 90 mM,
about 95 mM, or about 100 mM sodium phosphate. In
embodiments, the pH of the solution comprising sodium
phosphate is about 6.5, about 6.6, about 6.7, about 6.8, about
6.9, about 7.0, about 7.1, about 7.2, about 7.3, about 7.4, or
about 7.5. In embodiments, the dialysis solution comprising
sodium chloride comprises about 50 mM NaCl to about 500
mM NaCl, for example, about 50 mM, about 60 mM, about
70 mM, about 80 mM, about 90 mM, about 100 mM, about
110 mM, about 120 mM, about 130 mM, about 140 mM,
about 150 mM, about 160 mM, about 170 mM, about 180
mM, about 190 mM, about 200 mM, about 210 mM, about
220 mM, about 230 mM, about 240 mM, about 250 mM,
about 260 mM, about 270 mM, about 280 mM, about 290
mM, about 300 mM, about 310 mM, about 320 mM, about
330 mM, about 340 mM, about 350 mM, about 360 mM,
about 370 mM, about 380 mM, about 390 mM, about 400
mM, about 410 mM, about 420 mM, about 430 mM, about
440 mM, about 450 mM, about 460 mM, about 470 mM,
about 480 mM, about 490 mM, or about 500 mM NaCl. In
embodiments, the dialysis solution comprising PS80 com-
prises about 0.005% (v/v), about 0.006% (v/v), about
0.007% (v/v), about 0.008% (v/v), about 0.009% (v/v),
about 0.01% (v/v), about 0.015% (v/v), about 0.02% (v/v),
about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), or about 0.1% (v/v) PS80. In embodiments, the dialysis solution comprises about 25 mM sodium phosphate (pH 7.2), about 300 mM NaCl, and about 0.01% (v/v) PS80.

Detergent exchange may be performed with proteins purified as discussed above and purified, frozen for storage, and then thawed for detergent exchange.

Figure 12B:
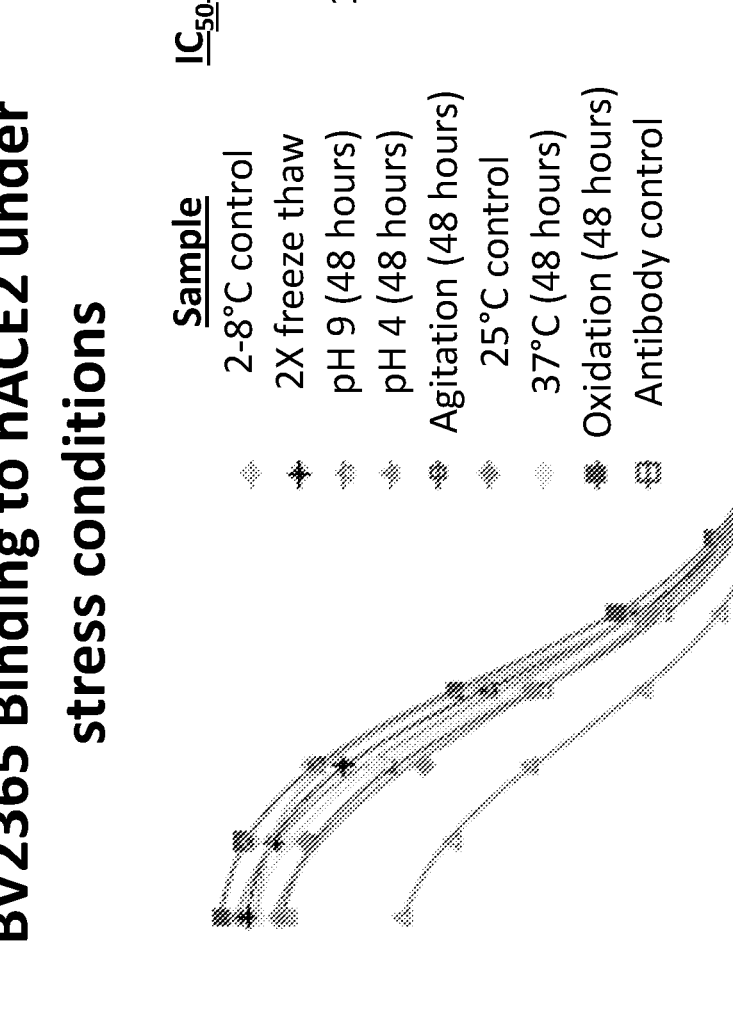
Figure 33:
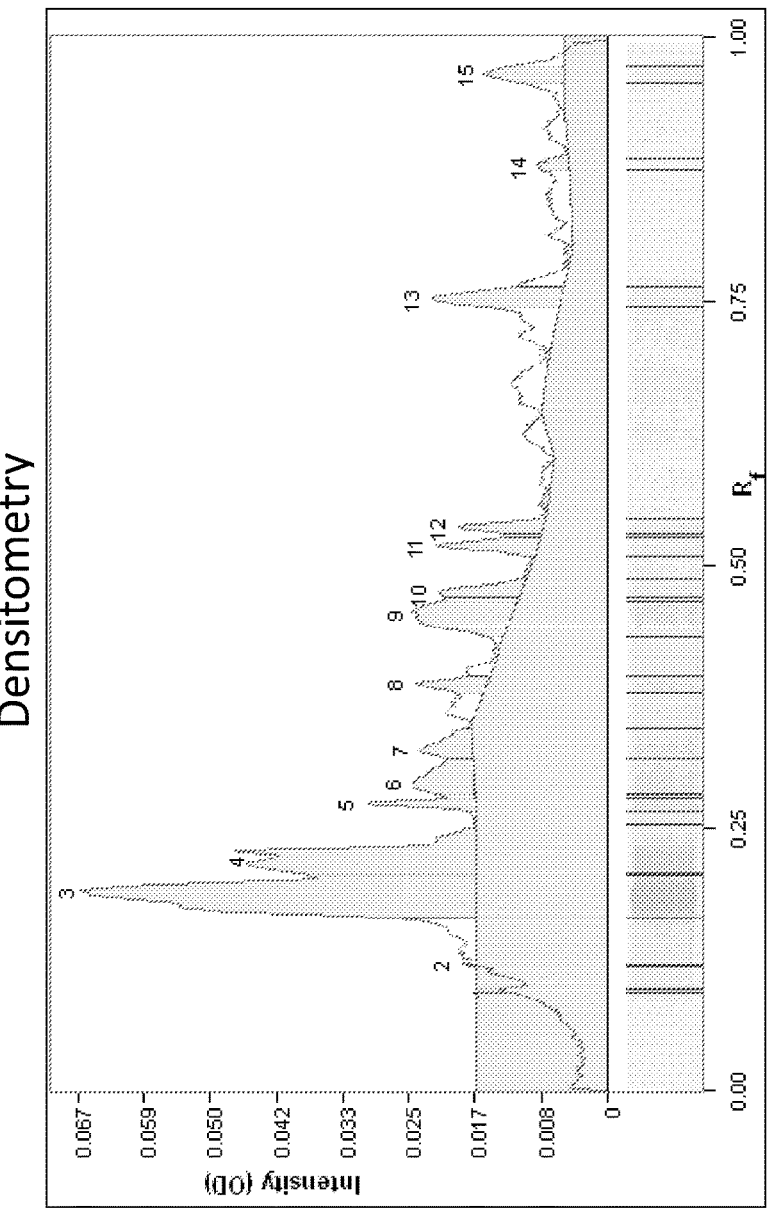
FIG. 33 shows a scanning densitometry plot of BV2384 (SEQ ID NO: 109) purity after purification.
Figure 34:
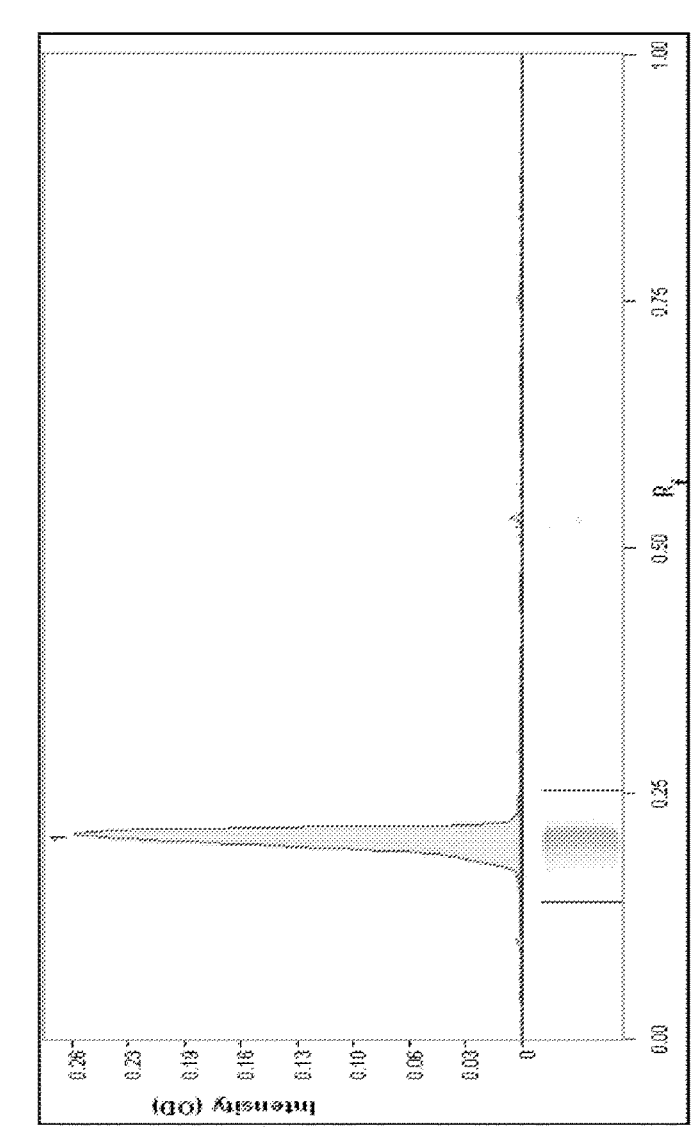
FIG. 34 shows a scanning densitometry plot of BV2373 (SEQ ID NO: 87) purity after purification

Stability of compositions disclosed herein may be measured in a variety of ways. In one approach, a peptide map may be prepared to determine the integrity of the antigen protein after various treatments designed to stress the nanoparticles by mimicking harsh storage conditions. Thus, a measure of stability is the relative abundance of antigen peptides in a stressed sample compared to a control sample. For example, the stability of nanoparticles containing the CoV S polypeptides may be evaluated by exposing the nanoparticles to various pHs, proteases, salt, oxidizing agents, including but not limited to hydrogen peroxide, various temperatures, freeze/thaw cycles, and agitation. FIGS. 12A-B show that BV2373 (SEQ ID NO: 87) and BV2365 (SEQ ID NO: 4) retain binding to hACE2 under a variety of stress conditions. It is thought that the position of the glycoprotein anchored into the detergent core provides enhanced stability by reducing undesirable interactions. For example, the improved protection against protease-based degradation may be achieved through a shielding effect whereby anchoring the glycoproteins into the core at the molar ratios disclosed herein results in steric hindrance blocking protease access. Stability may also be measured by monitoring intact proteins. FIG. 33 and FIG. 34 compare nanoparticles containing CoV polypeptides having amino acid sequences of SEQ ID NOS: 109 and 87, respectively. FIG. 34 indicates that CoV polypeptides having an amino acid sequence of SEQ ID NO: 87 show particularly good stability during purification. The polypeptide of FIG. 34 comprises a furin cleavage site having an amino acid sequence of QQAQ (SEQ ID NO: 7).

Vaccine Compositions Containing CoV S Polypeptide Antigens

The disclosure provides vaccine compositions comprising CoV S polypeptides, for example, in a nanoparticle. In some aspects, the vaccine composition may contain nanoparticles with antigens from more than one viral strain from the same species of virus. In another embodiment, the disclosures provide for a pharmaceutical pack or kit comprising one or more containers filled with one or more of the components of the vaccine compositions.

Compositions disclosed herein may be used either prophylactically or therapeutically, but will typically be prophylactic. Accordingly, the disclosure includes methods for treating or preventing infection. The methods involve administering to the subject a therapeutic or prophylactic amount of the immunogenic compositions of the disclosure. Preferably, the pharmaceutical composition is a vaccine composition that provides a protective effect. In other aspects, the protective effect may include amelioration of a symptom associated with infection in a percentage of the exposed population. For example, the composition may prevent or reduce one or more virus disease symptoms selected from: fever fatigue, muscle pain, headache, sore throat, vomiting, diarrhea, rash, symptoms of impaired kidney and liver function, internal bleeding and external bleeding, compared to an untreated subject.

The nanoparticles may be formulated for administration as vaccines in the presence of various excipients, buffers, and the like. For example, the vaccine compositions may contain sodium phosphate, sodium chloride, and/or histidine. Sodium phosphate may be present at about 10 mM to about 50 mM, about 15 mM to about 25 mM, or about 25 mM; in particular cases, about 22 mM sodium phosphate is present. Histidine may be present about 0.1% (w/v), about 0.5% (w/v), about 0.7% (w/v), about 1% (w/v), about 1.5% (w/v), about 2% (w/v), or about 2.5% (w/v). Sodium chloride, when present, may be about 150 mM. In certain compositions, the sodium chloride may be present in higher concentrations, for example from about 200 mM to about 500 mM. In embodiments, the sodium chloride is present in a high concentration, including but not limited to about 200 mM, about 250 mM, about 300 mM, about 350 mM, about 400 mM, about 450 mM, or about 500 mM.

In embodiments, the nanoparticles described herein have improved stability at certain pH levels. In embodiments, the nanoparticles are stable at slightly acidic pH levels. For example, the nanoparticles that are stable at a slightly acidic pH, for example from pH 5.8 to pH 7.0. In embodiments, the nanoparticles and compositions containing nanoparticles may be stable at pHs ranging from about pH 5.8 to about pH 7.0, including about pH 5.9 to about pH 6.8, about pH 6.0 to about pH 6.5, about pH 6.1 to about pH 6.4, about pH 6.1 to about pH 6.3, or about pH 6.2. In embodiments, the nanoparticles and compositions described herein are stabile at neutral pHs, including from about pH 7.0 to about pH 7.4. In embodiments, the nanoparticles and compositions described herein are stable at slightly alkaline pHs, for example from about pH 7.0 to about pH 8.5, from about pH 7.0 to about pH 8.0, or from about pH 7.0 to about pH 7.5, including all values and ranges in between.

Adjuvants

In certain embodiments, the compositions disclosed herein may be combined with one or more adjuvants to enhance an immune response. In other embodiments, the compositions are prepared without adjuvants, and are thus available to be administered as adjuvant-free compositions. Advantageously, adjuvant-free compositions disclosed herein may provide protective immune responses when administered as a single dose. Alum-free compositions that induce robust immune responses are especially useful in adults about 60 and older.

Aluminum-Based Adjuvants

In embodiments, the adjuvant may be alum (e.g. $AlPO_4$ or $Al(OH)_3$). Typically, the nanoparticle is substantially bound to the alum. For example, the nanoparticle may be at least 80% bound, at least 85% bound, at least 90% bound or at least 95% bound to the alum. Often, the nanoparticle is 92% to 97% bound to the alum in a composition. The amount of alum is present per dose is typically in a range between about 400 µg to about 1250 µg. For example, the alum may be present in a per dose amount of about 300 µg to about 900 µg, about 400 µg to about 800 about 500 µg to about 700 µg, about 400 µg to about 600 µg, or about 400 µg to about 500 µg. Typically, the alum is present at about 400 µg for a dose of 120 µg of the protein nanoparticle.

Saponin Adjuvants

Adjuvants containing saponin may also be combined with the immunogens disclosed herein. Saponins are glycosides derived from the bark of the *Quillaja saponaria* Molina tree. Typically, saponin is prepared using a multi-step purification process resulting in multiple fractions. As used, herein, the term "a saponin fraction from *Quillaja saponaria* Molina" is used generically to describe a semi-purified or defined saponin fraction of *Quillaja saponaria* or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semi-preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (Nor-Feed, AS Denmark), *Quillaja saponaria* Molina Spikoside (lsconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

ISCOM Structures

Saponin fractions may be administered in the form of a cage-like particle referred to as an ISCOM (Immune Stimulating COMplex). ISCOMs may be prepared as described in EP0109942B1, EP0242380B1 and EP0180546 B1. In particular embodiments a transport and/or a passenger antigen may be used, as described in EP 9600647-3 (PCT/SE97/00289).

Matrix Adjuvants

In embodiments, the ISCOM is an ISCOM matrix complex. An ISCOM matrix complex comprises at least one saponin fraction and a lipid. The lipid is at least a sterol, such as cholesterol. In particular aspects, the ISCOM matrix complex also contains a phospholipid. The ISCOM matrix complexes may also contain one or more other immunomodulatory (adjuvant-active) substances, not necessarily a glycoside, and may be produced as described in EP0436620B1, which is incorporated by reference in its entirety herein.

In other aspects, the ISCOM is an ISCOM complex. An ISCOM complex contains at least one saponin, at least one lipid, and at least one kind of antigen or epitope. The ISCOM complex contains antigen associated by detergent treatment such that that a portion of the antigen integrates into the particle. In contrast, ISCOM matrix is formulated as an admixture with antigen and the association between ISCOM matrix particles and antigen is mediated by electrostatic and/or hydrophobic interactions.

According to one embodiment, the saponin fraction integrated into an ISCOM matrix complex or an ISCOM complex, or at least one additional adjuvant, which also is integrated into the ISCOM or ISCOM matrix complex or mixed therewith, is selected from fraction A, fraction B, or fraction C of *Quillaja saponaria*, a semipurified preparation of *Quillaja saponaria*, a purified preparation of *Quillaja saponaria*, or any purified sub-fraction e.g., QA 1-21.

In particular aspects, each ISCOM particle may contain at least two saponin fractions. Any combinations of weight % of different saponin fractions may be used. Any combination of weight % of any two fractions may be used. For example, the particle may contain any weight % of fraction A and any weight % of another saponin fraction, such as a crude saponin fraction or fraction C, respectively. Accordingly, in particular aspects, each ISCOM matrix particle or each ISCOM complex particle may contain from 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60% by weight, or 50% by weight of one saponin fraction, e.g. fraction A and the rest up to 100% in each case of another saponin e.g. any crude fraction or any other faction e.g. fraction C. The weight is calculated as the total weight of the saponin fractions. Examples of ISCOM matrix complex and ISCOM complex adjuvants are disclosed in U.S Published Application No. 2013/0129770, which is incorporated by reference in its entirety herein.

In particular embodiments, the ISCOM matrix or ISCOM complex comprises from 5-99% by weight of one fraction, e.g. fraction A and the rest up to 100% of weight of another fraction e.g. a crude saponin fraction or fraction C. The weight is calculated as the total weight of the saponin fractions.

In another embodiment, the ISCOM matrix or ISCOM complex comprises from 40% to 99% by weight of one fraction, e.g. fraction A and from 1% to 60% by weight of another fraction, e.g. a crude saponin fraction or fraction C. The weight is calculated as the total weight of the saponin fractions.

In yet another embodiment, the ISCOM matrix or ISCOM complex comprises from 70% to 95% by weight of one fraction e.g., fraction A, and from 30% to 5% by weight of another fraction, e.g., a crude saponin fraction, or fraction C. The weight is calculated as the total weight of the saponin fractions. In other embodiments, the saponin fraction from *Quillaja saponaria* Molina is selected from any one of QA 1-21.

In addition to particles containing mixtures of saponin fractions, ISCOM matrix particles and ISCOM complex particles may each be formed using only one saponin fraction. Compositions disclosed herein may contain multiple particles wherein each particle contains only one saponin fraction. That is, certain compositions may contain one or more different types of ISCOM-matrix complexes particles and/or one or more different types of ISCOM complexes particles, where each individual particle contains one saponin fraction from *Quillaja saponaria* Molina, wherein the saponin fraction in one complex is different from the saponin fraction in the other complex particles.

In particular aspects, one type of saponin fraction or a crude saponin fraction may be integrated into one ISCOM matrix complex or particle and another type of substantially pure saponin fraction, or a crude saponin fraction, may be integrated into another ISCOM matrix complex or particle. A composition or vaccine may comprise at least two types of complexes or particles each type having one type of saponins integrated into physically different particles.

In the compositions, mixtures of ISCOM matrix complex particles and/or ISCOM complex particles may be used in which one saponin fraction *Quillaja saponaria* Molina and another saponin fraction *Quillaja saponaria* Molina are separately incorporated into different ISCOM matrix complex particles and/or ISCOM complex particles.

The ISCOM matrix or ISCOM complex particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix or complex containing a first saponin fraction with the remaining portion made up by an ISCOM matrix or complex containing a different saponin fraction. In some aspects, the remaining portion is one or more ISCOM matrix or complexes where each matrix or complex particle contains only one saponin fraction. In other aspects, the ISCOM matrix or complex particles may contain more than one saponin fraction.

In particular compositions, the only saponin fraction in a first ISCOM matrix or ISCOM complex particle is Fraction A and the only saponin fraction in a second ISCOM matrix or ISCOM complex particle is Fraction C.

Preferred compositions comprise a first ISCOM matrix containing Fraction A and a second ISCOM matrix containing Fraction C, wherein the Fraction A ISCOM matrix constitutes about 70% per weight of the total saponin adjuvant, and the Fraction C ISCOM matrix constitutes about 30% per weight of the total saponin adjuvant. In another preferred composition, the Fraction A ISCOM matrix constitutes about 85% per weight of the total saponin adjuvant, and the Fraction C ISCOM matrix constitutes about 15% per weight of the total saponin adjuvant. Thus, in certain compositions, the Fraction A ISCOM matrix is present in a range of about 70% to about 85%, and Fraction C ISCOM matrix is present in a range of about 15% to about 30%, of the total weight amount of saponin adjuvant in the composition. In embodiments, the Fraction A ISCOM matrix accounts for 50-96% by weight and Fraction C ISCOM matrix accounts for the remainder, respectively, of the sums of the weights of Fraction A ISCOM matrix and Fraction C ISCOM in the adjuvant. In a particularly preferred composition, referred to herein as MATRIX-M™, the Fraction A ISCOM matrix is present at about 85% and Fraction C ISCOM matrix is present at about 15% of the total weight amount of saponin adjuvant in the composition. MATRIX-M™ may be referred to interchangeably as Matrix-M1.

Exemplary QS-7 and QS-21 fractions, their production and their use is described in U.S. Pat. Nos. 5,057,540; 6,231,859; 6,352,697; 6,524,584; 6,846,489; 7,776,343, and 8,173,141, which are incorporated by reference herein.

In some, compositions other adjuvants may be used in addition or as an alternative. The inclusion of any adjuvant described in Vogel et al., "A Compendium of Vaccine Adjuvants and Excipients (2nd Edition)," herein incorporated by reference in its entirety for all purposes, is envisioned within the scope of this disclosure. Other adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/TWEEN® polysorbate 80 emulsion. In embodiments, the adjuvant may be a paucilamellar lipid vesicle; for example, NOVASOMES®. NOVASOMES® are paucilamellar non-phospholipid vesicles ranging from about 100 nm to about 500 nm. They comprise BRIJ® alcohol ethoxylate 72, cholesterol, oleic acid and squalene. NOVASOMES® have been shown to be an effective adjuvant (see, U.S. Pat. Nos. 5,629,021, 6,387,373, and 4,911,928.

Administration and Dosage

In embodiments, the disclosure provides a method for eliciting an immune response against one or more coronaviruses. In embodiments, the response is against one or more of the SARS-CoV-2 virus, MERS, and SARS. The method involves administering an immunologically effective amount of a composition containing a nanoparticle or containing a recombinant CoV Spike (S) polypeptide to a subject. Advantageously, the proteins disclosed herein induce one or more of particularly useful anti-coronavirus responses.

In embodiments, the nanoparticles or CoV S polypeptides are administered with an adjuvant. In other aspects, the nanoparticles or CoV S polypeptides are administered without an adjuvant. In some aspects, the adjuvant may be bound to the nanoparticle, such as by a non-covalent interaction. In other aspects, the adjuvant is co-administered with the nanoparticle but the adjuvant and nanoparticle do not interact substantially.

In embodiments, the nanoparticles may be used for the prevention and/or treatment of one or more of a SARS-CoV-2 infection, a SARS infection, or a MERS infection. Thus, the disclosure provides a method for eliciting an immune response against one or more of the SARS-CoV-2 virus, MERS, and SARS. The method involves administering an immunologically effective amount of a composition containing a nanoparticle or a CoV S polypeptide to a subject. Advantageously, the proteins disclosed herein induce particularly useful anti-coronavirus responses.

Compositions disclosed herein may be administered via a systemic route or a mucosal route or a transdermal route or directly into a specific tissue. As used herein, the term "systemic administration" includes parenteral routes of administration. In particular, parenteral administration includes subcutaneous, intraperitoneal, intravenous, intraarterial, intramuscular, or intrasternal injection, intravenous, or kidney dialytic infusion techniques. Typically, the systemic, parenteral administration is intramuscular injection. As used herein, the term "mucosal administration" includes oral, intranasal, intravaginal, intra-rectal, intra-tracheal, intestinal and ophthalmic administration. Preferably, administration is intramuscular.

Compositions may be administered on a single dose schedule or a multiple dose schedule. Multiple doses may be used in a primary immunization schedule or in a booster immunization schedule. In a multiple dose schedule the various doses may be given by the same or different routes a parenteral prime and mucosal boost, a mucosal prime and parenteral boost, etc. In some aspects, a follow-on boost dose is administered about 2 weeks, about 3 weeks, about 4 weeks, about 5 weeks, or about 6 weeks after the prior dose. In embodiments, the follow-on boost dose is administered 3 weeks after administration of the prior dose. In embodiments, the first dose is administered at day 0, and the boost dose is administered at day 21. In embodiments, the first dose is administered at day 0, and the boost dose is administered at day 28.

In embodiments, the dose, as measured in µg, may be the total weight of the dose including the solute, or the weight of the CoV S polypeptide nanoparticles, or the weight of the CoV S polypeptide. Dose is measured using protein concentration assay either A280 or ELISA.

The dose of antigen, including for pediatric administration, may be in the range of about 5 µg to about 25 µg, about 1 µg to about 300 µg, about 90 µg to about 270 µg, about 100 µg to about 160 µg, about 110 µg to about 150 µg, about 120 µg to about 140 µg, or about 140 µg to about 160 µg. In embodiments, the dose is about 120 µg, administered with alum. In some aspects, a pediatric dose may be in the range of about 1 µg to about 90 µg. In embodiments, the dose of CoV Spike (S) polypeptide is about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21, about 22, about 23, about 24, about 25 µg, about 26 µg, about 27 µg, about 28 µg, about 29 µg, about 30 µg, about 40 µg, about 50, about 60, about 70, about 80, about 90 about 100 µg, about 110 µg, about 120 µg about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, or about 300 µg, including all values and ranges in between. In embodiments, the dose of CoV S polypeptide is 5 µg. In embodiments, the dose of CoV S polypeptide is 25 µg.

Certain populations may be administered with or without adjuvants. In certain aspects, compositions may be free of added adjuvant. In such circumstances, the dose may be increased by about 10%.

In embodiments, the dose of the adjuvant administered with a non-naturally occurring CoV S polypeptide is from about 1 µg to about 100 µg, for example, about 1 µg, about 2 µg, about 3 µg, about 4 µg, about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21, about 22, about 23, about 24, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 61 µg, about 62 µg, about 63 µg, about 64 µg, about 65 µg, about 66 µg, about 67 µg, about 68 µg, about 69 µg, about 70 µg, about 71 µg, about 72 µg, about 73 µg, about 74 µg, about 75 µg, about 76 µg, about 77 µg, about 78 µg, about 79 µg, about 80 µg, about 81 µg, about 82 µg, about 83 µg, about 84 µg, about 85 µg, about 86 µg, about 87 µg, about 88 µg, about 89 µg, about 90 µg, about 91 µg, about 92 µg, about 93 µg, about 94 µg, about 95 µg, about 96 µg, about 97 µg, about 98 µg, about 99 µg, or about 100 µg of adjuvant. In embodiments, the dose of adjuvant is about 50 µg. In embodiments, the adjuvant is a saponin adjuvant, e.g., MATRIX-M™.

In embodiments, the dose is administered in a volume of about 0.1 mL to about 1.5 mL, for example, about 0.1 mL, about 0.2 mL, about 0.25 mL, about 0.3 mL, about 0.4 mL, about 0.5 mL, about 0.6 mL, about 0.7 mL, about 0.8 mL, about 0.9 mL, about 1.0 mL, about 1.1 mL, about 1.2 mL, about 1.3 mL, about 1.4 mL, or about 1.5 mL. In embodiments, the dose is administered in a volume of 0.25 mL. In embodiments, the dose is administered in a volume of 0.5 mL. In embodiments, the dose is administered in a volume of 0.6 mL.

In particular embodiments for a vaccine against MERS, SARS, or the SARS-CoV-2 coronavirus, the dose may comprise a CoV S polypeptide concentration of about 1 µg/mL to about 50 µg/mL, 10 µg/mL to about 100 µg/mL, about 10 µg/mL to about 50 µg/mL, about 175 µg/mL to about 325 µg/mL, about 200 µg/mL to about 300 µg/mL, about 220 µg/mL to about 280 µg/mL, or about 240 µg/mL to about 260 µg/mL.

In another embodiment, the disclosure provides a method of formulating a vaccine composition that induces immunity to an infection or at least one disease symptom thereof to a mammal, comprising adding to the composition an effective dose of a nanoparticle or a CoV S polypeptide. The disclosed CoV S polypeptides and nanoparticles are useful for preparing compositions that stimulate an immune response that confers immunity or substantial immunity to infectious agents. Thus, in one embodiment, the disclosure provides a method of inducing immunity to infections or at least one disease symptom thereof in a subject, comprising administering at least one effective dose of a nanoparticle and/or a CoV S polypeptide.

In embodiments, the CoV S polypeptides or nanoparticles comprising the same are administered in combination with an additional immunogenic composition. In embodiments, the additional immunogenic composition induces an immune response against SARS-CoV-2. In embodiments, the additional immunogenic composition is administered within about 1 minute, about 5 minutes, about 10 minutes, about 20 minutes, about 30 minutes, about 40 minutes, about 50 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, or about 31 days of the disclosed CoV S polypeptides or nanoparticles comprising the same. In embodiments, the additional composition is administered with a first dose of a composition comprising a CoV S polypeptide or nanoparticle comprising the same. In embodiments, the additional composition is administered with a boost dose of a composition comprising a CoV S polypeptide or nanoparticle comprising the same.

In embodiments, the additional immunogenic composition comprises an mRNA encoding a SARS-Cov-2 Spike glycoprotein, a plasmid DNA encoding a SARS-Cov-2 Spike glycoprotein, an viral vector encoding a SARS-Cov-2 Spike glycoprotein, or an inactivated SARS-CoV-2 virus.

In embodiments, the additional immunogenic composition comprises mRNA that encodes for a CoV S polypeptide. In embodiments, the mRNA encodes for a CoV S polypeptide comprising proline substitutions at positions 986 and 987 of SEQ ID NO: 1. In embodiments, the mRNA encodes for a CoV S polypeptide comprising an intact furin cleavage site. In embodiments, the mRNA encodes for a CoV S polypeptide comprising proline substitutions at positions 986 and 987 of SEQ ID NO: 1 and an intact furin cleavage site. In embodiments, the mRNA encodes for a CoV S polypeptide comprising proline substitutions at positions 986 and 987 of SEQ ID NO: 1 and an inactive furin cleavage site. In embodiments, the mRNA encodes for a CoV S polypeptide having an amino acid sequence of SEQ ID NO: 87. In embodiments, the mRNA encoding for a CoV S polypeptide is encapsulated in a lipid nanoparticle. An exemplary immunogenic composition comprising mRNA that encodes for a CoV S polypeptide is described in Jackson et al. N. Eng. J. Med. 2020. An mRNA Vaccine against SARS-CoV-2-preliminary report, which is incorporated by reference in its entirety herein. In embodiments, the composition comprising mRNA that encodes for a CoV S polypeptide is administered at a dose of 25 μg, 100 μg, or 250 μg.

In embodiments, the additional immunogenic composition comprises an adenovirus vector encoding for a CoV S polypeptide. In embodiments, the AAV vector encodes for a wild-type CoV S polypeptide. In embodiments, the AAV vector encodes for a CoV S polypeptide comprising proline substitutions at positions 986 and 987 of SEQ ID NO: 1 and an intact furin cleavage site. In embodiments, the AAV vector encodes for a CoV S polypeptide comprising proline substitutions at positions 986 and 987 of SEQ ID NO: 1 and an inactive furin cleavage site. In embodiments, the AAV vector encodes for a CoV S polypeptide having an amino acid sequence of SEQ ID NO: 87. The following publications describe immunogenic compositions comprising an adenovirus vector encoding for a CoV S polypeptide, each of which is incorporated by reference in its entirety herein: van Doremalen N. et al. A single dose of ChAdOx1 MERS provides protective immunity in rhesus macaques. Science Advances, 2020; van Doremalen N. et al. ChAdOx1 nCoV-19 vaccination prevents SARS-CoV-2 pneumonia in rhesus macaques. bioRxiv, (2020).

In embodiments, the additional immunogenic composition comprises deoxyribonucleic acid (DNA). In embodiments, the additional immunogenic composition comprises plasmid DNA. In embodiments, the plasmid DNA encodes for a CoV S polypeptide. In embodiments, the DNA encodes for a CoV S polypeptide comprising proline substitutions at positions 986 and 987 of SEQ ID NO: 1 and an intact furin cleavage site. In embodiments, the DNA encodes for a CoV S polypeptide comprising proline substitutions at positions 986 and 987 of SEQ ID NO: 1 and an inactive furin cleavage site. In embodiments, the DNA encodes for a CoV S polypeptide having an amino acid sequence of SEQ ID NO: 87.

In embodiments, the additional immunogenic composition comprises an inactivated virus vaccine.

In embodiments, the CoV S proteins or nanoparticles comprising CoV S proteins are useful for preparing immunogenic compositions to stimulate an immune response that confers immunity or substantial immunity to one or more of MERS, SARS, and SARS-CoV-2. Both mucosal and cellular immunity may contribute to immunity to infection and disease. Antibodies secreted locally in the upper respiratory tract are a major factor in resistance to natural infection. Secretory immunoglobulin A (sIgA) is involved in protection of the upper respiratory tract and serum IgG in protection of the lower respiratory tract. The immune response induced by an infection protects against reinfection with the same virus or an antigenically similar viral strain. The antibodies produced in a host after immunization with the nanoparticles disclosed herein can also be administered to others, thereby providing passive administration in the subject.

In embodiments, the CoV S proteins or nanoparticles comprising CoV S proteins induce cross-neutralizing antibodies against SARS-CoV-2 viruses containing S proteins with one or more modifications selected from:

(a) deletion of one or more amino acids of the NTD, wherein the one or more amino acids are selected from the group consisting of amino acid 56, 57, 131, 132, 229, 230, 231, or combinations thereof; and (b) mutation of one or more amino acids of the NTD, wherein the one or more mutations are selected from the group consisting of amino acid 67, 229, 202, 139, 5, 233, 7, 13, 125, 177, or combinations thereof;

(c) mutation of one or more amino acids of the RBD wherein the one or more mutations is selected from the group consisting of amino acid 488, 404, 471, 439, 426, 440, and combinations thereof;

(d) mutation to one or more amino acids of the SD1/2, wherein the one or more amino acids is selected from the group consisting of 601, 557, 668, 642, and combinations thereof;

(e) an inactive furin cleavage site (corresponding to one or more mutations in amino acids 669-672);

(f) deletion of one or more amino acids of the S2 subunit, wherein the amino acids are selected from the group consisting of 676-702, 702-711, 775-793, 806-815; and combinations thereof (g) mutation of one or more amino acids of the S2 subunit, wherein the amino acids are selected from the group consisting of 973, 974, 703, 1105, 688, 969, and 1014; and combinations thereof (h) deletion of one or more amino acids from the TMCT (amino acids 1201-1260), wherein the amino acids of the CoV S glycoprotein are numbered with respect to SEQ ID NO: 2.

In embodiments, the CoV S proteins or nanoparticles comprising CoV S proteins induce cross-neutralizing antibodies against SARS-CoV-2 viruses containing S proteins with one or more modifications selected from: deletions of amino acid 56, deletion of amino acid 57, deletion of amino acid 131, N488Y, A557D, D601G, P668H, 17031, 5969A, D1105H, N426K, and Y440F, wherein the amino acids are numbered with respect to a CoV S polypeptide having an amino acid sequence of SEQ ID NO: 2.

In embodiments, the present disclosure provides a method of producing one or more of high affinity anti-MERS-CoV, anti-SARS-CoV, and anti-SARS-CoV-2 virus antibodies. The high affinity antibodies produced by immunization with the nanoparticles disclosed herein are produced by administering an immunogenic composition comprising an S CoV polypeptide or a nanoparticle comprising an S CoV polypeptide to an animal, collecting the serum and/or plasma from the animal, and purifying the antibody from the serum/ and or plasma. In one embodiment, the animal is a human. In embodiments, the animal is a chicken, mouse, guinea pig, rat, rabbit, goat, human, horse, sheep, or cow. In one embodiment, the animal is bovine or equine. In another embodiment, the bovine or equine animal is transgenic. In yet a further embodiment, the transgenic bovine or equine animal produces human antibodies. In embodiments, the animal produces monoclonal antibodies. In embodiments, the animal produces polyclonal antibodies. In one embodiment, the method further comprises administration of an adjuvant or immune stimulating compound. In a further embodiment, the purified high affinity antibody is administered to a human subject. In one embodiment, the human subject is at risk for infection with one or more of MERS, SARS, and SARS-CoV-2.

In embodiments, the CoV S proteins or nanoparticles are co-administered with an influenza glycoprotein or nanoparticle comprising an influenza glycoprotein. Suitable glycoproteins and nanoparticles are described in US Publication No. 2018/0133308 and US Publication No. 2019/0314487, each of which is incorporated by reference herein in its entirety. In embodiments, the CoV S protein or nanoparticle is coadministered with: (a) a detergent-core nanoparticle, wherein the detergent-core nanoparticle comprises a recombinant influenza hemagglutinin (HA) glycoprotein from a Type B influenza strain; and (b) a Hemagglutinin Saponin Matrix Nanoparticle (HaSMaN), wherein the HaSMaN comprises a recombinant influenza HA glycoprotein from a Type A influenza strain and ISCOM matrix adjuvant. In embodiments, the CoV S protein or nanoparticle is coadministered with a nanoparticle comprising a non-ionic detergent core and an influenza HA glycoprotein, wherein the influenza HA glycoprotein contains a head region that projects outward from the non-ionic detergent core and a transmembrane domain that is associated with the non-ionic detergent core, wherein the influenza HA glycoprotein is a HA0 glycoprotein, wherein the amino acid sequence of the influenza HA glycoprotein has 100% identity to the amino acid sequence of the native influenza HA protein. In embodiments, the influenza glycoprotein or nanoparticle is coformulated with the CoV S protein or nanoparticle.

All patents, patent applications, references, and journal articles cited in this disclosure are expressly incorporated herein by reference in their entireties for all purposes.

EXAMPLES

Example 1

Expression and Purification of Coronavirus Spike (5) Polypeptide Nanoparticles

Figure 4:
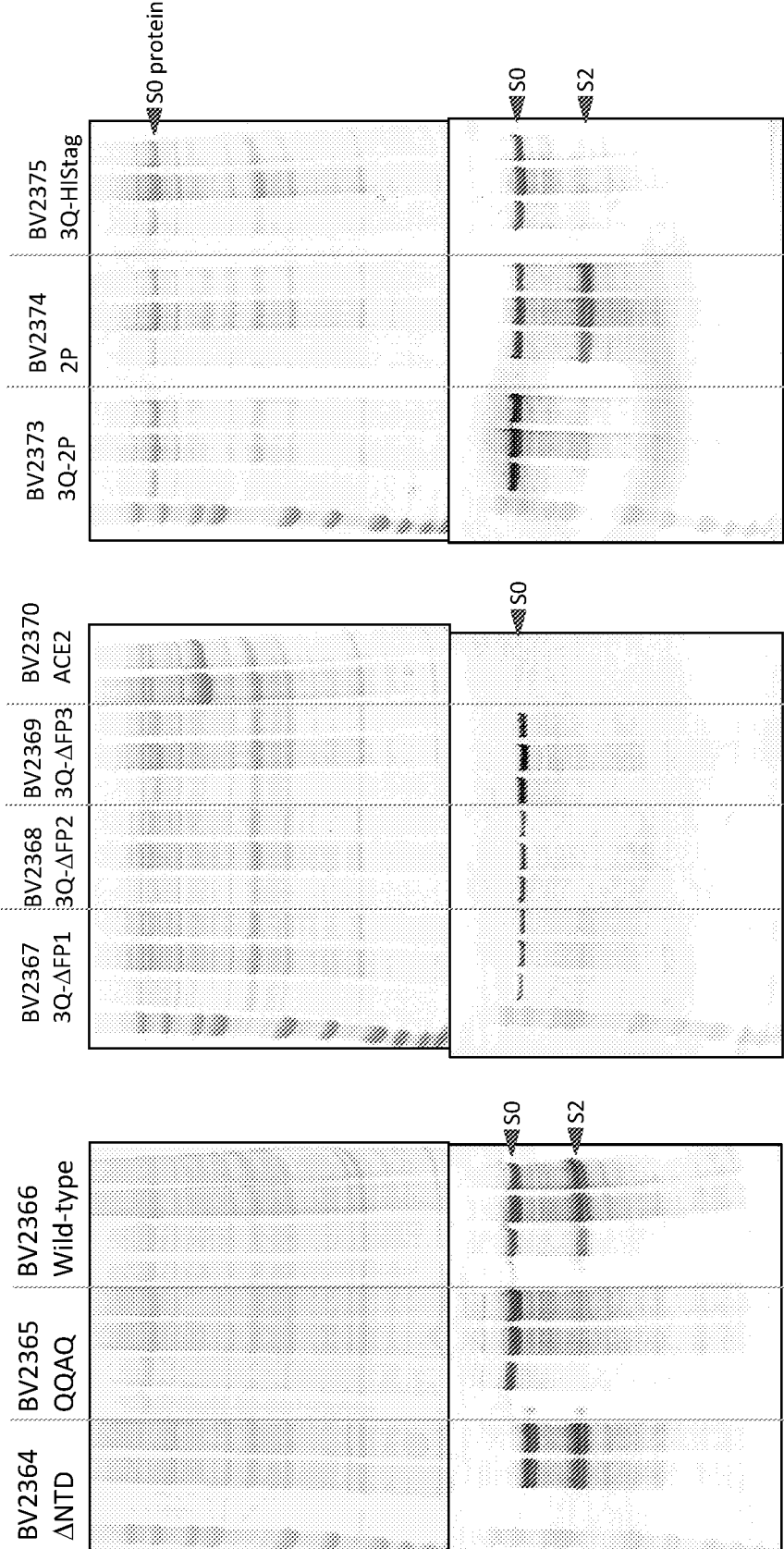
FIG. 4 shows purification of the CoV S polypeptides BV2364, BV2365, BV2366, BV2367, BV2368, BV2369, BV2373, BV2374, and BV2375. The data reveal that BV2365 (SEQ ID NO: 4) and BV2373 (SEQ ID NO: 87) which has an inactive furin cleavage site having an amino acid sequence of QQAQ (SEQ ID NO: 7) is expressed as a single chain (S0). In contrast, CoV S polypeptides containing an intact furin cleavage site (e.g. BV2364, BV2366, and BV2374) are cleaved, as evident by the presence of the cleavage product S2.
Figure 5:
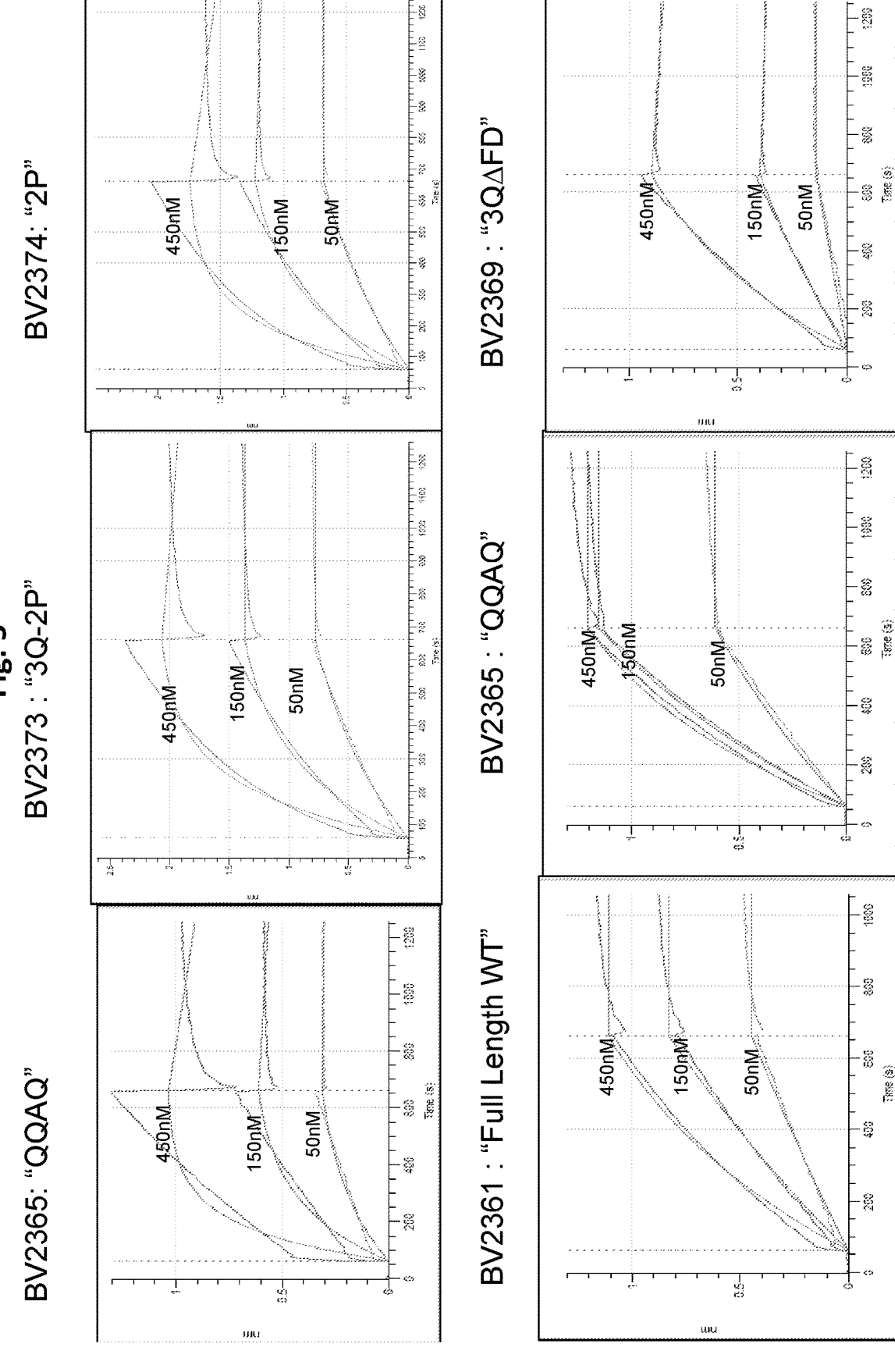
FIG. 5 shows that the CoV S polypeptides BV2361, BV2365, BV2369, BV2365, BV2373, and BV2374 bind to human angiotensin-converting enzyme 2 precursor (hACE2) by bio-layer interferometry.
Figure 6:
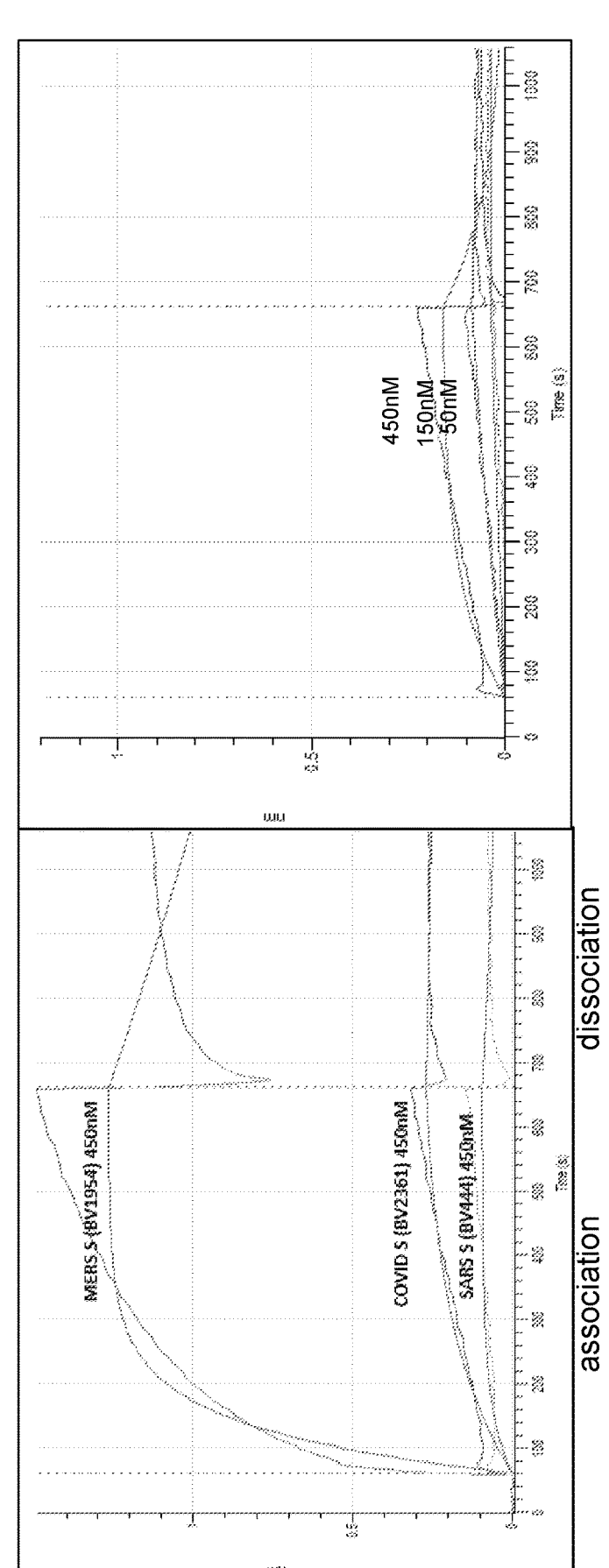
FIG. 6 shows that BV2361 from SARS-CoV-2 does not bind the MERS-CoV receptor, dipeptidyl peptidase IV (DPP4) and the MERS S protein does not bind to human angiotensin-converting enzyme 2 precursor (hACE2) by bio-layer interferometry.
Figure 7:
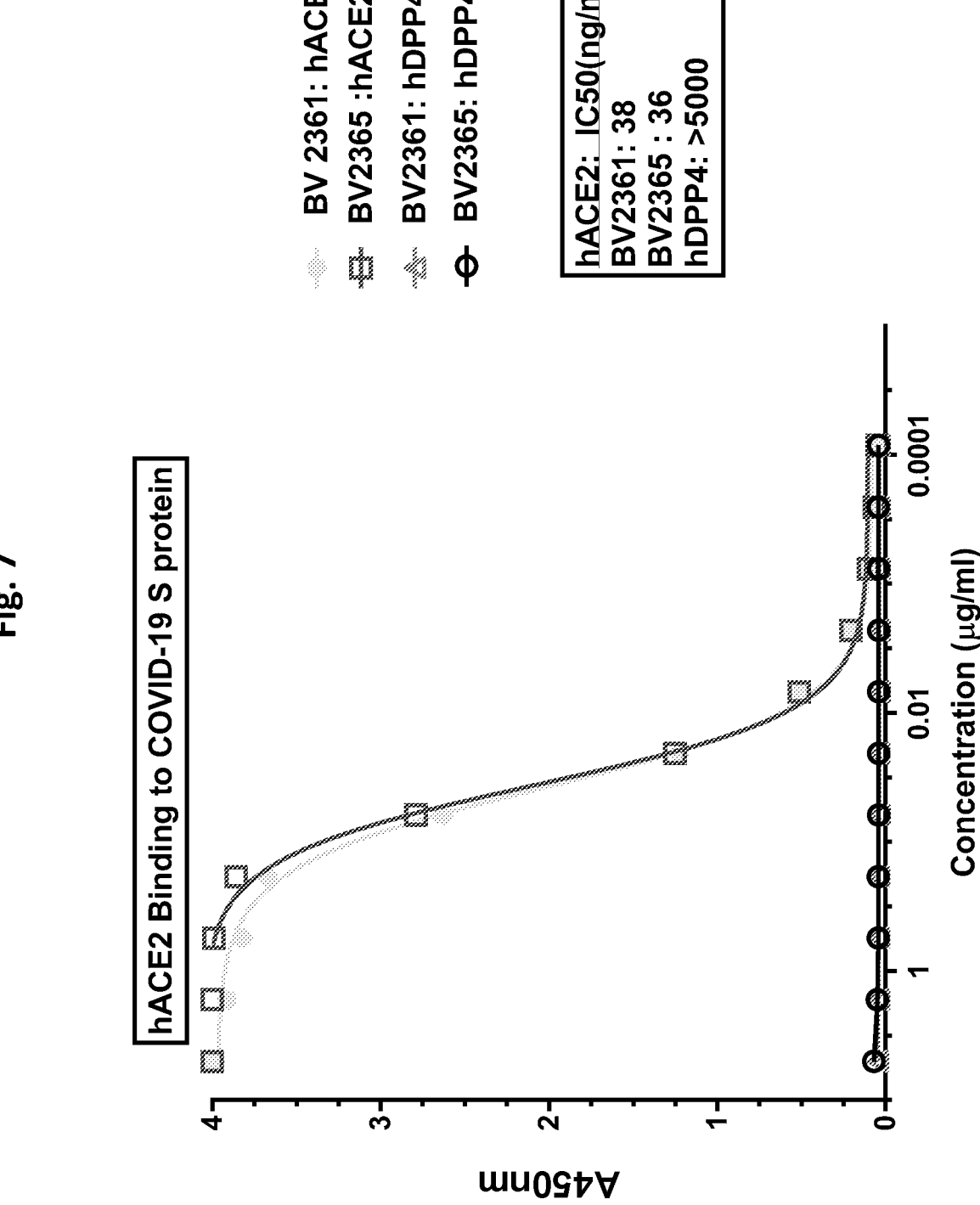
FIG. 7 shows that BV2361 binds to hACE2 by enzyme-linked immunosorbent assay (ELISA).
Figure 9:
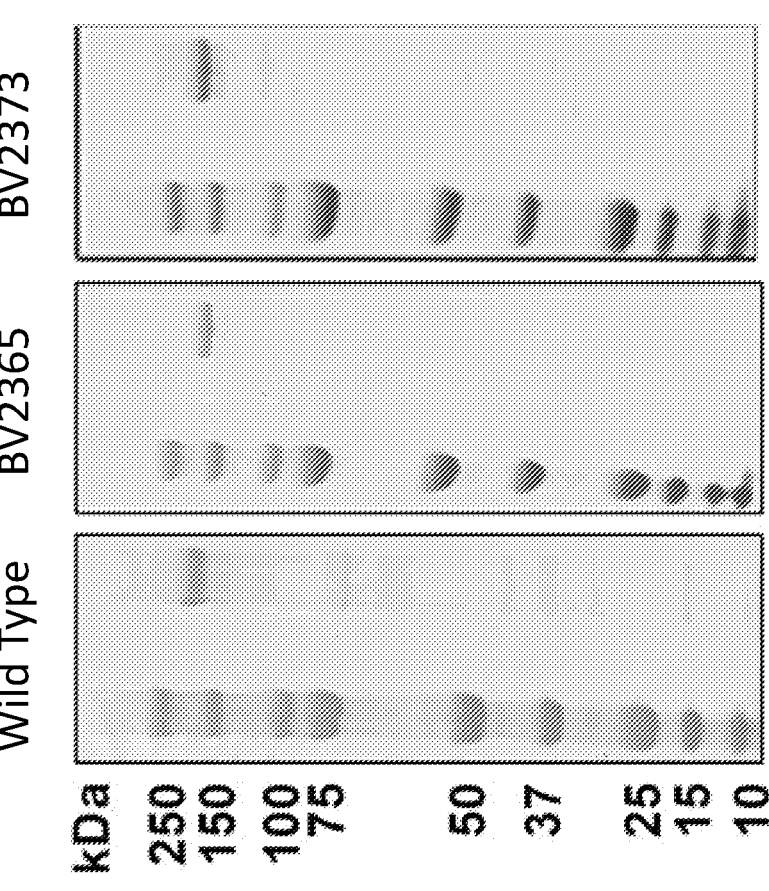
FIG. 9 shows purification of the wild type CoV S polypeptide and the CoV S polypeptides BV2365 and BV2373.

The native coronavirus Spike (S) polypeptide (SEQ ID NO: 1 and SEQ ID NO:2) and CoV Spike polypeptides which have amino acid sequences corresponding to SEQ ID NOS: 3, 4, 38, 41, 44, 48, 51, 54, 58, 61, 63, 65, 67, 73, 75, 78, 79, 82, 83, 85, 87, 106, 108, and 89 have been expressed in a baculovirus expression system and recombinant plaques expressing the coronavirus Spike (5) polypeptides were picked and confirmed. In each case the signal peptide is SEQ ID NO: 5. FIG. 4 and FIG. 9 show successful purification of the CoV Spike polypeptides BV2364, BV2365, BV2366, BV2367, BV2368, BV2369, BV2373, BV2374, and BV2375. Table 2 shows the sequence characteristics of the aforementioned CoV Spike polypeptides.

TABLE 2

| Selected CoV Spike Polypeptides | | |
| --- | --- | --- |
| CoV S polypeptide | Modification | SEQ ID NO. |
| BV2364 | Deleted N-Terminal Domain | 48 |
| BV2365 | Inactive furin cleavage site | 4 |
| BV2361/BV2366 | Wild-type | 2 |
| BV2367 | Deletion of amino acids 676-685, inactive furin cleavage site | 63 |
| BV2368 | Deletion of amino acids 702-711, inactive furin cleavage site | 65 |
| BV2369 | Deletion of amino acids 806-815, inactive furin cleavage site | 67 |
| BV2373, formulated into a composition referred to herein as "NVX-CoV2373" | Inactive furin cleavage site, K973P mutation, V974P mutation | 87 |
| BV2374 | K973P mutation, V974P mutation | 85 |
| BV2374 | Inactive furin cleavage site and His-tag | 58 |
| BV2384 | Inactive furin cleavage site (GSAS), K973P, V974P mutation | 110 |

The wild-type BV2361 protein (SEQ ID NO: 2) binds to human angiotensin-converting enzyme 2 precursor (hACE2). Bio-layer interferometry and ELISA were performed to assess binding of the CoV S polypeptides.

Bio-Layer Interferometry (BLI):

The BLI experiments were performed using an Octet QK384 system (Pall Forte Bio, Fremont, CA). His-tagged human ACE2 (2 µg mL-1) was immobilized on nickel-charged Ni-NTA biosensor tips. After baseline, SARS-CoV-2 S protein containing samples were 2-fold serially diluted and were allowed to associate for 600 seconds followed by dissociation for an additional 900 sec. Data was analyzed with Octet software HT 101:1 global curve fit.

The CoV S polypeptides BV2361, BV2365, BV2369, BV2365, BV2373, BV2374 retain the ability to bind to hACE2 (FIG. 5, FIGS. 11A-C). Dissociation kinetics showed that the S-proteins remained tightly bound as evident by minimal or no dissociation over 900 seconds of observation in the absence of fluid phase S protein (FIGS. 11A-C).

Furthermore, binding is specific. The wild-type CoV S protein, BV2361 and the CoV S polypeptides BV2365 and BV2373 do not bind the MERS-CoV receptor, dipeptidyl peptidase IV (DPP4). Additionally, the MERS S protein does not bind to human angiotensin-converting enzyme 2 precursor (hACE2) (FIG. 6 and FIGS. 11D-F).

ELISA

The specificity of the CoV S polypeptides for hACE2 was confirmed by ELISA. Ninety-six well plates were coated with 100 µL SARS-CoV-2 spike protein (2 µg/mL) overnight at 4° C. Plates were washed with phosphate buffered saline with 0.05% Tween (PBS-T) buffer and blocked with TBS Startblock blocking buffer (ThermoFisher, Scientific). His-tagged hACE2 and hDPP4 receptors were 3-fold serially diluted (5-0.0001 µg mL-1) and added to coated wells for 2 hours at room temperature. The plates were washed with PBS-T. Optimally diluted horseradish peroxidase (HRP) conjugated anti-histidine was added and color developed by addition of and 3,3',5,5'-tetramethylbenzidine peroxidase substrate (TMB, T0440-IL, Sigma, St. Louis, MO, USA). Plates were read at an OD of 450 nm with a SpectraMax Plus plate reader (Molecular Devices, Sunnyvale, CA, USA) and data analyzed with SoftMax software. EC50 values were calculated by 4-parameter fitting using GraphPad Prism 7.05 software.

The ELISA results showed that the wild-type CoV S polypeptide (B V2361), BV2365, and BV2373 proteins specifically bound hACE2 but failed to bind the hDPP-4 receptor used by MERS-CoV ($IC_{50}$>5000 ng mL-1). The wild-type CoV S polypeptide and BV2365 bound to hACE2 with similar affinity ($IC_{50}$=36-38 ng/mL), while BV2373 attained 50% saturation of hACE2 binding at 2-fold lower concentration ($IC_{50}$=18 ng/mL) (FIG. 7, FIGS. 11D-F).

Protein and Nanoparticle Production

The recombinant virus is amplified by infection of Sf9 insect cells. A culture of insect cells is infected at ~3 MOI (Multiplicity of infection=virus ffu or pfu/cell) with baculovirus. The culture and supernatant is harvested 48-72 hrs post-infection. The crude cell harvest, approximately 30 mL, is clarified by centrifugation for 15 minutes at approximately 800×g. The resulting crude cell harvests containing the coronavirus Spike (5) protein are purified as nanoparticles as described below.

To produce nanoparticles, non-ionic surfactant TERGITOL® nonylphenol ethoxylate NP-9 is used in the membrane protein extraction protocol. Crude extraction is further purified by passing through anion exchange chromatography, lentil lectin affinity/HIC and cation exchange chromatography. The washed cells are lysed by detergent treatment and then subjected to low pH treatment which leads to precipitation of BV and Sf9 host cell DNA and protein. The neutralized low pH treatment lysate is clarified and further purified on anion exchange and affinity chromatography before a second low pH treatment is performed.

Affinity chromatography is used to remove Sf9/BV proteins, DNA and NP-9, as well as to concentrate the coronavirus Spike (S) protein. Briefly, lentil lectin is a metalloprotein containing calcium and manganese, which reversibly binds polysaccharides and glycosylated proteins containing glucose or mannose. The coronavirus Spike (S) protein-containing anion exchange flow through fraction is loaded onto the lentil lectin affinity chromatography resin (Capto Lentil Lectin, GE Healthcare). The glycosylated coronavirus Spike (S) protein is selectively bound to the resin while non-glycosylated proteins and DNA are removed in the column flow through. Weakly bound glycoproteins are removed by buffers containing high salt and low molar concentration of methyl alpha-D-mannopyranoside (MMP).

The column washes are also used to detergent exchange the NP-9 detergent with the surfactant polysorbate 80 (PS80). The coronavirus Spike (S) polypeptides are eluted in nanoparticle structure from the lentil lectin column with a high concentration of MMP. After elution, the coronavirus Spike (S) protein trimers are assembled into nanoparticles composed of coronavirus Spike (5) protein trimers and PS80 contained in a detergent core.

Example 2

Immunogenicity of Coronavirus Spike (S) Polypeptide Nanoparticle Vaccines in Mice The coronavirus Spike (5) protein composition comprising a CoV S polypeptide of SEQ ID NO: 87 (also called "BV2373") as described in Example 1 was evaluated for immunogenicity and toxicity in a murine model, using female BALB/c mice (7-9 weeks old; Harlan Laboratories Inc., Frederick, MD). The compositions were evaluated in the presence and in the absence of a saponin adjuvant, e.g., MATRIX-M™. Compositions containing MATRIX-M™ contained 5 µg of MATRIX-M™. Vaccines containing coronavirus Spike (S) polypeptide at various doses, including 0.01 µg, 0.1 µg, 1 µg, and 10 µg, were administered intramuscularly as a single dose (also referred to as a single priming dose) (study day 14) or as two doses (also referred to as a prime/boost regimen) spaced 14-days apart (study day 0 and 14). A placebo group served as a non-immunized control. Serum was collected for analysis on study days −1, 13, 21, and 28. Vaccinated and control animals were intranasally challenged with SARS-CoV-2 42 days following one (a single dose) or two (two doses) immunizations.

Vaccine Immunogenicity

Figure 13A:
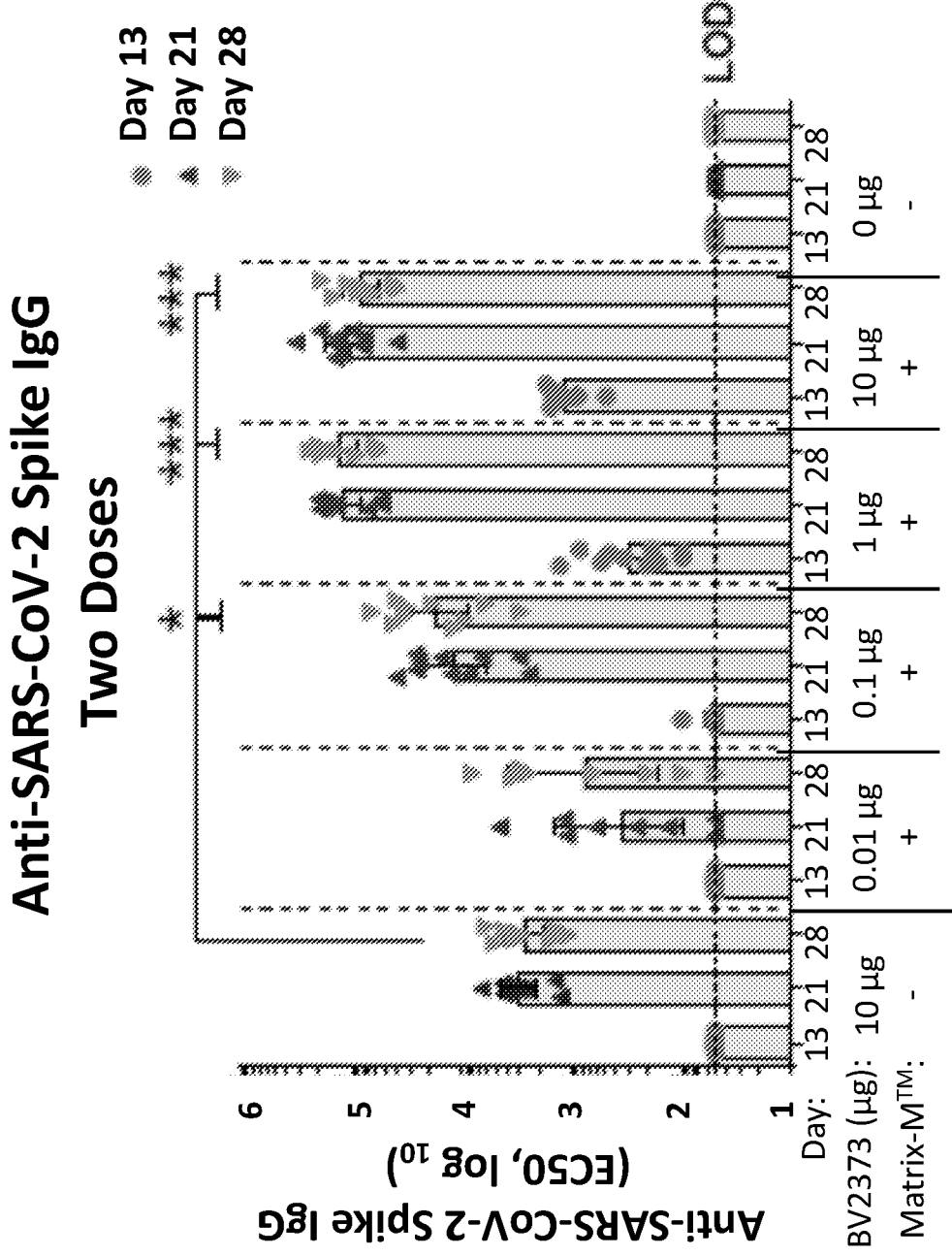
FIGS. 13A-B show anti-CoV S polypeptide IgG titers 13 days, 21 days, and 28 days after immunization of mice with two doses (FIG. 13A) and one dose of 0.1 μg to 10 μg of BV2373 with or without Fraction A and Fraction C iscom matrix (e.g., MATRIX-M™) (FIG. 13B).
Figure 13B:
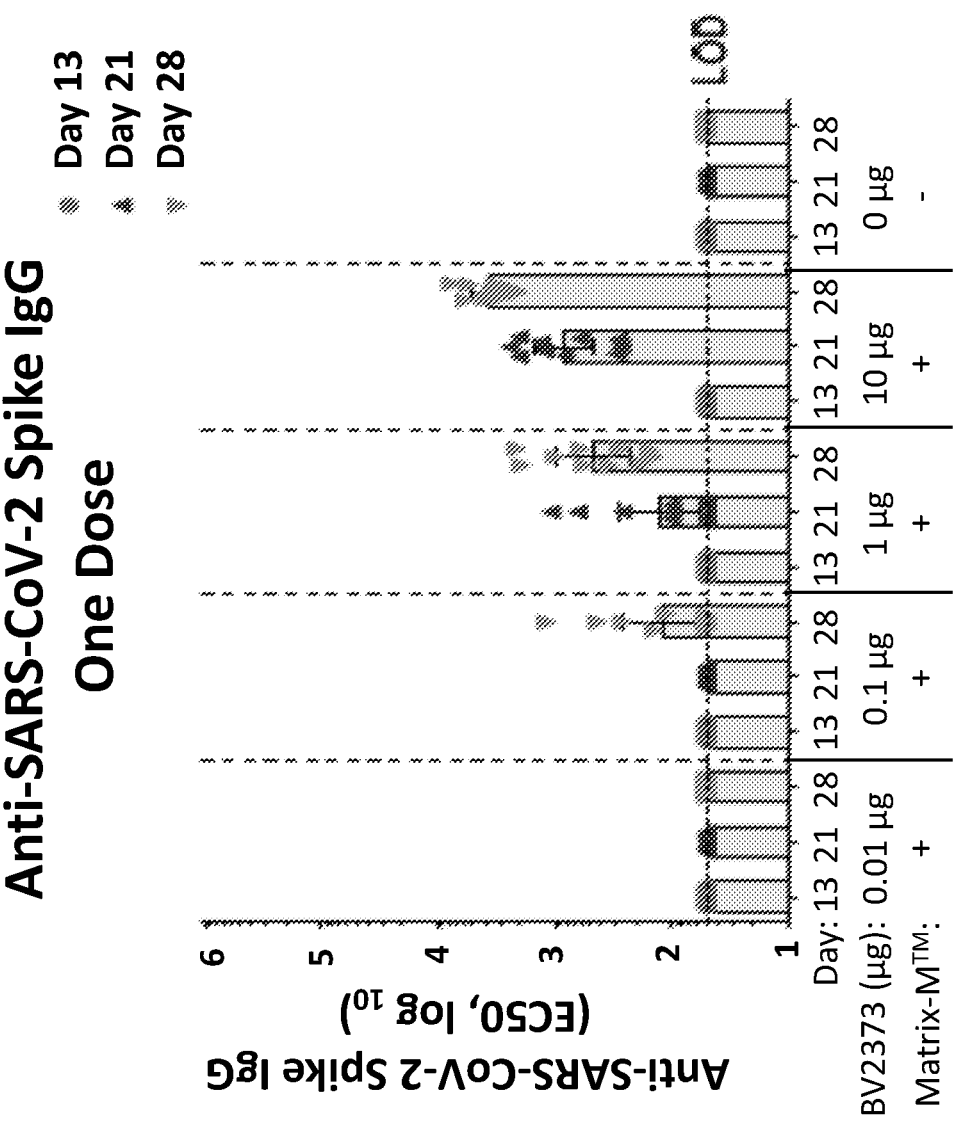
Figure 14:
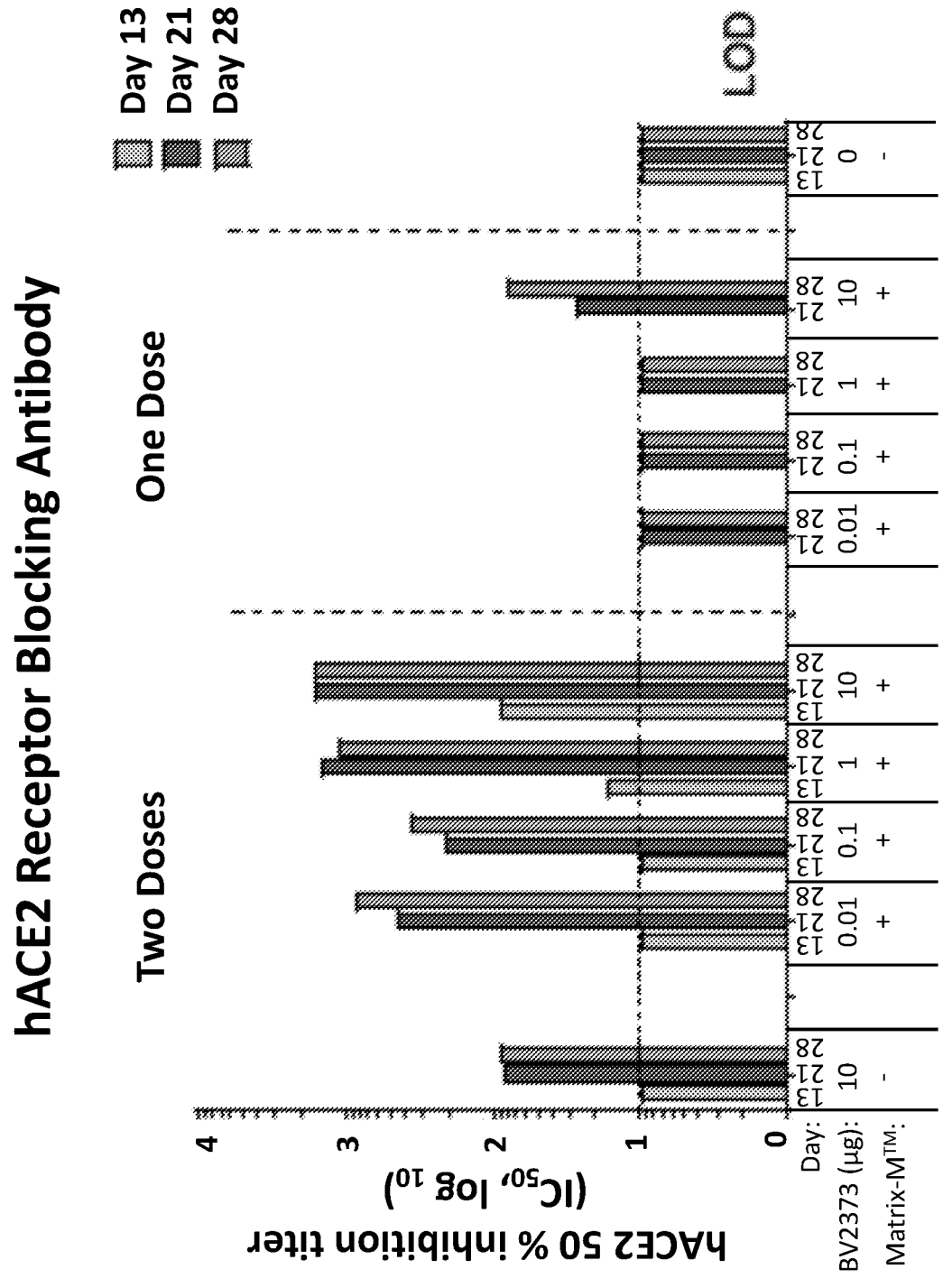
FIG. 14 shows the induction of antibodies that block interaction of hACE2 in mice immunized with one dose or two doses of 0.1 μg to 10 μg of BV2373 with or without MATRIX-M™.
Figure 15:
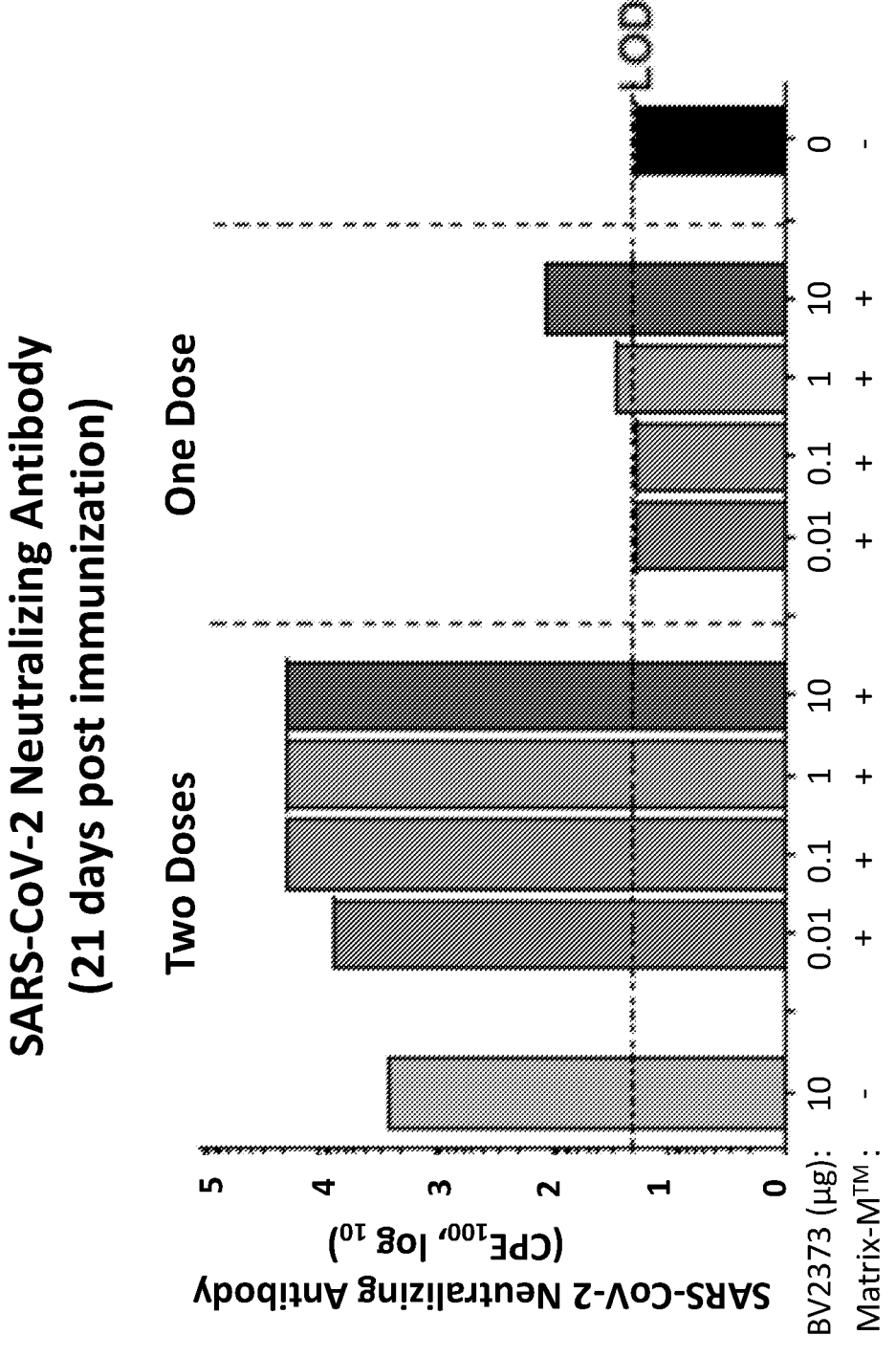
FIG. 15 shows virus neutralizing antibodies detected in mice immunized with one dose or two doses of 0.1 μg to 10 μg of BV2373 with or without MATRIX-M™.

Animals immunized with a single priming dose of 0.1-10 µg BV2373 and MATRIX-M™ had elevated anti-S IgG titers that were detected 21-28 days after a single immunization (FIG. 13B). Mice immunized with a 10 µg dose of BV2373 and MATRIX-M™ produced antibodies that blocked hACE2 receptor binding to the CoV S protein and virus neutralizing antibodies that were detected 21-28 days after a single priming dose (FIG. 14 and FIG. 15) Animals immunized with the prime/boost regimen (two doses) had significantly elevated anti-S IgG titers that were detected 7-16 days following the booster immunization across all dose levels (FIG. 13A). Animals immunized with BV2373 (1 µg and 10 µg) and MATRIX-M™ had similar high anti-S IgG titers following immunization (GMT=139,000 and 84,000, respectively). Mice immunized with BV2373 (0.1 µg, 1 µg, or 10 µg) and MATRIX-M™ had significantly ($p \leq 0.05$ and $p \leq 0.0001$) higher anti-S IgG titers compared to mice immunized with 10 µg BV2373 without adjuvant (FIG. 13A). These results indicate the potential for 10- to 100-fold dose sparing provided by the MATRIX-M™ adjuvant. Furthermore, immunization with two doses of BV2373 and MATRIX-M™ elicited high titer antibodies that blocked hACE2 receptor binding to S-protein (IC50=218-1642) and neutralized the cytopathic effect (CPE) of SARS-CoV-2 on Vero E6 cells (100% blocking of CPE=7680-20,000) across all dose levels (FIG. 14 and FIG. 15).

SARS CoV-2 Challenge

To evaluate the induction of protective immunity, immunized mice were challenged with SARS-CoV-2. Since mice do not support replication of the wild-type SARS-CoV-2 virus, on day 52 post initial vaccination, mice were intranasally infected with an adenovirus expressing hACE2 (Ad/hACE2) to render them permissive. Mice were intranasally inoculated with $1.5 \times 10^5$ pfu of SARS-CoV-2 in 50 µL divided between nares. Challenged mice were weighed on the day of infection and daily for up to 7 days post infection. At 4- and 7-days post infection, 5 mice were sacrificed from each vaccination and control group, and lungs were harvested and prepared for pulmonary histology.

Figure 16:
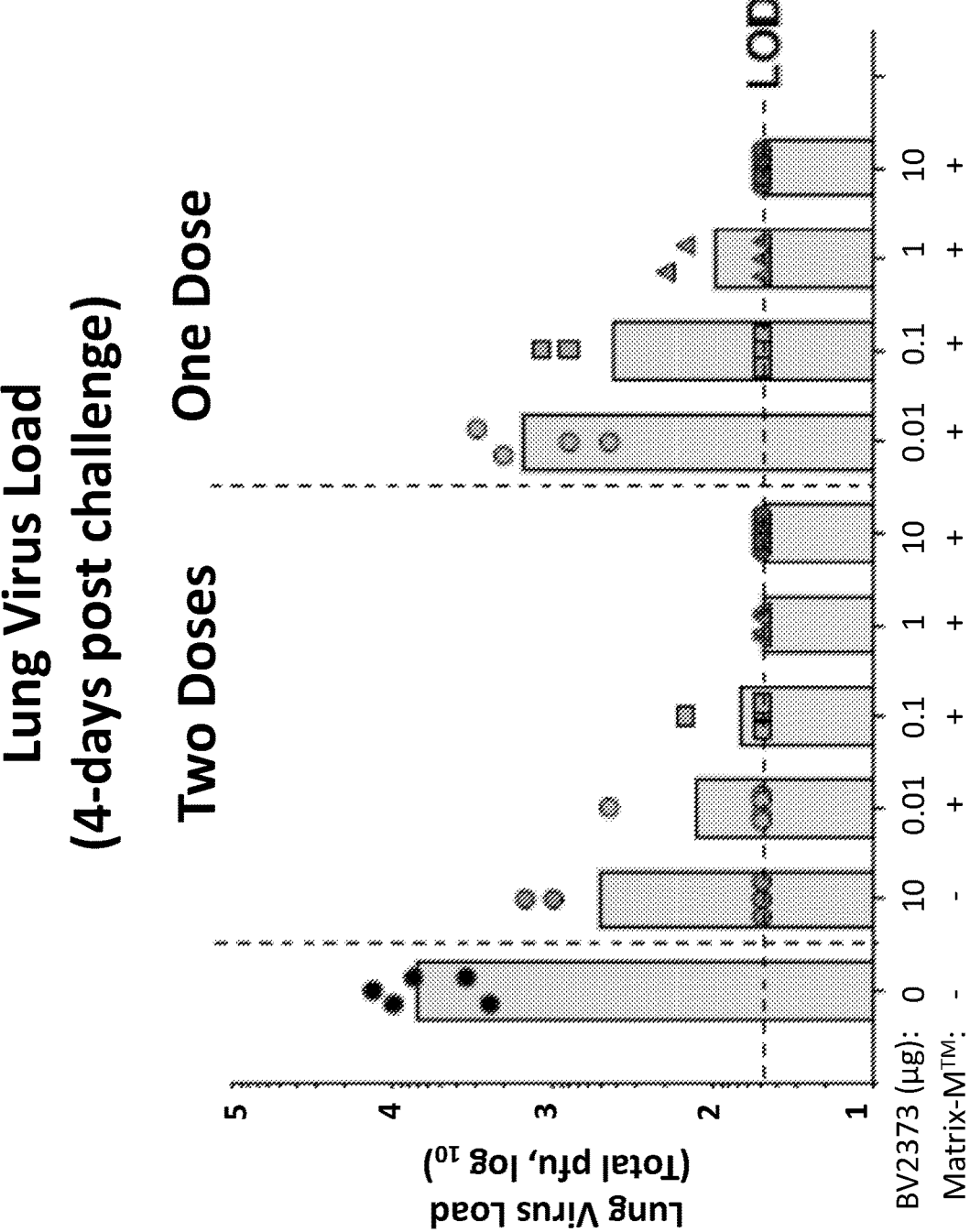
FIG. 16 shows the virus load (SARS-CoV-2) in the lungs of Ad/CMV/hACE2 mice immunized with either a single dose of BV2373 or two doses of BV2373 spaced 14 days apart with or without MATRIX-M™.

The viral titer was quantified by a plaque assay. Briefly, the harvested lungs were homogenized in PBS using 1.0 mm glass beads (Sigma Aldrich) and a Beadruptor (Omini International Inc.). Homogenates were added to Vero E6 near confluent cultures and SARS-CoV-2 virus titers determined by counting plaque forming units (pfu) using a 6-point dilution curve At 4 days post infection, placebo-treated mice had $10^4$ SARS-CoV-2 pfu/lung, while the mice immunized with BV2363 without MATRIX-M™ had $10^3$ pfu/lung (FIG. 16). The BV2373 with MATRIX-M™ prime-only groups of mice exhibited a dose dependent reduction in virus titer, with recipients of the 10 µg BV2373 dose having no detectable virus at day 4 post infection. Mice receiving 1 µg, 0.1 µg and 0.01 µg BV2373 doses all showed a marked reduction in titer compared to placebo-vaccinated mice. In the prime/ boost groups, mice immunized with 10 μg, 1 μg and 0.1 μg doses had almost undetectable lung virus loads, while the 0.01 μg group displayed a reduction of 1 log reduction relative to placebo animals.

Figure 17A:
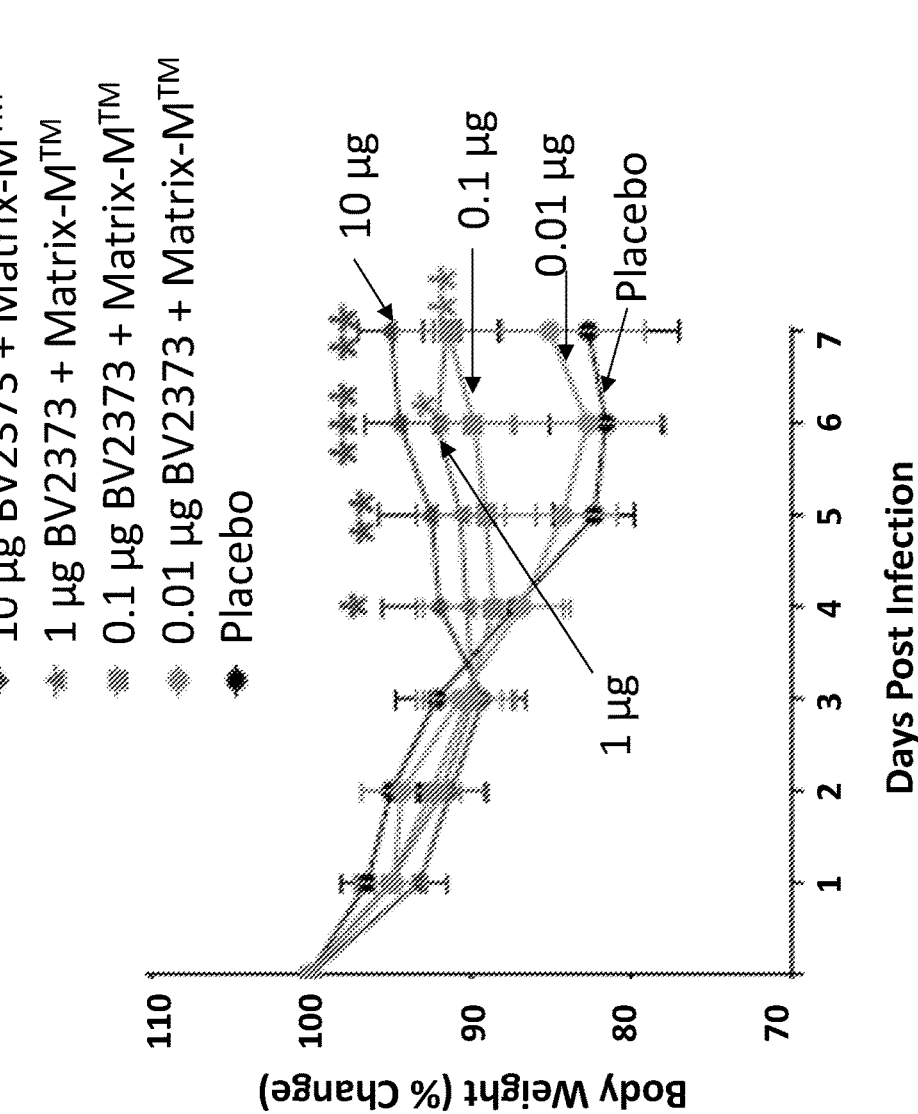
FIGS. 17A-C shows weight loss exhibited by mice after immunization with BV2373.
Figure 17B:
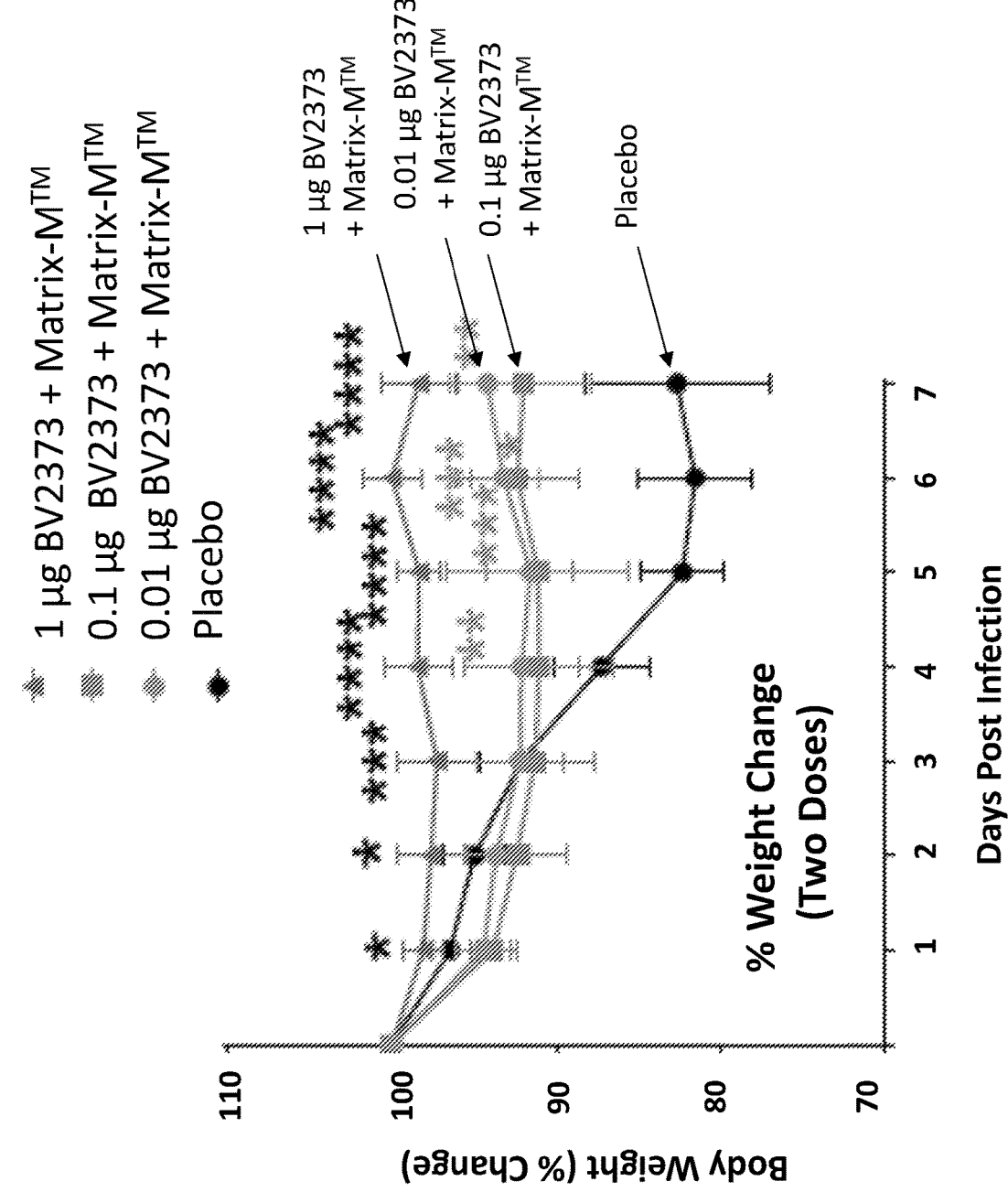
Figure 17C:
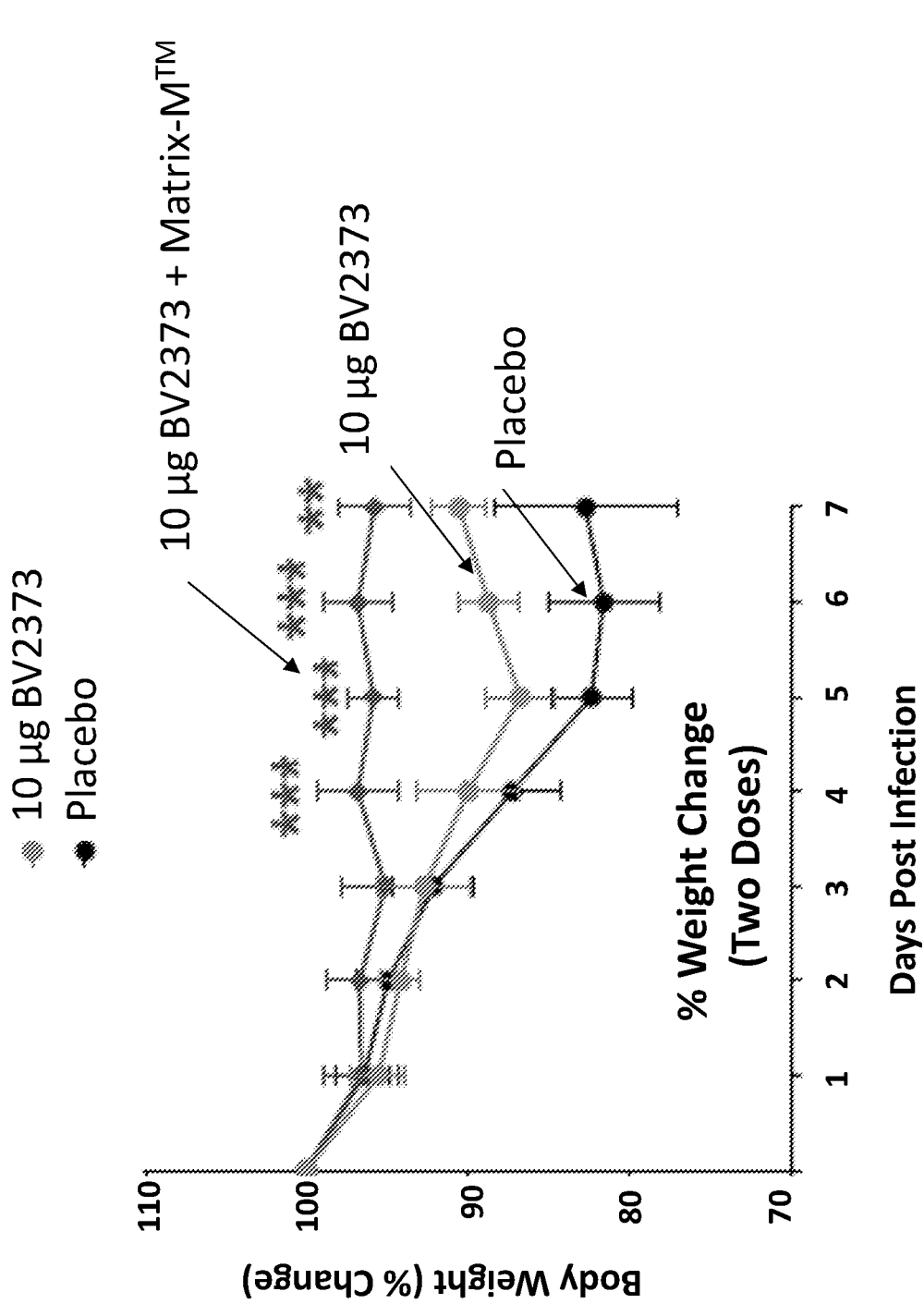

Weight loss paralleled the viral load findings. Animals receiving a single dose of BV2373 (0.1 μg, 1 μg, and 10 μg) and MATRIX-M™ showed marked protection from weight loss compared to the unvaccinated placebo animals (FIG. 17A). The mice receiving a prime and boost dose with adjuvant also demonstrated significant protection against weight loss at all dose levels (FIGS. 17B-C). The effect of the presence of adjuvant on protection against weight loss was evaluated. Mice receiving the prime/boost (two doses) plus adjuvant were significantly protected from weight loss relative to placebo, while the group immunized without adjuvant was not (FIG. 17C). These results showed that BV2373 confers protection against SARS-CoV-2 and that low doses of the vaccine associated with lower serologic responses do not exacerbate weight loss or demonstrate exaggerated illness.

Figure 18A:
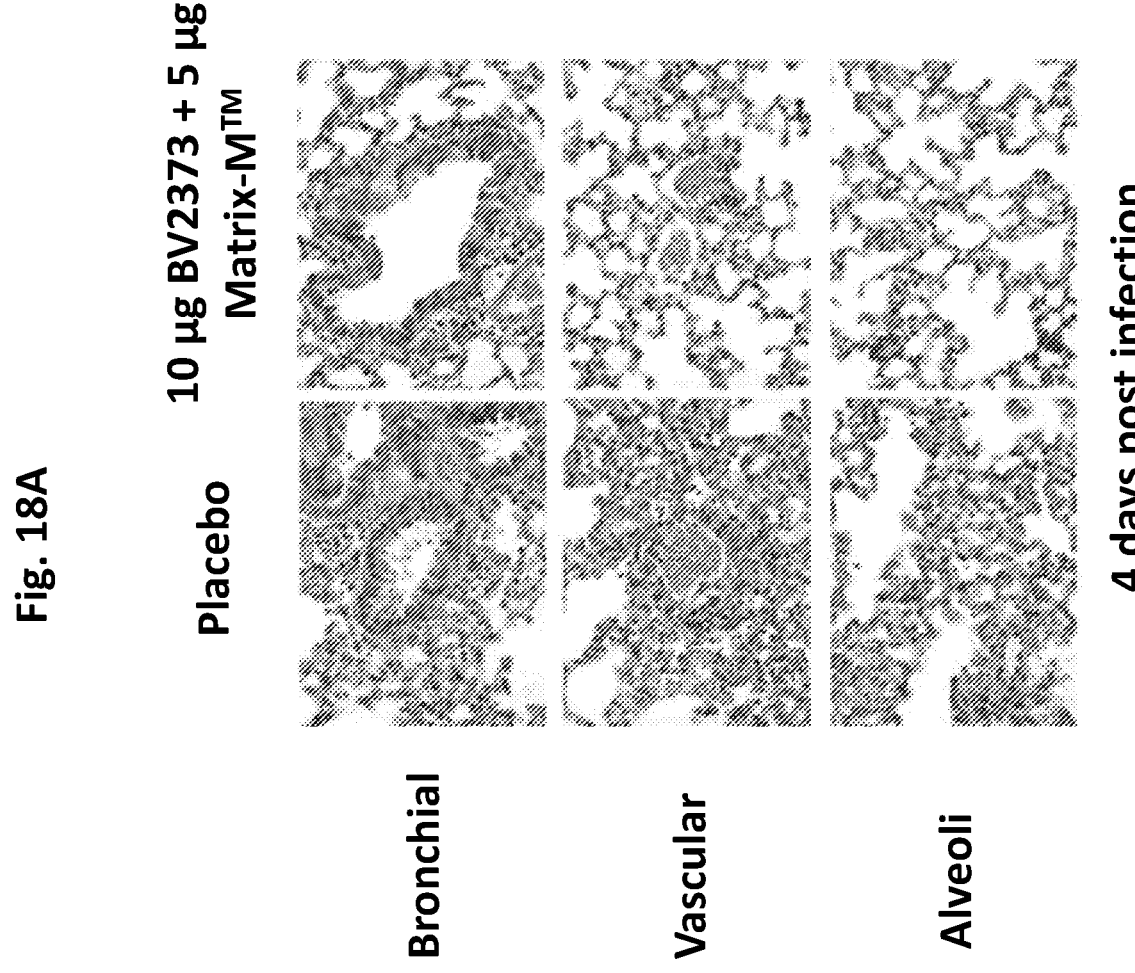
Figure 18B:
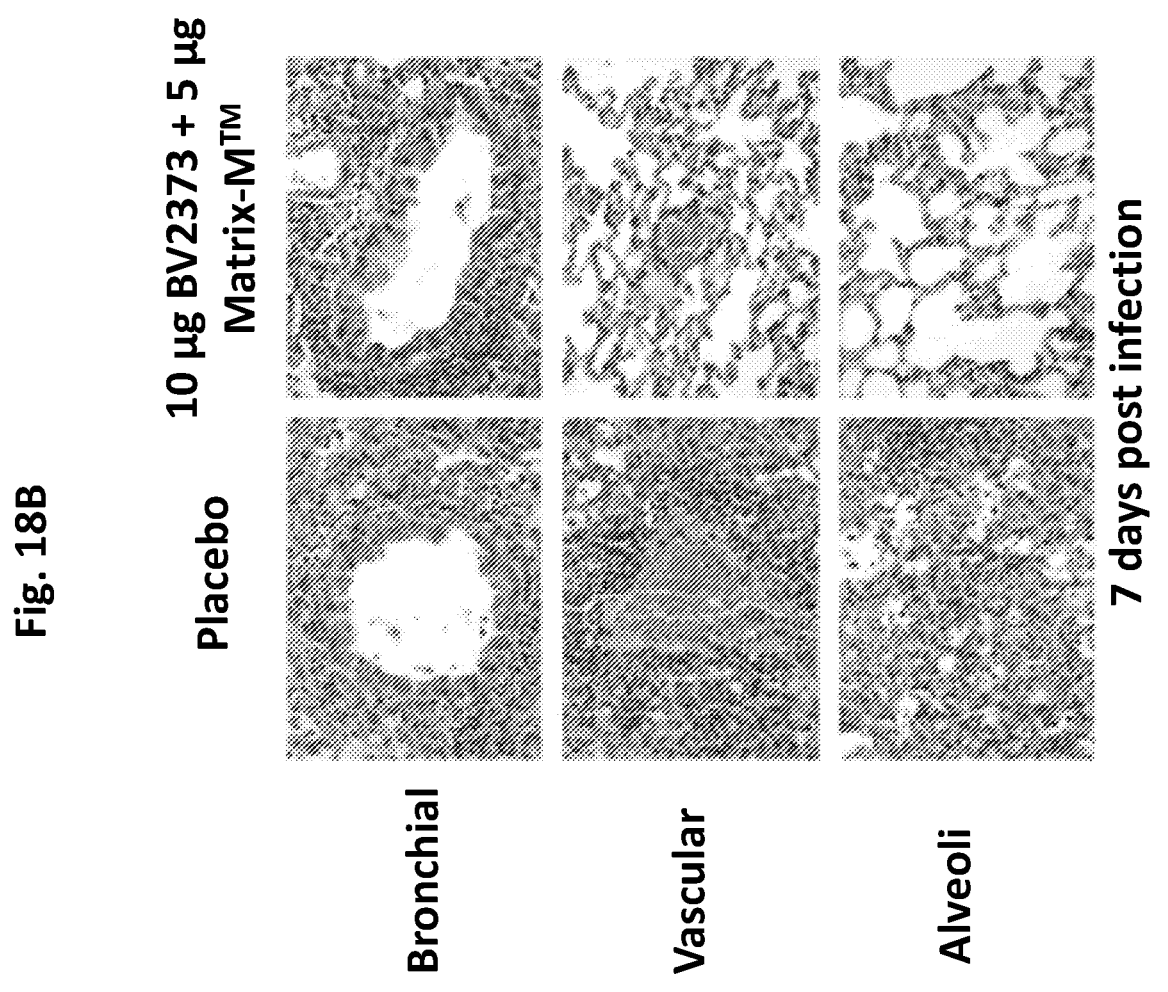

Lung histopathology was evaluated on days 4 and day 7 post infection (FIG. 18A and FIG. 18B). At day 4 post infection, placebo-immunized mice showed denudation of epithelial cells in the large airways with thickening of the alveolar septa surrounded by a mixed inflammatory cell population. Periarteriolar cuffing was observed throughout the lungs with inflammatory cells consisting primarily of neutrophils and macrophages. By day 7 post infection, the placebo-treated mice displayed peribronchiolar inflammation with increased periarteriolar cuffing. The thickened alveolar septa remained with increased diffuse interstitial inflammation throughout the alveolar septa (FIG. 18B).

The BV2373 immunized mice showed significant reduction in lung pathology at both day 4 and day 7 post infection in a dose-dependent manner. The prime only group displays reduced inflammation at the 10 μg and 1 μg dose with a reduction in inflammation surrounding the bronchi and arterioles compared to placebo mice. In the lower doses of the prime-only groups, lung inflammation resembles that of the placebo groups, correlating with weight loss and lung virus titer. The prime/boost immunized groups displayed a significant reduction in lung inflammation for all doses tested, which again correlated with lung viral titer and weight loss data. The epithelial cells in the large and small bronchi at day 4 and 7 were substantially preserved with minimal bronchiolar sloughing and signs of viral infection. The arterioles of animals immunized with 10 μg, 1 μg and 0.1 μg doses have minimal inflammation with only moderate cuffing seen with the 0.01 μg dose, similar to placebo. Alveolar inflammation was reduced in animals that received the higher doses with only the lower 0.01 μg dose associated with inflammation (FIGS. 18A-18B). These data demonstrate that BV2373 reduces lung inflammation after challenge and that even doses and regimens of BV2373 that elicit minimal or no detectable neutralizing activity are not associated with exacerbation of the inflammatory response to the virus. Furthermore, the vaccine does not cause vaccine associated enhanced respiratory disease (VAERD) in challenged mice.

T Cell Response

The effect of the vaccine composition comprising a CoV S polypeptide of SEQ ID NO: 87 on the T cell response was evaluated. BALB/c mice (N=6 per group) were immunized intramuscularly with 10 μg BV2373 with or without 5 μg MATRIX-M™ in 2 doses spaced 21-days apart. Spleens were collected 7-days after the second immunization (study day 28). A non-vaccinated group (N=3) served as a control.

Figure 19:
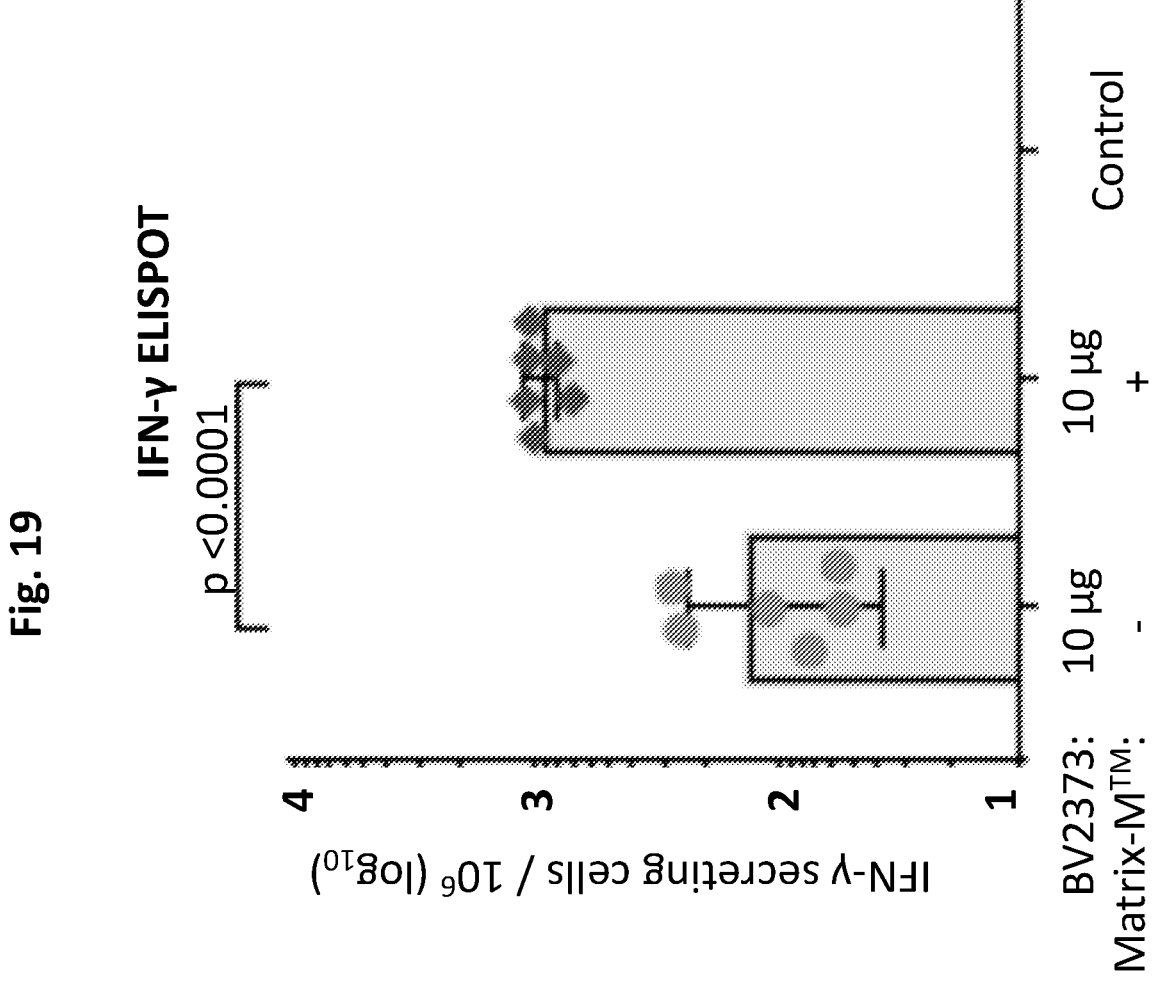
FIG. 19 shows the number of IFN-γ secreting cells after ex vivo stimulation in the spleens of mice immunized with BV2373 in the absence of adjuvant compared to mice immunized with BV2373 in the presence of MATRIX-M™.
Figure 20A:
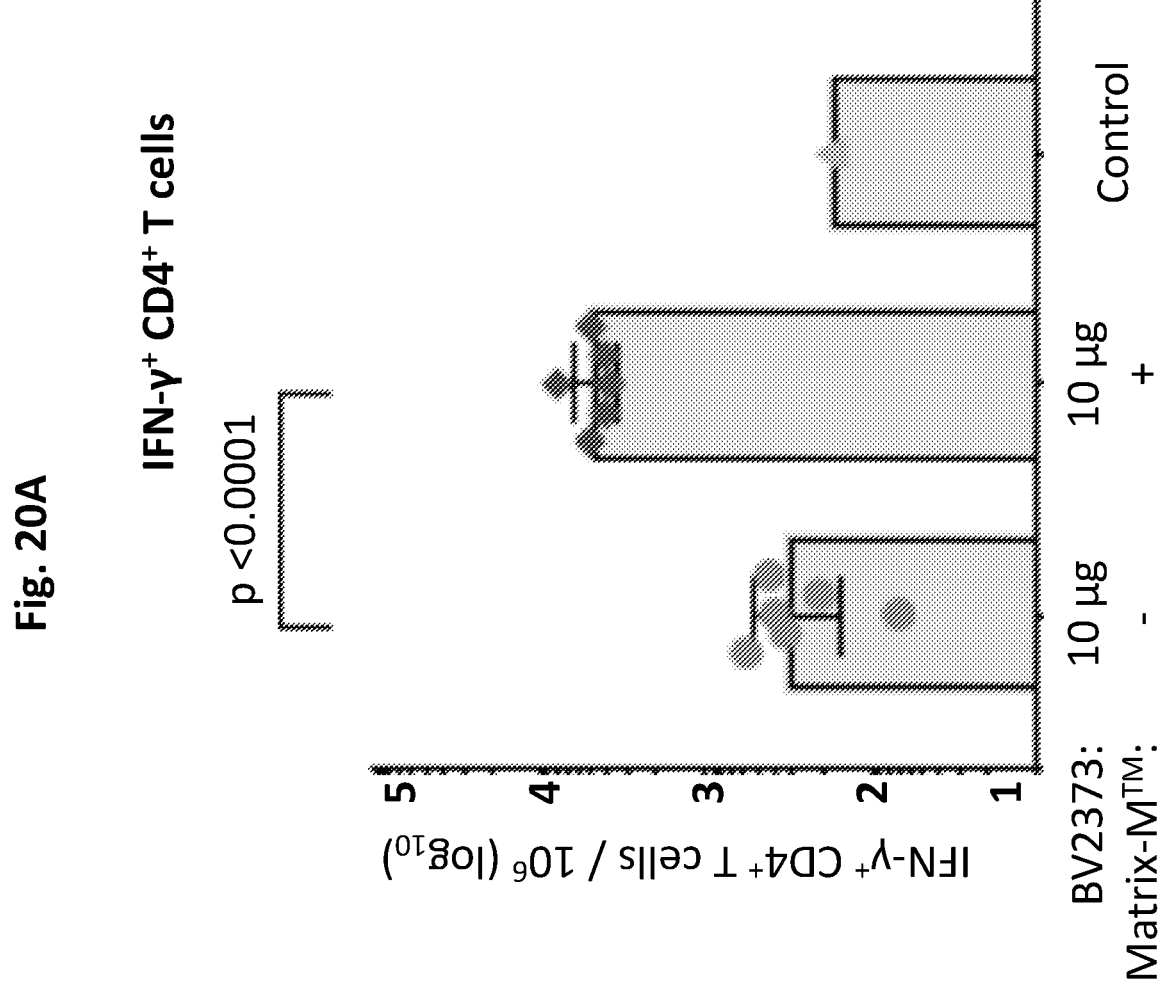
FIGS. 20A-E shows the frequency of cytokine secreting CD4+ T cells in the spleens of mice immunized with BV2373 in the presence or absence of MATRIX-M™.
Figure 20B:
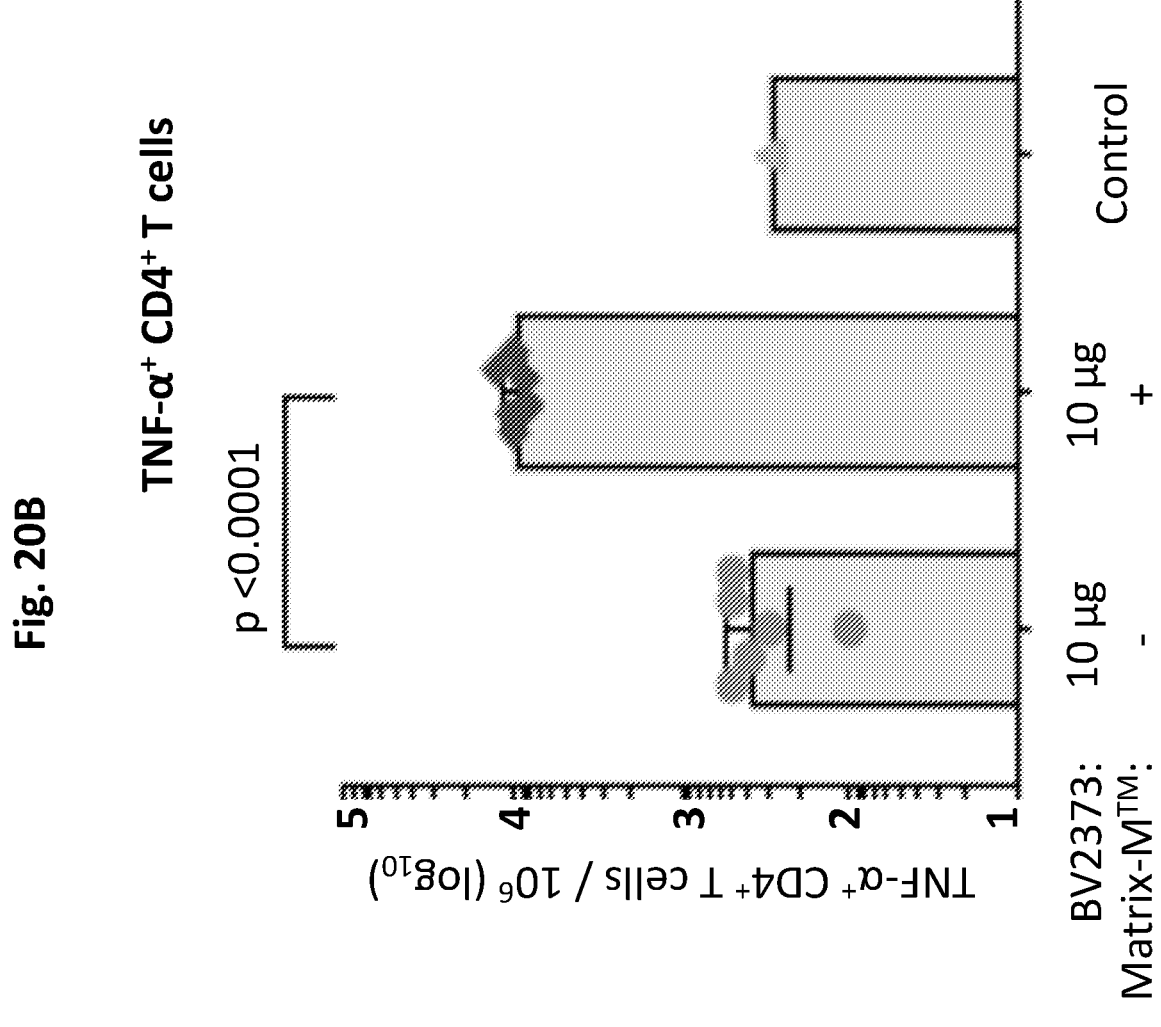
Figure 20C:
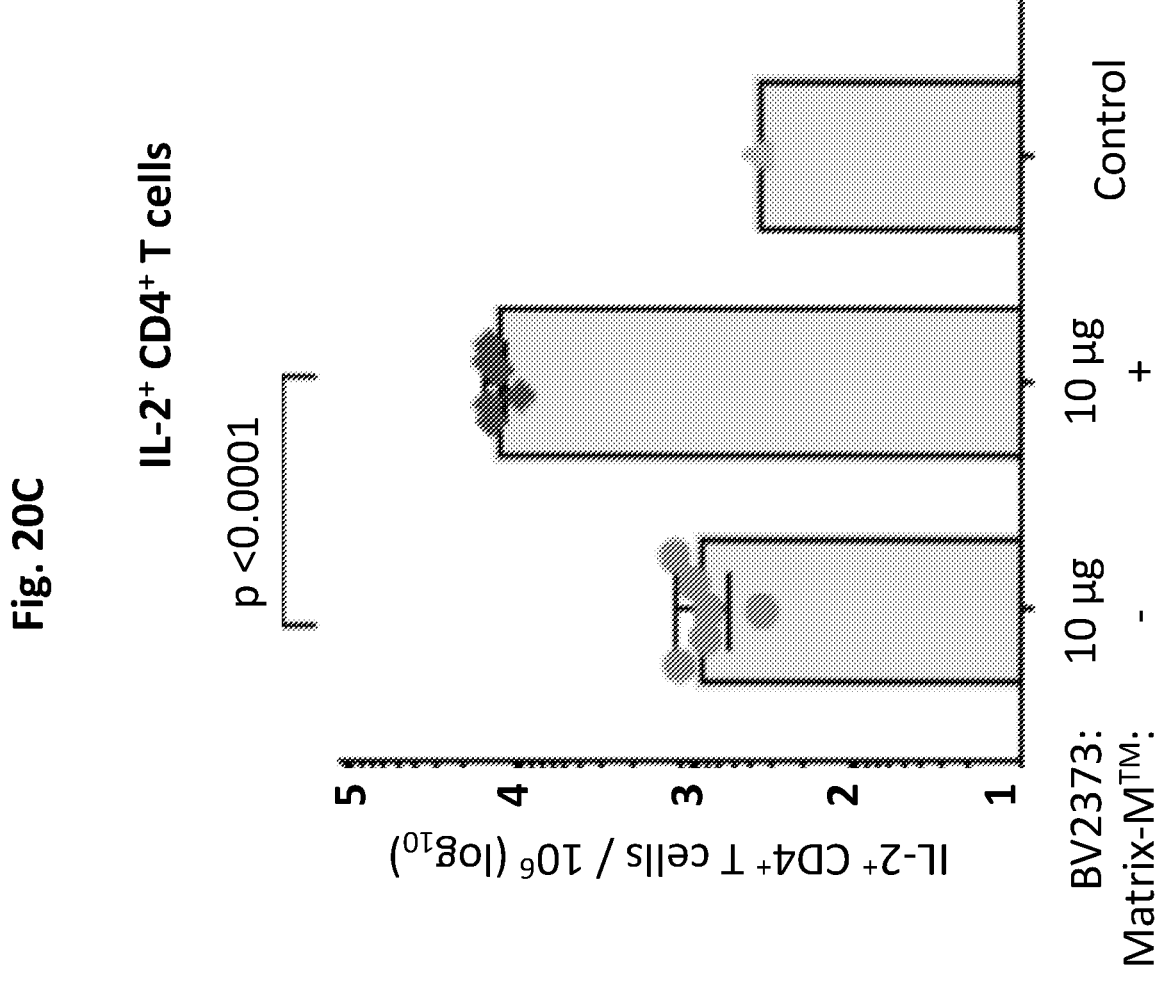
Figure 20D:
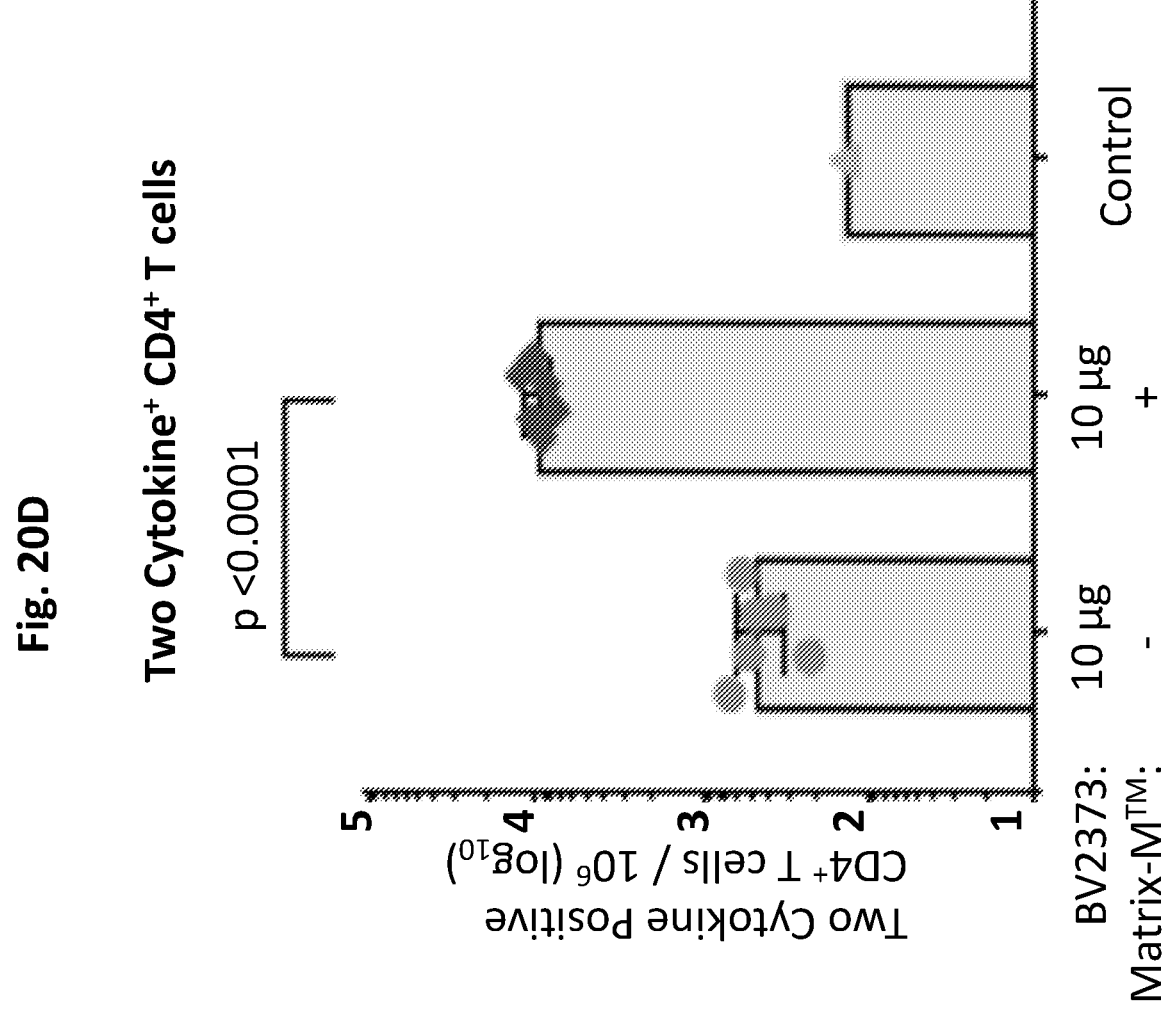
Figure 20E:
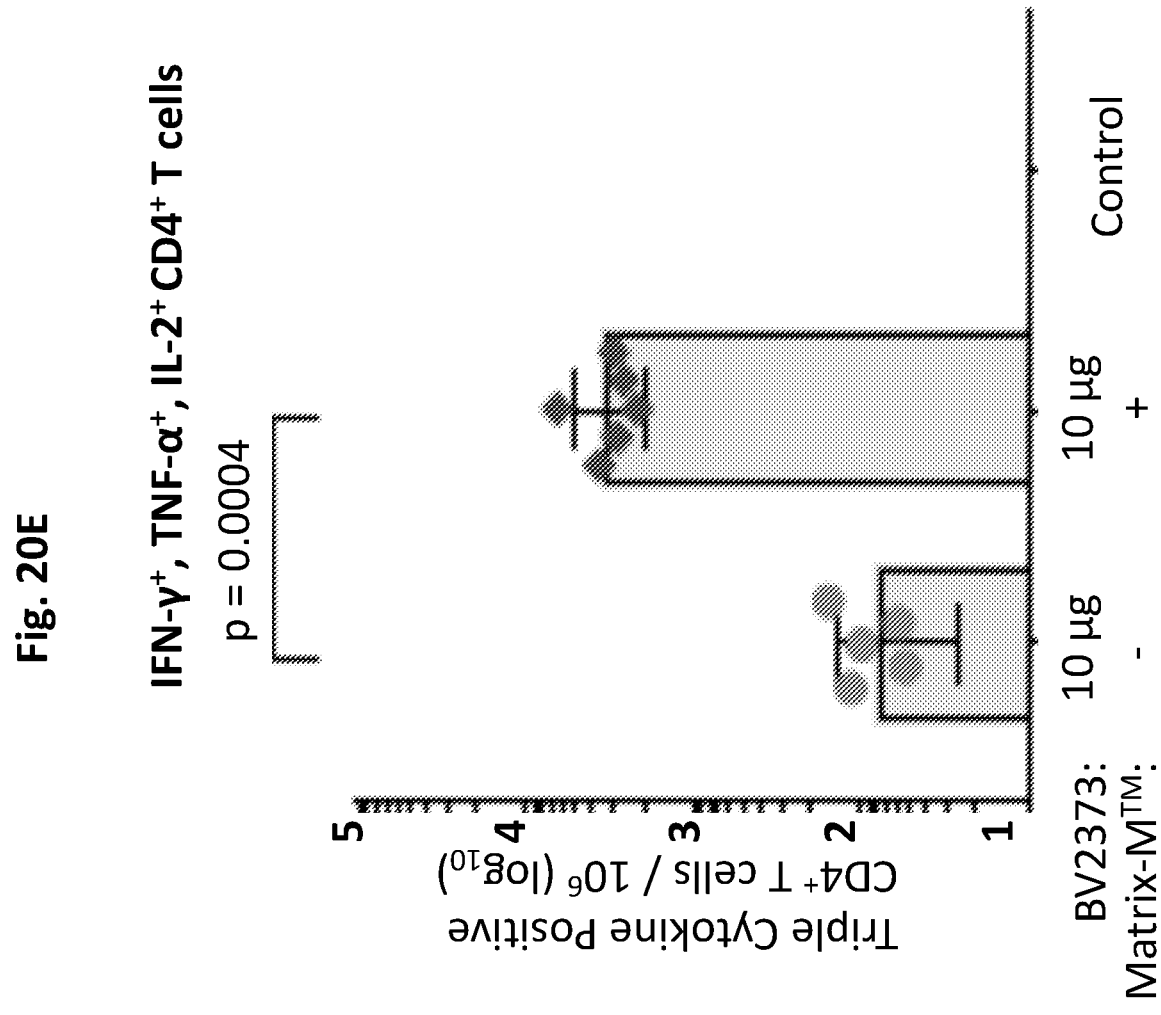
Figure 21A:
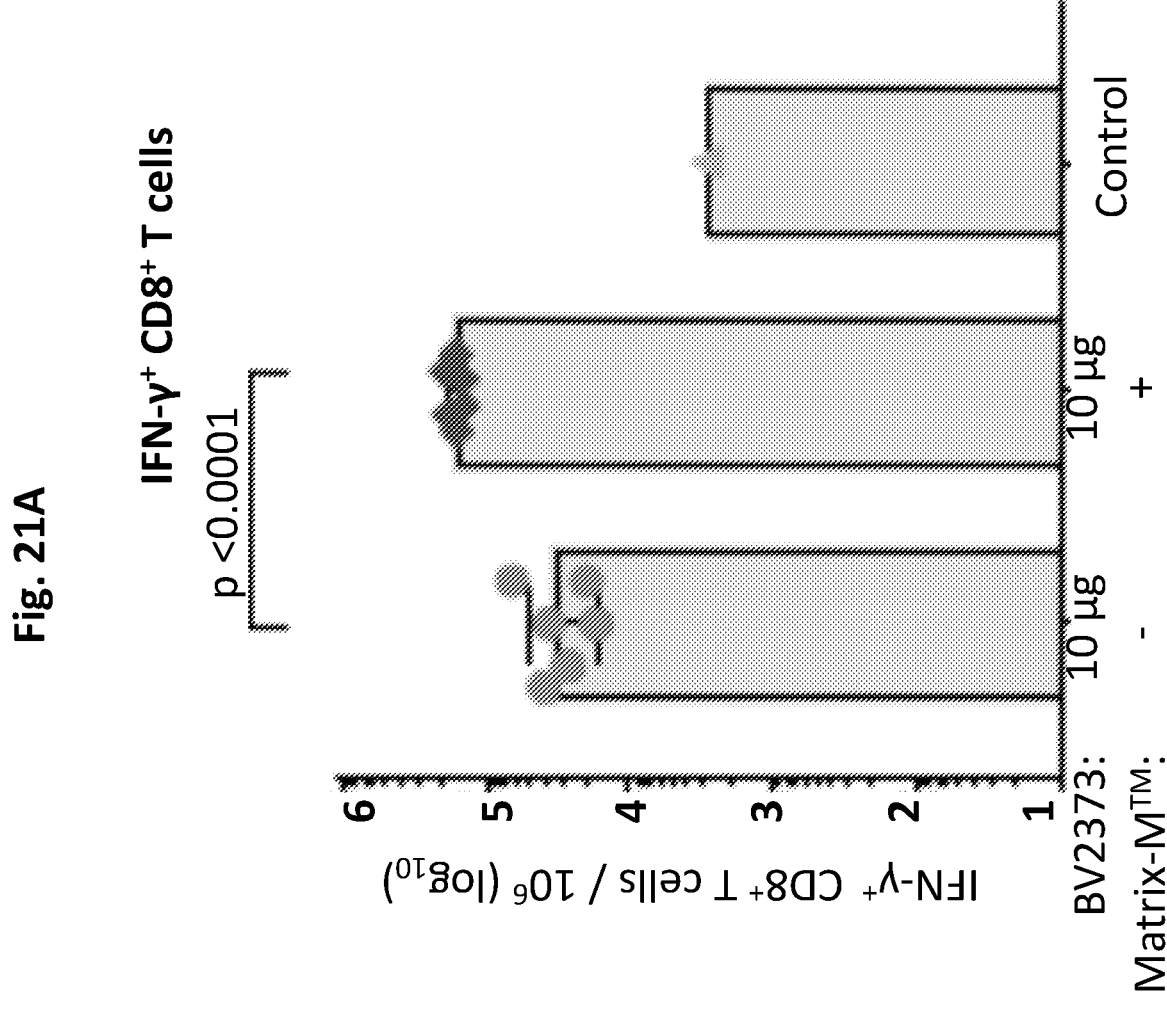
FIGS. 21A-E shows the frequency of cytokine secreting CD8+ T cells in the spleens of mice immunized with BV2373 in the presence or absence of MATRIX-M™.
Figure 21B:
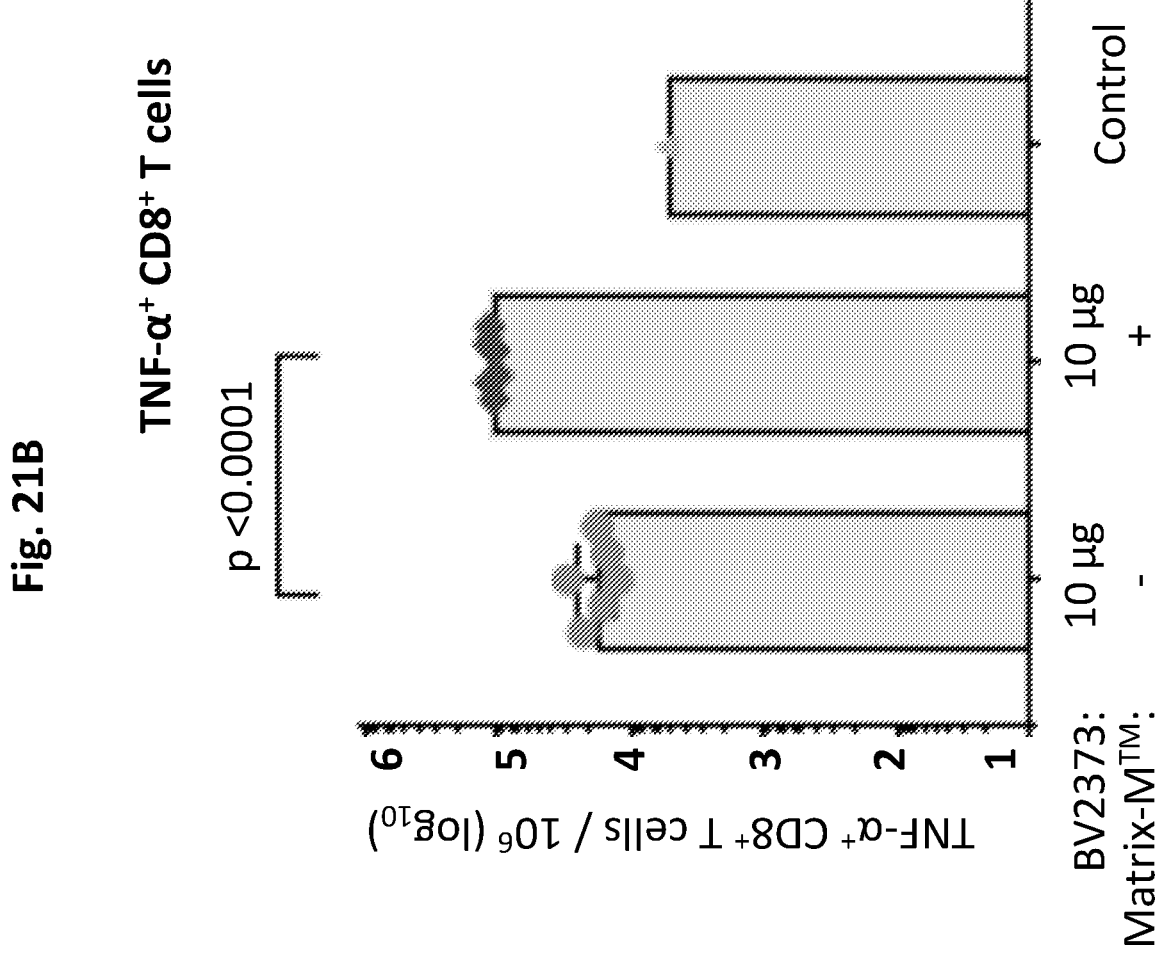
Figure 21C:
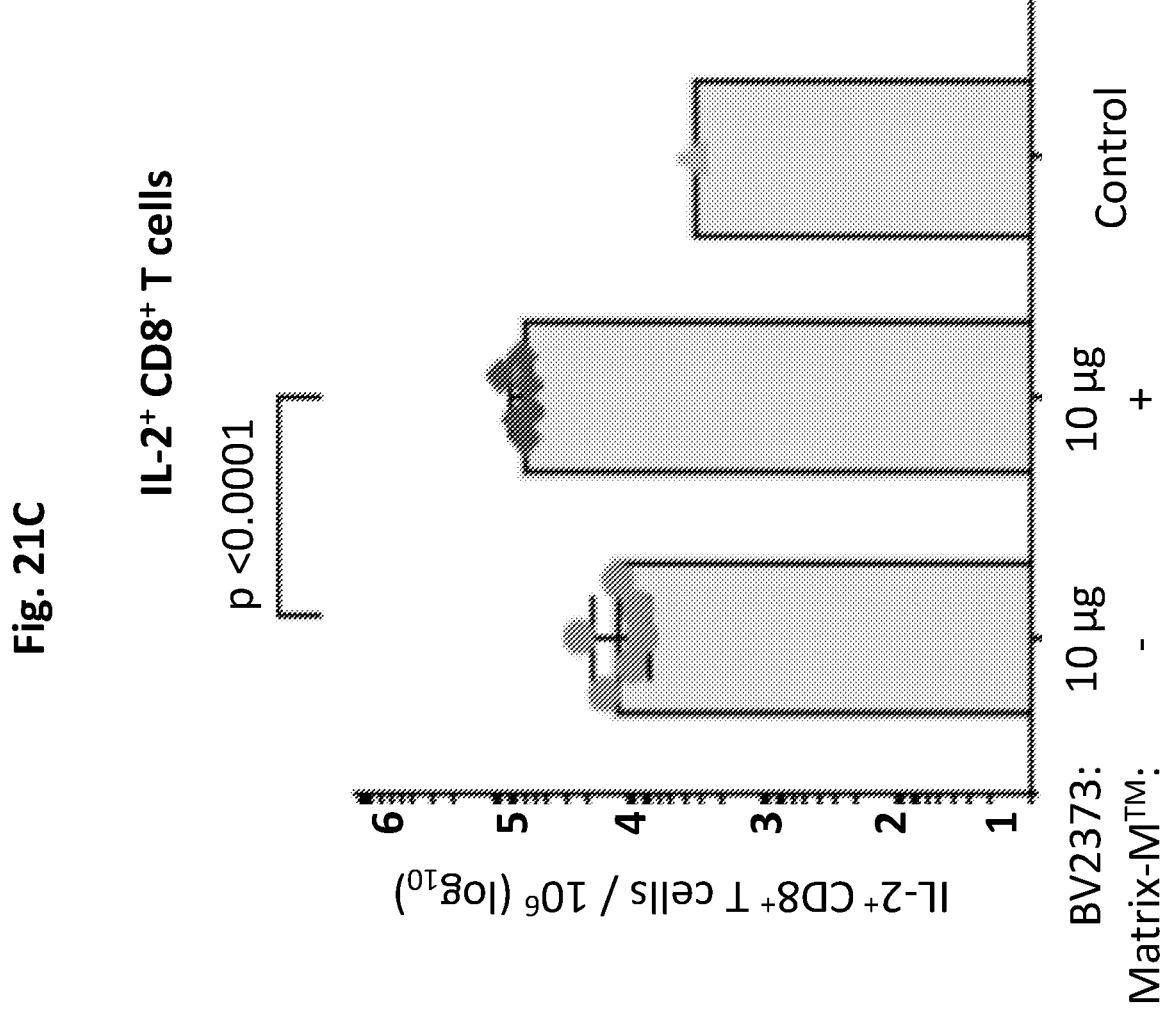
Figure 21D:
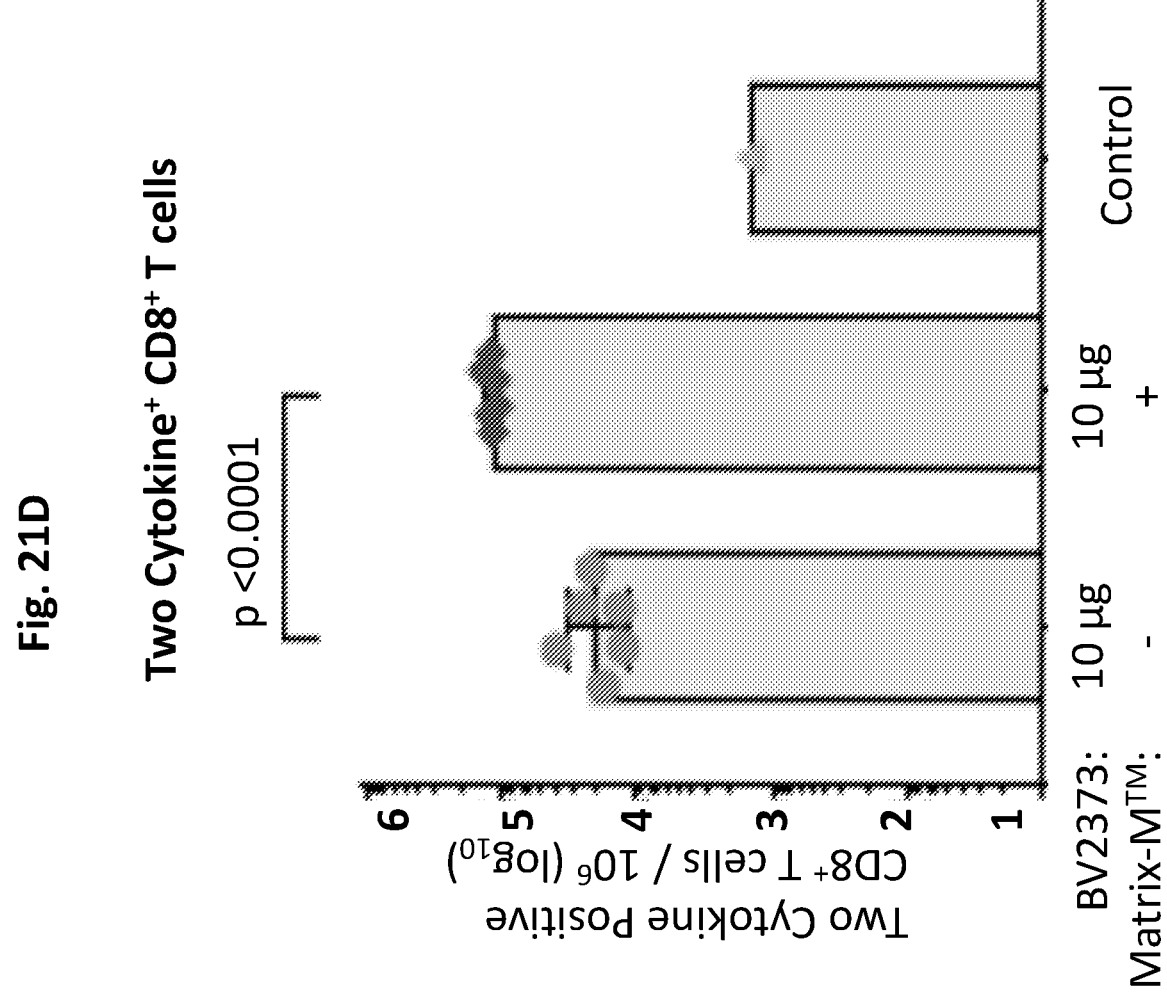
Figure 21E:
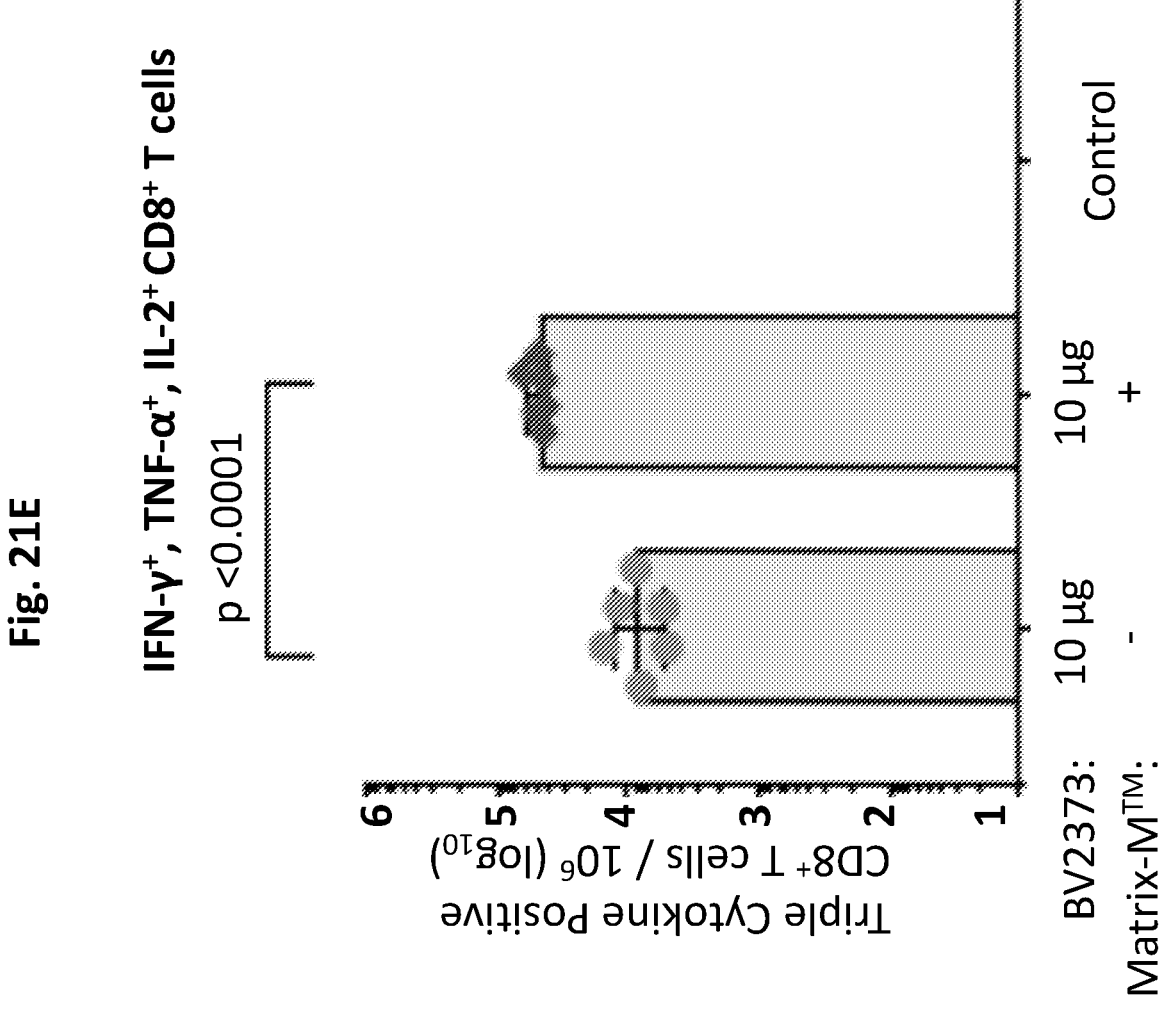
Figure 22:
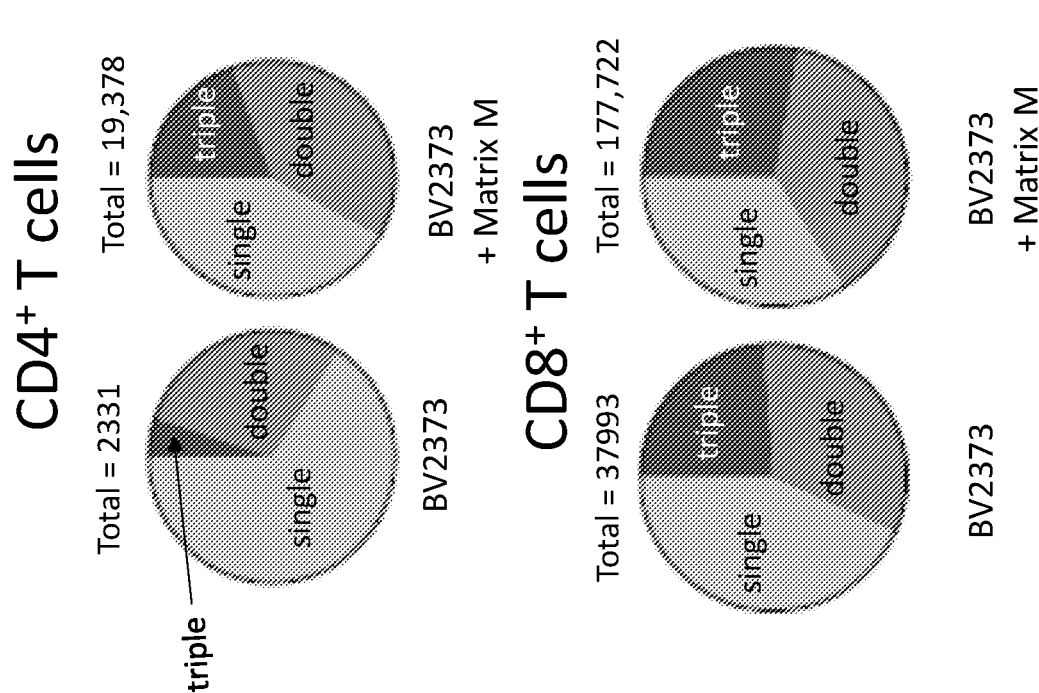
FIG. 22 illustrates the frequency of CD4+ or CD8+ cells that express one (single), two (double), or three (triple) cytokines selected from IFN-γ, TNF-α, and IL-2 in the spleens of mice immunized with BV2373 in the presence or absence of MATRIX-M™.

Antigen-specific T cell responses were measured by ELISPOT™ enzyme linked immunosorbent assay and intracellular cytokine staining (ICCS) from spleens collected 7-days after the second immunization (study day 28). The number of IFN-γ secreting cells after ex vivo stimulation increased 20-fold (p=0.002) in spleens of mice immunized with BV2373 and MATRIX-M™ compared to BV2373 alone as measured by the ELISPOT™ assay (FIG. 19). In order to examine CD4+ and CD8+ T cell responses separately, ICCS assays were performed in combination with surface marker staining. Data shown are gated on CD44hi CD62L-effector memory T cell population. The frequency of IFN-γ+, TNF-α+, and IL-2+ cytokine-secreting CD4+ and CD8+ T cells was significantly higher (p<0.0001) in spleens from mice immunized with BV2373 as compared to mice immunized without adjuvant (FIG. 20A-C and FIG. 21A-C). Further, the frequency of multifunctional CD4+ and CD8+ T cells, which simultaneously produce at least two or three cytokines was also significantly increased (p<0.0001) in spleens from the BV2373/MATRIX-M™ immunized mice as compared to mice immunized in the absence of adjuvant (FIGS. 20D-E and FIGS. 21D-E). Immunization with BV2373/MATRIX-M™ resulted in higher proportions of multifunctional phenotypes (e.g., T cells that secrete more than one of IFN-γ, TNF-α, and IL-2) within both CD4+ and CD8+ T cell populations. The proportions of multifunctional phenotypes detected in memory CD4+ T cells were higher than those in CD8+ T cells (FIG. 22).

Figure 23A:
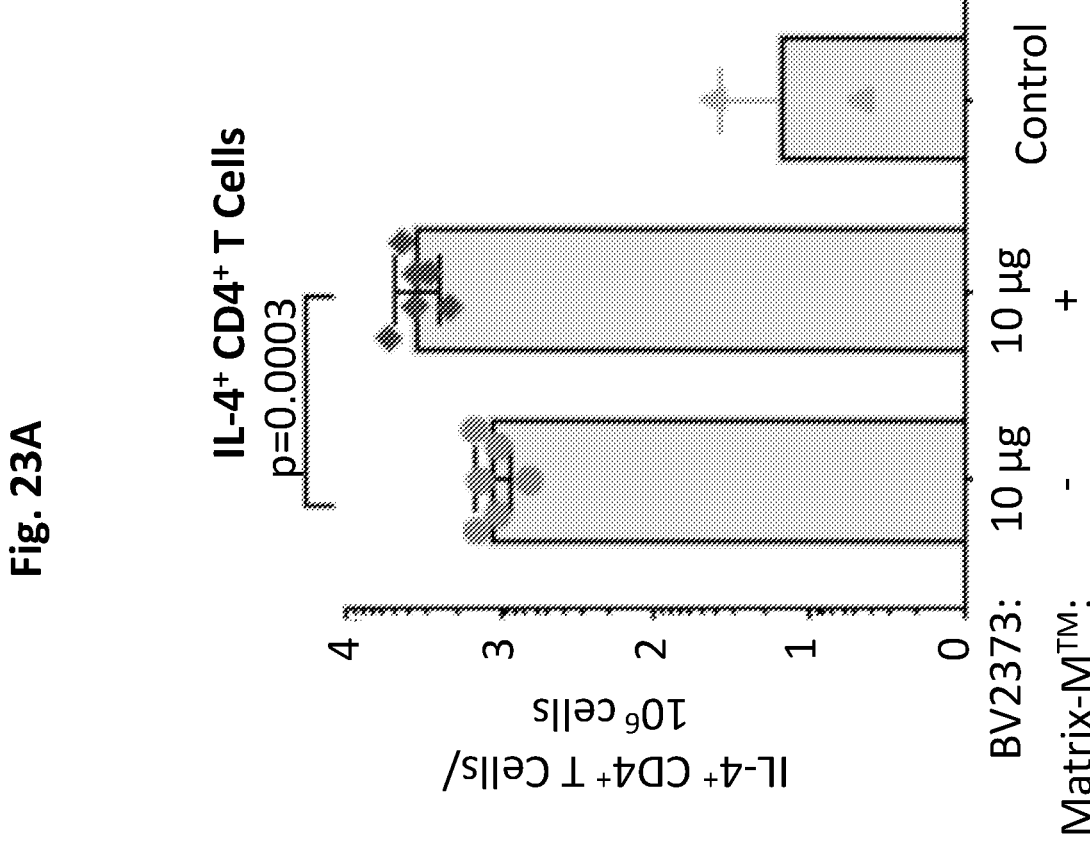
FIGS. 23A-C illustrate the effect of immunization with BV2373 in the presence or absence of MATRIX-M™ on type 2 cytokine secretion from CD4+ T cells.
Figure 23B:
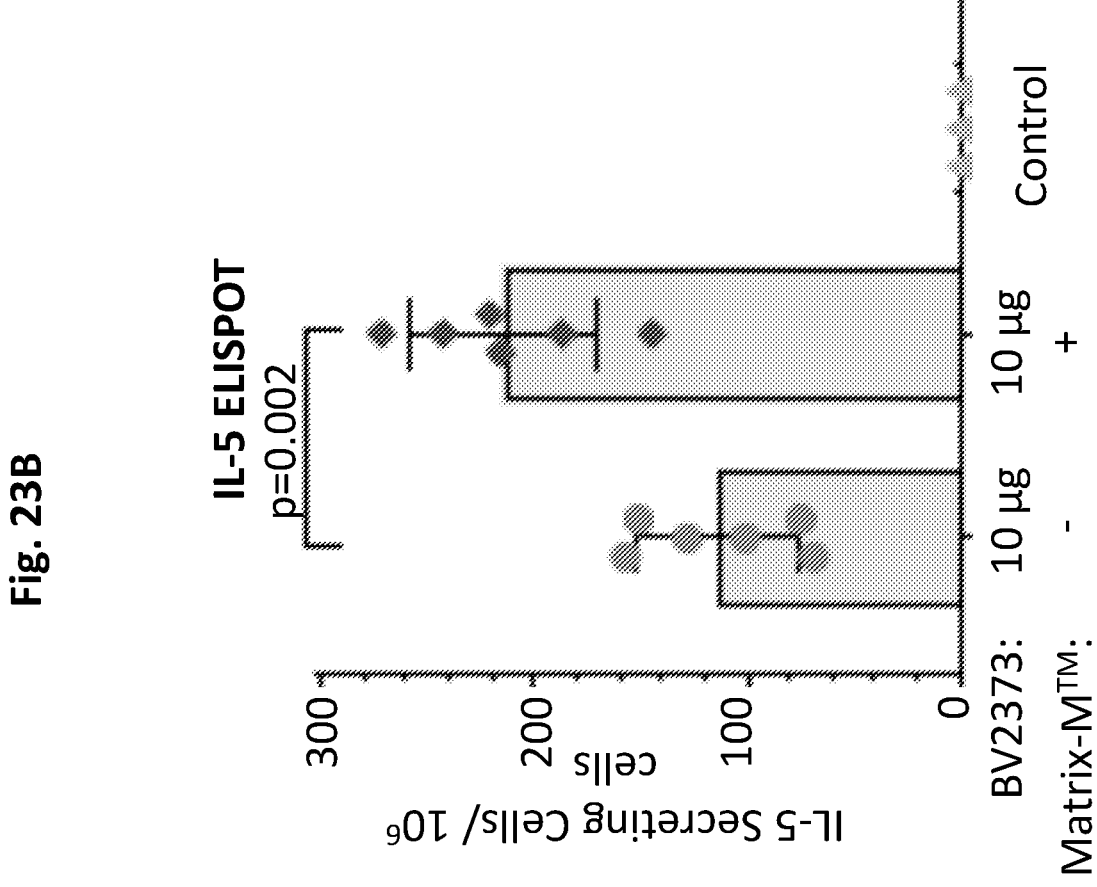
Figure 23C:
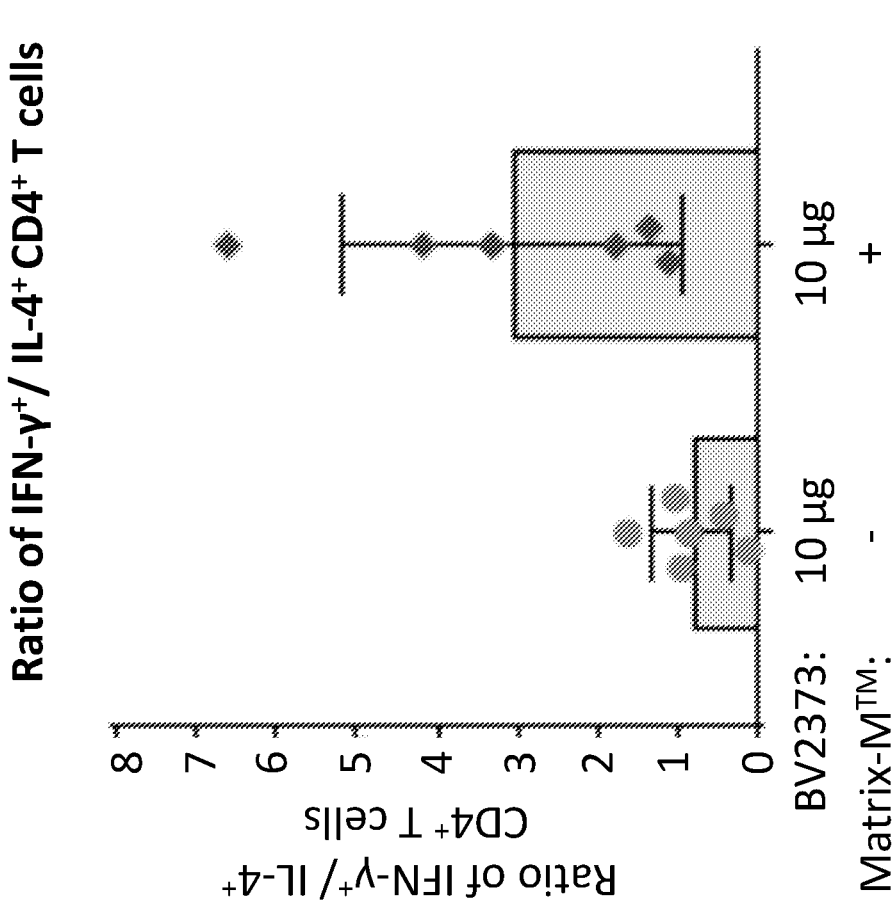
Figure 24A:
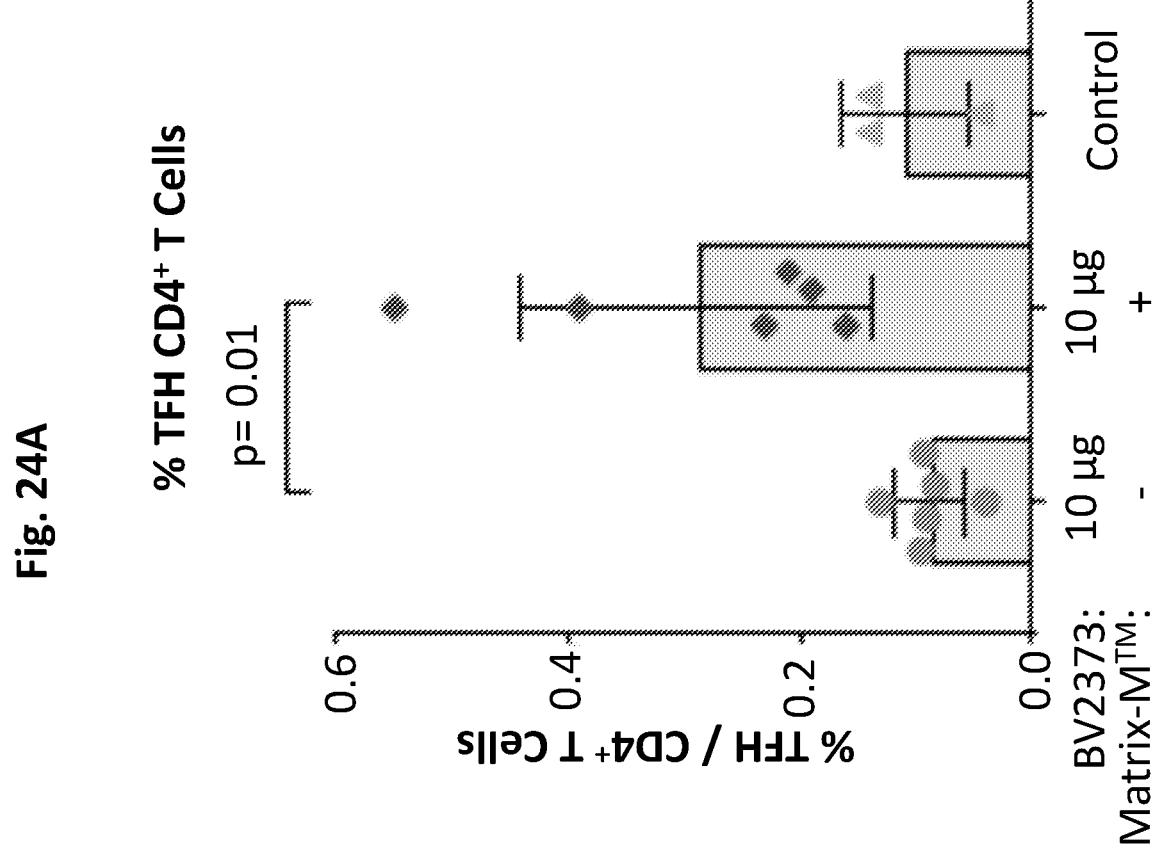
FIGS. 24A-B illustrate the effect of mouse immunization with BV2373 in the presence or absence of MATRIX-M™ on germinal center formation by assessing the presence of CD4+ T follicular helper cells (TFH).
Figure 24B:
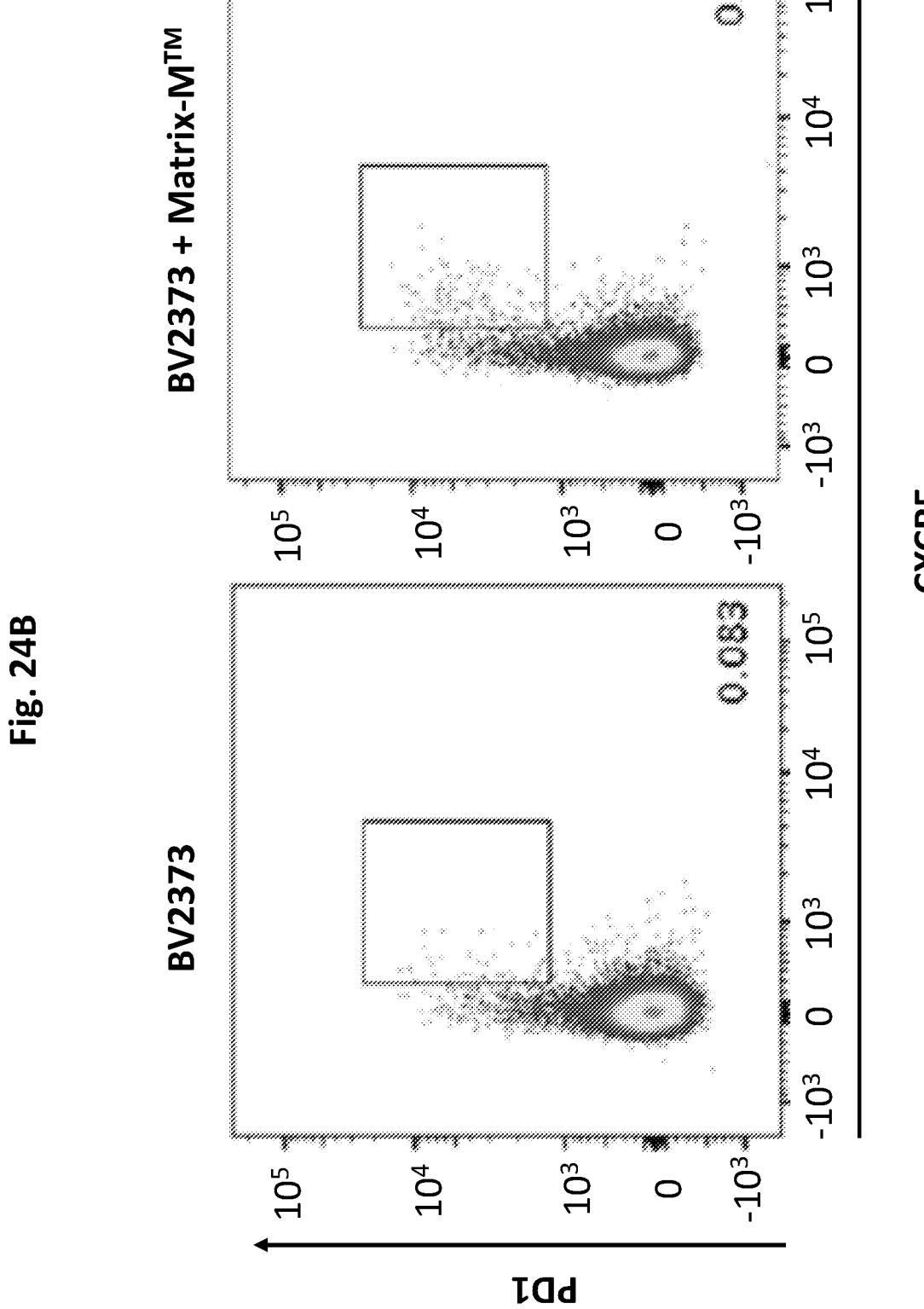
Figure 25B:
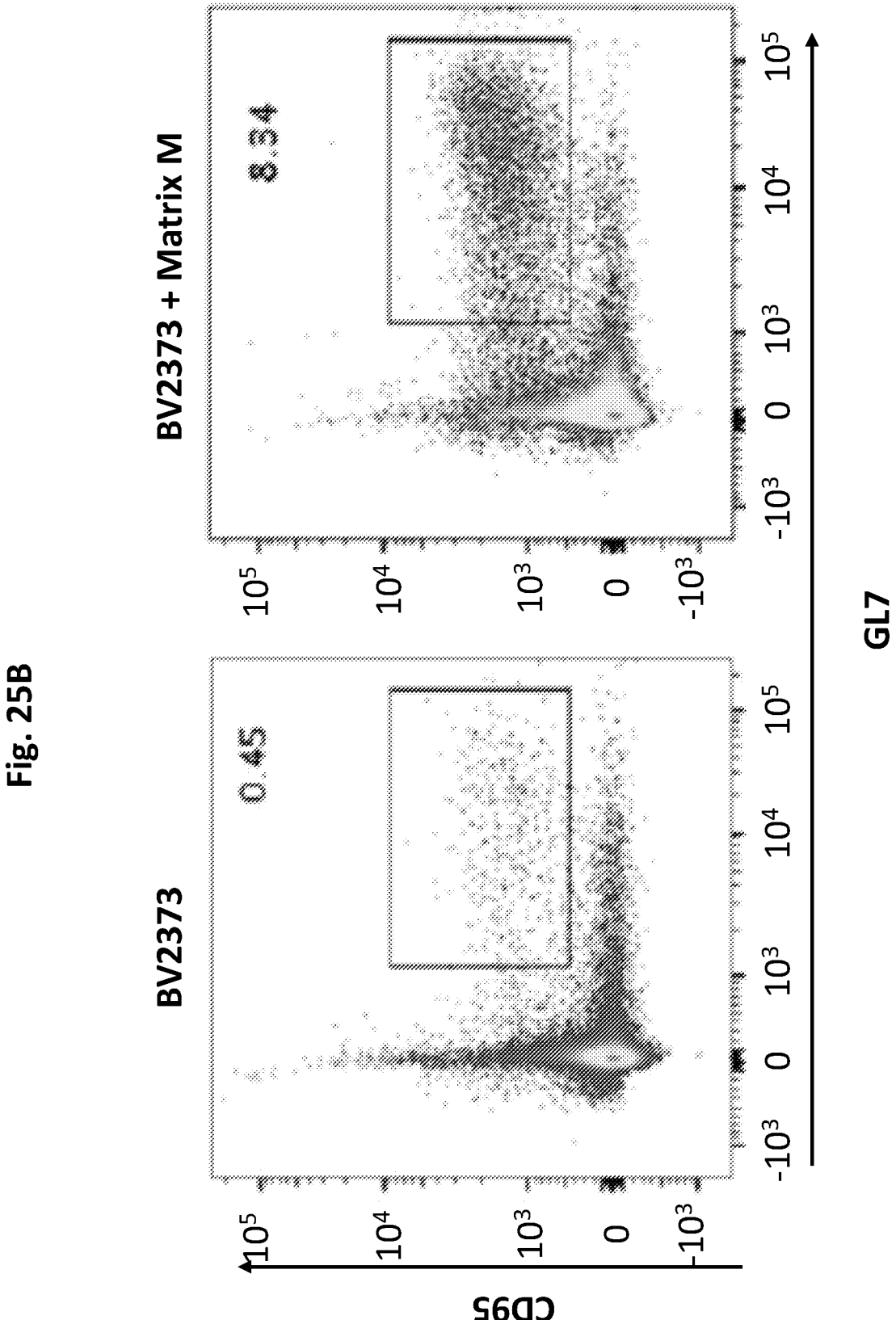

Type 2 cytokine IL-4 and IL-5 secretion from CD4+ T cells was also determined by ICCS and ELISPOT™ respectively Immunization with BV2373/MATRIX-M™ also increased type 2 cytokine IL-4 and IL-5 secretion (2-fold) compared to immunization with BV2373 alone, but to a lesser degree than enhancement of type 1 cytokine production (e.g. IFN-γ increased 20-fold) (FIGS. 23A-C). These results indicate that administration of the MATRIX-M™ adjuvant skewed the CD4+ T cell development toward Th1 responses.

The effect of immunization on germinal center formation was assessed by measuring the frequency of CD4+ T follicular helper (TFH) cells and germinal center (GC) B cells in spleens. MATRIX-M™ administration significantly increased the frequency of TFH cells (CD4+ CXCR5+ PD-1+) was significantly increased (p=0.01), as well as the frequency of GC B cells (CD19+GL7+CD95+) (p=0.0002) in spleens (FIGS. 24A-B and FIGS. 25A-B).

Example 3

Figure 26A:
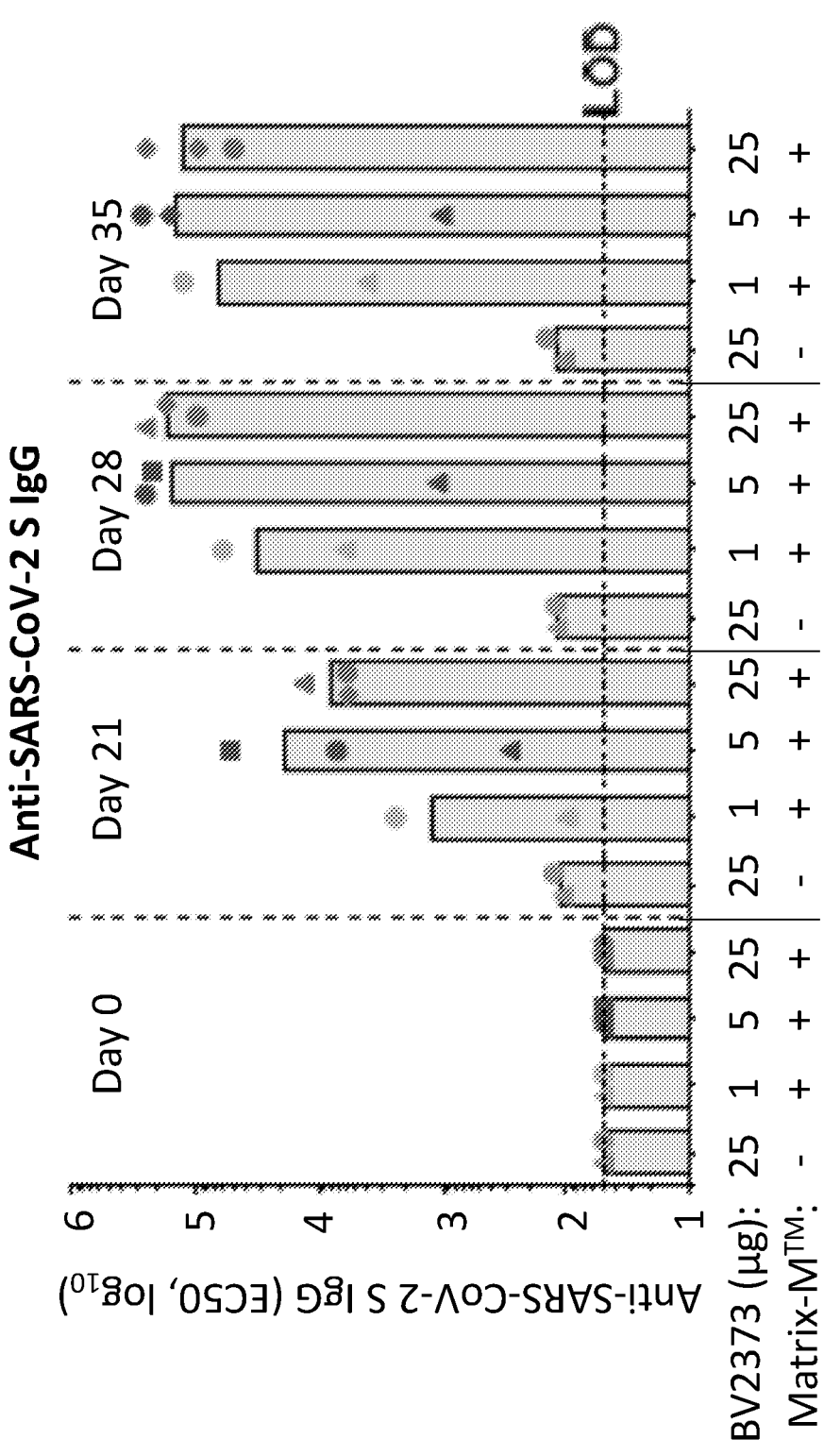
FIGS. 26A-C show the effect of immunization with BV2373 in the presence or absence of MATRIX-M™ on antibody response in olive baboons.

Immunogenicity of Coronavirus Spike (S) Polypeptide Nanoparticle Vaccines in Olive Baboons The immunogenicity of a vaccine composition comprising BV2373 in baboons was assessed. Adult olive baboons were immunized with a dose range (1 μg, 5 μg and 25 μg) of BV2373 and 50 μg MATRIX-M™ adjuvant administered by intramuscular (IM) injection in two doses spaced 21-days apart. To assess the adjuvanting activity of MATRIX-M™ in non-human primates, another group of animals was immunized with 25 μg of BV2373 without MATRIX-M™. Anti-S protein IgG titers were detected within 21-days of a single priming immunization in animals immunized with BV2373/ MATRIX-M™ across all the dose levels (GMT=1249-19, 000). Anti-S protein IgG titers increased over a log (GMT=33,000-174,000) within 1 to 2 weeks following a booster immunization (days 28 and 35) across all of the dose levels. (FIG. 26A).

Figure 26B:
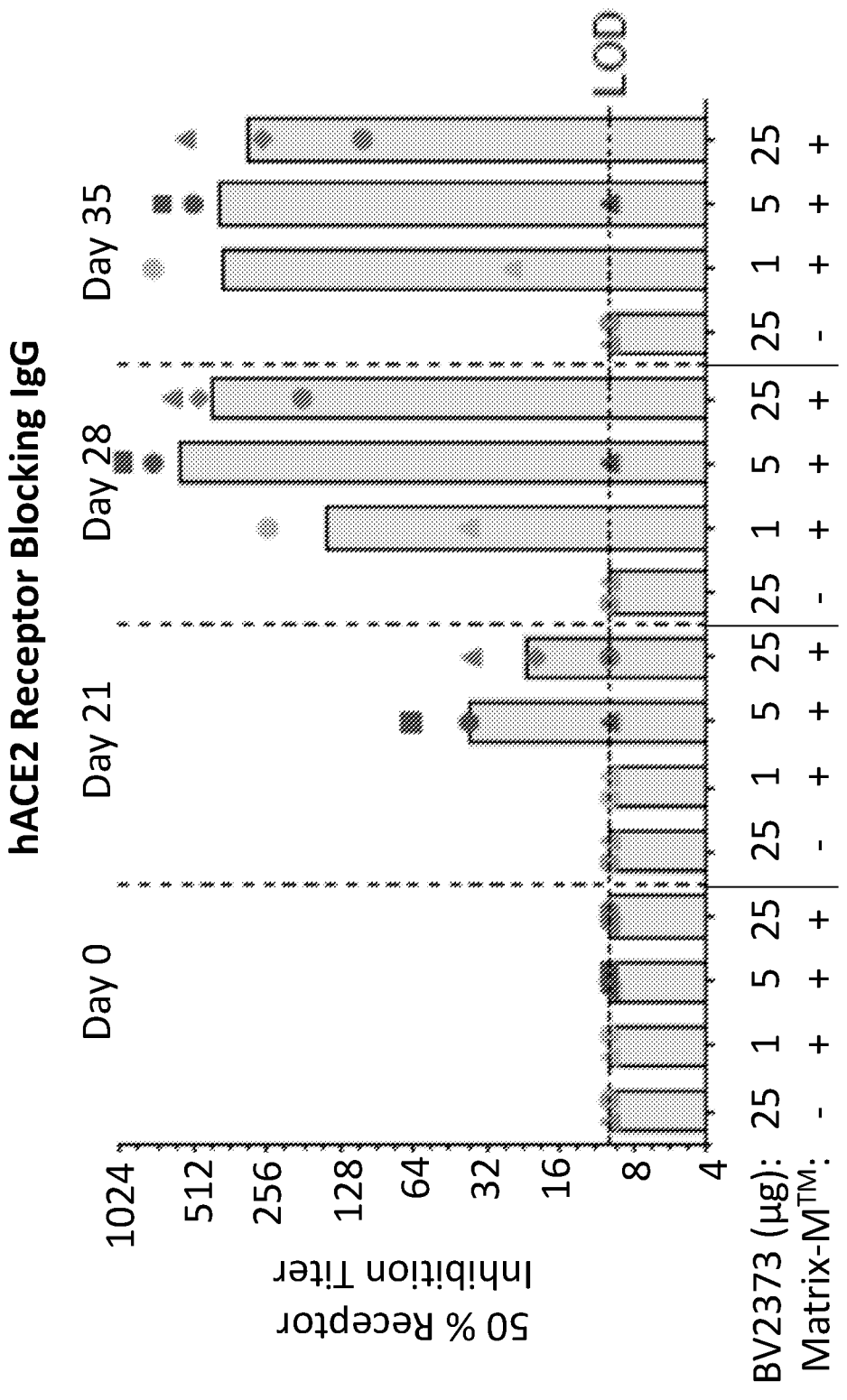
Figure 26C:
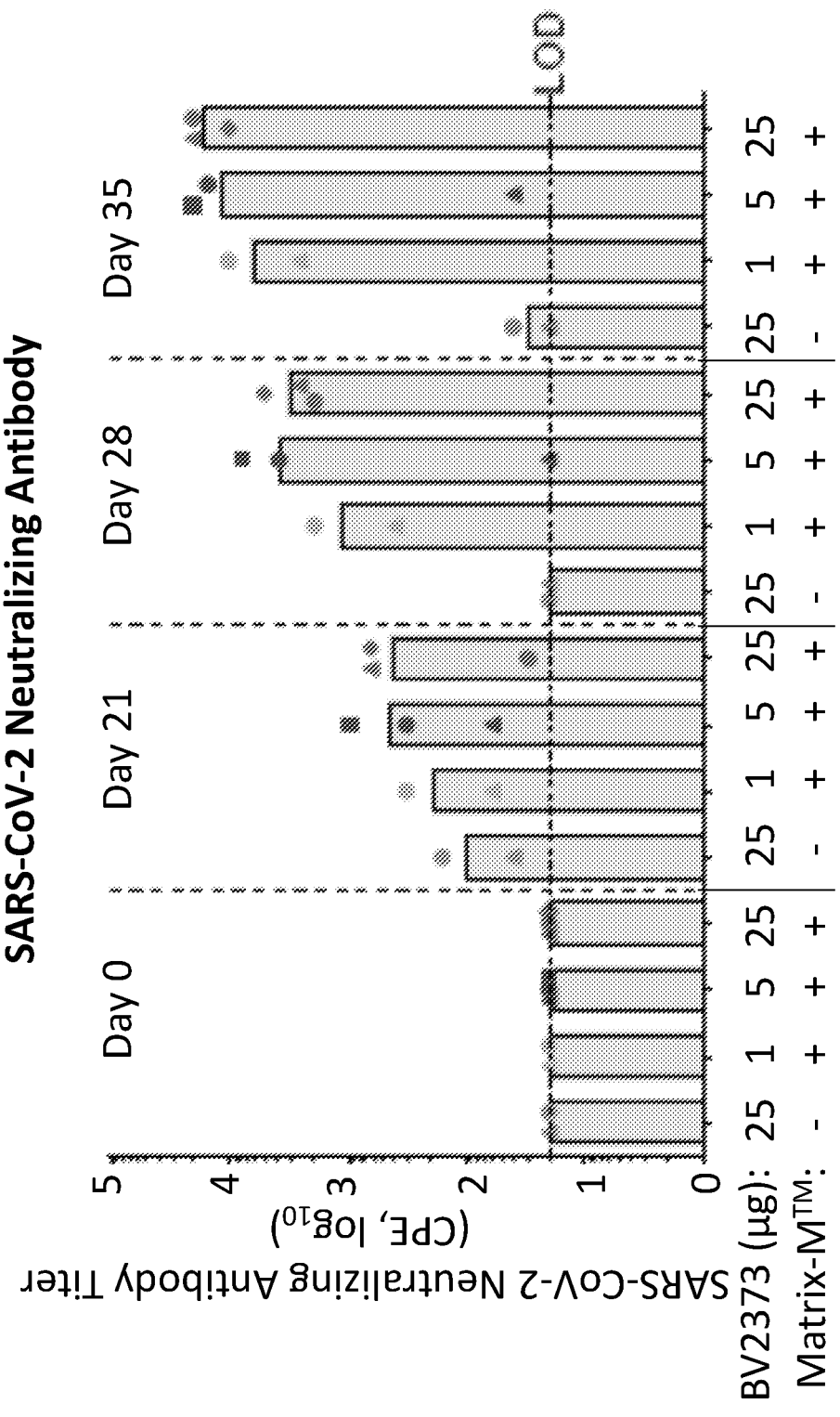
Figure 27:
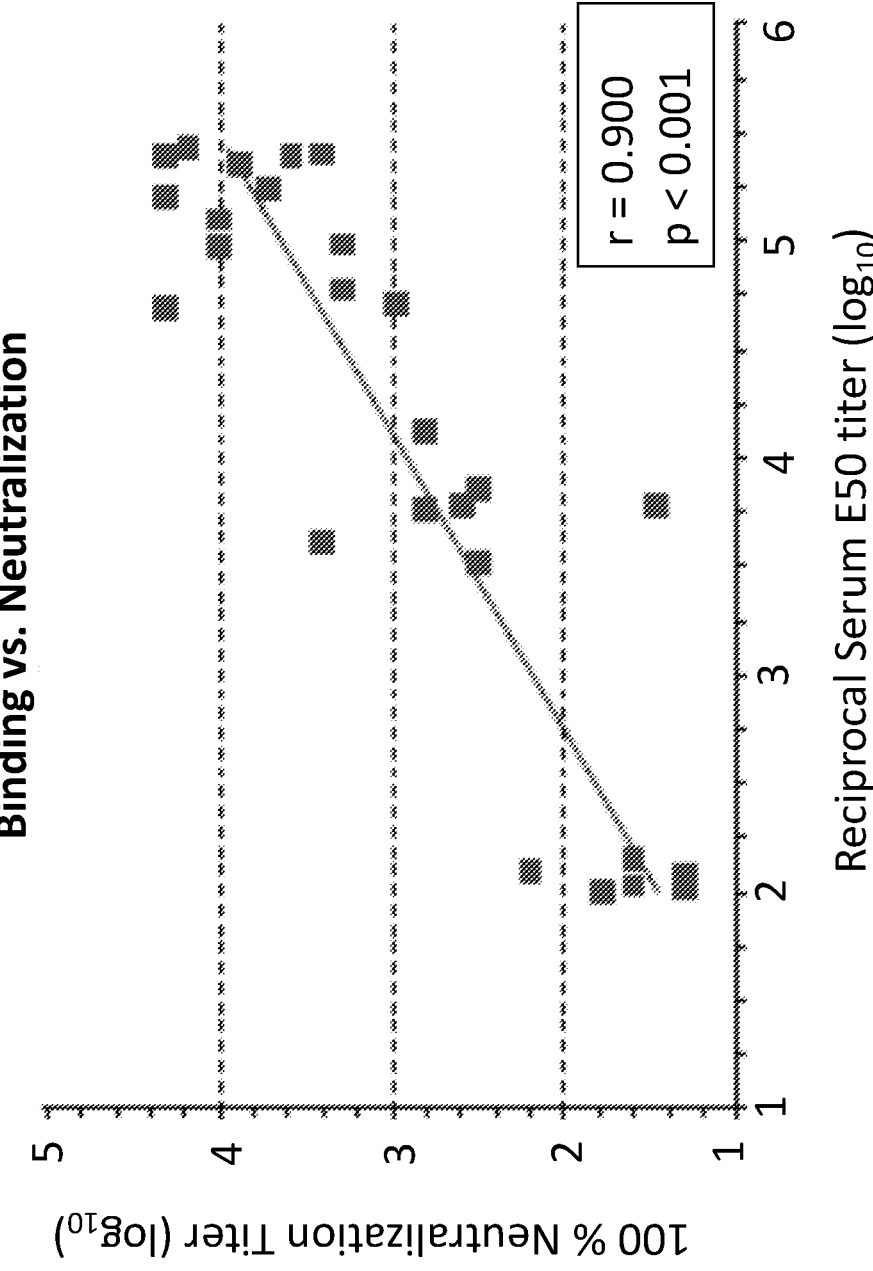
FIG. 27 shows the significant correlation between anti-SARS-CoV-2 S polypeptide IgG and neutralizing antibody titers in olive baboons after immunization with BV2373.

Low levels of hACE2 receptor blocking antibodies were detected in animals following a single immunization with BV2373 (5 μg or 25 μg) and MATRIX-M™ (GMT=22-37). Receptor blocking antibody titers were significantly increased within one to two weeks of the booster immunization across all groups immunized with BV2373/MATRIX-M™ (GMT=150-600) (FIG. 26B). Virus neutralizing antibodies were elevated (GMT=190-446) across all dose groups after a single immunization with BV2373/MATRIX-M™. Animals immunized with 25 μg BV2373 alone had no detectable antibodies that block S-protein binding to hACE2 (FIG. 26C). Neutralizing titers were increased 6- to 8-fold one week following the booster immunization (GMT=1160-3846). Neutralizing titers increased an additional 25- to 38-fold following the second immunization (GMT=6400-17,000) (FIG. 26C). There was a significant correlation (p<0.0001) between anti-S IgG levels and neutralizing antibody titers (FIG. 27). The immunogenicity of the adjuvanted vaccine in nonhuman primates is consistent with the results of Example 2 and further supports the role of MATRIX-M™ in promoting the generation of neutralizing antibodies and dose sparing.

Figure 28:
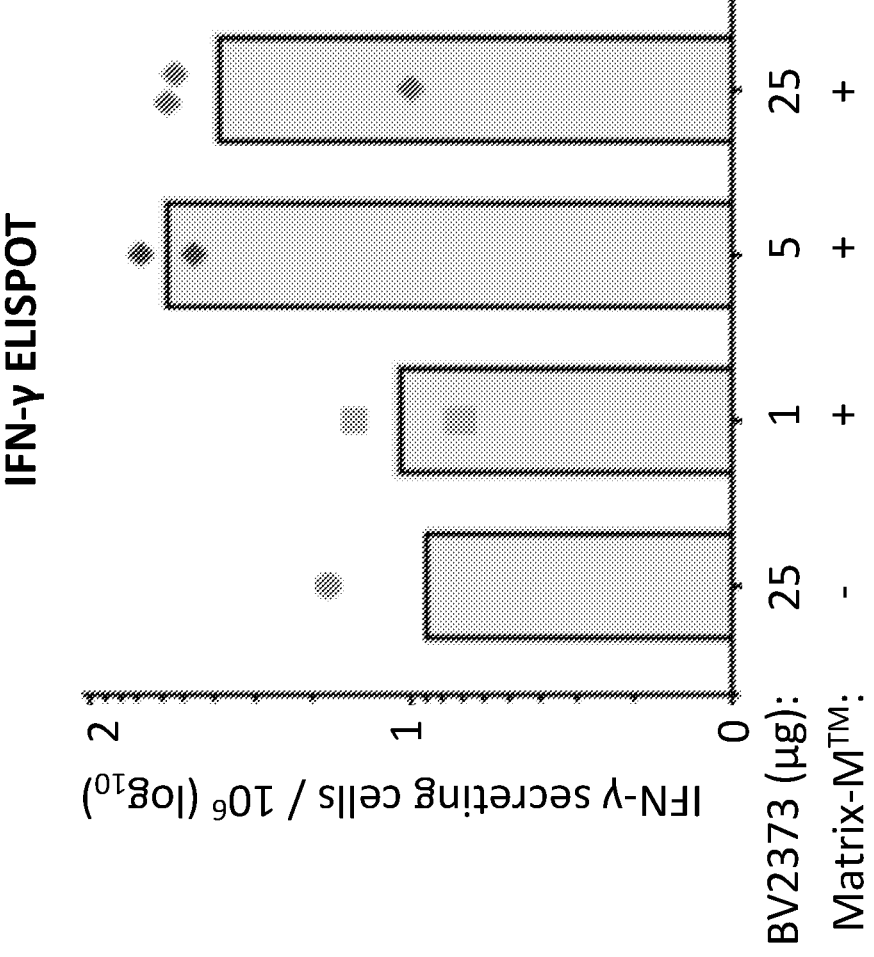
FIG. 28 shows the frequency of IFN-γ secreting cells in peripheral blood mononuclear cells (PBMC) of olive baboons immunized with BV2373 in the presence or absence of MATRIX-M™.
Figure 29A:
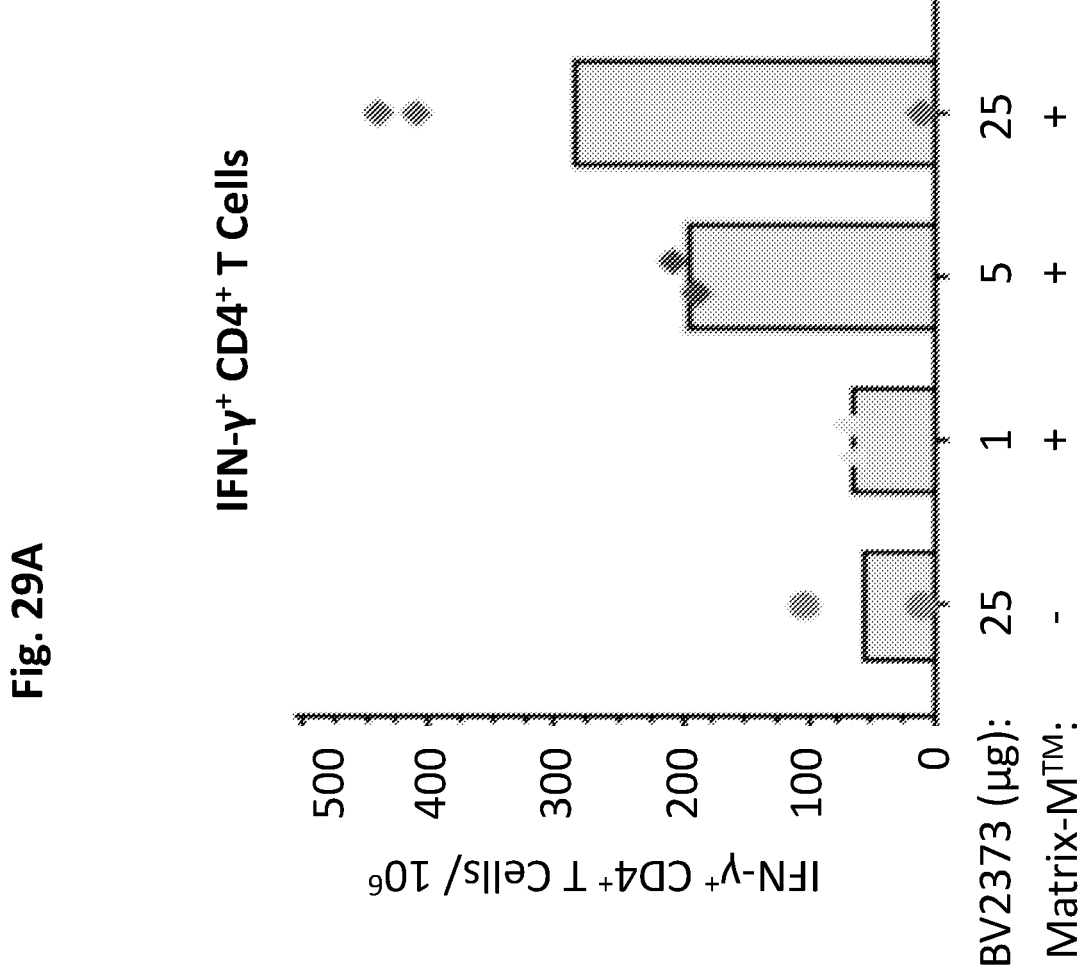
FIGS. 29A-E shows the frequency of cytokine secreting CD4+ T cells in the PBMC of olive baboons immunized with BV2373 in the presence or absence of MATRIX-M™.
Figure 29B:
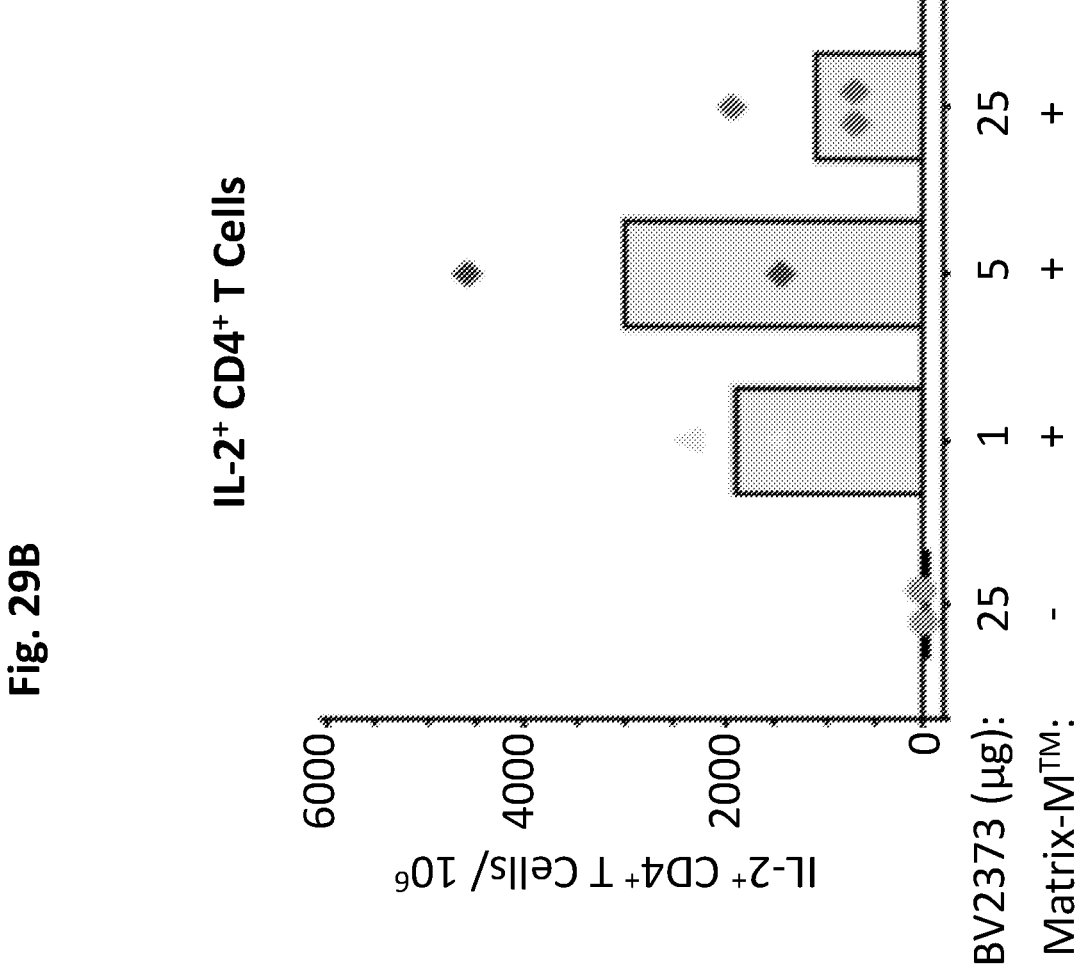
Figure 29C:
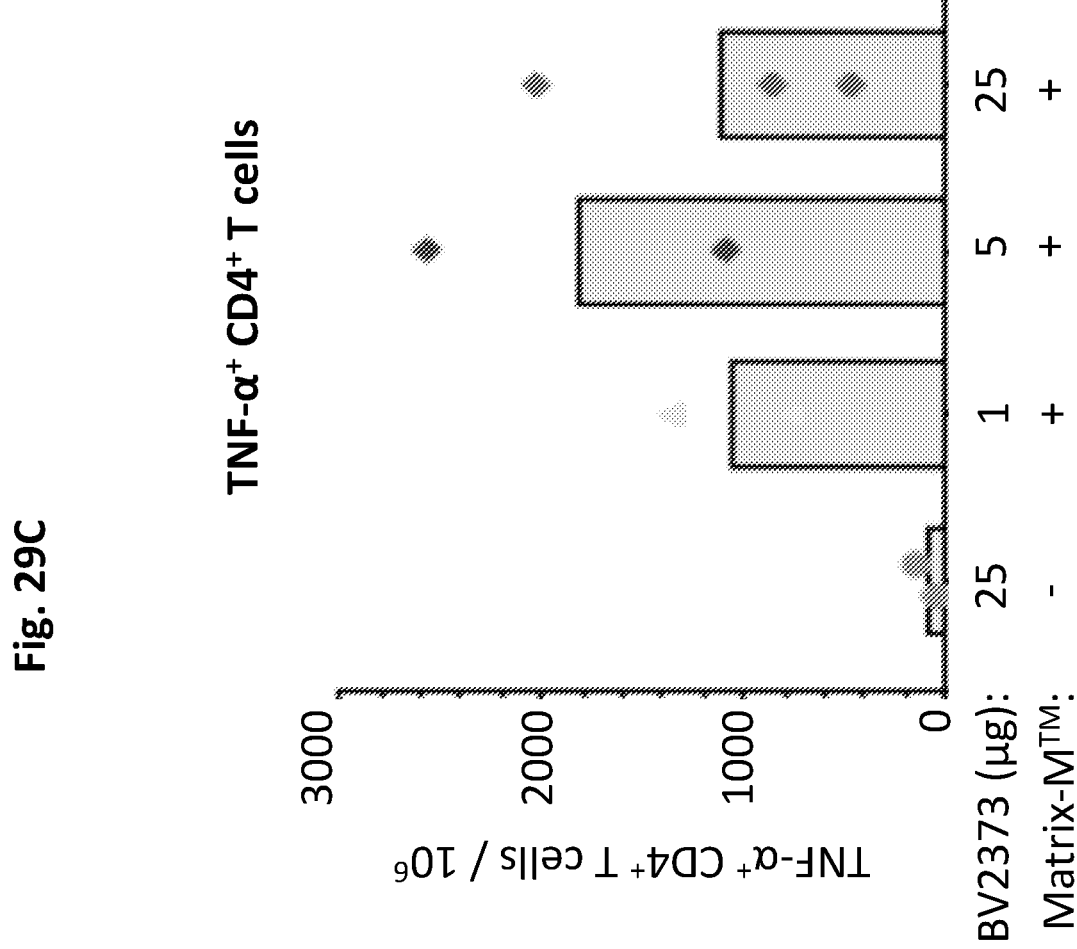
Figure 29D:
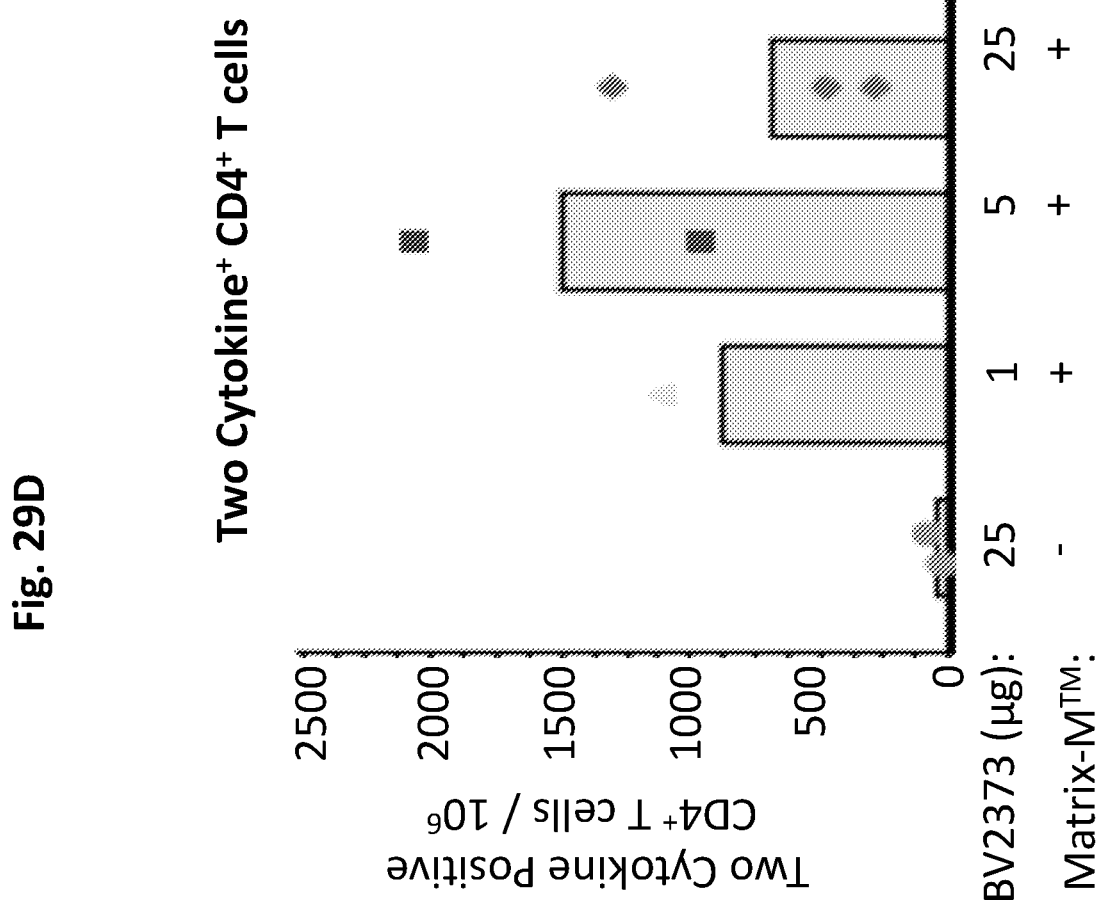
Figure 29E:
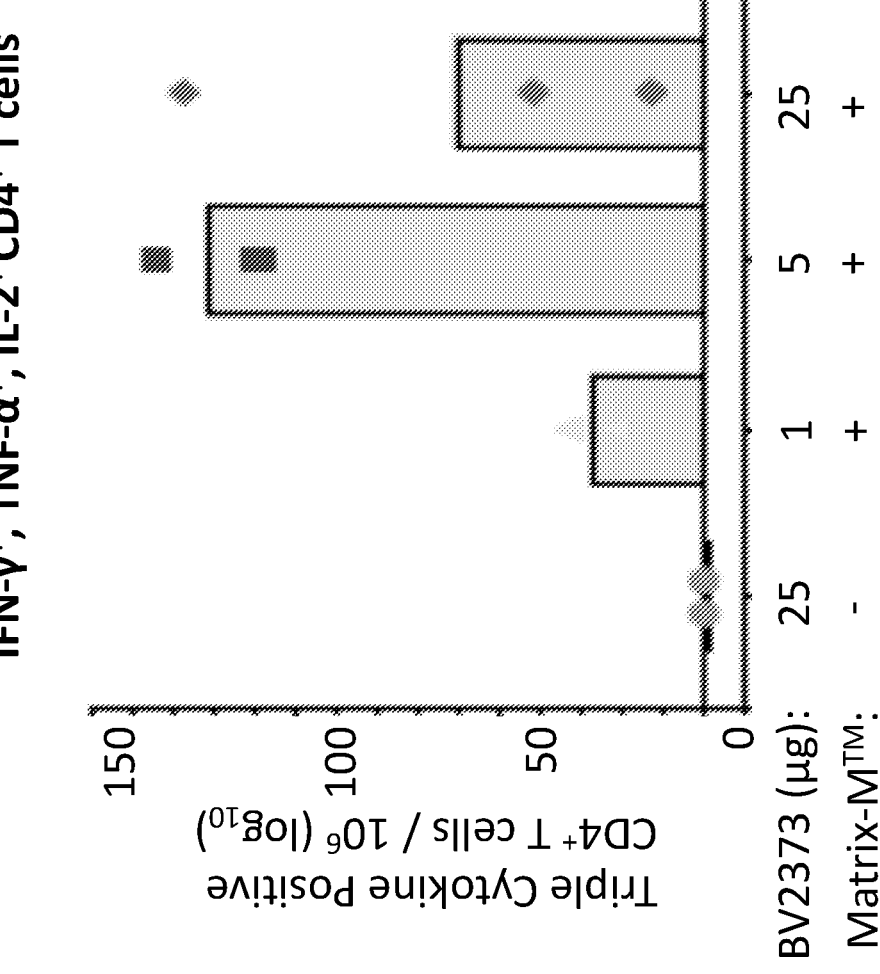

PBMCs were collected 7 days after the second immunization (day 28), and the T cell response was measured by ELISPOT assay. PBMCs from animals immunized with BV2373 (5 μg or 25 μg) and MATRIX-M™ had the highest number of IFN-γ secreting cells, which was 5-fold greater compared to animals immunized with 25 μg BV2373 alone or BV2373 (1 μg) and MATRIX-M™ (FIG. 28). By ICCS analysis, immunization with BV2373 (5 μg) and MATRIX-M™ showed the highest frequency of IFN-γ+, IL-2+, and TNF-α+ CD4+ T cells (FIGS. 29A-C). This trend was also true for multifunctional CD4+ T cells, in which at least two or three type 1 cytokines were produced simultaneously (FIGS. 29D-E).

Example 4

Structural Characterization of Coronavirus Spike (S) Polypeptide Nanoparticle Vaccines Transmission electron microscopy (TEM) and two dimensional (2D) class averaging were used to determine the ultrastructure of BV2373. High magnification (67,000× and 100,000×) TEM images of negatively stained BV2373 showed particles corresponding to S-protein homotrimers.

An automated picking protocol was used to construct 2D class average images (Lander G. C. et al. *J Strict Biol.* 166, 95-102 (2009); Sorzano C. O. et al., *J Struct Biol.* 148, 194-204 (2004).). Two rounds of 2D class averaging of homotrimeric structures revealed a triangular particle appearance with a 15 nm length and 13 nm width (FIG. 10, top left). Overlaying the recently solved cryoEM structure of the SARS-CoV-2 spike protein (EMD ID: 21374) over the 2D BV2373 image showed a good fit with the crown-shaped S1 (NTD and RBD) and the S2 stem (FIG. 10, bottom left). Also apparent in the 2D images was a faint projection that protruded from the tip of the trimeric structure opposite of the NTD/RBD crown (FIG. 10, top right). 2D class averaging using a larger box size showed these faint projections form a connection between the S-trimer and an amorphous structure. (FIG. 10, bottom right).

Dynamic light scattering (DLS) show that the wild-type CoV S protein had a Z-avg particle diameter of 69.53 nm compared to a 2-fold smaller particle size of BV2365 (33.4 nm) and BV2373 (27.2 nm). The polydispersity index (PDI) indicated that BV2365 and BV2373 particles were generally uniform in size, shape, and mass (PDI=0.25-0.29) compared to the wild-type spike-protein (PDI=0.46) (Table 3).

TABLE 3

Particle Size and Thermostability of SARS-CoV-2 Trimeric Spike Proteins

| SARS-CoV-2 S protein | Differential Scanning Calorimetry (DSC) | | Dynamic Light Scattering (DLS) | |
|---|---|---|---|---|
| | $T_{max}$ (° C.)[1] | ΔHcal (kj/mol) | Z- avg diameter[2] (nm) | PDI[3] |
| Wild-type | 58.6 | 153 | 69.53 | 0.46 |
| BV2365 | 61.3 | 466 | 33.40 | 0.25 |
| BV2373 | 60.4 | 732 | 27.21 | 0.29 |

[1]$T_{max}$: melting temperature
[2]Z-avg: Z-average particle size
[3]PDI: polydispersity index The thermal stability of the S-trimers was determined by differential scanning calorimetry (DSC). The thermal transition temperature of the wild-type CoV S-protein ($T_{max}$=58.6° C.) was similar to BV2365 and BV2373 with a $T_{max}$=61.3° C. and 60.4° C., respectively (Table 3). Of greater significance, was the 3-5 fold increased enthalpy of transition required to unfold the BV2365 and BV2373 variants (ΔHcal=466 and 732 kJ/mol, respectively) compared to the lower enthalpy required to unfold the WT spike protein (ΔHcal=153 kJ/mol). These results are consistent with improved thermal stability of the BV2365 and BV2373 compared to that of WT spike protein (Table 3).

The stability of the CoV Spike (S) polypeptide nanoparticle vaccines was evaluated by dynamic light scattering. Various pHs, temperatures, salt concentrations, and proteases were used to compare the stability of the CoV Spike (5) polypeptide nanoparticle vaccines to nanoparticle vaccines containing the native CoV Spike (S) polypeptide.

Example 5

Stability of Coronavirus Spike (S) Polypeptide Nanoparticle Vaccines

The stability of the CoV Spike (S) polypeptide nanoparticle vaccines was evaluated by dynamic light scattering. Various pHs, temperatures, salt concentrations, and proteases were used to compare the stability of the CoV Spike (S) polypeptide nanoparticle vaccines to nanoparticle vaccines containing the native CoV Spike (5) polypeptide. The stability of BV2365 without the 2-proline substitutions and BV2373 with two prolines substitution was assessed under different environmental stress conditions using the hACE2 capture ELISA. Incubation of BV2373 at pH extremes (48 hours at pH 4 and pH 9), with prolonged agitation (48 hours), and through freeze/thaw (2 cycles), and elevated temperature (48 hours at 25° C. and 37° C.) had no effect on hACE2 receptor binding (IC50=14.0-18.3 ng mL-1).

Oxidizing conditions with hydrogen peroxide reduced binding of hACE2 binding to BV2373 8-fold (IC50=120 ng mL-1) (FIG. 12A). BV2365 without the 2-proline substitutions was less stable as determined by a significant loss of hACE2 binding under multiple conditions (FIG. 12B).

Figure 32:
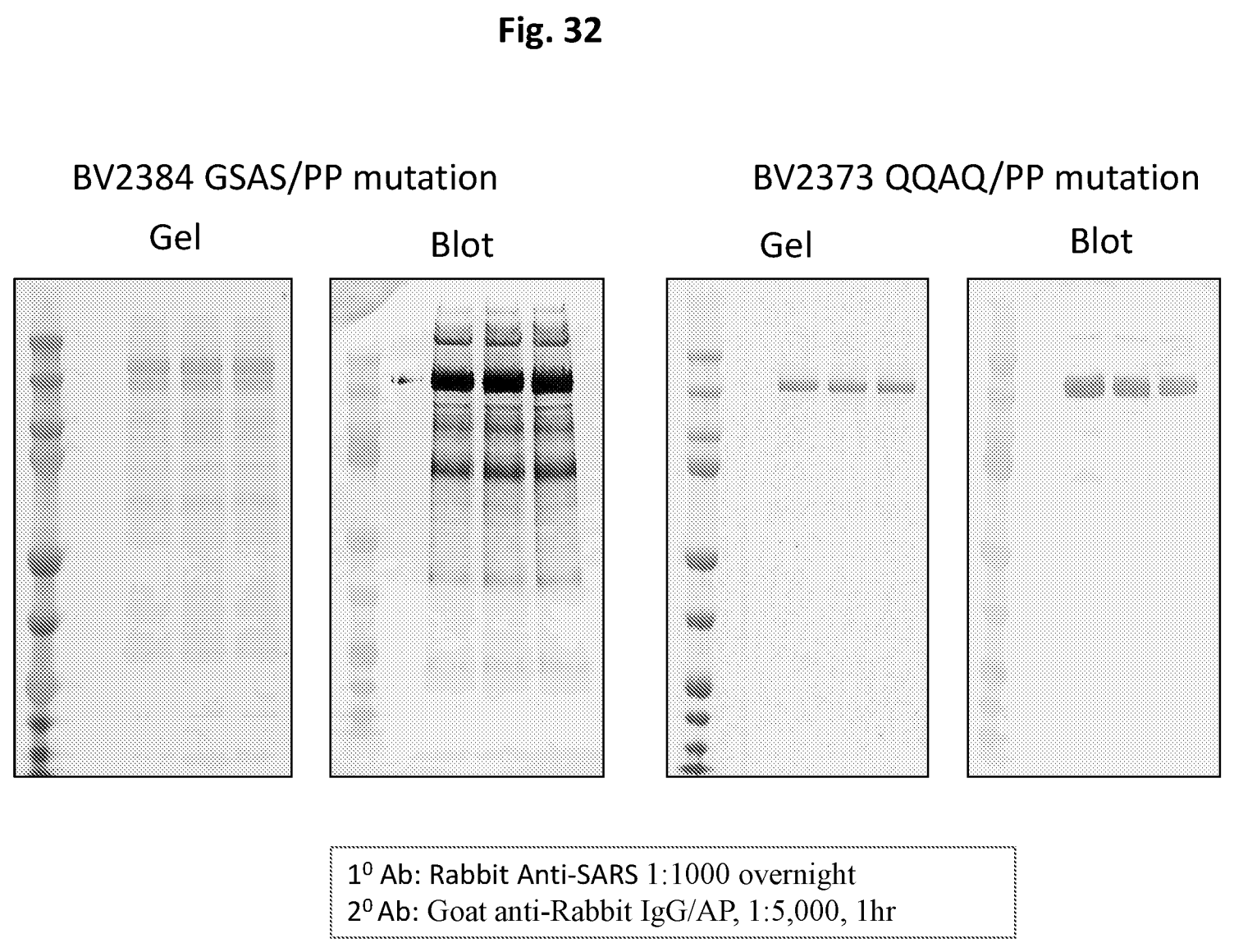

The stability of BV2384 (SEQ ID NO: 110) and BV2373 (SEQ ID NO: 87) were compared. BV2384 has a furin cleavage site sequence of GSAS (SEQ ID NO: 97), whereas BV2373 has a furin cleavage site of QQAQ (SEQ ID NO: 7). As demonstrated by SDS-PAGE and Western Blot, BV2384 showed extensive degradation in comparison to BV2373 (FIG. 32). Furthermore, scanning densitometry and recovery data demonstrate the unexpected loss of full length CoV S protein BV2384, lower purity, and recovery (FIG. 33) in comparison to BV2373 (FIG. 34).

Example 6

Immune Response in Cynomolgus Macaques

We assessed the immune response induced by BV2373 in a Cynomolgus macaque model of SARS-CoV-2 infection. Groups 1-6 were treated as shown in Table 4.

TABLE 4

| | | | | | |
|---|---|---|---|---|---|
| | Groups 1-6 of Cynomolgus macaque study | | | | |
| Group (N = 4) | BV2373 Dose | MATRIX-M ™ Dose | Immunization (Days) | Blood Draw (days) | Challenge (Day) |
| 1 | Placebo | — | 0, 21 | 0, 21, 33 | 35 |
| 2 | 2.5 µg | 25 µg | 0, 21 | 0, 21, 33 | 35 |
| 3 | 5 µg | 25 µg | 0 | 0, 21, 33 | 35 |
| 4 | 5 µg | 50 µg | 0, 21 | 0, 21, 33 | 35 |
| 5 | 5 µg | 50 µg | 0 | 0, 21, 33 | 35 |
| 6 | 25 µg | 50 µg | 0, 21 | 0, 21, 33 | 35 |

Figure 35A:
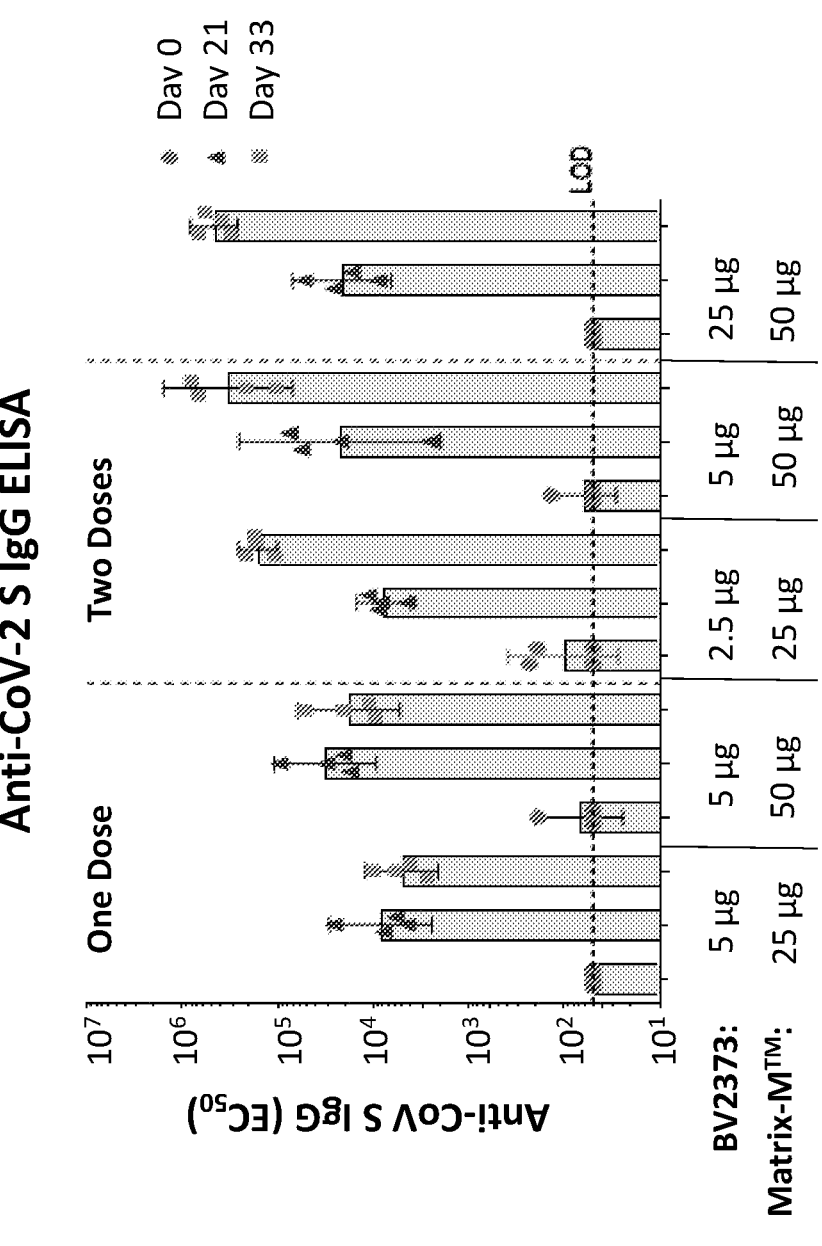
FIGS. 35A-B illustrates induction of anti-S antibodies (FIG. 35A) and neutralizing antibodies (FIG. 35B) in response to administration of BV2373 and MATRIX-M™. Cynomolgus macaques were administered one or two doses (Day 0 and Day 21) of 2.5 µg, 5 µg, or 25 µg of BV2373 with 25 µg or 50 µg MATRIX-M™ adjuvant. Controls received neither BV2373 or MATRIX-M™. Antibodies were measured at Days 21 and 33.
Figure 35B:
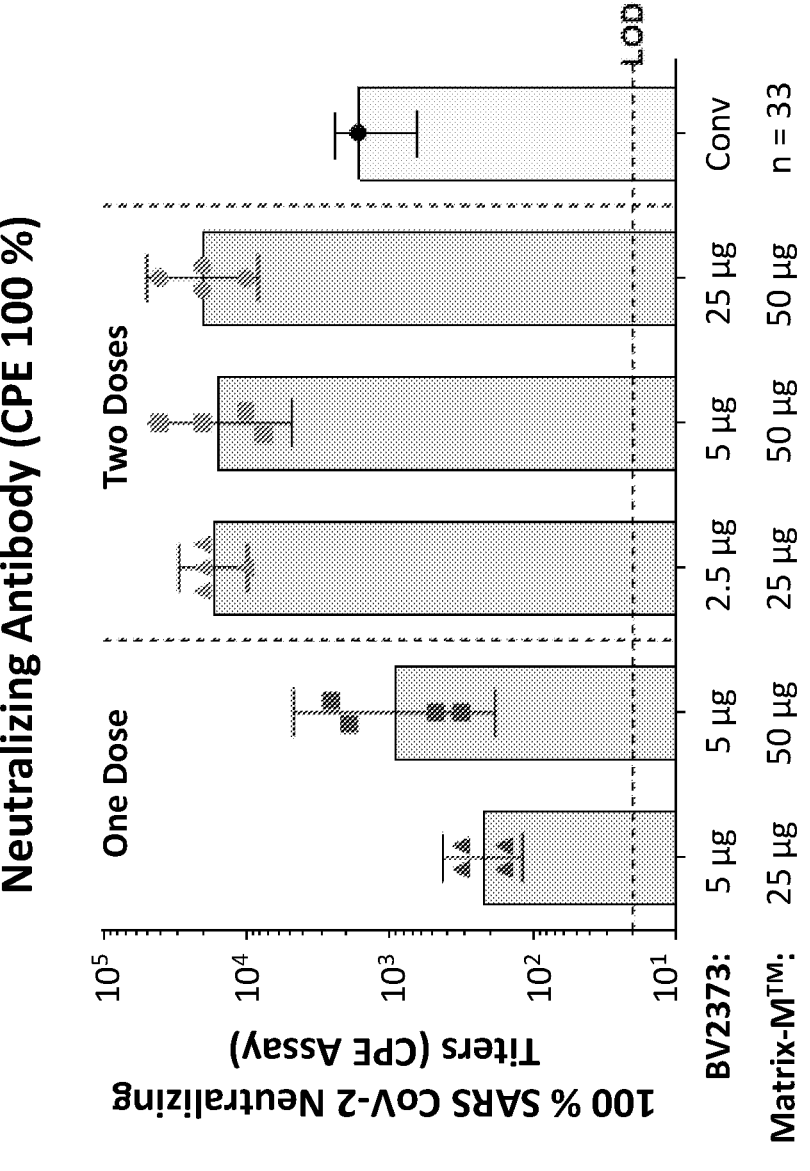
Figure 38A:
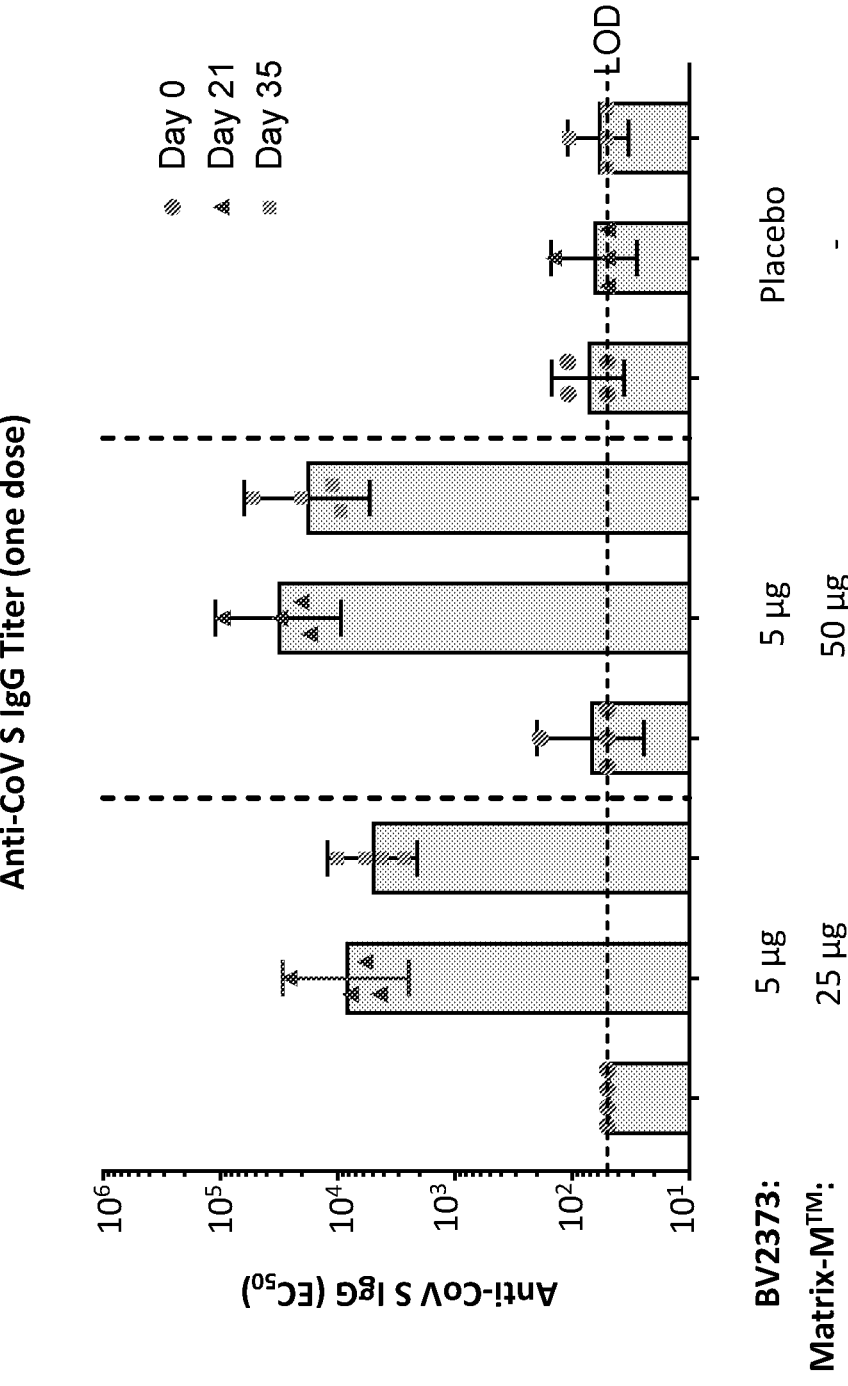
FIGS. 38A-B show anti-CoV S polypeptide IgG titers 21 days and 35 days after immunization of Cynomolgus macaques with one dose (FIG. 38A) or two doses of BV2373 and 25 µg or 50 µg of MATRIX-M™ (FIG. 38B).
Figure 38B:
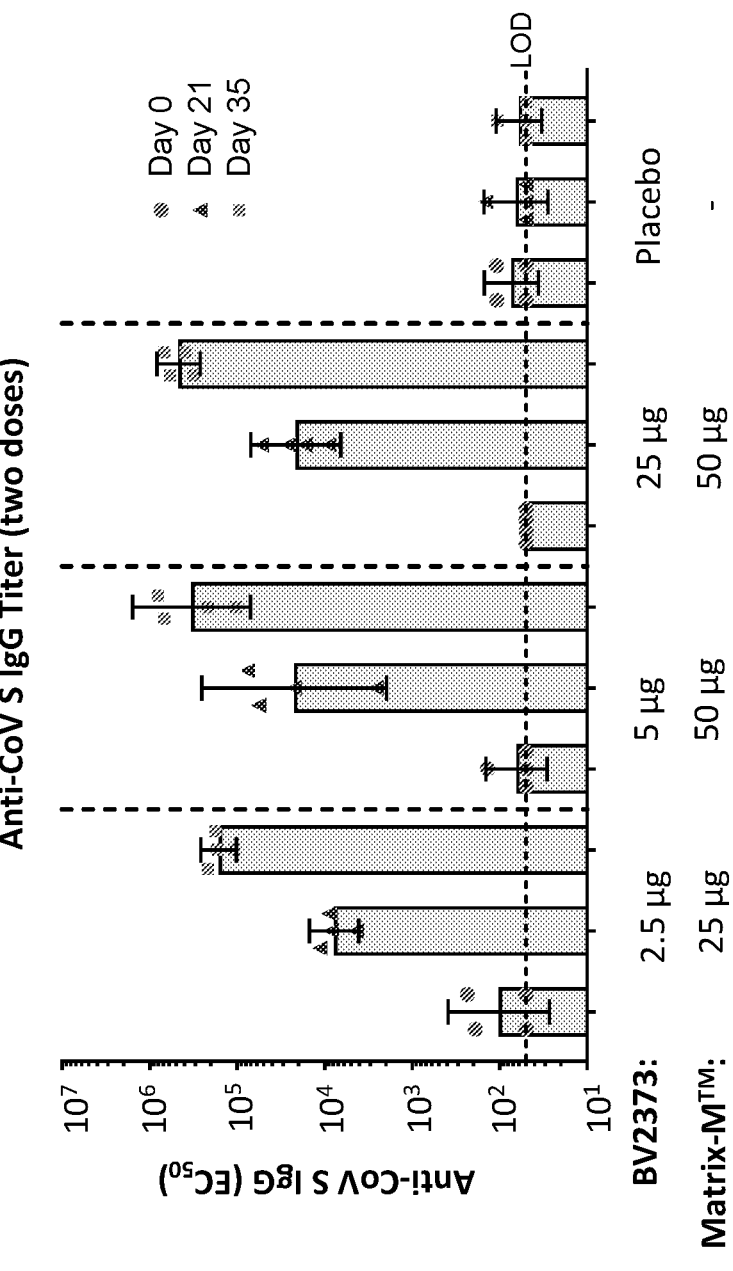
Figure 38C:
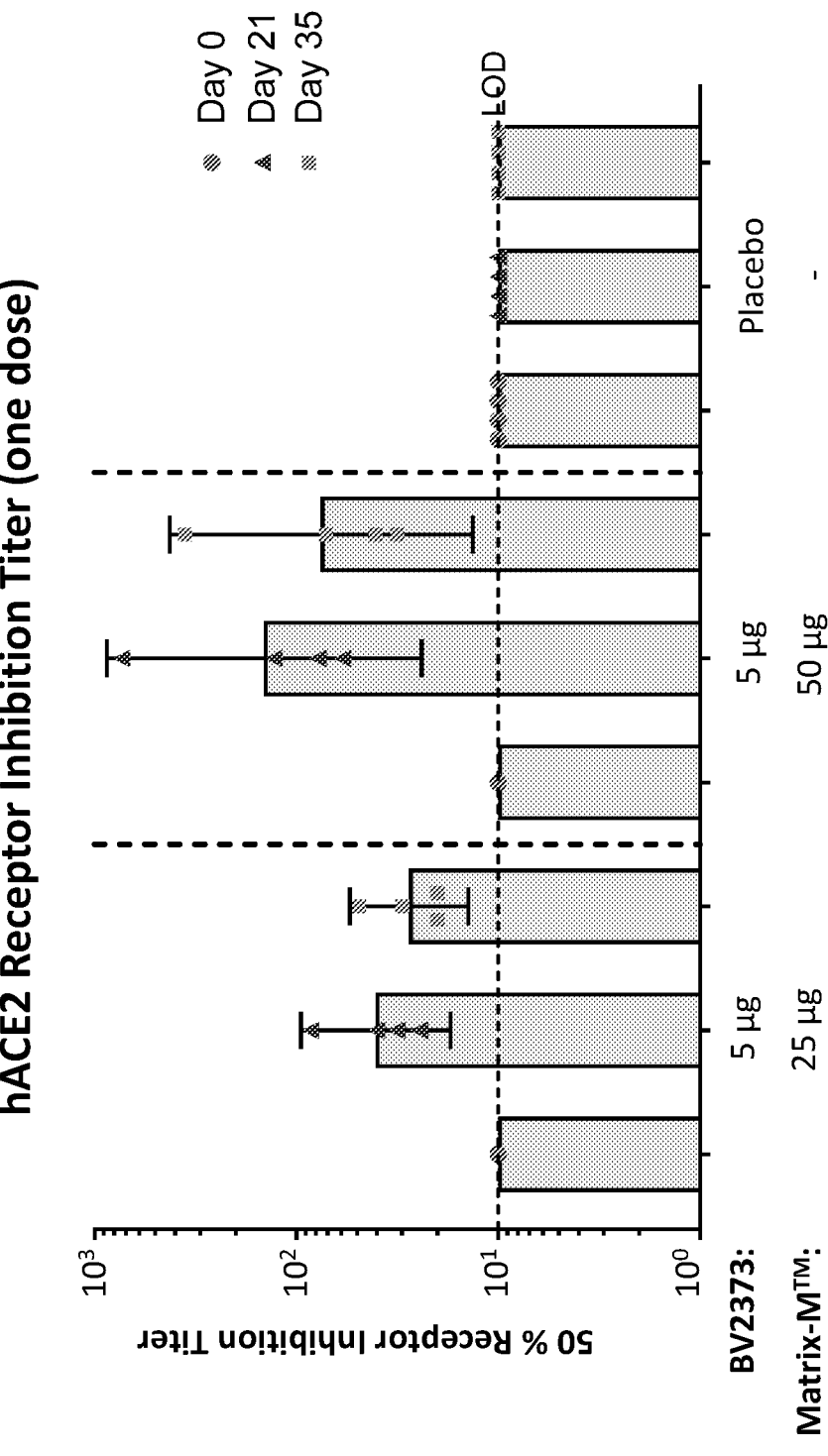
FIGS. 38C-38D shows the hACE2 inhibition titer of Cynomolgus macaques 21 days and 35 days after immunization of Cynomolgus macaques with one dose (FIG. 38C) or two doses of BV2373 (5 µg) and MATRIX-M™ (25 µg or 50 µg) (FIG. 38D).
Figure 38D:
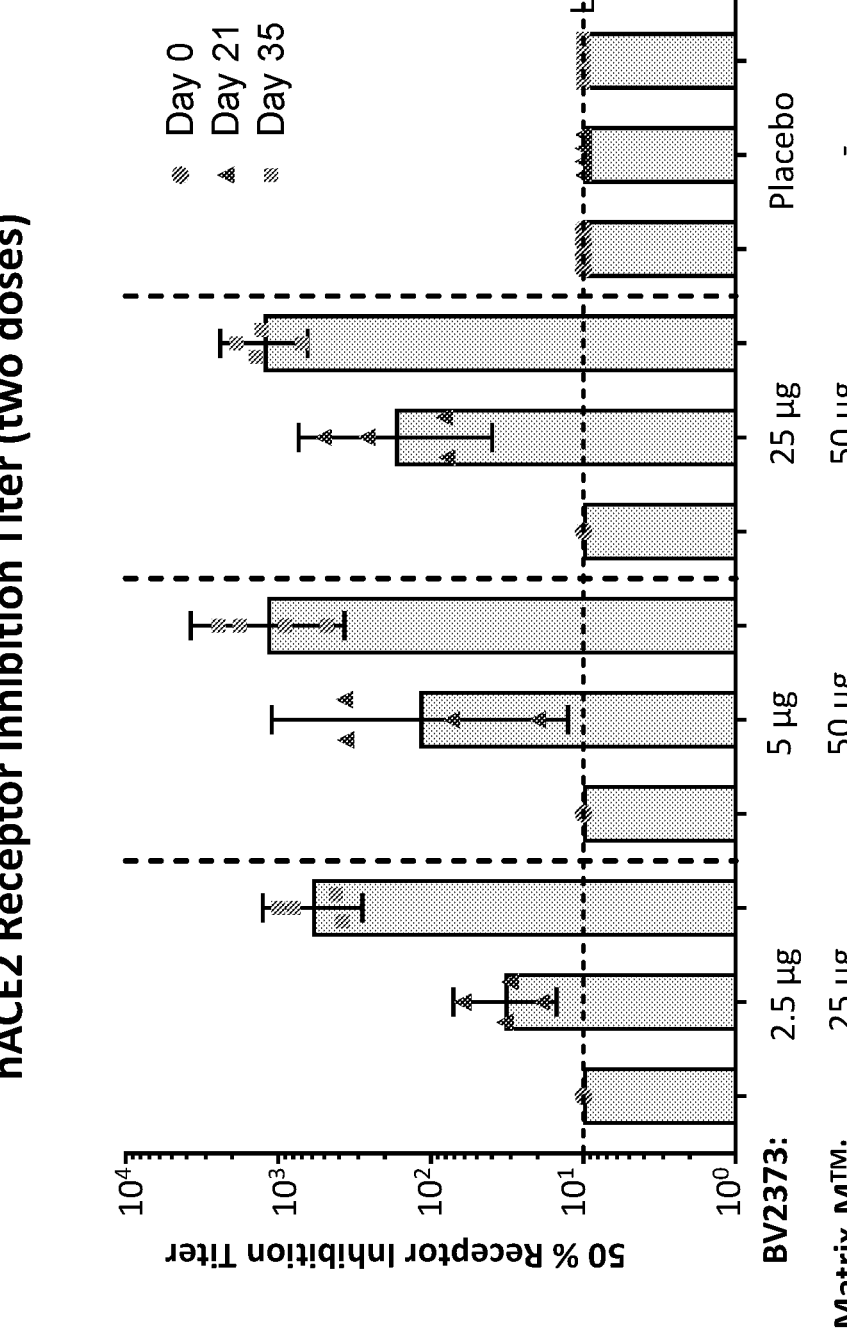
Figure 38E:
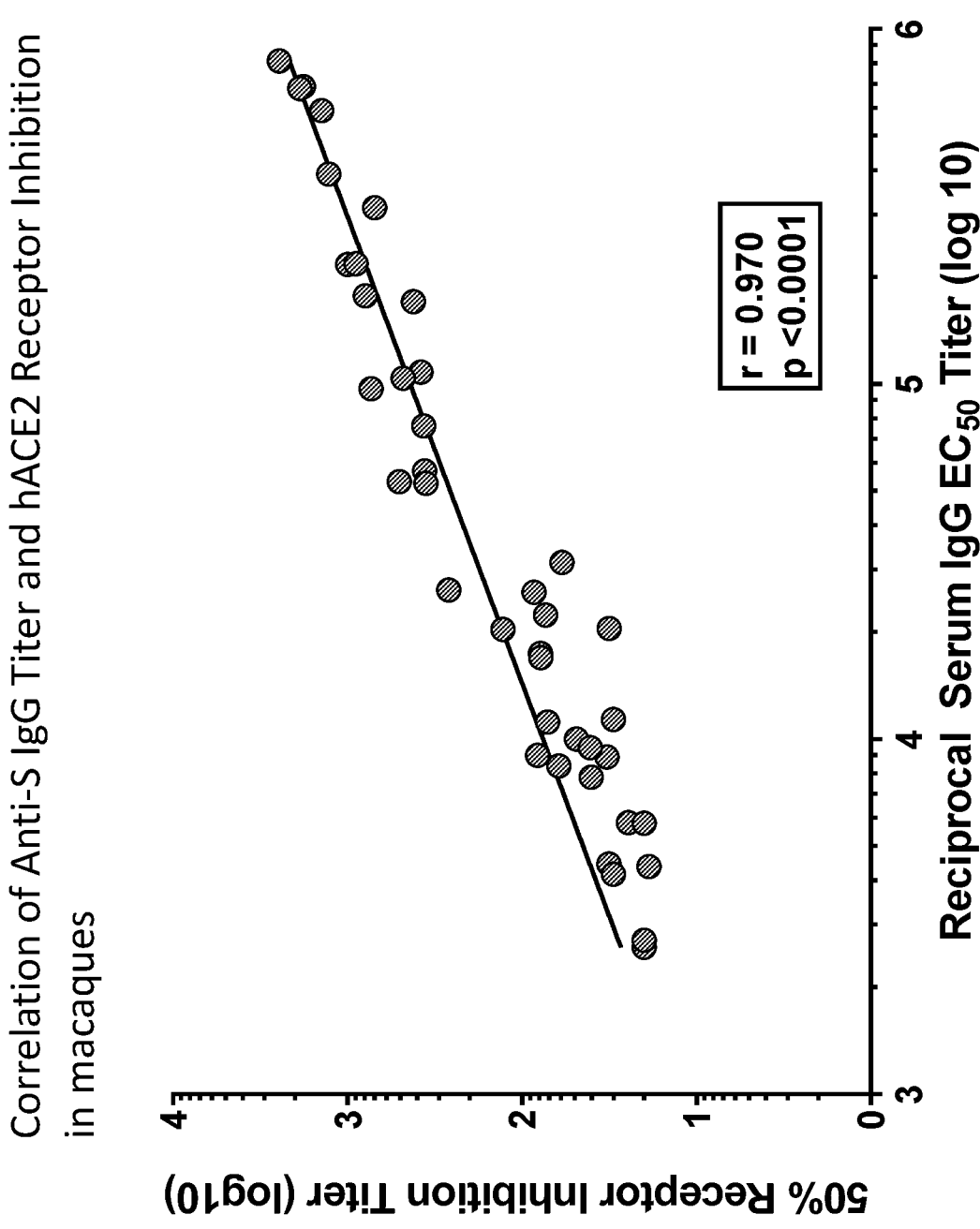
FIG. 38E shows the significant correlation between anti-CoV S polypeptide IgG titer and hACE2 inhibition titer in Cynomolgus macaques after administration of BV2373 and MATRIX-M™. Data is shown for Groups 2-6 of Table 4.
Figure 40A:
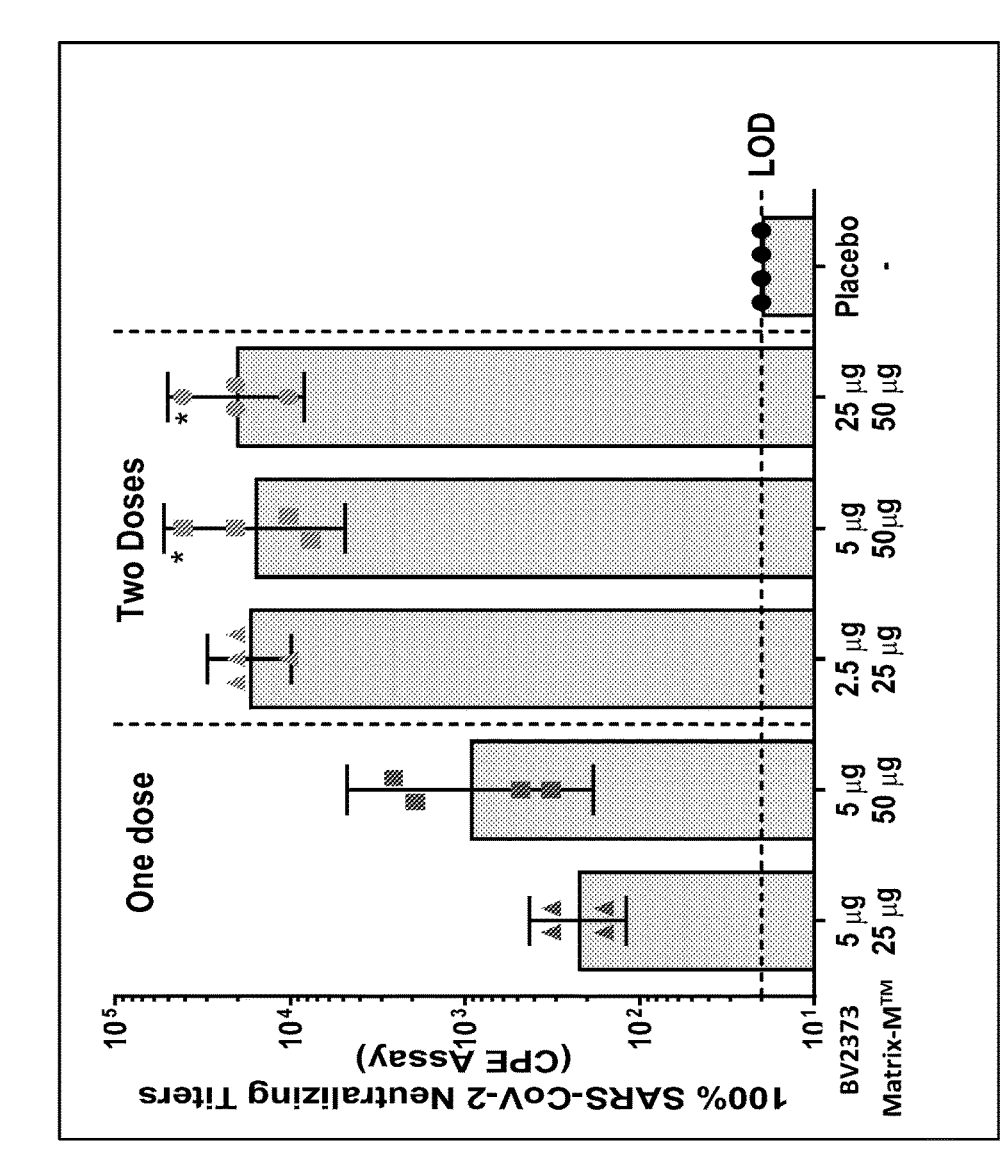
FIGS. 40A-B shows the SARS-CoV-2 neutralizing titers of Cynomolgus macaques immunized with BV2373 and MATRIX-M™ as determined by cytopathic effect (CPE) (FIG. 40A) and plaque reduction neutralization test (PRNT) (FIG. 40B).
Figure 40B:
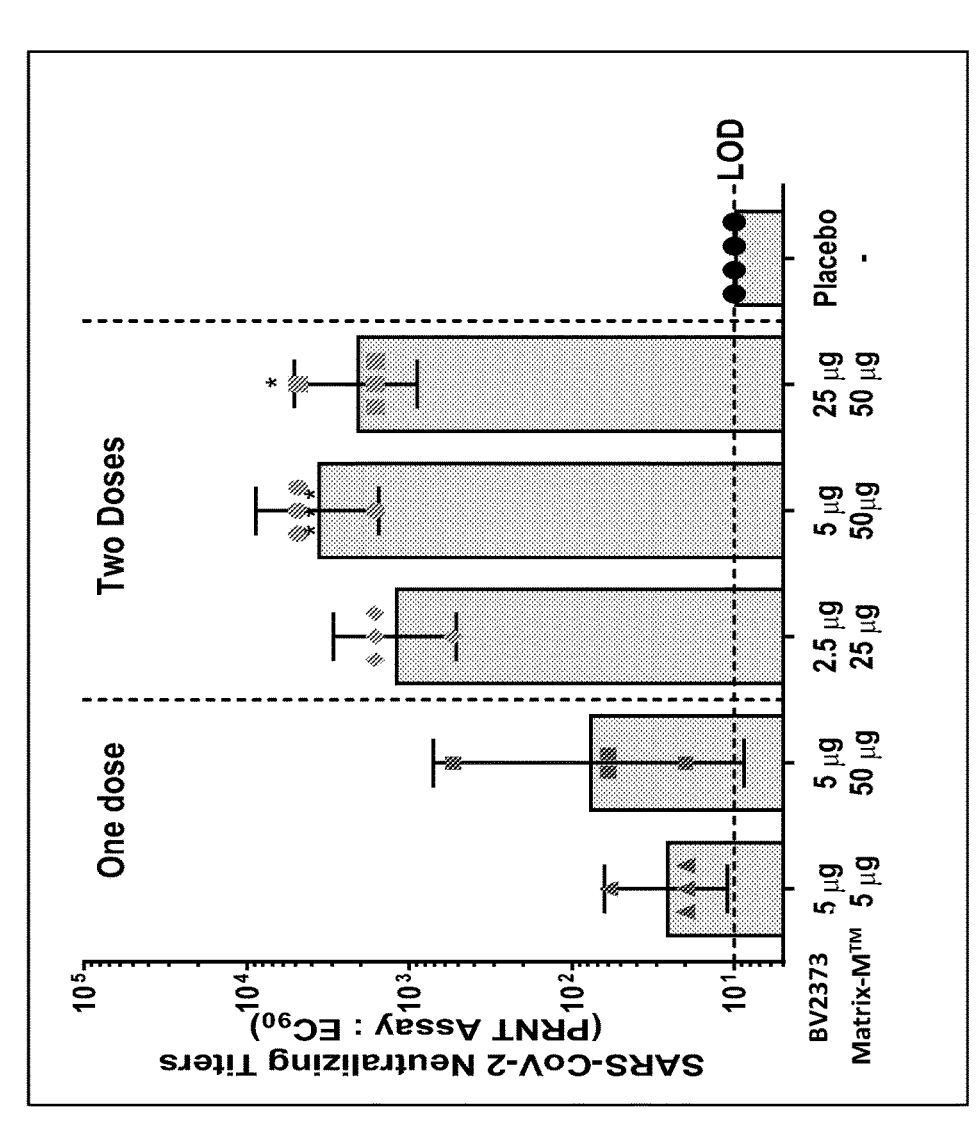

Administration of a vaccine comprising BV2373 resulted in the induction of anti-CoV-S antibodies (FIG. 35A) including neutralizing antibodies (FIG. 35B). Anti-CoV-S antibodies were induced after administration of one (FIG. 38A) or two doses (FIG. 38B) of BV2373. Administration of the vaccine comprising BV2373 also resulted in the production of antibodies that blocked binding of the CoV S protein to hACE2 (FIG. 38C and FIG. 38D). There was a significant correlation between anti-CoV S polypeptide IgG titer and hACE2 inhibition titer in Cynomolgus macaques after administration of BV2373 (FIG. 38E). The ability of BV2373 to induce the production of neutralizing antibodies was evaluated by cytopathic effect (CPE) (FIG. 40A) and plaque reduction neutralization test (PRNT) (FIG. 40B). The data revealed that vaccine formulations of Table 4 produced SARS-CoV-2 neutralizing titers, in contrast to the control.

Figure 39:
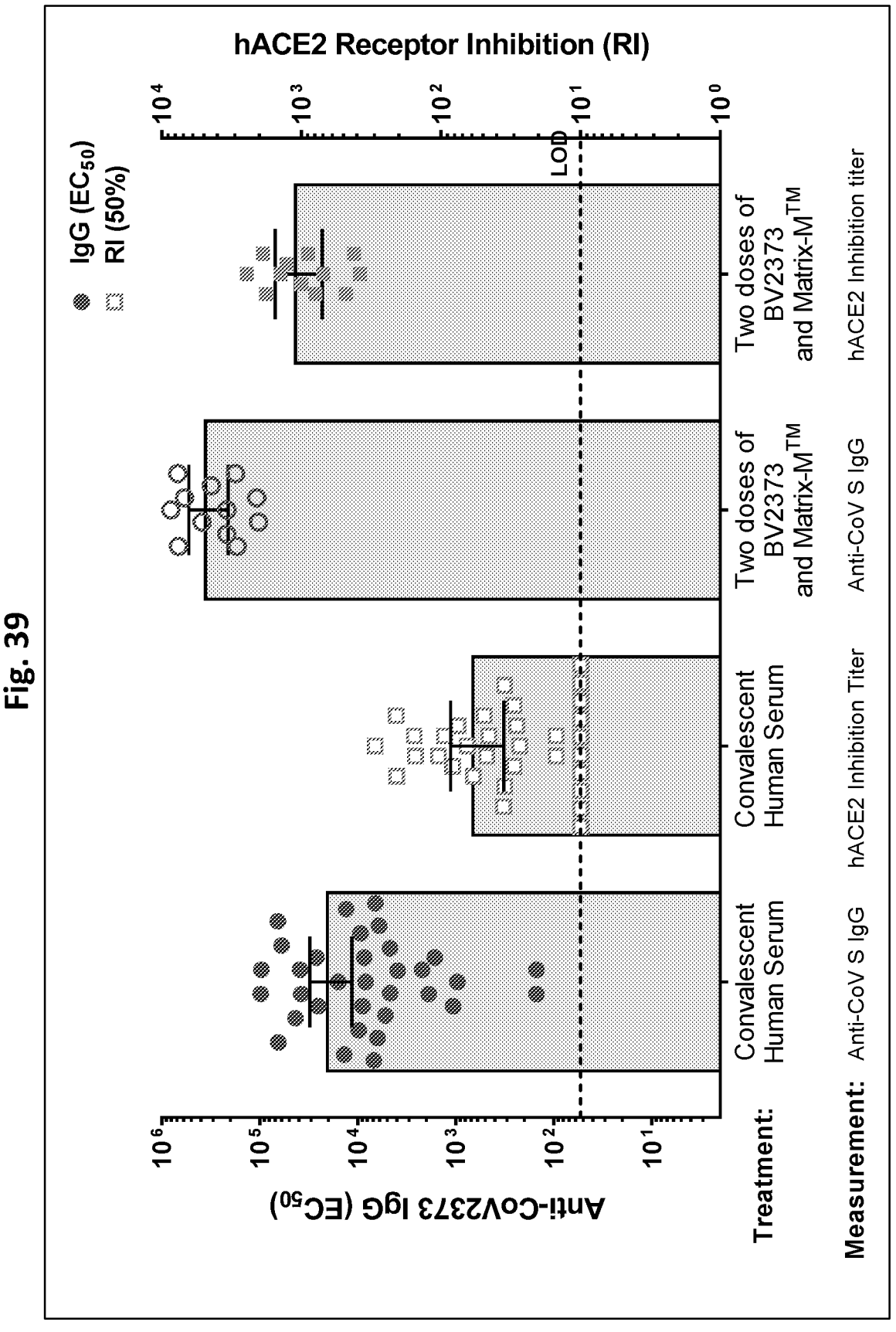
FIG. 39 shows the anti-CoV S polypeptide titers and hACE2 inhibition titer of Cynomolgus macaques 35 days after immunization with two doses of BV2373 and MATRIX-M™ or after immunization with convalescent human serum (Groups 2, 4, and 6) of Table 4. These data show that the anti-CoV S polypeptide and hACE2 inhibition titers of Cynomologus macaques immunized with BV2373 and MATRIX-M™ is superior to Cynomolgus macaques immunized with convalescent serum.

The vaccine comprising BV2373's ability to induce anti-CoV-S antibodies and antibodies that block binding of hACE2 to the CoV S protein in Cynomolgus macaques was compared to human convalescent serum. The data revealed that the BV2373 vaccine formulation induced superior anti-CoV S polypeptide and hACE2 inhibition titers as compared to human convalescent serum (FIG. 39).

Figure 36A:
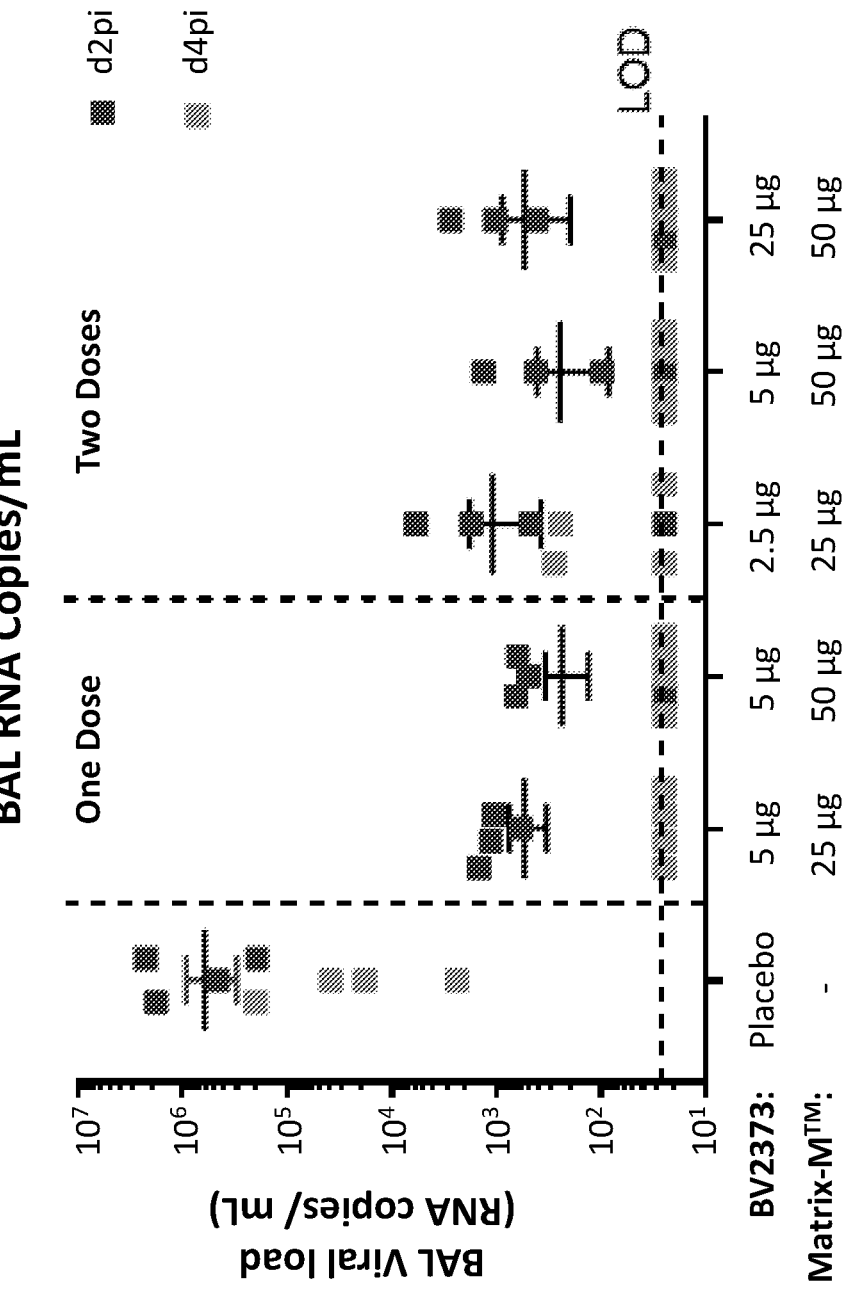
FIGS. 36A-B illustrates a decrease of SARS-CoV-2 viral replication by vaccine formulations disclosed herein as assessed in broncheoalveol lavage (BAL) in Cynomolgus macaques. Cynomolgus macaques were administered BV2373 and MATRIX-M™ as shown. Subjects were immunized Day 0 and in the groups with two doses Day 0 and Day 21. Subject animals were challenged Day 37 with $1\times10^4$ pfu SARS-CoV-2 virus. Viral RNA (FIG. 36A, corresponding to total RNA present) and viral sub-genomic RNA (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 µg. Sub-genomic RNA was not detected at either 2 Days or 4 days except for 1 subject, again at the lowest dose.
Figure 36B:
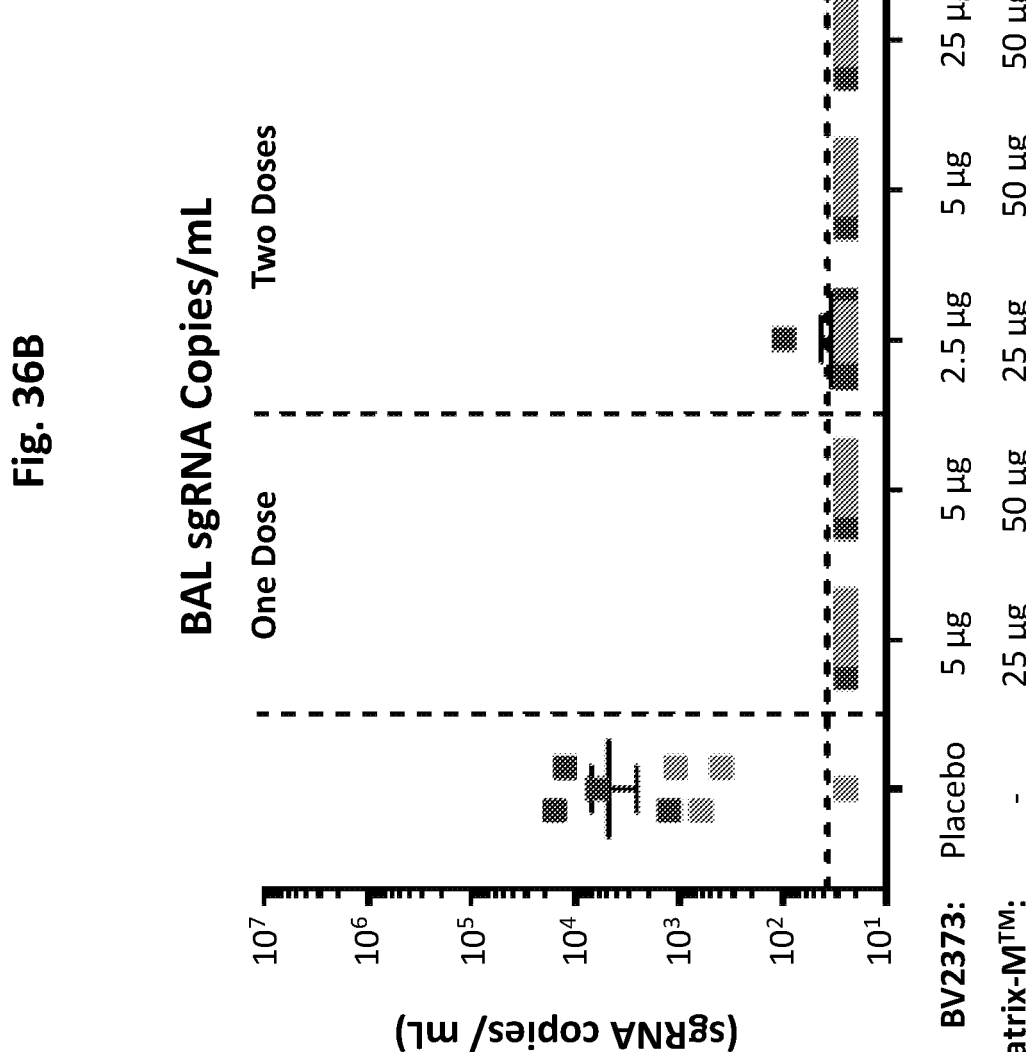
Figure 37A:
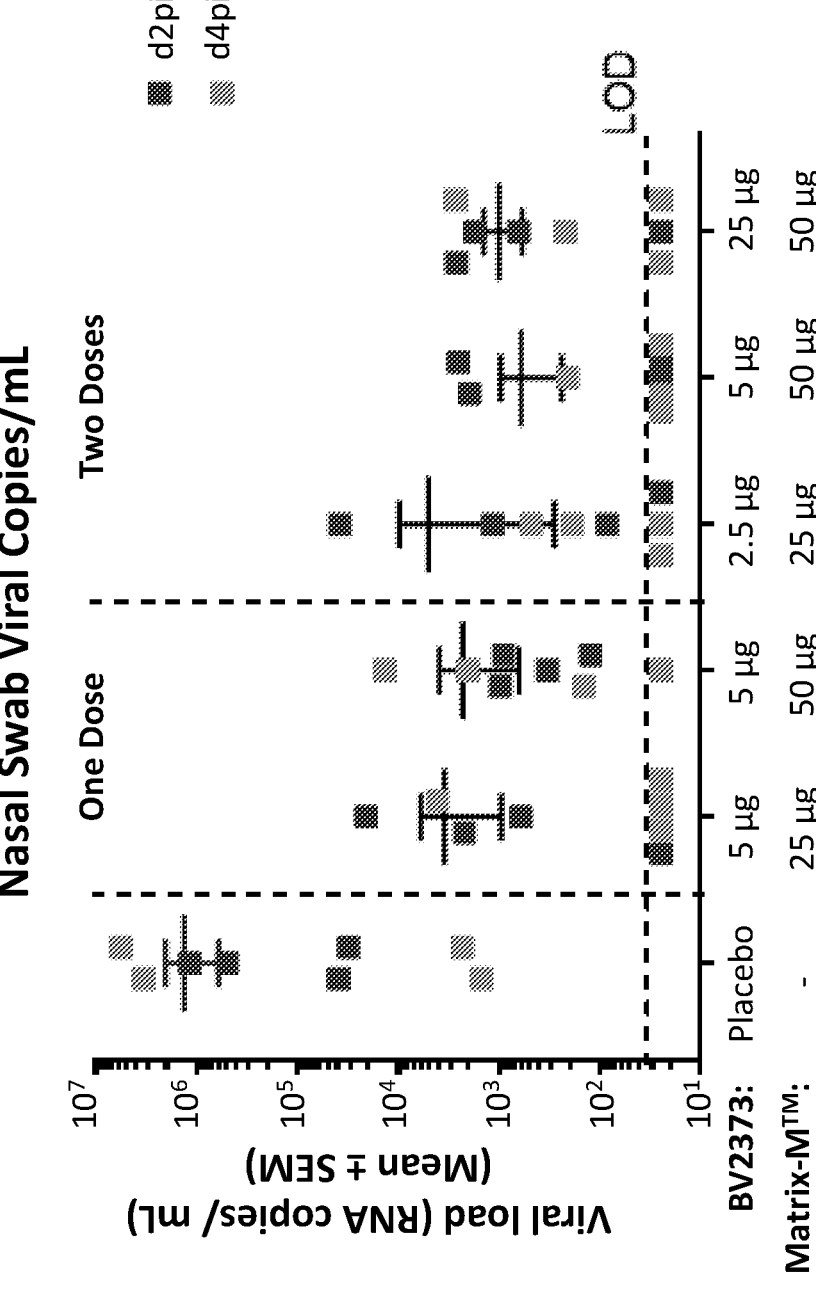
FIGS. 37A-B illustrates a decrease of SARS-CoV-2 viral replication by vaccine formulations disclosed herein as assessed in nasal swab in Cynomolgus macaques. Cynomolgus macaques were administered BV2373 with MATRIX-M™ as shown. Subjects were immunized Day 0 and in the groups with two doses Day 0 and Day 21. Subject animals were challenged Day 37 with $1\times10^4$ SARS-CoV-2 virus. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.
Figure 37B:
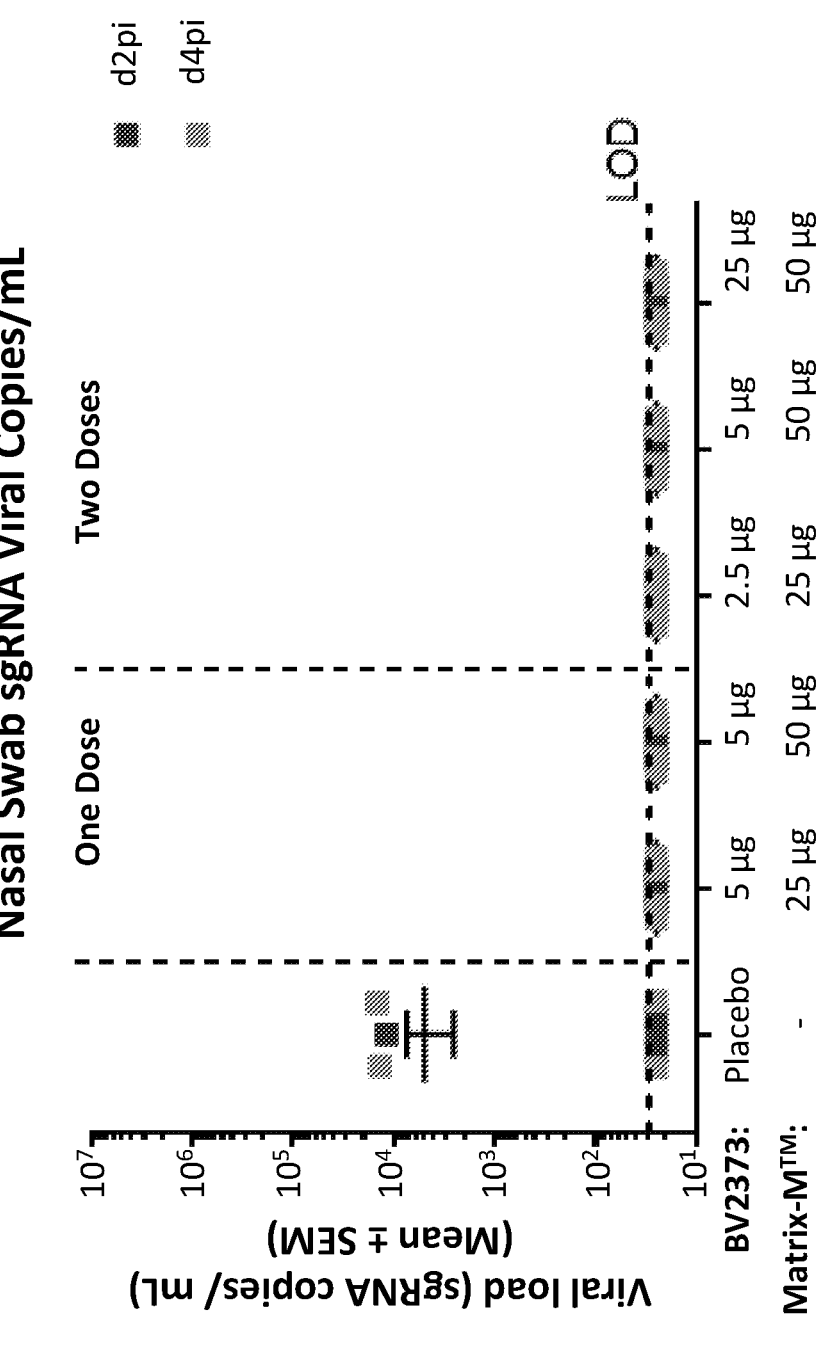

The BV2373 vaccine formulation also caused a decrease of SARS-CoV-2 viral replication (FIGS. 36A-B). Viral RNA (FIG. 36A, corresponding to total RNA present) and viral sub-genomic RNA (sgRNA) (FIG. 36B, corresponding to replicating virus) levels were assessed in bronchiolar lavage (BAL) at 2 days and 4 days post-challenge with infectious virus (d2pi and d4pi). Most subjects showed no viral RNA. At Day 2 small amounts of RNA were measured in some subjects. By Day 4, no RNA was measured except for two subjects at the lowest dose of 2.5 µg. Sub-genomic RNA was not detected at either 2 days or 4 days except for 1 subject, again at the lowest dose. Viral RNA (FIG. 37A) and viral sub-genomic (sg) RNA (FIG. 37B) were assessed by nasal swab at 2 days and 4 days post-infection (d2pi and d4pi). Most subjects showed no viral RNA. At Day 2 and Day 4 small amounts of RNA were measured in some subjects. Sub-genomic RNA was not detected at either 2 Days or 4 days. Subjects were immunized Day 0 and in the groups with two doses Day 0 and Day 21. These data show that the vaccine decreases nose total virus RNA by 100-1000 fold and sgRNA to undetectable levels, and confirm that immune response to the vaccine will block viral replication and prevent viral spread.

Example 7

Evaluation of CoV S Polypeptide Nanoparticle Vaccines in Humans

Figure 41:
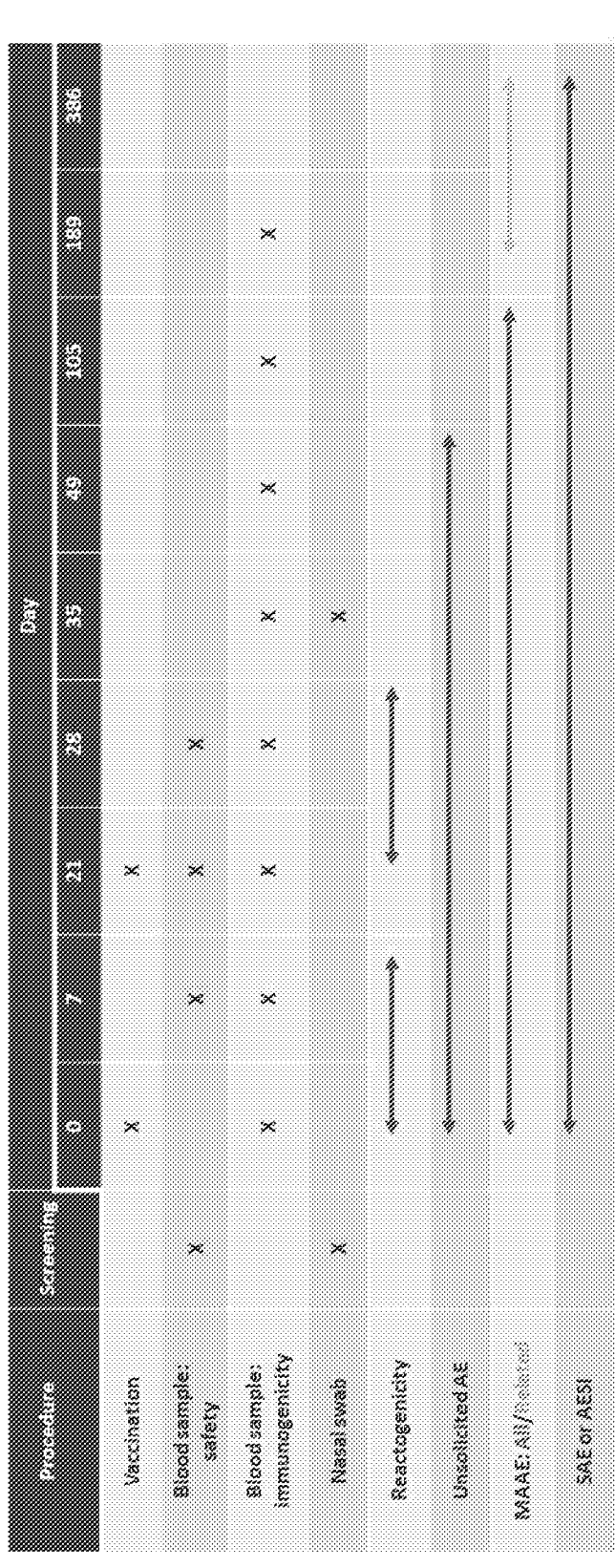
FIG. 41 shows administration timings of a clinical trial that evaluated the safety and efficacy of a vaccine comprising BV2373 and optionally MATRIX-M™. AESI denotes an adverse event of special interest. MAEE denotes a medically attended adverse event, and SAE denotes a serious adverse event.

We assessed the safety and efficacy of a vaccine comprising BV2373 in a randomized, observer-blinded, placebo-controlled Phase 1 clinical trial in 131 healthy participants 18-59 years of age. Participants were immunized with two intramuscular injections, 21 days apart. Participants received BV2373 with or without MATRIX-M™ (n=106) or placebo (n=25). Groups A-E were treated as shown in Table 5. FIG. 41 shows a timeline of the evaluation of clinical endpoints.

TABLE 5

| | | | | | | |
|---|---|---|---|---|---|---|
| | Groups A-E of Phase 1 Human Study | | | | | |
| | | | Day 0 | | Day 21 (+5 days) | |
| | Participants | | MATRIX- | | MATRIX- | |
| Group (N = 25) | Random-ized | Sen-tinel | BV2373 Dose | M ™ Dose | BV2373 Dose | M ™ Dose |
| A | 25 | — | 0 µg | 0 µg | 0 µg | 0 µg |
| B | 25 | — | 25 µg | 0 µg | 25 µg | 0 µg |
| C | 25 | 3 | 5 µg | 50 µg | 5 µg | 50 µg |
| D | 25 | 3 | 25 µg | 50 µg | 25 µg | 50 µg |
| E | 25 | — | 25 µg | 50 µg | 0 µg | 0 µg |

Figure 42A:
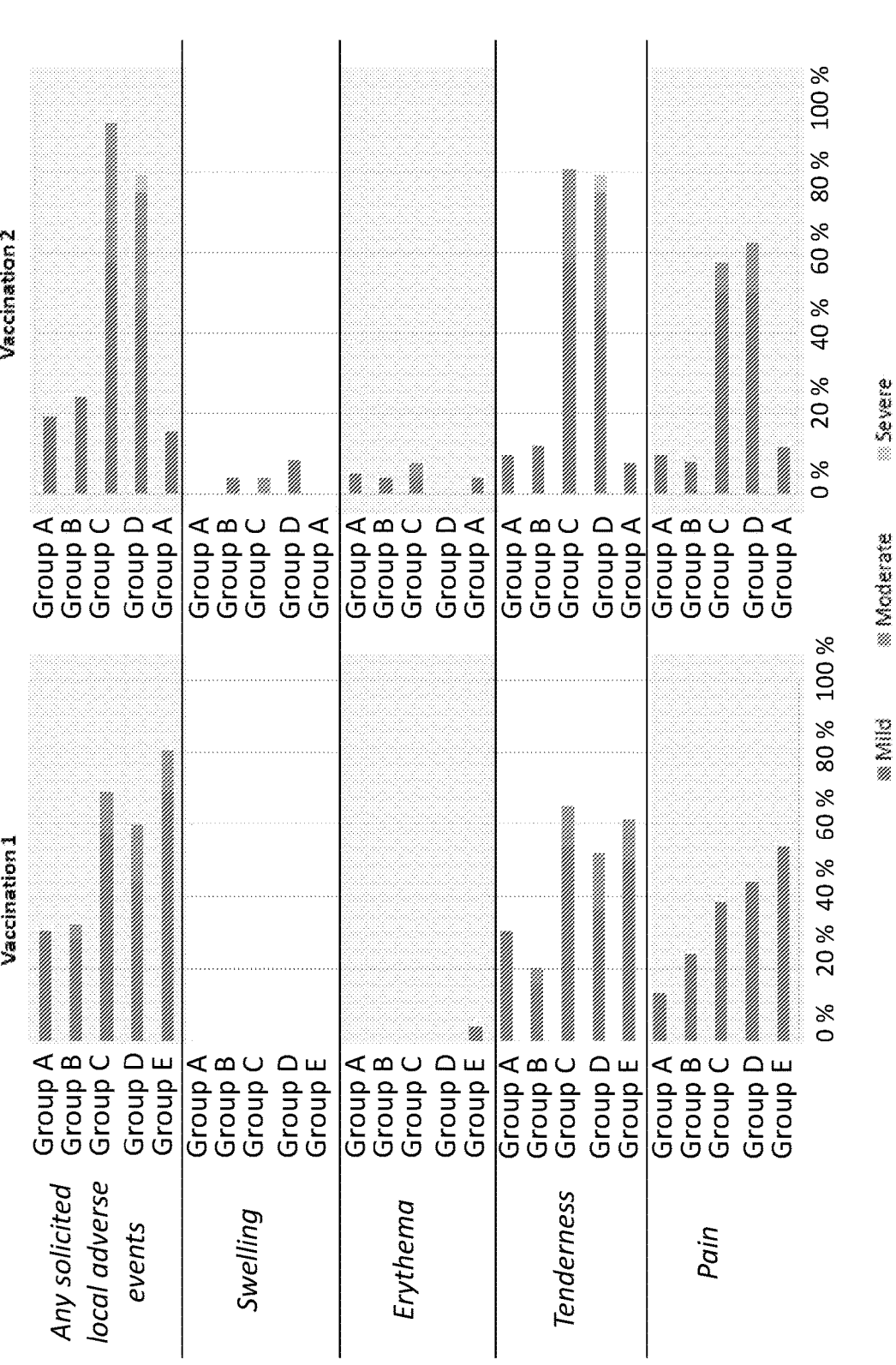
FIGS. 42A-B show the local (FIG. 42A) and systemic adverse events (FIG. 42B) experienced by patients in a clinical trial which evaluated a vaccine comprising BV2373 and MATRIX-M™. Groups A-E are identified in Table 5. The data shows that the vaccine was well tolerated and safe.
Figure 42B:
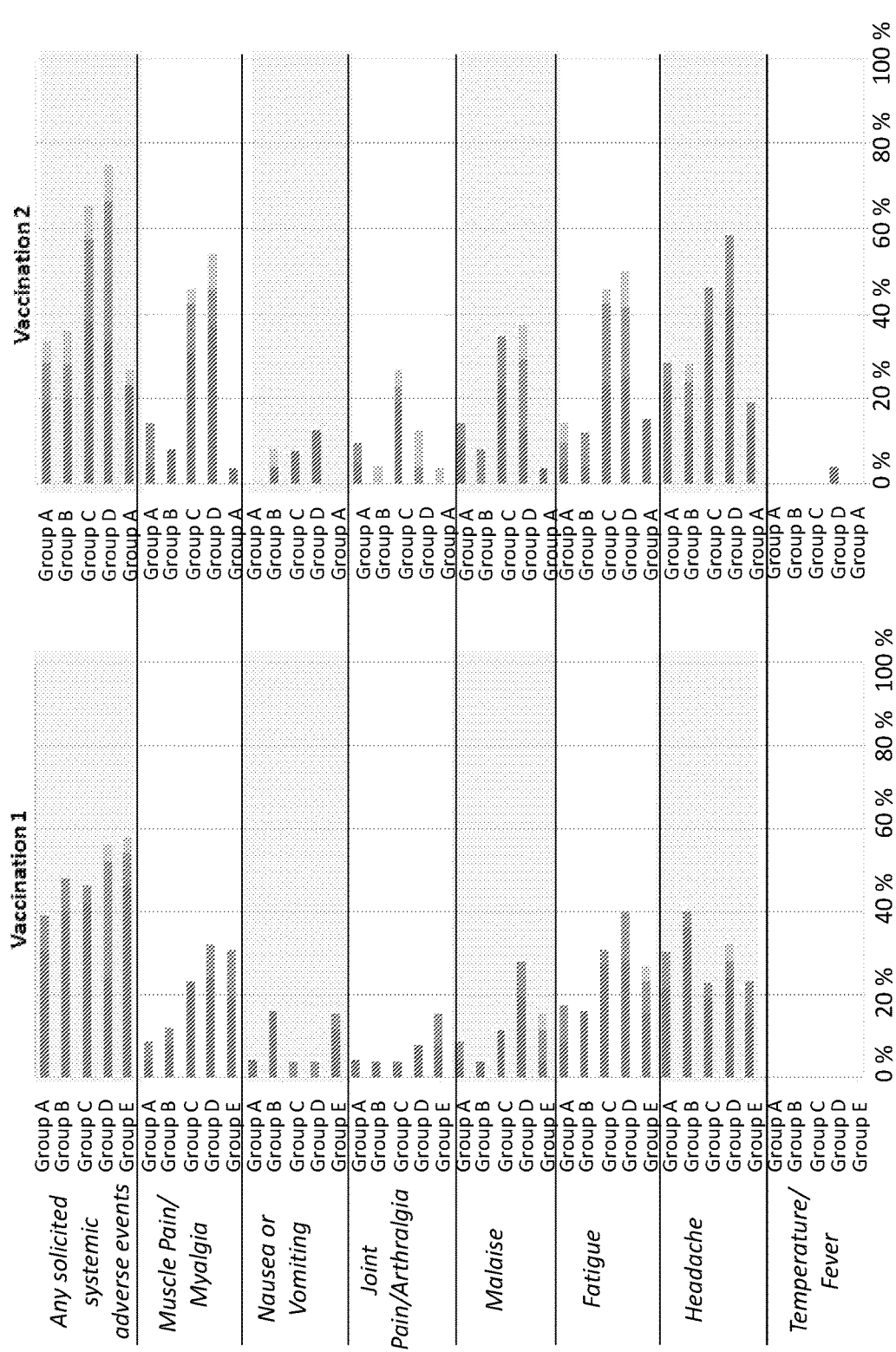

Overall reactogenicity was mild, and the vaccinations were well tolerated. Local reactogenicity was more frequent in patients treated with BV2373 and MATRIX-M™ (FIGS. 42A-B).

Figure 43A:
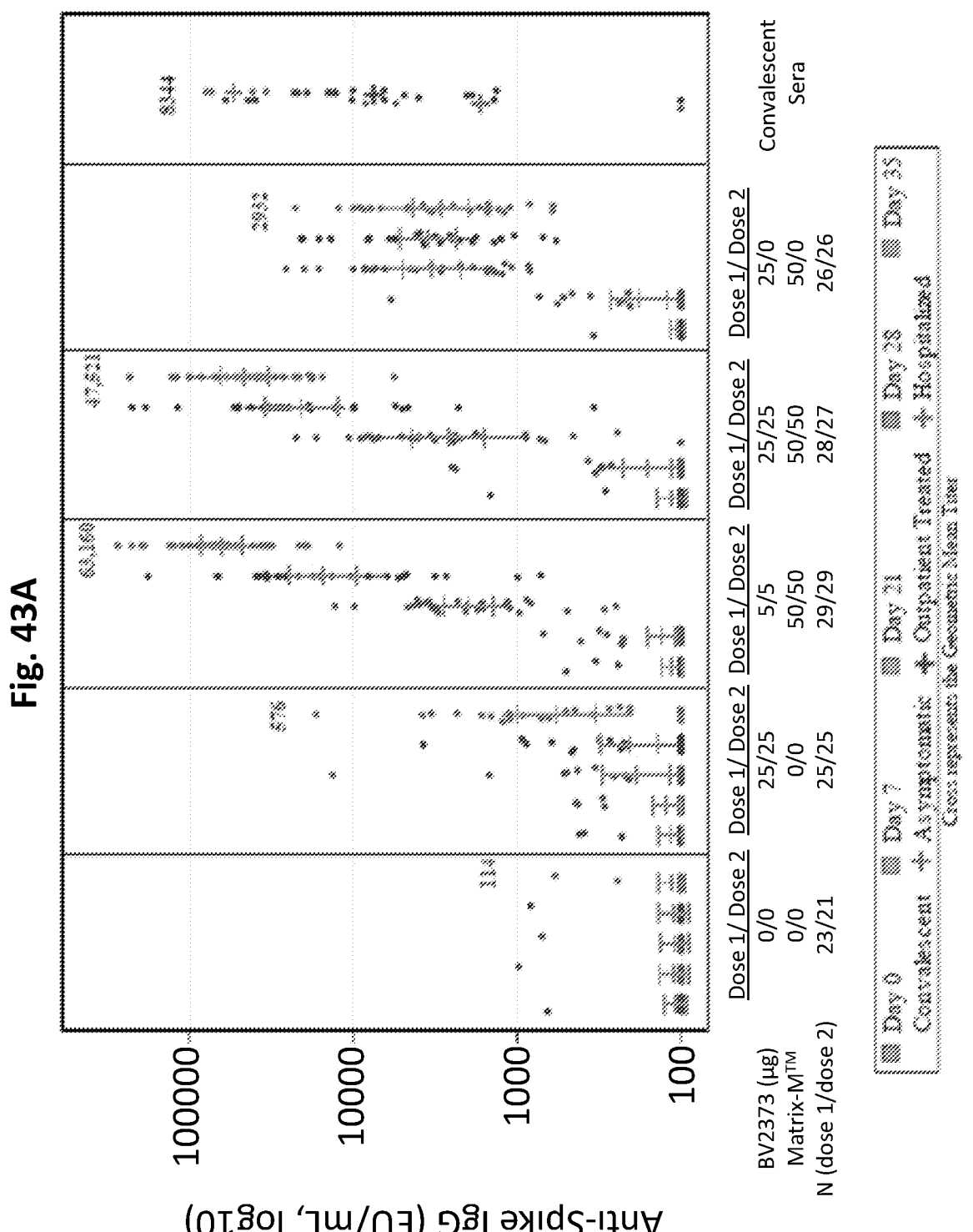
FIGS. 43A-B show the anti-CoV S polypeptide IgG (FIG. 43A) and neutralization titers (FIG. 43B) 21 days and 35 days after immunization of participants in a clinical trial which evaluated a vaccine comprising BV2373 and MATRIX-M™. Horizontal bars represent interquartile range (IRQ) and median area under the curve, respectively. Whisker endpoints are equal to the maximum and minimum values below or above the median±1.5 times the IQR. The convalescent serum panel includes specimens from PCR-confirmed COVID-19 participants from Baylor College of Medicine (29 specimens for ELISA and 32 specimens for microneutralization (MN $IC_{>99}$). Severity of COVID-19 is denoted as a red mark for hospitalized patients (including intensive care setting), a blue mark for outpatient-treated patients (sample collected in emergency department), and a green mark for asymptomatic (exposed) patients (sample collected from contact/exposure assessment).

The immunogenicity of BV2373 with and without MATRIX-M™ was evaluated. 21 days after vaccination, anti-CoV-S antibodies were detected for all vaccine regimens (FIG. 43A). Geometric mean fold rises (GMFR) in vaccine regimens comprising MATRIX-M™ exceeded those induced by unadjuvanted BV2373.? days after a second vaccination (day 28), the anti-CoV-S titer increased an additional eight-fold over responses seen with first vaccination and within 14 days (Day 35) responses had more than doubled yet again, achieving GMFRs approximately 100-fold over those observed with BV2373 alone. A single vaccination with BV2373/MATRIX-M™ achieved similar anti-CoV-S titer levels to those in asymptomatic (exposed) COVID-19 patients. A second vaccination achieved GMEU levels that exceeded convalescent serum from outpatient-treated COVID-19 patients by six-fold, achieved levels similar to convalescent serum from patients hospitalized with COVID-19, and exceeded overall convalescent serum anti-CoV-S antibodies by nearly six-fold. The responses in the two-dose 5-µg and 25-µg BV2373/MATRIX-M™ regimens were similar. This highlights the ability of the adjuvant (MATRIX-M™) to enable dose sparing.

Figure 43B:
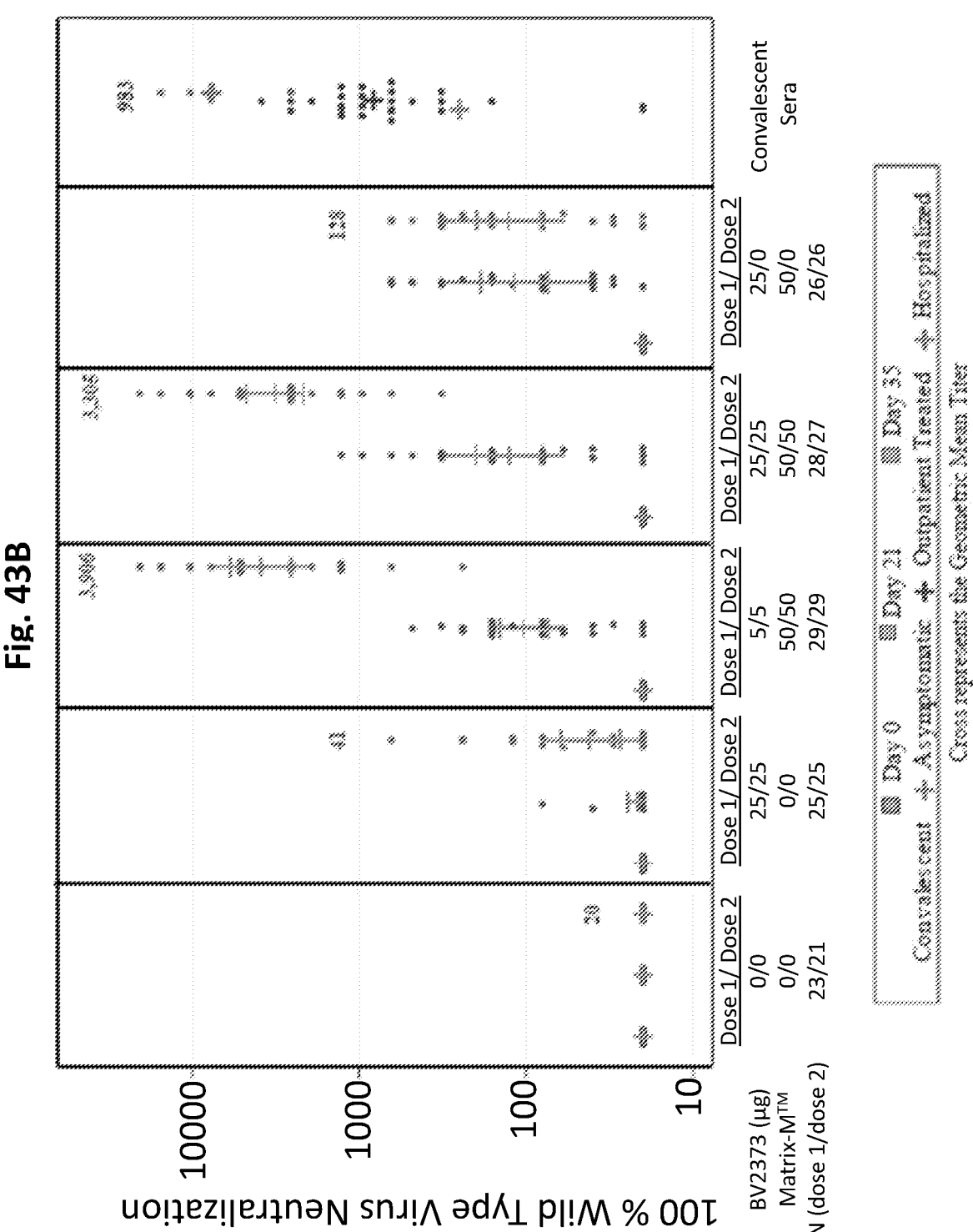

Neutralizing antibodies were induced in all groups treated with BV2373 (FIG. 43B). Groups treated with BV2373 and MATRIX-M™ regimens exhibited an approximately five-fold GMFR than groups treated with BV2373 alone (FIG. 43B). Second vaccinations with adjuvant had a profound effect on neutralizing antibody titers—inducing >100 fold rise over single vaccinations without adjuvant. When compared to convalescent serum, second vaccinations with BV2373/MATRIX-M™ achieved GMT levels four-fold greater than outpatient-treated COVID-19 patients, levels spanning those of patients hospitalized with COVID-19, and exceeded overall convalescent serum GMT by four fold.

Convalescent serum, obtained from COVID-19 patients with clinical symptoms requiring medical care, demonstrated proportional anti-CoV-S IgG and neutralization titers that increased with illness severity (FIGS. 43A-B).

Figure 44A:
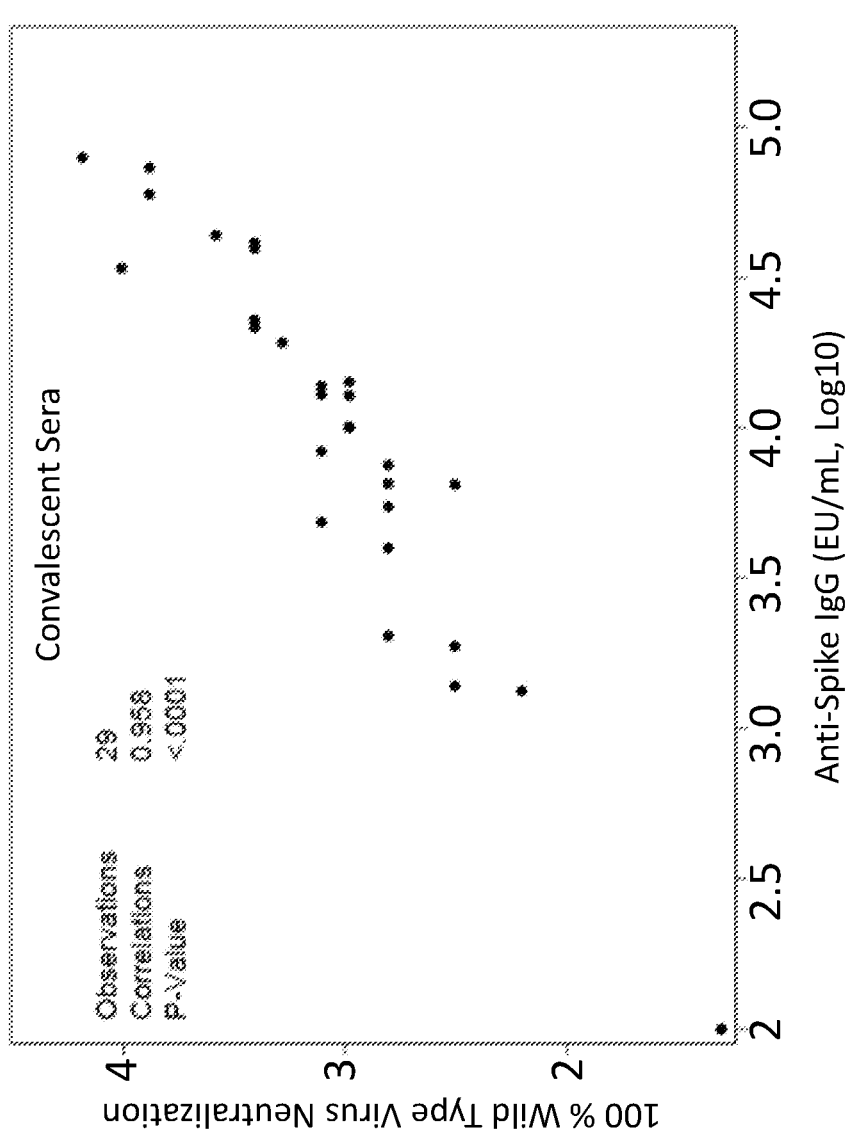
FIGS. 44A-C shows the correlation between anti-CoV S polypeptide IgG and neutralizing antibody titers in patients administered convalescent sera (FIG. 44A), two 25 µg doses of BV2373 (FIG. 44B), and two doses (5 µg and 25 µg) of BV2373 with MATRIX-M™ (FIG. 44C). A strong correlation was observed between neutralizing antibody titers and anti-CoV-S IgG titers in patients treated with convalescent sera or with adjuvanted BV2373, but not in patients treated with BV2373 in the absence of adjuvant.
Figure 44B:
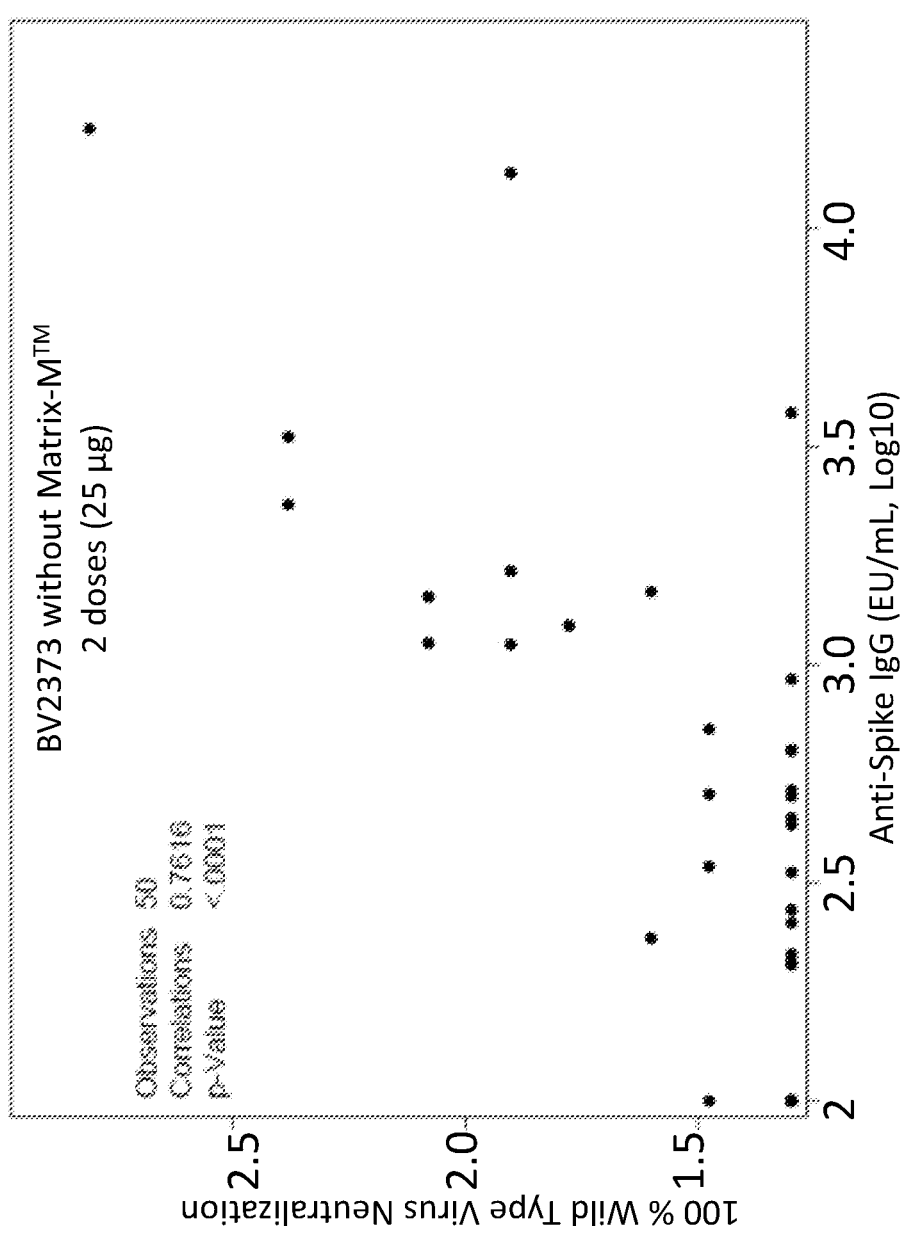
Figure 44C:
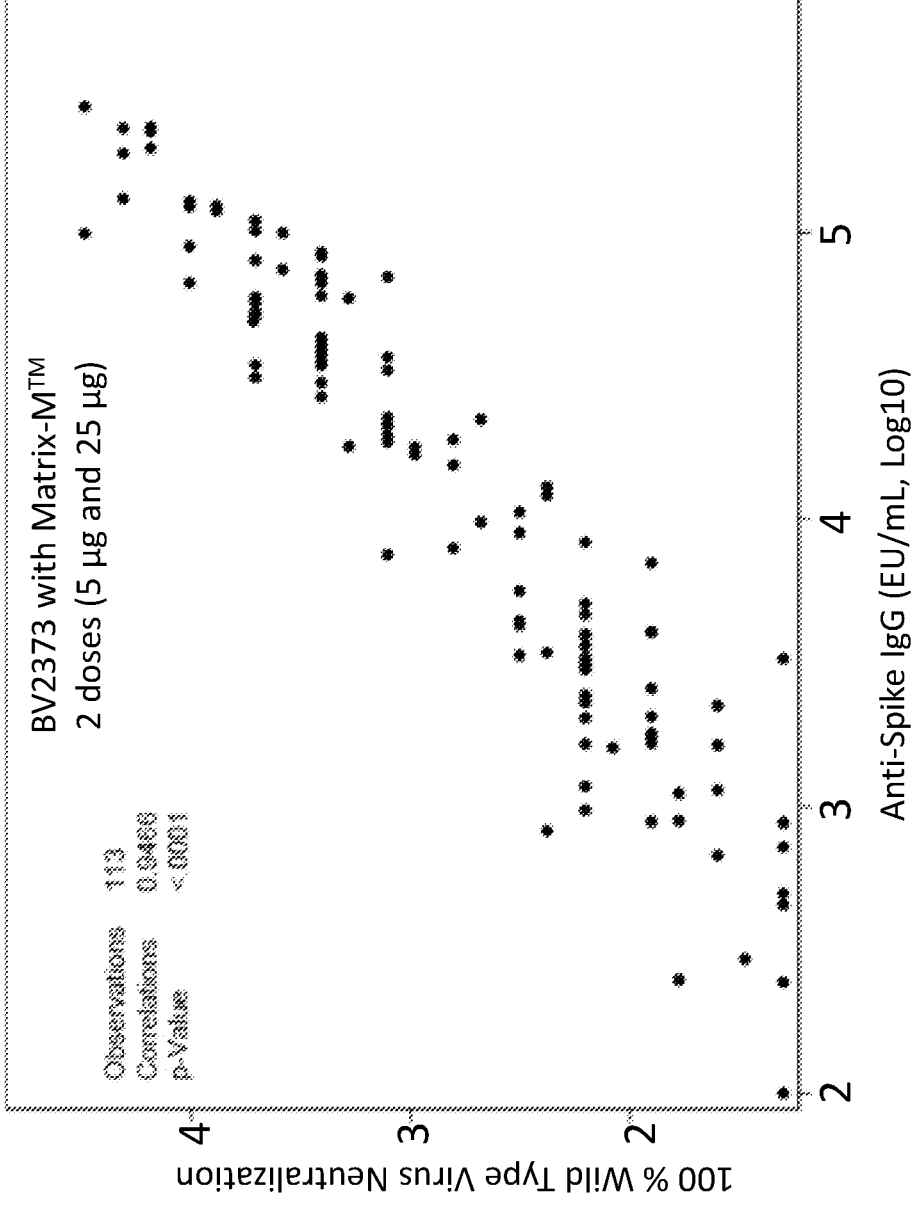
Figure 45B:
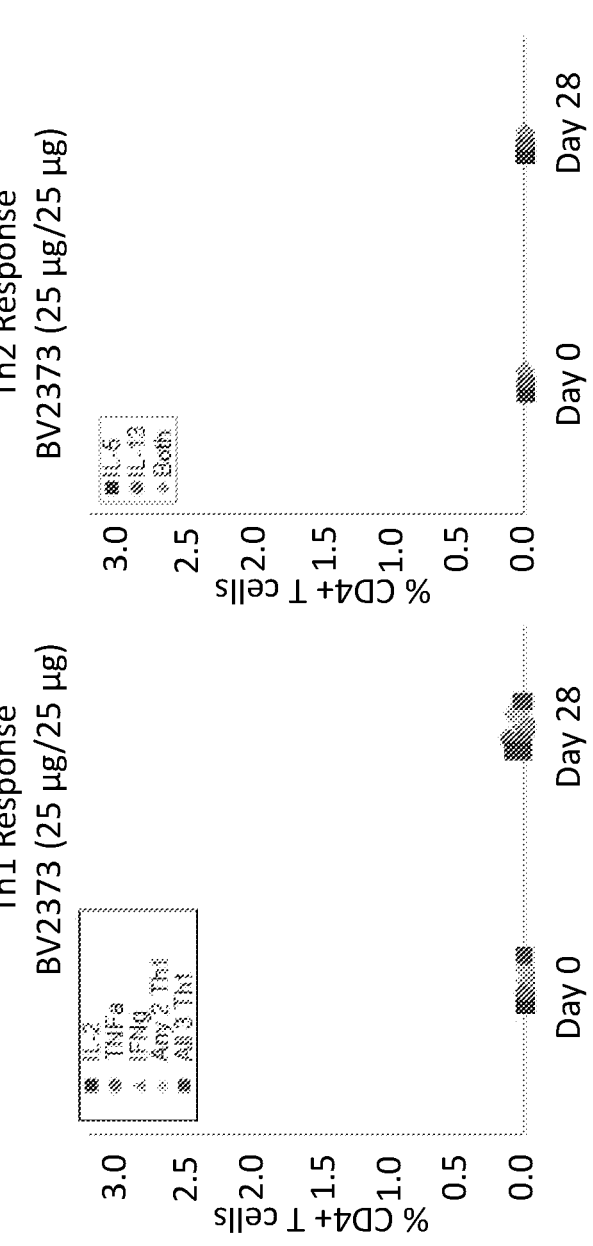
Figure 45C:
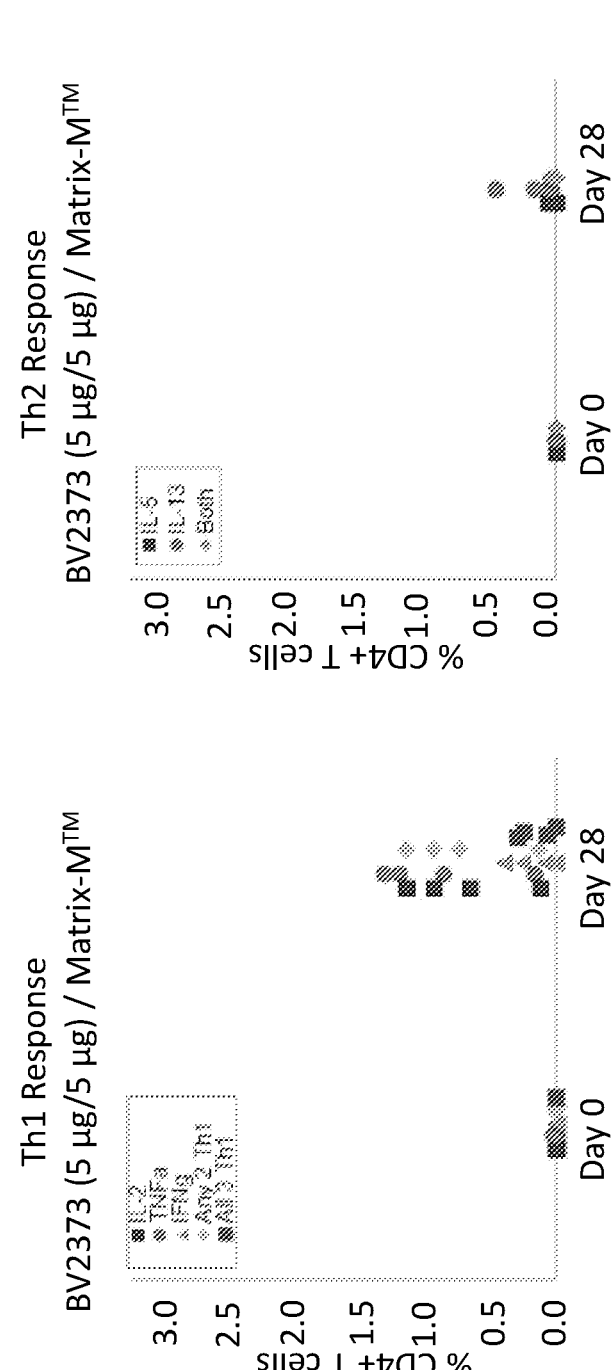

A strong correlation was observed between neutralizing antibody titers and anti-CoV-S IgG in patients treated with BV2373 and MATRIX-M™ (r=0.9466, FIG. 44C) similar to that observed in patients treated with convalescent sera (r=0.958) (FIG. 44A). This correlation was not observed in subjected administered unadjuvanted BV2373 (r=0.7616) (FIG. 44B). Both 5 μg and 25 μg BV2373/MATRIX-M™ groups (groups C-E of Table 5) demonstrated similar magnitudes of two-dose responses and every participant seroconverted using either assay measurement when a two-dose regimen was utilized.

T-cell responses in 16 participants (four participants from each of Groups A through D) showed that BV2373/MATRIX-M™ regimens induced antigen-specific polyfunctional CD4+ T-cell responses in terms of IFN-γ, IL-2, and TNF-α production upon stimulation with BV2373. There was a strong bias toward production of Th1 cytokines (FIGS. 45A-D).

Example 8

Expression, Purification, and Evaluation of Next-Generation CoV S Polypeptide Nanoparticles CoV S polypeptides having the amino acid sequence of SEQ ID NO: 112, SEQ ID NO: 113, SEQ ID NO: 114, or SEQ ID NO: 115 are expressed in a baculovirus expression system and recombinant plaques expressing the coronavirus Spike (5) polypeptides are picked and confirmed. CoV S polypeptides having a sequence of SEQ ID NO: 112, SEQ ID NO: 113, SEQ ID NO: 114, and SEQ ID NO: 115 are expressed using an N-terminal signal peptide having an amino acid sequence of SEQ ID NO: 5.

The CoV S polypeptide having a sequence of SEQ ID NO: 112 comprises a mutation of Asn-488 to tyrosine, mutations of Lys-973 and Val-974 to proline, and an inactivated furin cleavage site having the amino acid sequence of QQAQ (SEQ ID NO: 7).

The CoV S polypeptide having a sequence of SEQ ID NO: 113 comprises mutation of Asp-601 to glycine, mutation of Asn-488 to tyrosine, mutations of Lys-973 and Val-974 to proline, and an inactivated furin cleavage site having the amino acid sequence of QQAQ (SEQ ID NO: 7).

The CoV S polypeptide having a sequence of SEQ ID NO: 114 comprises deletion of amino acids 56, 57, and 131, mutation of Asn-488 to tyrosine, a mutation of Ala-557 to aspartate, mutation of Asp-601 to glycine, mutation of Pro-668 to histidine, mutation of Thr-703 to isoleucine, mutation of Ser-969 to alanine, mutation of Asp-1105 to histidine, mutations of Lys-973 and Val-974 to proline, and an inactivated furin cleavage site having the amino acid sequence of QQAQ (SEQ ID NO: 7).

The CoV S polypeptide having a sequence of SEQ ID NO: 115 comprises mutation of Asn-488 to tyrosine, mutation of Asp-67 to alanine, mutation of Leu-229 to histidine, mutation of Asp-202 to glycine, mutation of Lys-404 to asparagine, mutation of Glu-471 to lysine, mutation of Ala-688 to valine, mutation of Asp-601 to glycine, mutations of Lys-973 and Val-974 to proline, and an inactivated furin cleavage site having the amino acid sequence of QQAQ.

CoV S polypeptide nanoparticles are generated as in Example 1. The stability and immunogenicity of CoV S polypeptides having an amino acid sequence of SEQ ID NO: 112, SEQ ID NO: 112, SEQ ID NO: 113, and SEQ ID NO: 115 is evaluated as in Examples 2-7.

Numbered Embodiments

1. An immunogenic composition comprising:
   (i) a nanoparticle comprising a coronavirus S (CoV S) glycoprotein having the amino acid sequence of SEQ ID NO: 87, and a non-ionic detergent core;
   (ii) a pharmaceutically acceptable buffer, and
   (iii) a saponin adjuvant.
2. The immunogenic composition of embodiment 1, comprising between about 5 μg and about 25 μg of CoV S glycoprotein.
3. The immunogenic composition of embodiment 2, comprising about 5 μg of CoV S glycoprotein.
4. The immunogenic composition of embodiment 1, wherein the saponin adjuvant comprises at least two iscom particles, wherein:
   the first iscom particle comprises fraction A of *Quillaja saponaria* Molina and not fraction C of *Quillaja saponaria* Molina; and
   the second iscom particle comprises fraction C of *Quillaja saponaria* Molina and not fraction A of *Quillaja saponaria* Molina.
5. The immunogenic composition of embodiment 4, wherein fraction A of *Quillaja saponaria* Molina accounts for 50-96% by weight and fraction C of *Quillaja saponaria* Molina accounts for the remainder, respectively, of the sum of the weights of fraction A of *Quillaja saponaria* Molina and fraction C of *Quillaja saponaria* Molina in the adjuvant.
6. The immunogenic composition of embodiment 4, wherein fraction A of *Quillaja saponaria* Molina and fraction C of *Quillaja saponaria* Molina account for about 85% by weight and about 15% by weight, respectively, of the sum of the weights of fraction A of *Quillaja saponaria* Molina and fraction C of *Quillaja saponaria* Molina in the adjuvant.
7. The immunogenic composition of embodiment 1, comprising about 50 μg of saponin adjuvant.
8. The immunogenic composition of embodiment 1, wherein the non-ionic detergent core is selected from the group consisting of polysorbate-20 (PS20), polysorbate-40 (PS40), polysorbate-60 (PS60), polysorbate-65 (PS65), and polysorbate-80 (PS80).
9. A method of stimulating an immune response against SARS-CoV-2 in a subject comprising administering the immunogenic composition of embodiment 1.
10. The method of embodiment 9, comprising between about 5 μg and about 25 μg of CoV S glycoprotein.
11. The method of embodiment 10, comprising 5 μg of CoV S glycoprotein.
12. The method of embodiment 9, wherein the saponin adjuvant comprises at least two iscom particles, wherein:
    the first iscom particle comprises fraction A of *Quillaja saponaria* Molina and not fraction C of *Quillaja saponaria* Molina; and the second iscom particle comprises fraction C of *Quillaja saponaria* Molina and not fraction A of *Quillaja saponaria* Molina.

13. The method of embodiment 12, wherein fraction A of *Quillaja saponaria* Molina accounts for 50-96% by weight and fraction C of *Quillaja saponaria* Molina accounts for the remainder, respectively, of the sum of the weights of fraction A of *Quillaja saponaria* Molina and fraction C of *Quillaja saponaria* Molina in the adjuvant.

14. The method of embodiment 12, wherein fraction A of *Quillaja saponaria* Molina and fraction C of *Quillaja saponaria* Molina account for about 85% by weight and about 15% by weight, respectively, of the sum of the weights of fraction A of *Quillaja saponaria* Molina and fraction C of *Quillaja saponaria* Molina in the adjuvant.

15. The method of embodiment 9, comprising about 50 μg of saponin adjuvant.

16. The method of embodiment 9, wherein the non-ionic detergent core is selected from the group consisting of polysorbate-20 (PS20), polysorbate-40 (PS40), polysorbate-60 (PS60), polysorbate-65 (PS65), and polysorbate-80 (PS80).

17. The method of embodiment 9, wherein the subject is administered a first dose at day 0 and a boost dose at day 21.

18. The method of embodiment 9, wherein a single dose of the immunogenic composition is administered.

19. The method of embodiment 9, comprising administering a second immunogenic composition different from the first immunogenic composition.

20. The method of embodiment 19, wherein the second immunogenic composition comprises an mRNA encoding a SARS-Cov-2 Spike glycoprotein, a plasmid DNA encoding a SARS-Cov-2 Spike glycoprotein, a viral vector encoding a SARS-Cov-2 Spike glycoprotein, or an inactivated SARS-CoV-2 virus.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

---

The invention claimed is:

1. A coronavirus (CoV) Spike(S) glycoprotein comprising:
   (i) an S1 subunit comprising an inactivated furin cleavage site having the amino acid sequence of QQAQ (SEQ ID NO: 7); wherein the S1 subunit comprises an N-terminal domain (NTD); a receptor binding domain (RBD), and subdomains 1 and 2 (SD1/2);
   wherein the N-terminal domain comprises up to about 20 modifications compared to a NTD of a CoV S glycoprotein of SEQ ID NO: 2;
   wherein the RBD comprises up to about 30 modifications compared to a RBD of a CoV S glycoprotein of SEQ ID NO: 2;
   wherein the SD1/2 comprises up to about 15 modifications compared to a SD1/2 of a CoV S glycoprotein of SEQ ID NO: 2; and
   (ii) an S2 subunit, wherein amino acids 973 and 974 are proline,
   wherein the S2 subunit comprises up to 15 additional modifications compared to the S2 subunit of a CoV S glycoprotein of SEQ ID NO: 2;
   wherein the amino acids of the CoV S glycoprotein are numbered with respect to the CoV S glycoprotein of SEQ ID NO: 2;
   wherein each modification is a mutation, deletion, or addition of one amino acid.

2. The CoV S glycoprotein of claim 1, wherein the NTD of the CoV S glycoprotein comprises between about 5 and about 10 modifications compared to the NTD of SEQ ID NO: 2.

3. The CoV S glycoprotein of claim 1, wherein the NTD of the CoV S glycoprotein comprises between about 8 and about 12 modifications compared to the NTD of SEQ ID NO: 2.

4. The CoV S glycoprotein of claim 1, wherein the RBD of the CoV S glycoprotein comprises between about 18 and about 23 modifications compared to the RBD of SEQ ID NO: 2.

5. The CoV S glycoprotein of claim 1, wherein the RBD of the CoV S glycoprotein comprises between about 12 and about 17 modifications compared to the RBD of SEQ ID NO: 2.

6. The CoV S glycoprotein of claim 1, wherein the RBD of the CoV S glycoprotein comprises between about 5 and about 10 modifications compared to the RBD of SEQ ID NO: 2.

7. The CoV S glycoprotein of claim 1, wherein the RBD of the CoV S glycoprotein comprises between about 15 and about 20 modifications compared to the RBD of SEQ ID NO: 2.

8. The CoV S glycoprotein of claim 1, wherein the SD1/2 of the CoV S glycoprotein comprises between about 3 and about 10 modifications compared to the SD1/2 of SEQ ID NO: 2.

9. The CoV S glycoprotein of claim 1, wherein the S2 subunit of the CoV S glycoprotein comprises between about 3 and about 10 modifications compared to the S2 subunit of SEQ ID NO: 2.

10. The CoV S glycoprotein of claim 1, wherein the CoV S glycoprotein comprises one or more modifications at a position selected from the group consisting of 56, 57, 131, 404, 488, 439, 471, 601, 642, and 668, wherein the CoV S glycoprotein is numbered according to SEQ ID NO: 2.

11. A nanoparticle comprising the CoV S glycoprotein of claim 1 and a non-ionic detergent.

12. The nanoparticle of claim 11, wherein the non-ionic detergent is selected from the group consisting of polysorbate-20 (PS20), polysorbate-40 (PS40), polysorbate-60 (PS60), polysorbate-65 (PS65), and polysorbate-80 (PS80).

13. An immunogenic composition comprising the nanoparticle of claim 11 and a pharmaceutically acceptable buffer.

14. The immunogenic composition of claim 13, comprising an adjuvant.

15. The immunogenic composition of claim 14, wherein the adjuvant is a saponin adjuvant.

16. The immunogenic composition of claim 13, wherein the saponin adjuvant comprises at least two iscom particles, wherein:

the first iscom particle comprises fraction A of *Quillaja Saponaria* Molina and not fraction C of *Quillaja Saponaria* Molina; and the second iscom particle comprises fraction C of *Quillaja Saponaria* Molina and not fraction A of *Quillaja Saponaria* Molina.

17. The immunogenic composition of claim 16, wherein fraction A of *Quillaja Saponaria* Molina accounts for 50-96% by weight and fraction C of *Quillaja Saponaria* Molina accounts for the remainder, respectively, of the sum of the weights of fraction A of *Quillaja Saponaria* Molina and fraction C of *Quillaja Saponaria* Molina in the adjuvant.

18. The immunogenic composition of claim 16, wherein fraction A of *Quillaja Saponaria* Molina and fraction C of *Quillaja Saponaria* Molina account for about 85% by weight and about 15% by weight, respectively, of the sum of the weights of fraction A of *Quillaja Saponaria* Molina and fraction C of *Quillaja Saponaria* Molina in the adjuvant.

19. The immunogenic composition of claim 13, comprising from about 3 μg to about 25 μg of CoV S glycoprotein.

20. The immunogenic composition of claim 13, comprising about 5 μg of CoV S glycoprotein.

21. The immunogenic composition of claim 14, comprising about 50 μg of adjuvant.

22. A method of stimulating an immune response against SARS-COV-2 in a human comprising administering the immunogenic composition of claim 13.

23. The method of claim 22, wherein the immunogenic composition comprises an adjuvant.

24. The method of claim 23, wherein the adjuvant is a saponin adjuvant.

25. The method of claim 24, wherein the saponin adjuvant comprises at least two iscom particles, wherein:

the first iscom particle comprises fraction A of *Quillaja Saponaria* Molina and not fraction C of *Quillaja Saponaria* Molina; and the second iscom particle comprises fraction C of *Quillaja Saponaria* Molina and not fraction A of *Quillaja Saponaria* Molina.

26. The method of claim 25, wherein fraction A of *Quillaja Saponaria* Molina accounts for 50-96% by weight and fraction C of *Quillaja Saponaria* Molina accounts for the remainder, respectively, of the sum of the weights of fraction A of *Quillaja Saponaria* Molina and fraction C of *Quillaja Saponaria* Molina in the adjuvant.

27. The method of claim 25, wherein fraction A of *Quillaja Saponaria* Molina and fraction C of *Quillaja Saponaria* Molina account for about 85% by weight and about 15% by weight, respectively, of the sum of the weights of fraction A of *Quillaja Saponaria* Molina and fraction C of *Quillaja Saponaria* Molina in the adjuvant.

28. The method of claim 22, comprising from about 3 μg to about 25 μg of CoV S glycoprotein.

29. The method of claim 22, comprising about 5 μg of CoV S glycoprotein.

30. The method of claim 23, comprising about 50 μg of adjuvant.

* * * * *